United States Patent
Schaub et al.

(10) Patent No.: US 8,252,913 B2
(45) Date of Patent: Aug. 28, 2012

(54) APTAMERS TO TISSUE FACTOR PATHWAY INHIBITOR AND THEIR USE AS BLEEDING DISORDER THERAPEUTICS

(75) Inventors: Robert G. Schaub, Pelham, NH (US); Kathleen McGinness, Cambridge, MA (US); Jennifer Nelson, Boston, MA (US); Ryan Genga, Somerville, MA (US); Emily Waters, Jamaica Plain, MA (US); Jeffrey C. Kurz, Winchester, MA (US); John L. Diener, Cambridge, MA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 72 days.

(21) Appl. No.: 12/858,369

(22) Filed: Aug. 17, 2010

(65) Prior Publication Data

US 2011/0098345 A1    Apr. 28, 2011

Related U.S. Application Data

(60) Provisional application No. 61/234,939, filed on Aug. 18, 2009, provisional application No. 61/353,374, filed on Jun. 10, 2010, provisional application No. 61/366,362, filed on Jul. 21, 2010, provisional application No. 61/367,766, filed on Jul. 26, 2010.

(51) Int. Cl.
*C07H 21/02* (2006.01)
*C07H 21/04* (2006.01)
*C12N 15/11* (2006.01)

(52) U.S. Cl. ..................... 536/23.1; 514/44 A
(58) Field of Classification Search ........................ None
See application file for complete search history.

(56) References Cited

U.S. PATENT DOCUMENTS

| | | |
|---|---|---|
| 5,981,471 A | 11/1999 | Papathassiu et al. |
| 6,207,646 B1 | 3/2001 | Krieg et al. |
| 6,214,806 B1 | 4/2001 | Krieg et al. |
| 6,239,116 B1 | 5/2001 | Krieg et al. |
| 6,410,278 B1 | 6/2002 | Notomi et al. |
| 6,426,334 B1 | 7/2002 | Agrawal et al. |
| 6,429,199 B1 | 8/2002 | Krieg et al. |
| 6,498,148 B1 | 12/2002 | Raz |
| 6,514,948 B1 | 2/2003 | Raz et al. |
| 6,653,292 B1 | 11/2003 | Krieg et al. |
| 7,250,496 B2 | 7/2007 | Bentwich |

OTHER PUBLICATIONS

Bates, S.M. et al., "The status of new anticoagulants," *British Journal of Haemotology*, 2006, vol. 134, pp. 3-19.
Baugh, R.J. et al., "Regulation of Extrinsic Pathway Factor Xa Formation by Tissue Factor Pathway Inhibitor," *The Journal of Biological Chemistry*, Feb. 20, 1998, vol. 273, No. 8, pp. 4378-4386.
Broze, Jr, G.J., "Tissue Factor Pathway Inhibitor and the Revised Theory of Coagulation," *Annual Review of Medicine*, 1995, vol. 46, pp. 103-112.
Ecker, J.R. et al., GenBank: BH755568.1, Mar. 1, 2002, retrieved on Dec. 1, 2010, <http://www.ncbi.nlm.nih.gov/nucgss/BH755568>, 1 pages.
Franssen, J. et al., "Prothrombinase is protected from inactivation by tissue factor pathway inhibitor: competition between prothrombin and inhibitor," *Biochem. J.*, 1997, vol. 323, pp. 33-37.
Girard, T.J. et al., "Functional significance of the Kunitz-type inhibitory domains of lipoprotein-associated coagulation inhibitor," *Nature*, Apr. 6, 1989, vol. 338, pp. 518-520.
Huang, Z-F. et al., "Kinetics of Factor Xa Inhibition by Tissue Factor Pathway Inhibitor," *The Journal of Biological Chemistry*, Dec. 25, 1993, vol. 268, No. 36, pp. 26950-26955.
International Search Report mailed on Dec. 15, 2010, for International Application No. PCT/US10/45797 filed on Aug. 17, 2010, 4 pages.
Kreig, A.M., "CpG Motifs in Bacterial DNA and Their Immune Effects," *Annu. Rev. Immunol.*, 2002, vol. 20, pp. 709-760.
Liu, T. et al., "Improved coagulation in bleeding disorders by Non-Anticoagulant Sulfated Polysaccharides (NASP)," *Thromb. Haemost.*, 2006, vol. 95, pp. 68-76.
Ovanesov, M.V. et al., "Initiation and propagation of coagulation from tissue factor-bearing cell monolayers to plasma: initiator cells do not regulate spatial growth rate," *Journal of Thrombosis and Homeostasis*, 2005, vol. 3, pp. 321-331.
Panteleev, M.A. et al., "Spatial Propagation and Localization of Blood Coagulation Are Regulated by Intrinsic and Protein C Pathways, Respectively," *Biophysical Journal*, Mar. 2008, vol. 90, No. 5, pp. 1489-1500.
Petersen, L.C. et al., "Inhibitory properties of separate recombinant Kunitz-type-protease-inhibitor domains from tissue-factor-pathway inhibitor," *Eur. J. Biochem.*, 1996, vol. 235, pp. 310-316.
Prasad, S. et al., "Efficacy and safety of a new-class hemostatic drug candidate, AV513, in dogs with hemophilia A," *Blood*, Jan. 15, 2008, vol. 111, No. 2, pp. 672-679.
Robert, S. et al., "Is thrombin generation the new rapid, reliable and relevant pharmacological tool for the development of anticoagulant drugs?" *Pharmacological Research*, 2009, vol. 59, pp. 160-166.
Wesselschmidt, R. et al., "Structural requirements for tissue factor pathway inhibitor interactions with factor Xa and heparin," *Blood Coagulation and Fibrinolysis*, 1993, vol. 4, pp. 661-669.

*Primary Examiner* — Richard Schnizer
(74) *Attorney, Agent, or Firm* — Morgan, Lewis & Bockius LLP

(57) ABSTRACT

The invention relates generally to the field of nucleic acids and more particularly to aptamers that bind to TFPI, which are useful as therapeutics in and diagnostics of bleeding disorders and/or other diseases or disorders in which TFPI has been implicated. In addition, the TFPI aptamers may be used before, during and/or after medical procedures to reduce complications or side effects thereof. The invention further relates to materials and methods for the administration of aptamers that bind to TFPI.

36 Claims, 142 Drawing Sheets

```
DSEEDEEHTIITDTELPPLKLMHSFCAFKADDGPCKAIMKRFFFNIFTRQCEEFIYGGCEGNQNRFESLEECKK
MCTRDNANRIIKTTLQQEKPDFCFLEEDPGICRGYITRYFYNNQTKQCERFKYGGCLGNMNNFETLEECKNICE
DGPNGFQVDNYGTQLNAVNNSLTPQSTKVPSLFEFHGPSWCLTPADRGLCRANENRFYYNSVIGKCRPFKYSGC
GGNENNFTSKQECLRACKKGFIQRISKGGLIKTKRKRKKQRVKIAYEEIFVKNM (SEQ ID NO:11)
```

SEQ ID NO:2 WITH A 40 kDa PEG MOIETY

SEQ ID NO:2 WITH A LINKER AND A 40 kDa PEG MOIETY

SEQ ID NO:4

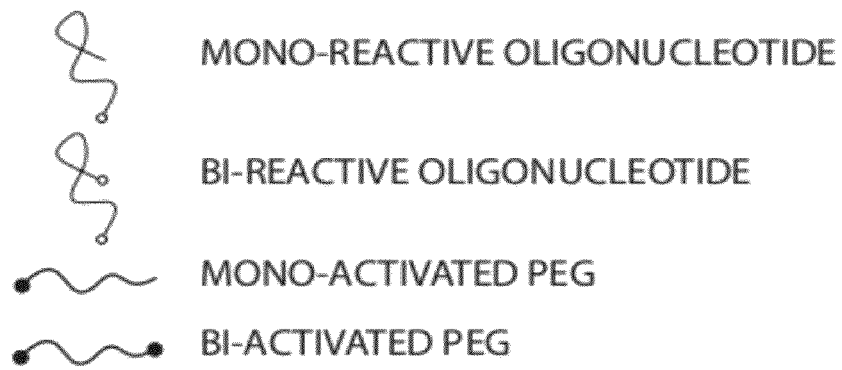
STANDARD PEGYLATION
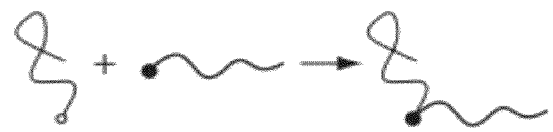
MULTIPLE PEGYLATION
DIMERIZATION VIA PEGYLATION
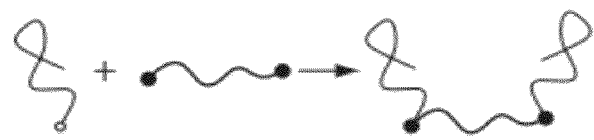
Fig. 11

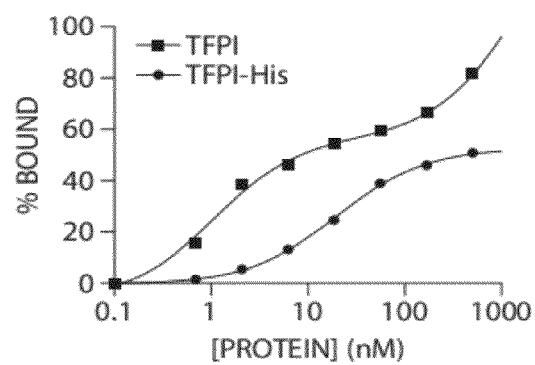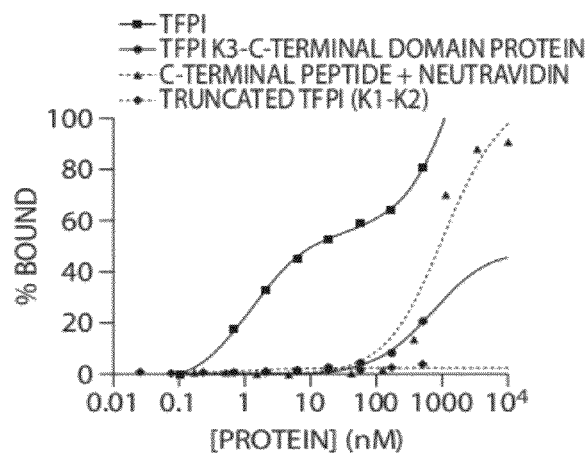
Fig. 17A
Fig. 17B
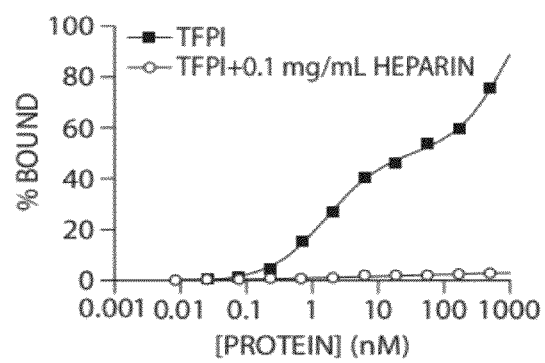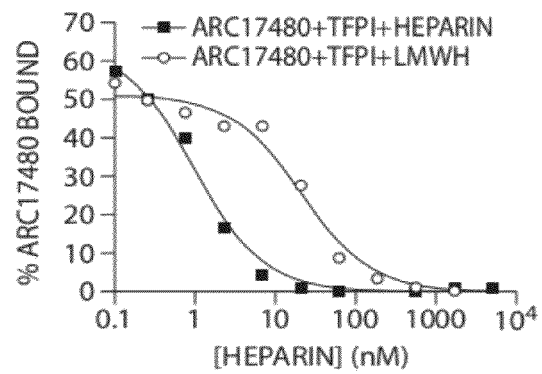
Fig. 18A
Fig. 18B

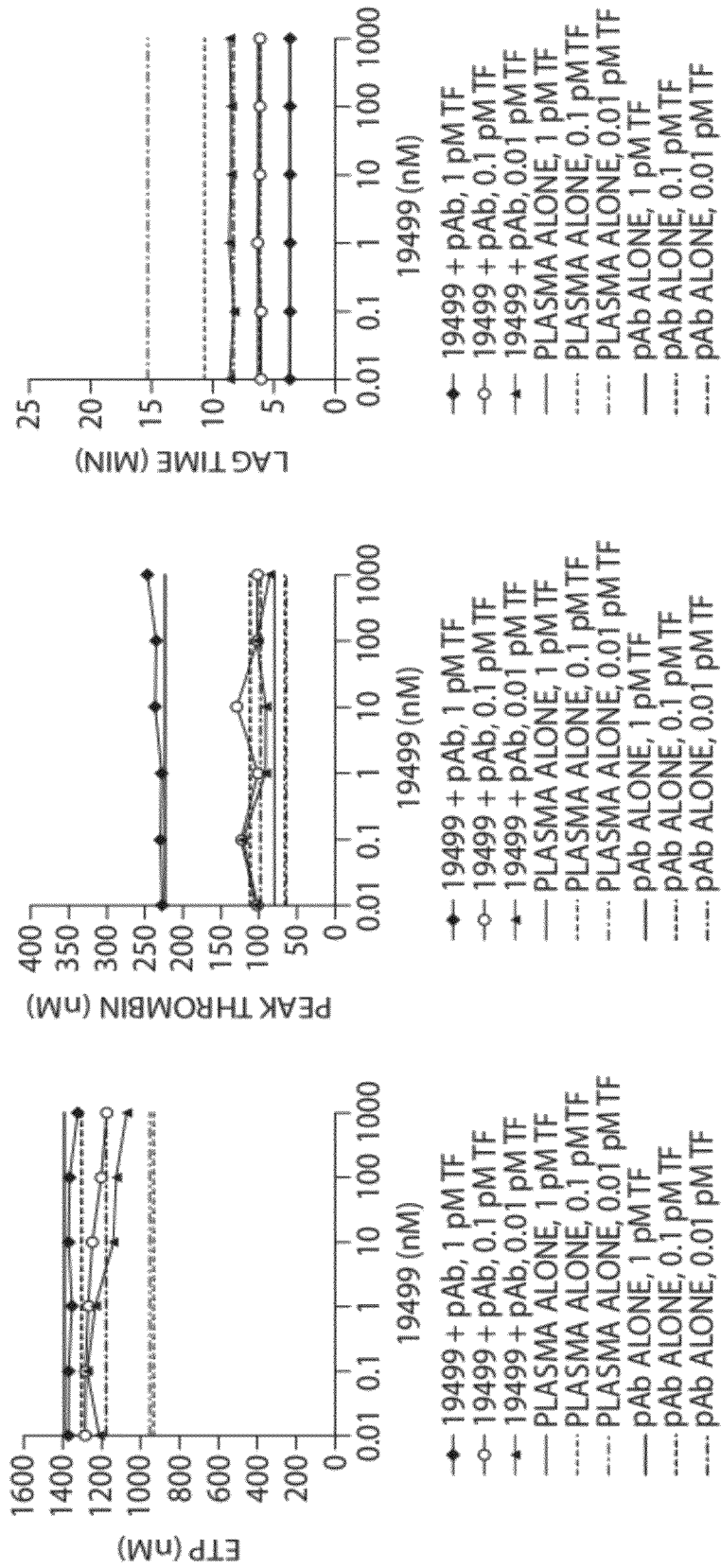

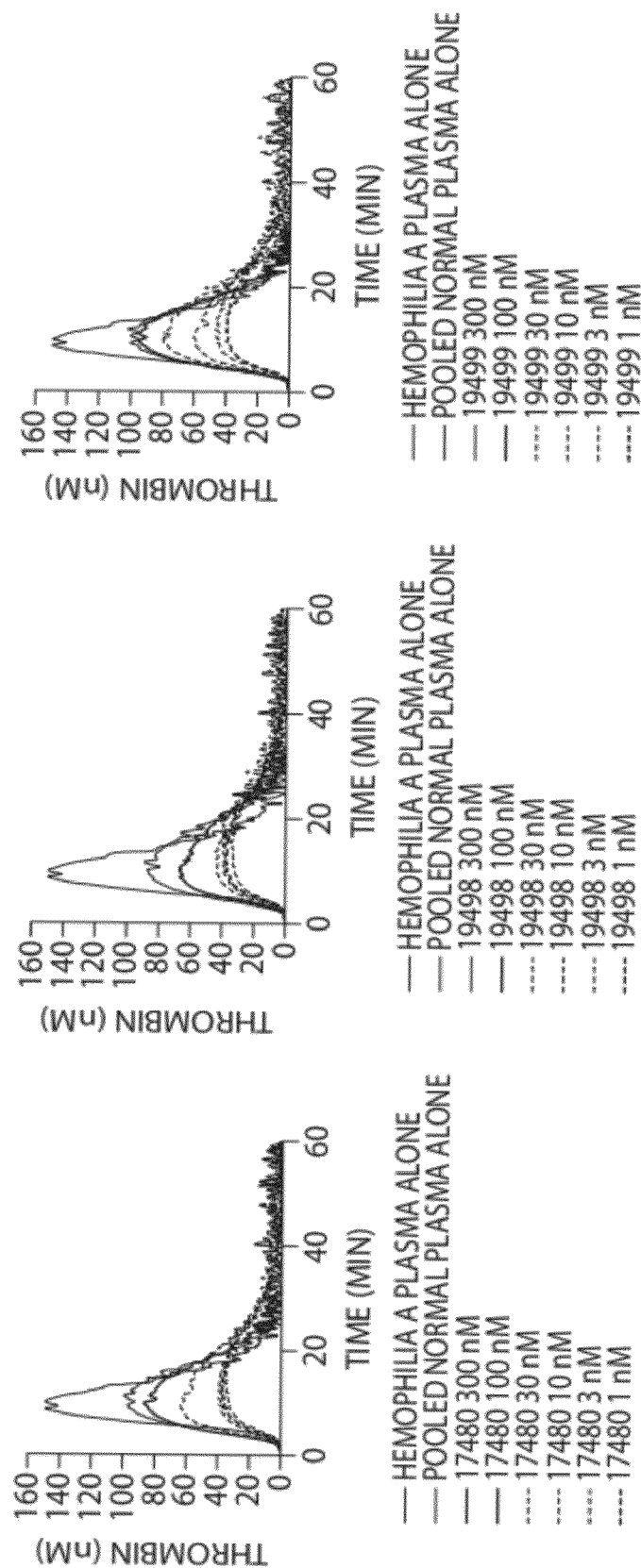

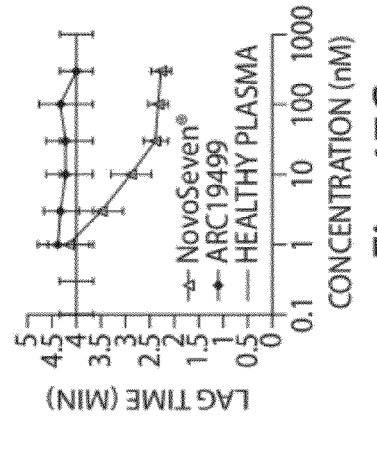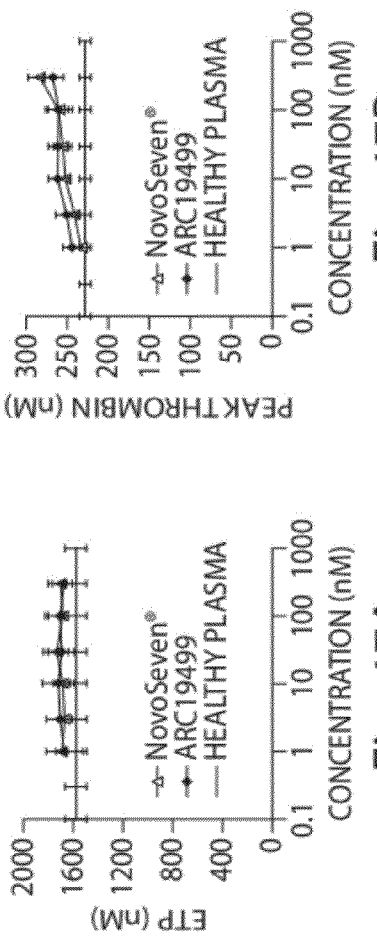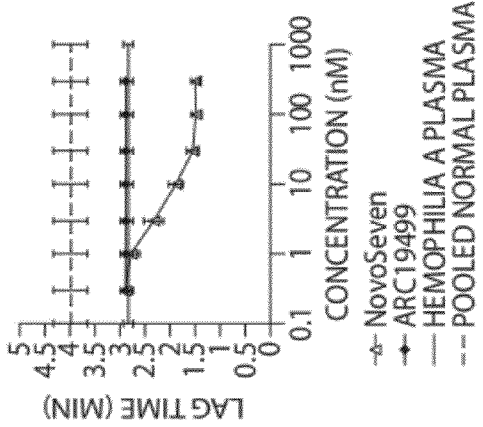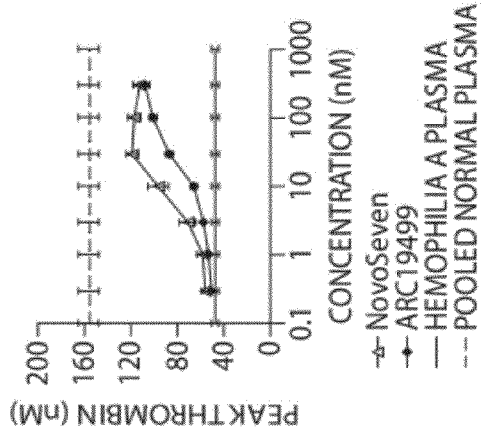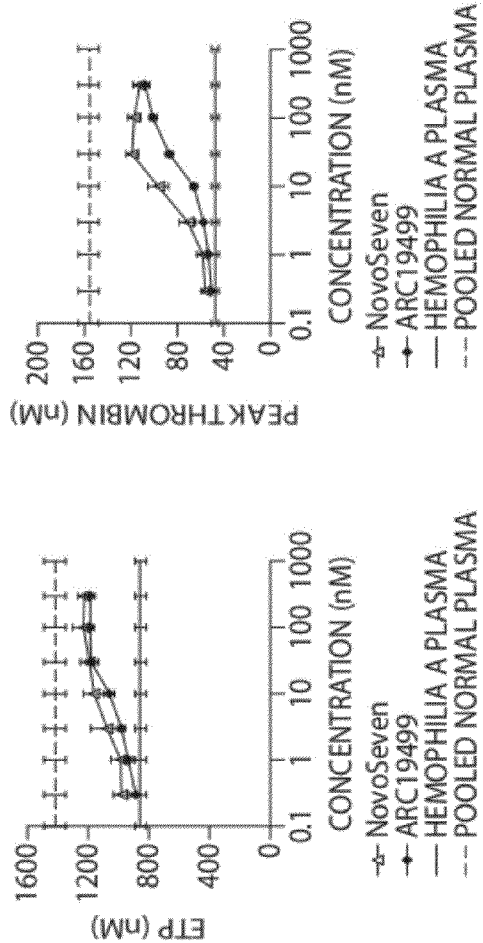

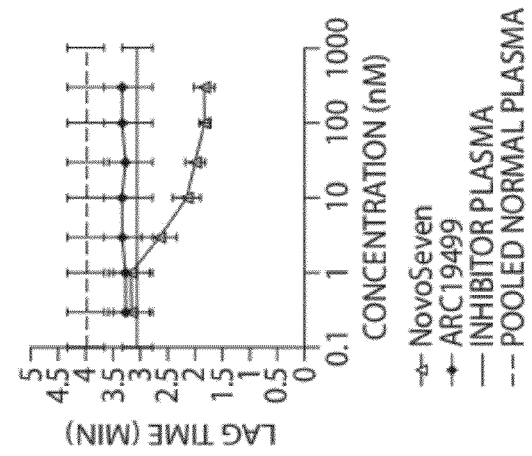
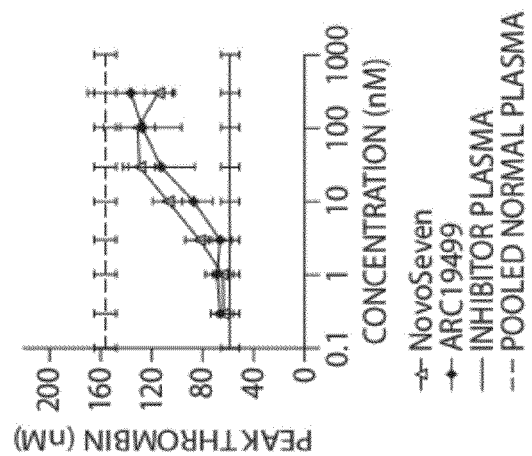
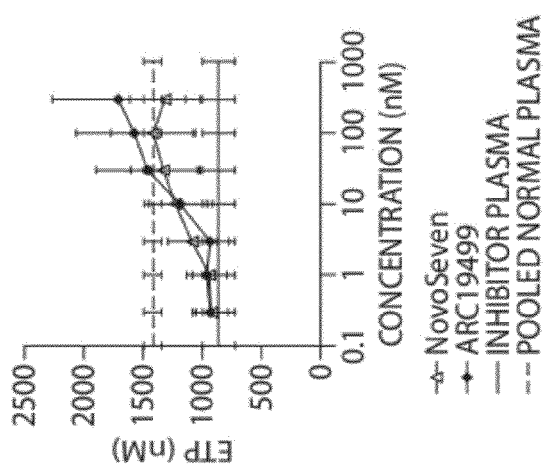
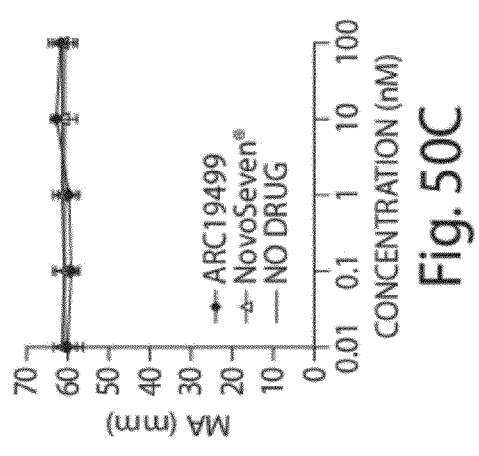
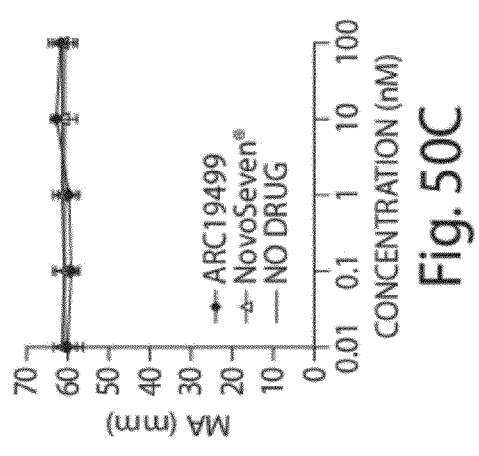
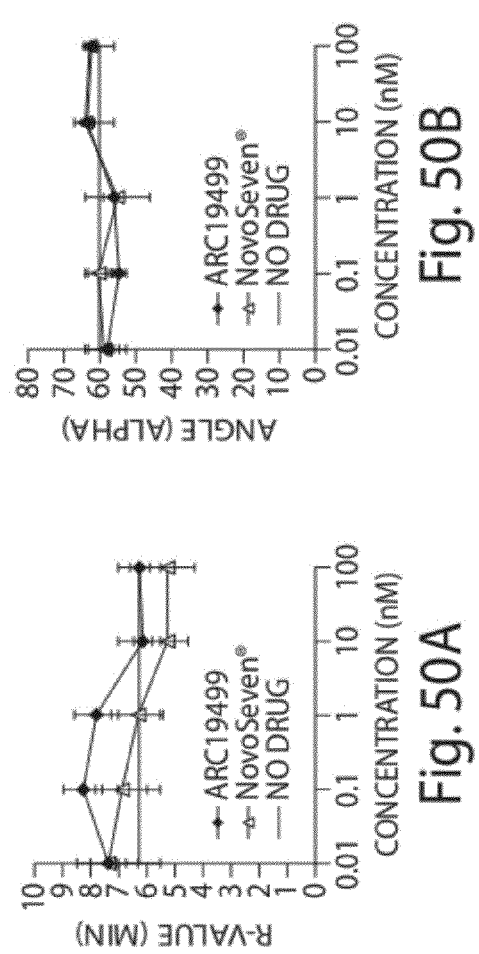

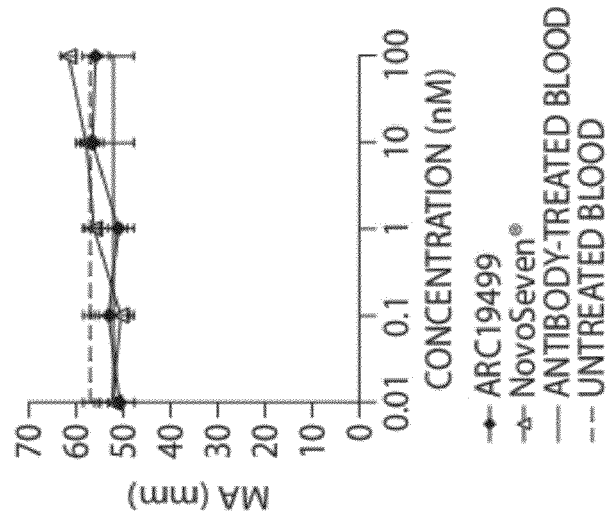
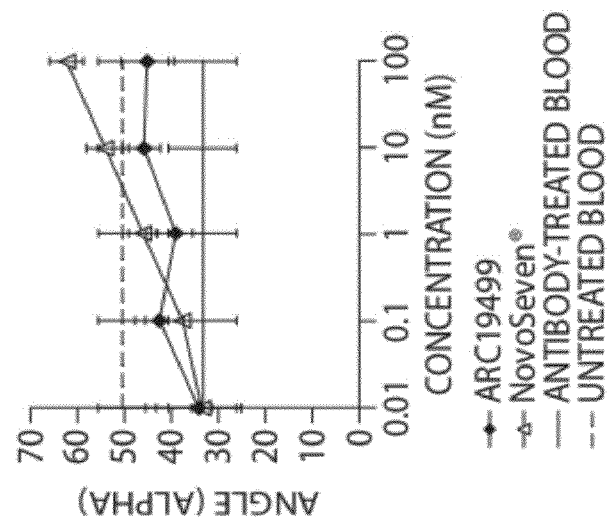
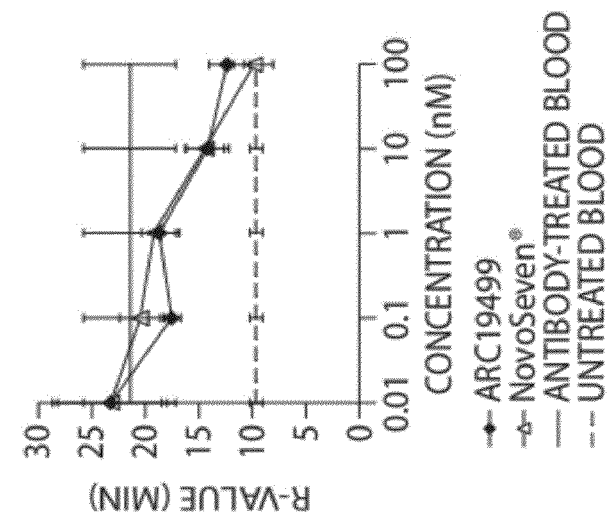
Fig. 51C
Fig. 51B
Fig. 51A

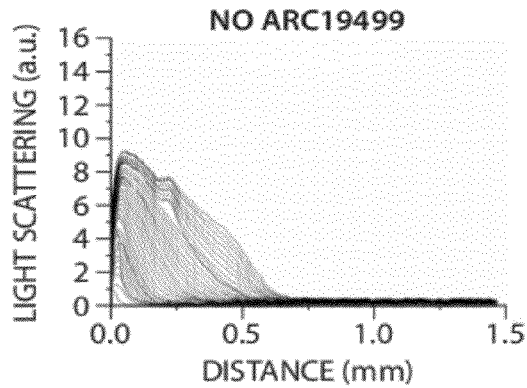
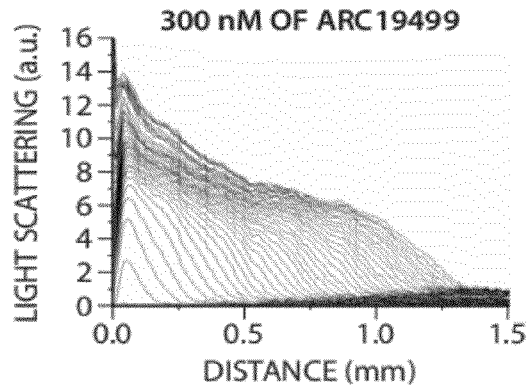
Fig. 55A    Fig. 55B
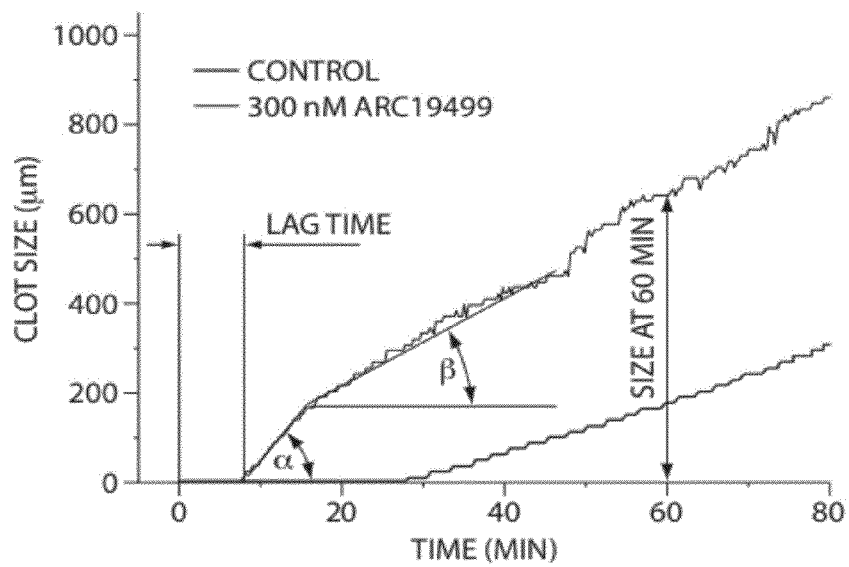
Fig. 56

| PATIENT NUMBER | AGE | MONTHLY BLEEDING EVENTS | FACTOR VIII LEVEL IN THE DAY OF EXPERIMENT, % | APTT, sec |
|---|---|---|---|---|
| 1 | 21 | 0-1 | <1 | 103 |
| 2 | 24 | 1-2 | 2.1 | 82 |
| 3 | 43 | 1-2 | 1.2 | 86 |
| 4 | 48 | 1-2 | 1.4 | 80 |
| 5 | 21 | 1-2 | <1 | 120 |
| 6 | 36 | 2-3 | <1 | 102 |
| 7 | 19 | 3-5 | 2.8 | 99 |
| 8 | 30 | 0-1 | <1 | 124 |

Fig. 65

| TF-ACT IN WHOLE BLOOD FROM NORMAL SUBJECTS | | | |
|---|---|---|---|
| [ARC19499] (nM) | #2 (N) (SECONDS) | #6 (N) (SECONDS) | #7 (N) (SECONDS) |
| 700 | | 311 | |
| 350 | 317 | 287 | 277 |
| 175 | 278 | 295 | 293 |
| 88 | 319 | 305 | 258 |
| 44 | | | 267 |
| 0 | 353 | 342 | 311 |

| TF-ACT IN WHOLE BLOOD FROM HEMOPHILIA B SUBJECTS | | |
|---|---|---|
| [ARC19499] (nM) | #4 (B) (SECONDS) | #9 (B) (SECONDS) |
| 350 | 438 | 522 |
| 175 | 435 | 457/510 |
| 88 | 323 | 420 |
| 44 | 460 | 510 |
| 0 | 528 | 580 |

| TF-ACT IN WHOLE BLOOD FROM HEMOPHILIA A SUBJECTS | | | | | | | |
|---|---|---|---|---|---|---|---|
| [ARC19499] (nM) | #1 (A) (SECONDS) | #3 (A) (SECONDS) | #5(A) (SECONDS) | #8(A) (SECONDS) | #10(A) (SECONDS) | #11(A) (SECONDS) | #12(A) (SECONDS) |
| 3115 | 264 | | | | | | |
| 1558 | 313 | | | | | | |
| 1400 | | | | | | 455 | 299 |
| 800 | 256 | | | | | | |
| 700 | | 551/500 | 489 | | 416 | 634 | 281 |
| 350 | | 444 | 434 | 483 | 418 | 347 | 295 |
| 175 | | 457 | 392 | 453 | 456 | 491 | 291 |
| 88 | | | 468 | 464 | | 456 | 306 |
| 44 | | | | | 477 | | |
| 0 | 578 | 651 | 540 | 642 | 527 | 783 | 328 |

Fig. 81

| DILUTE PT IN PLASMA FROM NORMAL SUBJECTS | | | |
|---|---|---|---|
| [ARC19499] (nM) | #2 (N) (SECONDS) | #6 (N) (SECONDS) | #7 (N) (SECONDS) |
| 500 | 179 | 185 | 174 |
| 125 | 183 | 225 | 168 |
| 32 | 181 | 242 | 170 |
| 8 | 191 | 246 | 176 |
| 2 | 294 | 274 | 265 |
| 0 | >360 | >360 | >360 |

| DILUTE PT IN PLASMA FROM HEMOPHILIA B SUBJECTS | | |
|---|---|---|
| [ARC19499] (nM) | #4 (B) (SECONDS) | #9 (B) (SECONDS) |
| 500 | 215 | 185 |
| 125 | 227 | 189 |
| 32 | 225 | 192 |
| 8 | 241 | 210 |
| 2 | >360 | >360 |
| 0 | >360 | >360 |

| DILUTE PT IN PLASMA FROM HEMOPHILIA A SUBJECTS | | | | | | | |
|---|---|---|---|---|---|---|---|
| [ARC19499] (nM) | #1 (A) (SECONDS) | #3 (A) (SECONDS) | #5 (A) (SECONDS) | #8 (A) (SECONDS) | #10 (A) (SECONDS) | #11 (A) (SECONDS) | #12 (A) (SECONDS) |
| 500 | 163 | 162 | 162 | 156 | 154 | 162 | >360 |
| 125 | 167 | 164 | 163 | 157 | 156 | 168 | >360 |
| 32 | 171 | 168 | 164 | 163 | 157 | 171 | >360 |
| 8 | 185 | 193 | 175 | 192 | 163 | 195 | >360 |
| 2 | >360 | >360 | >360 | >360 | 169 | >360 | >360 |
| 0 | >360 | >360 | >360 | >360 | 169 | >360 | >360 |

| SEQ ID | RESIDUE | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | |
|---|---|---|---|---|---|---|---|---|---|---|---|---|---|---|---|---|---|---|---|---|---|---|---|---|---|---|---|---|---|---|---|---|---|---|
| 101 | ARC17443 | mG | mG | mA | mA | mU | mA | mU | mA | dC | mU | mU | mG | mG | dC | mU | dC | mG | mU | mU | mA | mG | mG | mU | mG | dC | mG | mU | mA | smU | mA | mU | mA | 3T |
| 102 | ARC17444 | mG | mG | mA | mA | mU | mA | mU | mA | dC | mU | mU | mG | mG | dC | mU | dC | mG | mU | mU | mA | mG | mG | mU | mG | dC | mG | mU | mA | mU | smA | mU | mA | 3T |
| 103 | ARC19445 | mG | mG | mA | mA | mU | mA | mU | mA | dC | mU | mU | mG | mG | dC | mU | dC | mG | mU | mU | mA | mG | mG | mU | mG | dC | mG | mU | mA | mU | mA | smU | mA | 3T |
| 104 | ARC19446 | mG | mG | mA | mA | mU | mA | mU | mA | dC | mU | mU | mG | mG | dC | mU | dC | mG | mU | mU | mA | mG | mG | mU | mG | dC | mG | mU | mA | mU | mA | mU | smA | 3T |
| 105 | ARC19447 | mG | mG | mA | mA | mU | mA | mU | mA | dC | mU | mU | mG | mG | dC | mU | dC | mG | mU | mU | mA | mG | mG | mU | mG | dC | mG | mU | mA | mU | mA | mU | mA | s3T |

Fig. 141-2

| SEQ ID | | RESIDUE 9 | RESIDUE 14 | RESIDUE 16 | RESIDUE 25 | TOLERATED? |
|---|---|---|---|---|---|---|
| 2 | ARC17480 | dC | dC | dC | dC | YES |
| 66 | ARC18545 | dC | mC | mC | dC | YES |
| 8 | ARC18546 | dC | mC | dC | mC | YES |
| 67 | ARC18549 | dC | mC | mC | mC | YES |
| 68 | ARC19476 | fC | mC | dC | dC | YES |
| 69 | ARC19477 | dC | mC | fC | dC | YES |
| 70 | ARC19478 | dC | mC | dC | fC | YES |
| 71 | ARC19484 | dC | fC | dC | mC | YES |
| 72 | ARC19490 | fC | mC | dC | mC | YES |
| 73 | ARC19491 | dC | mC | fC | mC | YES |

| SEQ ID | RESIDUE | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | |
|---|---|---|---|---|---|---|---|---|---|---|---|---|---|---|---|---|---|---|---|---|---|---|---|---|---|---|---|---|---|---|---|---|---|---|
| 133 | ARC33144 | mG | mG |  |  | mU | mA | mU | mA | dC | mU | mU | mG | mG | dC | mU | dC | mG | mU | mU | mA | mG | mG | mU | mG | dC | mG | mU | mA | mU | mA | mU | mA | 3T |
| 134 | ARC33145 | mG | mG | mA | mA | mU | mA | mU | mA | dC | mU | mU | mG | mG | dC | mU | dC | mG | mU | mU | mA | mG | mG | mU | mG | dC | mG | mU | mA | mU | mA | mU | mA | 3T |
| 135 | ARC33146 | mG | mG | mA | mA | mU | mA | mU | mA | dC | mU | mU | mG | mG | dC | mU | dC | mG | mU | mU | mA | mG | mG | mU | mG | dC | mG | mU | mA | mU | mA | mU | mA | 3T |
| 136 | ARC33147 | mG | mG | mA | mA | mU | mA | mU | mA | dC | mU | mU | mG | mG | dC | mU | dC | mG | mU | mU | mA | mG | mG | mU | mG | dC | mG | mU | mA | mU | mA | mU | mA | 3T |
| 137 | ARC33148 | mG | mG | mA | mA | mU | mA | mU | mA | dC | mU | mU | mG | mG | dC | mU | dC | mG | mU | mU | mA | mG | mG | mU | mG | dC | mG | mU | mA | mU | mA | mU | mA | 3T |
| 138 | ARC32303 |  |  |  | mA | mU | mA | mU | mA | dC | mU |  |  | mG | dC | mU | dC | mG | mU | mU | mA | mG | mG | mU | mG | dC | mG | mU | mA | mU | mA | mU |  | 3T |
| 139 | ARC32305 | mG | mG | mA | mA | mU | mA | mU | mA | dC | mU | mU | mG | mG | dC | mU | dC | mG | mU | mU | mA | mG | mG | mU | mG | dC | mG | mU | mA | mU | mA | mU |  | 3T |
| 140 | ARC32306 |  |  | mA | mA | mU | mA | mU | mA | dC | mU | mU | mG | mG | dC | mU | dC | mG | mU | mU | mA | mG | mG | mU | mG | dC | mG | mU | mA | mU | mA |  |  | 3T |
| 141 | ARC32307 |  |  | mA | mA | mU | mA | mU | mA | dC | mU | mU | mG | mG | dC | mU | dC | mG | mU | mU | mA | mG | mG | mU | mG | dC | mG | mU | mA | mU | mA |  |  | 3T |
| 142 | ARC33889 |  |  | mA | mA | mU | mA | mU | mA | dC | mU | mU | mG | mG | dC | mU | dC | mG | mU | mU | mA | mG | mG | mU | mG | dC | mG | mU | mA | mU | mA |  |  | 3T |
| 143 | ARC33890 |  |  | mA | mA | mU | mA | mU | mA | dC | mU | mU | mG | mG | dC | mU | dC | mG | mU | mU | mA | mG | mG | mU | mG | dC | mG | mU | mA | mU | mA |  |  | 3T |
| 144 | ARC33891 |  |  | mA | mA | mU | mA | mU | mA | dC | mU | mU | mG | mG | dC | mU | dC | mG | mU | mU | mA | mG | mG | mU | mG | dC | mG | mU | mA | mU | mA |  |  | 3T |
| 145 | ARC33895 |  |  | mA | mA | mU | mA | mU | mA | dC | mU | mU | mG | mG | dC | mU | dC | mG | mU | mU | mA | mG | mG | mU | mG | dC | mG | mU | mA | mU | mA |  |  | 3T |
| 146 | ARC33900 | mG | mG | mA | mA | mU | mA | mU | mA | dC | mU | mU | mG | mG | dC | mU | dC | mG | mU | mU | mA | mG | mG | mU | mG | dC | mG | mU | mA | mU | mA | mU |  | 3T |
| 147 | ARC33907 | mG | mG | mA | mA | mU |  | mU | mA | dC | mU | mU | mG | mG | dC | mU | dC | mG | mU | mU | mA | mG | mG | mU | mG | dC | mG | mU | mA | mU | mA | mU | mA | 3T |

SEQUENCE LISTING

```
<160> NUMBER OF SEQ ID NOS: 153

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
```

```
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified

<400> SEQUENCE: 1
ggaauauacu uggcucguua ggugcguaua ua                              32

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 2
ggaauauacu uggcucguua ggugcguaua uat                             33
```

```
<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-NH2
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 3
ggaauauacu uggcucguua ggugcguaua uat                                  33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-PEG40K-NH
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
```

```
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 4
ggaauauacu uggcucguua ggugcguaua uat                                33

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-NH2
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
```

```
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<223> OTHER INFORMATION: 3'-NH2

<400> SEQUENCE: 5
ggaauauacu uggcucguua ggugcguaua ua                                 32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-PEG20K-NH
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<223> OTHER INFORMATION: 3'-NH-PEG20K

<400> SEQUENCE: 6
ggaauauacu uggcucguua ggugcguaua ua                                 32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(32)
<223> OTHER INFORMATION: 2'-O Methyl modified

<400> SEQUENCE: 7
ggaauauacu uggcucguua ggugcguaua ua                              32

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 8
ggaauauacu uggcucguua ggugcguaua uat                             33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-NH2
<220> FEATURE:
<221> NAME/KEY: modified_base
```

```
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 9
ggaauauacu uggcucguua ggugcguaua uat                                 33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-PEG40K-NH
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 10
ggaauauacu uggcucguua ggugcguaua uat                                 33

<210> SEQ ID NO 11
<211> LENGTH: 276
<212> TYPE: PRT
<213> ORGANISM: Homo sapiens

<400> SEQUENCE: 11

Asp Ser Glu Glu Asp Glu Glu His Thr Ile Ile Thr Asp Thr Glu Leu
1               5                   10                  15
```

```
Pro Pro Leu Lys Leu Met His Ser Phe Cys Ala Phe Lys Ala Asp Asp
            20                  25                  30

Gly Pro Cys Lys Ala Ile Met Lys Arg Phe Phe Asn Ile Phe Thr
        35                  40                  45

Arg Gln Cys Glu Glu Phe Ile Tyr Gly Gly Cys Glu Gly Asn Gln Asn
50                      55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
            275

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aacgttcgag                                                              10

<210> SEQ ID NO 13
<211> LENGTH: 276
<212> TYPE: PRT
<213> ORGANISM: Homo sapiens

<400> SEQUENCE: 13

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Asn Ile Phe Thr
        35                  40                  45
```

```
Arg Gln Cys Glu Glu Phe Ile Tyr Gly Gly Cys Glu Gly Asn Gln Asn
    50                  55                  60

Arg Phe Glu Ser Leu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
                100                 105                 110

Tyr Phe Ile Asn Asn Gln Thr Lys Gly Cys Glu Arg Phe Lys Tyr Gly
            115                 120                 125

Gly Cys Leu Gly Asn Met Asn Asn Phe Glu Thr Leu Glu Glu Cys Lys
    130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
                180                 185                 190

Ala Asp Arg Gly Ile Cys Arg Ala Asn Glu Asn Arg Phe Tyr Tyr Asn
            195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
                260                 265                 270

Val Lys Asn Met
            275

<210> SEQ ID NO 14
<211> LENGTH: 193
<212> TYPE: PRT
<213> ORGANISM: Homo sapiens

<400> SEQUENCE: 14

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Phe Asn Ile Phe Thr
            35                  40                  45

Arg Gln Cys Glu Glu Phe Ile Tyr Gly Gly Cys Glu Gly Asn Gln Asn
    50                  55                  60

Arg Phe Glu Ser Leu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
                100                 105                 110

Tyr Phe Ile Asn Asn Gln Thr Lys Gly Cys Glu Arg Phe Lys Tyr Gly
            115                 120                 125

Gly Cys Leu Gly Asn Met Asn Asn Phe Glu Thr Leu Glu Glu Cys Lys
    130                 135                 140
```

```
Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
            165                 170                 175

Val Pro Ser Leu Phe Val Thr Lys Glu Gly Thr Asn Asp Gly Trp Lys
            180                 185                 190

Asn

<210> SEQ ID NO 15
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: 2'-O Methyl modified

<400> SEQUENCE: 15
agccaaguau auucc                                                     15

<210> SEQ ID NO 16
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: 2'-O Methyl modified

<400> SEQUENCE: 16
uauauacgca ccuaa                                                     15

<210> SEQ ID NO 17
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: 2'-O Methyl modified

<400> SEQUENCE: 17
cuaacgagcc                                                           10

<210> SEQ ID NO 18
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: 2'-O Methyl modified

<400> SEQUENCE: 18
caccuaacga gccaa                                                     15
```

```
<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 19
ggaauauacu uggcucguua ggugcguaua uat                                  33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
```

```
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 20
ggaauauacu uggcucguua ggugcguaua uat                             33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 21
ggaauauacu uggcucguua ggugcguaua uat                             33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
```

```
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 22
ggaauauacu uggcucguua ggugcguaua uat                                 33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: 2'-fluoro modified
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
```

```
<221> NAME/KEY: modified_base
<222> LOCATION: (33)..(33)
<223> OTHER INFORMATION: Inverted deoxythymidine

<400> SEQUENCE: 23
ggaauauacu uggcucguua ggugcguaua uat                              33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: 2'-fluoro modified
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 24
ggaauauacu uggcucguua ggugcguaua uat                              33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
```

```
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: 2'-fluoro modified
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 25
ggaauauacu uggcucguua ggugcguaua uat                                   33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
```

```
<221> NAME/KEY: modified_base
<222> LOCATION: (25)..(25)
<223> OTHER INFORMATION: 2'-fluoro modified
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 26
ggaauauacu uggcucguua ggugcguaua uat                            33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: deoxynucleotide
<220> FEATURE:
<221> NAME/KEY: modified_base
<222> LOCATION: (2)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 27
ggaauauacu uggcucguua ggugcguaua uat                            33

<210> SEQ ID NO 28
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-O Methyl modified
<220> FEATURE:
<221> NAME/KEY: modified_base
<222> LOCATION: (2)..(2)
<223> OTHER INFORMATION: deoxynucleotide
<220> FEATURE:
<221> NAME/KEY: modified_base
<222> LOCATION: (3)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 28
ggaauauacu uggcucguua ggugcguaua uat                                  33

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'-O Methyl modified
<220> FEATURE:
<221> NAME/KEY: modified_base
<222> LOCATION: (3)..(3)
<223> OTHER INFORMATION: deoxynucleotide
<220> FEATURE:
```

```
<221> NAME/KEY: modified_base
<222> LOCATION: (4)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 29
ggaauauacu uggcucguua ggugcguaua uat                               33

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-O Methyl modified
<220> FEATURE:
<221> NAME/KEY: modified_base
<222> LOCATION: (4)..(4)
<223> OTHER INFORMATION: deoxynucleotide
<220> FEATURE:
<221> NAME/KEY: modified_base
<222> LOCATION: (5)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
```

```
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 30
ggaauauacu uggcucguua ggugcguaua uat                              33

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(4)
<223> OTHER INFORMATION: 2'-O Methyl modified
<220> FEATURE:
<221> NAME/KEY: modified_base
<222> LOCATION: (5)..(5)
<223> OTHER INFORMATION: deoxynucleotide
<220> FEATURE:
<221> NAME/KEY: modified_base
<222> LOCATION: (6)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
```

```
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 31
ggaatauacu uggcucguua ggugcguaua uat                                33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'-O Methyl modified
<220> FEATURE:
<221> NAME/KEY: modified_base
<222> LOCATION: (6)..(6)
<223> OTHER INFORMATION: deoxynucleotide
<220> FEATURE:
<221> NAME/KEY: modified_base
<222> LOCATION: (7)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 32
ggaauauacu uggcucguua ggugcguaua uat                                33

<210> SEQ ID NO 33
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O Methyl modified
<220> FEATURE:
<221> NAME/KEY: modified_base
<222> LOCATION: (7)..(7)
<223> OTHER INFORMATION: deoxynucleotide
<220> FEATURE:
<221> NAME/KEY: modified_base
<222> LOCATION: (8)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 33
ggaauatacu uggcucguua ggugcguaua uat                                33

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(7)
<223> OTHER INFORMATION: 2'-O Methyl modified
<220> FEATURE:
<221> NAME/KEY: modified_base
<222> LOCATION: (8)..(9)
<223> OTHER INFORMATION: deoxynucleotide
<220> FEATURE:
```

```
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 34
ggaauauacu uggcucguua ggugcguaua uat                                 33

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(10)
<223> OTHER INFORMATION: deoxynucleotide
<220> FEATURE:
<221> NAME/KEY: modified_base
<222> LOCATION: (11)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
```

```
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 35
ggaauauact uggcucguua ggugcguaua uat                                33

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(10)
<223> OTHER INFORMATION: 2'-O Methyl modified
<220> FEATURE:
<221> NAME/KEY: modified_base
<222> LOCATION: (11)..(11)
<223> OTHER INFORMATION: deoxynucleotide
<220> FEATURE:
<221> NAME/KEY: modified_base
<222> LOCATION: (12)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 36
ggaauauacu tggcucguua ggugcguaua uat                                33

<210> SEQ ID NO 37
<211> LENGTH: 33
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(11)
<223> OTHER INFORMATION: 2'-O Methyl modified
<220> FEATURE:
<221> NAME/KEY: modified_base
<222> LOCATION: (12)..(12)
<223> OTHER INFORMATION: deoxynucleotide
<220> FEATURE:
<221> NAME/KEY: modified_base
<222> LOCATION: (13)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 37
ggaauauacu uggcucguua ggugcguaua uat                                   33

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:

```
<221> NAME/KEY: modified_base
<222> LOCATION: (10)..(12)
<223> OTHER INFORMATION: 2'-O Methyl modified
<220> FEATURE:
<221> NAME/KEY: modified_base
<222> LOCATION: (13)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 38
ggaauauacu uggcucguua ggugcguaua uat                                    33

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine
```

```
<400> SEQUENCE: 39
ggaauauacu uggctcguua ggugcguaua uat                                33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(17)
<223> OTHER INFORMATION: deoxynucleotide
<220> FEATURE:
<221> NAME/KEY: modified_base
<222> LOCATION: (18)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 40
ggaauauacu uggcucguua ggugcguaua uat                                33

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
```

<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(17)
<223> OTHER INFORMATION: 2'-O Methyl modified
<220> FEATURE:
<221> NAME/KEY: modified_base
<222> LOCATION: (18)..(18)
<223> OTHER INFORMATION: deoxynucleotide
<220> FEATURE:
<221> NAME/KEY: modified_base
<222> LOCATION: (19)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 41
ggaauauacu uggcucgtua ggugcguaua uat                                      33

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:

```
<221> NAME/KEY: modified_base
<222> LOCATION: (17)..(18)
<223> OTHER INFORMATION: 2'-O Methyl modified
<220> FEATURE:
<221> NAME/KEY: modified_base
<222> LOCATION: (19)..(19)
<223> OTHER INFORMATION: deoxynucleotide
<220> FEATURE:
<221> NAME/KEY: modified_base
<222> LOCATION: (20)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 42
ggaauauacu uggcucguta ggugcguaua uat                                33

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(19)
<223> OTHER INFORMATION: 2'-O Methyl modified
<220> FEATURE:
<221> NAME/KEY: modified_base
<222> LOCATION: (20)..(20)
<223> OTHER INFORMATION: deoxynucleotide
<220> FEATURE:
<221> NAME/KEY: modified_base
<222> LOCATION: (21)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
```

```
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 43
ggaauauacu uggcucguua ggugcguaua uat                              33

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(20)
<223> OTHER INFORMATION: 2'-O Methyl modified
<220> FEATURE:
<221> NAME/KEY: modified_base
<222> LOCATION: (21)..(21)
<223> OTHER INFORMATION: deoxynucleotide
<220> FEATURE:
<221> NAME/KEY: modified_base
<222> LOCATION: (22)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 44
ggaauauacu uggcucguua ggugcguaua uat                              33

<210> SEQ ID NO 45
<211> LENGTH: 33
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(21)
<223> OTHER INFORMATION: 2'-O Methyl modified
<220> FEATURE:
<221> NAME/KEY: modified_base
<222> LOCATION: (22)..(22)
<223> OTHER INFORMATION: deoxynucleotide
<220> FEATURE:
<221> NAME/KEY: modified_base
<222> LOCATION: (23)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 45
ggaauauacu uggcucguua ggugcguaua uat                                33

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
```

```
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(22)
<223> OTHER INFORMATION: 2'-O Methyl modified
<220> FEATURE:
<221> NAME/KEY: modified_base
<222> LOCATION: (23)..(23)
<223> OTHER INFORMATION: deoxynucleotide
<220> FEATURE:
<221> NAME/KEY: modified_base
<222> LOCATION: (24)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 46
ggaauauacu uggcucguua ggtgcguaua uat                                   33

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
```

```
<221> NAME/KEY: modified_base
<222> LOCATION: (17)..(23)
<223> OTHER INFORMATION: 2'-O Methyl modified
<220> FEATURE:
<221> NAME/KEY: modified_base
<222> LOCATION: (24)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 47
ggaauauacu uggcucguua ggugcguaua uat                                33

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(26)
<223> OTHER INFORMATION: deoxynucleotide
<220> FEATURE:
<221> NAME/KEY: modified_base
<222> LOCATION: (27)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 48
ggaauauacu uggcucguua ggugcguaua uat                                33

<210> SEQ ID NO 49
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(26)
<223> OTHER INFORMATION: 2'-O Methyl modified
<220> FEATURE:
<221> NAME/KEY: modified_base
<222> LOCATION: (27)..(27)
<223> OTHER INFORMATION: deoxynucleotide
<220> FEATURE:
<221> NAME/KEY: modified_base
<222> LOCATION: (28)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 49
ggaauauacu uggcucguua ggugcgtaua uat                               33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
```

```
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(27)
<223> OTHER INFORMATION: 2'-O Methyl modified
<220> FEATURE:
<221> NAME/KEY: modified_base
<222> LOCATION: (28)..(28)
<223> OTHER INFORMATION: deoxynucleotide
<220> FEATURE:
<221> NAME/KEY: modified_base
<222> LOCATION: (29)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 50
ggaauauacu uggcucguua ggugcguaua uat                                    33

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
```

```
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(28)
<223> OTHER INFORMATION: 2'-O Methyl modified
<220> FEATURE:
<221> NAME/KEY: modified_base
<222> LOCATION: (29)..(29)
<223> OTHER INFORMATION: deoxynucleotide
<220> FEATURE:
<221> NAME/KEY: modified_base
<222> LOCATION: (30)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 51
ggaauauacu uggcucguua ggugcguata uat                                    33

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(29)
<223> OTHER INFORMATION: 2'-O Methyl modified
<220> FEATURE:
<221> NAME/KEY: modified_base
<222> LOCATION: (30)..(30)
<223> OTHER INFORMATION: deoxynucleotide
<220> FEATURE:
```

```
<221> NAME/KEY: modified_base
<222> LOCATION: (31)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 52
ggaauauacu uggcucguua ggugcguaua uat                          33

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(30)
<223> OTHER INFORMATION: 2'-O Methyl modified
<220> FEATURE:
<221> NAME/KEY: modified_base
<222> LOCATION: (31)..(31)
<223> OTHER INFORMATION: deoxynucleotide
<220> FEATURE:
<221> NAME/KEY: modified_base
<222> LOCATION: (32)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 53
ggaauauacu uggcucguua ggugcguaua tat                          33

<210> SEQ ID NO 54
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(31)
<223> OTHER INFORMATION: 2'-O Methyl modified
<220> FEATURE:
<221> NAME/KEY: modified_base
<222> LOCATION: (32)..(32)
<223> OTHER INFORMATION: deoxynucleotide
<220> FEATURE:
<221> NAME/KEY: modified_base
<222> LOCATION: (33)..(33)
<223> OTHER INFORMATION: Inverted deoxythymidine

<400> SEQUENCE: 54
ggaauauacu uggcucguua ggugcguaua uat                                   33

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(4)
<223> OTHER INFORMATION: 2'-O Methyl modified
<220> FEATURE:
<221> NAME/KEY: modified_base
<222> LOCATION: (5)..(5)
<223> OTHER INFORMATION: deoxynucleotide
<220> FEATURE:
<221> NAME/KEY: modified_base
<222> LOCATION: (6)..(8)
<223> OTHER INFORMATION: 2'-O Methyl modified
<220> FEATURE:
```

```
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 55
ggaauauacu uggcucguua ggugcguaua uat                            33

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O Methyl modified
<220> FEATURE:
<221> NAME/KEY: modified_base
<222> LOCATION: (7)..(7)
<223> OTHER INFORMATION: deoxynucleotide
<220> FEATURE:
<221> NAME/KEY: modified_base
<222> LOCATION: (8)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
```

```
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 56
ggaauauacu uggcucguua ggugcguaua uat                                    33

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(10)
<223> OTHER INFORMATION: deoxynucleotide
<220> FEATURE:
<221> NAME/KEY: modified_base
<222> LOCATION: (11)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 57
ggaauauacu uggcucguua ggugcguaua uat                                    33
```

```
<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(10)
<223> OTHER INFORMATION: 2'-O Methyl modified
<220> FEATURE:
<221> NAME/KEY: modified_base
<222> LOCATION: (11)..(11)
<223> OTHER INFORMATION: deoxynucleotide
<220> FEATURE:
<221> NAME/KEY: modified_base
<222> LOCATION: (12)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 58
ggaauauacu uggcucguua ggugcguaua uat                           33

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
```

```
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 59
ggaauauacu uggcucguua ggugcguaua uat                                33

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(17)
<223> OTHER INFORMATION: 2'-O Methyl modified
<220> FEATURE:
<221> NAME/KEY: modified_base
<222> LOCATION: (18)..(18)
<223> OTHER INFORMATION: deoxynucleotide
<220> FEATURE:
<221> NAME/KEY: modified_base
<222> LOCATION: (19)..(24)
<223> OTHER INFORMATION: 2'-O Methyl modified
<220> FEATURE:
```

```
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 60
ggaauauacu uggcucguua ggugcguaua uat                                33

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(18)
<223> OTHER INFORMATION: 2'-O Methyl modified
<220> FEATURE:
<221> NAME/KEY: modified_base
<222> LOCATION: (19)..(19)
<223> OTHER INFORMATION: deoxynucleotide
<220> FEATURE:
<221> NAME/KEY: modified_base
<222> LOCATION: (20)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 61
ggaauauacu uggcucguua ggugcguaua uat                                33
```

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(22)
<223> OTHER INFORMATION: 2'-O Methyl modified
<220> FEATURE:
<221> NAME/KEY: modified_base
<222> LOCATION: (23)..(23)
<223> OTHER INFORMATION: deoxynucleotide
<220> FEATURE:
<221> NAME/KEY: modified_base
<222> LOCATION: (24)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 62
ggaauauacu uggcucguua ggugcguaua uat                                33

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:

```
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(26)
<223> OTHER INFORMATION: 2'-O Methyl modified
<220> FEATURE:
<221> NAME/KEY: modified_base
<222> LOCATION: (27)..(27)
<223> OTHER INFORMATION: deoxynucleotide
<220> FEATURE:
<221> NAME/KEY: modified_base
<222> LOCATION: (28)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 63
ggaauauacu uggcucguua ggugcguaua uat                           33

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
```

```
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(28)
<223> OTHER INFORMATION: 2'-O Methyl modified
<220> FEATURE:
<221> NAME/KEY: modified_base
<222> LOCATION: (29)..(29)
<223> OTHER INFORMATION: deoxynucleotide
<220> FEATURE:
<221> NAME/KEY: modified_base
<222> LOCATION: (30)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 64
ggaauauacu uggcucguua ggugcguaua uat                                   33

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(30)
<223> OTHER INFORMATION: 2'-O Methyl modified
<220> FEATURE:
```

```
<221> NAME/KEY: modified_base
<222> LOCATION: (31)..(31)
<223> OTHER INFORMATION: deoxynucleotide
<220> FEATURE:
<221> NAME/KEY: modified_base
<222> LOCATION: (32)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 65
ggaauauacu uggcucguua ggugcguaua uat                          33

<210> SEQ ID NO 66
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 66
ggaauauacu uggcucguua ggugcguaua uat                          33

<210> SEQ ID NO 67
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(32)
<223> OTHER INFORMATION: 2'-O Methyl modified
<220> FEATURE:
```

```
<221> NAME/KEY: modified_base
<222> LOCATION: (33)..(33)
<223> OTHER INFORMATION: Inverted deoxythymidine

<400> SEQUENCE: 67
ggaauauacu uggcucguua ggugcguaua uat                              33

<210> SEQ ID NO 68
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: 2'-fluoro modified
<220> FEATURE:
<221> NAME/KEY: modified_base
<222> LOCATION: (10)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 68
ggaauauacu uggcucguua ggugcguaua uat                              33

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(15)
<223> OTHER INFORMATION: 2'-O Methyl modified
<220> FEATURE:
```

```
<221> NAME/KEY: modified_base
<222> LOCATION: (16)..(16)
<223> OTHER INFORMATION: 2'-fluoro modified
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 69
ggaauauacu uggcucguua ggugcguaua uat                              33

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: 2'-fluoro modified
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 70
ggaauauacu uggcucguua ggugcguaua uat                              33

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: 2'-fluoro modified
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 71
ggaauauacu uggcucguua ggugcguaua uat                                33

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: 2'-fluoro modified
<220> FEATURE:
<221> NAME/KEY: modified_base
<222> LOCATION: (10)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 72
ggaauauacu uggcucguua ggugcguaua uat                                33
```

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(15)
<223> OTHER INFORMATION: 2'-O Methyl modified
<220> FEATURE:
<221> NAME/KEY: modified_base
<222> LOCATION: (16)..(16)
<223> OTHER INFORMATION: 2'-fluoro modified
<220> FEATURE:
<221> NAME/KEY: modified_base
<222> LOCATION: (17)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 73
ggaauauacu uggcucguua ggugcguaua uat                                33

<210> SEQ ID NO 74
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:

```
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 74
ggaauauacu uggcucguua ggugcguaua uat                               33

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 75
ggaauauacu uggcucguua ggugcguaua uat                               33
```

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 76
ggaauauacu uggcucguua ggugcguaua uat                             33

<210> SEQ ID NO 77
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: misc_feature
<222> LOCATION: (4)..(5)
<223> OTHER INFORMATION: Phosphorothioate linkage
<220> FEATURE:

```
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 77
ggaauauacu uggcucguua ggugcguaua uat                              33

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: misc_feature
<222> LOCATION: (5)..(6)
<223> OTHER INFORMATION: Phosphorothioate linkage
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
```

```
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 78
ggaauauacu uggcucguua ggugcguaua uat                            33

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: misc_feature
<222> LOCATION: (6)..(7)
<223> OTHER INFORMATION: Phosphorothioate linkage
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 79
ggaauauacu uggcucguua ggugcguaua uat                            33
```

-continued

```
<210> SEQ ID NO 80
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: misc_feature
<222> LOCATION: (7)..(8)
<223> OTHER INFORMATION: Phosphorothioate linkage
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 80
ggaauauacu uggcucguua ggugcguaua uat                                   33

<210> SEQ ID NO 81
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: misc_feature
<222> LOCATION: (8)..(9)
<223> OTHER INFORMATION: Phosphorothioate linkage
<220> FEATURE:
```

```
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 81
ggaauauacu uggcucguua ggugcguaua uat                                     33

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: misc_feature
<222> LOCATION: (9)..(10)
<223> OTHER INFORMATION: Phosphorothioate linkage
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
```

```
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 82
ggaauauacu uggcucguua ggugcguaua uat                              33

<210> SEQ ID NO 83
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: misc_feature
<222> LOCATION: (10)..(11)
<223> OTHER INFORMATION: Phosphorothioate linkage
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 83
ggaauauacu uggcucguua ggugcguaua uat                              33
```

```
<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 84
ggaauauacu uggcucguua ggugcguaua uat                           33

<210> SEQ ID NO 85
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
```

```
<221> NAME/KEY: modified_base
<222> LOCATION: (10)..(13)
<223> OTHER INFORMATION: 2'-O Methyl modified
<220> FEATURE:
<221> NAME/KEY: misc_feature
<222> LOCATION: (12)..(13)
<223> OTHER INFORMATION: Phosphorothioate linkage
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 85
ggaauauacu uggcucguua ggugcguaua uat                              33

<210> SEQ ID NO 86
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
```

```
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 86
ggaauauacu uggcucguua ggugcguaua uat                               33

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 87
ggaauauacu uggcucguua ggugcguaua uat                               33
```

<210> SEQ ID NO 88
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: misc_feature
<222> LOCATION: (15)..(16)
<223> OTHER INFORMATION: Phosphorothioate linkage
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 88
ggaauauacu uggcucguua ggugcguaua uat                                    33

<210> SEQ ID NO 89
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:

```
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: misc_feature
<222> LOCATION: (16)..(17)
<223> OTHER INFORMATION: Phosphorothioate linkage
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 89
ggaauauacu uggcucguua ggugcguaua uat                                33

<210> SEQ ID NO 90
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
```

```
<221> NAME/KEY: misc_feature
<222> LOCATION: (17)..(18)
<223> OTHER INFORMATION: Phosphorothioate linkage
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 90
ggaauauacu uggcucguua ggugcguaua uat                              33

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: misc_feature
<222> LOCATION: (18)..(19)
<223> OTHER INFORMATION: Phosphorothioate linkage
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 91
ggaauauacu uggcucguua ggugcguaua uat                              33
```

```
<210> SEQ ID NO 92
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: misc_feature
<222> LOCATION: (19)..(20)
<223> OTHER INFORMATION: Phosphorothioate linkage
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 92
ggaauauacu uggcucguua ggugcguaua uat                                33

<210> SEQ ID NO 93
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
```

```
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 93
ggaauauacu uggcucguua ggugcguaua uat                                 33

<210> SEQ ID NO 94
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
```

```
<221> NAME/KEY: misc_feature
<222> LOCATION: (21)..(22)
<223> OTHER INFORMATION: Phosphorothioate linkage
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 94
ggaauauacu uggcucguua ggugcguaua uat                                   33

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: misc_feature
<222> LOCATION: (22)..(23)
<223> OTHER INFORMATION: Phosphorothioate linkage
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 95
ggaauauacu uggcucguua ggugcguaua uat                                   33
```

```
<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: misc_feature
<222> LOCATION: (23)..(24)
<223> OTHER INFORMATION: Phosphorothioate linkage
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 96
ggaauauacu uggcucguua ggugcguaua uat                             33

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
```

```
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: misc_feature
<222> LOCATION: (24)..(25)
<223> OTHER INFORMATION: Phosphorothioate linkage
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 97
ggaauauacu uggcucguua ggugcguaua uat                                    33

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
```

```
<221> NAME/KEY: modified_base
<222> LOCATION: (25)..(25)
<223> OTHER INFORMATION: deoxynucleotide
<220> FEATURE:
<221> NAME/KEY: misc_feature
<222> LOCATION: (25)..(26)
<223> OTHER INFORMATION: Phosphorothioate linkage
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 98
ggaauauacu uggcucguua ggugcguaua uat                                   33

<210> SEQ ID NO 99
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: misc_feature
<222> LOCATION: (26)..(27)
<223> OTHER INFORMATION: Phosphorothioate linkage
<220> FEATURE:
<221> NAME/KEY: modified_base
<222> LOCATION: (33)..(33)
<223> OTHER INFORMATION: Inverted deoxythymidine

<400> SEQUENCE: 99
ggaauauacu uggcucguua ggugcguaua uat                                   33
```

-continued

```
<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: misc_feature
<222> LOCATION: (27)..(28)
<223> OTHER INFORMATION: Phosphorothioate linkage
<220> FEATURE:
<221> NAME/KEY: modified_base
<222> LOCATION: (33)..(33)
<223> OTHER INFORMATION: Inverted deoxythymidine

<400> SEQUENCE: 100
ggaauauacu uggcucguua ggugcguaua uat                                 33

<210> SEQ ID NO 101
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
```

```
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: misc_feature
<222> LOCATION: (28)..(29)
<223> OTHER INFORMATION: Phosphorothioate linkage
<220> FEATURE:
<221> NAME/KEY: modified_base
<222> LOCATION: (33)..(33)
<223> OTHER INFORMATION: Inverted deoxythymidine

<400> SEQUENCE: 101
ggaauauacu uggcucguua ggugcguaua uat                                    33

<210> SEQ ID NO 102
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
```

```
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: misc_feature
<222> LOCATION: (29)..(30)
<223> OTHER INFORMATION: Phosphorothioate linkage
<220> FEATURE:
<221> NAME/KEY: modified_base
<222> LOCATION: (33)..(33)
<223> OTHER INFORMATION: Inverted deoxythymidine

<400> SEQUENCE: 102
ggaauauacu uggcucguua ggugcguaua uat                              33

<210> SEQ ID NO 103
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: misc_feature
<222> LOCATION: (30)..(31)
<223> OTHER INFORMATION: Phosphorothioate linkage
<220> FEATURE:
<221> NAME/KEY: modified_base
<222> LOCATION: (33)..(33)
<223> OTHER INFORMATION: Inverted deoxythymidine

<400> SEQUENCE: 103
ggaauauacu uggcucguua ggugcguaua uat                              33
```

```
<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: misc_feature
<222> LOCATION: (31)..(32)
<223> OTHER INFORMATION: Phosphorothioate linkage
<220> FEATURE:
<221> NAME/KEY: modified_base
<222> LOCATION: (33)..(33)
<223> OTHER INFORMATION: Inverted deoxythymidine

<400> SEQUENCE: 104
ggaauauacu uggcucguua ggugcguaua uat                                   33

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
```

```
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: misc_feature
<222> LOCATION: (32)..(33)
<223> OTHER INFORMATION: Phosphorothioate linkage
<220> FEATURE:
<221> NAME/KEY: modified_base
<222> LOCATION: (33)..(33)
<223> OTHER INFORMATION: Inverted deoxythymidine

<400> SEQUENCE: 105
ggaauauacu uggcucguua ggugcguaua uat                                33

<210> SEQ ID NO 106
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(7)
<223> OTHER INFORMATION: 2'-O Methyl modified
<220> FEATURE:
<221> NAME/KEY: modified_base
<222> LOCATION: (8)..(8)
<223> OTHER INFORMATION: deoxynucleotide
<220> FEATURE:
<221> NAME/KEY: modified_base
<222> LOCATION: (9)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
```

```
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 106
gaauauacuu ggcucguuag gugcguauau at                               32

<210> SEQ ID NO 107
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(7)
<223> OTHER INFORMATION: 2'-O Methyl modified
<220> FEATURE:
<221> NAME/KEY: modified_base
<222> LOCATION: (8)..(8)
<223> OTHER INFORMATION: deoxynucleotide
<220> FEATURE:
<221> NAME/KEY: modified_base
<222> LOCATION: (9)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 107
ggauauacuu ggcucguuag gugcguauau at                               32

<210> SEQ ID NO 108
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(7)
<223> OTHER INFORMATION: 2'-O Methyl modified
<220> FEATURE:
<221> NAME/KEY: modified_base
<222> LOCATION: (8)..(8)
<223> OTHER INFORMATION: deoxynucleotide
<220> FEATURE:
<221> NAME/KEY: modified_base
<222> LOCATION: (9)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 108
ggaaauacuu ggcucguuag gugcguauau at                                    32

<210> SEQ ID NO 109
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(7)
<223> OTHER INFORMATION: 2'-O Methyl modified
<220> FEATURE:
<221> NAME/KEY: modified_base
<222> LOCATION: (8)..(8)
<223> OTHER INFORMATION: deoxynucleotide
<220> FEATURE:
<221> NAME/KEY: modified_base
<222> LOCATION: (9)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:
```

```
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 109
ggaauuacuu ggcucguuag gugcguauau at                              32

<210> SEQ ID NO 110
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(7)
<223> OTHER INFORMATION: 2'-O Methyl modified
<220> FEATURE:
<221> NAME/KEY: modified_base
<222> LOCATION: (8)..(8)
<223> OTHER INFORMATION: deoxynucleotide
<220> FEATURE:
<221> NAME/KEY: modified_base
<222> LOCATION: (9)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 110
ggaauaacuu ggcucguuag gugcguauau at                              32
```

-continued

<210> SEQ ID NO 111
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(7)
<223> OTHER INFORMATION: 2'-O Methyl modified
<220> FEATURE:
<221> NAME/KEY: modified_base
<222> LOCATION: (8)..(8)
<223> OTHER INFORMATION: deoxynucleotide
<220> FEATURE:
<221> NAME/KEY: modified_base
<222> LOCATION: (9)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 111
ggaauaucuu ggcucguuag gugcguauau at                                    32

<210> SEQ ID NO 112
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:

```
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 112
ggaauauauu ggcucguuag gugcguauau at                                     32

<210> SEQ ID NO 113
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 113
ggaauauacu ggcucguuag gugcguauau at                                     32
```

<210> SEQ ID NO 114
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 114
ggaauauacu ugcucguuag gugcguauau at                                     32

<210> SEQ ID NO 115
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(14)
<223> OTHER INFORMATION: 2'-O Methyl modified
<220> FEATURE:

```
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 115
ggaauauacu uggucguuag gugcguauau at                                32

<210> SEQ ID NO 116
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 116
ggaauauacu uggccguuag gugcguauau at                                32

<210> SEQ ID NO 117
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 117
ggaauauacu uggcuguuag gugcguauau at                                       32

<210> SEQ ID NO 118
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(23)
<223> OTHER INFORMATION: 2'-O Methyl modified
<220> FEATURE:
```

```
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 118
ggaauauacu uggcucuuag gugcguauau at                              32

<210> SEQ ID NO 119
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 119
ggaauauacu uggcucguag gugcguauau at                              32

<210> SEQ ID NO 120
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 120
ggaauauacu uggcucguug gugcguauau at                                      32

<210> SEQ ID NO 121
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
```

```
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 121
ggaauauacu uggcucguua gugcguauau at                              32

<210> SEQ ID NO 122
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 122
ggaauauacu uggcucguua gggcguauau at                              32
```

<210> SEQ ID NO 123
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 123
ggaauauacu uggcucguua ggucguauau at                                  32

<210> SEQ ID NO 124
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:

```
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 124
ggaauauacu uggcucguua ggugguauau at                                32

<210> SEQ ID NO 125
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 125
ggaauauacu uggcucguua ggugcuauau at                                32
```

-continued

<210> SEQ ID NO 126
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 126
ggaauauacu uggcucguua ggugcgauau at                                    32

<210> SEQ ID NO 127
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:

```
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 127
ggaauauacu uggcucguua ggugcguuau at                                    32

<210> SEQ ID NO 128
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(31)
<223> OTHER INFORMATION: 2'-O Methyl modified
<220> FEATURE:
```

```
<221> NAME/KEY: modified_base
<222> LOCATION: (32)..(32)
<223> OTHER INFORMATION: Inverted deoxythymidine

<400> SEQUENCE: 128
ggaauauacu uggcucguua ggugcguaau at                               32

<210> SEQ ID NO 129
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 129
ggaauauacu uggcucguua ggugcguauu at                               32

<210> SEQ ID NO 130
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
```

<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 130
ggaauauacu uggcucguua ggugcguaua at                                   32

<210> SEQ ID NO 131
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:

```
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(31)
<223> OTHER INFORMATION: 2'-O Methyl modified
<220> FEATURE:
<221> NAME/KEY: modified_base
<222> LOCATION: (32)..(32)
<223> OTHER INFORMATION: Inverted deoxythymidine

<400> SEQUENCE: 131
ggaauauacu uggcucguua ggugcguaua ut                                  32

<210> SEQ ID NO 132
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O Methyl modified
<220> FEATURE:
<221> NAME/KEY: modified_base
<222> LOCATION: (7)..(7)
<223> OTHER INFORMATION: deoxynucleotide
<220> FEATURE:
<221> NAME/KEY: modified_base
<222> LOCATION: (8)..(11)
<223> OTHER INFORMATION: 2'-O Methyl modified
<220> FEATURE:
<221> NAME/KEY: modified_base
<222> LOCATION: (12)..(12)
<223> OTHER INFORMATION: deoxynucleotide
<220> FEATURE:
<221> NAME/KEY: modified_base
<222> LOCATION: (13)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(22)
<223> OTHER INFORMATION: 2'-O Methyl modified
<220> FEATURE:
<221> NAME/KEY: modified_base
<222> LOCATION: (23)..(23)
<223> OTHER INFORMATION: deoxynucleotide
<220> FEATURE:
<221> NAME/KEY: modified_base
<222> LOCATION: (24)..(30)
<223> OTHER INFORMATION: 2'-O Methyl modified
<220> FEATURE:
<221> NAME/KEY: modified_base
<222> LOCATION: (31)..(31)
<223> OTHER INFORMATION: Inverted deoxythymidine

<400> SEQUENCE: 132
aauauacuug gcucguuagg ugcguauaua t                                   31

<210> SEQ ID NO 133
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O Methyl modified
<220> FEATURE:
<221> NAME/KEY: modified_base
<222> LOCATION: (7)..(7)
<223> OTHER INFORMATION: deoxynucleotide
<220> FEATURE:
<221> NAME/KEY: modified_base
<222> LOCATION: (8)..(11)
<223> OTHER INFORMATION: 2'-O Methyl modified
<220> FEATURE:
<221> NAME/KEY: modified_base
<222> LOCATION: (12)..(12)
<223> OTHER INFORMATION: deoxynucleotide
<220> FEATURE:
<221> NAME/KEY: modified_base
<222> LOCATION: (13)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(22)
<223> OTHER INFORMATION: 2'-O Methyl modified
<220> FEATURE:
<221> NAME/KEY: modified_base
<222> LOCATION: (23)..(23)
<223> OTHER INFORMATION: deoxynucleotide
<220> FEATURE:
<221> NAME/KEY: modified_base
<222> LOCATION: (24)..(30)
<223> OTHER INFORMATION: 2'-O Methyl modified
<220> FEATURE:
<221> NAME/KEY: modified_base
<222> LOCATION: (31)..(31)
<223> OTHER INFORMATION: Inverted deoxythymidine

<400> SEQUENCE: 133
gguauacuug gcucguuagg ugcguauaua t                              31

<210> SEQ ID NO 134
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(11)
<223> OTHER INFORMATION: 2'-O Methyl modified
<220> FEATURE:
<221> NAME/KEY: modified_base
<222> LOCATION: (12)..(12)
<223> OTHER INFORMATION: deoxynucleotide
<220> FEATURE:
<221> NAME/KEY: modified_base
<222> LOCATION: (13)..(13)
<223> OTHER INFORMATION: 2'-O Methyl modified
<220> FEATURE:
```

```
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(22)
<223> OTHER INFORMATION: 2'-O Methyl modified
<220> FEATURE:
<221> NAME/KEY: modified_base
<222> LOCATION: (23)..(23)
<223> OTHER INFORMATION: deoxynucleotide
<220> FEATURE:
<221> NAME/KEY: modified_base
<222> LOCATION: (24)..(30)
<223> OTHER INFORMATION: 2'-O Methyl modified
<220> FEATURE:
<221> NAME/KEY: modified_base
<222> LOCATION: (31)..(31)
<223> OTHER INFORMATION: Inverted deoxythymidine

<400> SEQUENCE: 134
ggaauauacg gcucguuagg ugcguauaua t            31

<210> SEQ ID NO 135
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(11)
<223> OTHER INFORMATION: 2'-O Methyl modified
<220> FEATURE:
<221> NAME/KEY: modified_base
<222> LOCATION: (12)..(12)
<223> OTHER INFORMATION: deoxynucleotide
<220> FEATURE:
<221> NAME/KEY: modified_base
<222> LOCATION: (13)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(22)
<223> OTHER INFORMATION: 2'-O Methyl modified
<220> FEATURE:
<221> NAME/KEY: modified_base
<222> LOCATION: (23)..(23)
<223> OTHER INFORMATION: deoxynucleotide
<220> FEATURE:
<221> NAME/KEY: modified_base
<222> LOCATION: (24)..(30)
<223> OTHER INFORMATION: 2'-O Methyl modified
<220> FEATURE:
<221> NAME/KEY: modified_base
<222> LOCATION: (31)..(31)
<223> OTHER INFORMATION: Inverted deoxythymidine

<400> SEQUENCE: 135
ggaauauacu ucucguuagg ugcguauaua t            31
```

-continued

<210> SEQ ID NO 136
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(22)
<223> OTHER INFORMATION: 2'-O Methyl modified
<220> FEATURE:
<221> NAME/KEY: modified_base
<222> LOCATION: (23)..(23)
<223> OTHER INFORMATION: deoxynucleotide
<220> FEATURE:
<221> NAME/KEY: modified_base
<222> LOCATION: (24)..(30)
<223> OTHER INFORMATION: 2'-O Methyl modified
<220> FEATURE:
<221> NAME/KEY: modified_base
<222> LOCATION: (31)..(31)
<223> OTHER INFORMATION: Inverted deoxythymidine

<400> SEQUENCE: 136
ggaauauacu uggcucgagg ugcguauaua t                              31

<210> SEQ ID NO 137
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:

```
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(22)
<223> OTHER INFORMATION: 2'-O Methyl modified
<220> FEATURE:
<221> NAME/KEY: modified_base
<222> LOCATION: (23)..(23)
<223> OTHER INFORMATION: deoxynucleotide
<220> FEATURE:
<221> NAME/KEY: modified_base
<222> LOCATION: (24)..(30)
<223> OTHER INFORMATION: 2'-O Methyl modified
<220> FEATURE:
<221> NAME/KEY: modified_base
<222> LOCATION: (31)..(31)
<223> OTHER INFORMATION: Inverted deoxythymidine

<400> SEQUENCE: 137
ggaauauacu uggcucguua ugcguauaua t                              31

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'-O Methyl modified
<220> FEATURE:
<221> NAME/KEY: modified_base
<222> LOCATION: (6)..(6)
<223> OTHER INFORMATION: deoxynucleotide
<220> FEATURE:
<221> NAME/KEY: modified_base
<222> LOCATION: (7)..(10)
<223> OTHER INFORMATION: 2'-O Methyl modified
<220> FEATURE:
<221> NAME/KEY: modified_base
<222> LOCATION: (11)..(11)
<223> OTHER INFORMATION: deoxynucleotide
<220> FEATURE:
<221> NAME/KEY: modified_base
<222> LOCATION: (12)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(21)
<223> OTHER INFORMATION: 2'-O Methyl modified
<220> FEATURE:
<221> NAME/KEY: modified_base
<222> LOCATION: (22)..(22)
<223> OTHER INFORMATION: deoxynucleotide
<220> FEATURE:
<221> NAME/KEY: modified_base
<222> LOCATION: (23)..(29)
<223> OTHER INFORMATION: 2'-O Methyl modified
<220> FEATURE:
```

```
<221> NAME/KEY: modified_base
<222> LOCATION: (30)..(30)
<223> OTHER INFORMATION: Inverted deoxythymidine

<400> SEQUENCE: 138
auauacuugg cucguuaggu gcguauauat                                            30

<210> SEQ ID NO 139
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(7)
<223> OTHER INFORMATION: 2'-O Methyl modified
<220> FEATURE:
<221> NAME/KEY: modified_base
<222> LOCATION: (8)..(8)
<223> OTHER INFORMATION: deoxynucleotide
<220> FEATURE:
<221> NAME/KEY: modified_base
<222> LOCATION: (9)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(14)
<223> OTHER INFORMATION: 2'-O Methyl modified
<220> FEATURE:
<221> NAME/KEY: modified_base
<222> LOCATION: (15)..(15)
<223> OTHER INFORMATION: deoxynucleotide
<220> FEATURE:
<221> NAME/KEY: modified_base
<222> LOCATION: (16)..(23)
<223> OTHER INFORMATION: 2'-O Methyl modified
<220> FEATURE:
<221> NAME/KEY: modified_base
<222> LOCATION: (24)..(24)
<223> OTHER INFORMATION: deoxynucleotide
<220> FEATURE:
<221> NAME/KEY: modified_base
<222> LOCATION: (25)..(30)
<223> OTHER INFORMATION: 2'-O Methyl modified
<220> FEATURE:
<221> NAME/KEY: modified_base
<222> LOCATION: (31)..(31)
<223> OTHER INFORMATION: Inverted deoxythymidine

<400> SEQUENCE: 139
gaauauacuu ggcucguuag gugcguauau t                                          31

<210> SEQ ID NO 140
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O Methyl modified
<220> FEATURE:
```

```
<221> NAME/KEY: modified_base
<222> LOCATION: (7)..(7)
<223> OTHER INFORMATION: deoxynucleotide
<220> FEATURE:
<221> NAME/KEY: modified_base
<222> LOCATION: (8)..(11)
<223> OTHER INFORMATION: 2'-O Methyl modified
<220> FEATURE:
<221> NAME/KEY: modified_base
<222> LOCATION: (12)..(12)
<223> OTHER INFORMATION: deoxynucleotide
<220> FEATURE:
<221> NAME/KEY: modified_base
<222> LOCATION: (13)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(22)
<223> OTHER INFORMATION: 2'-O Methyl modified
<220> FEATURE:
<221> NAME/KEY: modified_base
<222> LOCATION: (23)..(23)
<223> OTHER INFORMATION: Inverted deoxythymidine
<220> FEATURE:
<221> NAME/KEY: modified_base
<222> LOCATION: (24)..(28)
<223> OTHER INFORMATION: 2'-O Methyl modified
<220> FEATURE:
<221> NAME/KEY: modified_base
<222> LOCATION: (29)..(29)
<223> OTHER INFORMATION: Inverted deoxythymidine

<400> SEQUENCE: 140
aauauacuug gcucguuagg ugcguauat                                      29

<210> SEQ ID NO 141
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'-O Methyl modified
<220> FEATURE:
<221> NAME/KEY: modified_base
<222> LOCATION: (6)..(6)
<223> OTHER INFORMATION: deoxynucleotide
<220> FEATURE:
<221> NAME/KEY: modified_base
<222> LOCATION: (7)..(10)
<223> OTHER INFORMATION: 2'-O Methyl modified
<220> FEATURE:
<221> NAME/KEY: modified_base
<222> LOCATION: (11)..(11)
<223> OTHER INFORMATION: deoxynucleotide
<220> FEATURE:
<221> NAME/KEY: modified_base
<222> LOCATION: (12)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(21)
<223> OTHER INFORMATION: 2'-O Methyl modified
<220> FEATURE:
```

```
<221> NAME/KEY: modified_base
<222> LOCATION: (22)..(22)
<223> OTHER INFORMATION: deoxynucleotide
<220> FEATURE:
<221> NAME/KEY: modified_base
<222> LOCATION: (23)..(26)
<223> OTHER INFORMATION: 2'-O Methyl modified
<220> FEATURE:
<221> NAME/KEY: modified_base
<222> LOCATION: (27)..(27)
<223> OTHER INFORMATION: Inverted deoxythymidine

<400> SEQUENCE: 141
auauacuugg cucguuaggu gcguaut                                    27

<210> SEQ ID NO 142
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(4)
<223> OTHER INFORMATION: 2'-O Methyl modified
<220> FEATURE:
<221> NAME/KEY: modified_base
<222> LOCATION: (5)..(5)
<223> OTHER INFORMATION: deoxynucleotide
<220> FEATURE:
<221> NAME/KEY: modified_base
<222> LOCATION: (6)..(9)
<223> OTHER INFORMATION: 2'-O Methyl modified
<220> FEATURE:
<221> NAME/KEY: modified_base
<222> LOCATION: (10)..(10)
<223> OTHER INFORMATION: deoxynucleotide
<220> FEATURE:
<221> NAME/KEY: modified_base
<222> LOCATION: (11)..(11)
<223> OTHER INFORMATION: 2'-O Methyl modified
<220> FEATURE:
<221> NAME/KEY: modified_base
<222> LOCATION: (12)..(12)
<223> OTHER INFORMATION: deoxynucleotide
<220> FEATURE:
<221> NAME/KEY: modified_base
<222> LOCATION: (13)..(20)
<223> OTHER INFORMATION: 2'-O Methyl modified
<220> FEATURE:
<221> NAME/KEY: modified_base
<222> LOCATION: (21)..(21)
<223> OTHER INFORMATION: deoxynucleotide
<220> FEATURE:
<221> NAME/KEY: modified_base
<222> LOCATION: (22)..(25)
<223> OTHER INFORMATION: 2'-O Methyl modified
<220> FEATURE:
<221> NAME/KEY: modified_base
<222> LOCATION: (26)..(26)
<223> OTHER INFORMATION: Inverted deoxythymidine

<400> SEQUENCE: 142
uauacuuggc ucguuaggug cguaut                                     26

<210> SEQ ID NO 143
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'-O Methyl modified
<220> FEATURE:
<221> NAME/KEY: modified_base
<222> LOCATION: (6)..(6)
<223> OTHER INFORMATION: deoxynucleotide
<220> FEATURE:
<221> NAME/KEY: modified_base
<222> LOCATION: (7)..(10)
<223> OTHER INFORMATION: 2'-O Methyl modified
<220> FEATURE:
<221> NAME/KEY: modified_base
<222> LOCATION: (11)..(11)
<223> OTHER INFORMATION: 2'-O Methyl modified
<220> FEATURE:
<221> NAME/KEY: modified_base
<222> LOCATION: (12)..(12)
<223> OTHER INFORMATION: 2'-O Methyl modified
<220> FEATURE:
<221> NAME/KEY: modified_base
<222> LOCATION: (13)..(13)
<223> OTHER INFORMATION: deoxynucleotide
<220> FEATURE:
<221> NAME/KEY: modified_base
<222> LOCATION: (14)..(21)
<223> OTHER INFORMATION: 2'-O Methyl modified
<220> FEATURE:
<221> NAME/KEY: modified_base
<222> LOCATION: (22)..(22)
<223> OTHER INFORMATION: deoxynucleotide
<220> FEATURE:
<221> NAME/KEY: modified_base
<222> LOCATION: (23)..(27)
<223> OTHER INFORMATION: 2'-O Methyl modified
<220> FEATURE:
<221> NAME/KEY: modified_base
<222> LOCATION: (28)..(28)
<223> OTHER INFORMATION: Inverted deoxythymidine

<400> SEQUENCE: 143
auauacuugg cucguuaggu gcguauat                                          28

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(4)
<223> OTHER INFORMATION: 2'-O Methyl modified
<220> FEATURE:
<221> NAME/KEY: modified_base
<222> LOCATION: (5)..(5)
<223> OTHER INFORMATION: deoxynucleotide
<220> FEATURE:
<221> NAME/KEY: modified_base
<222> LOCATION: (6)..(9)
<223> OTHER INFORMATION: 2'-O Methyl modified
<220> FEATURE:
<221> NAME/KEY: modified_base
<222> LOCATION: (10)..(10)
<223> OTHER INFORMATION: deoxynucleotide
<220> FEATURE:
<221> NAME/KEY: modified_base
<222> LOCATION: (11)..(11)
<223> OTHER INFORMATION: 2'-O Methyl modified
<220> FEATURE:
```

```
<221> NAME/KEY: modified_base
<222> LOCATION: (12)..(12)
<223> OTHER INFORMATION: deoxynucleotide
<220> FEATURE:
<221> NAME/KEY: modified_base
<222> LOCATION: (13)..(20)
<223> OTHER INFORMATION: 2'-O Methyl modified
<220> FEATURE:
<221> NAME/KEY: modified_base
<222> LOCATION: (21)..(21)
<223> OTHER INFORMATION: deoxynucleotide
<220> FEATURE:
<221> NAME/KEY: modified_base
<222> LOCATION: (22)..(26)
<223> OTHER INFORMATION: 2'-O Methyl modified
<220> FEATURE:
<221> NAME/KEY: modified_base
<222> LOCATION: (27)..(27)
<223> OTHER INFORMATION: Inverted deoxythymidine

<400> SEQUENCE: 144
uauacuuggc ucguuaggug cguauat                                              27

<210> SEQ ID NO 145
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-O Methyl modified
<220> FEATURE:
<221> NAME/KEY: modified_base
<222> LOCATION: (4)..(4)
<223> OTHER INFORMATION: deoxynucleotide
<220> FEATURE:
<221> NAME/KEY: modified_base
<222> LOCATION: (5)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(10)
<223> OTHER INFORMATION: 2'-O Methyl modified
<220> FEATURE:
<221> NAME/KEY: modified_base
<222> LOCATION: (11)..(11)
<223> OTHER INFORMATION: deoxynucleotide
<220> FEATURE:
<221> NAME/KEY: modified_base
<222> LOCATION: (12)..(19)
<223> OTHER INFORMATION: 2'-O Methyl modified
<220> FEATURE:
<221> NAME/KEY: modified_base
<222> LOCATION: (20)..(20)
<223> OTHER INFORMATION: deoxynucleotide
<220> FEATURE:
<221> NAME/KEY: modified_base
<222> LOCATION: (21)..(25)
<223> OTHER INFORMATION: 2'-O Methyl modified
<220> FEATURE:
<221> NAME/KEY: modified_base
<222> LOCATION: (26)..(26)
<223> OTHER INFORMATION: Inverted deoxythymidine

<400> SEQUENCE: 145
auacuuggcu cguuaggugc guauat                                               26
```

```
<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-O Methyl modified
<220> FEATURE:
<221> NAME/KEY: modified_base
<222> LOCATION: (4)..(4)
<223> OTHER INFORMATION: deoxynucleotide
<220> FEATURE:
<221> NAME/KEY: modified_base
<222> LOCATION: (5)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(10)
<223> OTHER INFORMATION: 2'-O Methyl modified
<220> FEATURE:
<221> NAME/KEY: modified_base
<222> LOCATION: (11)..(11)
<223> OTHER INFORMATION: deoxynucleotide
<220> FEATURE:
<221> NAME/KEY: modified_base
<222> LOCATION: (12)..(19)
<223> OTHER INFORMATION: 2'-O Methyl modified
<220> FEATURE:
<221> NAME/KEY: modified_base
<222> LOCATION: (20)..(20)
<223> OTHER INFORMATION: deoxynucleotide
<220> FEATURE:
<221> NAME/KEY: modified_base
<222> LOCATION: (21)..(25)
<223> OTHER INFORMATION: 2'-O Methyl modified
<220> FEATURE:
<221> NAME/KEY: modified_base
<222> LOCATION: (26)..(26)
<223> OTHER INFORMATION: Inverted deoxythymidine

<400> SEQUENCE: 146
uuacuuggcu cguuaggugc guauat                                          26

<210> SEQ ID NO 147
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O Methyl modified
<220> FEATURE:
<221> NAME/KEY: modified_base
<222> LOCATION: (7)..(7)
<223> OTHER INFORMATION: deoxynucleotide
<220> FEATURE:
<221> NAME/KEY: modified_base
<222> LOCATION: (8)..(11)
<223> OTHER INFORMATION: 2'-O Methyl modified
<220> FEATURE:
```

```
<221> NAME/KEY: modified_base
<222> LOCATION: (12)..(12)
<223> OTHER INFORMATION: deoxynucleotide
<220> FEATURE:
<221> NAME/KEY: modified_base
<222> LOCATION: (13)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(22)
<223> OTHER INFORMATION: 2'-O Methyl modified
<220> FEATURE:
<221> NAME/KEY: modified_base
<222> LOCATION: (23)..(23)
<223> OTHER INFORMATION: deoxynucleotide
<220> FEATURE:
<221> NAME/KEY: modified_base
<222> LOCATION: (24)..(30)
<223> OTHER INFORMATION: 2'-O Methyl modified
<220> FEATURE:
<221> NAME/KEY: modified_base
<222> LOCATION: (31)..(31)
<223> OTHER INFORMATION: Inverted deoxythymidine

<400> SEQUENCE: 147
ggaauacuug gcucguuagg ugcguauaua t                                    31

<210> SEQ ID NO 148
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-PEG40K-NH
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
```

-continued

<223> OTHER INFORMATION: 2'-O Methyl modified

<400> SEQUENCE: 148
ggaauauacu uggcucguua ggugcguaua ua        32

<210> SEQ ID NO 149
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-PEG40K-NH
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(31)
<223> OTHER INFORMATION: 2'-O Methyl modified

<400> SEQUENCE: 149
ggaauauacu uggcucguua ggugcguaua u        31

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-PEG40K-NH
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)

```
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(30)
<223> OTHER INFORMATION: 2'-O Methyl modified

<400> SEQUENCE: 150
ggaauauacu uggcucguua ggugcguaua                                        30

<210> SEQ ID NO 151
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5'-PEG40K-NH
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(15)
<223> OTHER INFORMATION: 2'-O Methyl modified
<220> FEATURE:
<221> NAME/KEY: modified_base
<222> LOCATION: (16)..(16)
<223> OTHER INFORMATION: deoxynucleotide
<220> FEATURE:
<221> NAME/KEY: modified_base
<222> LOCATION: (17)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
```

```
<221> NAME/KEY: modified_base
<222> LOCATION: (26)..(29)
<223> OTHER INFORMATION: 2'-O Methyl modified

<400> SEQUENCE: 151
ggaauauacu uggcucguua ggugcguau                                           29

<210> SEQ ID NO 152
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-O Methyl modified
<220> FEATURE:
<221> NAME/KEY: modified_base
<222> LOCATION: (9)..(9)
<223> OTHER INFORMATION: deoxynucleotide
<220> FEATURE:
<221> NAME/KEY: modified_base
<222> LOCATION: (10)..(13)
<223> OTHER INFORMATION: 2'-O Methyl modified
<220> FEATURE:
<221> NAME/KEY: modified_base
<222> LOCATION: (14)..(14)
<223> OTHER INFORMATION: deoxynucleotide
<220> FEATURE:
<221> NAME/KEY: modified_base
<222> LOCATION: (15)..(16)
<223> OTHER INFORMATION: 2'-O Methyl modified
<220> FEATURE:
<221> NAME/KEY: modified_base
<222> LOCATION: (17)..(17)
<223> OTHER INFORMATION: deoxynucleotide
<220> FEATURE:
<221> NAME/KEY: modified_base
<222> LOCATION: (18)..(24)
<223> OTHER INFORMATION: 2'-O Methyl modified
<220> FEATURE:
<221> NAME/KEY: modified_base
<222> LOCATION: (25)..(25)
<223> OTHER INFORMATION: deoxynucleotide
<220> FEATURE:
<221> NAME/KEY: modified_base
<222> LOCATION: (26)..(32)
<223> OTHER INFORMATION: 2'-O Methyl modified
<220> FEATURE:
<221> NAME/KEY: modified_base
<222> LOCATION: (33)..(33)
<223> OTHER INFORMATION: Inverted deoxythymidine

<400> SEQUENCE: 152
ggaauauacu uggcugcuua ggugcguaua uat                                      33

<210> SEQ ID NO 153
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ggaauauacu uggcucguua ggugcguaua ua                                       32
```

APTAMERS TO TISSUE FACTOR PATHWAY INHIBITOR AND THEIR USE AS BLEEDING DISORDER THERAPEUTICS

CROSS-REFERENCE TO RELATED APPLICATIONS

This non-provisional patent application claims the benefit of priority under 35 U.S.C. §119(e) to U.S. Provisional Patent Application Ser. Nos. 61/234,939, filed Aug. 18, 2009; 61/353,374, filed Jun. 10, 2010; 61/366,362, filed Jul. 21, 2010; and 61/367,766, filed Jul. 26, 2010; the contents of each of which are hereby incorporated by reference in their entirety.

INCORPORATION-BY-REFERENCE OF SEQUENCE LISTING

The contents of the text file named "ARC612USsubseqlist.txt," which was created on Jan. 3, 2011 and is 149 KB in size, are hereby incorporated by reference in their entirety.

FIELD OF THE INVENTION

The invention relates generally to the field of nucleic acids and more particularly to aptamers that bind to tissue factor pathway inhibitor (TFPI), which are useful as therapeutics in and diagnostics of bleeding disorders and/or other pathologies, diseases or disorders in which TFPI has been implicated. The invention further relates to materials and methods for the administration of aptamers that bind to TFPI.

BACKGROUND OF THE INVENTION

Aptamers

An aptamer is an isolated or purified nucleic acid that binds with high specificity and affinity to a target through interactions other than Watson-Crick base pairing. An aptamer has a three dimensional structure that provides chemical contacts to specifically bind to a target. Unlike traditional nucleic acid binding, aptamer binding is not dependent upon a conserved linear base sequence, but rather a particular secondary or tertiary structure. That is, the nucleic acid sequences of aptamers are non-coding sequences. Any coding potential that an aptamer may possess is entirely fortuitous and plays no role whatsoever in the binding of an aptamer to a target. A typical minimized aptamer is 5-15 kDa in size (15-45 nucleotides), binds to a target with nanomolar to sub-nanomolar affinity, and discriminates against closely related targets (e.g., aptamers will typically not bind to other proteins from the same gene or functional family).

Aptamers have been generated to many targets, such as small molecules, carbohydrates, peptides and proteins, including growth factors, transcription factors, enzymes, immunoglobulins and receptors.

Aptamers are capable of specifically binding to selected targets and modulating the target's activity or binding interactions, e.g., through binding, aptamers may inhibit or stimulate a target's ability to function. Specific binding to a target is an inherent property of an aptamer. Functional activity, i.e., inhibiting or stimulating a target's function, is not. Often times, an aptamer binds to a target and has little or no effect on the function of the target. Sometimes, an aptamer binds to a target and has an inhibitory or stimulatory effect on a target's function.

Aptamers have a number of desirable characteristics for use as therapeutics and diagnostics, including high specificity and affinity, biological activity, low immunogenicity, tunable pharmacokinetic properties and stability.

Bleeding Disorders

Coagulation is the formation of a stable fibrin/cellular hemostatic plug that is sufficient to stop bleeding. The coagulation process, which is illustrated in FIG. 1, involves complex biochemical and cellular interactions that can be divided into three stages. Stage 1 is the formation of activated Factor X by either the contact (intrinsic) or the tissue factor/VIIa (extrinsic) pathway. Stage 2 is the formation of thrombin from prothrombin by Factor Xa. Stage 3 is the formation of fibrin from fibrinogen stabilized by Factor XIIIa.

Hemophilia is defined as a congenital or acquired disorder of coagulation that usually, but not always, involves a quantitative and/or functional deficiency of a single coagulation protein. Deficiency of coagulation Factors VIII (hemophilia A) and IX (hemophilia B) are the two most common inherited bleeding disorders. The total overall number of hemophilia A and B patients worldwide is approximately 400,000; however, only about ¼ (100,000) of these individuals are treated. Hemophilia A and B can be further divided in regard to the extent of factor deficiency. Mild hemophilia is 5-40% of normal factor levels and represents approximately 25% of the total hemophilia population. Moderate hemophilia is 1-5% of normal factor levels and represents approximately 25% of the total hemophilia population. Severe hemophilia is <1% of normal factor levels and represents approximately 50% of the total hemophilia population and the highest users of currently available therapies.

Since the discovery of cryoprecipitation by Pool (Pool et al., "High-potency antihaemophilic factor concentrate prepared from cryoglobulin precipitate", *Nature*, vol. 203, p. 312 (1964)), treatment of these life threatening deficiencies has focused on factor replacement, with a continued effort directed toward improvement in the quality of the Factor VIII and IX concentrates. The most significant improvement has been the availability of recombinant forms of Factors VIII and IX. These highly purified recombinant molecules have a safety and efficacy profile that has made them the primary form of replacement factors used for the treatment of hemophilia. The majority of mild and moderate patients are treated "on demand", that is when a bleed occurs. Approximately 50-60% of severe patients are treated "on demand", while the remainder of this population uses prophylactic therapy, which involves administering intravenous factor 2-3 times weekly.

Unfortunately, recombinant factors still retain some of the limitations of concentrates and more highly purified plasma derived factors. These limitations include the relatively short half-life of the molecules, which require frequent injection to maintain effective plasma concentration; high cost; and the development of antibody responses, especially to Factor VIII, in a subpopulation of patients called inhibitor patients.

In a majority of patients who develop inhibitory antibodies, the antibody is only transient. In those patients with a sustained antibody response (~15%), some respond to complex and expensive tolerization protocols. Those who do not respond to tolerization (~5-10%) require the use of non-Factor VIII/Factor IX products to control bleeding. Prothrombin Complex Concentrations (PCC), Factor Eight Inhibitor Bypass Agent (FEIBA) and recombinant Factor VIIa (NovoSeven®, FVIIa) are effective Factor VIII/Factor IX bypass treatments for inhibitor patients.

Recombinant Factor VIIa (rFVIIa) treatment is the most used of these bypass agents. Factor VIIa complexes with endogenous tissue factor to activate the extrinsic pathway. It also can directly activate Factor X. The response to rFVIIa treatment is variable. The variable response, along with the poor pharmacokinetic (PK) profile of rFVIIa, can require multiple injections to control bleeding and significantly limits its utility for prophylactic treatment.

A major effort is currently underway towards development of modified Factor VIII, IX and VIIa molecules with improved potency, stability and circulating half-life. It should be noted that in all instances, the products represent incremental improvements to stability, pharmacokinetics and/or formulation of existing replacement factors.

The tissue factor/VIIa (extrinsic) pathway provides for rapid formation of low levels of thrombin that can serve as the initial hemostatic response to initiate and accelerate the Factor VIII, V and IX dependent intrinsic pathway. Tissue factor, Factor VIIa and Factor Xa have a central role in this pathway and it is closely regulated by an endothelial cell associated Kunitz Type proteinase inhibitor, tissue factor pathway inhibitor (TFPI).

Tissue factor pathway inhibitor is a 40 kDa serine protease inhibitor that is synthesized in and found bound to endothelial cell surfaces ("surface TFPI"), in plasma at a concentration of 2-4 nM ("plasma TFPI") and is stored (200 pM/$10^8$ platelets) and released from activated platelets. Approximately 10% of plasma TFPI is unassociated, while 90% is associated with oxidized LDL particles and is inactive. There are two primary forms of TFPI, TFPIα and TFPIβ (FIGS. 2 and 3).

TFPIα contains 3 Kunitz decoy domains, K1, K2 and K3. K1 and K2 mimic protease substrates and inhibit by tight but reversible binding to the target proteases. In the case of TFPIα, K1 binds to and inhibits tissue factor/VIIa, while K2 binds to and inhibits Factor Xa. The role for K3 is unknown at this time, but it may have a role in cell-surface binding and enhancing the inhibition of Factor Xa by K2. TFPIα has a basic C-terminal tail peptide that is the membrane binding site region for the molecule. It is estimated that 80% of the surface TFPI is TFPIα. TFPIα is primarily bound to the endothelial surface associated with the membrane proteoglycans. Heparin has been shown to release TFPIα from cultured endothelium, isolated veins and following intravenous (IV) heparin (unfractionated and LMWH) injection. The exact nature of the release mechanism is unclear (competition or induced release), but TFPI levels can be increased 3-8 fold following IV heparin administration. Some TFPIα can also be found bound to glycosylated phosphatidylinositol (GPI) via an unidentified co-receptor.

TFPIβ is an alternatively spliced version of TFPI that is post-translationally modified with a glycosylated phosphatidylinositol (GPI) anchor. It is estimated that it represents about 20% of the surface TFPI in cultured endothelial cells. Although it has in vitro inhibitory activity, the functional in vivo role is less clear.

Surface TFPI may have a more important role in regulation of coagulation based on its localization to the site of vascular injury and thrombus formation. Surface TFPI represents the largest proportion of active TFPI. Data from several laboratories suggest that TFPI can also have complementary/synergistic effects via interactions with antithrombin III (ATIII) and protein C.

TFPI binds to Factor VIIa and Factor Xa via its K1 and K2 domains and to proteoglycans via its K3 and C-terminal domains. The fact that TFPI has a key role in the inhibition of both tissue factor/VIIa and Xa suggests that TFPI inhibition could provide a single treatment or an adjuvant treatment that is given in addition to or combined with recombinant purified factors. An approach to promote a prothrombotic state could be via the upregulation of the tissue factor mediated extrinsic pathway of coagulation. It has been suggested that inhibition of TFPI might improve coagulation in the hemophilia patient.

Studies have demonstrated that TFPI deficiency in mice can increase thrombus formation, and that TFPI antibodies improve bleeding times in Factor VIII deficient rabbits and shorten clotting in plasma from hemophilia patients. In the rabbit, transient hemophilia A was induced by treating rabbits with a Factor VIII antibody. This was followed by treatment with either Factor VIII replacement or an antibody specific to rabbit TFPI. The anti-TFPI treatment produced a reduction in bleeding and a correction of coagulation that was similar to that observed with Factor VIII replacement. Liu et al. (Liu et al., "Improved coagulation in bleeding disorders by Non-Anticoagulant Sulfated Polysaccharides (NASP)", Thromb. Haemost., vol. 95, pp. 68-76 (2006)) reported the effects of a non-anticoagulant polysaccharide isolated from brown algae that inhibits TFPI. A subsequent paper by Prasad et al. (Prasad et al., "Efficacy and safety of a new-class of hemostatic drug candidate, AV513, in dogs with hemophilia A", Blood, vol. 111, pp. 672-679 (2008)) also assessed this polysaccharide in hemophilia A dogs. In both studies, it was found that TFPI inhibition had a positive effect on restoration of a normal coagulation profile and, in the dog model, an improvement in hemostatic profile, including an improved thromboelastogram (TEG) and a reduction in nail bleeding time. These data suggest that inhibition of TFPI could provide an approach to treating hemophilia.

Accordingly, it would be beneficial to identify novel therapies for antagonizing TFPI in the treatment of bleeding disorders, or that are used in conjunction with medical procedures, or that are used in combination with another drug or another therapy to induce a pro-coagulant state. The present invention provides materials and methods to meet these and other needs.

SUMMARY OF THE INVENTION

The invention provides aptamers that bind to tissue factor pathway inhibitor (TFPI), referred to herein as "TFPI aptamers", and methods for using such aptamers in the treatment of bleeding disorders and other TFPI-mediated pathologies, diseases or disorders, with or without other agents. In addition, the TFPI aptamers may be used before, during and/or after medical procedures, with or without other agents, in order to reduce the complications or side effects thereof.

The TFPI aptamers bind to or otherwise interact with TFPI or one or more portions (or regions) thereof. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. Preferably, the TFPI is human TFPI. Preferably, the TFPI aptamers bind to TFPI and require binding contacts, at least in part, outside of the K1 and K2 regions, such as the K3/C-terminal region. More preferably, the TFPI aptamers bind at least in part to one or more portions of mature TFPI (for example, FIG. 3A) that are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. Preferably, the TFPI aptamer has a dissociation constant for TFPI of 100 nM or less.

Examples of TFPI aptamers include, but are not limited to, aptamers that comprise a nucleic acid sequence selected from the group consisting of SEQ ID NO: 1, which is referred to herein as ARC26835; SEQ ID NO: 2, which is referred to herein as ARC17480; SEQ ID NO: 3, which is referred to herein as ARC 19498; SEQ ID NO: 4, which is referred to herein as ARC19499; SEQ ID NO: 5, which is referred to herein as ARC19500; SEQ ID NO: 6, which is referred to herein as ARC19501; SEQ ID NO: 7, which is referred to herein as ARC31301; SEQ ID NO: 8, which is referred to herein as ARC 18546; SEQ ID NO: 9, which is referred to herein as ARC19881; and SEQ ID NO: 10, which is referred to herein as ARC19882.

Preferably, the TFPI aptamer is an aptamer or a salt thereof comprising the following nucleic acid sequence: mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA (SEQ ID NO: 1) (ARC26835), wherein "dN" is a deoxynucleotide and "mN" is a 2'-O Methyl containing nucleotide (which is also known in the art as a 2'-OMe, 2'-methoxy or 2'-OCH$_3$ containing nucleotide). In some embodiments, the TFPI aptamer is an aptamer or a salt thereof that consists of the nucleic acid sequence of SEQ ID NO: 1.

More preferably, the TFPI aptamer is an aptamer or a salt thereof comprising the following nucleic acid sequence: mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 2) (ARC17480), wherein "3T" is an inverted deoxythymidine, "dN" is a deoxynucleotide and "mN" is a 2'-O Methyl containing nucleotide. In some embodiments, the TFPI aptamer is an aptamer or a salt thereof that consists of the nucleic acid sequence of SEQ ID NO: 2.

Even more preferably, the TFPI aptamer is an aptamer or a salt thereof comprising the following nucleic acid sequence: NH$_2$-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 3) (ARC19498), wherein "NH$_2$" is from a 5'-hexylamine linker phosphoramidite, "3T" is an inverted deoxythymidine, "dN" is a deoxynucleotide and "mN" is a 2'-O Methyl containing nucleotide. In some embodiments, the TFPI aptamer is an aptamer or a salt thereof that consists of the nucleic acid sequence of SEQ ID NO: 3.

Most preferably, the TFPI aptamer is an aptamer or a salt thereof comprising the following nucleic acid sequence: PEG40K-NH-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 4) (ARC19499), wherein "NH" is from a 5'-hexylamine linker phosphoramidite, "3T" is an inverted deoxythymidine, "dN" is a deoxynucleotide, "mN" is a 2'-O Methyl containing nucleotide and "PEG" is a polyethylene glycol. In some embodiments, the TFPI aptamer is an aptamer or a salt thereof that consists of the nucleic acid sequence of SEQ ID NO: 4. In some embodiments, the PEG40K moiety of SEQ ID NO: 4 is a branched PEG moiety having a total molecular weight of 40 kDa. In other embodiments, the PEG40K moiety of SEQ ID NO: 4 is a linear PEG moiety having a molecular weight of 40 kDa. In further embodiments, the PEG40K moiety of SEQ ID NO: 4 is a methoxypolyethylene glycol (mPEG) moiety having a molecular weight of 40 kDa. In still further embodiments, the PEG40K moiety of SEQ ID NO: 4 is a branched mPEG moiety that contains two mPEG20K moieties, each having a molecular weight of 20 kDa, as shown in FIGS. 6-9, where "20KPEG" refers to a mPEG moiety having a molecular weight of 20 kDa. In a preferred embodiment, the PEG40K moiety of SEQ ID NO: 4 is the branched PEG40K moiety shown in FIG. 6, where "20KPEG" refers to a mPEG moiety having a molecular weight of 20 kDa, and is connected to the aptamer as shown in FIG. 7. In a more preferred embodiment, the PEG40K moiety is connected to the aptamer using a 5'-amine linker phosphoramidite, as shown in FIG. 8, where "20KPEG" refers to a mPEG moiety having a molecular weight of 20 kDa. In a most preferred embodiment, the PEG40K moiety is a mPEG moiety having a total molecular weight of 40 kDa and is connected to the aptamer using a 5'-hexylamine linker phosphoramidite, as shown in FIGS. 9A and 9B.

Alternatively, the TFPI aptamer is an aptamer or a salt thereof comprising the following nucleic acid sequence: NH$_2$-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-NH$_2$ (SEQ ID NO: 5) (ARC19500), wherein "dN" is a deoxynucleotide, "mN" is a 2'-O Methyl containing nucleotide and "NH$_2$" is from a hexylamine linker phosphoramidite. In some embodiments, the TFPI aptamer is an aptamer or a salt thereof that consists of the nucleic acid sequence of SEQ ID NO: 5.

Preferable to the TFPI aptamer of paragraph [0029] is an aptamer or a salt thereof comprising the following nucleic acid sequence: PEG20K-NH-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-NH-PEG20K (SEQ ID NO: 6) (ARC19501), wherein "dN" is a deoxynucleotide, "mN" is a 2'-O Methyl containing nucleotide, "NH" is from a hexylamine linker phosphoramidite and "PEG" is a polyethylene glycol. In some embodiments, the TFPI aptamer is an aptamer or a salt thereof that consists of the nucleic acid sequence of SEQ ID NO: 6. In some embodiments, the PEG20K moieties of SEQ ID NO: 6 are branched PEG moieties. In other embodiments, the PEG20K moieties of SEQ ID NO: 6 are linear PEG moieties. In further embodiments, the PEG20K moieties of SEQ ID NO: 6 are methoxypolyethylene glycol (mPEG) moieties having a molecular weight of 20 kDa. In still further embodiments, the PEG20K moieties of SEQ ID NO: 6 are branched mPEG moieties that contain two mPEG10K moieties each having a molecular weight of 10 kDa.

Alternatively, the TFPI aptamer is an aptamer or a salt thereof comprising the following nucleic acid sequence: mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA (SEQ ID NO: 7) (ARC31301), wherein "dN" is a deoxynucleotide and "mN" is a 2'-O Methyl containing nucleotide. In some embodiments, the TFPI aptamer is an aptamer or a salt thereof that consists of the nucleic acid sequence of SEQ ID NO: 7.

Preferable to the TFPI aptamer of paragraph [0031] is an aptamer or a salt thereof comprising the following nucleic acid sequence: mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA-3T (SEQ ID NO: 8) (ARC18546), wherein "3T" is an inverted deoxythymidine, "dN" is a deoxynucleotide and "mN" is a 2'-O Methyl containing nucleotide. In some embodiments, the TFPI aptamer is an aptamer or a salt thereof that consists of the nucleic acid sequence of SEQ ID NO: 8.

More preferable to the TFPI aptamer of paragraph [0031] is an aptamer or a salt thereof comprising the following nucleic acid sequence: NH$_2$-mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA-3T (SEQ ID NO: 9) (ARC19881), wherein "NH$_2$" is from a 5'-hexylamine linker phosphoramidite, "3T" is an inverted deoxythymidine, "dN" is a deoxynucleotide and "mN" is a 2'-O Methyl containing nucleotide. In some embodiments, the TFPI aptamer is an aptamer or a salt thereof that consists of the nucleic acid sequence of SEQ ID NO: 9.

Even more preferable to the TFPI aptamer of paragraph [0031] is an aptamer or a salt thereof comprising the following nucleic acid sequence: PEG40K-NH-mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA-3T (SEQ ID NO: 10) (ARC19882), wherein "NH" is from a 5'-hexylamine linker phosphoramidite, "3T" is an inverted deoxythymidine, "dN" is a deoxynucleotide, "mN" is a 2'-O Methyl containing nucleotide and "PEG" is a polyethylene glycol. In some embodiments, the TFPI aptamer is an aptamer or a salt thereof that consists of the nucleic acid sequence of SEQ ID NO: 10. In some embodiments, the PEG40K moiety of SEQ ID NO: 10 is a branched PEG moiety having a total molecular weight of 40 kDa. In other embodiments, the PEG40K moiety of SEQ ID NO: 10 is a linear PEG moiety having a molecular weight of 40 kDa. In further embodiments, the PEG40K moiety of SEQ ID NO: 10 is a methoxypolyethylene glycol (mPEG) moiety having a molecular weight of 40 kDa. In still further embodiments, the PEG40K moiety of SEQ ID NO: 10 is a branched mPEG moiety that contains two mPEG20K moieties, each having a molecular weight of 20 kDa, as shown in FIGS. 6-9, where "20KPEG" refers to a mPEG moiety having a molecular weight of 20 kDa. In a preferred embodiment, the PEG40K moiety of SEQ ID NO: 10 is the branched PEG40K moiety shown in FIG. 6, where "20KPEG" refers to a mPEG moiety having a molecular weight of 20 kDa, and is connected to the aptamer as shown in FIG. 7. In a more preferred embodiment, the PEG40K moiety is connected to the aptamer using a 5'-amine linker phosphoramidite, as shown in FIG. 8, where "20KPEG" refers to a mPEG moiety having a molecular weight of 20 kDa. In a most preferred embodiment, the PEG40K moiety is a mPEG moiety having a total molecular weight of 40 kDa and is connected to the aptamer using a 5'-hexylamine linker phosphoramidite, as shown in FIGS. 9A and 9B.

Preferably, the TFPI aptamers are connected to one or more PEG moieties, with or without one or more linkers. The PEG moieties may be any type of PEG moiety. For example, the PEG moiety may be linear, branched, multiple branched, star shaped, comb shaped or a dendrimer. In addition, the PEG moiety may have any molecular weight. Preferably, the PEG moiety has a molecular weight ranging from 5-100 kDa in size. More preferably, the PEG moiety has a molecular weight ranging from 10-80 kDa in size. Even more preferably, the PEG moiety has a molecular weight ranging from 20-60 kDa in size. Yet even more preferably, the PEG moiety has a molecular weight ranging from 30-50 kDa in size. Most preferably, the PEG moiety has a molecular weight of 40 kDa in size, also referred to herein as "40 KPEG". The same or different PEG moieties may be connected to a TFPI aptamer. The same or different linkers or no linkers may be used to connect the same or different PEG moieties to a TFPI aptamer.

Alternatively, the TFPI aptamers may be connected to one or more PEG alternatives (rather than to one or more PEG moieties), with or without one or more linkers. Examples of PEG alternatives include, but are not limited to, polyoxazoline (POZ), PolyPEG, hydroxyethylstarch (HES) and albumin. The PEG alternative may be any type of PEG alternative, but it should function the same as or similar to a PEG moiety, i.e., to reduce renal filtration and increase the half-life of the TFPI aptamer in the circulation. The same or different PEG alternatives may be connected to a TFPI aptamer. The same or different linkers or no linkers may be used to connect the same or different PEG alternatives to a TFPI aptamer. Alternatively, a combination of PEG moieties and PEG alternatives may be connected to a TFPI aptamer, with or without one or more of the same or different linkers.

Preferably, the TFPI aptamers are connected to a PEG moiety or a PEG alternative via one or more linkers. However, the TFPI aptamers may be connected to a PEG moiety or PEG alternative directly, without the use of a linker. The linker may be any type of molecule. Examples of linkers include, but are not limited to, amines, thiols and azides. The linkers can include a phosphate group. Preferably, the linker is from a 5'-amine linker phosphoramidite. In some embodiments, the 5'-amine linker phosphoramidite comprises 2-18 consecutive CH$_2$ groups. In more preferred embodiments, the 5'-amine linker phosphoramidite comprises 2-12 consecutive CH$_2$ groups. In even more preferred embodiments, the 5'-amine linker phosphoramidite comprises 4-8 consecutive CH$_2$ groups. In most preferred embodiments, the 5'-amine linker phosphoramidite comprises 6 consecutive CH$_2$ groups, i.e., is a 5'-hexylamine linker phosphoramidite. One or more of the same or different linkers or no linkers may be used to connect one or more of the same or different PEG moieties or one or more of the same or different PEG alternatives to a TFPI aptamer.

In preferred embodiments, an aptamer, or a salt thereof, comprising the following structure is provided:

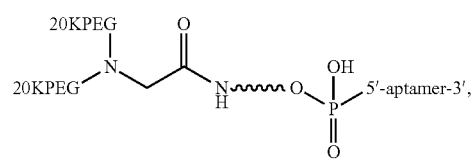

wherein HN$\sim\sim\sim$PO$_3$H is from a 5'-amine linker phosphoramidite, and the aptamer is a TFPI aptamer of the invention. Preferably, the aptamer is selected from the group consisting of SEQ ID NOs: 2 and 8. The 20KPEG moiety can be any PEG moiety having a molecular weight of 20 kDa. Preferably, the 20KPEG moiety is a mPEG moiety having a molecular weight of 20 kDa.

In alternative preferred embodiments, an aptamer, or a salt thereof, comprising the following structure is provided:

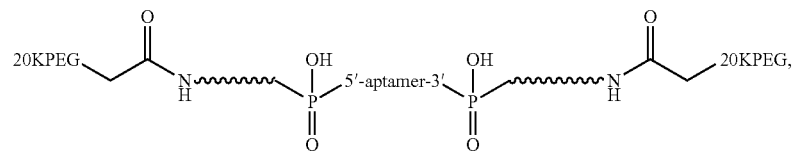

wherein HN〜〜〜PO₂H is from a 5'-amine linker phosphoramidite, and the aptamer is a TFPI aptamer of the invention. Preferably, the aptamer is selected from the group consisting of SEQ ID NO: 1. The 20KPEG moiety can be any PEG moiety having a molecular weight of 20 kDa. Preferably, the 20KPEG moiety is a mPEG moiety having a molecular weight of 20 kDa In more preferred embodiments, an aptamer, or a salt thereof, comprising the following structure is provided:

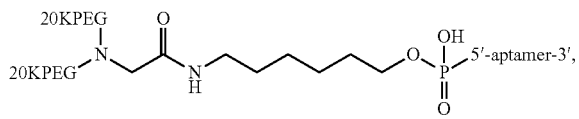

wherein the aptamer is a TFPI aptamer of the invention. Preferably, the aptamer is selected from the group consisting of SEQ ID NOs: 2 and 8. The 20KPEG moiety can be any PEG moiety having a molecular weight of 20 kDa. Preferably, the 20KPEG moiety is a mPEG moiety having a molecular weight of 20 kDa In alternative more preferred embodiments, an aptamer, or a salt thereof, comprising the following structure is provided:

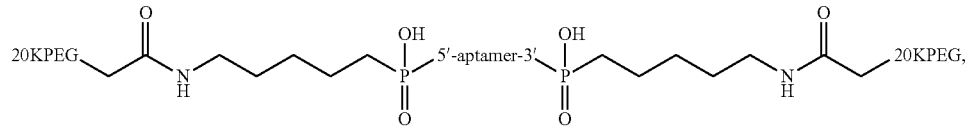

wherein the aptamer is a TFPI aptamer of the invention. Preferably, the aptamer is selected from the group consisting of SEQ ID NO: 1. The 20KPEG moiety can be any PEG moiety having a molecular weight of 20 kDa. Preferably, the 20KPEG moiety is a mPEG moiety having a molecular weight of 20 kDa In most preferred embodiments, an aptamer, or a salt thereof, comprising the following structure is provided:

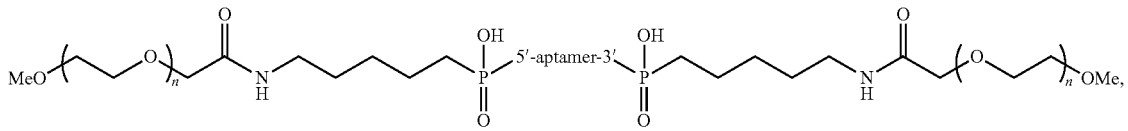

wherein "n" is about 454 ethylene oxide units (PEG=20 kDa), and the aptamer is a TFPI aptamer of the invention. "n" is about 454 ethylene oxide units because the number of n's may vary slightly for a PEG having a particular molecular weight. Preferably, "n" ranges from 400-500 ethylene oxide units. More preferably, "n" ranges from 425-475 ethylene oxide units. Even more preferably, "n" ranges from 440-460 ethylene oxide units. Most preferably, "n" is 454 ethylene oxide units. Preferably, the aptamer is selected from the group consisting of SEQ ID NOs: 2 and 8.

In alternative most preferred embodiments, an aptamer, or a salt thereof, comprising the following structure is provided:

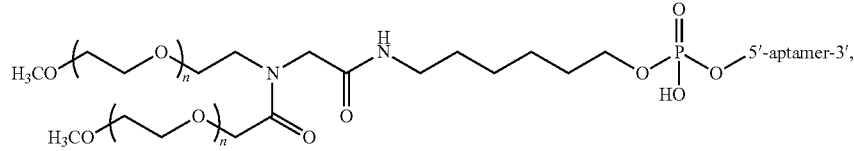

wherein "n" is about 454 ethylene oxide units (PEG=20 kDa), and the aptamer is a TFPI aptamer of the invention. "n" is about 454 ethylene oxide units because the number of n's may vary slightly for a PEG having a particular molecular weight. Preferably, "n" ranges from 400-500 ethylene oxide units. More preferably, "n" ranges from 425-475 ethylene oxide units. Even more preferably, "n" ranges from 440-460 ethylene oxide units. Most preferably, "n" is 454 ethylene oxide units. Preferably, the aptamer is selected from the group consisting of SEQ ID NO: 1.

The invention also provides aptamers that have substantially the same ability to bind to TFPI as any one of the aptamers shown in SEQ ID NOs: 1, 2, 3, 4, 5, 6, 7, 8, 9 or 10. In some embodiments, the aptamers have substantially the same structure as any one of the aptamers shown in SEQ ID NOs: 1, 2, 3, 4, 5, 6, 7, 8, 9 or 10. In some embodiments, the aptamers have substantially the same ability to bind to TFPI and substantially the same structure as any one of the aptamers shown in SEQ ID NOs: 1, 2, 3, 4, 5, 6, 7, 8, 9 or 10. The invention also provides aptamers that have substantially the same ability to bind to TFPI and substantially the same ability to modulate a biological function of TFPI as any one of the aptamers shown in SEQ ID NOs: 1, 2, 3, 4, 5, 6, 7, 8, 9 or 10. The invention further provides aptamers that have substantially the same ability to bind to TFPI and substantially the same ability to modulate blood coagulation as any one of the aptamers shown in SEQ ID NOs: 1, 2, 3, 4, 5, 6, 7, 8, 9 or 10. The invention also provides aptamers that have substantially the same structure and substantially the same ability to modulate a biological function of TFPI as any one of the aptamers shown in SEQ ID NOs: 1, 2, 3, 4, 5, 6, 7, 8, 9 or 10. The invention also provides aptamers that have substantially the same structure and substantially the same ability to modulate blood coagulation as any one of the aptamers shown in SEQ ID NOs: 1, 2, 3, 4, 5, 6, 7, 8, 9 or 10. In some embodiments, the aptamers have substantially the same ability to bind to TFPI, substantially the same structure and substantially the same ability to modulate a biological function of TFPI as any one of the aptamers shown in SEQ ID NOs: 1, 2, 3, 4, 5, 6, 7, 8, 9 or 10. In some embodiments, the aptamers have substantially the same ability to bind to TFPI, substantially the same structure and substantially the same ability to modulate blood coagulation as any one of the aptamers shown in SEQ ID NOs: 1, 2, 3, 4, 5, 6, 7, 8, 9 or 10.

The TFPI aptamers may comprise at least one chemical modification. Preferably, the modification is selected from the group consisting of: a chemical substitution at a sugar position, a chemical substitution at an internucleotide linkage and a chemical substitution at a base position. Alternatively, the modification is selected from the group consisting of: incorporation of a modified nucleotide; a 3' cap; a 5' cap; conjugation to a high molecular weight, non-immunogenic compound; conjugation to a lipophilic compound; incorporation of a CpG motif; and incorporation of a phosphorothioate or phosphorodithioate into the phosphate backbone. The high molecular weight, non-immunogenic compound is preferably polyethylene glycol. In some embodiments, the polyethylene glycol is methoxypolyethylene glycol (mPEG). The 3' cap is preferably an inverted deoxythymidine cap.

The invention also provides aptamers that bind to TFPI and have one or more of the following characteristics: (i) includes the primary nucleotide sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA (SEQ ID NO: 1); (ii) includes a primary nucleotide sequence that has at least 70%, 75%, 80%, 85%, 90%, 91%, 92%, 93%, 94%, 95%, 96%, 97%, 98% or 99% sequence identity to the primary nucleotide sequence shown in SEQ ID NO: 1 or 7; (iii) has substantially the same or better ability to bind to TFPI as that of an aptamer that comprises a primary nucleotide sequence selected from the group consisting of SEQ ID NOs: 1, 2, 3, 4, 5, 6, 7, 8, 9 or 10; and/or (iv) has substantially the same or better ability to modulate or inhibit TFPI as that of an aptamer comprising a primary nucleotide sequence selected from the group consisting of SEQ ID NOs: 1, 2, 3, 4, 5, 6, 7, 8, 9 or 10. As used herein, the term primary nucleotide sequence refers to the 5' to 3' linear sequence of nucleotide bases of the nucleic acid sequence that forms an aptamer, without regard to 3' or 5' modifications. For example, ARC26835, ARC17480, ARC19498, ARC19499, ARC19500 and ARC19501 all have the same primary nucleotide sequence.

The invention additionally provides pharmaceutical compositions comprising a therapeutically effective amount of a TFPI aptamer or a salt thereof, and a pharmaceutically acceptable carrier or diluent.

The invention further provides a method for treating, preventing, delaying the progression of, or ameliorating a pathology, disease or disorder mediated by TFPI by administering to a subject the above pharmaceutical composition. Preferably, the subject is a mammal. More preferably, the subject is a human. Preferably, the pathology, disease or disorder is selected from the group consisting of: coagulation factor deficiencies, congenital or acquired, mild or moderate or severe, including hemophilia A (Factor VIII deficiency), hemophilia B (Factor IX deficiency) and hemophilia C (Factor XI deficiency); hemophilia A or B with inhibitors; other factor deficiencies (V, VII, X, XIII, prothrombin, fibrinogen); deficiency of α2-plasmin inhibitor; deficiency of plasminogen activator inhibitor 1; multiple factor deficiency; functional factor abnormalities (e.g., dysprothrombinemia); joint hemorrhage (hemarthrosis), including, but not limited to, ankle, elbow and knee; spontaneous bleeding in other locations (muscle, gastrointestinal, mouth, etc.); hemorrhagic stroke; intracranial hemorrhage; lacerations and other hemorrhage associated with trauma; acute traumatic coagulopathy; coagulopathy associated with cancer (e.g., acute promyelocytic leukemia); von Willebrand's Disease; disseminated intravascular coagulation; liver disease; menorrhagia; thrombocytopenia and hemorrhage associated with the use of anticoagulants (e.g., vitamin K antagonists, FXa antagonists, etc.).

The pharmaceutical compositions may be administered by numerous routes of administration. Preferably, the compositions are administered intravenously (IV). Most preferably, the compositions are administered subcutaneously (SC or SQ).

The pharmaceutical compositions may be administered using various treatment regimens. For example, the compositions may be administered as a maintenance therapy at a defined dose for a defined period of time, such as when a patient is not suffering from a bleeding episode. Alternatively, the compositions may be administered on demand, i.e., as needed, such as when a patient is suffering from a bleeding episode. In a further alternative embodiment, the compositions may be administered as a combination of maintenance therapy and on demand therapy. In such an embodiment, the compositions may be administered as a maintenance therapy at a defined dose for a defined period of time until a bleed occurs, in which case the dosage of the compositions would be increased on an as needed basis until the bleeding stopped, at which point the dosage of the compositions would be decreased back to the prior maintenance level. In another such embodiment, the compositions may be administered as a maintenance therapy at a defined dose for a defined period of time until a bleed occurs, in which case another bleeding disorder therapy would be administered to the patient (such as Factor VIII) until the bleeding stopped, at which point the other bleeding disorder therapy would be discontinued. During this entire time, the compositions would continue to be administered as a maintenance therapy. In yet another such embodiment, the compositions may be administered as a maintenance therapy at a defined dose for a defined period of time until a bleed occurs, in which case the dosage of the compositions would be decreased and another bleeding disorder therapy would be administered to the patient (such as Factor VIII) until the bleeding stopped, at which point the dosage of the compositions would be increased back to the prior maintenance level and the other bleeding disorder therapy would be discontinued. In another such embodiment, another bleeding disorder therapy (such as Factor VIII) may be administered as a maintenance therapy at a defined dose for a defined period of time until a bleed occurs, in which case the compositions would be administered to the patient until the bleeding stopped, at which point therapy with the compositions would be discontinued. During this entire time, the other bleeding disorder therapy would continue to be administered as a maintenance therapy. In yet another such embodiment, another bleeding disorder therapy (such as Factor VIII) may be administered as a maintenance therapy at a defined dose for a defined period of time until a bleed occurs, in which case the dosage of the other bleeding disorder therapy would be decreased and the compositions would be administered to the patient until the bleeding stopped, at which point the dosage of the other bleeding disorder therapy would be increased back to the prior maintenance level and therapy with the compositions would be discontinued.

The pharmaceutical compositions may also be administered prior to, during and/or after a medical procedure. For example, the pharmaceutical compositions may be administered in conjunction (before, during and/or after) with medical procedures, such as: prophylaxis and/or treatment associated with bleeding caused by dental procedures, orthopedic surgery including but not limited to arthroplasty (e.g., hip replacement), surgical or radionuclide synovectomy (RSV), major surgery, venipuncture, transfusion and amputation.

The pharmaceutical compositions may also be administered in combination with another drug, such as: activated prothrombin complex concentrates (APCC), Factor Eight Inhibitor Bypass Agent (FEIBA®), recombinant Factor VIIa (e.g., NovoSeven®), recombinant Factor VIII (Advate®, Kogenate®, Recombinate®, Helixate®, ReFacto®), plasma-derived Factor VIII (Humate P®, Hemofil M®, recombinant Factor IX)(BeneFIX®, plasma-derived Factor IX (Bebulin VH®, Konyne®, Mononine®), cryoprecipitate, desmopressin acetate (DDAVP), epsilon-aminocaproic acid or tranexamic acid. Alternatively, the pharmaceutical compositions may be administered in combination with another therapy, such as: blood or blood-product transfusion, plasmapheresis, immune tolerance induction therapy with high doses of replacement factor, immune tolerance therapy with immunosuppressive agents (e.g., prednisone, rituximab) or pain therapy.

The TFPI aptamers may be used for identification of the TFPI protein. Specifically, the TFPI aptamers may be used to identify, quantify or otherwise detect the presence of the TFPI protein in a sample, such as a biological sample or other subject-derived sample. For example, the TFPI aptamers may be used in in vitro assays, e.g., ELISA, to detect TFPI levels in a patient sample.

The invention also provides a method for regulating TFPI in which a molecule binds or otherwise interacts with one or more portions of TFPI, wherein at least one portion is outside of the K1 and K2 domains of TFPI, such as the K3/C terminal region. The molecule can be any type of molecule, such as, for example, a small molecule organic compound, an antibody, a protein or peptide, a polysaccharide, a nucleic acid, an siRNA, an aptamer, or any combination thereof. Preferably, the molecule is a small molecule organic compound. More preferably, the molecule is an antibody. Most preferably, the molecule is an aptamer. For example, the molecule may bind to or otherwise interact with a linear portion or a conformational portion of TFPI. A molecule binds to or otherwise interacts with a linear portion of TFPI when the molecule binds to or otherwise interacts with a contiguous stretch of amino acid residues that are linked by peptide bonds. A molecule binds to or otherwise interacts with a conformational portion of TFPI when the molecule binds to or otherwise interacts with non-contiguous amino acid residues that are brought together by folding or other aspects of the secondary and/or tertiary structure of the polypeptide chain. Preferably, the molecule binds at least in part to one or more portions of mature TFPI (for example, FIG. 3A) that are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The molecule preferably comprises a dissociation constant for human TFPI, or a variant thereof, of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

The invention further provides for the use of a TFPI aptamer in the manufacture of a medicament in the treatment, prevention, delaying progression, and/or amelioration of a bleeding disorder. For example, ARC26835, ARC17480, ARC19498, ARC19499, ARC19500, ARC19501, ARC31301, ARC18546, ARC19881 and ARC19882 are used in the manufacture of a medicament for treating, preventing, delaying progression of or otherwise ameliorating a bleeding disorder.

In one embodiment, the invention provides a TFPI aptamer for use in a method of treatment, prevention, delaying progression and/or amelioration of a bleeding disorder.

In one embodiment, the invention provides for the use of a TFPI aptamer in the manufacture of a diagnostic composition or product for use in a method of diagnosis practiced on the human or animal body. In some embodiments, the method of diagnosis is for the diagnosis of a bleeding disorder.

In one embodiment, the invention provides a TFPI aptamer for use in a method of diagnosis practiced on the human or animal body. In some embodiments, the method of diagnosis is for the diagnosis of a bleeding disorder.

In one embodiment, the invention provides the use of a TFPI aptamer for diagnosis in vitro. In some embodiments, the in vitro use is for the diagnosis of a bleeding disorder.

The invention further relates to agents that reverse the effects of the TFPI aptamers, referred to herein as "TFPI reversal agents". The TFPI reversal agent can be any type of molecule, such as a protein, antibody, small molecule organic compound or an oligonucleotide. Preferably, a TFPI reversal agent is an oligonucleotide that is 10-15 nucleotides in length. Preferably, a TFPI reversal agent binds to a TFPI aptamer. Preferably, such binding is via complementary base pairing. Without wishing to be bound by theory, a TFPI reversal agent acts by hybridizing to a TFPI aptamer, thereby disrupting the TFPI aptamer's structure and preventing the binding of the TFPI aptamer to TFPI.

Examples of TFPI reversal agents include, but are not limited to: SEQ ID NO: 15, which is ARC23085; SEQ ID NO: 16, which is ARC23087; SEQ ID NO: 17, which is ARC23088; and SEQ ID NO: 18, which is ARC23089.

Preferably, the TFPI reversal agent is a nucleic acid comprising the structure set forth below: mA-mG-mC-mC-mA-mA-mG-mU-mA-mU-mA-mU-mU-mC-mC (SEQ ID NO: 15), wherein "mN" is a 2'-O Methyl containing residue (which is also known in the art as a 2'-OMe, 2'-methoxy or 2'-OCH$_3$ containing residue).

Alternatively, the TFPI reversal agent is a nucleic acid comprising the structure set forth below: mU-mA-mU-mA-mU-mA-mC-mG-mC-mA-mC-mC-mU-mA-mA (SEQ ID NO: 16), wherein "mN" is a 2'-O Methyl containing residue.

Alternatively, the TFPI reversal agent is a nucleic acid comprising the structure set forth below: mC-mU-mA-mA-mC-mG-mA-mG-mC-mC (SEQ ID NO: 17), wherein "mN" is a 2'-O Methyl containing residue.

Alternatively, the TFPI reversal agent is a nucleic acid comprising the structure set forth below: mC-mA-mC-mC-mU-mA-mA-mC-mG-mA-mG-mC-mC-mA-mA (SEQ ID NO: 18), wherein "mN" is a 2'-O Methyl containing residue.

The invention further provides a method for treating, preventing, delaying the progression of and/or ameliorating a bleeding disorder, the method comprising the step of administering a TFPI reversal agent to a patient in need of such treatment.

The invention provides for the use of a TFPI reversal agent in the manufacture of a medicament for the treatment, prevention, delaying progression and/or amelioration of a bleeding disorder.

Accordingly, the invention provides for the use of a TFPI reversal agent in the manufacture of a medicament for the treatment, prevention, delaying progression and/or amelioration of a bleeding disorder in a patient wherein the method involves administering the TFPI reversal agent to the patient to control and/or modulate the therapeutic effect of a TFPI aptamer administered to the patient. The TFPI aptamer may be administered prior to the TFPI reversal agent, simultaneously with the TFPI reversal agent or after the TFPI reversal agent, and may be administered as part of a combination therapy. Preferably, the TFPI aptamer is administered to the patient in order to treat, prevent, delay progression of and/or ameliorate a bleeding disorder in the patient.

The invention also provides the use of a TFPI reversal agent in the manufacture of a medicament for use in controlling and/or modulating the treatment of a bleeding disorder, wherein the bleeding disorder is being treated with a TFPI aptamer.

In one embodiment, the invention provides a TFPI reversal agent for use in the treatment, prevention, delaying progression and/or amelioration of a bleeding disorder.

Accordingly, the invention provides a TFPI reversal agent for use in the treatment, prevention, delaying progression and/or amelioration of a bleeding disorder in a patient wherein the method involves administering the TFPI reversal agent to the patient to control and/or modulate the therapeutic effect of a TFPI aptamer administered to the patient.

The invention also provides a TFPI reversal agent for use in the treatment, prevention, delaying progression and/or amelioration of a bleeding disorder, wherein the bleeding disorder is being treated with a TFPI aptamer.

In one embodiment, the invention provides for the use of a TFPI reversal agent in the manufacture of a diagnostic composition or product for use in a method of diagnosis practiced on the human or animal body. In some embodiments, the method of diagnosis is for the diagnosis of a bleeding disorder.

In one embodiment, the invention provides a TFPI reversal agent for use in a method of diagnosis practiced on the human or animal body. In some embodiments, the method of diagnosis is for the diagnosis of a bleeding disorder.

In one embodiment, the invention provides the use of a TFPI reversal agent for diagnosis in vitro. In some embodiments, the in vitro use is for the diagnosis of a bleeding disorder.

The invention also provides a kit comprising at least one container comprising a quantity of one or more TFPI aptamers, along with instructions for using the one or more TFPI aptamers in the treatment, prevention, delaying progression and/or amelioration of a bleeding disorder. For example, the kit includes ARC26835, ARC17480, ARC19498, ARC19499, ARC19500, ARC19501, ARC31301, ARC18546, ARC19881 or ARC19882 and combinations thereof. In some embodiments, the aptamers are formulated as a pharmaceutical composition. The kit may further comprise a TFPI reversal agent, along with instructions regarding administration of the reversal agent.

The invention also provides a method for producing an aptamer that binds to TFPI, the method comprising the step of chemically synthesizing a nucleic acid having a nucleic acid sequence of an aptamer that binds to TFPI as described herein. The method may further comprise the step of formulating a pharmaceutical composition by mixing the synthesized nucleic acid sequence, or a salt thereof, with a pharmaceutically acceptable carrier or diluent.

The invention additionally provides a method for producing a reversal agent, the method comprising the step of chemically synthesizing a nucleic acid having a nucleic acid sequence of a TFPI reversal agent as described herein. The method may further comprise the step of formulating a pharmaceutical composition by mixing the synthesized nucleic acid sequence or a salt thereof, with a pharmaceutically acceptable carrier or diluent.

The invention further provides aptamers that have been identified by the SELEX™ process, which comprises the steps of (a) contacting a mixture of nucleic acids with TFPI under conditions in which binding occurs; (b) partitioning unbound nucleic acids from those nucleic acids that have bound to TFPI; (c) amplifying the bound nucleic acids to yield a ligand-enriched mixture of nucleic acids; and, optionally, (d) reiterating the steps of binding, partitioning and amplifying through as many cycles as desired to obtain aptamer(s) that bind to TFPI.

The invention further provides methods for identifying aptamers that bind at least in part to or otherwise interact with one or more portions of TFPI, which comprise the steps of (a) contacting a mixture of nucleic acids with one or more portions of TFPI under conditions in which binding occurs; (b) partitioning unbound nucleic acids from those nucleic acids that have bound to TFPI; (c) amplifying the bound nucleic acids to yield a ligand-enriched mixture of nucleic acids; and, optionally, (d) reiterating the steps of contacting, partitioning and amplifying through as many cycles as desired, to obtain aptamer(s) that bind to a portion of TFPI. This method may also include intervening or additional cycles with binding to full-length TFPI, followed by partitioning and amplification. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. Preferably, the one or more portions of mature TFPI (for example, FIG. 3A) are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The aptamer preferably comprises a dissociation constant for human TFPI or a variant or one or more portions thereof, of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

The invention also provides methods for identifying aptamers that bind at least in part to or otherwise interact with one or more portions of TFPI, which comprise the steps of (a) contacting a mixture of nucleic acids with full-length TFPI or one or more portions of TFPI under conditions in which binding occurs; (b) partitioning unbound nucleic acids from those nucleic acids that have bound to full-length TFPI or one or more portions of TFPI; (c) specifically eluting the bound nucleic acids with a portion of TFPI, or a ligand that binds to full-length TFPI or a portion of TFPI; (d) amplifying the bound nucleic acids to yield a ligand-enriched mixture of nucleic acids; and, optionally, (e) reiterating the steps of contacting, partitioning, eluting and amplifying through as many cycles as desired to obtain aptamer(s) that bind to one or more portions of TFPI. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. Preferably, the one or more portions of mature TFPI (for example, FIG. 3A) are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The aptamer preferably comprises a dissociation constant for human TFPI or a variant or one or more portions thereof of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

The invention further provides methods for identifying aptamers that bind at least in part to or otherwise interact with one or more portions of TFPI, which comprise the steps of (a) contacting a mixture of nucleic acids with full-length TFPI or one or more portions of TFPI under conditions in which binding occurs in the presence of a TFPI ligand (a ligand that binds to TFPI) that blocks one or more epitopes on TFPI from aptamer binding; (b) partitioning unbound nucleic acids from those nucleic acids that have bound to full-length TFPI or one or more portions of TFPI; (c) amplifying the bound nucleic acids to yield a ligand-enriched mixture of nucleic acids; and, optionally, (d) reiterating the steps of contacting, partitioning and amplifying through as many cycles as desired to obtain aptamer(s) that bind to one or more portions of TFPI. In other embodiments of this method, inclusion of a TFPI ligand that blocks one or more portions on TFPI from aptamer binding can occur during the contacting step, the partitioning step, or both. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. Preferably, the one or more portions of mature TFPI (for example, FIG. 3A) are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The aptamer preferably comprises a dissociation constant for human TFPI or a variant or one or more portions thereof of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

The invention further provides methods for identifying aptamers that bind at least in part to or otherwise interact with one or more portions of TFPI, which comprise the steps of (a) contacting a mixture of nucleic acids with full-length TFPI or one or more portions of TFPI under conditions in which binding occurs; (b) partitioning unbound nucleic acids from those nucleic acids that have bound to full-length TFPI or one or more portions of TFPI; (c) partitioning bound nucleic acids that have a desired functional property from bound nucleic acids that do not have a desired functional property; (d) amplifying the bound nucleic acids that have a desired functional property to yield a ligand-enriched mixture of nucleic acids; and, optionally, (e) reiterating the steps of contacting, partitioning, partitioning and amplifying through as many cycles as desired to obtain aptamer(s) that bind to one or more portions of TFPI. Steps (b) and (c) can occur sequentially or simultaneously. Preferably, the desired functional property is inhibition of TFPI's interaction with FXa, FVIIa, TFPI receptor or the glycocalyx. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. Preferably, the one or more portions of mature TFPI (for example, FIG. 3A) are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The aptamer preferably comprises a dissociation constant for human TFPI or a variant or one or more portions thereof of less than 100 μM, less than 1 μM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

The invention also provides an aptamer that binds to a human tissue factor pathway inhibitor (TFPI) polypeptide having the amino acid sequence of SEQ ID NO: 11, wherein the aptamer modulates TFPI-mediated inhibition of blood coagulation, and wherein the aptamer competes for binding to TFPI with a reference aptamer comprising a nucleic acid sequence selected from the group consisting of: SEQ ID NO: 4 (ARC19499), SEQ ID NO: 1 (ARC26835), SEQ ID NO: 2 (ARC17480), SEQ ID NO: 3 (ARC19498), SEQ ID NO: 5 (ARC19500), SEQ ID NO:6 (ARC19501), SEQ ID NO: 7 (ARC31301), SEQ ID NO: 8 (ARC18546), SEQ ID NO: 9 (ARC19881) and SEQ ID NO: 10 (ARC19882). Preferably, the reference aptamer comprises the nucleic acid sequence of SEQ ID NO: 4 (ARC 19499).

The invention further provides an aptamer that binds to a human tissue factor pathway inhibitor (TFPI) polypeptide having the amino acid sequence of SEQ ID NO: 11, wherein the aptamer binds to a linear portion or a conformational portion of TFPI in which at least a portion of the region recognized by the aptamer is different than the TFPI region bound by Factor VIIa, Factor Xa, or both Factor VIIa and Factor Xa. Preferably, the aptamer binds to one or more regions comprising at least a portion of the amino acid sequence of SEQ ID NO: 11 selected from the group consisting of: amino acid residues 148-170, amino acid residues 150-170, amino acid residues 155-175, amino acid residues 160-180, amino acid residues 165-185, amino acid residues 170-190, amino acid residues 175-195, amino acid residues 180-200, amino acid residues 185-205, amino acid residues 190-210, amino acid residues 195-215, amino acid residues 200-220, amino acid residues 205-225, amino acid residues 210-230, amino acid residues 215-235, amino acid residues 220-240, amino acid residues 225-245, amino acid residues 230-250, amino acid residues 235-255, amino acid residues 240-260, amino acid residues 245-265, amino acid residues 250-270, amino acid residues 255-275, amino acid residues 260-276, amino acid residues 148-175, amino acid residues 150-175, amino acid residues 150-180, amino acid residues 150-185, amino acid residues 150-190, amino acid residues 150-195, amino acid residues 150-200, amino acid residues 150-205, amino acid residues 150-210, amino acid residues 150-215, amino acid residues 150-220, amino acid residues 150-225, amino acid residues 150-230, amino acid residues 150-235, amino acid residues 150-240, amino acid residues 150-245, amino acid residues 150-250, amino acid residues 150-255, amino acid residues 150-260, amino acid residues 150-265, amino acid residues 150-270, amino acid residues 150-275, amino acid residues 150-276, amino acid residues 190-240, amino acid residues 190-276, amino acid residues 240-276, amino acid residues 242-276, amino acid residues 161-181, amino acid residues 162-181, amino acid residues 182-240, amino acid residues 182-241, and amino acid residues 182-276. More preferably, the aptamer competes with a reference aptamer comprising the nucleic acid sequence of SEQ ID NO: 4 (ARC 19499) for binding to TFPI.

The invention also provides an aptamer that binds to the same region on a human tissue factor pathway inhibitor (TFPI) polypeptide having the amino acid sequence of SEQ ID NO: 11 as the region bound by a TFPI aptamer comprising the nucleic acid sequence of SEQ ID NO: 4 (ARC19499).

The invention further provides an aptamer that binds to a region on a human tissue factor pathway inhibitor (TFPI) polypeptide comprising one or more portions of SEQ ID NO: 11, wherein the one or more portions is selected from the group consisting of: amino acid residues 148-170, amino acid residues 150-170, amino acid residues 155-175, amino acid residues 160-180, amino acid residues 165-185, amino acid residues 170-190, amino acid residues 175-195, amino acid residues 180-200, amino acid residues 185-205, amino acid residues 190-210, amino acid residues 195-215, amino acid residues 200-220, amino acid residues 205-225, amino acid residues 210-230, amino acid residues 215-235, amino acid residues 220-240, amino acid residues 225-245, amino acid residues 230-250, amino acid residues 235-255, amino acid residues 240-260, amino acid residues 245-265, amino acid residues 250-270, amino acid residues 255-275, amino acid residues 260-276, amino acid residues 148-175, amino acid residues 150-175, amino acid residues 150-180, amino acid residues 150-185, amino acid residues 150-190, amino acid residues 150-195, amino acid residues 150-200, amino acid residues 150-205, amino acid residues 150-210, amino acid residues 150-215, amino acid residues 150-220, amino acid residues 150-225, amino acid residues 150-230, amino acid residues 150-235, amino acid residues 150-240, amino acid residues 150-245, amino acid residues 150-250, amino acid residues 150-255, amino acid residues 150-260, amino acid residues 150-265, amino acid residues 150-270, amino acid residues 150-275, amino acid residues 150-276, amino acid residues 190-240, amino acid residues 190-276, amino acid residues 240-276, amino acid residues 242-276, amino acid residues 161-181, amino acid residues 162-181, amino acid residues 182-240, amino acid residues 182-241, and amino acid residues 182-276.

The invention additionally provides an aptamer that binds to human tissue factor pathway inhibitor (TFPI) and exhibits one or more of the following properties: a) competes for binding to TFPI with any one of SEQ ID NOs: 1-10; b) inhibits TFPI inhibition of Factor Xa; c) increases thrombin generation in hemophilia plasma; d) inhibits TFPI inhibition of the intrinsic tenase complex; e) restores normal hemostasis, as measured by thromboelastography (TEG®) in whole blood and plasma; f) restores normal clotting, as indicated by shorter clot time, more rapid clot formation or more stable clot development, as measured by thromboelastography (TEG®) or rotational thromboelastometry (ROTEM) in whole blood and plasma; or g) decreases the clot time, as measured by dilute prothrombin time (dPT), tissue factor activated clotting time (TF-ACT) or any other TFPI-sensitive clot-time measurement.

The invention also provides an aptamer that binds to human tissue factor pathway inhibitor wherein the aptamer competes for binding to TFPI with a reference aptamer selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

The invention further provides an aptamer that binds to tissue factor pathway inhibitor (TFPI) wherein the aptamer competes, either directly or indirectly, for binding to TFPI with a reference antibody selected from the group consisting of: AD4903.

The invention also provides an aptamer that binds to human tissue factor pathway inhibitor (TFPI) and comprises a stem and loop motif having the nucleotide sequence of SEQ ID NO: 4, wherein: a) any one or more of nucleotides 1, 2, 3, 4, 6, 8, 11, 12, 13, 17, 20, 21, 22, 24, 28, 30 and 32 may be modified from a 2'-OMe substitution to a 2'-deoxy substitution; b) any one or more of nucleotides 5, 7, 15, 19, 23, 27, 29 and 31 may be modified from a 2'-OMe uracil to either a 2'-deoxy uracil or a 2'-deoxy thymine; c) nucleotide 18 may be modified from a 2'-OMe uracil to a 2'-deoxy uracil; and/or d) any one or more of nucleotides 14, 16 and 25 may be modified from a 2'-deoxy cytosine to either a 2'-OMe cytosine or a 2'-fluoro cytosine.

The invention additionally provides an aptamer that binds to human tissue factor pathway inhibitor (TFPI) and comprises nucleotides 7-28 of SEQ ID NO: 2.

The invention further provides a method for treating a bleeding disorder comprising administering any one of the above aptamers.

The invention further provides an aptamer that binds to tissue factor pathway inhibitor (TFPI), wherein the aptamer comprises a primary nucleic acid sequence selected from the group consisting of SEQ ID NOs.: 4, 1, 2, 3, 5, 6, 7, 8, 9 and 10.

BRIEF DESCRIPTION OF THE DRAWINGS

FIG. 11 is an illustration depicting various PEGylation strategies, such as standard mono-PEGylation, multiple PEGylation and oligomerization via PEGylation.

FIG. 14 is a set of graphs showing binding experiments with ARC17480 and various proteins, including coagulation factors, protease inhibitors and coagulation zymogens.

FIG. 17A depicts the results of a binding assay with radiolabeled ARC17480, full-length TFPI and TFPI-His. FIG. 17B depicts the results of a binding assay with radiolabeled ARC17480, full-length TFPI, truncated TFPI-K1K2, TFPI K3-C-terminal domain protein, and the peptide that contains the C-terminal region of TFPI in the presence of neutravidin.

FIG. 18A depicts the results of a binding assay with radiolabeled ARC17480 and full-length TFPI in the absence or presence of 0.1 mg/mL heparin. FIG. 18B depicts the results of a binding-competition assay with radiolabeled ARC17480, 12.5 nM full-length TFPI, and different concentrations of heparin and low molecular weight heparin (LMWH) as competitors.

FIG. 21 is a series of graphs showing the activity of ARC19499 in the extrinsic Xase inhibition assay.

FIG. 39 is a series of graphs showing the activity of ARC19499 in the calibrated automated thrombogram (CAT) assay in pooled normal plasma (PNP) previously treated with a neutralizing, polyclonal anti-TFPI antibody. The assay was initiated with 0.01 pM tissue factor (TF; FIG. 39D), peak thrombin (FIG. 39E) and lag time (FIG. 39F) remained largely unchanged at all ARC19499 concentrations independent of the TF concentration.

FIG. 47 is a series of graphs from thrombin generation experiments showing the effect of NovoSeven® (empty triangles) and ARC19499 (filled diamonds) on endogenous thrombin potential (ETP; FIG. 47A), peak thrombin (FIG. 47B) and lag time (FIG. 47C) in normal plasma. The solid black line designates the level of each parameter in the absence of any drug. Data represent mean±standard error, n=3.

FIG. 48 is a series of graphs from thrombin generation experiments showing the effect of NovoSeven® (empty triangles) and ARC19499 (filled diamonds) on endogenous thrombin potential (ETP; FIG. 48A), peak thrombin (FIG. 48B) and lag time (FIG. 48C) in hemophilia A plasma. The solid black line designates the level of each parameter in the absence of any drug. The dashed line designates the level of each parameter in pooled normal plasma (PNP) without any additional drug. Data represent mean±standard error, n=3.

FIG. 49 is a series of graphs from thrombin generation experiments showing the effect of NovoSeven® (empty triangles) and ARC19499 (filled diamonds) on endogenous thrombin potential (ETP; FIG. 49A), peak thrombin (FIG. 49B) and lag time (FIG. 49C) in hemophilia A inhibitor plasma. The solid black line designates the level of each parameter in the absence of any drug. The dashed line designates the level of each parameter in pooled normal plasma (PNP) without any additional drug. Data represent mean±standard error, n=3.

FIG. 50 is a series of graphs from experiments showing the effect of NovoSeven® (empty triangles) and ARC19499 (filled diamonds) on R-value (FIG. 50A), angle (FIG. 50B) and maximum amplitude (MA; FIG. 50C) in a thromboelastography (TEG®) assay in citrated whole blood from healthy volunteers. The solid black line designates the level of each parameter in the absence of any drug. Data represent mean±standard error, n=3.

FIG. 51 is a series of graphs from experiments showing the effect of NovoSeven® (empty triangles) and ARC19499 (filled diamonds) on R-value (FIG. 51A), angle (FIG. 51B) and maximum amplitude (MA; FIG. 51C) in a thromboelastography (TEG®) assay in citrated whole blood from healthy volunteers treated with an anti-FVIII antibody. The solid black line designates the level of each parameter in the absence of any drug. The dashed line designates the level of each parameter in whole blood not treated with antibody. Data represent mean±standard error, n=3.

FIG. 52 is a series of graphs from thromboelastography experiments showing the lag time (FIG. 52A), peak thrombin (FIG. 52B) and endogenous thrombin potential (ETP.

FIG. 53 is a series of graphs from thrombin generation experiments demonstrating ARC19499 activity in plasma with various concentrations of Factor VIII (FVIII).

FIG. 54 illustrates the experimental design of the spatial clotting model.

FIG. 55 shows two graphs illustrating clot propagation in the spatial clotting model, as measured by light scattering, plotted as a function of distance from the activating surface. Clotting was activated by low density tissue factor in normal pooled plasma in the absence (FIG. 55A) and in the presence (FIG. 55B) of 300 nM ARC19499.

FIG. 56 is a graph of clot size versus time, in the absence (thick black line) and the presence (thin grey line) of 300 nM ARC19499 in normal pooled plasma. The parameters that can be derived from this graph include the lag time (time until beginning of clot growth), initial velocity ($\alpha$ or $V_{initial}$; mean slope during the first 10 minutes of growth), stationary velocity ($\beta$ or $V_{stationary}$; mean slope during the next 30 minutes of growth) and clot size after 60 minutes (an integral parameter of clot formation efficiency).

FIG. 65 is a table summarizing the demographics of hemophilia A patients from which plasma samples were drawn for spatial clot formation experiments.

FIG. 81 is a series of tables showing the effects of ARC19499 on the TF-activated clotting time (TF-ACT) assay in whole blood samples from normal, severe hemophilia B and severe hemophilia A individuals.

FIG. 82 is a series of tables showing the effects of ARC19499 on the dilute prothrombin time (dPT) assay in plasma samples from normal, severe hemophilia B and severe hemophilia A individuals.

FIG. 120 shows the schedule for bleeding time assessment and related FVIII antibody and ARC19499 dosing and blood sampling in the non-human primate (NHP) bleeding model.

FIG. 121 is a series of graphs showing FVIII activity levels in plasma samples from various dosing groups of cynomolgus monkeys treated with FVIII antibody and ARC19499: Group 1, monkeys whose bleeding times were corrected with one dose of 1 mg/kg ARC19499 (FIG. 121A); Group 2, monkeys whose bleeding times were corrected with two doses of 1 mg/kg ARC19499 (FIG. 121B); Group 3, monkey whose bleeding time was corrected with three doses of 1 mg/kg ARC19499 (FIG. 121C); and Group 4, monkey whose bleeding time was not corrected with three doses of 1 mg/kg ARC19499 (FIG. 121D).

Figure 122A:
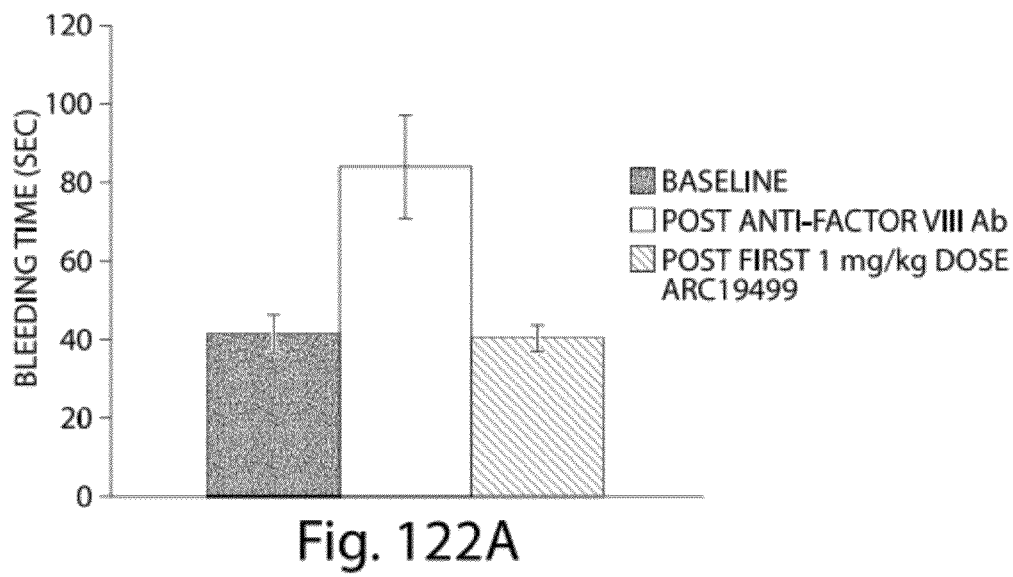
Figure 122B:
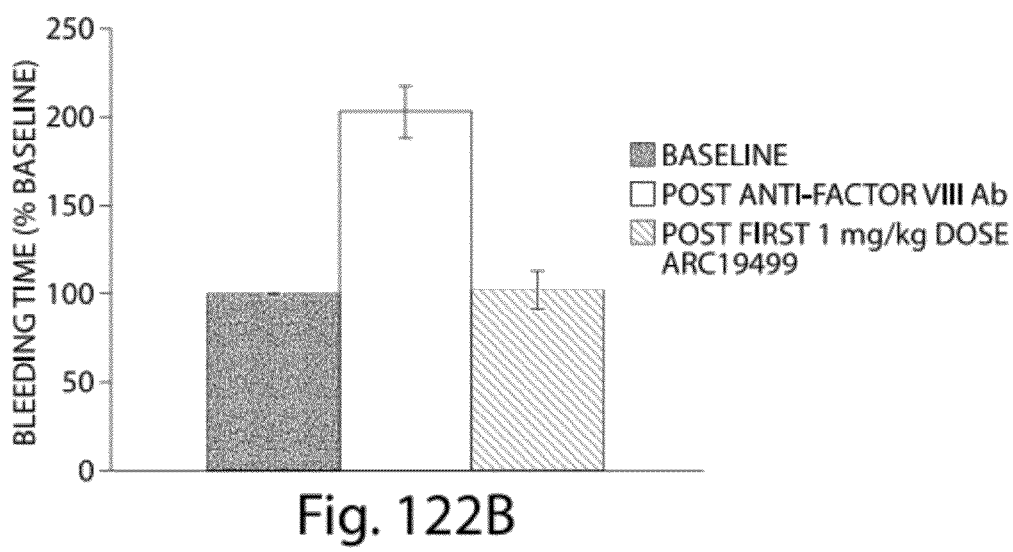

FIG. 122 shows mean group bleeding times for Group 1 monkeys in seconds (FIG. 122A) and in terms of % of baseline bleeding time (FIG. 122B).

Figure 123A:
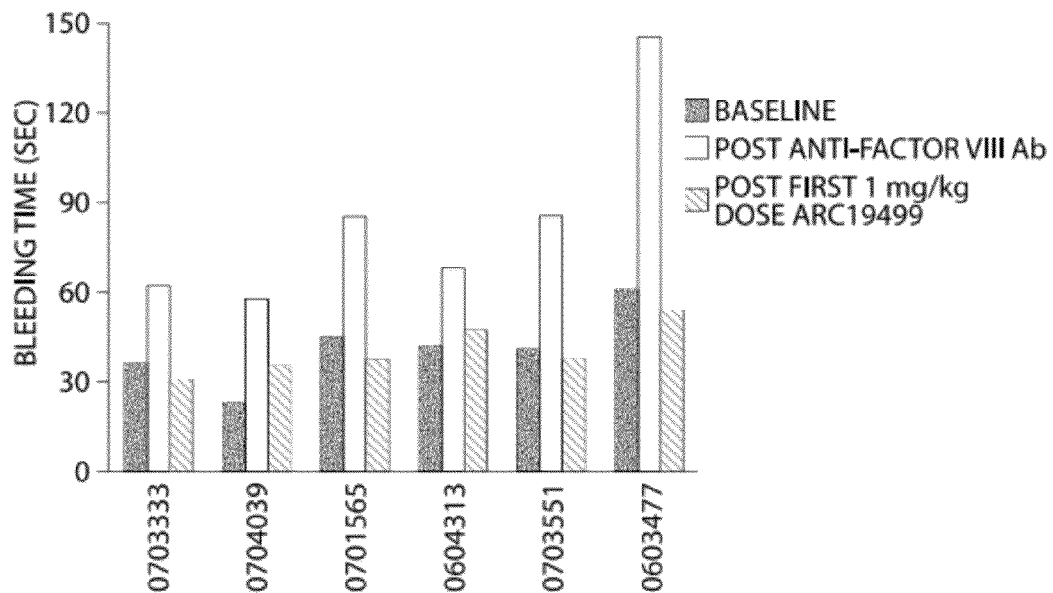
Figure 123B:
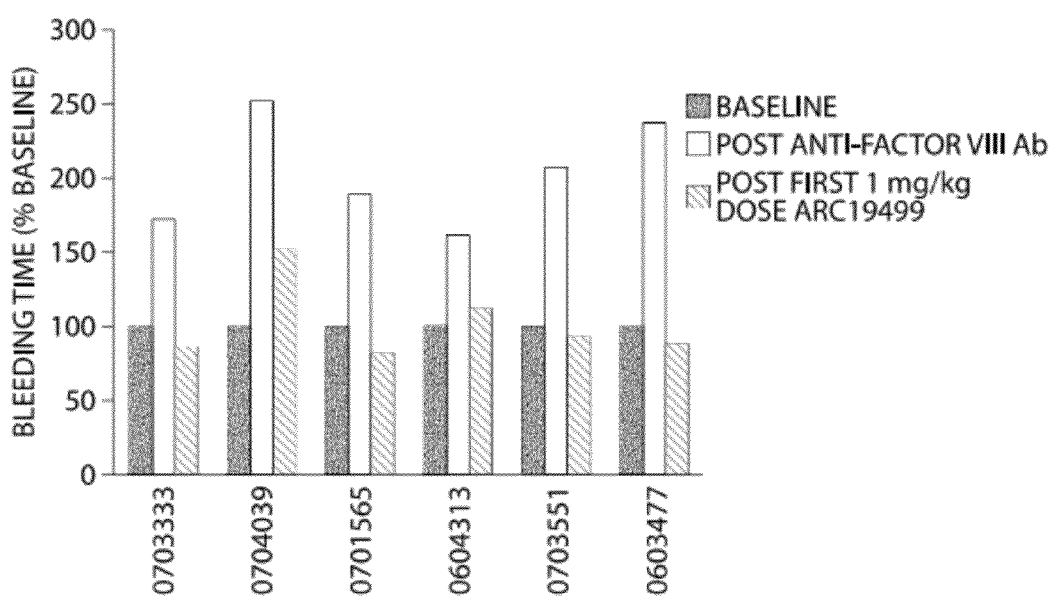

FIG. 123 shows individual bleeding times for Group 1 monkeys in seconds (FIG. 123A) and in terms of % of baseline bleeding time (FIG. 123B).

Figure 124A:
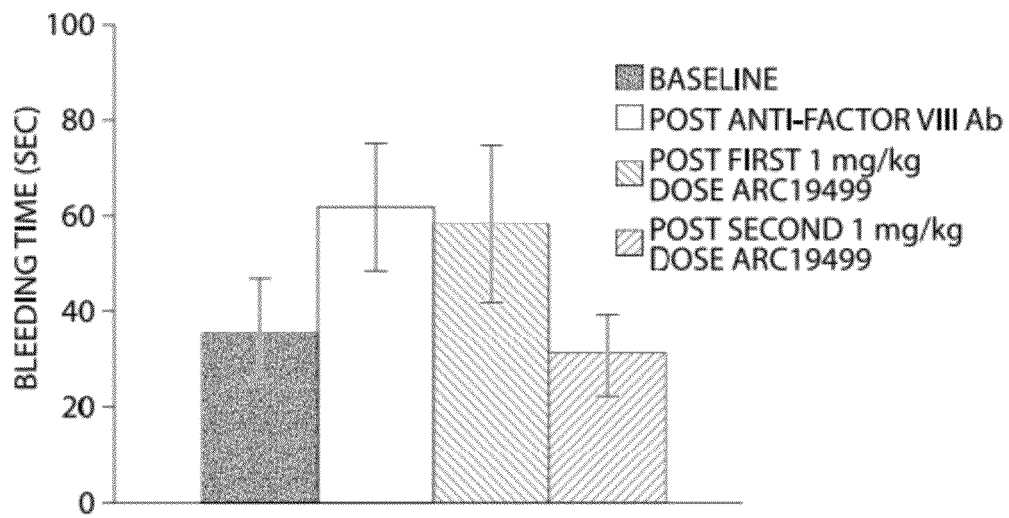
Figure 124B:
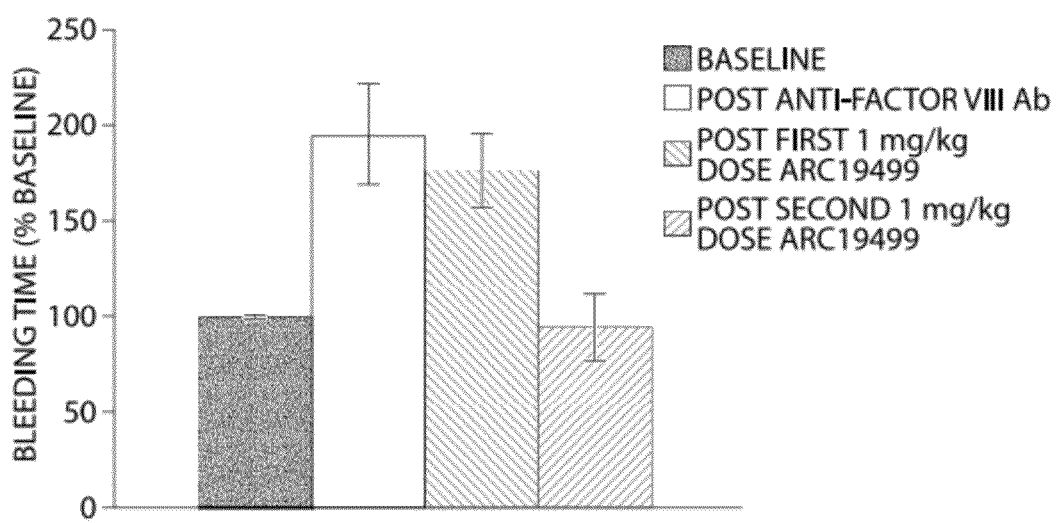

FIG. 124 shows mean group bleeding times for Group 2 monkeys in seconds (FIG. 124A) and in terms of % of baseline bleeding time (FIG. 124B).

Figure 125A:
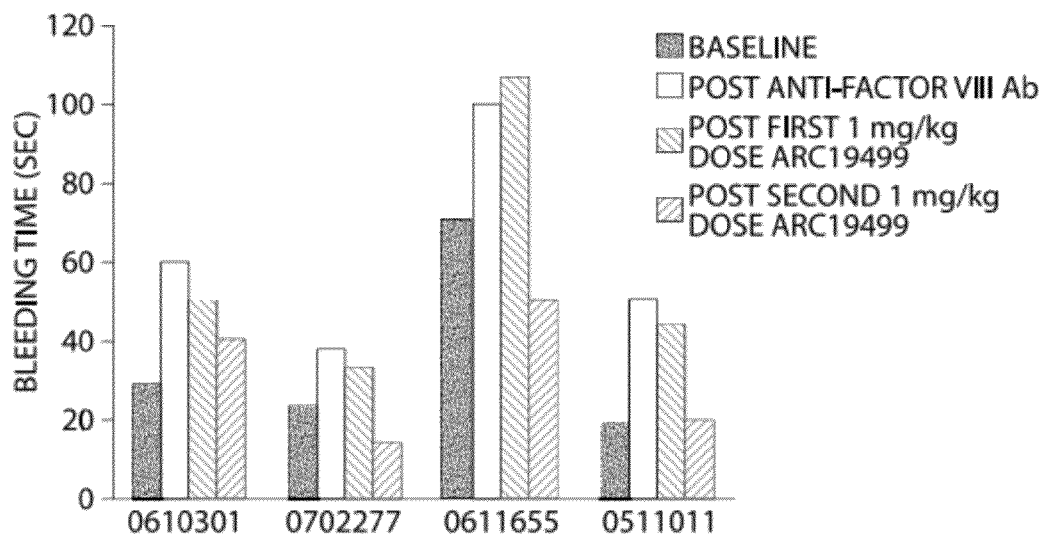
Figure 125B:
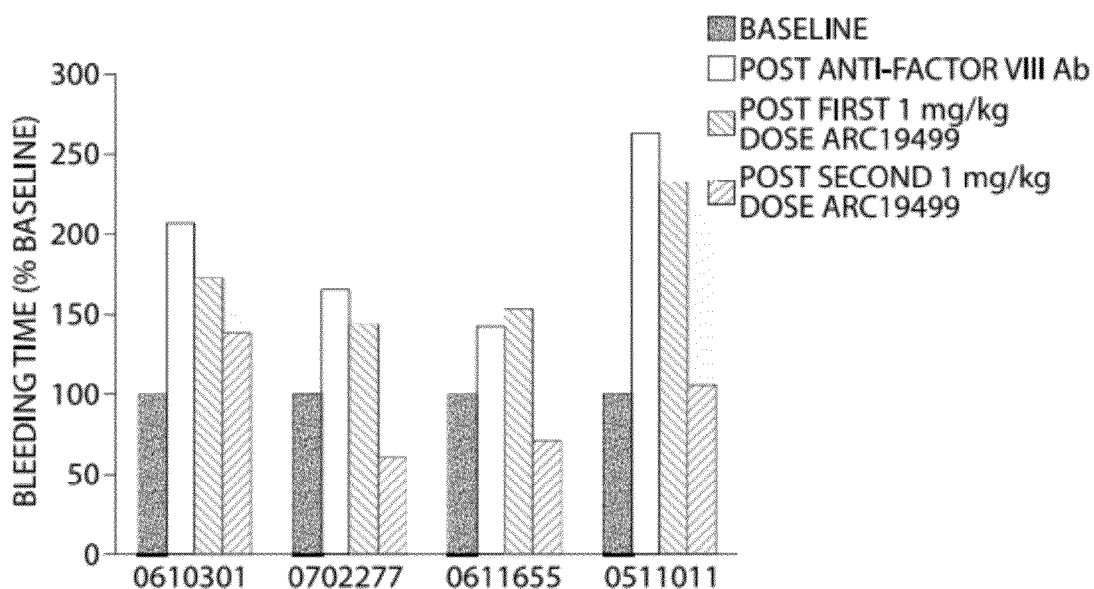

FIG. 125 shows individual bleeding times for Group 2 monkeys in seconds (FIG. 125A) and in terms of % of baseline bleeding time (FIG. 125B).

Figure 126A:
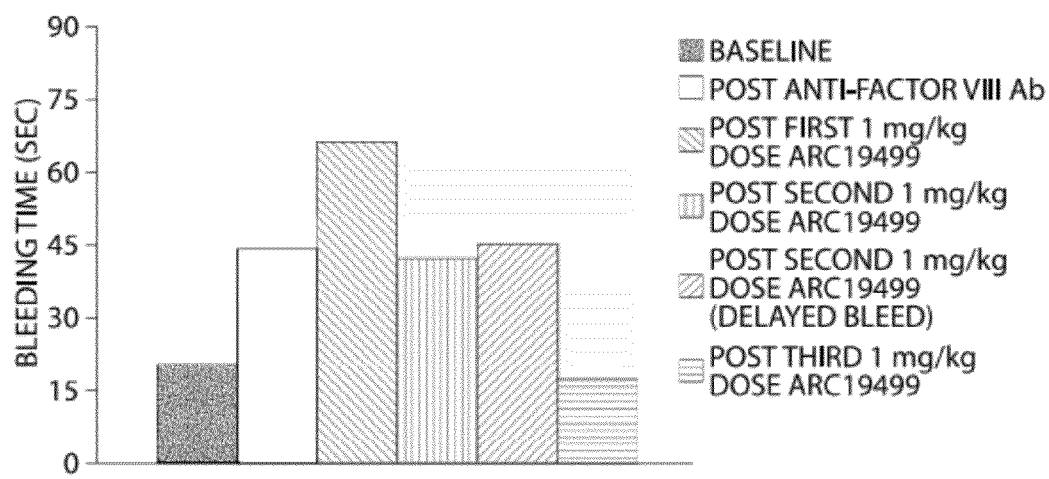
Figure 126B:
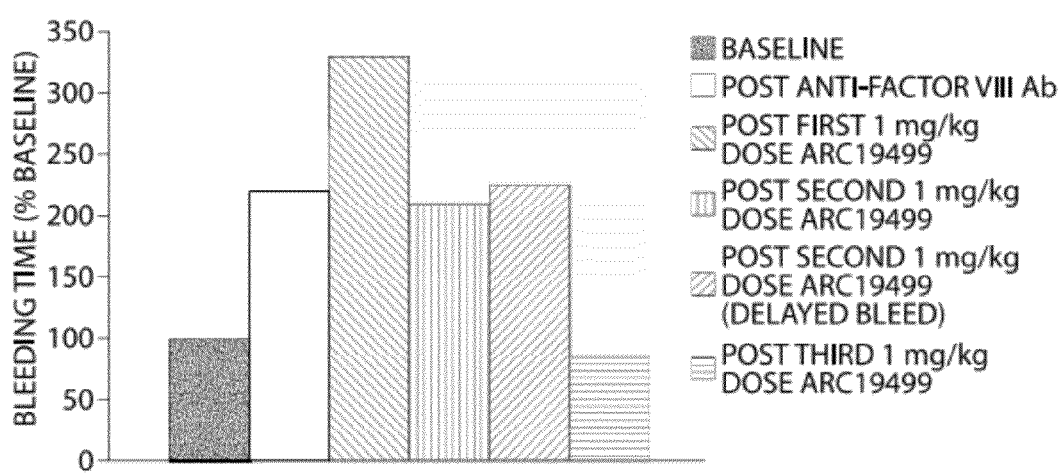

FIG. 126 shows bleeding times for the Group 3 monkey in seconds (FIG. 126A) and in terms of % of baseline bleeding time (FIG. 126B).

Figure 127A:
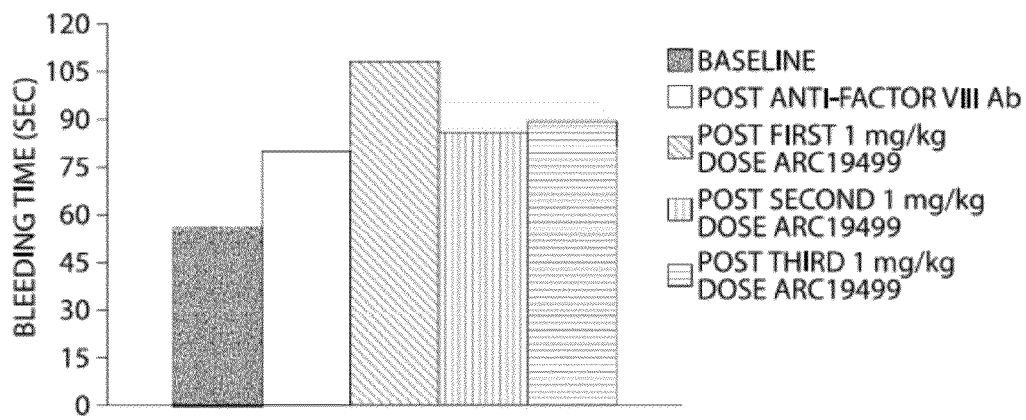
Figure 127B:
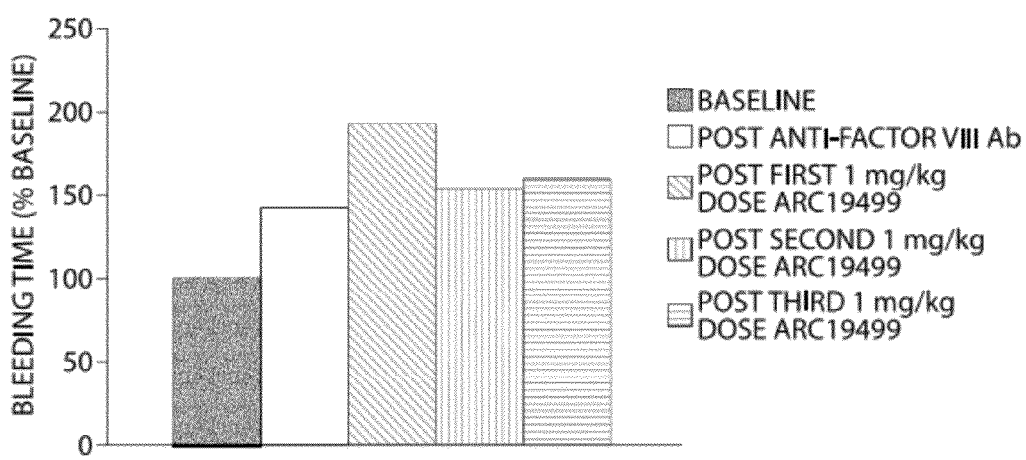

FIG. 127 shows bleeding times for the Group 4 monkey in seconds (FIG. 127A) and in terms of % of baseline bleeding time (FIG. 127B).

Figure 128:
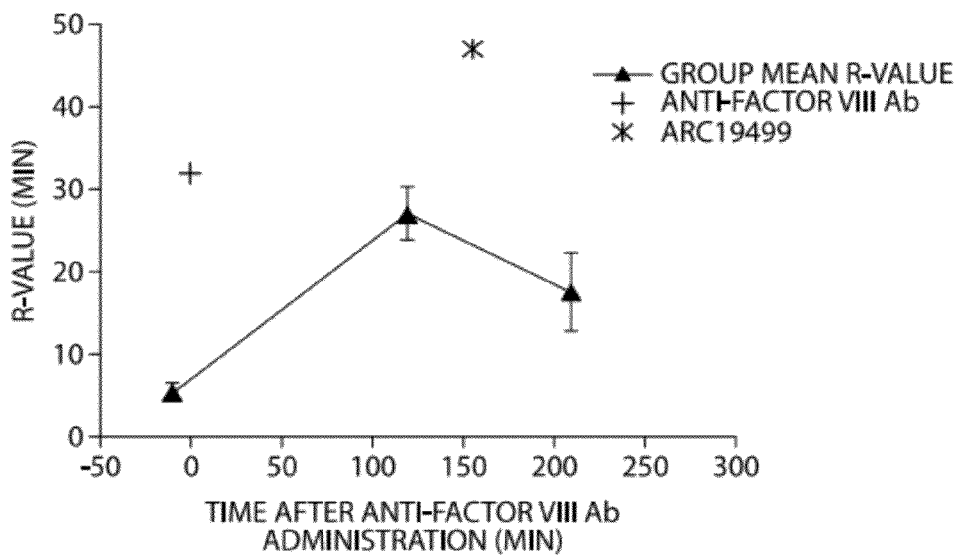

FIG. 128 is a graph of mean group whole blood thromboelastography (TEG®) R-values plotted against sampling timepoint for Group 1 monkeys. The time of anti-Factor VIII antibody dosing is indicated by a plus-sign (+) and the time of ARC19499 dosing is indicated by an asterisk (*).

Figure 129:
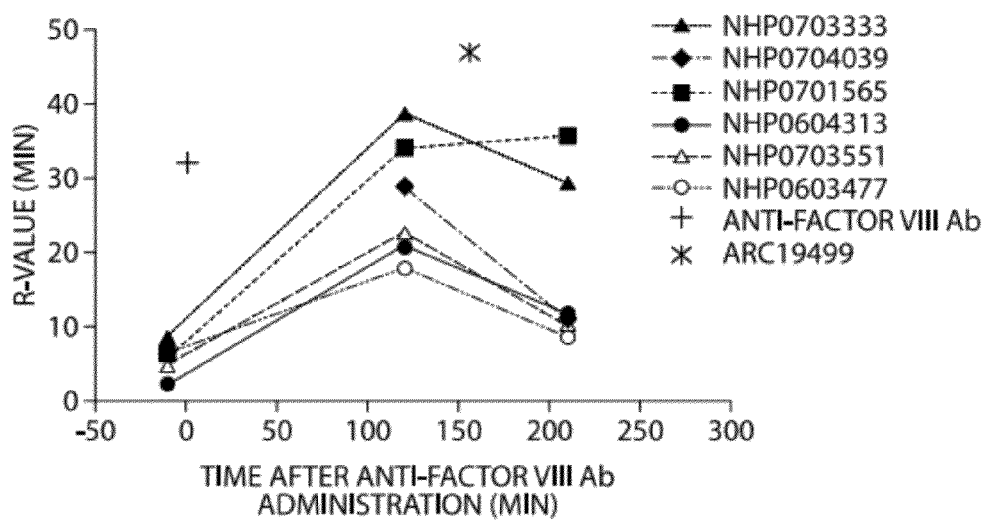

FIG. 129 is a graph of individual whole blood thromboelastography (TEG®) R-values plotted against sampling timepoint for Group 1 monkeys. The time of anti-Factor VIII antibody dosing is indicated by a plus-sign (+) and the time of ARC19499 dosing is indicated by an asterisk (*).

Figure 130:
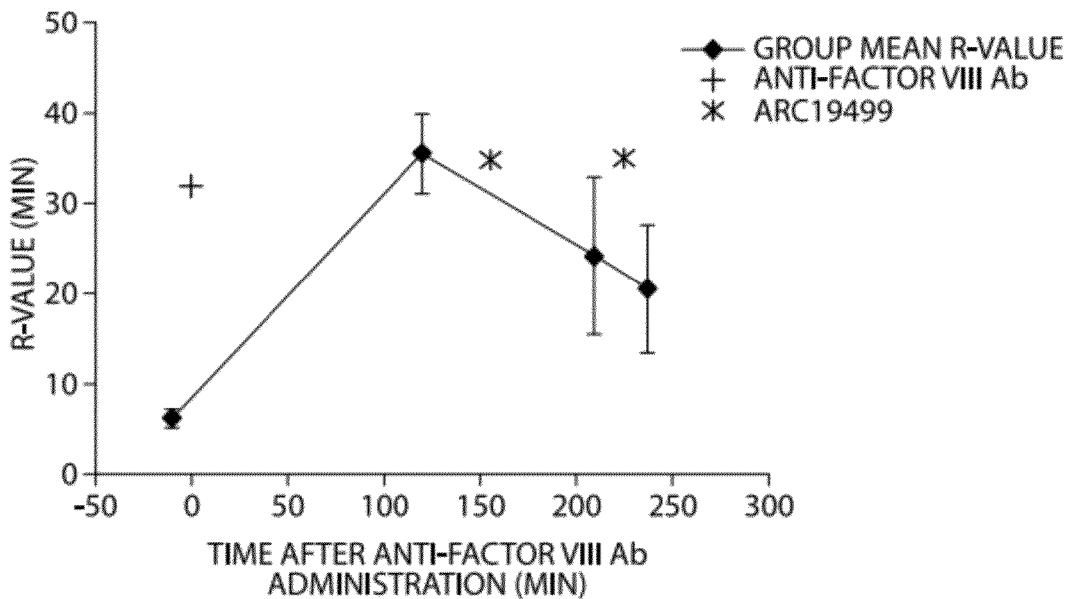

FIG. 130 is a graph of mean group whole blood thromboelastography (TEG®) R-values plotted against sampling timepoint for Group 2 monkeys. The time of anti-Factor VIII antibody dosing is indicated by a plus-sign (+) and the times of ARC19499 dosing are indicated by asterisks (*).

Figure 131:
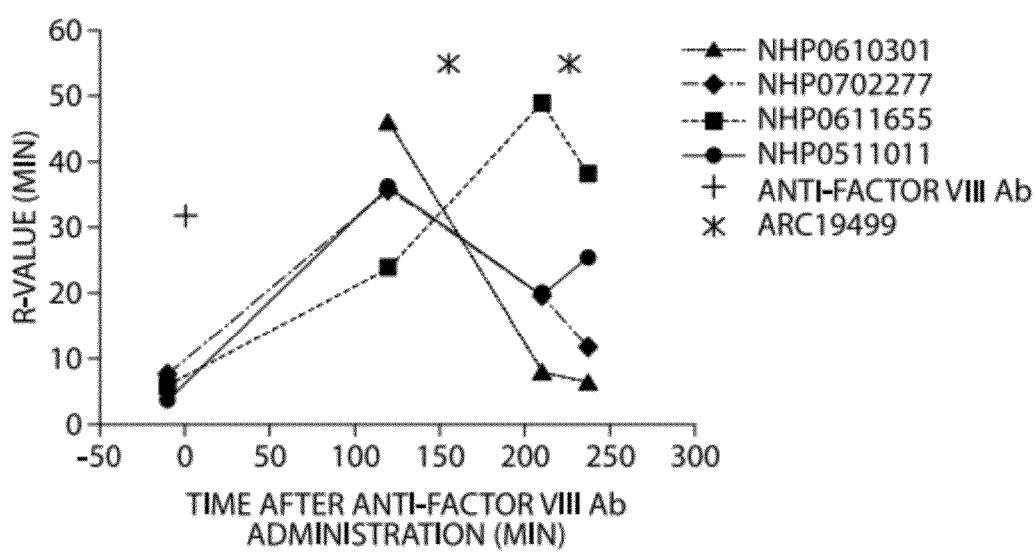

FIG. 131 is a graph of individual whole blood thromboelastography (TEG®) R-values plotted against sampling timepoint for Group 2 monkeys. The time of anti-Factor VIII antibody dosing is indicated by a plus-sign (+) and the times of ARC19499 dosing are indicated by asterisks (*).

Figure 132:
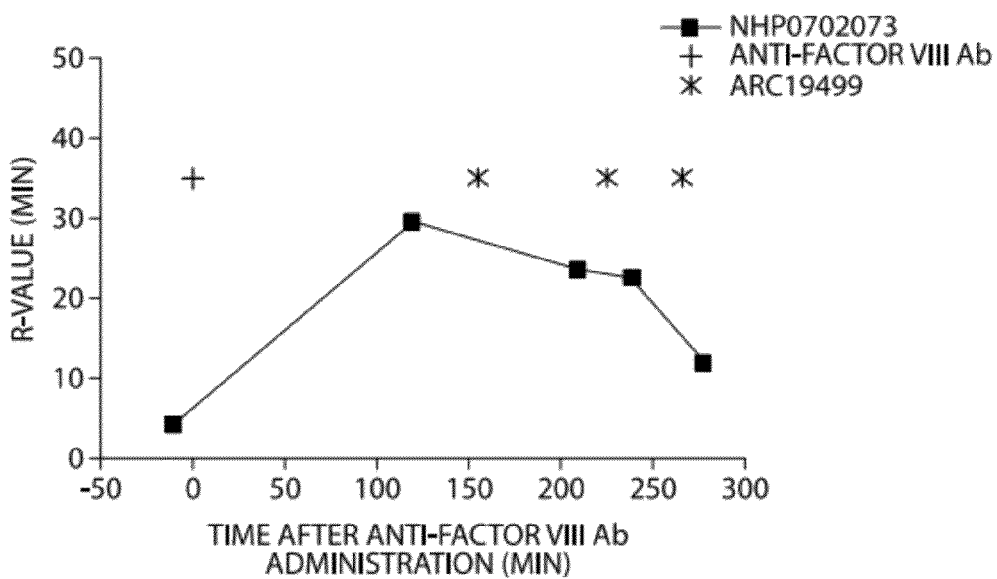

FIG. 132 is a graph of individual whole blood thromboelastography (TEG®) R-values plotted against sampling timepoint for the Group 3 monkey. The time of anti-Factor VIII antibody dosing is indicated by a plus-sign (+) and the times of ARC19499 dosing are indicated by asterisks (*).

Figure 133:
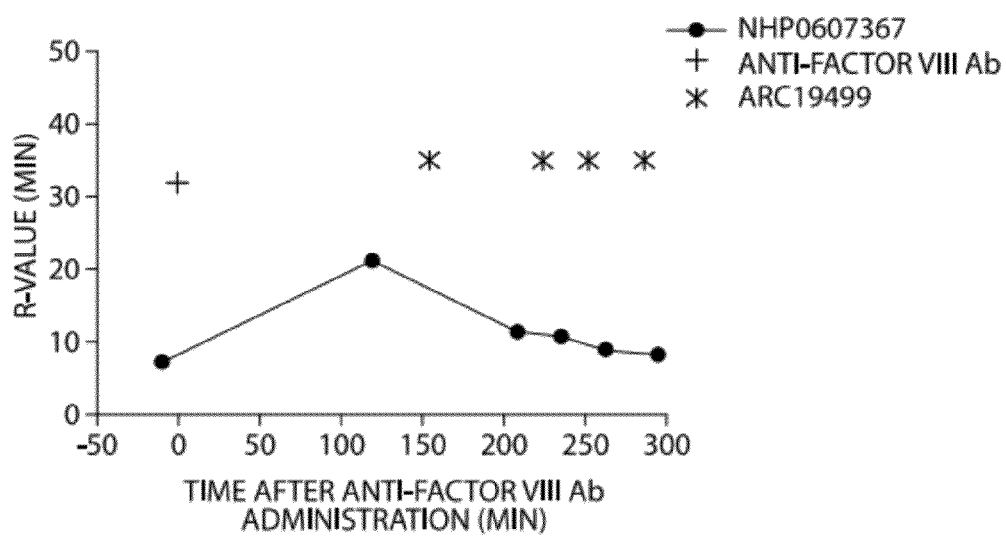

FIG. 133 is a graph of individual whole blood thromboelastography (TEG®) R-values plotted against sampling timepoint for the Group 4 monkey. The time of anti-Factor VIII antibody dosing is indicated by a plus-sign (+) and the times of ARC19499 dosing are indicated by asterisks (*).

Figure 134:
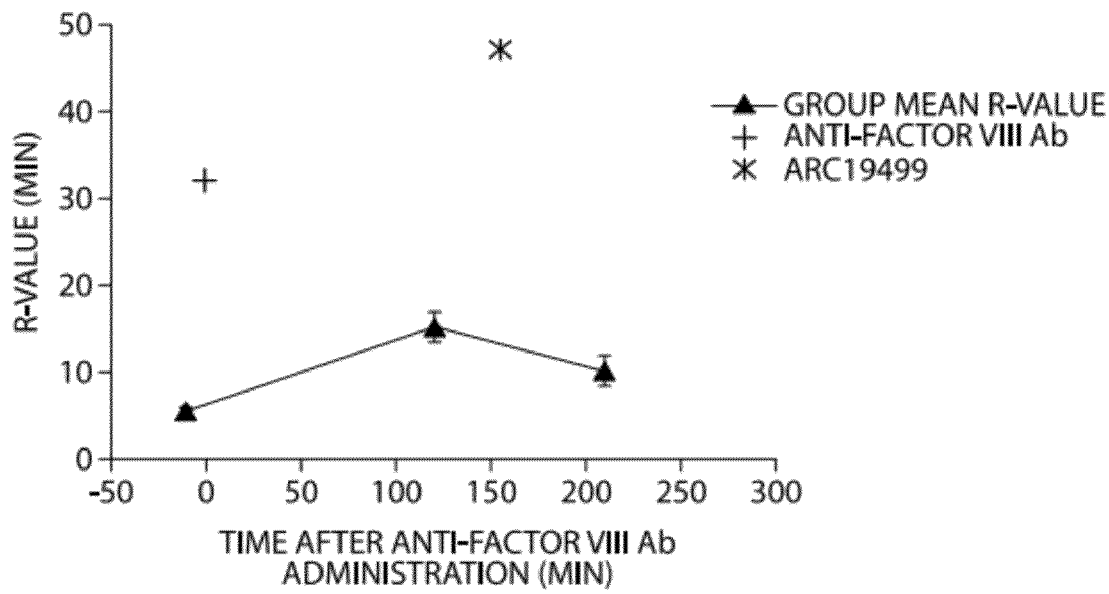

FIG. 134 is a graph of mean group plasma thromboelastography (TEG®) R-values plotted against sampling timepoint for Group 1 monkeys. The time of anti-Factor VIII antibody dosing is indicated by a plus-sign (+) and the time of ARC19499 dosing is indicated by an asterisk (*).

Figure 135:
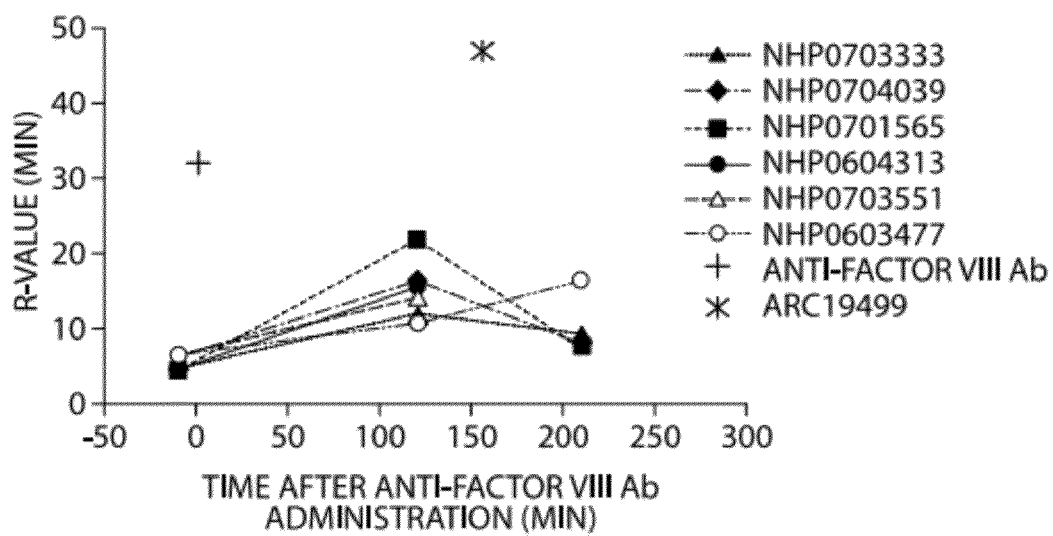

FIG. 135 is a graph of individual plasma thromboelastography (TEG®) R-values plotted against sampling timepoint for Group 1 monkeys. The time of anti-Factor VIII antibody dosing is indicated by a plus-sign (+) and the time of ARC19499 dosing is indicated by an asterisk (*).

Figure 136:
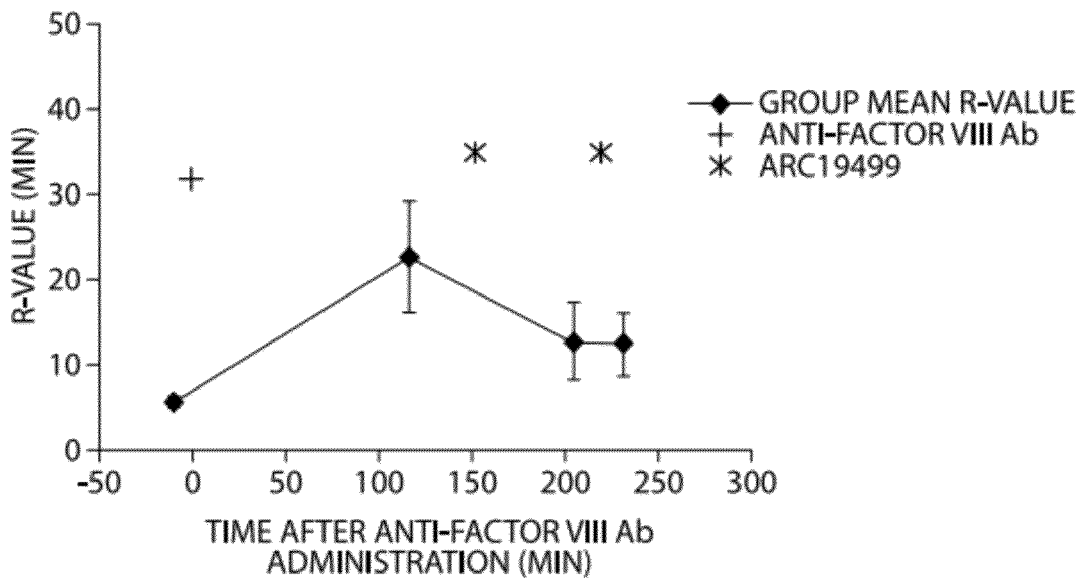

FIG. 136 is a graph of mean group plasma thromboelastography (TEG®) R-values plotted against sampling timepoint for Group 2 monkeys. The time of anti-Factor VIII antibody dosing is indicated by a plus-sign (+) and the times of ARC19499 dosing are indicated by asterisks (*).

Figure 137:
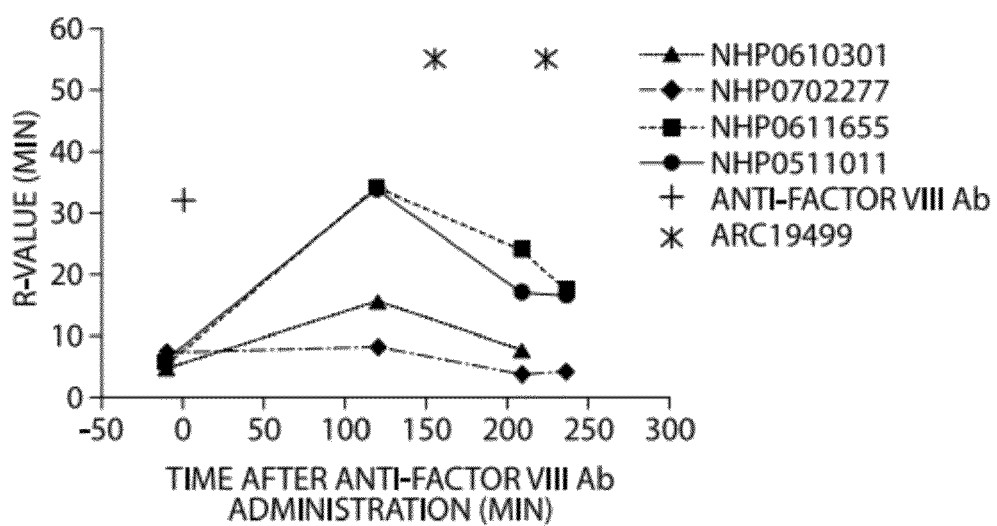

FIG. 137 is a graph of individual plasma thromboelastography (TEG®) R-values plotted against sampling timepoint for Group 2 monkeys. The time of anti-Factor VIII antibody dosing is indicated by a plus-sign (+) and the times of ARC19499 dosing are indicated by asterisks (*).

Figure 138:
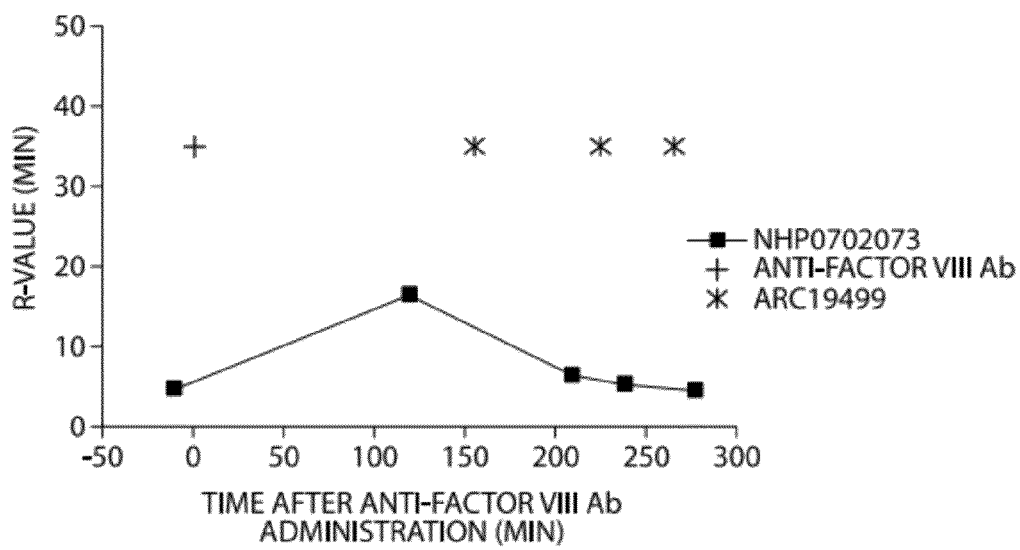

FIG. 138 is a graph of individual plasma thromboelastography (TEG®) R-values plotted against sampling timepoint for the Group 3 monkey. The time of anti-Factor VIII antibody dosing is indicated by a plus-sign (+) and the times of ARC19499 dosing are indicated by asterisks (*).

Figure 139:
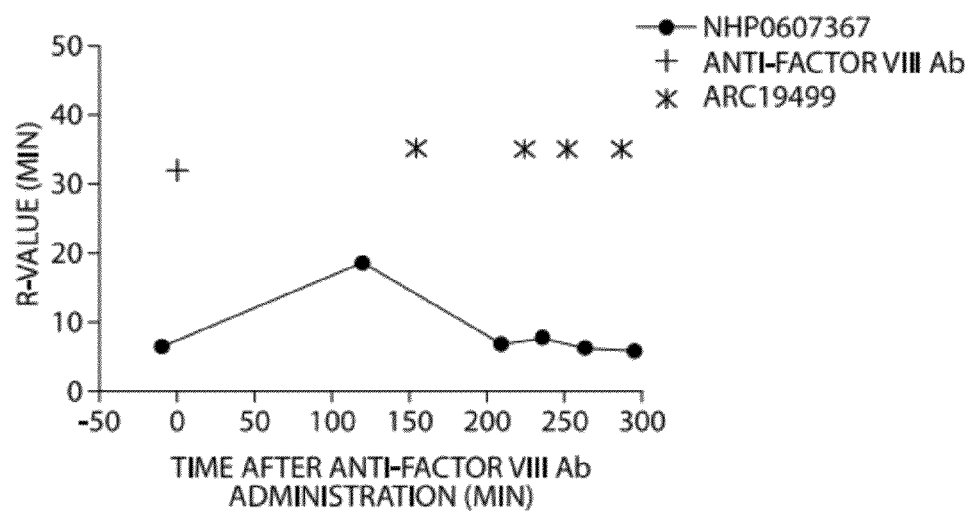

FIG. 139 is a graph of individual plasma thromboelastography (TEG®) R-values plotted against sampling timepoint for the Group 4 monkey. The time of anti-Factor VIII antibody dosing is indicated by a plus-sign (+) and the times of ARC19499 dosing are indicated by asterisks (*).

FIG. 140 depicts derivatives of ARC17480 that contain single and multiple 2'-substitutions in the ARC17480 sequence. Differences relative to ARC17480 are shaded.

FIG. 141 depicts derivatives of ARC17480 that contain a single phosphorothioate substitution between each pair of residues in the ARC17480 sequence. Each phosphorothioate is indicated by an "s" between the pairs of residues in the sequence. Differences relative to ARC17480 are shaded.

Figures 142A, 142B:
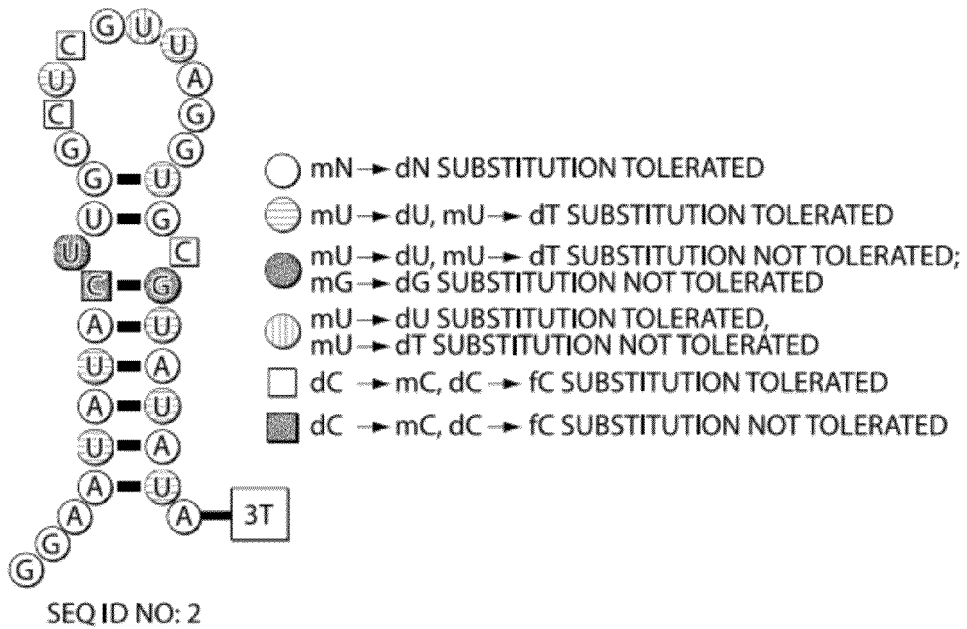

FIG. 142A depicts tolerated and non-tolerated 2'-substitutions mapped onto the putative secondary structure of ARC17480. FIG. 142B depicts active ARC17480 derivatives with multiple 2'-deoxy to 2'-O Methyl and/or 2'-fluoro substitutions at the four deoxycytidine residues of ARC17480 (residues 9, 14, 16 and 25).

FIG. 143 depicts derivatives of ARC17480 that contain single or multiple deletions in the ARC17480 sequence. Differences relative to ARC17480 are highlighted in black.

Figure 144A:
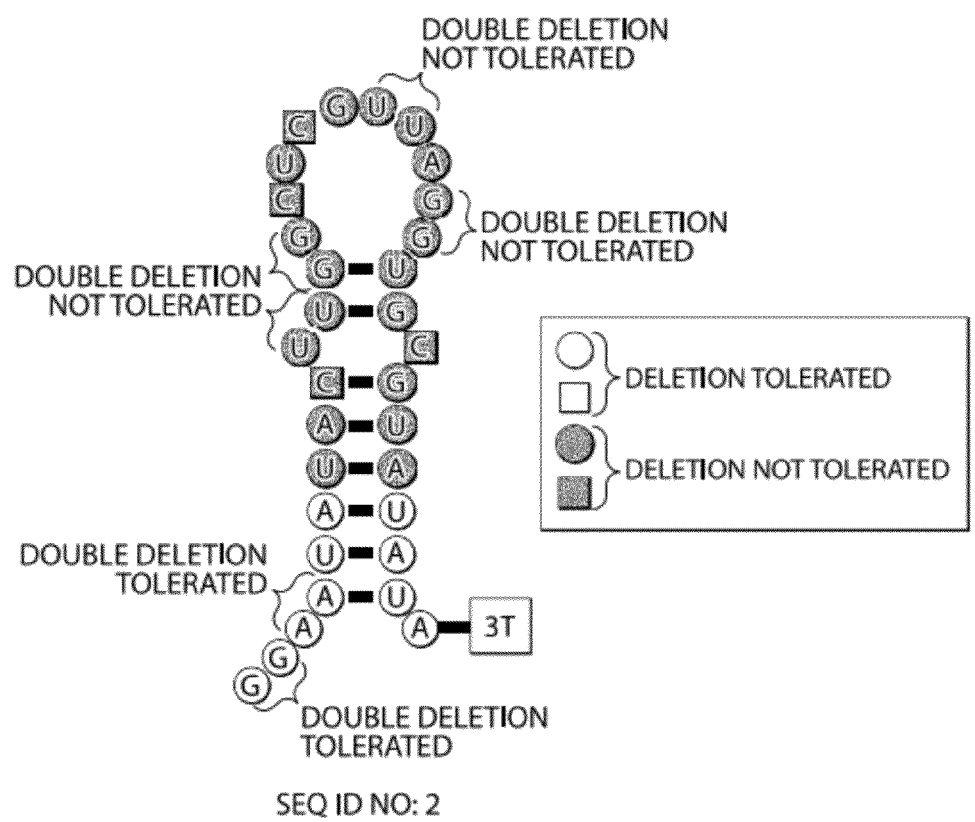
Figure 144B:
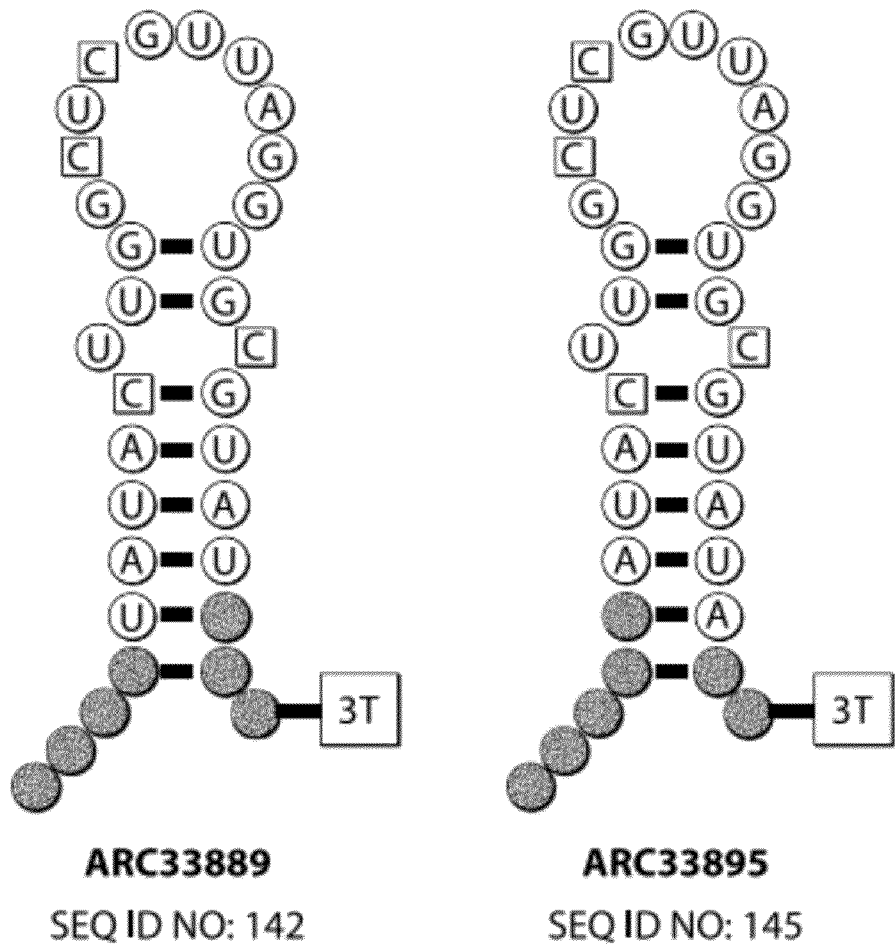

FIG. 144A depicts tolerated and non-tolerated single residue deletions mapped onto the putative secondary structure of ARC17480. ARC17480 is comprised of 2'-O Methyl (circles) and 2'-deoxy (squares) nucleotides and is modified at its 3'-terminus with an inverted deoxythymidine residue (3T). The corresponding double residue deletion is also depicted in cases where two adjacent nucleotides were identical. Tolerated deletions are highlighted in gray and non-tolerated deletions are highlighted in black. Tolerated and non-tolerated double deletions are indicated. FIG. 144B depicts active ARC17480 derivatives ARC33889 and ARC33895. These molecules each have seven of the ARC17480 residues deleted, which are represented by black circles.

Figure 145A:
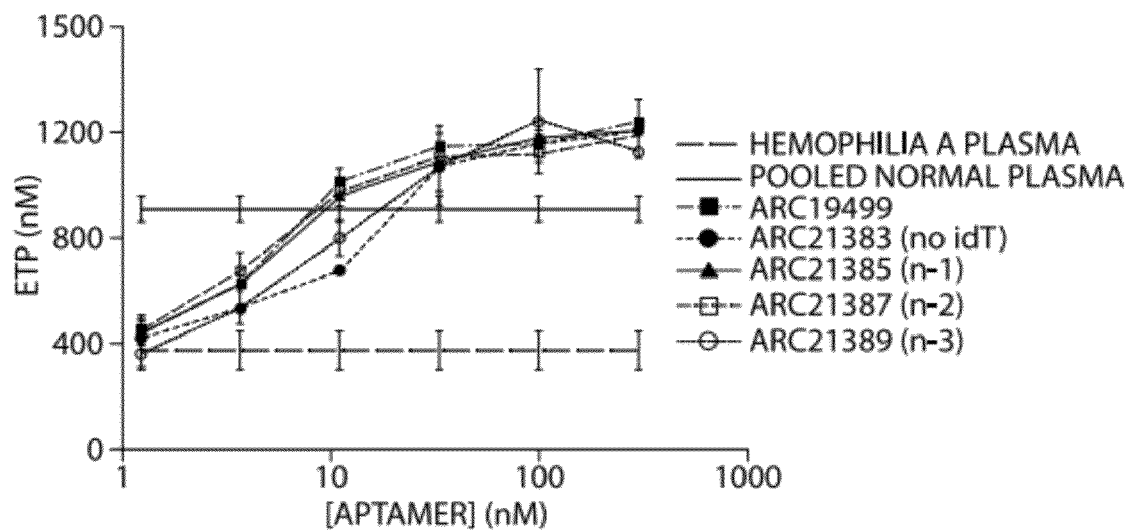
Figure 145B:
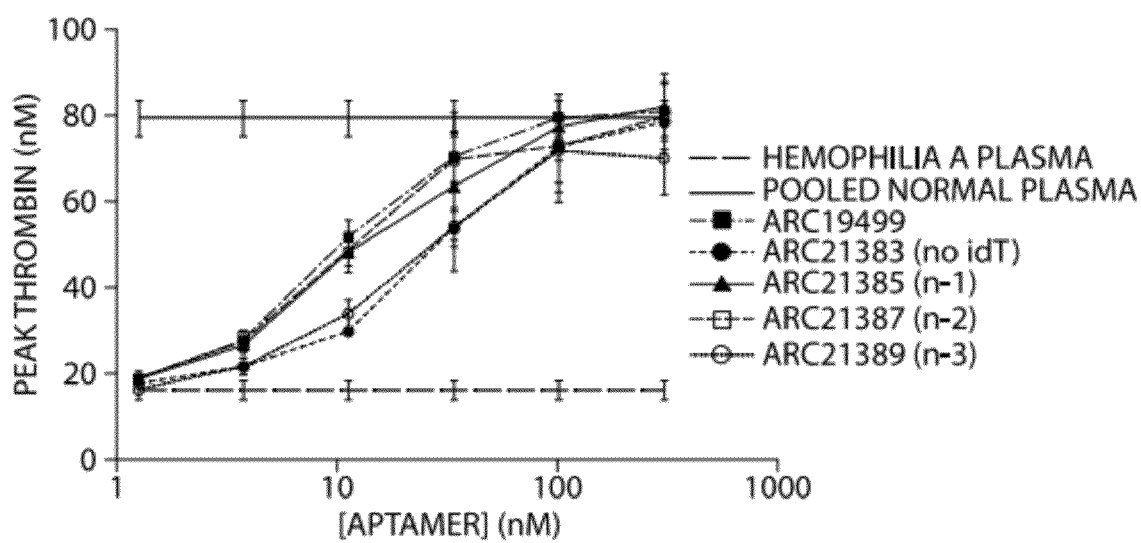

FIG. 145 depicts the results of a thrombin generation experiment with 3'-truncated ARC19499 derivatives. ARC19499, ARC21383, ARC21385, ARC21387 and ARC21389 all increase thrombin generation in a concentration-dependent manner in hemophilia A plasma, as measured by endogenous thrombin potential (ETP; FIG. 145A) and peak thrombin (FIG. 145B).

DETAILED DESCRIPTION OF THE INVENTION

The details of one or more embodiments of the invention are set forth in the accompanying description below. Although any methods and materials similar or equivalent to those described herein can be used in the practice or testing of the invention, the preferred methods and materials are now described. Other features, objects and advantages of the invention will be apparent from the description. In the description, the singular form also includes the plural unless the context clearly dictates otherwise. Unless defined otherwise, all technical and scientific terms used herein have the same meaning as commonly understood by one of ordinary skill in the art to which this invention belongs. In the case of conflict, the present description will control.

The invention provides aptamers that bind to TFPI, which are described herein as "TFPI aptamers", and methods for using such aptamers in the treatment of bleeding disorders and other TFPI-mediated pathologies, diseases and disorders, with or without other agents. In addition, the TFPI aptamers may be used before, during and/or after medical procedures, with or without other agents, in order to reduce or otherwise delay the progression of the complications or side effects thereof.

Identification of Aptamers

Figures 4, 5:
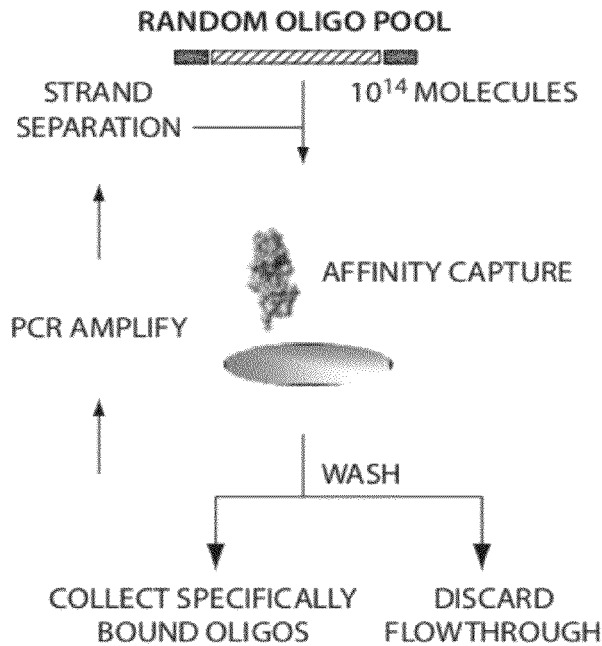
FIG. 4 is a schematic representation of the in vitro aptamer selection (SELEX™) process from pools of random sequence oligonucleotides.
FIG. 5 is an illustration of the amino acid sequence of the mature human TFPI protein.

The aptamers described herein are preferably identified through a method known in the art as Systematic Evolution of Ligands by EXponential Enrichment, or SELEX™, which is shown generally in FIG. 4. More specifically, starting with a mixture containing a starting pool of nucleic acids, the SELEX™ method includes steps of: (a) contacting the mixture with a target under conditions favorable for binding; (b) partitioning unbound nucleic acids from those nucleic acids that have bound to the target; (c) amplifying the bound nucleic acids to yield a ligand-enriched mixture of nucleic acids; and, optionally, (d) reiterating the steps of contacting, partitioning and amplifying through as many cycles as desired to yield highly specific, high affinity aptamers to the target. In those instances where transcribed aptamers, such as RNA aptamers, are being selected, the amplification step of the SELEX™ method includes the steps of: (i) reverse transcribing the nucleic acids dissociated from the nucleic acid-target complexes or otherwise transmitting the sequence information into a corresponding DNA sequence; (ii) PCR amplification; and (iii) transcribing the PCR amplified nucleic acids or otherwise transmitting the sequence information into a corresponding RNA sequence before restarting the process. The starting pool of nucleic acids can be modified or unmodified DNA, RNA or DNA/RNA hybrids, and acceptable modifications include modifications at a base, sugar and/or internucleotide linkage. The composition of the starting pool is dependent upon the desired properties of the final aptamer. Selections can be performed with nucleic acid sequences incorporating modified nucleotides to, e.g., stabilize the aptamers against degradation in vivo. For example, resistance to nuclease degradation can be greatly increased by the incorporation of modifying groups at the 2'-position.

In one embodiment, the invention provides aptamers including single 2' substitutions at all bases or combinations of 2'-OH, 2'-F, 2'-deoxy, 2'-NH$_2$ and 2'-OMe modifications of the adenosine triphosphate (ATP), guanosine triphosphate (GTP), cytidine triphosphate (CTP), thymidine triphosphate (TTP) and uridine triphosphate (UTP) nucleotides. In another embodiment, the invention provides aptamers including combinations of 2'-OH, 2'-F, 2'-deoxy, 2'-OMe, 2'-NH$_2$ and 2'-methoxyethyl modifications of the ATP, GTP, CTP, TTP and UTP nucleotides. In a further embodiment, the invention provides aptamers including all or substantially all 2'-OMe modified ATP, GTP, CTP, TTP and/or UTP nucleotides.

In some embodiments, 2'-modified aptamers of the invention are created using modified polymerases, e.g., a modified RNA polymerase having a rate of incorporation of modified nucleotides having bulky substituents at the furanose 2' position that is higher than that of wild-type polymerases. In one embodiment, the modified RNA polymerase is a mutant T7 polymerase in which the tyrosine at position 639 has been changed to phenylalanine (Y639F). In another embodiment, the modified RNA polymerase is a mutant T7 polymerase in which the tyrosine at position 639 has been changed to phenylalanine and the lysine at position 378 has been changed to arginine (Y639F/K378R). In yet another embodiment, the modified RNA polymerase is a mutant T7 polymerase in which the tyrosine at position 639 has been changed to phenylalanine, the histidine at position 784 has been changed to an alanine, and the lysine at position 378 has been changed to arginine (Y639F/H784A/K378R), and the transcription reaction mixture requires a spike of 2'-OH GTP for transcription. In a further embodiment, the modified RNA polymerase is a mutant T7 polymerase in which the tyrosine at position 639 has been changed to phenylalanine and the histidine at position 784 has been changed to an alanine (Y639F/H784A).

In one embodiment, the modified RNA polymerase is a mutant T7 polymerase in which the tyrosine at position 639 has been changed to leucine (Y639L). In another embodiment, the modified RNA polymerase is a mutant T7 polymerase in which the tyrosine at position 639 has been changed to leucine and the histidine at position 784 has been changed to an alanine (Y639L/H784A). In yet another embodiment, the modified RNA polymerase is a mutant T7 polymerase in which the tyrosine at position 639 has been changed to leucine, the histidine at position 784 has been changed to alanine, and the lysine at position 378 has been changed to arginine (Y639L/H784A/K378R).

Another suitable RNA polymerase having a rate of incorporation of modified nucleotides having bulky substituents at the furanose 2' position that is higher than that of wild-type polymerases is, for example, a mutant T3 RNA polymerase. In one embodiment, the mutant T3 RNA polymerase has a mutation at position 640, wherein the tyrosine at position 640 is replaced with a phenylalanine (Y640F). In another embodiment, the mutant T3 RNA polymerase has mutations at positions 640 and 785, wherein the tyrosine at position 640 is replaced with a leucine and the histidine at position 785 is replaced with an alanine (Y640L/H785A).

2'-modified oligonucleotides may be synthesized entirely of modified nucleotides or with a subset of modified nucleotides. The modifications can be the same or different. Some or all nucleotides may be modified, and those that are modified may contain the same modification. For example, all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this way, transcripts, or pools of transcripts, are generated using any combination of modifications, including for example, ribonucleotides (2'-OH), deoxyribonucleotides (2'-deoxy), 2'-amino nucleotides (2'-NH$_2$), 2'-fluoro nucleotides (2'-F) and 2'-O-methyl (2'-OMe) nucleotides.

As used herein, a transcription mixture containing only 2'-OMe A, G, C and U and/or T triphosphates (2'-OMe ATP, 2'-OMe UTP and/or 2'-OMe TTP, 2'-OMe CTP and 2'-OMe GTP) is referred to as an MNA or mRmY mixture, and aptamers selected therefrom are referred to as MNA aptamers or mRmY aptamers and contain only 2'-O-methyl nucleotides. A transcription mixture containing 2'-OMe C and U and/or T, and 2'-OH A and G is referred to as an "rRmY" mixture, and aptamers selected therefrom are referred to as "rRmY" aptamers. A transcription mixture containing deoxy A and G, and 2'-OMe U and/or T, and C is referred to as a "dRmY"

mixture, and aptamers selected therefrom are referred to as "dRmY" aptamers. A transcription mixture containing 2'-OMe A, C and U and/or T, and 2'-OH G is referred to as a "rGmH" mixture, and aptamers selected therefrom are referred to as "rGmH" aptamers. A transcription mixture alternately containing 2'-OMe A, C, U and/or T and G, and 2'-OMe A, U and/or T, and C, and 2'-F G is referred to as an "alternating mixture", and aptamers selected therefrom are referred to as "alternating mixture" aptamers. A transcription mixture containing 2'-OH A and G, and 2'-F C and U and/or T is referred to as an "rRfY" mixture, and aptamers selected therefrom are referred to as "rRfY" aptamers. A transcription mixture containing 2'-OMe A and G, and 2'-F C and U and/or T is referred to as an "mRfY" mixture, and aptamers selected therefrom are referred to as "mRfY" aptamers. A transcription mixture containing 2'-OMe A, U and/or T, and C, and 2'-F G is referred to as a "fGmH" mixture, and aptamers selected therefrom are referred to as "fGmH" aptamers. A transcription mixture containing 2'-OMe A, U and/or T, C and G, where up to 10% of the G's are ribonucleotides is referred to as a "r/mGmH" mixture, and aptamers selected therefrom are referred to as "r/mGmH" aptamers. A transcription mixture containing 2'-OMe A, U and/or T, and C, and deoxy G is referred to as a "dGmH" mixture, and aptamers selected therefrom are referred to as "dGmH" aptamers. A transcription mixture containing deoxy A, and 2'-OMe C, G and U and/or T is referred to as a "dAmB" mixture, and aptamers selected therefrom are referred to as "dAmB" aptamers. A transcription mixture containing 2'-OH A, and 2'-OMe C, G and U and/or T is referred to as a "rAmB" mixture, and aptamers selected therefrom are referred to as "rAmB" aptamers. A transcription mixture containing 2'-OH A and 2'-OH G, and 2'-deoxy C and 2'-deoxy T is referred to as an rRdY mixture, and aptamers selected therefrom are referred to as "rRdY" aptamers. A transcription mixture containing 2'-OMe A, U and/or T, and G, and deoxy C is referred to as a "dCmD" mixture, and aptamers selected there from are referred to as "dCmD" aptamers. A transcription mixture containing 2'-OMe A, G and C, and deoxy T is referred to as a "dTmV" mixture, and aptamers selected there from are referred to as "dTmV" aptamers. A transcription mixture containing 2'-OMe A, C and G, and 2'-OH U is referred to as a "rUmV" mixture, and aptamers selected there from are referred to as "rUmV" aptamers. A transcription mixture containing 2'-OMe A, C and G, and 2'-deoxy U is referred to as a "dUmV" mixture, and aptamers selected therefrom are referred to as "dUmV" aptamers. A transcription mixture containing all 2'-OH nucleotides is referred to as a "rN" mixture, and aptamers selected therefrom are referred to as "rN", "rRrY" or RNA aptamers. A transcription mixture containing all deoxy nucleotides is referred to as a "dN" mixture, and aptamers selected therefrom are referred to as "dN", "dRdY" or DNA aptamers. A transcription mixture containing 2'-F C and 2'-OMe A, G and U and/or T is referred to as a "fCmD" mixture, and aptamers selected therefrom are referred to as "fCmD" aptamers. A transcription mixture containing 2'-F U and 2'-OMe A, G and C is referred to as a "fUmV" mixture, and aptamers selected therefrom are referred to as "fUmV" aptamers. A transcription mixture containing 2'-F A and G, and 2'-OMe C and U and/or T is referred to as a "fRmY" mixture, and aptamers selected therefrom are referred to as "fRmY" aptamers. A transcription mixture containing 2'-F A and 2'-OMe C, G and U and/or T is referred to as a "fAmB" mixture, and aptamers selected therefrom are referred to as "fAmB" aptamers.

A number of factors have been determined to be useful for optimizing the transcription conditions used to produce the aptamers disclosed herein. For example, a leader sequence can be incorporated into the fixed sequence at the 5' end of a DNA transcription template. The leader sequence is typically 6-15 nucleotides long, e.g., 6, 7, 8, 9, 10, 11, 12, 13, 14 or 15 nucleotides long, and may be composed of all purines, or a mixture of purine and pyrimidine nucleotides.

For compositions that contain 2'-OMe GTP, another useful factor can be the presence or concentration of 2'-OH guanosine or guanosine monophosphate (GMP). Transcription can be divided into two phases: the first phase is initiation, during which the RNA is extended by about 10-12 nucleotides; the second phase is elongation, during which transcription proceeds beyond the addition of the first about 10-12 nucleotides. It has been found that 2'-OH GMP or guanosine added to a transcription mixture containing an excess of 2'-OMe GTP is sufficient to enable the polymerase to initiate transcription. Priming transcription with 2'-OH guanosine e.g., or GMP is useful due to the specificity of the polymerase for the initiating nucleotide. The preferred concentration of GMP is 0.5 mM and even more preferably 1 mM.

Another useful factor for optimizing the incorporation of 2'-OMe substituted nucleotides into transcripts is the use of both divalent magnesium and manganese in the transcription mixture. Different combinations of concentrations of magnesium chloride and manganese chloride have been found to affect yields of 2'-O modified transcripts, the optimum concentration of the magnesium and manganese chloride being dependent upon the concentration of NTPs in the transcription reaction mixture that complex divalent metal ions.

Other reagents that can be included in the transcription reaction include buffers such as N-2-hydroxyethylpiperazine-N'-2-ethanesulfonic acid (HEPES) buffer, a redox reagent such as dithiothreitol (DTT), a polycation such as spermidine, spermine, a surfactant such as Triton X100, and any combinations thereof.

In one embodiment, the HEPES buffer concentration can range from 0 to 1 M. The invention also contemplates the use of other buffering agents having a pKa between 5 and 10, including, for example, Tris-hydroxymethyl-aminomethane. In some embodiments, the DTT concentration can range from 0 to 400 mM. The methods of the invention also provide for the use of other reducing agents, including, for example, mercaptoethanol. In some embodiments, the spermidine and/or spermine concentration can range from 0 to 20 mM. In some embodiments, the PEG-8000 concentration can range from 0 to 50% (w/v). The methods of the invention also provide for the use of other hydrophilic polymers, including, for example, other molecular weight PEGs or other polyalkylene glycols. In some embodiments, the Triton X-100 concentration can range from 0 to 0.1% (w/v). The methods of the invention also provide for the use of other non-ionic detergents, including, for example, other detergents, including other Triton-X detergents. In some embodiments, the $MgCl_2$ concentration can range from 0.5 mM to 50 mM. The $MnCl_2$ concentration can range from 0.15 mM to 15 mM. In some embodiments, the 2'-OMe NTP concentration (each NTP) can range from 5 μM to 5 mM. In some embodiments, the 2'-OH GTP concentration can range from 0 μM to 300 μM. In some embodiments, the 2'-OH GMP concentration can range from 0 to 5 mM. The pH can range from pH 6 to pH 9.

Variations of the SELEX process may also be used to identify aptamers. For example, one may use agonist SELEX, toggle SELEX, 2'-Modified SELEX or Counter SELEX. Each of these variations of the SELEX process is known in the art.

TFPI Aptamers

The invention includes nucleic acid aptamers, preferably of 20-55 nucleotides in length, that bind to tissue factor pathway inhibitor (TFPI) and which, in some embodiments, functionally modulate, e.g., stimulate, block or otherwise inhibit or stimulate, the activity of TFPI.

The TFPI aptamers bind at least in part to TFPI or a variant or one or more portions (or regions) thereof. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain.

A TFPI variant, as used herein, encompasses variants that perform essentially the same function as TFPI functions, preferably includes substantially the same structure and in some embodiments includes at least 70% sequence identity, preferably at least 80% sequence identity, more preferably at least 90% sequence identity, and more preferably at least 95%, 96%, 97%, 98% or 99% sequence identity to the amino acid sequence of human TFPI, which is shown in FIG. 5 as SEQ ID NO: 11.

Figure 1:
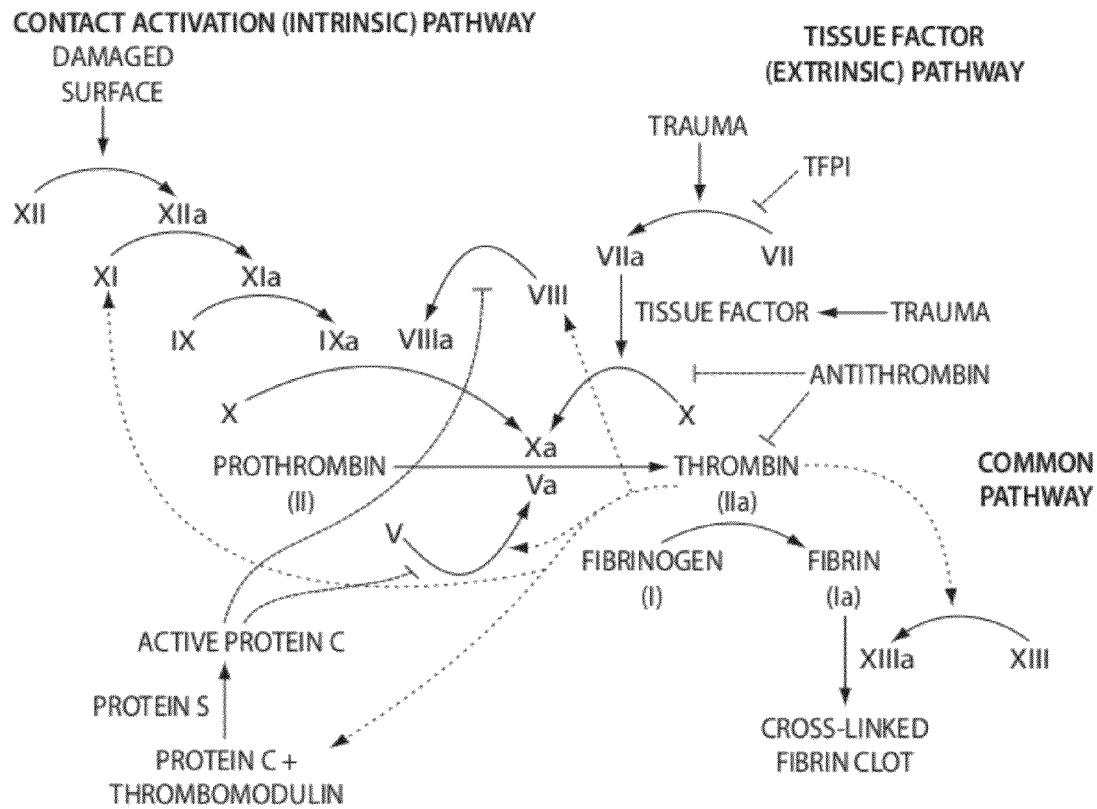
FIG. 1 is a schematic representation of the coagulation cascade.
Figure 2:
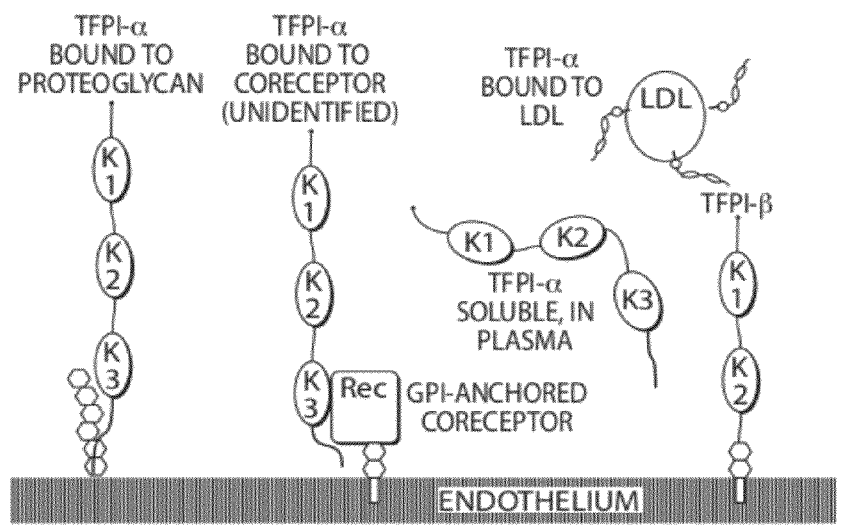
FIG. 2 is an illustration of the forms of TFPI, which are associated with the vascular endothelium or in the plasma pool.
Figure 3A:
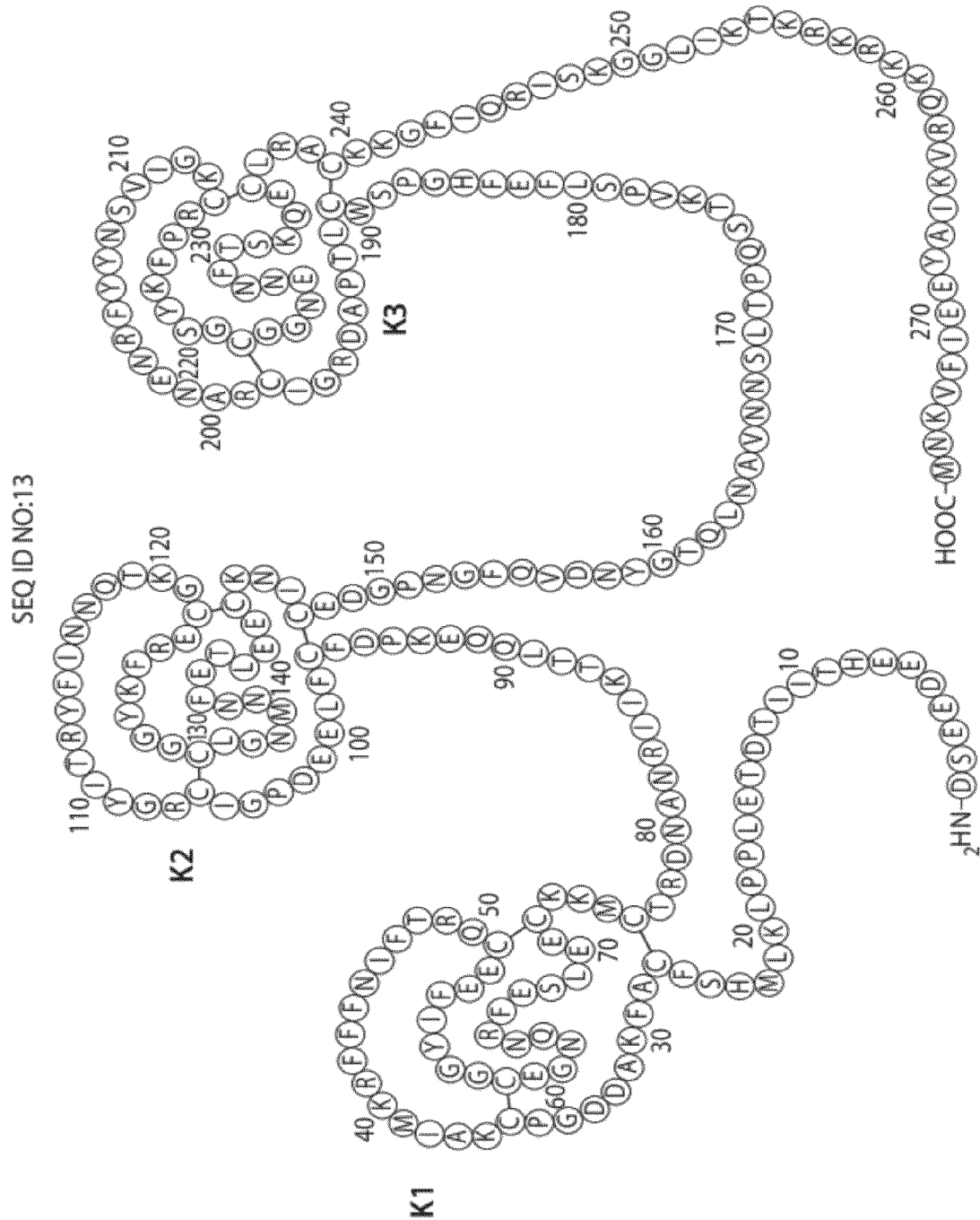
FIG. 3 is a schematic representation of the two forms of TFPI found on the endothelium, (FIG. 3A) TFPIα and (FIG. 3B) TFPIβ.
Figure 3B:
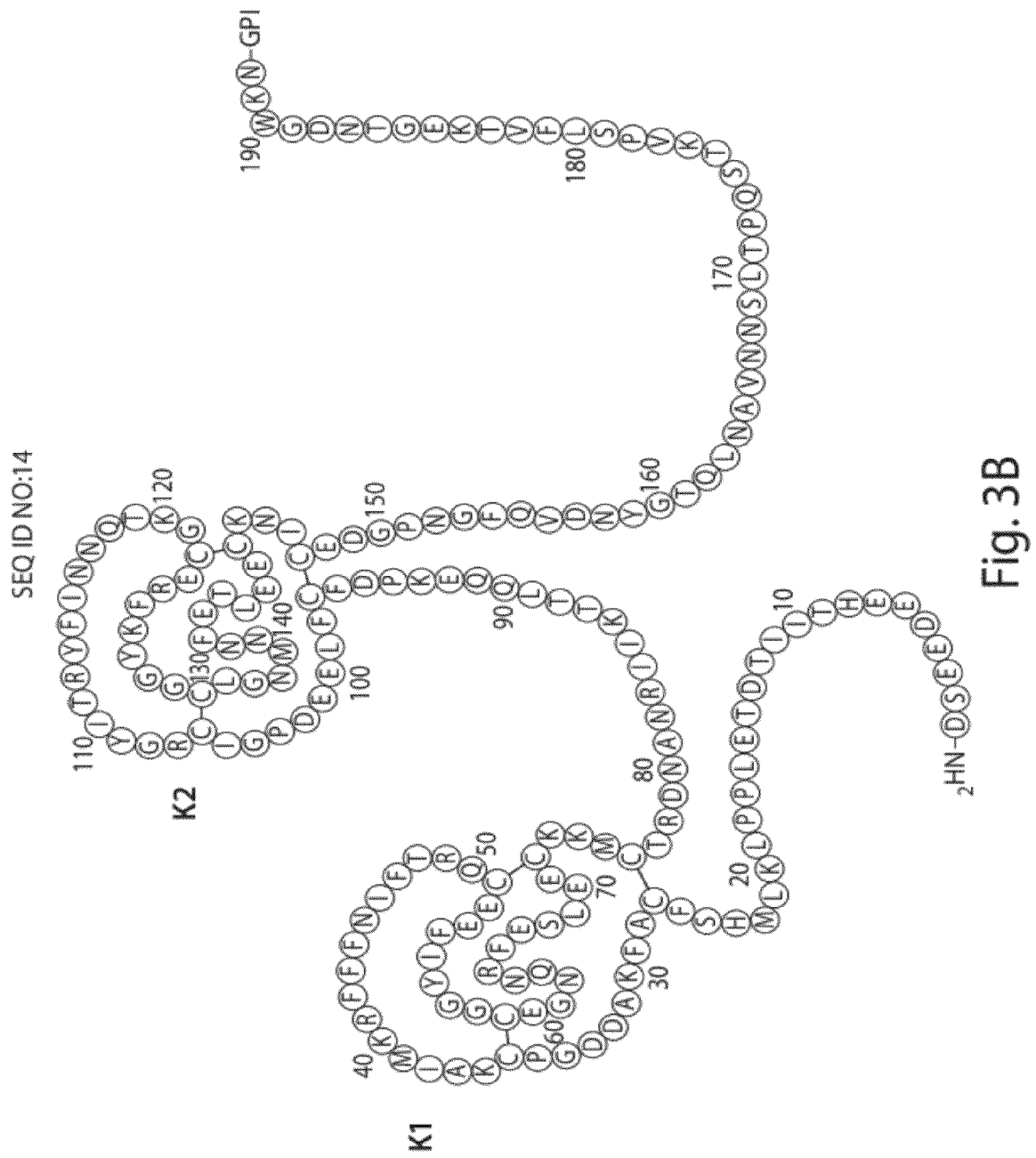

Preferably, the TFPI aptamers bind to full length TFPI. If an aptamer binds to one or more portions of TFPI, it is preferable that the aptamer require binding contacts or other interaction with a portion of TFPI, at least in part, outside of the K1 and K2 regions, such as the K3/C-terminal region. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. More preferably, the TFPI aptamers bind at least in part to one or more portions of mature TFPI (for example, FIG. 3A) that are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276.

The TFPI may be from any species, but is preferably human.

The TFPI aptamers preferably comprise a dissociation constant for human TFPI, or a variant thereof, of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less. In some embodiments, the dissociation constant is determined by dot blot titration.

The TFPI aptamers may be ribonucleic acid, deoxyribonucleic acid, modified nucleic acids (for example, 2'-modified) or mixed ribonucleic acid, deoxyribonucleic acid and modified nucleic acids, or any combination thereof. The aptamers may be single stranded ribonucleic acid, deoxyribonucleic acid, modified nucleic acids (for example, 2'-modified), ribonucleic acid and modified nucleic acid, deoxyribonucleic acid and modified nucleic acid, or mixed ribonucleic acid, deoxyribonucleic acid and modified nucleic acids, or any combination thereof.

In some embodiments, the TFPI aptamers comprise at least one chemical modification. In some embodiments, the chemical modification is selected from the group consisting of: a chemical substitution at a sugar position, a chemical substitution at an internucleotide linkage and a chemical substitution at a base position. In other embodiments, the chemical modification is selected from the group consisting of: incorporation of a modified nucleotide; a 3' cap; a 5' cap; conjugation to a high molecular weight, non-immunogenic compound; conjugation to a lipophilic compound; incorporation of a CpG motif; and incorporation of a phosphorothioate or phosphorodithioate into the phosphate backbone. In a preferred embodiment, the non-immunogenic, high molecular weight compound is polyalkylene glycol, and more preferably is polyethylene glycol (PEG). In some embodiments, the polyethylene glycol is methoxypolyethylene glycol (mPEG). In another preferred embodiment, the 3' cap is an inverted deoxythymidine cap.

The modifications described herein may affect aptamer stability, e.g., incorporation of a capping moiety may stabilize the aptamer against endonuclease degradation. Additionally, the modifications described herein may affect the binding affinity of an aptamer to its target, e.g., site specific incorporation of a modified nucleotide or conjugation to a PEG may affect binding affinity. The effect of such modifications on binding affinity can be determined using a variety of art-recognized techniques, such as, e.g., functional assays, such as an ELISA, or binding assays in which labeled trace aptamer is incubated with varying target concentrations and complexes are captured on nitrocellulose and quantitated, to compare the binding affinities pre- and post-incorporation of a modification.

Preferably, the TFPI aptamers bind at least in part to TFPI or a variant or one or more portions thereof and act as an antagonist to inhibit the function of TFPI.

The TFPI aptamers completely or partially inhibit, reduce, block or otherwise modulate TFPI-mediated inhibition of blood coagulation. The TFPI aptamers are considered to completely modulate, block, inhibit, reduce, antagonize, neutralize or otherwise interfere with TFPI biological activity, such as TFPI-mediated inhibition of blood coagulation, when the level of TFPI-mediated inhibition in the presence of the TFPI aptamer is decreased by at least 95%, e.g., by 96%, 97%, 98%, 99% or 100% as compared to the level TFPI-mediated inhibition in the absence of the TFPI aptamer. The TFPI aptamers are considered to partially modulate, block, inhibit, reduce, antagonize, neutralize or otherwise interfere with TFPI biological activity, such as TFPI-mediated inhibition, when the level of TFPI-mediated inhibition in the presence of the TFPI aptamer is decreased by less than 95%, e.g., 10%, 15%, 20%, 25%, 30%, 35%, 40%, 45%, 50%, 55%, 60%, 65%, 70%, 75%, 80%, 85% or 90% as compared to the level of TFPI activity in the absence of the TFPI aptamer.

Examples of aptamers that bind to and modulate the function of TFPI for use as therapeutics and/or diagnostics include, but are not limited to, ARC26835, ARC17480, ARC19498, ARC19499, ARC19500, ARC19501, ARC31301, ARC18546, ARC19881 and ARC19882.

Preferably, the TFPI aptamers comprise one of the following nucleic acid sequences:
(ARC26835) mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA (SEQ ID NO: 1), wherein "dN" is a deoxynucleotide and "mN" is a 2'-O Methyl containing nucleotide (which is also known in the art as a 2'-OMe, 2'-methoxy or 2'-OCH$_3$ containing nucleotide); and
(ARC17480) mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 2), wherein "3T" is an inverted deoxythymidine, "dN" is a deoxynucleotide and "mN" is a 2'-O Methyl containing nucleotide; and
(ARC19498) NH$_2$-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 3), wherein "NH$_2$" is from a 5'-hexylamine linker phosphoramidite, "3T" is an inverted deoxythymidine, "dN" is a deoxynucleotide and "mN" is a 2'-O Methyl containing nucleotide; and
(ARC19499) PEG40K-NH-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 4), wherein "NH" is from a 5'-hexylamine linker phosphoramidite, "3T" is an inverted deoxythymidine, "dN" is a deoxynucleotide, "mN" is a 2'-O Methyl containing nucleotide and "PEG" is a polyethylene glycol; and
(ARC19500) NH$_2$-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-NH$_2$ (SEQ Id No: 5), Wherein "dN" is a deoxynucleotide, "mN" is a 2'-O Methyl containing nucleotide and "NH$_2$" is from a hexylamine linker phosphoramidite; and
(ARC19501) PEG20K-NH-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-NH-PEG20K (SEQ Id No: 6), wherein "dN" is a deoxynucleotide, "mN" is a 2'-O Methyl containing nucleotide, "NH" is from a hexylamine linker phosphoramidite and "PEG" is a polyethylene glycol; and
(ARC31301) mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA (SEQ ID NO: 7), wherein "dN" is a deoxynucleotide and "mN" is a 2'-O Methyl containing nucleotide; and
(ARC18546) mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA-3T (SEQ ID NO: 8), wherein "3T" is an inverted deoxythymidine, "dN" is a deoxynucleotide and "mN" is a 2'-O Methyl containing nucleotide; and
(ARC19881) NH$_2$-mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA (SEQ ID NO: 9), wherein "NH$_2$" is from a 5'-hexylamine linker phosphoramidite, "3T" is an inverted deoxythymidine, "dN" is a deoxynucleotide and "mN" is a 2'-O Methyl containing nucleotide; and
(ARC19882) PEG40K-NH-mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA-3T (SEQ ID NO: 10), wherein "NH" is from a 5'-hexylamine linker phosphoramidite, "3T" is an inverted deoxythymidine, "dN" is a deoxynucleotide, "mN" is a 2'-O Methyl containing nucleotide and "PEG" is a polyethylene glycol.

The chemical name of ARC26835 is 2'-OMe-guanylyl-(3'→5')-2'-OMe-guanylyl-(3'→5')-2'-OMe-adenylyl-(3'→5')-2'-OMe-adenylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-2'-deoxycytidylyl-(3'→5')-2'-OMe-uracylyl-(3'→5')-2'-OMe-uracylyl-(3'→5')-2'-OMe-guanylyl-(3'→5')-2'-OMe-guanylyl-(3'→5')-2'-deoxycytidylyl-(3'→5')-2'-OMe-uracylyl-(3'→5')-2'-deoxycytidylyl-(3'→5')-2'-OMe-guanylyl-(3'→5')-2'-OMe-uracylyl-(3'→5')-2'-OMe-uracylyl-(3'→5')-2'-OMe-adenylyl-(3'→5')-2'-OMe-guanylyl-(3'→5')-2'-OMe-guanylyl-(3'→5')-2'-OMe-uracylyl-(3'→5')-2'-OMe-guanylyl-(3'→5')-2'-deoxycytidylyl-(3'→5')-2'-OMe-guanylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-2'-OMe-uracylyl-(3'→5')-2'-OMe-adenylyl.

The chemical name of ARC17480 is 2'-OMe-guanylyl-(3'→5')-2'-OMe-guanylyl-(3'→5')-2'-OMe-adenylyl-(3'→5')-2'-OMe-adenylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-2'-deoxycytidylyl-(3'→5')-2'-OMe-uracylyl-(3'→5')-2'-OMe-uracylyl-(3'→5')-2'-OMe-guanylyl-(3'→5')-2'-OMe-guanylyl-(3'→5')-2'-deoxycytidylyl-(3'→5')-2'-OMe-uracylyl-(3'→5')-2'-deoxycytidylyl-(3'→5')-2'-OMe-guanylyl-(3'→5')-2'-OMe-uracylyl-(3'→5')-2'-OMe-uracylyl-(3'→5')-2'-OMe-adenylyl-(3'→5')-2'-OMe-guanylyl-(3'→5')-2'-OMe-guanylyl-(3'→5')-2'-OMe-uracylyl-(3'→5')-2'-OMe-guanylyl-(3'→5')-2'-deoxycytidylyl-(3'→5')-2'-OMe-guanylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-(3'→3')-2'-deoxythymidine.

The chemical name of ARC19498 is 6-aminohexylyl-(1→5')-2'-OMe-guanylyl-(3'→5')-2'-OMe-guanylyl-(3'→5')-2'-OMe-adenylyl-(3'→5')-2'-OMe-adenylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-2'-deoxycytidylyl-(3'→5')-2'-OMe-uracylyl-(3'→5')-2'-OMe-uracylyl-(3'→5')-2'-OMe-guanylyl-(3'→5')-2'-OMe-guanylyl-(3'→5')-2'-deoxycytidylyl-(3'→5')-2'-OMe-uracylyl-(3'→5')-2'-deoxycytidylyl-(3'→5')-2'-OMe-guanylyl-(3'→5')-2'-OMe-uracylyl-(3'→5')-2'-OMe-uracylyl-(3'→5')-2'-OMe-adenylyl-(3'→5')-2'-OMe-guanylyl-(3'→5')-2'-OMe-guanylyl-(3'→5')-2'-OMe-uracylyl-(3'→5')-2'-OMe-guanylyl-(3'→5')-2'-deoxycytidylyl-(3'→5')-2'-OMe-guanylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-(3'→3')-2'-deoxythymidine.

The chemical name of ARC19499 is N-(methoxy-polyethyleneglycol)-6-aminohexylyl-(1→5')-2'-OMe-guanylyl-(3'→5')-2'-OMe-guanylyl-(3'→5')-2'-OMe-adenylyl- (3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-deoxycytidylyl-
(3'→5')-2'-OMe-uracylyl-(3'→5')-2'-OMe-uracylyl-
(3'→5')-2'-OMe-guanylyl-(3'→5')-2'-OMe-guanylyl-
(3'→5')-2'-deoxycytidylyl-(3'→5')-2'-OMe-uracylyl-
(3'→5')-2'-deoxycytidylyl-(3'→5')-2'-OMe-guanylyl-
(3'→5')-2'-OMe-uracylyl-(3'→5')-2'-OMe-uracylyl-
(3'→5')-2'-OMe-adenylyl-(3'→5')-2'-OMe-guanylyl-
(3'→5')-2'-OMe-guanylyl-(3'→5')-2'-OMe-uracylyl-
(3'→5')-2'-OMe-guanylyl-(3'→5')-2'-deoxycytidylyl-
(3'→5')-2'-OMe-guanylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-(3'→3')-2'-deoxythymidine.

The chemical name of ARC19500 is 6-aminohexylyl-(1→5')-2'-OMe-guanylyl-(3'→5')-2'-OMe-guanylyl-
(3'→5')-2'-OMe-adenylyl-(3'→5')-2'-OMe-adenylyl-
(3'→5')-2'-OMe-uracylyl-(3'→5')-2'-OMe-adenylyl-
(3'→5')-2'-OMe-uracylyl-(3'→5')-2'-OMe-adenylyl-
(3'→5')-2'-deoxycytidylyl-(3'→5')-2'-OMe-uracylyl-
(3'→5')-2'-OMe-uracylyl-(3'→5')-2'-OMe-guanylyl-
(3'→5')-2'-OMe-guanylyl-(3'→5')-2'-deoxycytidylyl-
(3'→5')-2'-OMe-uracylyl-(3'→5')-2'-deoxycytidylyl-
(3'→5')-2'-OMe-guanylyl-(3'→5')-2'-OMe-uracylyl-
(3'→5')-2'-OMe-uracylyl-(3'→5')-2'-OMe-adenylyl-
(3'→5')-2'-OMe-guanylyl-(3'→5')-2'-OMe-guanylyl-
(3'→5')-2'-OMe-uracylyl-(3'→5')-2'-OMe-guanylyl-
(3'→5')-2'-deoxycytidylyl-(3'→5')-2'-OMe-guanylyl-
(3'→5')-2'-OMe-uracylyl-(3'→5')-2'-OMe-adenylyl-
(3'→5')-2'-OMe-uracylyl-(3'→5')-2'-OMe-adenylyl-
(3'→5')-2'-OMe-uracylyl-(3'→5')-2'-OMe-adenylyl-6-aminohexylyl.

The chemical name of ARC19501 is N-(methoxy-polyethyleneglycol)-6-aminohexylyl-(1→5')-2'-OMe-guanylyl-
(3'→5')-2'-OMe-guanylyl-(3'→5')-2'-OMe-adenylyl-
(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-deoxycytidylyl-
(3'→5')-2'-OMe-uracylyl-(3'→5')-2'-OMe-uracylyl-
(3'→5')-2'-OMe-guanylyl-(3'→5')-2'-OMe-guanylyl-
(3'→5')-2'-deoxycytidylyl-(3'→5')-2'-OMe-uracylyl-
(3'→5')-2'-deoxycytidylyl-(3'→5')-2'-OMe-guanylyl-
(3'→5')-2'-OMe-uracylyl-(3'→5')-2'-OMe-uracylyl-
(3'→5')-2'-OMe-adenylyl-(3'→5')-2'-OMe-guanylyl-
(3'→5')-2'-OMe-guanylyl-(3'→5')-2'-OMe-uracylyl-
(3'→5')-2'-OMe-guanylyl-(3'→5')-2'-deoxycytidylyl-
(3'→5')-2'-OMe-guanylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-6-aminohexylyl-N-(methoxy-polyethyleneglycol).

The chemical name of ARC31301 is 2'-OMe-guanylyl-(3'→5')-2'-OMe-guanylyl-(3'→5')-2'-OMe-adenylyl-
(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-deoxycytidylyl-
(3'→5')-2'-OMe-uracylyl-(3'→5')-2'-OMe-uracylyl-
(3'→5')-2'-OMe-guanylyl-(3'→5')-2'-OMe-guanylyl-
(3'→5')-2'-OMe-cytidylyl-(3'→5')-2'-OMe-uracylyl-
(3'→5')-2'-deoxycytidylyl-(3'→5')-2'-OMe-guanylyl-
(3'→5')-2'-OMe-uracylyl-(3'→5')-2'-OMe-uracylyl-
(3'→5')-2'-OMe-adenylyl-(3'→5')-2'-OMe-guanylyl-
(3'→5')-2'-OMe-guanylyl-(3'→5')-2'-OMe-cytidylyl-
(3'→5')-2'-OMe-guanylyl-(3'→5')-2'-OMe-uracylyl-
(3'→5')-2'-OMe-adenylyl-(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-(3'→3')-2'-deoxythymidine.

The chemical name of ARC18546 is 2'-OMe-guanylyl-(3'→5')-2'-OMe-guanylyl-(3'→5')-2'-OMe-adenylyl-
(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-deoxycytidylyl-
(3'→5')-2'-OMe-uracylyl-(3'→5')-2'-OMe-uracylyl-
(3'→5')-2'-OMe-guanylyl-(3'→5')-2'-OMe-guanylyl-
(3'→5')-2'-OMe-cytidylyl-(3'→5')-2'-OMe-uracylyl-
(3'→5')-2'-deoxycytidylyl-(3'→5')-2'-OMe-guanylyl-
(3'→5')-2'-OMe-uracylyl-(3'→5')-2'-OMe-uracylyl-
(3'→5')-2'-OMe-adenylyl-(3'→5')-2'-OMe-guanylyl-
(3'→5')-2'-OMe-guanylyl-(3'→5')-2'-OMe-uracylyl-
(3'→5')-2'-OMe-guanylyl-(3'→5')-2'-OMe-cytidylyl-
(3'→5')-2'-OMe-guanylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-(3'→3')-2'-deoxythymidine.

The chemical name of ARC19881 is 6-aminohexylyl-(1→5')-2'-OMe-guanylyl-(3'→5')-2'-OMe-guanylyl-
(3'→5')-2'-OMe-adenylyl-(3'→5')-2'-OMe-adenylyl-
(3'→5')-2'-OMe-uracylyl-(3'→5')-2'-OMe-adenylyl-
(3'→5')-2'-OMe-uracylyl-(3'→5')-2'-OMe-adenylyl-
(3'→5')-2'-deoxycytidylyl-(3'→5')-2'-OMe-uracylyl-
(3'→5')-2'-OMe-uracylyl-(3'→5')-2'-OMe-guanylyl-
(3'→5')-2'-OMe-guanylyl-(3'→5')-2'-OMe-cytidylyl-
(3'→5')-2'-OMe-uracylyl-(3'→5')-2'-deoxycytidylyl-
(3'→5')-2'-OMe-guanylyl-(3'→5')-2'-OMe-uracylyl-
(3'→5')-2'-OMe-uracylyl-(3'→5')-2'-OMe-adenylyl-
(3'→5')-2'-OMe-guanylyl-(3'→5')-2'-OMe-guanylyl-
(3'→5')-2'-OMe-uracylyl-(3'→5')-2'-OMe-guanylyl-
(3'→5')-2'-OMe-cytidylyl-(3'→5')-2'-OMe-guanylyl-
(3'→5')-2'-OMe-uracylyl-(3'→5')-2'-OMe-adenylyl-
(3'→5')-2'-OMe-uracylyl-(3'→5')-2'-OMe-adenylyl-
(3'→5')-2'-OMe-uracylyl-(3'→5')-2'-OMe-adenylyl-
(3'→5')-(3'→3')-2'-deoxythymidine.

The chemical name of ARC19882 is N-(methoxy-polyethyleneglycol)-6-aminohexylyl-(1→5')-2'-OMe-guanylyl-
(3'→5')-2'-OMe-guanylyl-(3'→5')-2'-OMe-adenylyl-
(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-deoxycytidylyl-
(3'→5')-2'-OMe-uracylyl-(3'→5')-2'-OMe-uracylyl-
(3'→5')-2'-OMe-guanylyl-(3'→5')-2'-OMe-guanylyl-
(3'→5')-2'-OMe-cytidylyl-(3'→5')-2'-OMe-uracylyl-
(3'→5')-2'-deoxycytidylyl-(3'→5')-2'-OMe-guanylyl-
(3'→5')-2'-OMe-uracylyl-(3'→5')-2'-OMe-uracylyl-
(3'→5')-2'-OMe-adenylyl-(3'→5')-2'-OMe-guanylyl-
(3'→5')-2'-OMe-guanylyl-(3'→5')-2'-OMe-uracylyl-
(3'→5')-2'-OMe-guanylyl-(3'→5')-2'-OMe-cytidylyl-
(3'→5')-2'-OMe-guanylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-2'-OMe-uracylyl-
(3'→5')-2'-OMe-adenylyl-(3'→5')-(3'→3')-2'-deoxythymidine.

Figure 10A:
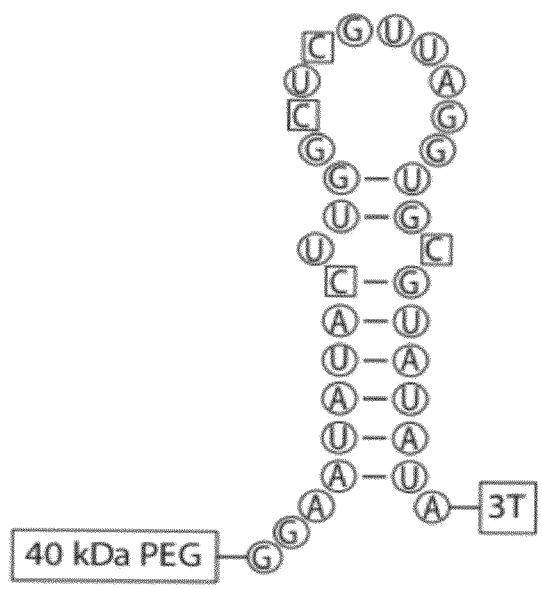
FIG. 10A is an illustration of a TFPI aptamer, which is comprised of 2'-O Methyl (circles) and 2'-deoxy (squares) nucleotides and is modified at its 5'-terminus with a 40 kDa PEG moiety and at its 3'-terminus with an inverted deoxythymidine residue (3T, which is also known in the art as idT).

The TFPI aptamers of the invention may have any secondary structure. Preferably, the TFPI aptamers comprise a stem and a loop motif, such as in FIGS. 10A and B. The putative secondary structure of ARC19499 is depicted in FIG. 10C, which comprises a stem and a loop motif.

Preferably, the TFPI aptamers are connected to one or more PEG moieties, with (FIG. 10B) or without (FIG. 10A) one or more linkers. The PEG moieties may be any type of PEG moiety. For example, the PEG moiety may be linear, branched, multiple branched, star shaped, comb shaped or a dendrimer. In addition, the PEG moiety may have any molecular weight. Preferably, the PEG moiety has a molecular weight ranging from 5-100 kDa in size. More preferably, the PEG moiety has a molecular weight ranging from 10-80 kDa in size. Even more preferably, the PEG moiety has a molecular weight ranging from 20-60 kDa in size. Yet even more preferably, the PEG moiety has a molecular weight ranging from 30-50 kDa in size. Most preferably, the PEG moiety has a molecular weight of 40 kDa in size. The same or different PEG moieties may be connected to a TFPI aptamer. The same or different linkers or no linkers may be used to connect the same or different PEG moieties to a TFPI aptamer Alternatively, the TFPI aptamers may be connected to one or more PEG alternatives (rather than to one or more PEG moieties), with or without one or more linkers. Examples of PEG alternatives include, but are not limited to, polyoxazoline (POZ), PolyPEG, hydroxyethylstarch (HES) and albumin. The PEG alternative may be any type of PEG alternative, but it should function the same as or similar to a PEG moiety, i.e., to reduce renal filtration and increase the half-life of the TFPI aptamer in the circulation. The same or different PEG alternatives may be connected to a TFPI aptamer. The same or different linkers or no linkers may be used to connect the same or different PEG alternatives to a TFPI aptamer. Alternatively, a combination of PEG moieties and PEG alternatives may be connected to a TFPI aptamer, with or without one or more of the same or different linkers.

Figure 10B:
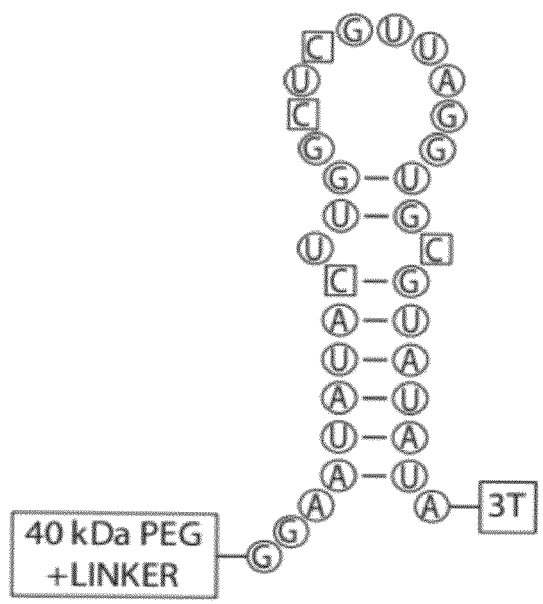
FIG. 10B is an illustration of a TFPI aptamer, which is comprised of 2'-O Methyl (circles) and 2'-deoxy (squares) nucleotides and is modified at its 5'-terminus with a 40 kDa PEG moiety and linker, and at its 3'-terminus with an inverted deoxythymidine residue (3T).
Figure 10C:
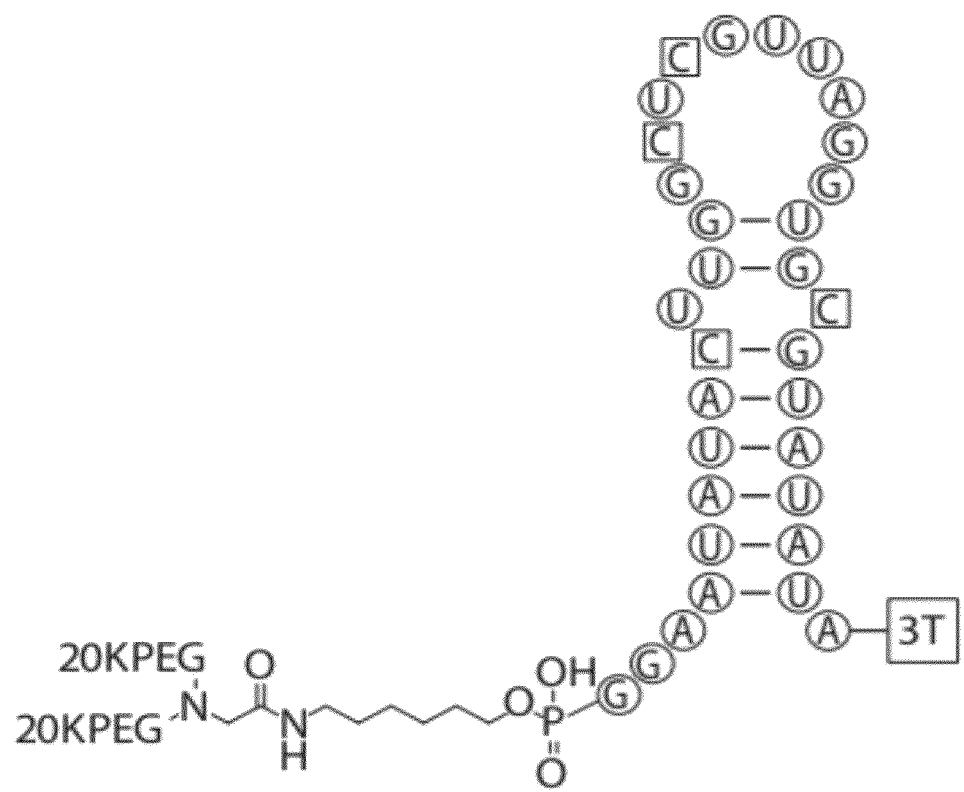
FIG. 10C is an illustration of the putative structure of ARC19499, which is comprised of 2'-O Methyl (circles) and 2'-deoxy (squares) nucleotides and is modified at its 5'-terminus with a 40 kDa branched PEG moiety and a hexylamine phosphate-containing linker, and at its 3'-terminus with an inverted deoxythymidine residue (3T).

Preferably, the TFPI aptamers are connected to a PEG moiety via a linker (FIG. 10B). However, the TFPI aptamers may be connected to a PEG moiety directly, without the use of a linker (FIG. 10A). The linker may be any type of molecule. Examples of linkers include, but are not limited to, amines, thiols and azides. For example, amines ($RNH_2$) and activated esters ($R'C(=O)OR''$) or anhydrides ($R'C(=O)OC(=O)R''$) can be used as linkers to yield an amide ($R'(C=O)NR$). Activated esters include, without limitation, NHS (N-hydroxysuccinimide) and sulfo derivatives of NHS, nitrophenyl esters and other substituted aromatic derivatives. Anhydrides can by cyclic, such as succinic acid anhydride derivatives. Amines ($RNH_2$) and activated carbonates ($R'OC(=O)OR''$) can be used to yield carbamates ($ROC(=O)NR$). Activated carbamates include, without limitation, NHS (N-hydroxysuccinimide) and sulfo derivatives of NHS, nitrophenyl carbamates. Amines ($RNH_2$) and isothiocyanates ($R'N=C=S$) can be used as linkers to yield isothioureas ($RNHC(=S)NHR'$). Amines ($RNH_2$) and isocyanates ($R'N=C=O$) can be used as linkers to yield isoureas ($RNH(C=O)NHR'$). Amines ($RNH_2$) and acyl azides ($R'(C=O)N_2$) can be used as linkers to yield amides ($RNH(C=O)R'$). Amines ($RNH_2$) and aldehydes or glyoxals ($R'(C=O)H$) can be used as linkers to yield imines ($R'CH=NR$) or amines via reduction ($R'CH_2=NHR$). Amines ($RNH_2$) and sulfonyl chlorides ($R'SO_2Cl$) can be used as linkers to yield sulfoamides ($R'SO_2NHR$). Amines ($RNH_2$) and epoxides and oxiranes can be used as linkers to give α-hydroxyamines. Thiols (RSH) and iodoacetyls ($R'(C=O)CH_2I$) can be used as linkers to yield thioethers ($RSCH_2(O=C)R'$). Thiols (RSH) and maleimides or maleimide derivatives can be used as linkers to give thioethers. Thiols (RSH) and aziridines can be used as linkers to give α-amine thioethers. Thiols (RSH) and acryloyl derivatives ($R'CH=CH2$) can be used as linkers to give thioethers ($R'CH_2CH_2SR$). Thiols (RSH) and disulfides (R'SSR") can be used as linkers to give disulfides (RSSR' or R"). Thiols (RSH) and vinylsulfones ($CH_2=CHSO_2R'$) can be used as linkers to yield thiol ethers ($RSCH_2CH_2SO_2R'$). Azides ($RN_3$) and alkynes ($R'C=H$) can be used as linkers to yield triazolines. Preferably, the linker contains a phosphate group. Preferably, the linker is from a 5'-amine linker phosphoramidite. In some embodiments, the 5'-amine linker phosphoramidite comprises 2-18 consecutive $CH_2$ groups. In more preferred embodiments, the 5'-amine linker phosphoramidite comprises 2-12 consecutive $CH_2$ groups. In even more preferred embodiments, the 5'-amine linker phosphoramidite comprises 4-8 consecutive $CH_2$ groups. In most preferred embodiments, the 5'-amine linker phosphoramidite comprises 6 consecutive $CH_2$ groups, i.e., is a 5'-hexylamine linker phosphoramidite. One or more of the same or different linkers or no linkers may be used to connect one or more of the same or different PEG moieties or one or more of the same or different PEG alternatives to a TFPI aptamer.

In preferred embodiments, an aptamer, or a salt thereof, comprising the following structure is provided:

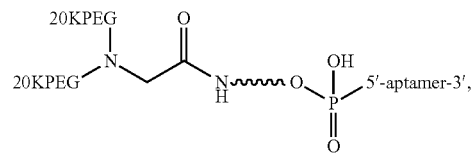

wherein HN〰〰$PO_3H$ is from a 5'-amine linker phosphoramidite, and the aptamer is a TFPI aptamer of the invention. The 20KPEG moiety can be any PEG moiety having a molecular weight of 20 kDa. Preferably, the 20KPEG moiety is a mPEG moiety having a molecular weight of 20 kDa.

In a particular embodiment, the aptamer, or a salt thereof, comprises the following structure:

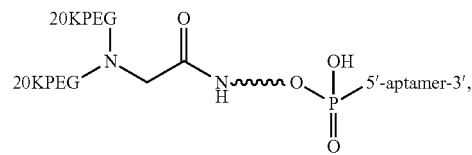

wherein HN〰〰$PO_3H$ is from a 5'-amine linker phosphoramidite, and the aptamer has the nucleic acid sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 2), wherein "3T" is an inverted deoxythymidine, "dN" is a deoxynucleotide and "mN" is a 2'-O Methyl containing nucleotide. In some embodiments, the 5'-amine linker phosphoramidite comprises 2-18 consecutive $CH_2$ groups. In more preferred embodiments, the 5'-amine linker phosphoramidite comprises 2-12 consecutive $CH_2$ groups. In even more preferred embodiments, the 5'-amine linker phosphoramidite comprises 4-8 consecutive $CH_2$ groups. In most preferred embodiments, the 5'-amine linker phosphoramidite comprises 6 consecutive $CH_2$ groups. The 20KPEG moiety can be any PEG moiety having a molecular weight of 20 kDa. Preferably, the 20KPEG moiety is a mPEG moiety having a molecular weight of 20 kDa.

In a particular embodiment, the aptamer, or a salt thereof, comprises the following structure:

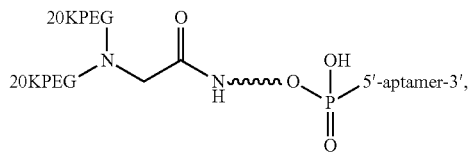

wherein HN~~~~PO₃H is from a 5'-amine linker phosphoramidite, and the aptamer has the nucleic acid sequence of mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA-3T (SEQ ID NO: 8), wherein "3T" is an inverted deoxythymidine, "dN" is a deoxynucleotide and "mN" is a 2'-O Methyl containing nucleotide. In some embodiments, the 5'-amine linker phosphoramidite comprises 2-18 consecutive CH₂ groups. In more preferred embodiments, the 5'-amine linker phosphoramidite comprises 2-12 consecutive CH₂ groups. In even more preferred embodiments, the 5'-amine linker phosphoramidite comprises 4-8 consecutive CH₂ groups. In most preferred embodiments, the 5'-amine linker phosphoramidite comprises 6 consecutive CH₂ groups. The 20KPEG moiety can be any PEG moiety having a molecular weight of 20 kDa. Preferably, the 20KPEG moiety is a mPEG moiety having a molecular weight of 20 kDa.

In alternative preferred embodiments, an aptamer, or a salt thereof, comprising the following structure is provided:

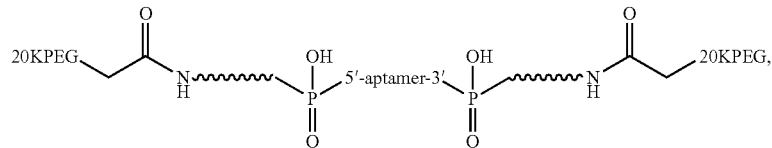

wherein HN~~~~PO₂H is from a 5'-amine linker phosphoramidite, and the aptamer is a TFPI aptamer of the invention. The 20KPEG moiety can be any PEG moiety having a molecular weight of 20 kDa. Preferably, the 20KPEG moiety is a mPEG moiety having a molecular weight of 20 kDa.

In a particular alternative embodiment, the aptamer, or a salt thereof, comprises the following structure:

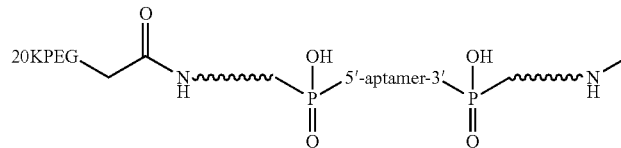

wherein HN~~~~PO₂H is from a 5'-amine linker phosphoramidite, and the aptamer has the nucleic acid sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA (SEQ ID NO: 1), wherein "dN" is a deoxynucleotide and "mN" is a 2'-O Methyl containing nucleotide. In some embodiments, the 5'-amine linker phosphoramidite comprises 2-18 consecutive CH₂ groups. In more preferred embodiments, the 5'-amine linker phosphoramidite comprises 2-12 consecutive CH₂ groups. In even more preferred embodiments, the 5'-amine linker phosphoramidite comprises 4-8 consecutive CH₂ groups. In most preferred embodiments, the 5'-amine linker phosphoramidite comprises 6 consecutive CH₂ groups. The 20KPEG moiety can be any PEG moiety having a molecular weight of 20 kDa. Preferably, the 20KPEG moiety is a mPEG moiety having a molecular weight of 20 kDa.

In more preferred embodiments, an aptamer, or a salt thereof, comprising the following structure is provided:

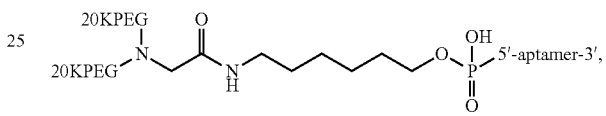

wherein the aptamer is a TFPI aptamer of the invention. The 20KPEG moiety can be any PEG moiety having a molecular weight of 20 kDa. Preferably, the 20KPEG moiety is a mPEG moiety having a molecular weight of 20 kDa.

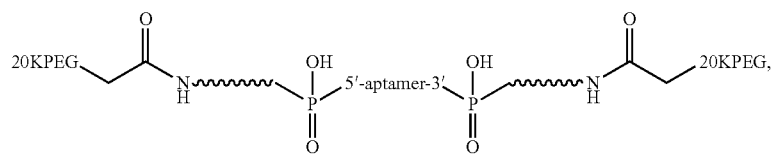

In a particular embodiment, the aptamer, or a salt thereof, comprises the following structure:

[Chemical structure: 20KPEG-N(20KPEG)-CH2-C(=O)-NH-(CH2)5-O-P(=O)(OH)-O-5'-aptamer-3']

wherein the aptamer has the nucleic acid sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 2), wherein "3T" is an inverted deoxythymidine, "dN" is a deoxynucleotide and "mN" is a 2'-O Methyl containing nucleotide. The 20KPEG moiety can be any PEG moiety having a molecular weight of 20 kDa. Preferably, the 20KPEG moiety is a mPEG moiety having a molecular weight of 20 kDa.

In a particular embodiment, the aptamer, or a salt thereof, comprises the following structure:

[Chemical structure: 20KPEG-N(20KPEG)-CH2-C(=O)-NH-(CH2)5-O-P(=O)(OH)-O-5'-aptamer-3']

wherein the aptamer has the nucleic acid sequence of mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA-3T (SEQ ID NO: 8), wherein "3T" is an inverted deoxythymidine, "dN" is a deoxynucleotide and "mN" is a 2'-O Methyl containing nucleotide. The 20KPEG moiety can be any PEG moiety having a molecular weight of 20 kDa. Preferably, the 20KPEG moiety is a mPEG moiety having a molecular weight of 20 kDa.

In alternative more preferred embodiments, an aptamer, or a salt thereof, comprising the following structure is provided:

[Chemical structure: 20KPEG-C(=O)-NH-(CH2)5-P(=O)(OH)-O-5'-aptamer-3'-O-P(=O)(OH)-(CH2)5-NH-C(=O)-20KPEG]

wherein the aptamer is a TFPI aptamer of the invention. The 20KPEG moiety can be any PEG moiety having a molecular weight of 20 kDa. Preferably, the 20KPEG moiety is a mPEG moiety having a molecular weight of 20 kDa.

In a particular alternative embodiment, the aptamer, or a salt thereof, comprises the following structure:

[Chemical structure: 20KPEG-C(=O)-NH-(CH2)5-P(=O)(OH)-O-5'-aptamer-3'-O-P(=O)(OH)-(CH2)5-NH-C(=O)-20KPEG]

wherein the aptamer has the nucleic acid sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA (SEQ ID NO: 1), wherein "dN" is a deoxynucleotide and "mN" is a 2'-O Methyl containing nucleotide. The 20KPEG moiety can be any PEG moiety having a molecular weight of 20 kDa. Preferably, the 20KPEG moiety is a mPEG moiety having a molecular weight of 20 kDa.

In most preferred embodiments, an aptamer, or a salt thereof, comprising the following structure is provided:

[Chemical structure: H3CO-(CH2CH2O)n-CH2-N(-C(=O)-(OCH2CH2)n-OCH3)-C(=O)-NH-(CH2)5-O-P(=O)(OH)-O-5'-aptamer-3']

wherein "n" is about 454 ethylene oxide units (PEG=20 kDa), and the aptamer is a TFPI aptamer of the invention. "n" is about 454 ethylene oxide units because the number of n's may vary slightly for a PEG having a particular molecular weight. Preferably, "n" ranges from 400-500 ethylene oxide units. More preferably, "n" ranges from 425-475 ethylene oxide units. Even more preferably, "n" ranges from 440-460 ethylene oxide units. Most preferably, "n" is 454 ethylene oxide units.

In a particular embodiment, the aptamer, or a salt thereof, comprises the following structure:

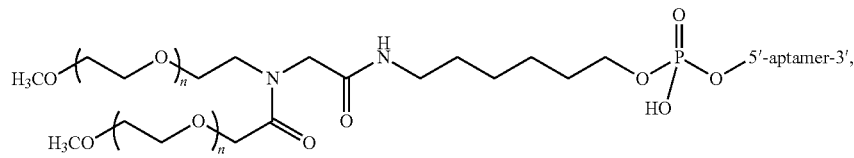

wherein the aptamer has the nucleic acid sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 2), wherein "n" is approximately 450, "3T" is an inverted deoxythymidine, "dN" is a deoxynucleotide and "mN" is a 2'-O Methyl containing nucleotide. This aptamer is also known as ARC19499.

In a particular embodiment, the aptamer, or a salt thereof, comprises the following structure:

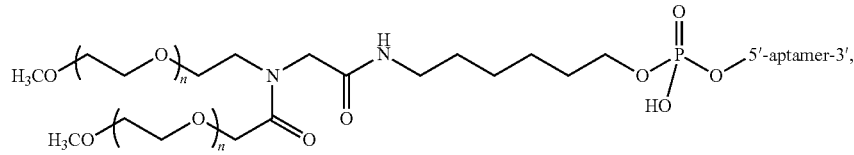

wherein the aptamer has the nucleic acid sequence of mG-mG-mA-mA-mU-mA-mU-mA-dC-mU-mU-mG-mG-mC-mU-dC-mG-mU-mU-mA-mG-mG-mU-mG-mC-mG-mU-mA-mU-mA-mU-mA-3T (SEQ ID NO: 8), wherein "n" is approximately 450, "3T" is an inverted deoxythymidine, "dN" is a deoxynucleotide and "mN" is a 2'-O Methyl containing nucleotide. This aptamer is also known as ARC19882.

In alternative most preferred embodiments, an aptamer, or a salt thereof, comprising the following structure is provided:

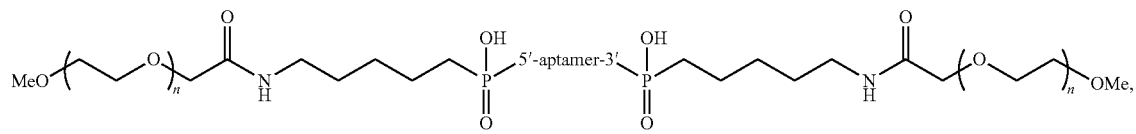

wherein "n" is about 454 ethylene oxide units (PEG=20 kDa), and the aptamer is a TFPI aptamer of the invention. "n" is about 454 ethylene oxide units because the number of n's may vary slightly for a PEG having a particular molecular weight. Preferably, "n" ranges from 400-500 ethylene oxide units. More preferably, "n" ranges from 425-475 ethylene oxide units. Even more preferably, "n" ranges from 440-460 ethylene oxide units. Most preferably, "n" is 454 ethylene oxide units.

In a particular alternative embodiment, the aptamer, or a salt thereof, comprises the following structure:

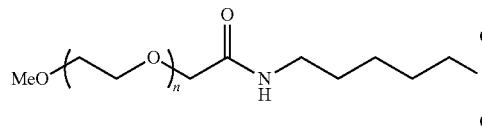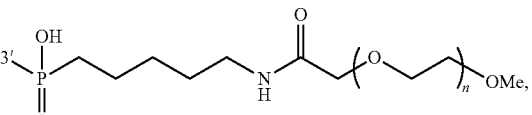

wherein the aptamer has the nucleic acid sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA (SEQ ID NO: 1), wherein "n" is approximately 450, "dN" is a deoxynucleotide and "mN" is a 2'-O Methyl containing nucleotide. This aptamer is also known as ARC19501.

The invention also provides aptamers that have substantially the same ability to bind to TFPI as any one of the aptamers shown in SEQ ID NOs: 1, 2, 3, 4, 5, 6, 7, 8, 9 or 10. In some embodiments, the aptamers have substantially the same structure as any one of the aptamers shown in SEQ ID NOs: 1, 2, 3, 4, 5, 6, 7, 8, 9 or 10. In some embodiments, the aptamers have substantially the same ability to bind to TFPI and substantially the same structure as any one of the aptamers shown in SEQ ID NOs: 1, 2, 3, 4, 5, 6, 7, 8, 9 or 10. The invention also provides aptamers that have substantially the same ability to bind to TFPI and substantially the same ability to modulate a biological function of TFPI as any one of the aptamers shown in SEQ ID NOs: 1, 2, 3, 4, 5, 6, 7, 8, 9 or 10. The invention further provides aptamers that have substantially the same ability to bind to TFPI and substantially the same ability to modulate blood coagulation as any one of the aptamers shown in SEQ ID NOs: 1, 2, 3, 4, 5, 6, 7, 8, 9 or 10. The invention also provides aptamers that have substantially the same structure and substantially the same ability to modulate a biological function of TFPI as any one of the aptamers shown in SEQ ID NOs: 1, 2, 3, 4, 5, 6, 7, 8, 9 or 10. The invention also provides aptamers that have substantially the same structure and substantially the same ability to modulate blood coagulation as any one of the aptamers shown in SEQ ID NOs: 1, 2, 3, 4, 5, 6, 7, 8, 9 or 10. In some embodiments, the aptamers have substantially the same ability to bind to TFPI, substantially the same structure and substantially the same ability to modulate a biological function of TFPI as any one of the aptamers shown in SEQ ID NOs: 1, 2, 3, 4, 5, 6, 7, 8, 9 or 10. In some embodiments, the aptamers have substantially the same ability to bind to TFPI, substantially the same structure and substantially the same ability to modulate blood coagulation as any one of the aptamers shown in SEQ ID NOs: 1, 2, 3, 4, 5, 6, 7, 8, 9 or 10. As used herein, substantially the same ability to bind to TFPI means that the affinity is within one or two orders of magnitude of the affinity of the nucleic acid sequences and/or aptamers described herein. It is well within the skill of those of ordinary skill in the art to determine whether a given sequence has substantially the same ability to bind to TFPI. In some embodiments, the aptamer that binds to TFPI has a nucleic acid sequence at least 70%, 80%, 90% or 95% identical to SEQ ID NOs: 1, 2, 3, 4, 5, 6, 7, 8, 9 or 10.

The ability of an aptamer to bind to TFPI may be assessed in a binding-competition assay, e.g., as described in Example 34, in which one of the aptamers shown in SEQ ID NOs: 1, 2, 3, 4, 5, 6, 7, 8, 9 or 10 may be selected as the competitor acting as a control aptamer. For example, a suitable assay may involve incubating 10 nM human TFPI (American Diagnos-tica, Stamford, Conn., catalog #4500PC) with trace amounts of radiolabeled control aptamer and 5000 nM, 16667 nM, 556 nM, 185 nM, 61.7 nM, 20.6 nM, 6.86 nM, 2.29 nM, 0.76 nM or 0.25 nM of unlabeled competitor aptamer. A control aptamer is included in each experiment. For each molecule, the percentage of radiolabeled control aptamer bound at each competitor aptamer concentration is used for analysis. The percentage of radiolabeled control aptamer bound is plotted as a function of aptamer concentration and fitted to the equation $y=(max/(1+x/IC_{50}))+int$, where y=the percentage of radiolabeled control aptamer bound, x=the concentration of aptamer, max=the maximum radiolabeled control aptamer bound, and int=the y-intercept, to generate an $IC_{50}$ value for binding-competition. The $IC_{50}$ of each aptamer is compared to the $IC_{50}$ of the control aptamer evaluated in the same experiment. An aptamer having substantially the same ability to bind may include an aptamer having an $IC_{50}$ that is within one or two orders of magnitude of the $IC_{50}$ of the control aptamer, and/or an aptamer having an $IC_{50}$ that is not more than 5-fold greater than that of the control aptamer evaluated in the same experiment.

The ability of an aptamer to modulate a biological function and/or to modulate blood coagulation may be assessed in a calibrated automated thrombogram (CAT) assay, e.g., as described in Example 34, in which one of the aptamers shown in SEQ ID NOs: 1, 2, 3, 4, 5, 6, 7, 8, 9 or 10 may be selected as a control aptamer. For example, a suitable assay may involve evaluation in a CAT assay in pooled hemophilia A plasma at 500 nM, 167 nM, 55.6 nM, 18.5 nM, 6.17 nM and 2.08 nM aptamer concentration. A control aptamer is included in each experiment. For each molecule, the endogenous thrombin potential (ETP) and peak thrombin values at each aptamer concentration are used for analysis. The ETP or peak thrombin value for hemophilia A plasma alone is subtracted from the corresponding value in the presence of aptamer for each molecule at each concentration. Then, the corrected ETP and peak values are plotted as a function of aptamer concentration and fitted to the equation $y=(max/(1+IC_{50}/x))+int$, where y=ETP or peak thrombin, x=concentration of aptamer, max=the maximum ETP or peak thrombin, and int=the y-intercept, to generate an $IC_{50}$ value for both the ETP and the peak thrombin. The $IC_{50}$ of each aptamer is compared to the $IC_{50}$ of the control aptamer that is evaluated in the same experiment. An aptamer having substantially the same ability to modulate a biological function and/or to modulate blood coagulation may include an aptamer having an $IC_{50}$ that is within one or two orders of magnitude of the $IC_{50}$ of the control aptamer, and/or an aptamer for which one or both of the ETP and peak thrombin $IC_{50}$ of that molecule are not more than 5-fold greater than that of the control aptamer evaluated in the same experiment.

The ability of an aptamer to modulate a biological function and/or to modulate blood coagulation may be assessed by evaluating inhibition of TFPI in a Factor Xa (FXa) activity assay, e.g., as described in Example 34, in which one of the aptamers shown in SEQ ID NOs: 1, 2, 3, 4, 5, 6, 7, 8, 9 or 10 may be selected as a control aptamer. A suitable assay may involve measuring the ability of FXa to cleave a chromogenic substrate in the presence and absence of TFPI, with or without the addition of aptamer. For example, 2 nM human FXa is incubated with 8 nM human TFPI. Then, 500 μM chromogenic substrate and aptamers are added and FXa cleavage of the substrate is measured by absorbance at 405 nm ($A_{405}$) as a function of time. Aptamers are tested at 500 nM, 125 nM, 31.25 nM, 7.81 nM, 1.95 nM and 0.49 nM concentrations. A control aptamer is included in each experiment. For each aptamer concentration, the $A_{405}$ is plotted as a function of time and the linear region of each curve is fitted to the equation y=mx+b, where y=$A_{405}$, x=the aptamer concentration, m=the rate of substrate cleavage, and b=the y-intercept, to generate a rate of FXa substrate cleavage. The rate of FXa substrate cleavage in the presence of TFPI and the absence of aptamer is subtracted from the corresponding value in the presence of both TFPI and aptamer for each molecule at each concentration. Then, the corrected rates are plotted as a function of aptamer concentration and fitted to the equation y=($V_{max}$/(1+$IC_{50}$/x)), where y=the rate of substrate cleavage, x=concentration of aptamer, and $V_{max}$=the maximum rate of substrate cleavage, to generate an $IC_{50}$ and maximum ($V_{max}$) value. The $IC_{50}$ and $V_{max}$ values of each aptamer are compared to the $IC_{50}$ and $V_{max}$ values of the control aptamer evaluated in the same experiment. An aptamer having substantially the same ability to modulate a biological function and/or to modulate blood coagulation may include an aptamer having an $IC_{50}$ that is within one or two orders of magnitude of the $IC_{50}$ of the control aptamer, and/or an aptamer having an $IC_{50}$ that is not more than 5-fold greater than that of the control aptamer evaluated in the same experiment, and/or an aptamer having a $V_{max}$ value not less than 80% of the $V_{max}$ value of the control aptamer evaluated in the same experiment.

The terms "sequence identity" or "% identity", in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For sequence comparison, typically one sequence acts as a reference sequence to which test sequences are compared. Optimal alignment of sequences for comparison can be conducted, e.g., by the local homology algorithm of Smith & Waterman, Adv. Appl. Math. 2: 482 (1981); by the homology alignment algorithm of Needleman & Wunsch, J. Mol. Biol. 48: 443 (1970); by the search for similarity method of Pearson & Lipman, Proc. Nat'l. Acad. Sci. USA 85: 2444 (1988); by computerized implementations of these algorithms (GAP, BESTFIT, FASTA, and TFASTA in the Wisconsin Genetics Software Package, Genetics Computer Group, 575 Science Dr., Madison, Wis.); or by visual inspection (see generally, Ausubel, F. M. et al., Current Protocols in Molecular Biology, pub. by Greene Publishing Assoc. and Wiley-Interscience (1987)).

One example of an algorithm that is suitable for determining percent sequence identity is the algorithm used in the basic local alignment search tool (hereinafter "BLAST"), see, e.g. Altschul et al., J. Mol. Biol. 215: 403-410 (1990) and Altschul et al., Nucleic Acids Res., 15: 3389-3402 (1997), which is publicly available through the National Center for Biotechnology Information (hereinafter "NCBI").

Aptamers of the invention including, but not limited to, aptamers identified by the SELEX™ method, 2'-Modified SELEX™, minimized aptamers, optimized aptamers and chemically substituted aptamers, can be manufactured using any oligonucleotide synthesis technique that is well known in the art, such as solid phase oligonucleotide synthesis techniques (see, e.g., Gualtiere, F. Ed., New Trends in Synthetic Medicinal Chemistry, Ch. 9, Chemistry of Antisense Oligonucleotides, p. 261-335, 2000, Wiley-VCH, New York). The manufacturing of aptamers using solid phase oligonucleotide synthesis techniques can also be done at commercial scale. Solution phase methods, such as triester synthesis methods (see, e.g., Sood et al., Nucl. Acid Res. 4:2557 (1977) and Hirose et al., Tet. Lett., 28:2449 (1978)), may also be used to manufacture aptamers of the invention, as well as recombinant means.

In addition, a variety of functional groups can be introduced during the solid phase synthesis. The functionality can be a simple linker that results in a functional group, such as an amine or thiol, or may be a more complex construct, such as a biotin or a fluorescent dye. Typically, functional group linkers or more complex moieties are introduced using a phosphoramidite, or they can be introduced post-synthetically (i.e., after solid phase synthesis). Alternatively, by utilizing a modified solid support, a variety of functionalities can be introduced at the 3'-end of the oligonucleotide, thereby enabling a wider variety of conjugation techniques.

The invention further provides aptamers that have been identified by the SELEX™ process, which comprises the steps of (a) contacting a mixture of nucleic acids with TFPI under conditions in which binding occurs; (b) partitioning unbound nucleic acids from those nucleic acids that have bound to TFPI; (c) amplifying the bound nucleic acids to yield a ligand-enriched mixture of nucleic acids; and, optionally, (d) reiterating the steps of binding, partitioning and amplifying through as many cycles as desired to obtain aptamer(s) that bind to TFPI.

The invention further provides methods for identifying aptamers that bind at least in part to or otherwise interact with one or more portions of TFPI, which comprise the steps of (a) contacting a mixture of nucleic acids with one or more portions of TFPI under conditions in which binding occurs; (b) partitioning unbound nucleic acids from those nucleic acids that have bound to TFPI; (c) amplifying the bound nucleic acids to yield a ligand-enriched mixture of nucleic acids; and, optionally, (d) reiterating the steps of contacting, partitioning and amplifying through as many cycles as desired, to obtain aptamer(s) that bind to a portion of TFPI. This method may also include intervening or additional cycles with binding to full-length TFPI, followed by partitioning and amplification. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. Preferably, the one or more portions of mature TFPI (for example, FIG. 3A) are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The aptamer preferably comprises a dissociation constant for human TFPI or a variant or one or more portions thereof, of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

The invention also provides methods for identifying aptamers that bind at least in part to or otherwise interact with one or more portions of TFPI, which comprise the steps of (a) contacting a mixture of nucleic acids with full-length TFPI or one or more portions of TFPI under conditions in which binding occurs; (b) partitioning unbound nucleic acids from those nucleic acids that have bound to full-length TFPI or one or more portions of TFPI; (c) specifically eluting the bound nucleic acids with full-length TFPI or a portion of TFPI, or a ligand that binds to full-length TFPI or a portion of TFPI; (d) amplifying the bound nucleic acids to yield a ligand-enriched mixture of nucleic acids; and, optionally, (e) reiterating the steps of contacting, partitioning, eluting and amplifying through as many cycles as desired to obtain aptamer(s) that bind to one or more portions of TFPI. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. Preferably, the one or more portions of mature TFPI (for example, FIG. 3A) are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The aptamer preferably comprises a dissociation constant for human TFPI or a variant or one or more portions thereof of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

The invention further provides methods for identifying aptamers that bind at least in part to or otherwise interact with one or more portions of TFPI, which comprise the steps of (a) contacting a mixture of nucleic acids with full-length TFPI or one or more portions of TFPI under conditions in which binding occurs in the presence of a TFPI ligand (a ligand that binds to TFPI) that blocks one or more epitopes on TFPI from aptamer binding; (b) partitioning unbound nucleic acids from those nucleic acids that have bound to full-length TFPI or one or more portions of TFPI; (c) amplifying the bound nucleic acids to yield a ligand-enriched mixture of nucleic acids; and, optionally, (d) reiterating the steps of contacting, partitioning and amplifying through as many cycles as desired to obtain aptamer(s) that bind to one or more portions of TFPI. In other embodiments of this method, inclusion of a TFPI ligand that blocks one or more portions on TFPI from aptamer binding can occur during the contacting step, the partitioning step, or both. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. Preferably, the one or more portions of mature TFPI (for example, FIG. 3A) are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The aptamer preferably comprises a dissociation constant for human TFPI or a variant or one or more portions thereof of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

The invention further provides methods for identifying aptamers that bind at least in part to or otherwise interact with one or more portions of TFPI, which comprise the steps of (a) contacting a mixture of nucleic acids with full-length TFPI or one or more portions of TFPI under conditions in which binding occurs; (b) partitioning unbound nucleic acids from those nucleic acids that have bound to full-length TFPI or one or more portions of TFPI; (c) partitioning bound nucleic acids that have a desired functional property from bound nucleic acids that do not have a desired functional property; (d) amplifying the bound nucleic acids that have a desired functional property to yield a ligand-enriched mixture of nucleic acids; and, optionally, (e) reiterating the steps of contacting, partitioning, partitioning and amplifying through as many cycles as desired to obtain aptamer(s) that bind to one or more portions of TFPI. Steps (b) and (c) can occur sequentially or simultaneously. For example, the TFPI aptamers may bind to or otherwise interact with a linear portion or a conformational portion of TFPI. A TFPI aptamer binds to or otherwise interacts with a linear portion of TFPI when the aptamer binds to or otherwise interacts with a contiguous stretch of amino acid residues that are linked by peptide bonds. A TFPI aptamer binds to or otherwise interacts with a conformational portion of TFPI when the aptamer binds to or otherwise interacts with non-contiguous amino acid residues that are brought together by folding or other aspects of the secondary and/or tertiary structure of the polypeptide chain. Preferably, the one or more portions of mature TFPI (for example, FIG. 3A) are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The aptamer preferably comprises a dissociation constant for human TFPI or a variant or one or more portions thereof of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

The invention also provides an aptamer that binds to a human tissue factor pathway inhibitor (TFPI) polypeptide having the amino acid sequence of SEQ ID NO: 11, wherein the aptamer modulates TFPI-mediated inhibition of blood coagulation, and wherein the aptamer competes for binding to TFPI with a reference aptamer comprising a nucleic acid sequence selected from the group consisting of: SEQ ID NO: 4 (ARC19499), SEQ ID NO: 1 (ARC26835), SEQ ID NO: 2 (ARC17480), SEQ ID NO: 3 (ARC19498), SEQ ID NO: 5 (ARC19500), SEQ ID NO:6 (ARC19501), SEQ ID NO: 7 (ARC31301), SEQ ID NO: 8 (ARC18546), SEQ ID NO: 9 (ARC19881) and SEQ ID NO: 10 (ARC19882). Preferably, the reference aptamer comprises the nucleic acid sequence of SEQ ID NO: 4 (ARC19499).

The invention further provides an aptamer that binds to a human tissue factor pathway inhibitor (TFPI) polypeptide having the amino acid sequence of SEQ ID NO: 11, wherein the aptamer binds to a linear portion or a conformational portion of TFPI in which at least a portion of the region recognized by the aptamer is different than the TFPI region bound by Factor VIIa, Factor Xa, or both Factor VIIa and Factor Xa. Preferably, the aptamer binds to one or more regions comprising at least a portion of the amino acid sequence of SEQ ID NO: 11 selected from the group consisting of: amino acid residues 148-170, amino acid residues 150-170, amino acid residues 155-175, amino acid residues 160-180, amino acid residues 165-185, amino acid residues 170-190, amino acid residues 175-195, amino acid residues 180-200, amino acid residues 185-205, amino acid residues 190-210, amino acid residues 195-215, amino acid residues 200-220, amino acid residues 205-225, amino acid residues 210-230, amino acid residues 215-235, amino acid residues 220-240, amino acid residues 225-245, amino acid residues 230-250, amino acid residues 235-255, amino acid residues 240-260, amino acid residues 245-265, amino acid residues 250-270, amino acid residues 255-275, amino acid residues 260-276, amino acid residues 148-175, amino acid residues 150-175, amino acid residues 150-180, amino acid residues 150-185, amino acid residues 150-190, amino acid residues 150-195, amino acid residues 150-200, amino acid residues 150-205, amino acid residues 150-210, amino acid residues 150-215, amino acid residues 150-220, amino acid residues 150-225, amino acid residues 150-230, amino acid residues 150-235, amino acid residues 150-240, amino acid residues 150-245, amino acid residues 150-250, amino acid residues 150-255, amino acid residues 150-260, amino acid residues 150-265, amino acid residues 150-270, amino acid residues 150-275, amino acid residues 150-276, amino acid residues 190-240, amino acid residues 190-276, amino acid residues 240-276, amino acid residues 242-276, amino acid residues 161-181, amino acid residues 162-181, amino acid residues 182-240, amino acid residues 182-241, and amino acid residues 182-276. More preferably, the aptamer competes with a reference aptamer comprising the nucleic acid sequence of SEQ ID NO: 4 (ARC19499) for binding to TFPI.

The invention also provides an aptamer that binds to the same region on a human tissue factor pathway inhibitor (TFPI) polypeptide having the amino acid sequence of SEQ ID NO: 11 as the region bound by a TFPI aptamer comprising the nucleic acid sequence of SEQ ID NO: 4 (ARC19499).

The invention further provides an aptamer that binds to a region on a human tissue factor pathway inhibitor (TFPI) polypeptide comprising one or more portions of SEQ ID NO: 11, wherein the one or more portions is selected from the group consisting of: amino acid residues 148-170, amino acid residues 150-170, amino acid residues 155-175, amino acid residues 160-180, amino acid residues 165-185, amino acid residues 170-190, amino acid residues 175-195, amino acid residues 180-200, amino acid residues 185-205, amino acid residues 190-210, amino acid residues 195-215, amino acid residues 200-220, amino acid residues 205-225, amino acid residues 210-230, amino acid residues 215-235, amino acid residues 220-240, amino acid residues 225-245, amino acid residues 230-250, amino acid residues 235-255, amino acid residues 240-260, amino acid residues 245-265, amino acid residues 250-270, amino acid residues 255-275, amino acid residues 260-276, amino acid residues 148-175, amino acid residues 150-175, amino acid residues 150-180, amino acid residues 150-185, amino acid residues 150-190, amino acid residues 150-195, amino acid residues 150-200, amino acid residues 150-205, amino acid residues 150-210, amino acid residues 150-215, amino acid residues 150-220, amino acid residues 150-225, amino acid residues 150-230, amino acid residues 150-235, amino acid residues 150-240, amino acid residues 150-245, amino acid residues 150-250, amino acid residues 150-255, amino acid residues 150-260, amino acid residues 150-265, amino acid residues 150-270, amino acid residues 150-275, amino acid residues 150-276, amino acid residues 190-240, amino acid residues 190-276, amino acid residues 240-276, amino acid residues 242-276, amino acid residues 161-181, amino acid residues 162-181, amino acid residues 182-240, amino acid residues 182-241, and amino acid residues 182-276.

The invention additionally provides an aptamer that binds to human tissue factor pathway inhibitor (TFPI) and exhibits one or more of the following properties: a) competes for binding to TFPI with any one of SEQ ID NOs: 1-10; b) inhibits TFPI inhibition of Factor Xa; c) increases thrombin generation in hemophilia plasma; d) inhibits TFPI inhibition of the intrinsic tenase complex; e) restores normal hemostasis, as measured by thromboelastography (TEG®) in whole blood and plasma; f) restores normal clotting, as indicated by shorter clot time, more rapid clot formation or more stable clot development, as measured by thromboelastography (TEG®) or rotational thromboelastometry (ROTEM) in whole blood and plasma; or g) decreases the clot time, as measured by dilute prothrombin time (dPT), tissue factor activated clotting time (TF-ACT) or any other TFPI-sensitive clot-time measurement.

The invention also provides an aptamer that binds to human tissue factor pathway inhibitor wherein the aptamer competes for binding to TFPI with a reference aptamer selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

The invention further provides an aptamer that binds to tissue factor pathway inhibitor (TFPI) wherein the aptamer competes, either directly or indirectly, for binding to TFPI with a reference antibody selected from the group consisting of: AD4903.

The invention also provides an aptamer that binds to human tissue factor pathway inhibitor (TFPI) and comprises a stem and loop motif having the nucleotide sequence of SEQ ID NO: 4, wherein: a) any one or more of nucleotides 1, 2, 3, 4, 6, 8, 11, 12, 13, 17, 20, 21, 22, 24, 28, 30 and 32 may be modified from a 2'-OMe substitution to a 2'-deoxy substitution; b) any one or more of nucleotides 5, 7, 15, 19, 23, 27, 29 and 31 may be modified from a 2'-OMe uracil to either a 2'-deoxy uracil or a 2'-deoxy thymine; c) nucleotide 18 may be modified from a 2'-OMe uracil to a 2'-deoxy uracil; and/or d) any one or more of nucleotides 14, 16 and 25 may be modified from a 2'-deoxy cytosine to either a 2'-OMe cytosine or a 2'-fluoro cytosine.

The invention additionally provides an aptamer that binds to human tissue factor pathway inhibitor (TFPI) and comprises nucleotides 7-28 of SEQ ID NO: 2.

The invention further provides a method for treating a bleeding disorder comprising administering any one of the above aptamers.

The invention further provides an aptamer that binds to tissue factor pathway inhibitor (TFPI), wherein the aptamer comprises a primary nucleic acid sequence selected from the group consisting of SEQ ID NOs.: 4, 1, 2, 3, 5, 6, 7, 8, 9 and 10. A primary nucleic acid sequence of an aptamer refers solely to the nucleotides (adenine, guanine, cytosine, uracil, thymine), without any modifications (such as a 2'-O Methyl, 2'-fluoro modification, 3T or PEG).

Aptamer Medicinal Chemistry

Once aptamers that bind to TFPI are identified, several techniques may be optionally performed in order to further increase binding, stability, potency and/or functional characteristics of the identified aptamer sequences.

Aptamers that bind to TFPI may be truncated in order to obtain the minimal aptamer sequence having the desired binding and/or functional characteristics (also referred to herein as a "minimized construct" or a "minimized aptamer"). One method of accomplishing this is by using folding programs and sequence analysis, e.g., aligning clone sequences resulting from a selection to look for conserved motifs and/or covariation to inform the design of minimized constructs. Suitable folding programs include, for example, the RNA structure program (Mathews, D. H.; Disney, M. D.; Childs, J. L.; Schroeder, S. J.; Zuker, M.; and Turner, D. H., "Incorporating chemical modification constraints into a dynamic programming algorithm for prediction of RNA secondary structure," 2004. *Proceedings of the National Academy of Sciences, US,* 101, 7287-7292). Biochemical probing experiments can also be performed in order to determine the 5' and 3' boundaries of an aptamer sequence to inform the design of minimized constructs. Minimized constructs can then be chemically synthesized and tested for binding and functional characteristics, as compared to the non-minimized sequence from which they were derived. Variants of an aptamer sequence containing a series of 5', 3' and/or internal deletions may also be directly chemically synthesized and tested for binding and/or functional characteristics, as compared to the non-minimized aptamer sequence from which they were derived.

Additionally, doped reselections may be used to explore the sequence requirements within a single active aptamer sequence or a single minimized aptamer sequence. Doped reselections are performed using a synthetic, degenerate pool that has been designed based on the single sequence of interest. The level of degeneracy usually varies 70% to 85% from the wild type sequence, i.e., the single sequence of interest. In general, sequences with neutral mutations are identified through the doped reselection process, but in some cases sequence changes can result in improvements in affinity. The composite sequence information from clones identified using doped reselections can then be used to identify the minimal binding motif and aid in optimization efforts.

Aptamer sequences and/or minimized aptamer sequences may also be optimized post-SELEX™ using aptamer medicinal chemistry to perform random or directed mutagenesis of the sequence to increase binding affinity and/or functional characteristics, or alternatively to determine which positions in the sequence are essential for binding activity and/or functional characteristics.

Aptamer medicinal chemistry is an aptamer improvement technique in which sets of variant aptamers are chemically synthesized. These sets of variants typically differ from the parent aptamer by the introduction of a single substituent, and differ from each other by the location of this substituent. These variants are then compared to each other and to the parent. Improvements in characteristics may be profound enough that the inclusion of a single substituent may be all that is necessary to achieve a particular therapeutic criterion.

Alternatively the information gleaned from the set of single variants may be used to design further sets of variants in which more than one substituent is introduced simultaneously. In one design strategy, all of the single substituent variants are ranked, the top 4 are chosen and all possible double (6), triple (4) and quadruple (1) combinations of these 4 single substituent variants are synthesized and assayed. In a second design strategy, the best single substituent variant is considered to be the new parent and all possible double substituent variants that include this highest-ranked single substituent variant are synthesized and assayed. Other strategies may be used, and these strategies may be applied repeatedly such that the number of substituents is gradually increased while continuing to identify further-improved variants.

Aptamer medicinal chemistry may be used particularly as a method to explore the local, rather than the global, introduction of substituents. Because aptamers are discovered within libraries that are generated by transcription, any substituents that are introduced during the SELEX™ process must be introduced globally. For example, if it is desired to introduce phosphorothioate linkages between nucleotides then they can only be introduced at every A (or every G, C, T, U, etc.) if globally substituted. Aptamers that require phosphorothioates at some As (or some G, C, T, U, etc.) (locally substituted) but cannot tolerate it at other As (or some G, C, T, U, etc.) cannot be readily discovered by this process.

The kinds of substituents that can be utilized by the aptamer medicinal chemistry process are only limited by the ability to introduce them into an oligomer synthesis scheme. The process is certainly not limited to nucleotides alone. Aptamer medicinal chemistry schemes may include substituents that introduce steric bulk, hydrophobicity, hydrophilicity, lipophilicity, lipophobicity, positive charge, negative charge, neutral charge, zwitterions, polarizability, nuclease-resistance, conformational rigidity, conformational flexibility, protein-binding characteristics, mass, etc. Aptamer medicinal chemistry schemes may include base-modifications, sugar-modifications or phosphodiester linkage-modifications.

When considering the kinds of substituents that are likely to be beneficial within the context of a therapeutic aptamer, it may be desirable to introduce substitutions that fall into one or more of the following categories:
  (1) Substituents already present in the body, e.g., 2'-deoxy, 2'-ribo, 2'-O-methyl nucleotides, inosine or 5-methyl cytosine;
  (2) Substituents already part of an approved therapeutic, e.g., 2'-fluoro nucleotides; or
  (3) Substituents that hydrolyze, degrade or metabolize to one of the above two categories, e.g., methylphosphonate-linked oligonucleotides or phosphorothioate-linked oligonucleotides.

The aptamers of the invention include aptamers developed through aptamer medicinal chemistry, as described herein.

Target binding affinity of the aptamers of the invention can be assessed through a series of binding reactions between the aptamer and the target (e.g., a protein) in which trace $^{32}$P-labeled aptamer is incubated with a dilution series of the target in a buffered medium and then analyzed by nitrocellulose filtration using a vacuum filtration manifold. Referred to herein as the dot blot binding assay, this method uses a three layer filtration medium consisting (from top to bottom) of nitrocellulose, nylon filter and gel blot paper. Aptamer that is bound to the target is captured on the nitrocellulose filter, whereas the non-target bound aptamer is captured on the nylon filter. The gel blot paper is included as a supporting medium for the other filters. Following filtration, the filter layers are separated, dried and exposed on a phosphor screen and quantified using a phosphorimaging system. The quantified results can be used to generate aptamer binding curves from which dissociation constants ($K_D$) can be calculated. In a preferred embodiment, the buffered medium used to perform the binding reactions is 1× Dulbecco's PBS (with $Ca^{++}$ and $Mg^{++}$) plus 0.1 mg/mL BSA.

Generally, the ability of an aptamer to modulate the functional activity of a target can be assessed using in vitro and in vivo models, which will vary depending on the biological function of the target. In some embodiments, the aptamers of the invention may inhibit a known biological function of the target. In other embodiments, the aptamers of the invention may stimulate a known biological function of the target. The functional activity of aptamers of the invention can be assessed using in vitro and in vivo models designed to measure a known function of TFPI.

Aptamer sequences and/or minimized aptamer sequences may also be optimized using metabolic profile directed aptamer medicinal chemistry for site-specific identification of cleavage sites and modifications to optimize stability of the aptamer sequences and/or minimized aptamer sequences.

Metabolic profile directed aptamer medicinal chemistry involves incubating a parent aptamer with a test fluid to result in a mixture. Then, the mixture is analyzed to determine the rate of disappearance of the parent aptamer or the amount or percentage of aptamer remaining after incubation, the specific aptamer metabolic profile and the specific aptamer metabolite sequences. Knowledge of the sequences of the specific metabolites formed allows one to identify the sites of nuclease cleavage based on the mass of the metabolite(s). After systematically conducting metabolic profiling and identifying specific aptamer cleavage sites, the method involves introducing chemical substitutions or modifications at or near the cleavage sites that are designed to optimize the stability of the aptamer sequences and/or minimized aptamer sequences.

In one embodiment, an aptamer is identified and modified by a) incubating a parent aptamer with a test fluid to result in a mixture; b) analyzing the mixture to identify metabolites of the parent aptamer, thereby detecting at least one aptamer cleavage site in the parent aptamer; and c) introducing a chemical substitution at a position proximal to the at least one aptamer cleavage site to result in a modified aptamer. This enhances the stability of the aptamer, and, in particular, the stability of the aptamer to endonucleases and exonucleases.

In some embodiments, the test fluid is a biological matrix, particularly a biological matrix selected from the group consisting of one or more of: serum; plasma; cerebral spinal fluid; tissue extracts, including cytosolic fraction, S9 fraction and microsomal fraction; aqueous humour; vitreous humour and tissue homogenates. In some embodiments, the biological matrix is derived from a species selected from the group consisting of one or more of: mouse, rat, monkey, pig, human, dog, guinea pig and rabbit. In some embodiments, the test fluid comprises at least one purified enzyme, particularly at least one purified enzyme selected from the group consisting of: snake venom phosphodiesterase and DNAse I.

In some embodiments, the analyzing step includes analyzing the resulting aptamer using liquid chromatography and mass spectrometry, particularly electron spray ionization liquid chromatography mass spectrometry, polyacrylamide gel electrophoresis or capillary electrophoresis to determine a position of at least one aptamer cleavage site. In some embodiments, the analyzing step includes analyzing the resulting aptamer using a bioanalytical method selected from the group consisting of one or more of: denaturing polyacrylamide gel electrophoresis (PAGE); capillary electrophoresis; high performance liquid chromatography (HPLC) and liquid chromatography-mass spectrometry (LC/MS), particularly LC/MS/MS or LC/MS/MS/MS, and more particularly electrospray ionization LC/MS (ESI-LC/MS), ESI-LC/MS/MS and ESI-LC/MS/MS/MS.

In some embodiments, the proximal position includes a position selected from the group consisting of: a position immediately 5' to the aptamer cleavage site, a 5' position at or within three nucleotides of the aptamer cleavage site, a position immediately 3' to the aptamer cleavage site, a 3' position at or within three nucleotides of the aptamer cleavage site, and at the cleaved internucleotide linkage.

In some embodiments, the chemical substitution is selected from the group consisting of: a chemical substitution at a sugar position; a chemical substitution at a base position and a chemical substitution at an internucleotide linkage. More particularly, a substitution is selected from the group consisting of: a nucleotide substituted for a different nucleotide; a purine substitution for a pyrimidine; a 2'-amine substitution for any nucleotide; a 2'-deoxy dihydrouridine substitution for a uridine; a 2'-deoxy-5-methyl cytidine for a cytidine; a 2-amino purine substitution for a purine; a phosphorothioate substituted for a phosphodiester; a phosphorodithioate substituted for a phosphodiester; a 2'-deoxy nucleotide substituted for a 2'-OH nucleotide, a 2'-OMe nucleotide or a 2'-fluoro nucleotide; a 2'-OMe nucleotide substituted for a 2'-OH nucleotide, a 2'-deoxy nucleotide, or a 2'-fluoro nucleotide; a 2'-fluoro nucleotide substituted for a 2'-OH nucleotide, a 2'-deoxy nucleotide or a 2'-OMe nucleotide; or a 2'-O-methoxyethyl nucleotide substituted for a 2'-OH, 2'-fluoro or 2'-deoxy nucleotide; a 2'-β-methoxyethyl nucleotide or deoxy nucleotide for a 2'-fluoro nucleotide; and the addition of one or more PEG or other polymers or other PK or distribution-influencing entity.

In additional embodiments, the introducing step of these methods further includes introducing more than one chemical substitution at one or more cleavage sites or at a single cleavage site or both.

In another embodiment, wherein more than one aptamer cleavage site is detected, the introducing step of these methods further includes introducing at least one chemical substitution at the associated proximal position of the aptamer cleavage site determined to occur first in time during the incubating step or at any other cleavage site(s) that provides the desired properties upon introduction of a chemical substitution.

In other embodiments, these methods further include the step of testing the stability of the modified aptamer in the test fluid. In some embodiments, aptamer stability is assessed by determining the percent of modified aptamer that remains intact in the test fluid as compared to the percent of the parent aptamer that remains intact in the test fluid. In some embodiments, the percent of intact aptamer is assessed by a bioanalytical method selected from the group consisting of one or more of: denaturing polyacrylamide gel electrophoresis (PAGE); capillary electrophoresis; HPLC and LC/MS, particularly LC/MS/MS or LC/MS/MS/MS, and more particularly ESI-LC/MS, ESI-LC/MS/MS and ESI-LC/MS/MS/MS. In other embodiments, the modified aptamer is more stable in the test fluid than the parent aptamer, preferably at least 2 fold, more preferably at least 5 fold and most preferably at least 10 fold more stable.

In additional embodiments, these methods further include determining a dissociation constant or $IC_{50}$ of the modified aptamer for its target. In some embodiments, chemical substitutions are introduced singly at each position or in various combinations in the aptamer, and the dissociation constant or $IC_{50}$ for each resulting aptamer is determined. Chemical substitutions are introduced at a position proximal to the aptamer cleavage site such that a single chemical modification results in a dissociation constant for the modified aptamer that is the same or less than that of the parent aptamer. In another embodiment of the invention, the method includes selecting a modified aptamer having a dissociation constant or $IC_{50}$ for its target that is the same or less than that for the parent aptamer.

In other embodiments, the modified aptamer binds to a target having a biological activity, and the method further includes testing the biological activity of the target in the presence and absence of modified aptamer. In another embodiment, the method further includes selecting a modified aptamer that binds to a target having a biological activity that is the same or better than that of the parent aptamer. The biological activity may be measured in any relevant assay, such as an ELISA assay or a cell-based assay.

In some embodiments, the incubating, analyzing, introducing and testing steps are repeated iteratively until the desired stability is achieved.

The aptamers of the invention may be routinely adapted for diagnostic purposes according to any number of techniques employed by those skilled in the art. Diagnostic utilization may include both in vivo or in vitro diagnostic applications. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any aptamer by procedures known in the art to incorporate a labeling tag to track the presence of such ligand. Such a tag could be used in a number of diagnostic procedures.

Aptamers Having Immunostimulatory Motifs

The invention provides aptamers that bind to TFPI and modulate its biological function.

Recognition of bacterial DNA by the vertebrate immune system is based upon the recognition of unmethylated CG dinucleotides in particular sequence contexts ("CpG motifs"). One receptor that recognizes such a motif is Toll-like receptor 9 ("TLR 9"), a member of a family of Toll-like receptors (~10 members) that participate in the innate immune response by recognizing distinct microbial components. TLR 9 is activated by unmethylated oligodeoxynucleotide ("ODN") CpG sequences in a sequence-specific manner. The recognition of CpG motifs triggers defense mechanisms leading to innate and ultimately acquired immune responses. For example, activation of TLR 9 in mice induces activation of antigen presenting cells, up-regulation of MHC class I and II molecules, and expression of important co-stimulatory molecules and cytokines including IL-12 and IL-23. This activation both directly and indirectly enhances B and T cell responses, including a robust up-regulation of the TH1 cytokine IFN-gamma. Collectively, the response to CpG sequences leads to: protection against infectious diseases, improved immune response to vaccines, an effective response against asthma, and improved antibody-dependent cell-mediated cytotoxicity. Thus, CpG ODNs can provide protection against infectious diseases, function as immuno-adjuvants or cancer therapeutics (monotherapy or in combination with a mAb or other therapies), and can decrease asthma and allergic response.

A variety of different classes of CpG motifs have been identified, each resulting upon recognition in a different cascade of events, release of cytokines and other molecules, and activation of certain cell types. See, e.g., CpG Motifs in Bacterial DNA and Their Immune Effects, Annu Rev. Immunol. 2002, 20:709-760, which is incorporated herein by reference. Additional immunostimulatory motifs are disclosed in the following U.S. Patents, each of which is incorporated herein by reference: U.S. Pat. No. 6,207,646; U.S. Pat. No. 6,239,116; U.S. Pat. No. 6,429,199; U.S. Pat. No. 6,214,806; U.S. Pat. No. 6,653,292; U.S. Pat. No. 6,426,334; U.S. Pat. No. 6,514,948 and U.S. Pat. No. 6,498,148. Any of these CpG or other immunostimulatory motifs can be incorporated into an aptamer. The choice of aptamers is dependent upon the disease or disorder to be treated. Preferred immunostimulatory motifs are as follows (shown 5' to 3', left to right) wherein "r" designates a purine, "y" designates a pyrimidine, and "X" designates any nucleotide: AACGTTCGAG (SEQ ID NO: 12); AACGTT; ACGT; rCGy; rrCGyy; XCGX; XXCGXX; and $X_1X_2CGY_1Y_2$; wherein $X_1$ is G or A, $X_2$ is not C, $Y_1$ is not G and $Y_2$ is preferably T.

In those instances where a CpG motif is incorporated into an aptamer that binds to a specific target other than a target known to bind to CpG motifs, and upon binding stimulates an immune response (a "non-CpG target"), the CpG is preferably located in a non-essential region of the aptamer. Non-essential regions of aptamers can be identified by site-directed mutagenesis, deletion analyses and/or substitution analyses. However, any location that does not significantly interfere with the ability of the aptamer to bind to the non-CpG target may be used. In addition to being embedded within the aptamer sequence, the CpG motif may be appended to either or both of the 5' and 3' ends or otherwise attached to the aptamer. Any location or means of attachment may be used as long as the ability of the aptamer to bind to the non-CpG target is not significantly interfered with.

As used herein, "stimulation of an immune response" can mean either (1) the induction of a specific response (e.g., induction of a Th1 response) or the production of certain molecules, or (2) the inhibition or suppression of a specific response (e.g., inhibition or suppression of the Th2 response) or of certain molecules.

Aptamers of the invention, including aptamers having one or more CpG or other immunostimulatory sequences, can be identified or generated by a variety of strategies using, e.g., the SELEX™ process described herein. The incorporated immunostimulatory sequences can be DNA, RNA, substituted DNA or RNA, and/or a combination of substituted or unsubstituted DNA/RNA. In general, the strategies can be divided into two groups. For both groups of strategies, the CpG motifs are included to: a) stimulate the immune response to counteract situations where a repressed immune response is relevant to disease development (i.e., immune deficiency diseases such as AIDS), and b) to focus a stimulated immune response against a particular target or cell type (i.e., cancer cells), or to bias an immune response towards a TH1 state and away from TH2 or TH17 state (i.e., including CpG motifs in an aptamer against an anti-allergy target such as IgE to counteract an allergic condition).

In group one, the strategies are directed to identifying or generating aptamers including both a CpG motif or other immunostimulatory sequence as well as a binding site for a target, where the target (hereinafter "non-CpG target") is a target other than one known to recognize CpG motifs or other immunostimulatory sequences. In some embodiments of the invention, the non-CpG target is a TFPI target. The first strategy of this group includes performing SELEX™ to obtain an aptamer to a specific non-CpG target, preferably a target using an oligonucleotide pool wherein a CpG motif has been incorporated into each member of the pool as, or as part of, a fixed region, e.g., in some embodiments the randomized region of the pool members includes a fixed region having a CpG motif incorporated therein, and identifying an aptamer including a CpG motif. The second strategy of this group includes performing SELEX™ to obtain an aptamer to a specific non-CpG target, and following selection, appending a CpG motif to the 5' and/or 3' end or engineering a CpG motif into a region, preferably a non-essential region, of the aptamer. The third strategy of this group includes performing SELEX™ to obtain an aptamer to a specific non-CpG target, wherein during synthesis of the pool the molar ratio of the various nucleotides is biased in one or more nucleotide addition steps so that the randomized region of each member of the pool is enriched in CpG motifs, and identifying an aptamer including a CpG motif. The fourth strategy of this group includes performing SELEX™ to obtain an aptamer to a specific non-CpG target, and identifying an aptamer including a CpG motif. The fifth strategy of this group includes performing SELEX™ to obtain an aptamer to a specific non-CpG target, and identifying an aptamer which, upon binding, stimulates an immune response but that does not include a CpG motif.

In group two, the strategies are directed to identifying or generating aptamers including a CpG motif and/or other sequences that are bound by the receptors for the CpG motifs (e.g., TLR9 or the other toll-like receptors) and upon binding stimulate an immune response. The first strategy of this group includes performing SELEX™ to obtain an aptamer to a target known to bind to CpG motifs or other immunostimulatory sequences and upon binding stimulate an immune response using an oligonucleotide pool wherein a CpG motif has been incorporated into each member of the pool as, or as part of, a fixed region, e.g., in some embodiments the randomized region of the pool members include a fixed region having a CpG motif incorporated therein, and identifying an aptamer including a CpG motif. The second strategy of this group includes performing SELEX™ to obtain an aptamer to a target known to bind to CpG motifs or other immunostimulatory sequences and upon binding stimulate an immune response and then appending a CpG motif to the 5' and/or 3' end or engineering a CpG motif into a region, preferably a non-essential region, of the aptamer. The third strategy of this group includes performing SELEX™ to obtain an aptamer to a target known to bind to CpG motifs or other immunostimulatory sequences and upon binding stimulate an immune response, wherein during synthesis of the pool the molar ratio of the various nucleotides is biased in one or more nucleotide addition steps so that the randomized region of each member of the pool is enriched in CpG motifs, and identifying an aptamer including a CpG motif. The fourth strategy of this group includes performing SELEX™ to obtain an aptamer to a target known to bind to CpG motifs or other immunostimulatory sequences and upon binding stimulate an immune response, and identifying an aptamer including a CpG motif. The fifth strategy of this group includes performing SELEX™ to obtain an aptamer to a target known to bind to CpG motifs or other immunostimulatory sequences, and identifying an aptamer which, upon binding, stimulates an immune response but that does not include a CpG motif.

Modulation of Pharmacokinetics and Biodistribution of Aptamer Therapeutics

It is important to match the pharmacokinetic properties for all oligonucleotide-based therapeutics, including aptamers, to the desired pharmaceutical application. Aptamers must be able to be distributed to target organs and tissues, and remain in the body (unmodified) for a period of time consistent with the desired dosing regimen.

The invention provides materials and methods to affect the pharmacokinetics of aptamer compositions and, in particular, the ability to tune aptamer pharmacokinetics. The tunability of (i.e., the ability to modulate) aptamer pharmacokinetics is achieved through conjugation of modifying moieties (e.g., PEG polymers) to the aptamer and/or the incorporation of modified nucleotides (e.g., 2'-fluoro or 2'-O-methyl) or modified internucleotide linkages to alter the chemical composition of the aptamer. The ability to tune aptamer pharmacokinetics is used in the improvement of existing therapeutic applications, or alternatively, in the development of new therapeutic applications. For example, in some therapeutic applications, e.g., in anti-neoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it is desirable to increase the residence times of aptamers in the circulation.

In addition, the tunability of aptamer pharmacokinetics is used to modify the disposition, for example the absorption, distribution, metabolism and elimination (ADME) of an aptamer to fit its therapeutic objective in a subject. Tunability of the pharmacokinetics of an aptamer can affect the manner and extent of absorption of the aptamer, the distribution of an aptamer throughout the fluids and tissues of the body, the successive metabolic transformations of the aptamer and its metabolite(s) and finally, the elimination of the aptamer and its metabolite(s). For example, in some therapeutic applications, it may be desirable to alter the biodistribution of an aptamer therapeutic in an effort to target a particular type of tissue or a specific organ (or set of organs), or to increase the propensity to enter specific cell types. In these applications, the aptamer therapeutic preferentially distributes into specific tissues and/or organs and accumulates therein to cause a therapeutic effect. In other therapeutic applications, it may be desirable to target tissues displaying a cellular marker or a symptom associated with a given disease, cellular injury or other abnormal pathology, such that the aptamer therapeutic preferentially accumulates in the affected tissue. For example, PEGylation of an aptamer therapeutic (e.g., PEGylation with a 20 kDa PEG polymer or other polymer or conjugation entity) is used to target inflamed tissues, such that the PEGylated aptamer therapeutic preferentially accumulates in the inflamed tissue.

To determine the pharmacokinetic profiles of aptamer therapeutics (e.g., aptamer conjugates or aptamers having altered chemistries, such as modified nucleotides), a variety of parameters are studied in normal subjects, e.g., test animals or humans, or in diseased subjects, e.g., TFPI-specific animal models, such as animal models of hypercoagulation or hypocoagulation, or humans with a coagulation deficiency. Such parameters include, for example, the distribution or elimination half-life ($t_{1/2}$), the plasma clearance (CL), the volume of distribution (Vss), the area under the concentration-time curve (AUC), the maximum observed serum or plasma concentration ($C_{max}$), and the mean residence time (MRT) of an aptamer composition. As used herein, the term "AUC" refers to the area under the plasma concentration curve of an aptamer therapeutic versus the time after aptamer administration. The AUC value is used to estimate the exposure of the aptamer and also used to determine the bioavailability of an aptamer after an extravascular route of administration, such as, e.g., subcutaneous administration. Bioavailability is determined by taking the ratio of the AUC obtained after subcutaneous administration to the AUC obtained after intravenous administration and normalizing them to the doses used after each administration (i.e., the percent ratio of aptamer administered after subcutaneous administration as compared to the same aptamer administered by intravenous administration at the same dose or normalized dose). The CL value is the measurement of the removal of the parent aptamer therapeutic from the systemic circulation. The volume of distribution (Vd) is a term that relates the amount of aptamer in the body at one time to its plasma concentration. The Vd is used to determine how well a drug is removed from the plasma and distributed to tissues and/or organs. A larger Vd implies wide distribution, extensive tissue binding, or both a wide distribution and extensive tissue binding. There are three basic volumes of distribution: (i) the apparent or initial volume of distribution at time zero obtained from back extrapolation of the concentration-time curve; (ii) the volume calculated once distribution is complete, approximating to Vdss, where the area volume is dependent upon the elimination kinetics; and (iii) the volume of distribution calculated once distribution is complete. The parameter that should ideally be measured is the Vdss because this parameter is independent of the elimination kinetics. If the Vss for the aptamer is larger than the blood volume, it suggests that the aptamer is distributed outside of the systemic circulation and is likely to be found in the tissues or organs. Pharmacodynamic parameters may also be used to assess drug characteristics.

To determine the distribution of aptamer therapeutics (e.g., aptamer conjugates or aptamers having altered chemistries, such as modified nucleotides), a tissue distribution study or quantitative whole body autoradiography using a radiolabeled aptamer that is administered to a normal animal or a diseased target specific animal model is used. The accumulation of the radiolabeled-aptamer at a specific site can be quantified.

The pharmacokinetics and biodistribution of an aptamer described herein, such as a stabilized aptamer, can be modulated in a controlled manner by conjugating an aptamer to a modulating moiety, such as, but not limited to, a small molecule, peptide, or polymer, or by incorporating modified nucleotides into an aptamer. The conjugation of a modifying moiety and/or altering nucleotide chemical composition alters fundamental aspects of aptamer residence time in circulation and distribution within and to tissues and cells.

In addition to metabolism by nucleases, oligonucleotide therapeutics are subject to elimination via renal filtration. As such, a nuclease-resistant oligonucleotide administered intravenously typically exhibits an in vivo half-life of <30 minutes, unless filtration can be blocked. This can be accomplished by either facilitating rapid distribution out of the blood stream into tissues or by increasing the apparent molecular weight of the oligonucleotide above the effective size cut-off for the glomerulus. Conjugation of small molecular weight therapeutics to a PEG polymer (PEGylation), as described below, can dramatically lengthen residence times of aptamers in the circulation, thereby decreasing dosing frequency and enhancing effectiveness against vascular targets.

Modified nucleotides can also be used to modulate the plasma clearance of aptamers. For example, an unconjugated aptamer that incorporates for example, 2'-fluoro, 2'-OMe, and/or phosphorothioate stabilizing chemistries, which is typical of current generation aptamers as it exhibits a high degree of nuclease resistance in vitro and in vivo, displays rapid distribution into tissues, primarily into the liver and kidney, when compared to unmodified aptamer.

PAG-Derivatized Nucleic Acids

As described above and as shown in FIG. 11, derivatization of nucleic acids with high molecular weight non-immunogenic polymers has the potential to alter the pharmacokinetic and pharmacodynamic properties of nucleic acids making them more effective and/or safer therapeutic agents. Favorable changes in activity can include increased resistance to degradation by nucleases, decreased filtration by the kidneys, decreased exposure to the immune system, and altered distribution of the therapeutic through the body.

The aptamer compositions of the invention may be derivatized with one or more polyalkylene glycol ("PAG") moieties. Typical polymers used in the invention include polyethylene glycol ("PEG"), also known as polyethylene oxide ("PEO") and polypropylene glycol (including poly isopropylene glycol). Additionally, random or block copolymers of different alkylene oxides can be used in many applications. In a common form, a polyalkylene glycol, such as PEG, is a linear polymer terminated at each end with hydroxyl groups: HO—$CH_2CH_2O$—$(CH_2CH_2O)_n$—$CH_2CH_2$—OH. This polymer, alpha-, omega-dihydroxylpolyethylene glycol, can also be represented as HO-PEG-OH, where it is understood that the -PEG- symbol represents the following structural unit: —$CH_2CH_2O$—$(CH_2CH_2O)_n$—$CH_2CH_2$—, where n typically ranges from 4 to 10,000.

PAG polymers suitable for therapeutic indications typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995). PAG conjugates are often used not only to enhance solubility and stability, but also to prolong the blood circulation half-life of molecules and later distribution within the body.

Figure 6:
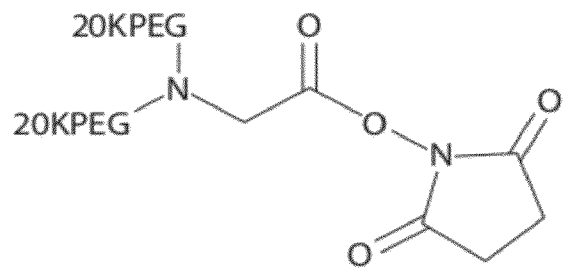
FIG. 6 is an illustration of a 40 kDa branched PEG.
Figure 7:
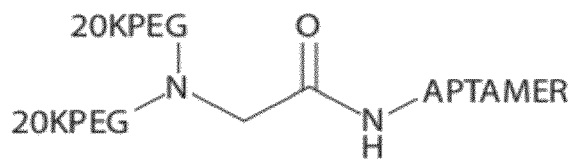
FIG. 7 is an illustration of a 40 kDa branched PEG that is attached to the 5' terminus of an amine aptamer.
Figure 8:
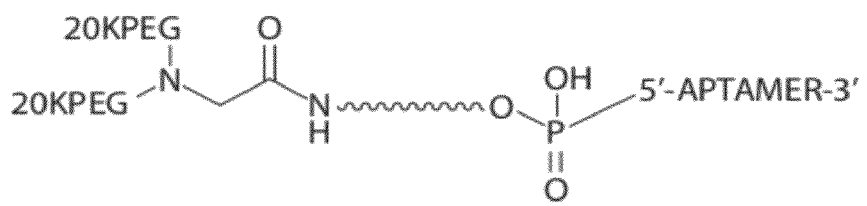
FIG. 8 is an illustration of a 40 kDa branched PEG that is attached to the 5' terminus of an aptamer using a 5'-amine linker phosphoramidite.
Figure 9A:
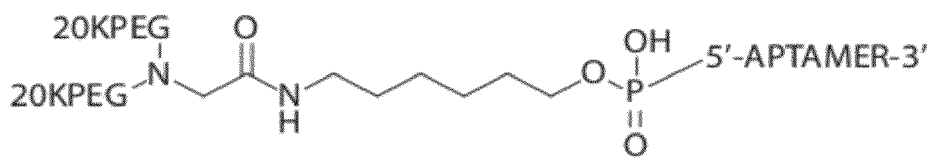
FIG. 9A is an illustration of a 40 kDa branched PEG that is attached to the 5' terminus of an aptamer using a 5'-hexylamine linker phosphoramidite.
Figure 9B:
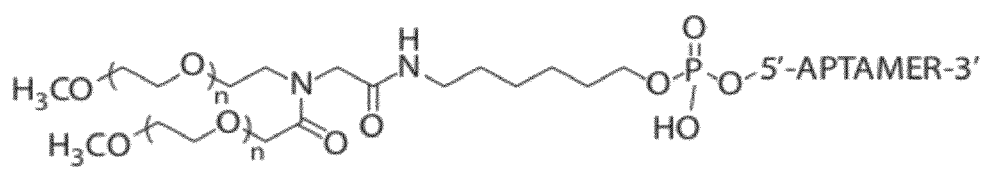
FIG. 9B is an alternative illustration of a 40 kDa branched PEG that is attached to the 5' terminus of an aptamer using a 5'-hexylamine linker phosphoramidite.

The PAG derivatized compounds conjugated to the aptamers of the invention are typically between 5 and 80 kDa in size, however any size can be used, the choice dependent on the aptamer and application. Other PAG derivatized compounds of the invention are between 10 and 80 kDa in size. Still other PAG derivatized compounds of the invention are between 10 and 60 kDa in size. In some embodiments, the PAG moieties derivatized to compositions of the invention are PEG moieties having a molecular weight ranging from 5, 10, 15, 20, 25, 30, 35, 40, 45, 50, 55, 60, 65, 70, 75, 80, 85, 90, 95 or 100 kDa in size. In some embodiments, the PEG is linear PEG, while in other embodiments, the PEG is branched PEG. In still other embodiments, the PEG is a 40 kDa branched PEG as depicted in FIG. 6. In some embodiments, the 40 kDa branched PEG is attached to the 5' end of the aptamer as depicted in FIG. 7.

Production of high molecular weight PEGs (>10 kDa) can be difficult, inefficient and expensive. To synthesize high molecular weight PEG-nucleic acid conjugates, higher molecular weight activated PEGs are generated. Methods for generating such molecules involve the formation of a linear activated PEG, or a branched activated PEG in which two or more PEGs are attached to a central core carrying the activated group. The terminal portions of these higher molecular weight PEG molecules, i.e., the relatively non-reactive hydroxyl (—OH) moieties, can be activated or converted to functional moieties for attachment of one or more of the PEGs to other compounds at reactive sites on the compound. Branched activated PEGs will have more than two termini, and in cases where two or more termini have been activated, such activated higher molecular weight PEG molecules are herein referred to as, multi-activated PEGs. In some cases, not all termini in a branched PEG molecule are activated. In cases where any two termini of a branched PEG molecule are activated, such PEG molecule is referred to as a bi-activated PEG. In some cases where only one terminus in a branched PEG molecule is activated, such PEG molecule is referred to as mono-activated. In other cases, the linear PEG molecule is di-functional and is sometimes referred to as "PEG diol". The terminal portions of the PEG molecule are relatively non-reactive hydroxyl moieties, the —OH groups, that can be activated or converted to functional moieties for attachment of the PEG to other compounds at reactive sites on the compounds. Such activated PEG diols are referred to herein as homo bi-activated PEGs. The molecules are generated using any of a variety of art-recognized techniques. In addition to activating PEG using one of the previously described methods, one or both of the terminal alcohol functionalities of the PEG molecule can be modified to allow for different types of conjugation to a nucleic acid. For example, converting one of the terminal alcohol functionalities to an amine or a thiol allows access to urea and thiourethane conjugates. Other functionalities include, e.g., maleimides and aldehydes.

In many applications, it is desirable to cap the PEG molecule on one end with an essentially non-reactive moiety so that the PEG molecule is mono-functional (or mono-activated). In the case of protein therapeutics, which generally display multiple reaction sites for activated PEGs, homo bi-functional activated PEGs lead to extensive cross-linking, yielding poorly functional aggregates. To generate mono-activated PEGs, one hydroxyl moiety on the terminus of the PEG diol molecule typically is substituted with a non-reactive methoxy end moiety, —$OCH_3$. In this embodiment, the polymer can be represented by MeO—$CH_2CH_2O$—$(CH_2CH_2O)_n$—$CH_2CH_2$—OH and is commonly referred to as "mPEG", where n typically ranges from 4 to 10,000.

The other, un-capped terminus of the PEG molecule typically is converted to a reactive end moiety that can be activated for attachment at a reactive site on a surface or a molecule, such as a protein, peptide or oligonucleotide.

In some cases, it is desirable to produce a hetero bi-functional PEG reagent, where one end of the PEG molecule has a reactive group, such as an N-hydroxysuccinimide or nitrophenyl carbonate, while the opposite end contains a maleimide or other activating group. In these embodiments, two different functionalities, for example, amine and thiol, may be conjugated to the activated PEG reagent at different times.

Pharmaceutical Compositions

The invention also includes pharmaceutical compositions comprising an aptamer that binds to TFPI. In some embodiments, the compositions include a therapeutically effective amount of a pharmacologically active TFPI aptamer or a pharmaceutically acceptable salt thereof, alone or in combination, with one or more pharmaceutically acceptable carriers or diluents.

The compositions may comprise one or more TFPI aptamers. For example, the compositions may comprise ARC19499. Alternatively, the compositions may comprise ARC19882. Alternatively, the compositions may comprise ARC19499 and another TFPI aptamer. In embodiments where the composition includes at least two aptamers that can be the same aptamer or two different aptamers, the aptamers may, optionally, be tethered or otherwise coupled together. Preferably, the compositions comprise ARC19499, either alone or in combination with another TFPI aptamer. Alternatively, the compositions comprise a TFPI aptamer in combination with another agent. Preferably, the compositions comprise ARC19499 in combination with another agent.

As used herein, the terms "pharmaceutically acceptable salt" refers to salt forms of the active compound that are prepared with counter ions that are non-toxic under the conditions of use and are compatible with a stable formulation. Examples of pharmaceutically acceptable salts of TFPI aptamers include hydrochlorides, sulfates, phosphates, acetates, fumarates, maleates and tartrates.

The terms "pharmaceutically acceptable carrier", "pharmaceutically acceptable medium" or "pharmaceutically acceptable excipient", as used herein, means being compatible with the other ingredients of the formulation and not deleterious to the recipient thereof. Pharmaceutically acceptable carriers are well known in the art. Examples of pharmaceutically acceptable carriers can be found, for example, in Goodman and Gillmans, *The Pharmacological Basis of Therapeutics*, latest edition.

The pharmaceutical compositions will generally include a therapeutically effective amount of the active component(s) of the therapy, e.g., a TFPI aptamer of the invention that is dissolved or dispersed in a pharmaceutically acceptable carrier or medium. Examples of preferred pharmaceutically acceptable carriers include, but are not limited to, physiological saline solution, phosphate buffered saline solution, and glucose solution. However it is contemplated that other pharmaceutically acceptable carriers may also be used. Examples of other pharmaceutically acceptable media or carriers include any and all solvents, dispersion media, coatings, antibacterial agents, antifungal agents, isotonic and absorption delaying agents and the like. Pharmaceutically acceptable carriers that may be used in the compositions include, but are not limited to, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The use of such media and agents for pharmaceutically active substances is well known in the art.

The pharmaceutical compositions may also contain pharmaceutically acceptable excipients, such as preserving, stabilizing, wetting or emulsifying agents, solution promoters, salts, or buffers for modifying or maintaining pH, osmolarity, viscosity, clarity, color, sterility, stability, rate of dissolution or absorption of the formulation. For solid compositions, excipients include pharmaceutical grades of mannitol, lactose, starch, magnesium stearate, sodium saccharin, talcum, cellulose, glucose, sucrose, magnesium carbonate and the like.

The pharmaceutical compositions are prepared according to conventional mixing, granulating or coating methods, and typically contain 0.1% to 99.9%, for example, 0.1% to 75%, 0.1% to 50%, 0.1% to 25%, 0.1% to 10%, 0.1 to 5%, preferably 1% to 50%, of the active component.

The formulation of pharmaceutical compositions is known to one of skill in the art. Typically, such compositions may be formulated as injectables, either as liquid solutions or suspensions; solid forms suitable for solution in, or suspension in, liquid prior to injection; as tablets or other solids for oral administration; as time release capsules for slow release formulations; or in any other form currently used, including eye drops, creams, lotions, salves, inhalants and the like. The compositions may also be formulated as suppositories, using for example, polyalkylene glycols as the carrier. In some embodiments, suppositories are prepared from fatty emulsions or suspensions. The use of sterile formulations, such as saline-based washes, by surgeons, physicians or health care workers to treat a particular area in the operating field may also be particularly useful.

The compositions may be formulated as oral dosage forms, such as tablets, capsules, pills, powders, granules, elixirs, tinctures, suspensions, syrups and emulsions. For instance, for oral administration in the form of a tablet or capsule (e.g., a gelatin capsule), the active drug component can be combined with an oral, non-toxic, pharmaceutically acceptable carrier, such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars, such as glucose or beta-lactose, corn sweeteners, natural and synthetic gums, such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethylene glycol and the like. Disintegrators include, without limitation, starch, methyl cellulose, agar, bentonite, xanthan gum starches, agar, alginic acid or its sodium salt, or effervescent mixtures and the like. Diluents, include, e.g., lactose, dextrose, sucrose, mannitol, sorbitol, cellulose and/or glycine.

Pharmaceutical compositions can also be formulated in liposome delivery systems, such as small unilamellar vesicles, large unilamellar vesicles and multilamellar vesicles. Liposomes can be formed from a variety of phospholipids containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the aptamers described herein can be provided as a complex with a lipophilic compound or non-immunogenic, high molecular weight compound constructed using methods known in the art. Additionally, liposomes may bear aptamers on their surface for targeting and carrying cytotoxic agents internally to mediate cell killing. An example of nucleic-acid associated complexes is provided in U.S. Pat. No. 6,011,020.

The compositions of the invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the compositions of the invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compositions of the invention may also be used in conjunction with medical devices.

The quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

Administration

The compositions may be administered to a vertebrate, preferably a mammal, and more preferably a human. The terms "patient" and "subject" are used interchangeably throughout the application, and these terms include both human and veterinary subjects.

In embodiments where the TFPI aptamers are antagonist aptamers, the TFPI aptamer compositions provided herein are administered to subjects in an amount effective to inhibit, reduce, block or otherwise modulate TFPI-mediated inhibition of blood coagulation. The TFPI aptamer compositions may completely or partially inhibit, reduce, block or otherwise modulate TFPI-mediated inhibition of blood coagulation. The TFPI aptamers are considered to inhibit or otherwise modulate TFPI activity when the aptamers cause an increase in thrombin generation (such as, for example, peak thrombin, endogenous thrombin potential or lag time) over hemophilic plasma that is equivalent to at least 1-2% of factor replacement.

The compositions may be administered by numerous routes of administration. Such routes of administration include, but are not limited to, oral routes; topical routes, such as intranasally, vaginally or rectally; and parenteral routes, such as intravenous, subcutaneous, intradermal, intramuscular, intraarticular and intrathecal administration. Suitable routes of administration may also be used in combination, such as intravenous administration followed by subcutaneous administration. The route of administration, however, is determined by the attending physician. Preferably, the formulations are administered intravenously. Most preferably, the formulations are administered subcutaneously.

Oral dosage forms may be administered as tablets, capsules, pills, powders, granules, elixirs, tinctures, suspensions, syrups or emulsions.

Topical dosage forms include creams, ointments, lotions, aerosol sprays and gels for intranasal vehicles, inhalants or transdermal patches.

Parenteral dosage forms include pre-filled syringes, and solutions and lyophilized powders that are reconstituted prior to administration.

The dosage regimen utilizing the aptamers of the invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

The pharmaceutical compositions may be administered using various treatment regimens. For example, the compositions may be administered as a maintenance therapy at a defined dose for a defined period of time, such as when a patient is not suffering from a bleeding episode. Alternatively, the compositions may be administered on demand, i.e., as needed, such as when a patient is suffering from a bleeding episode. In a further alternative embodiment, the compositions may be administered as a combination of maintenance therapy and on demand therapy. In such an embodiment, the compositions may be administered as a maintenance therapy at a defined dose for a defined period of time until a bleed occurs, in which case the dosage of the compositions would be increased on an as needed basis until the bleeding stopped, at which point the dosage of the compositions would be decreased back to the prior maintenance level. In another such embodiment, the compositions may be administered as a maintenance therapy at a defined dose for a defined period of time until a bleed occurs, in which case another bleeding disorder therapy would be administered to the patient (such as Factor VIII) until the bleeding stopped, at which point the other bleeding disorder therapy would be discontinued. During this entire time, the compositions would continue to be administered as a maintenance therapy. In yet another such embodiment, the compositions may be administered as a maintenance therapy at a defined dose for a defined period of time until a bleed occurs, in which case the dosage of the compositions would be decreased and another bleeding disorder therapy would be administered to the patient (such as Factor VIII) until the bleeding stopped, at which point the dosage of the compositions would be increased back to the prior maintenance level and the other bleeding disorder therapy would be discontinued. In another such embodiment, another bleeding disorder therapy (such as Factor VIII) may be administered as a maintenance therapy at a defined dose for a defined period of time until a bleed occurs, in which case the compositions would be administered to the patient until the bleeding stopped, at which point therapy with the compositions would be discontinued. During this entire time, the other bleeding disorder therapy would continue to be administered as a maintenance therapy. In yet another such embodiment, another bleeding disorder therapy (such as FVIII) may be administered as a maintenance therapy at a defined dose for a defined period of time until a bleed occurs, in which case the dosage of the other bleeding disorder therapy would be decreased and the compositions would be administered to the patient until the bleeding stopped, at which point the dosage of the other bleeding disorder therapy would be increased back to the prior maintenance level and therapy with the compositions would be discontinued.

Indications

The compositions are used to treat, prevent, delay the progression of or ameliorate tissue factor pathway inhibitor (TFPI)-mediated pathologies, including the treatment of bleeding disorder pathologies involving TFPI-mediated inhibition of blood coagulation. The pathologies to be treated, prevented, delayed or ameliorated are selected from the group consisting of: coagulation factor deficiencies, congenital or acquired, mild or moderate or severe, including hemophilia A (Factor VIII deficiency), hemophilia B (Factor IX deficiency) and hemophilia C (Factor XI deficiency); hemophilia A or B with inhibitors; other factor deficiencies (V, VII, X, XIII, prothrombin, fibrinogen); deficiency of α2-plasmin inhibitor; deficiency of plasminogen activator inhibitor 1; multiple factor deficiency; functional factor abnormalities (e.g., dysprothrombinemia); joint hemorrhage (hemarthrosis), including, but not limited to, ankle, elbow and knee; spontaneous bleeding in other locations (muscle, gastrointestinal, mouth, etc.); hemorrhagic stroke; intracranial hemorrhage; lacerations and other hemorrhage associate with trauma; acute traumatic coagulopathy; coagulopathy associated with cancer (e.g., acute promyelocytic leukemia); von Willebrand's Disease; disseminated intravascular coagulation; liver disease; menorrhagia; thrombocytopenia and hemorrhage associated with the use of anticoagulants (e.g., vitamin K antagonists, FXa antagonists, etc.).

The compositions may also be administered prior to, during and/or after a medical procedure. For example, the pharmaceutical compositions may be administered in conjunction (before, during and/or after) with medical procedures, such as: prophylaxis and/or treatment associated with bleeding caused by dental procedures, orthopedic surgery including but not limited to arthroplasty (e.g., hip replacement), surgical or radionuclide synovectomy (RSV), major surgery, venipuncture, transfusion and amputation.

Therapeutic Rationale

Without wishing to be bound by theory regarding mechanism of action, the following therapeutic rationale is offered by way of example only.

Inhibitors of tissue factor pathway inhibitor (TFPI) would be expected to enhance the generation of thrombin via the tissue factor/Factor VIIa pathway (also known as the extrinsic pathway). In a normal individual, activation of the extrinsic pathway stimulates initiation of the thrombin generation response, resulting in a small amount of activated thrombin. Following initiation, this pathway is rapidly deactivated by the inhibitory action of TFPI. Subsequent propagation of the thrombin generation response depends upon thrombin-mediated feedback activation of the intrinsic pathway, which includes Factor VIII (FVIII) and Factor IX (FIX). Propagation is necessary to generate a sufficiently large quantity of thrombin to catalyze the formation of a stable clot. Individuals with a deficiency of either Factor VIII (hemophilia A) or Factor IX (hemophilia B) have an impaired propagation response. Individuals with a severe deficiency (<1%) cannot produce thrombin via the intrinsic pathway that is dependent on these proteins. This condition results in the inability to produce sufficient thrombin to have adequate platelet activation, fibrin generation and stable clot formation. However, these individuals have an intact extrinsic pathway Inhibition of TFPI could permit continuation of the initiation response and enable propagation to occur via the extrinsic pathway, permitting sufficient thrombin generation to partially or completely replace the deficient intrinsic pathway and thus reduce bleeding risk. Individuals with mild or moderate deficiencies in these factors, who are also at risk for increased bleeding, may also benefit from the enhanced blood coagulation caused by TFPI inhibition. In addition, in patients with normal intrinsic and extrinsic pathways who are bleeding for other reasons, such as trauma, TFPI inhibition may provide a hemostatic stimulus that could control bleeding. Patients with other deficiencies of clotting factors, platelet deficiencies, and vascular defects associated with bleeding, might also benefit from a treatment that would inhibit TFPI.

Combination Therapy

One embodiment of the invention comprises a TFPI aptamer or a salt thereof or a pharmaceutical composition used in combination with one or more other treatments for bleeding diseases or disorders, such as other procoagulant factors or other inhibitors of coagulation cascade regulatory molecules. The pharmaceutical compositions may also be administered in combination with another drug, such as: activated prothrombin complex concentrates (APCC), Factor Eight Inhibitor Bypass Agent (FEIBA®), recombinant Factor VIIa (e.g., Novoseven®), recombinant Factor VIII (Advate®, Kogenate®, Recombinate®, Helixate®, ReFacto®), plasma-derived Factor VIII (Humate P®, Hemofil M®), recombinant Factor IX (BeneFIX®), plasma-derived Factor IX (Bebulin VH®, Konyne®, Mononine®), cryoprecipitate, desmopressin acetate (DDAVP), epsilon-aminocaproic acid or tranexamic acid. Alternatively, the pharmaceutical compositions may be administered in combination with another therapy, such as: blood or blood-product transfusion, plasmapheresis, immune tolerance induction therapy with high doses of replacement factor, immune tolerance therapy with immunosuppressive agents (e.g., prednisone, rituximab) or pain therapy. In general, the currently available dosage forms of the known therapeutic agents and the uses of non-drug therapies for use in such combinations will be suitable.

"Combination therapy" (or "co-therapy") includes the administration of a TFPI aptamer and at least a second agent or treatment as part of a specific treatment regimen intended to provide the beneficial effect from the co-action of these therapeutic agents or treatments. The beneficial effect of the combination includes, but is not limited to, pharmacokinetic or pharmacodynamic co-action resulting from the combination of therapeutic agent or treatments. Administration of these therapeutic agents or treatments in combination typically is carried out over a defined time period (usually minutes, hours, days or weeks depending upon the combination selected).

Combination therapy may, but generally is not, intended to encompass the administration of two or more of these therapeutic agents or treatments as part of separate monotherapy regimens that incidentally and arbitrarily result in the combinations of the invention. Combination therapy is intended to embrace administration of the therapeutic agents or treatments in a sequential manner. That is, wherein each therapeutic agent or treatment is administered at a different time, as well as administration of these therapeutic agents or treatments, or at least two of the therapeutic agents or treatments, in a substantially simultaneous manner. Substantially simultaneous administration can be accomplished, for example, by administering to the subject a single injection having a fixed ratio of each therapeutic agent or in multiple, single injections for each of the therapeutic agents.

Sequential or substantially simultaneous administration of each therapeutic agent or treatment can be effected by any appropriate route including, but not limited to, topical routes, oral routes, intravenous routes, subcutaneous routes, intramuscular routes, and direct absorption through mucous membrane tissues. The therapeutic agents or treatments can be administered by the same route or by different routes. For example, a first therapeutic agent or treatment of the combination selected may be administered by injection while the other therapeutic agents or treatments of the combination may be administered subcutaneously. Alternatively, for example, all therapeutic agents or treatments may be administered subcutaneously or all therapeutic agents or treatments may be administered by injection. The sequence in which the therapeutic agents or treatments are administered is not critical unless noted otherwise.

Combination therapy also can embrace the administration of the therapeutic agent or treatments as described above in further combination with other biologically active ingredients. Where the combination therapy comprises a non-drug treatment, the non-drug treatment may be conducted at any suitable time so long as a beneficial effect from the co-action of the combination of the therapeutic agent and non-drug treatment is achieved. For example, in appropriate cases, the beneficial effect is still achieved when the non-drug treatment is temporally removed from the administration of the therapeutic agent, perhaps by days or even weeks.

Reversal Agents

The invention further relates to agents that reverse the effects of the TFPI aptamers, referred to herein as "TFPI reversal agents". The agent can be any type of molecule, such as a protein, antibody, small molecule organic compound or an oligonucleotide.

Preferably, a TFPI reversal agent is a nucleic acid that is 10-15 nucleotides in length. However, there are no limits to the length of the reversal agent.

Preferably, a TFPI reversal agent binds to a TFPI aptamer. A TFPI reversal agent may bind to a full length TFPI aptamer or a fragment thereof. Such binding may be through ionic interactions, covalent bonding, complementary base pairing, hydrogen bonding, or any other type of chemical bond. Preferably, such binding is via complementary base pairing. Without wishing to be bound by theory, a TFPI reversal agent acts by hybridizing to a TFPI aptamer, thereby disrupting the TFPI aptamer's secondary and tertiary structure and preventing the binding of the TFPI aptamer to TFPI. By preventing the binding of the TFPI aptamer to TFPI, the effect of the binding interaction, e.g., therapeutic effect, and/or stimulation or inhibition of the molecular pathway, can be modulated, providing a means of controlling the extent of the binding interaction and the associated effect.

A TFPI reversal agent may be a ribonucleic acid, deoxyribonucleic acid or mixed ribonucleic and deoxyribonucleic acid. Preferably, a TFPI reversal agent is single stranded. Preferably, a TFPI reversal agent comprises all 2'-O Methyl residues and a 3'-inverted deoxythymidine. However, a TFPI reversal agent may contain any nucleotides, modified or unmodified, along with any other 3' or 5' modifications that may be found on aptamers.

Examples of TFPI reversal agents include, but are not limited to: SEQ ID NO: 15, which is ARC23085; SEQ ID NO: 16, which is ARC23087; SEQ ID NO: 17, which is ARC23088; and SEQ ID NO: 18, which is ARC23089.

Preferably, the TFPI reversal agent is a nucleic acid comprising the structure set forth below: mA-mG-mC-mC-mA-mA-mG-mU-mA-mU-mA-mU-mU-mC-mC (SEQ ID NO: 15), wherein "mN" is a 2'-O Methyl containing residue (which is also known in the art as a 2'-OMe, 2'-methoxy or 2'-OCH$_3$ containing residue).

Alternatively, the TFPI reversal agent is a nucleic acid comprising the structure set forth below: mU-mA-mU-mA-mU-mA-mC-mG-mC-mA-mC-mC-mU-mA-mA (SEQ ID NO: 16), wherein "mN" is a 2'-O Methyl containing residue.

Alternatively, the TFPI reversal agent is a nucleic acid comprising the structure set forth below: mC-mU-mA-mA-mC-mG-mA-mG-mC-mC (SEQ ID NO: 17), wherein "mN" is a 2'-O Methyl containing residue.

Alternatively, the TFPI reversal agent is a nucleic acid comprising the structure set forth below: mC-mA-mC-mC-mU-mA-mA-mC-mG-mA-mG-mC-mC-mA-mA (SEQ ID NO: 18), wherein "mN" is a 2'-O Methyl containing residue.

The chemical name of ARC23085 is 2'-OMe-adenylyl-(3'→5')-2'-OMe-guanylyl-(3'→5')-2'-OMe-cytidylyl-(3'→5')-2'-OMe-cytidylyl-(3'→5')-2'-OMe-adenylyl-(3'→5')-2'-OMe-adenylyl-(3'→5')-2'-OMe-guanylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-2'-OMe-uracylyl-(3'→5')-2'-OMe-uracylyl-(3'→5')-2'-OMe-cytidylyl-(3'→5')-2'-OMe-cytidylyl.

The chemical name of ARC23087 is 2'-OMe-uracylyl-(3'→5')-2'-OMe-adenylyl-(3'→5')-2'-OMe-uracylyl-(3'→5')-2'-OMe-adenylyl-(3'→5')-2'-OMe-uracylyl-(3'→5')-2'-OMe-adenylyl-(3'→5')-2'-OMe-cytidylyl-(3'→5')-2'-OMe-guanylyl-(3'→5')-2'-OMe-cytidylyl-(3'→5')-2'-OMe-adenylyl-(3'→5')-2'-OMe-cytidylyl-(3'→5')-2'-OMe-cytidylyl-(3'→5')-2'-OMe-uracylyl-(3'→5')-2'-OMe-adenylyl-(3'→5')-2'-OMe-adenylyl.

The chemical name of ARC23088 is 2'-OMe-cytidylyl-(3'→5')-2'-OMe-uracylyl-(3'→5')-2'-OMe-adenylyl-(3'→5')-2'-OMe-adenylyl-(3'→5')-2'-OMe-cytidylyl-(3'→5')-2'-OMe-guanylyl-(3'→5')-2'-OMe-adenylyl-(3'→5')-2'-OMe-guanylyl-(3'→5')-2'-OMe-cytidylyl-(3'→5')-2'-OMe-cytidylyl.

The chemical name of ARC23089 is 2'-OMe-cytidylyl-(3'→5')-2'-OMe-adenylyl-(3'→5')-2'-OMe-cytidylyl-(3'→5')-2'-OMe-cytidylyl-(3'→5')-2'-OMe-uracylyl-(3'→5')-2'-OMe-adenylyl-(3'→5')-2'-OMe-adenylyl-(3'→5')-2'-OMe-cytidylyl-(3'→5')-2'-OMe-guanylyl-(3'→5')-2'-OMe-adenylyl-(3'→5')-2'-OMe-guanylyl-(3'→5')-2'-OMe-cytidylyl-(3'→5')-2'-OMe-cytidylyl-(3'→5')-2'-OMe-adenylyl-(3'→5')-2'-OMe-adenylyl.

The invention also includes TFPI reversal agents that have 70% identity or more to any one of SEQ ID NOs: 15, 16, 17 or 18. For example, the TFPI reversal agents may have 70, 75, 80, 85, 90, 95 or 100% identity to one of SEQ ID NOs: 15, 16, 17 or 18.

The invention also includes pharmaceutical compositions containing TFPI reversal agents that bind to TFPI aptamers. In some embodiments, the compositions include an effective amount of a pharmacologically active TFPI reversal agent or a pharmaceutically acceptable salt thereof, alone or in combination, with one or more pharmaceutically acceptable carriers. The compositions may contain one or more different TFPI reversal agents. The TFPI reversal agents are administered to subjects in an amount effective to reverse the therapeutic effect of the TFPI aptamer. The compositions may be administered by numerous routes of administration, such as, for example, topically, intranasally or parenterally. The dosage regimen for a TFPI reversal agent will depend on a variety of factors including type, species, age, weight, sex and medical condition of the patient; the severity of the condition to be treated; the route of administration, the renal and hepatic function of the patient; the amount of TFPI aptamer used to treat a patient; and the particular TFPI reversal agent or salt thereof employed. An ordinary skilled physician or veterinarian can readily determine and prescribe the effective amount of the TFPI reversal agent required to reverse the therapeutic effect of a TFPI aptamer.

The invention further includes agents that neutralize the hemostatic activity of the TFPI aptamer. Such an agent may bind to TFPI and prevent its inhibition by the TFPI aptamer, or the agent may inhibit downstream coagulation factors (e.g., FXa or thrombin) in a manner that counteracts the hemostatic activity of the TFPI aptamer. Such an agent may include, but is not limited to, anticoagulants, such as unfractionated heparin or low molecular weight heparin. A study by Wesselschmidt (Wesselschmidt et al., "Structural requirements for tissue factor pathway inhibitor interactions with factor Xa and heparin", *Blood Coagul Fibrinolysis*, vol. 4, pp. 661-669 (1993)) shows that heparin binds to TFPI through interactions with the K3 and C-terminal domains, which could interfere either directly or indirectly with the ability of TFPI aptamers to bind to TFPI. Moreover, in the same study, heparin-binding was observed to facilitate the FXa inhibitory activity of TFPI, which would tend to further counteract the hemostatic activity of TFPI aptamers. Finally, heparin is well known to inhibit thrombin, FXa and other coagulation factors through an antithrombin-dependent mechanism. These activities could neutralize the ability of TFPI aptamers to stimulate thrombin generation and clot formation. In the event that the hemostatic effects of TFPI aptamers were to induce thrombosis, one of these agents could be administered to arrest its progression. An ordinary skilled physician or veterinarian can readily determine and prescribe the effective amount of the anticoagulant or other neutralizing agent required to reverse the hemostatic effect of a TFPI aptamer.

Kits

The pharmaceutical compositions may also be packaged in a kit. The kit will comprise the composition, along with instructions regarding administration of the TFPI aptamer. The kit may also comprise one or more of the following: a syringe or pre-filled syringe, an intravenous bag or bottle, a vial, the same TFPI aptamer in a different dosage form or another TFPI aptamer. For example, the kit may comprise both an intravenous formulation and a subcutaneous formulation of a TFPI aptamer of the invention. Alternatively, the kit may comprise lyophilized TFPI aptamer and an intravenous bag of physiological saline solution or phosphate buffered saline solution. The kit form is particularly advantageous when the separate components must be administered in different dosage forms (i.e., parenteral and oral) or are administered at different dosage intervals. The kit may further comprise a TFPI reversal agent, along with instructions regarding administration of the reversal agent. The kit may contain both an intravenous formulation and a subcutaneous formulation of the TFPI reversal agent. Alternatively, the kit may contain lyophilized TFPI reversal agent and an intravenous bag of solution.

Preferably, the kits are stored at 5±3° C. The kits can also be stored at room temperature or frozen at −20° C.

Regulating TFPI

The invention also provides a method for regulating TFPI in which a molecule binds or otherwise interacts with one or more portions of TFPI, wherein at least one portion is outside of the K1 and K2 domains of TFPI, such as the K3/C terminal region. The molecule can be any type of molecule, such as, for example, a small molecule organic compound, an antibody, a protein or peptide, a nucleic acid, a siRNA, an aptamer, or any combination thereof. Preferably, the molecule is a small molecule organic compound. More preferably, the molecule is an antibody. Most preferably, the molecule is an aptamer. For example, the molecule may bind to or otherwise interact with a linear portion or a conformational portion of TFPI. A molecule binds to or otherwise interacts with a linear portion of TFPI when the molecule binds to or otherwise interacts with a contiguous stretch of amino acid residues that are linked by peptide bonds. A molecule binds to or otherwise interacts with a conformational portion of TFPI when the molecule binds to or otherwise interacts with non-contiguous amino acid residues that are brought together by folding or other aspects of the secondary and/or tertiary structure of the polypeptide chain. Preferably, the molecule binds at least in part to one or more portions of mature TFPI (for example, FIG. 3A) that are selected from the group consisting of: amino acids 148-170, amino acids 150-170, amino acids 155-175, amino acids 160-180, amino acids 165-185, amino acids 170-190, amino acids 175-195, amino acids 180-200, amino acids 185-205, amino acids 190-210, amino acids 195-215, amino acids 200-220, amino acids 205-225, amino acids 210-230, amino acids 215-235, amino acids 220-240, amino acids 225-245, amino acids 230-250, amino acids 235-255, amino acids 240-260, amino acids 245-265, amino acids 250-270, amino acids 255-275, amino acids 260-276, amino acids 148-175, amino acids 150-175, amino acids 150-180, amino acids 150-185, amino acids 150-190, amino acids 150-195, amino acids 150-200, amino acids 150-205, amino acids 150-210, amino acids 150-215, amino acids 150-220, amino acids 150-225, amino acids 150-230, amino acids 150-235, amino acids 150-240, amino acids 150-245, amino acids 150-250, amino acids 150-255, amino acids 150-260, amino acids 150-265, amino acids 150-270, amino acids 150-275, amino acids 150-276, amino acids 190-240, amino acids 190-276, amino acids 240-276, amino acids 242-276, amino acids 161-181, amino acids 162-181, amino acids 182-240, amino acids 182-241, and amino acids 182-276. The molecule preferably comprises a dissociation constant for human TFPI, or a variant thereof, of less than 100 µM, less than 1 µM, less than 500 nM, less than 100 nM, preferably 50 nM or less, preferably 25 nM or less, preferably 10 nM or less, preferably 5 nM or less, more preferably 3 nM or less, even more preferably 1 nM or less, and most preferably 500 pM or less.

Many modifications and variations of the invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

In the examples, one or more of the following TFPI aptamers were used to conduct the various experiments. ARC26835 is the aptamer described in SEQ ID NO: 1. ARC17480 is the aptamer described in SEQ ID NO: 2. ARC19498 is the aptamer described in SEQ ID NO: 3. ARC19499 is the aptamer described in SEQ ID NO: 4. ARC19500 is the aptamer described in SEQ ID NO: 5. ARC19501 is the aptamer described in SEQ ID NO: 6. ARC26835 is the core aptamer sequence for each of ARC17480, ARC19498, ARC19499, ARC19500 and ARC19501. ARC31301 is the aptamer described in SEQ ID NO: 7. ARC18546 is the aptamer described in SEQ ID NO: 8. ARC19881 is the aptamer described in SEQ ID NO: 9. ARC19882 is the aptamer described in SEQ ID NO: 10. ARC31301 is the core aptamer sequence for each of ARC18546, ARC19881 and ARC19882.

Example 1

This example demonstrates how ARC19499 was generated.

In vitro selection experiments were performed using a pool of modified oligonucleotide molecules, each of which contained dC, mA, mG and mU residues, and recombinant human tissue factor pathway inhibitor (TFPI), which was obtained from American Diagnostica (catalog #4500PC, Stamford, Conn.). Iterative rounds of selection for binding to TFPI, followed by amplification, were performed to generate ARC14943, an 84 nucleotide long precursor to ARC19499. ARC14943 was minimized from 84 nucleotides to 32 nucleotides (ARC26835) using computational folding prediction programs and systematic deletion. Appendage of a 3'-inverted deoxythymidine residue to ARC26835 resulted in ARC17480, a 33 nucleotide long molecule. Addition of a 5'-hexylamine group to ARC17480 resulted in ARC19498. This molecule was then PEGylated via the 5'-hexylamine group with a 40 kDa PEG moiety to result in ARC19499.

Example 2

This example demonstrates that ARC17480 binds tightly to TFPI in vitro in a dot-blot binding experiment, in both the absence and presence of competitor tRNA.

Figure 12A:
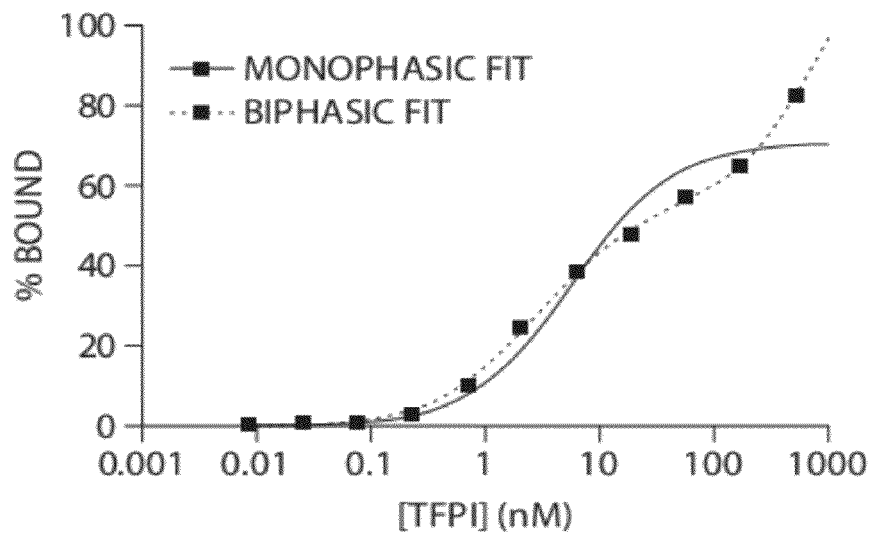
FIG. 12A is a graph showing that ARC17480 binds tightly to full-length TFPI. The data are fit to both monophasic and biphasic models to determine a $K_D$ for binding.
Figure 12B:
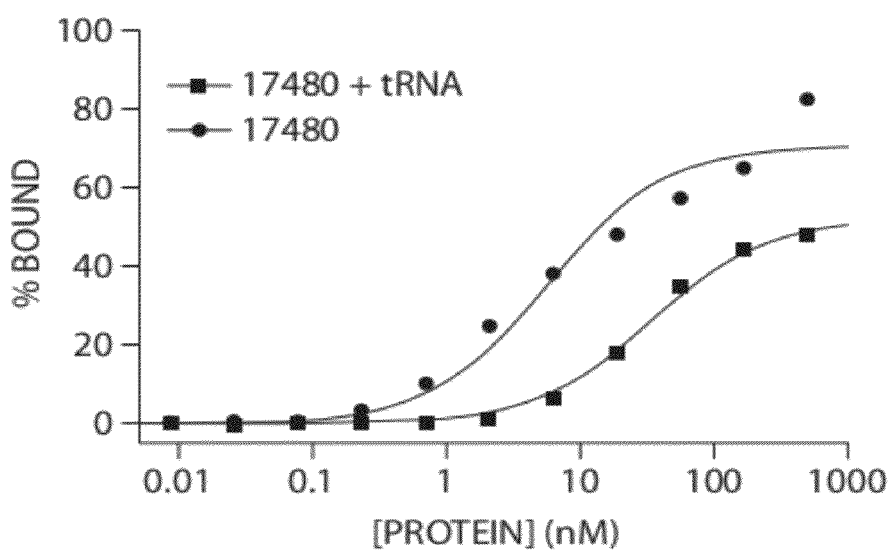
FIG. 12B is a graph showing that tRNA shifts the affinity of ARC17480 for TFPI. The aptamer still binds tightly to TFPI in the presence of tRNA, indicating that the binding of ARC17480 to TFPI is specific.
Figure 13A:
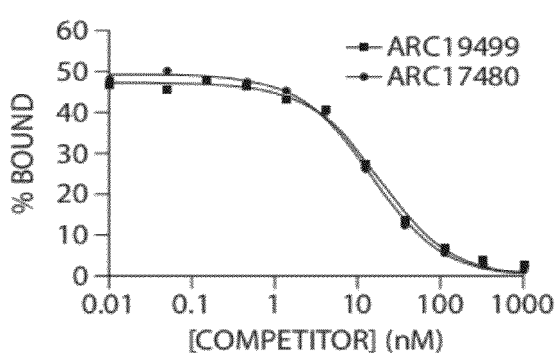
FIG. 13 depicts the results of binding-competition experiments with radiolabeled ARC17480, full-length TFPI and various unlabeled aptamers. Unlabeled ARC17480 and ARC19499 (FIG. 13A); ARC19498 (FIG. 13B), ARC18546 (FIG. 13C); ARC26835 and ARC31301 (FIG. 13D); ARC19500, ARC19501, ARC19881 and ARC19882 (FIG. 13E) all compete for binding with radiolabeled ARC17480.
Figure 13B:
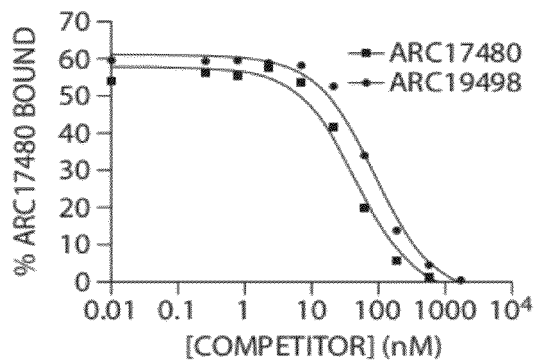
Figure 13C:
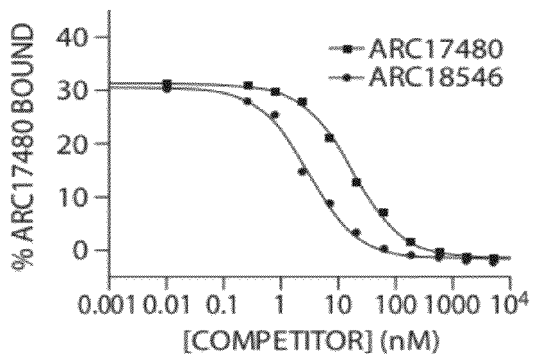
Figure 13D:
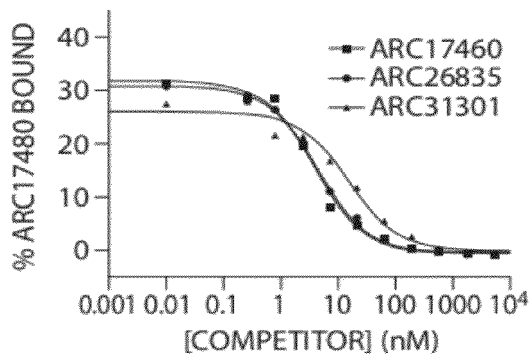
Figure 13E:
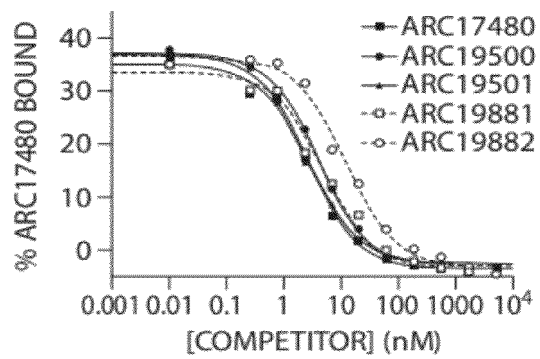
Figure 14A:
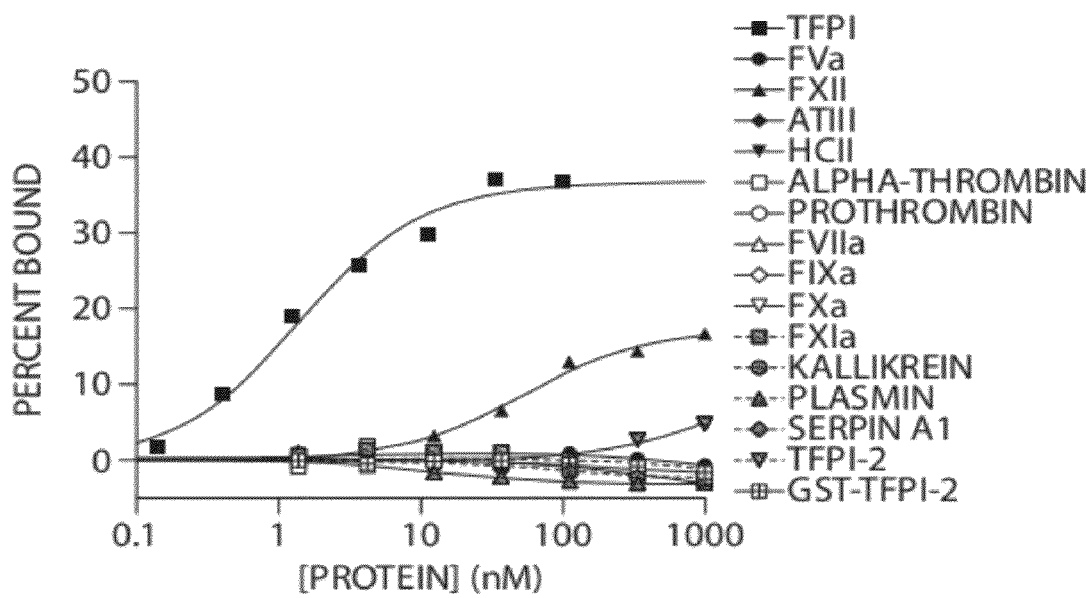
FIG. 14A is a graph of a binding experiment with ARC17480 and various proteins.
Figure 14B:
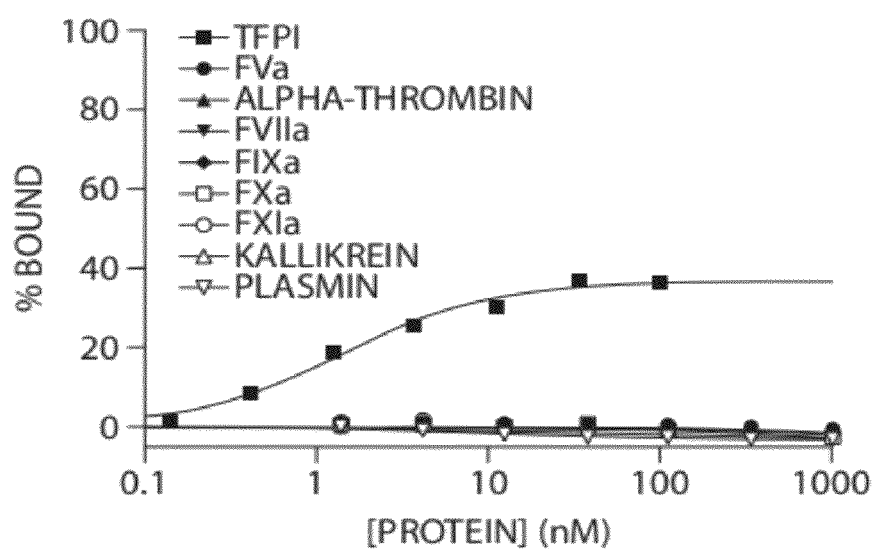
FIG. 14B is a graph of a binding experiment with ARC17480 and TFPI or various activated coagulation factors.
Figure 14C:
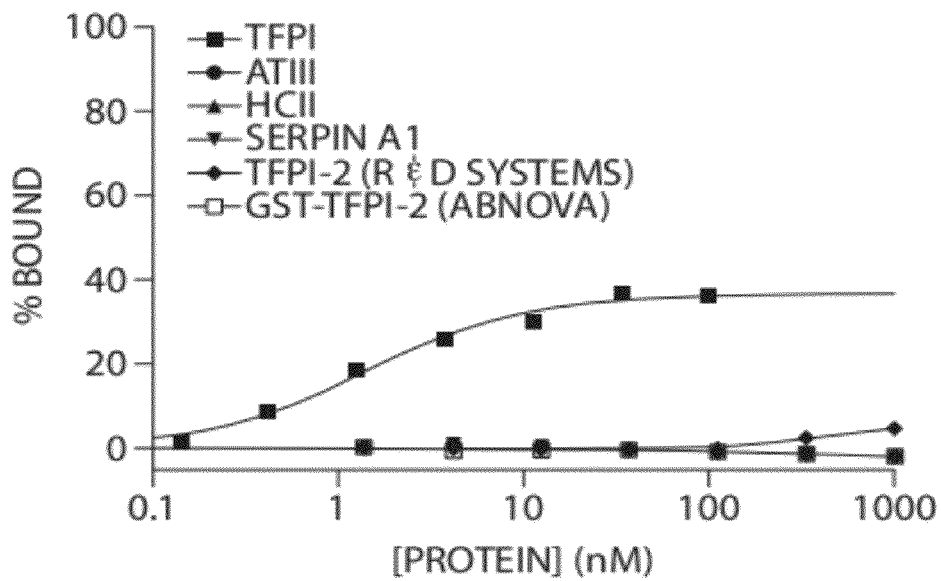
FIG. 14C is a graph of a binding experiment with ARC17480 and TFPI or various protease inhibitors.
Figure 14D:
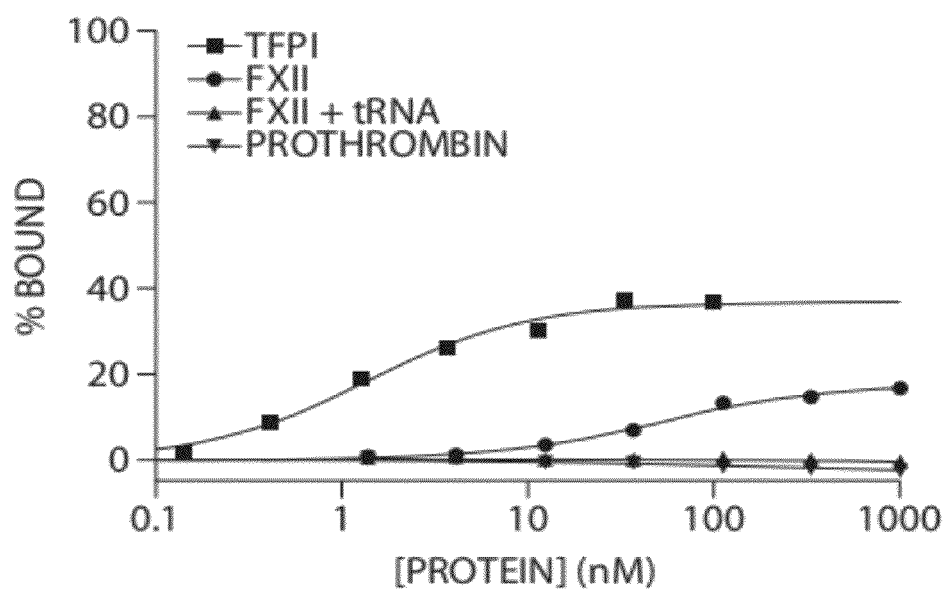
FIG. 14D is a graph of a binding experiment with ARC17480 and TFPI or various coagulation zymogens. ARC17480 showed significant binding to TFPI, but not to any of the other proteins tested.

Radiolabeled ARC17480 was incubated with different concentrations of TFPI. ARC17480 bound to TFPI was then captured on a nitrocellulose filter membrane. The ratio of radiolabeled ARC17480 bound to the nitrocellulose filter over total radiolabeled ARC17480 added was determined and plotted as the percentage of ARC17480 bound as a function of protein concentration. An example of an ARC17480/TFPI binding plot is shown in FIG. 12A. The data were fit to models for monophasic and biphasic aptamer-protein binding. This experiment was repeated eleven times and $K_D$s using both monophasic and biphasic binding models were determined for each data set. The mean $K_D$ determined using a monophasic fit was 4.0±1.5 nM and using a biphasic fit was 1.7±0.7 nM. Both monophasic and biphasic fits to the data assume different models for the interaction of ARC17480 to TFPI, although the fits in and of themselves do not explicitly support either binding model. Regardless of the model used to fit the data, the $K_D$ determined for binding of ARC17480 to TFPI was essentially the same. When the $K_D$s determined from both the monophasic and biphasic fits were taken into consideration, the mean $K_D$ of ARC17480 binding to TFPI was 2.9±1.6 nM. This mean $K_D$ does not assume a mode of binding interaction between ARC17480 and TFPI and, as such, is the most robust determination of the binding interaction between the aptamer and the protein. ARC17480 maintained binding to human TFPI in the presence of tRNA, indicating that the binding was specific. A shift in binding affinity of ARC17480 to TFPI was observed in the presence of 0.1 mg/mL tRNA with a mean $K_D$ of 42±12 nM. An example plot of ARC17480 binding to TFPI in both the presence and absence of tRNA is shown in FIG. 12B.

Example 3

This example demonstrates that unlabeled ARC17480, ARC19498, ARC19499, ARC26835, ARC19500, ARC19501, ARC31301, ARC18546, ARC19881 and ARC19882 compete with radiolabeled ARC17480 for binding to TFPI. This example also demonstrates that all of these aptamers have affinities for TFPI that are similar to that observed with ARC17480.

Each aptamer was evaluated for binding to TFPI in a binding-competition assay. For these experiments, human TFPI (American Diagnostica, Stamford, Conn., catalog #4500PC) was incubated with trace amounts of radiolabeled ARC17480 and different concentrations of unlabeled competitor aptamer (5000 nM-0.25 nM for all aptamers except ARC19499; 1000 nM-0.05 nM for ARC19499). For experiments with ARC17480 and ARC19499 in FIG. 13A, 60 nM TFPI was used. For all other experiments (FIG. 13B-E), 10 nM TFPI was used. ARC17480 was included as a competitor in every experiment as a control. For each aptamer, the percentage of radiolabeled ARC17480 bound at each competitor aptamer concentration was used for analysis. The percentage of radiolabeled ARC17480 bound was plotted as a function of aptamer concentration and fit to the equation $y=(max/(1+x/IC_{50}))+int$, where y=the percentage of radiolabeled ARC17480 bound, x=the concentration of aptamer, max=the maximum radiolabeled ARC17480 bound, and int=the y-intercept, to generate an $IC_{50}$ value for binding-competition. FIG. 13A-E shows graphs of competition experiments with ARC17480, ARC19498, ARC19499, ARC26835, ARC19500, ARC19501, ARC31301, ARC18546, ARC19881 and ARC19882. These molecules all competed similarly with radiolabeled ARC17480 for binding to TFPI. These experiments demonstrate that ARC17480, ARC19498, ARC19499, ARC26835, ARC19500, ARC19501, ARC31301, ARC18546, ARC19881 and ARC19882 all bind similarly to full-length TFPI.

Example 4

This example demonstrates that the TFPI aptamers bind specifically to TFPI.

In this experiment, ARC17480 was tested for binding to a variety of proteins that are key molecules in the coagulation cascade, molecules whose inhibition would show a similar profile to TFPI inhibition, or molecules that are similar in structure or function to TFPI. Proteins investigated were TFPI, Factor Va (FVa), Factor XII (FXII), antithrombin (ATIII), heparin cofactor II (HCII), alpha-thrombin, prothrombin, Factor VIIa (FVIIa), Factor IXa (FIXa), Factor Xa (FXa), Factor XIa (FXIa), kallikrein, plasmin, alpha-1 antitrypsin (serpin-A1), TFPI-2, and GST-TFPI-2. In the presence of up to 0.5-1 μM of each protein, ARC17480 did not have any significant affinity for the sequence- and mechanistically-related proteins tested (FIG. 14A-D). ARC17480 showed some binding to FXII at higher concentrations of protein. This binding was eliminated in the presence of 0.1 mg/mL tRNA (FIG. 14D), indicating that the binding was likely non-specific.

These experiments indicate that any effects on coagulation that are mediated by the TFPI aptamers are likely due to direct binding and inhibition of TFPI.

Example 5

This example demonstrates that ARC19499 binds tightly to TFPI in a plate-based binding assay. This example also demonstrates that ARC19498 binds tightly to TFPI due to its competition with ARC19499 for binding to TFPI in a plate-based binding assay.

Figure 15:
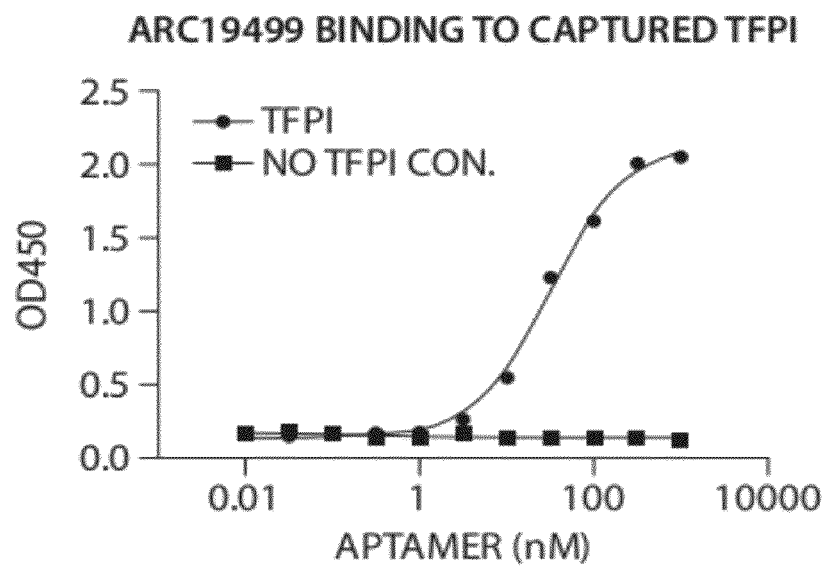
FIG. 15 is a graph showing data from a plate-based assay demonstrating binding of ARC19499 to recombinant TFPI.

In order to assess the binding affinity of ARC19499 to TFPI, recombinant human TFPI protein (0.5 mg/mL) was diluted in Dulbecco's Phosphate-buffered Saline (DPBS) to a final concentration of 15 μg/mL, and 100 μL was added to a 96-well Maxisorb plate and incubated overnight at 4° C. The TFPI solution was then removed and the plate was subsequently washed 3 times with 200 μL wash buffer (DPBS+ 0.05% Tween 20) at room temperature. The plate was then blocked with 200 μL of 10 mg/mL bovine serum albumin (BSA) in DPBS for 30 minutes at room temperature. The BSA blocking solution was then removed and the plate was washed again 3 times with 200 μL wash buffer. Serially diluted ARC19499 in DPBS with 0.1% BSA was then added to the plate and incubated for 3 hours at room temperature. After washing 3 times with 200 μL wash buffer, 100 μL of 0.5 μg/mL rabbit monoclonal anti-PEG antibody (Epitomics)

was added to the plate and incubated for 60 minutes at room temperature. The anti-PEG antibody solution was then removed and the plate was washed as described above. Then, 100 µL anti-rabbit IgG-HRP secondary antibody (Cell Signaling Technology), diluted 1000-fold in assay buffer, was added to each well and incubated for 30 minutes. After washing 3 times with 200 µL wash buffer, 100 µL of TMB solution (Pierce) was added to each well and incubated for 2 minutes before adding 100 µL stop solution (2N $H_2SO_4$) to each well to stop the reaction. The assay plate was then read at 450 nm using a Victor$^3$V 1420 multilabel counter (Perkin Elmer). Five different binding experiments suggested that the binding affinity between ARC19499 and recombinant TFPI is 30 nM in the plate-based binding assay. The data from one of these experiments is shown in FIG. 15.

Figure 16:
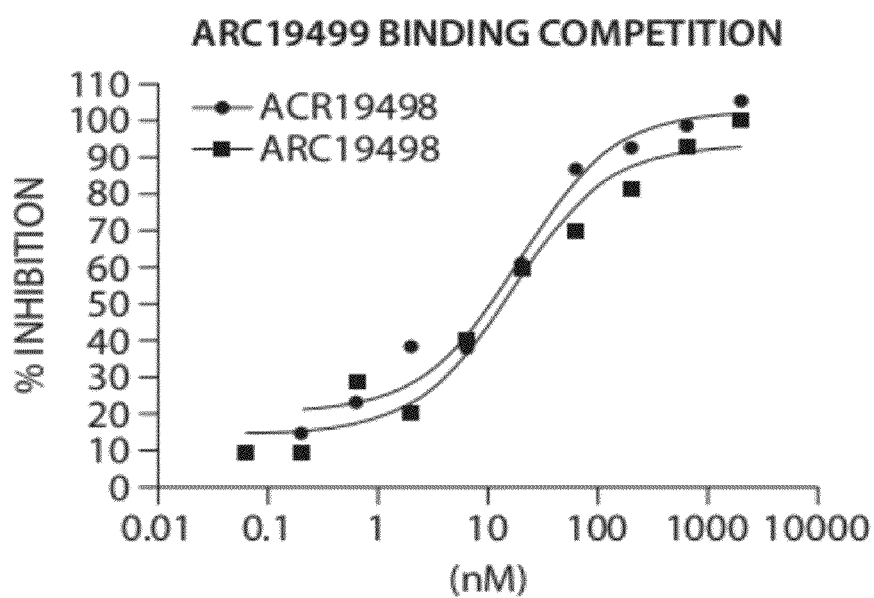
FIG. 16 is a graph showing data from a plate-based competition assay demonstrating binding of ARC19498 to TFPI in competition with ARC19499.

In order to assess the affinity of ARC19498 towards TFPI protein, an ARC19499:TFPI binding competition assay was set up. Recombinant human TFPI protein (0.5 mg/mL) was diluted in DPBS to a final concentration of 15 µg/mL, and 100 µL was added to a 96-well Maxisorb plate and incubated overnight at 4° C. The TFPI solution was then removed and the plate was subsequently washed 3 times with 200 µL wash buffer (DPBS+0.05% Tween 20) at room temperature. The plate was then blocked with 200 µL of 10 mg/mL BSA in DPBS for 30 minutes at room temperature. The BSA blocking solution was then removed and the plate was washed again 3 times with 200 µL wash buffer. ARC19498 was serially diluted and mixed at different concentrations with 20 nM ARC19499 in DPBS in 0.1% BSA. The ARC19498:ARC19499 mixtures were added to the plate and incubated for 3 hours at room temperature. After washing 3 times with 200 µL wash buffer, 100 µL of 0.5 µg/mL rabbit monoclonal anti-PEG antibody (Epitomics) was added to the plate and incubated for 60 minutes at room temperature. The anti-PEG antibody solution was then removed and the plate was washed as described above. Then, 100 µL anti-rabbit IgG-HRP secondary antibody (Cell Signaling Technology), diluted 1000-fold in assay buffer, was added to each well and incubated for 30 minutes. After washing 3 times with 200 µL wash buffer, 100 µL of TMB solution (Pierce) was added to each well and incubated for 2 minutes before adding 100 µL stop solution (2N $H_2SO_4$) to each well to stop the reaction. The assay plate was then read at 450 nm using a Victor$^3$V 1420 multilabel counter (Perkin Elmer). The percent inhibition of ARC19499 binding was calculated using 0 nM ARC19498 in 20 nM ARC19499 as 0% inhibition, and 0 nM ARC19498 and 0 nM ARC19499 as 100% inhibition. The $IC_{50}$ was calculated based on 4-parameter logistics using Graphpad Prism 4 software. FIG. 16 shows two replicates of this experiment, both of which gave an $IC_{50}$ of 20 nM for ARC19498 competition with ARC19499 in this assay. These results suggest that ARC19498 has a binding affinity for TFPI in the plate-based binding assay that is similar to that observed for ARC19499.

Example 6

This example examines the regions on TFPI where ARC17480 binds. Dot blot binding experiments were carried out with radiolabeled ARC17480 and various truncated TFPI proteins, and binding-competition experiments were carried out with radiolabeled ARC17480, TFPI, and heparin or low molecular weight heparin (LMWH). The proteins used for binding experiments are described in Table 1 below.

Trace amounts of radiolabeled ARC17480 were incubated with different concentrations (500 nM-0.7 nM) of full-length TFPI and TFPI-His (Table 1). FIG. 17A shows that ARC17480 had reduced binding to TFPI-His when compared to its binding to full-length TFPI. This experiment suggested that the C-terminal 20 amino acids of TFPI, which are missing in TFPI-His but present in full-length TFPI, contribute to binding of ARC17480 to TFPI.

Trace amounts of radiolabeled ARC17480 were incubated with different concentrations of truncated TFPI-K1K2 (500 nM-0.008 nM) and the K3-C-terminal domain protein (500 nM-0.7 nM) (Table 1). FIG. 17B shows that ARC17480 had no detectable binding to truncated TFPI-K1K2 and very weak binding to the K3-C-terminal domain protein that was only detectable at higher concentrations of the protein. Trace amounts of radiolabeled ARC17480 were incubated with different concentrations of the C-terminal peptide (10 µM-0.17 nM) (Table 1). Neutravidin (~100 nM monomer) was then added to the binding solution to assist in the capture of aptamer:peptide complexes on a nitrocellulose filter. The amount of radiolabeled aptamer captured on a nitrocellulose filter was quantitated and compared to the total amount of radiolabeled aptamer to generate a binding curve, which is shown in FIG. 17B. ARC17480 showed weak binding to the C-terminal peptide at high concentrations of peptide.

Trace amounts of radiolabeled ARC17480 were incubated with different concentrations of full-length TFPI (500 nM-0.008 nM) in the absence or presence of 0.1 mg/mL unfractionated heparin (FIG. 18A). The inclusion of heparin in the binding experiment completely abolished ARC17480 binding to TFPI. In a separate experiment, trace amounts of radiolabeled ARC17480 were incubated with 12.5 nM full-length TFPI and different concentrations (5 µM-0.25 nM) of unfractionated heparin or low molecular weight heparin (LMWH). FIG. 18B shows that both unfractionated heparin and LMWH competed with ARC17480 for binding to TFPI in a concentration-dependent manner. Heparin was a more effective competitor than LMWH. The K3-C-terminal regions of TFPI have been implicated in glycocalyx binding, and this is the region of the protein where heparin and LMWH should bind. These experiments suggest that the K3-C-terminal region of TFPI is important for ARC17480 binding to TFPI.

Taken together, these experiments demonstrate that the C-terminal domain likely participates in ARC17480 binding to TFPI. These experiments also demonstrate that the ARC17480 binding region on TFPI is not entirely contained within the K1-K2 region of the protein, or within the K3-C-terminal region of the protein. The regions required for ARC17480 binding likely spans more than one domain of the protein.

TABLE 1

Proteins used for binding experiments

| Protein | Description | Amino acids of mature TFPI |
|---|---|---|
| Full-length TFPI | American Diagnostica, E. coli expressed | 1-276 |
| TFPI-His | R&D systems, murine myeloma cell line expressed | 1-256 + C-terminal 10-His tag |
| Truncated TFPI-K1K2 | American Diagnostica, E. coli expressed | 1-161 |
| K3-C-terminal domain | E. coli expressed | N-terminal 6-His tag + 182-276 |
| C-terminal peptide | synthetic | N-terminal biotin + 242-276 |

Example 7

This example examines the regions on TFPI where ARC17480 and ARC19499 bind. For these experiments, antibodies that bind to different regions on TFPI were used to compete for binding to TFPI with ARC19499 in a plate-based binding assay, or to compete for binding to TFPI with ARC17480 in a dot-blot binding assay. The antibodies used for competition are shown in Table 2 below.

Figure 19A:
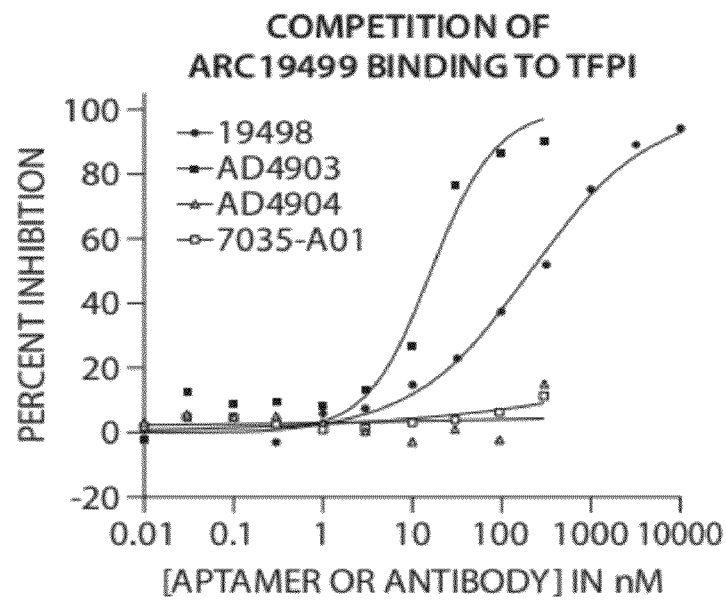
FIGS. 19, A and B, illustrates competition of various anti-TFPI antibodies with ARC19499 in a plate-based binding assay.
Figure 19B:
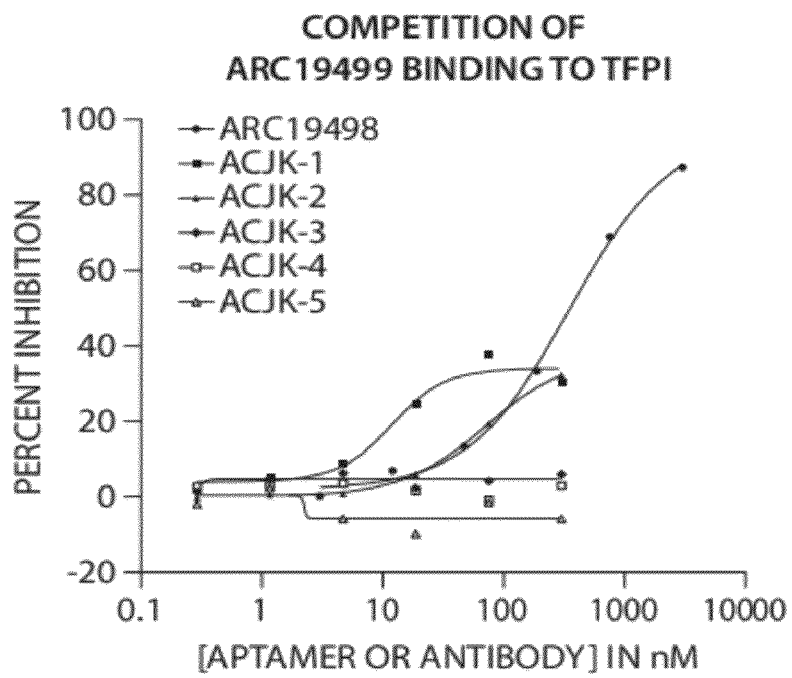
Figure 20A:
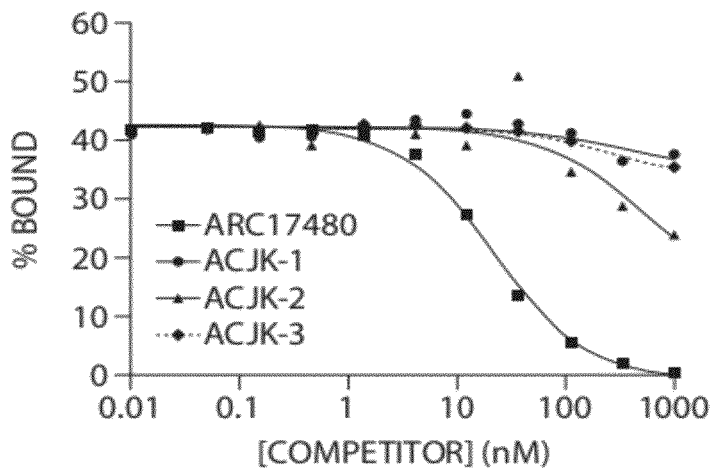
FIGS. 20, A, B and C, illustrates competition of various anti-TFPI antibodies with ARC19499 in a nitrocellulose filtration (dot-blot) assay.
Figure 20B:
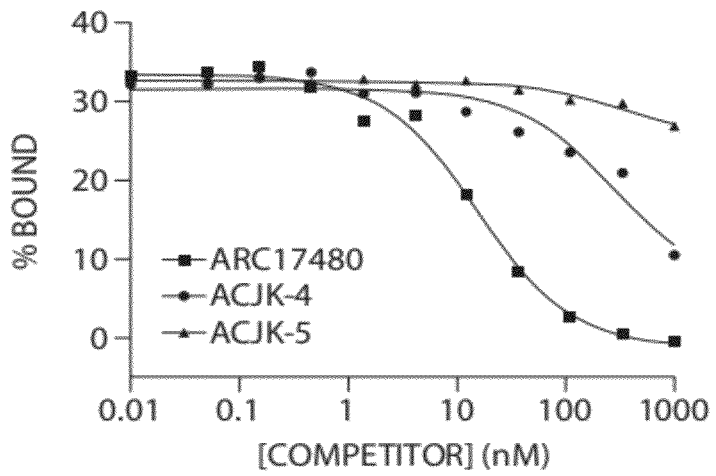
Figure 20C:
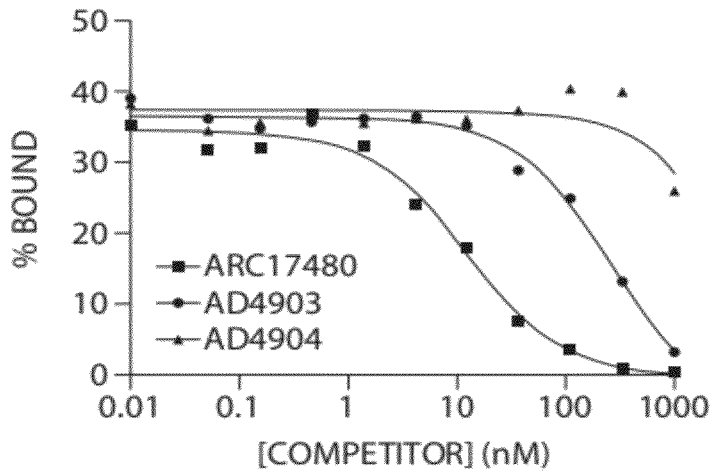

This example demonstrates that antibody AD4903 (American Diagnostica, catalog #4903) competed for binding of ARC19499 to TFPI in a plate-based binding assay and competed for binding of ARC17480 to TFPI in a dot blot-binding assay (FIG. 19A and FIG. 20C). Antibody AD4903 was raised against a fragment of TFPI containing K1 domain amino acid residues 22-87, and binds to TFPI somewhere in this region (Table 2). This example also demonstrates that antibody ACJK-4, which was raised against a peptide that contained amino acid residues 148-162 that are part of the intervening region between the K2 and K3 domains of TFPI, competed weakly with ARC17480 for binding to TFPI in a dot-blot binding assay (FIG. 20B). This example also demonstrates that antibodies ACJK-1 and ACJK-2, which were raised against peptides that contained amino acid residues 261-276 and 245-262, respectively, that are part of the C-terminal domain of TFPI, partially competed for ARC19499 binding to TFPI in a plate-based binding assay (FIG. 19B). This example further demonstrates that several other antibodies that bind to different regions of TFPI did not compete with ARC19499 binding to TFPI in a plate-based binding assay, and did not compete with ARC17480 for binding to TFPI in a dot blot-based binding assay. The antibodies used for the competition experiments are shown in Table 2 below.

For plate-based binding experiments, 400 ng/well of TFPI (American Diagnostics, cat#4900PC) in 100 µL Dulbecco's Phosphate-buffered Saline (DPBS) was used to coat a 96-well Maxisorb plate at 4° C. The TFPI solution was then removed and the plate was subsequently washed 3 times with 200 µL wash buffer (DPBS+0.05% Tween 20) at room temperature. The plate was then blocked with 200 µL of 10 mg/mL bovine serum albumin (BSA) in DPBS for 30 minutes at room temperature. The BSA blocking solution was then removed and the plate was washed 3 times with 200 µL wash buffer. The competing antibodies were serially diluted and mixed with ARC19499 at the final concentration of 25 nM ARC19499 and 0.1% BSA in DPBS, and the mixture was then added to the assay plate and incubated for 3 hours at room temperature. ARC19498 was similarly mixed with ARC19499 and used as a positive control in the antibody competition assay. Wells were then washed, as described above. For experiments using antibodies AD4903, AD4904 and 7035-A01 for competition, 100 µL of 0.5 µg/mL rabbit monoclonal anti-PEG antibody (Epitomics, cat #2061-1) in assay buffer was added to the plate and incubated for 3 hours at room temperature. Anti-PEG antibody solution was then removed and the plate was washed as described above, followed by addition of 100 µL of 1:1000-diluted anti-rabbit IgG-HRP secondary antibody in assay buffer to each well (Cell Signaling Technology, cat #7074) and incubated for 30 minutes. The secondary antibody solution was removed and the plate was washed, as described above. For antibodies ACJK1-ACJK5, 0.5 µg/mL of 100 µL biotinylated rabbit monoclonal anti-PEG antibody (Epitomics, cat #2173) in assay buffer was added to the assay plate and incubated for 3 hours at room temperature, followed by washing, as described above. The antibody was then removed and the plate was washed as described above, followed by addition of 100 µL of streptavidin-HRP (4800-30-06) from R&D Systems (Minneapolis, Minn.) diluted 200-fold in DPBS and incubated for an additional 1 hour at room temperature. The streptavidin-HRP was then removed and the plate was washed as described above. Then 100 µL of TMB solution (Pierce, #34028) solution was added to each well and incubated for 2 minutes, followed by addition of 100 µL stop solution (2N $H_2SO_4$) to each well to stop the reaction. The assay plate was then read at 450 nm using a Victor$^3$V 1420 multilabel counter (Perkin Elmer). Percent inhibition of binding was calculated using 0 nM antibody in 25 nM ARC19499 as 0% inhibition, and 0 nM antibody and 0 nM ARC19499 as 100% inhibition. The $IC_{50}$ was calculated based on 4-parameter logistics using Prism 4 Graphpad software.

As shown in FIG. 19A, antibody AD4903, which binds within the K1 domain of TFPI, competed with ARC19499 for binding to recombinant TFPI in the plate-based binding assay. Antibodies ACJK-1 and ACJK-2, which bind to regions within the C-terminal region of TFPI, partially competed for ARC19499 binding to TFPI in the plate-based binding assay (FIG. 19B). Antibodies AD4904, ACJK-3, ACJK-4, ACJK-5 and 7035-A01 showed no competition for ARC19499 binding to TFPI in the plate-based binding assay (FIGS. 19A and B). These experiments suggest that the K1 region and the C-terminal region of TFPI are involved in ARC19499 binding to TFPI.

The antibodies in Table 2 were also tested in a dot blot-based competition binding assay. In these experiments, trace amounts of radiolabeled ARC17480 were incubated with 10 nM recombinant TFPI, with or without the addition of antibody. Antibodies were tested at 1000 nM, 333 nM, 111 nM, 37.0 nM, 12.4 nM, 4.12 nM, 1.37 nM, 0.46 nM, 0.15 nM and 0.051 nM. ARC17480 was included as a competitor in every experiment as a control. For each molecule, the percentage of radiolabeled ARC17480 bound at each competitor aptamer concentration was used for analysis. The percentage of radiolabeled ARC17480 bound was plotted as a function of aptamer concentration and fit to the equation $y=(max/(1+x/IC_{50}))+int$, where y=the percentage of radiolabeled ARC17480 bound, x=the concentration of aptamer, max=the maximum radiolabeled ARC17480 bound, and int=the y-intercept, to generate an $IC_{50}$ value for binding-competition. FIG. 20 shows the binding-competition experiments carried out with ACJK-1, ACJK-2, ACJK-3, ACJK-4, ACJK-5, AD4903 and AD4904. These experiments demonstrate that antibody AD4903 competed for ARC17480 binding to TFPI in the dot blot competition assay (FIG. 20C). ACJK-4 partially competed for binding in this assay (FIG. 20B), while ACJK-1, ACJK-2, ACJK-3, ACJK-5 and AD4904 showed no significant competition for binding with ARC17480 (FIG. 20A-C). These experiments suggest that the K1 region and the K2-K3 intervening regions of TFPI are involved in ARC17480 binding to TFPI.

Taken together, these experiments demonstrate that the K1 region of TFPI is likely involved in ARC17480/ARC19499 binding to TFPI. These experiments also suggest that the C-terminal and the K2-K3 intervening regions of TFPI may be involved in aptamer binding. Lack of binding competition of antibodies to other regions of TFPI does not preclude their involvement in aptamer binding.

TABLE 2

Antibodies used in ARC19499 competition assays

| Antibody | Type | Region of mature TFPI used as an antigen for antibody generation | Antibody target region in TFPI |
|---|---|---|---|
| AD4903 | mouse monoclonal | 22-87 | K1 region |
| AD4904 | mouse monoclonal | 88-160 | K2 region |

TABLE 2-continued

Antibodies used in ARC19499 competition assays

| Antibody | Type | Region of mature TFPI used as an antigen for antibody generation | Antibody target region in TFPI |
|---|---|---|---|
| ACJK-1 | rabbit polyclonal | 261-276 | C-terminal peptide |
| ACJK-2 | rabbit polyclonal | 245-262 | C-terminal peptide |
| ACJK-3 | rabbit polyclonal | 192-204 | K3 peptide |
| ACJK-4 | rabbit polyclonal | 148-162 | K2-K3 intervening peptide |
| ACJK-5 | rabbit polyclonal | 54-69 | K1 peptide |
| 7035-A01 | mouse polyclonal | 152-252 | K3-C-terminal region |

Example 8

This example demonstrates that ARC19499 has in vitro activity inhibiting TFPI in the extrinsic tenase (Xase) inhibition assay.

Figure 21A:
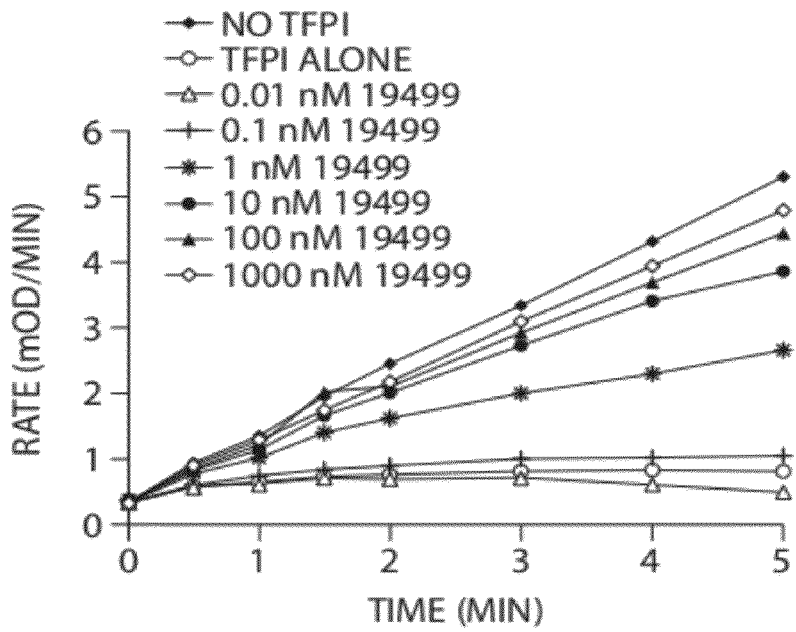
In FIG. 21A, the rate (mOD/min) was plotted vs time (minutes). In the absence of TFPI, the rate was linear. 1 nM TFPI decreased the rate dramatically. Increasing concentrations of ARC19499 from 0.01 to 1000 nM increased the rate in a dose-dependent manner until nearly the level of no TFPI.
Figure 21B:
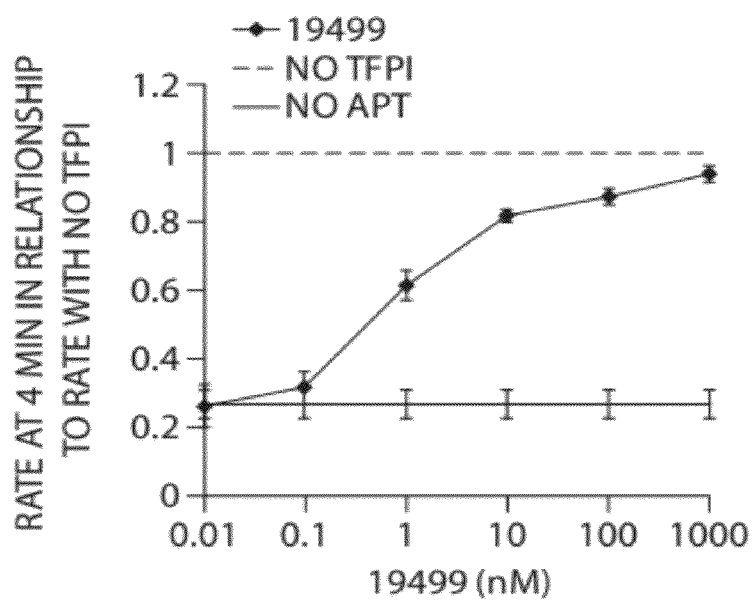
In FIG. 21B, the rates at the 4 minute time point were normalized to the rate in the absence of TFPI at 4 minutes. ARC19499 showed a dose-dependent improvement on the rate of the assay, reaching levels close to that of no TFPI by 10 nM aptamer. Data for FIG. 21A were representative from three experiments. Data for FIG. 21B represent mean±standard error, n=3.

In this assay, tissue factor (TF) was mixed with Factor VIIa (FVIIa) and phospholipid vesicles. Factor X (FX) was added and aliquots were removed and quenched at various time points. At this point, a chromogenic substrate for Factor Xa (FXa) was added and absorbance at 405 nm was measured over a course of an hour in order to determine rates of FXa generation. When 1 nM TFPI was included, the rate of FXa generation was significantly decreased. This was seen in FIG. 21A when comparing the filled diamonds (no TFPI) with the empty circles (1 nM TFPI). When increasing concentrations of ARC19499 were also included along with the 1 nM TFPI, there was a dose-dependent improvement on the rate of FXa generation. 1000 nM ARC19499 (empty diamonds) resulted in rates of FXa generation that were close to the rate of FXa generation in the absence of TFPI (filled diamonds) (FIG. 21A). These rates were normalized by dividing the rate at one specific time point (in this case, at 4 minutes) by the rate achieved with no TFPI at that same time point (FIG. 21B). In this manner, TFPI reduced the rate of FXa generation at 4 minutes by nearly 70%. Increasing concentrations of ARC19499 improved this rate, reaching levels close to that of no TFPI with 10-1000 nM aptamer (FIG. 21B).

This experiment indicates that ARC19499 inhibits TFPI in an in vitro extrinsic tenase inhibition assay.

Example 9

This example demonstrates that ARC26835, ARC17480, ARC19498, ARC19499, ARC19500, ARC19501, ARC31301, ARC18546, ARC19881 and ARC19882 have TFPI-inhibitory activity in the Factor Xa (FXa) activity assay.

Figure 22A:
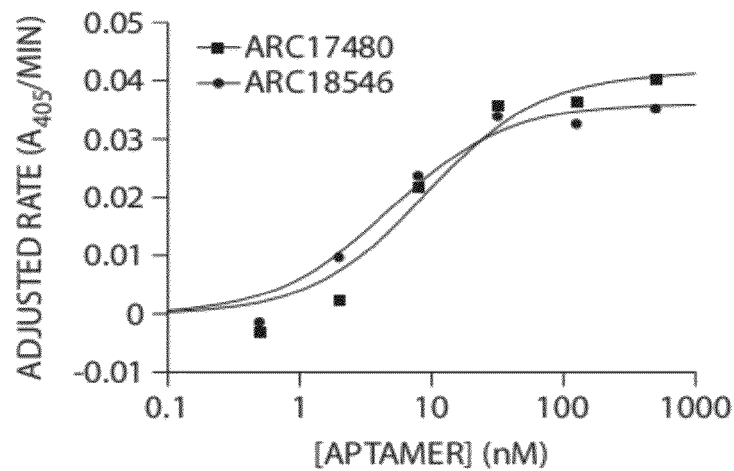
FIG. 22, A-C, depicts the results of a Factor Xa (FXa) activity assay with full-length TFPI and ARC17480, ARC18546, ARC26835, ARC31301, ARC19498, ARC19499, ARC19500, ARC19501, ARC19881 or ARC19882. The adjusted rate of FXa substrate degradation is plotted as a function of aptamer concentration. The rates are adjusted by subtraction of the rate observed with FXa and TFPI in the absence of aptamer. All of the aptamers inhibit TFPI, which results in a concentration-dependent increase in FXa activity in this assay.
Figure 22B:
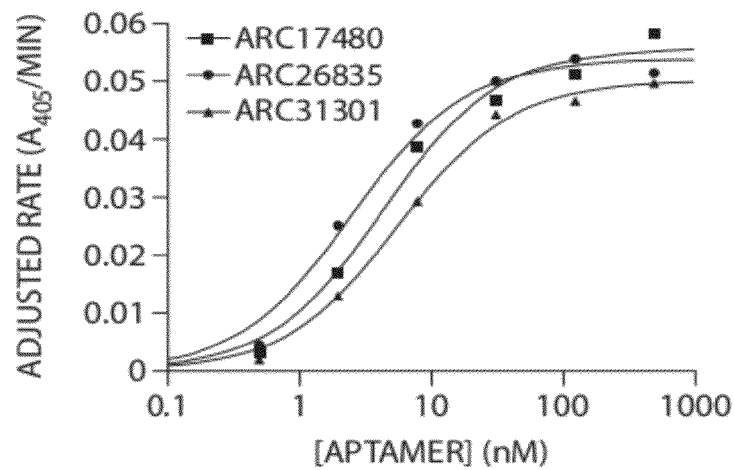
Figure 22C:
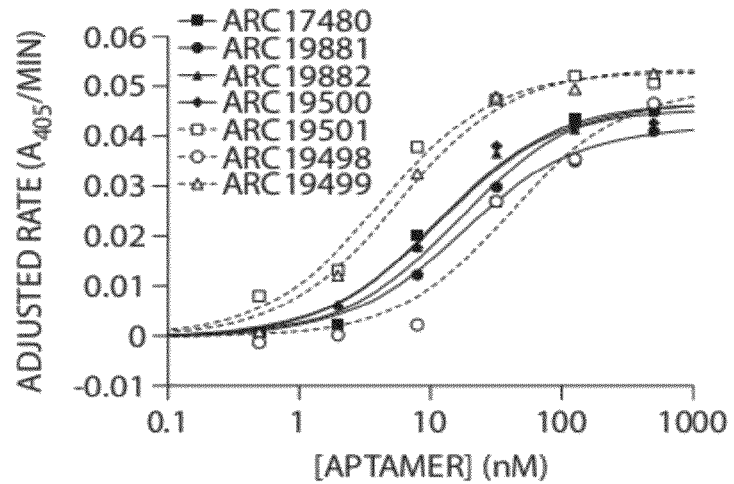

Each aptamer was evaluated for inhibition of TFPI in a Factor Xa (FXa) activity assay. The ability of FXa to cleave a chromogenic substrate was measured in the presence and absence of TFPI, with or without the addition of aptamer. For these experiments, 2 nM human FXa was incubated with 8 nM human TFPI. Then, 500 µM chromogenic substrate and aptamers were added, and FXa cleavage of the substrate was measured by absorbance at 405 nm ($A_{405}$) as a function of time. Aptamers were tested at 500 nM, 125 nM, 31.25 nM, 7.81 nM, 1.95 nM and 0.49 nM concentrations. ARC17480 was included as a control in each experiment. For each aptamer concentration, the $A_{405}$ was plotted as a function of time and the linear region of each curve was fit to the equation $y=mx+b$, where $y=A_{405}$, $x=$the aptamer concentration, $m=$the rate of substrate cleavage, and $b=$the y-intercept, to generate a rate of FXa substrate cleavage. The rate of FXa substrate cleavage in the presence of TFPI and the absence of aptamer was subtracted from the corresponding value in the presence of both TFPI and aptamer for each aptamer at each concentration. Then, the adjusted rates were plotted as a function of aptamer concentration and fit to the equation $y=(V_{max}/(1+IC_{50}/x))$, where $y=$the rate of substrate cleavage, $x=$concentration of aptamer, and $V_{max}$ the maximum rate of substrate cleavage, to generate an $IC_{50}$ and maximum ($V_{max}$) value. FIG. 22A-C show graphs of FXa activity assays with ARC26835, ARC17480, ARC19498, ARC19499, ARC19500, ARC19501, ARC31301, ARC18546, ARC19881 and ARC19882. These aptamers all inhibited TFPI in these assays, as evidenced by an increase in FXa activity as a function of aptamer concentration. These aptamers all had similar activity in the FXa assay.

Example 10

This example demonstrates that ARC19499 protects Factor Xa (FXa) from inhibition by TFPI in a chromogenic assay with purified components.

Figure 23:
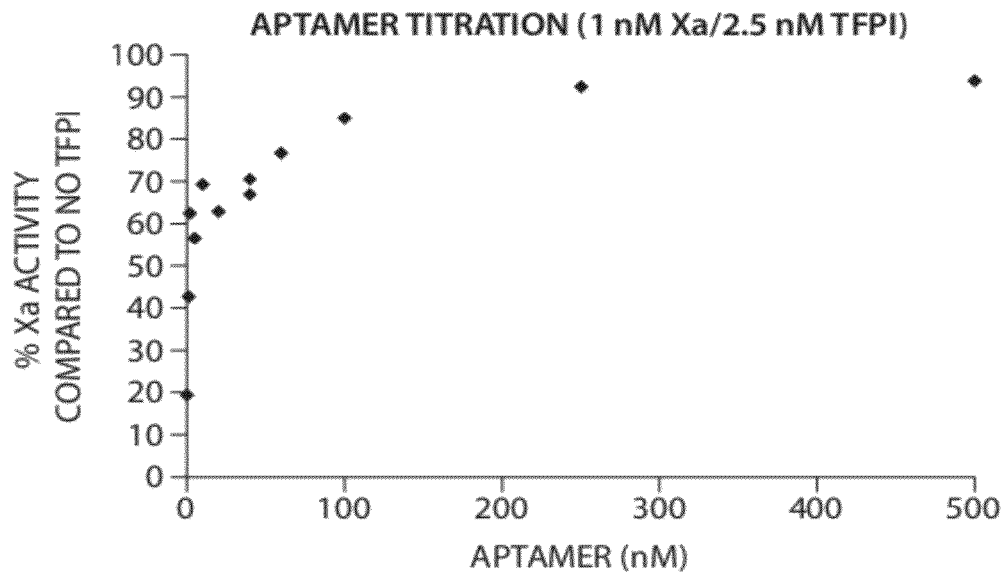
FIG. 23 is a graph that shows protection of Factor Xa (FXa) activity by ARC19499 from TFPI inhibition in a chromogenic FXa activity assay.

FXa (1 nM), TFPI (2.5 nM), ARC19499 (0-500 nM) and Spectrozyme Xa (American Diagnostica) chromogenic substrate (200 µM) were incubated in HEPES-buffered saline (20 mM HEPES, 150 mM NaCl, pH 7.4) containing 2 mM $CaCl_2$ and 0.1% PEG-6,000 (HBSP2 buffer) at 37° C. until equilibrium was achieved (5 minutes). The rate of Spectrozyme FXa hydrolysis was determined using a ThermoMax instrument (Molecular Devices) and plotted as the % FXa activity compared to no TFPI (100%). Increasing concentrations of ARC19499 caused an increase in FXa activity (FIG. 23), demonstrating that ARC19499 protected FXa from the inhibition by TFPI. Based on this data, the apparent dissociation constant ($K_D$) of ARC19499 for TFPI was 1.8 nM. ARC19499 is specific for TFPI and did not inhibit FXa activity in the absence of TFPI (data not shown).

Example 11

This example demonstrates that ARC19499 protects the extrinsic FXase complex, which is composed of tissue factor, Factor VIIa (FVIIa) and Factor Xa (FXa), from inhibition by TFPI in a chromogenic activity assay with purified components.

Figure 24:
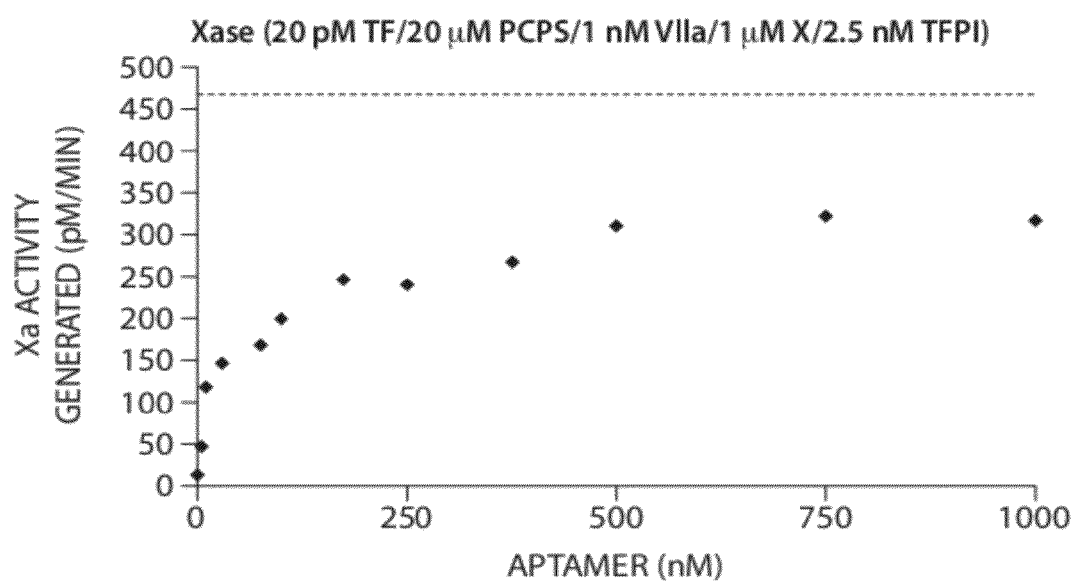
FIG. 24 is a graph that shows protection of the extrinsic FXase by ARC19499 from TFPI inhibition in a chromogenic assay of Factor X (FX) activation.

Relipidated tissue factor (TF; 20 pM), FVIIa (1 nM), PCPS vesicles (75% phosphatidyl choline/25% phosphatidyl serine; 20 µM) and ARC19499 (0-1000 nM) were incubated in HBSP2 buffer at 37° C. for 10 minutes, followed by the simultaneous addition of FX (1 µM) and TFPI (2.5 nM). Aliquots were removed every 30 seconds for 5 minutes and quenched into HBS buffer containing 20 mM EDTA and 0.1% PEG. Spectrozyme FXa substrate (200 µM) was added, the rate of substrate hydrolysis was measured, and the concentration of active FXa was estimated from a calibration curve. Increasing concentrations of ARC19499 caused an increase in FXa activity (FIG. 24) up to 70% of the rate measured in the absence of TFPI, demonstrating that ARC19499 substantially protected the extrinsic FXase complex from the inhibition by TFPI.

Example 12

This example demonstrates that ARC19499 protects the tissue factor:FVIIa complex from TFPI inhibition in a fluorogenic assay of tissue factor:FVIIa activity carried out with purified components.

Figure 25:
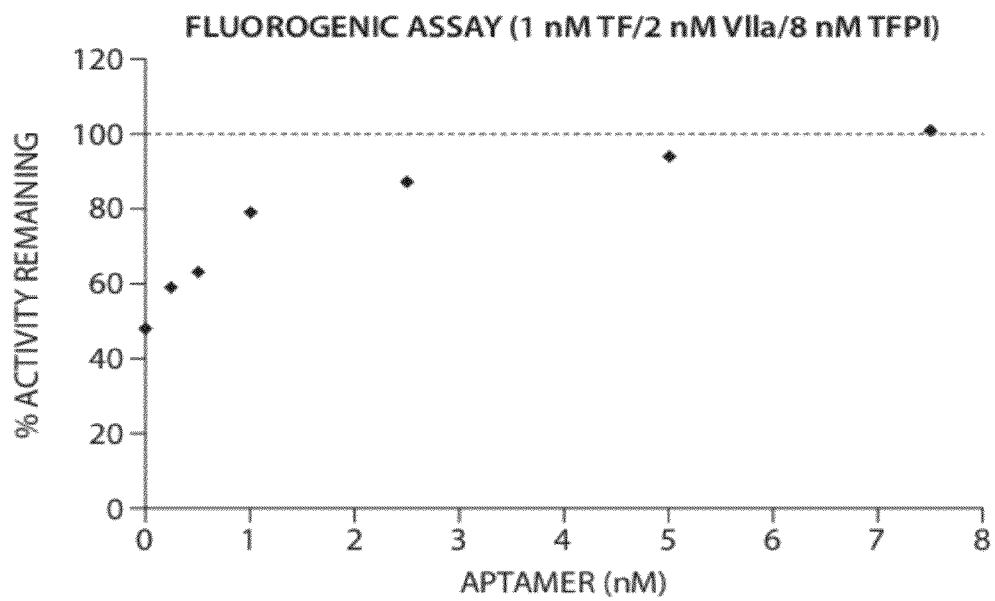
FIG. 25 is a graph that shows protection of the TF:FVIIa complex by ARC19499 from TFPI inhibition in a fluorogenic assay of TF:FVIIa activity.

Tissue factor (TF; 1 nM), FVIIa (2 nM) and ARC19499 (0-7.5 nM) were incubated in HBSP2 at 37° C. for 10 minutes, followed by the simultaneous addition of a fluorogenic substrate SN-17c (50 µM) and TFPI (8 nM). The rate of substrate hydrolysis was measured in a fluorescence plate reader (BioTek). TFPI inhibited approximately 50% of TF:FVIIa activity under these conditions (FIG. 25). The addition of a stoichiometric concentration of ARC19499 (8 nM) completely restored full TF:FVIIa activity compared to a no TFPI control (FIG. 25), demonstrating that ARC19499 efficiently protected the TF:FVIIa complex from TFPI inhibition. A titration of increasing ARC19499 concentrations in the presence of 8 nM TFPI increased the activity of the TF:FVIIa complex in an ARC19499 concentration-dependent manner, reaching the mid-point of activity at ~1 nM ARC19499. Data analysis indicated that the apparent $K_D$ of ARC19499 for TFPI in this assay was 1.2 nM. ARC19499 is specific for TFPI and did not inhibit TF:FVIIa activity in the absence of TFPI (data not shown).

Example 13

This example demonstrates that ARC19499 inhibits TFPI in a synthetic coagulation proteome that models hemophilia A and hemophilia B. These data show that ARC19499 restored normal thrombin generation in the presence of complete (0%) Factor VIII (FVIII) or Factor IX (FIX) deficiency. ARC19499 also restored normal thrombin generation in the presence of incomplete (2%, 5% or 40%) FVIII deficiency.

Thrombin generation was initiated with 5 µM relipidated tissue factor (TF) added to a mixture of procoagulants and coagulation inhibitors (Factors V, VII, VIIa, VIII, IX, X, XI, prothrombin, antithrombin and TFPI; all at mean physiologic concentrations) and 50 µM PCPS (75% phosphatidyl choline/25% phosphatidyl serine). Thrombin generation over time was measured in a chromogenic assay using the Spectrozyme TH substrate (American Diagnostica). ARC19499 was tested at increasing concentrations of 1 nM, 2.5 nM, 5 nM and 10 nM in a fully reconstituted system (healthy control) or in reconstituted systems in which either FVIII (severe hemophilia A) or FIX (severe hemophilia B) was omitted.

Figure 26:
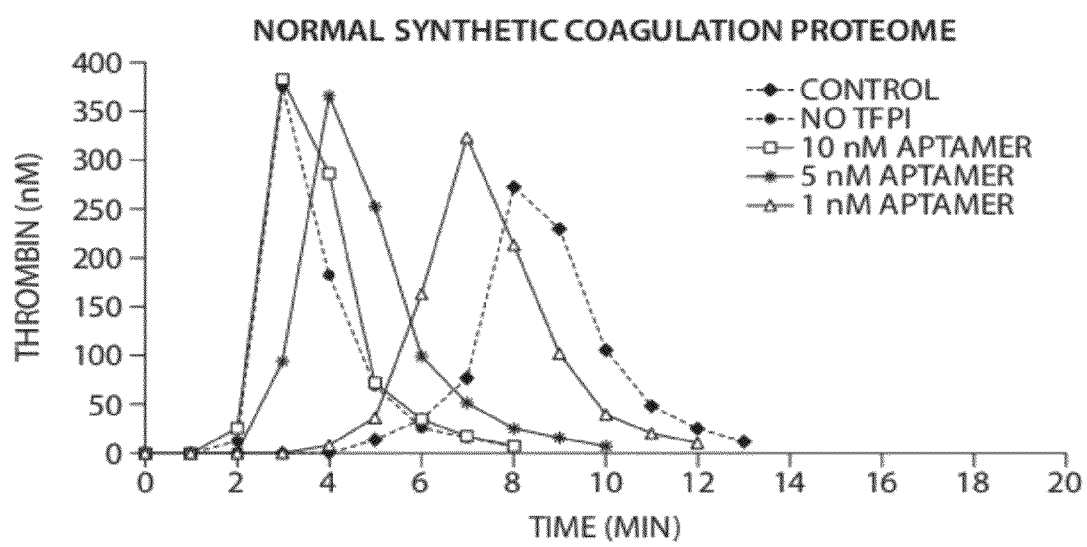
FIG. 26 is a graph that shows the effect of ARC19499 on tissue factor (TF)-initiated thrombin generation in a Normal Synthetic Coagulation Proteome (SCP).

In the presence of all proteins at their mean physiologic concentrations ("healthy control"; FIG. 26), the initiation (lag) phase of thrombin generation initiated with 5 pM relipidated TF was approximately 6 minutes, and the maximum concentration of active thrombin observed was 270 nM (filled diamonds). The omission of TFPI significantly shortened the initiation phase (to 2 minutes) and increased maximum thrombin concentration to 374 nM (filled circles). Additions of increasing ARC19499 concentrations in the presence of 2.5 nM TFPI decreased the duration of the initiation phase and increased maximum thrombin concentration in an ARC19499-dependent manner, and at 10 nM (empty squares) the ARC19499 thrombin generation profile was almost identical to that observed in the absence of both TFPI and ARC19499 (FIG. 26).

Figure 27:
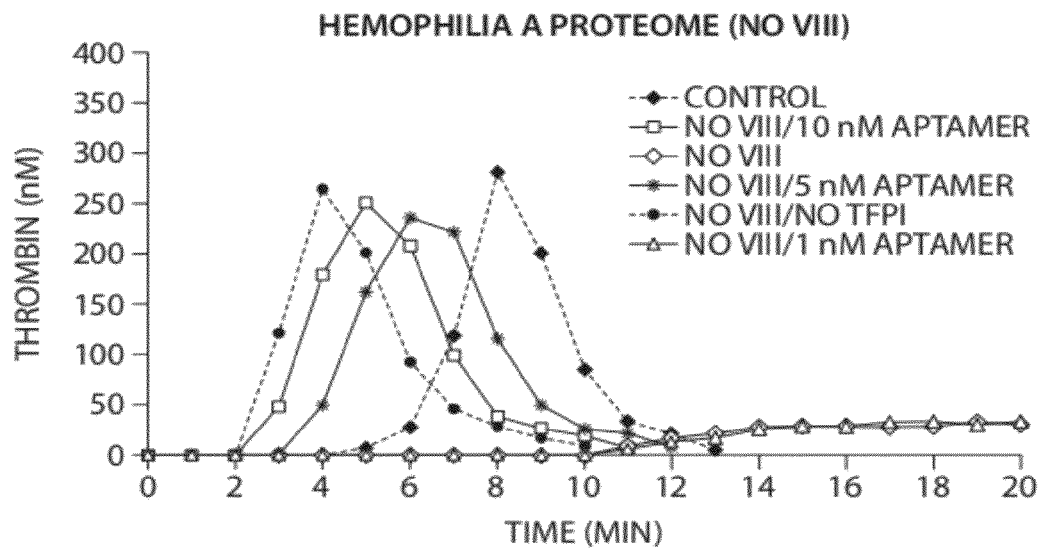
FIG. 27 is a graph that shows the effect of ARC19499 on tissue factor (TF)-initiated thrombin generation in a hemophilia A Synthetic Coagulation Proteome.

In the absence of FVIII, TF initiated thrombin generation was significantly suppressed (FIG. 27). The initiation phase was extended from 6 minutes in the "healthy control" (filled diamonds) to 10 minutes in hemophilia A (empty diamonds), and maximum thrombin activity decreased from 270 nM to 34 nM. The omission of TFPI in the absence of FVIII restored normal thrombin generation (maximum concentration of active thrombin increases to 264 nM and the duration of the initiation phase decreased to 2 minutes (filled circles). In the absence of FVIII and in the presence of 2.5 nM TFPI, the addition of 5 nM ARC19499 (asterisks) restored thrombin generation to the level observed in the "healthy control" with the initiation phase of 3 minutes. In the presence of 10 nM ARC19499 (empty squares) and 2.5 nM TFPI and in the absence of FVIII, the thrombin generation profile became similar to that observed in the absence of TFPI, FVIII and ARC19499.

Figure 28:
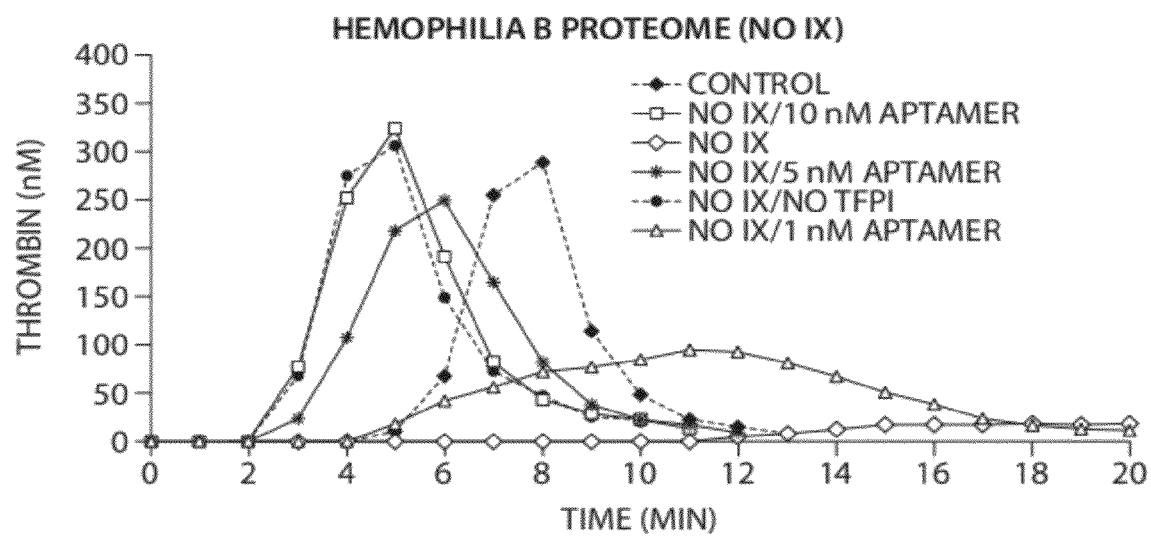
FIG. 28 is a graph that shows the effect of ARC19499 on tissue factor (TF)-initiated thrombin generation in a hemophilia B Synthetic Coagulation Proteome.

The effect of TFPI inhibition by ARC19499 in a hemophilia B (no FIX) synthetic coagulation proteome was similar to that observed for the hemophilia A model, i.e., ARC19499 at 5 nM concentration and in the absence of FIX restored thrombin generation to the level similar to that observed in "healthy control" (FIG. 28).

Figure 29:
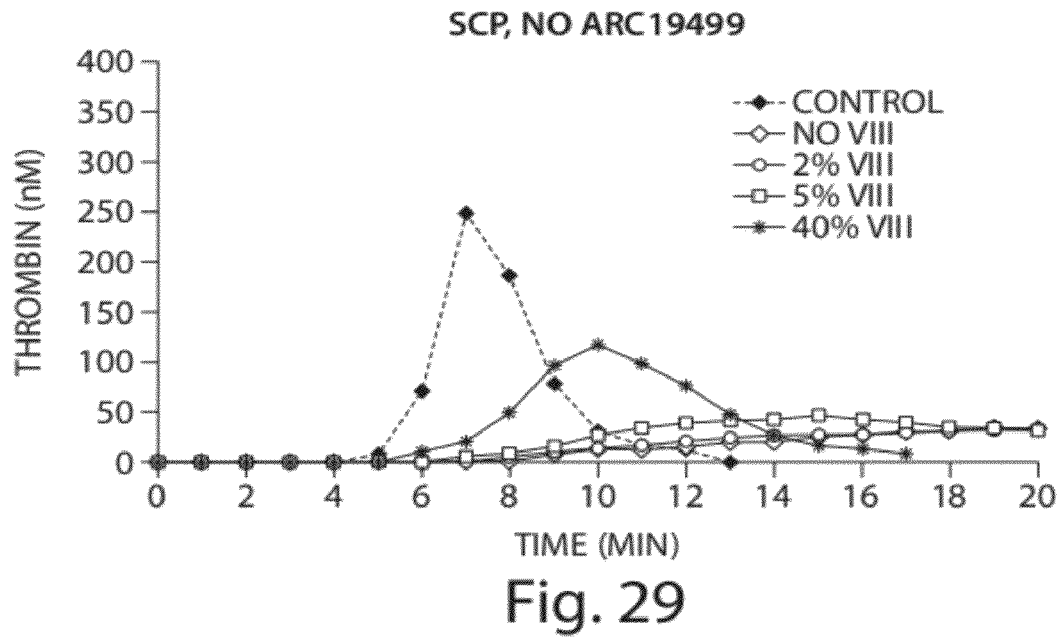
FIG. 29 is a graph that shows the effect of increasing Factor VIII (FVIII) concentrations on tissue factor (TF)-initiated thrombin generation in the absence of ARC19499.
Figure 30:
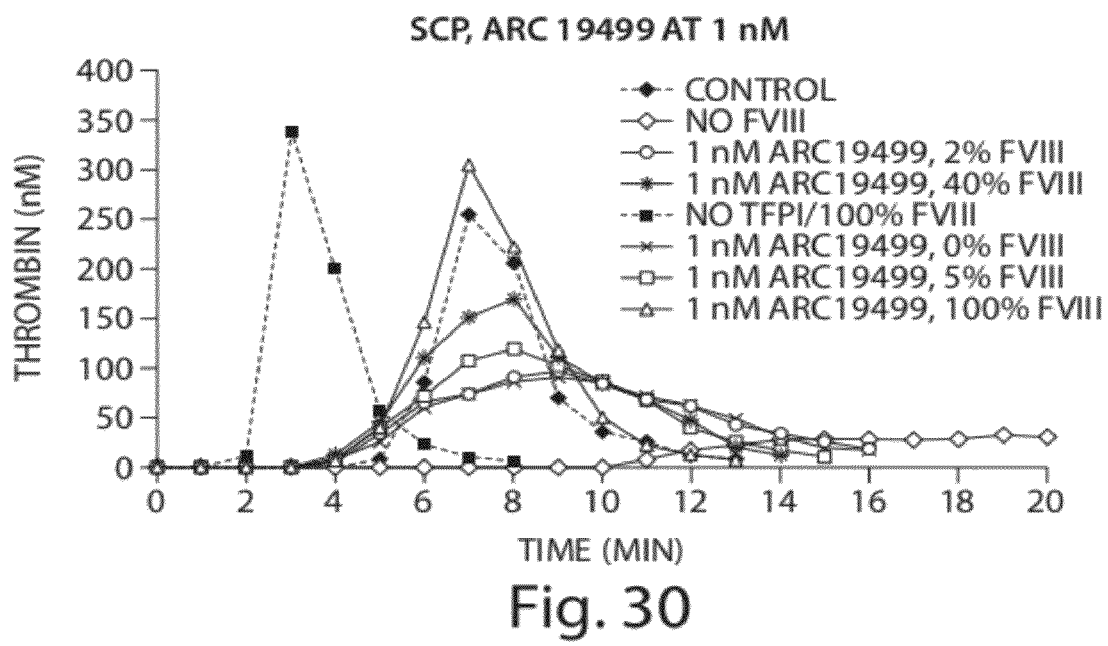
FIG. 30 is a graph that shows the effect of increasing Factor VIII (FVIII) concentrations on tissue factor (TF)-initiated thrombin generation in the presence of 1.0 nM ARC19499.
Figure 31:
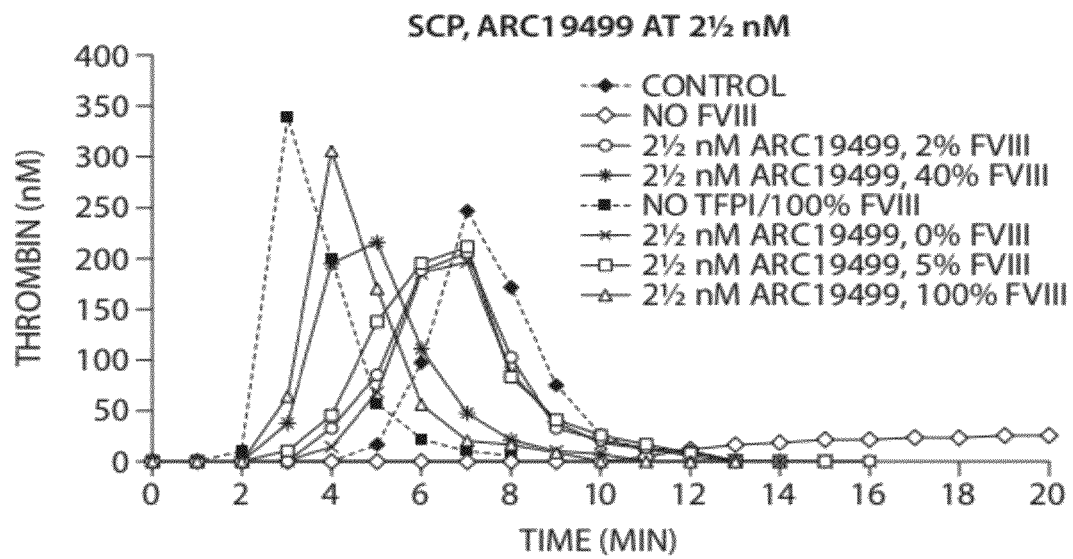
FIG. 31 is a graph that shows the effect of increasing Factor VIII (FVIII) concentrations on tissue factor (TF)-initiated thrombin generation in the presence of 2.5 nM ARC19499.

The effect of ARC19499 on TF-initiated thrombin generation was evaluated in the synthetic coagulation proteome model at 0%, 2% (0.014 nM), 5% (0.035 nM), 40% (0.28 nM) and 100% (0.7 nM) FVIII. The selected FVIII concentrations covered the range observed in severe (<1%), moderate (1-5%) and mild (5-40%) hemophilia A patients. In the absence of ARC19499 (FIG. 29), thrombin generation was suppressed at all FVIII concentrations tested, up to and including 40%. The peak thrombin level observed in the 40% FVIII proteome (asterisks) was approximately 50% of the "healthy control" (filled diamonds). The addition of ARC19499 at a concentration of 1 nM was sufficient to significantly boost thrombin generation by shortening the initiation phase and increasing peak thrombin levels (FIG. 30). The addition of 2.5 nM ARC19499 essentially normalized thrombin generation in the presence of 0-5% FVIII (FIG. 31), while at 40% and 100% FVIII, 2.5 nM ARC19499 induced further shortening of the initiation phase and increased peak thrombin, nearly to the extent of the "No TFPI" control.

Figure 32:
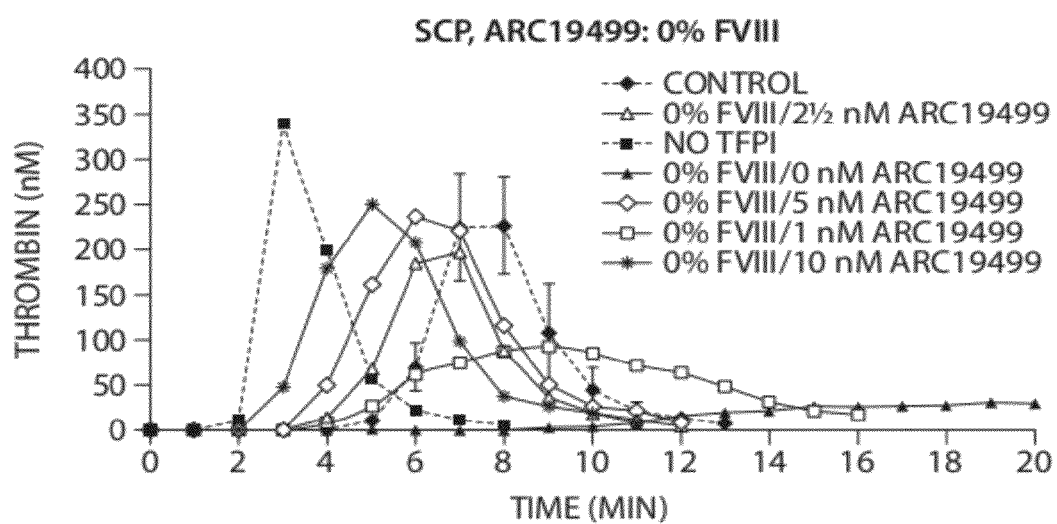
FIG. 32 is a graph that shows the effect of increasing ARC19499 concentrations on tissue factor (TF)-initiated thrombin generation in the absence of Factor VIII (FVIII).
Figure 33:
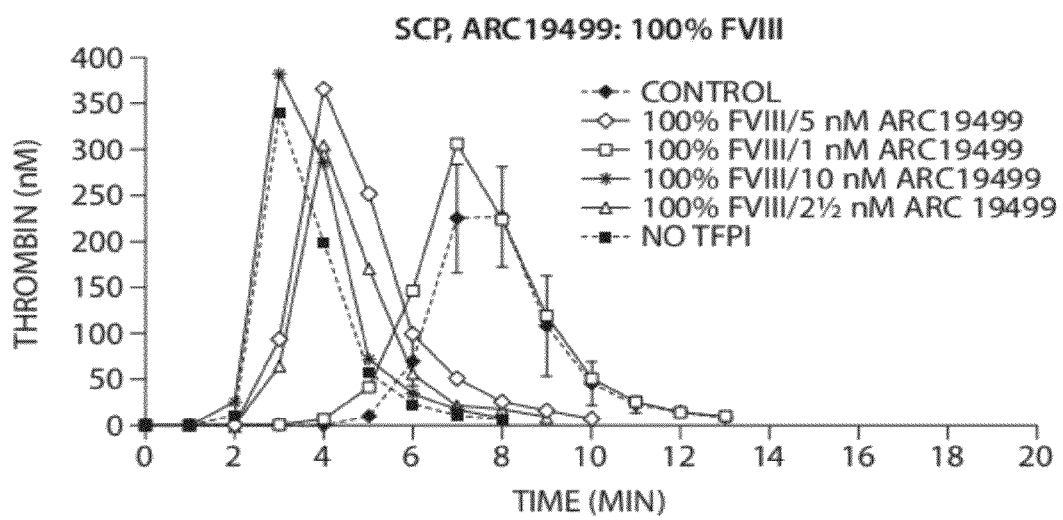
FIG. 33 is a graph that shows the effect of increasing ARC19499 concentrations on tissue factor (TF)-initiated thrombin generation in the presence of 100% Factor VIII (FVIII).
Figure 34:
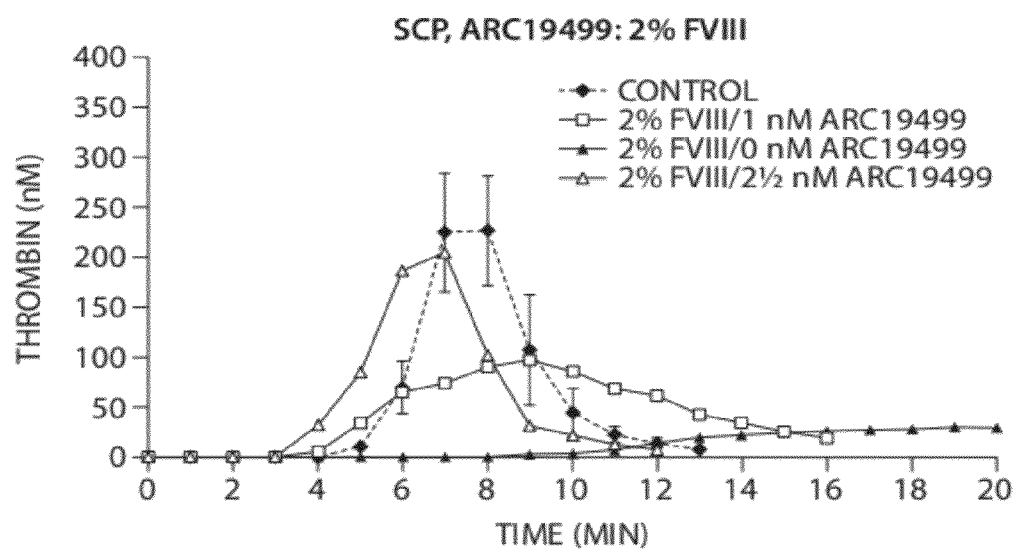
FIG. 34 is a graph that shows the effect of increasing ARC19499 concentrations on tissue factor (TF)-initiated thrombin generation in the presence of 2% Factor VIII (FVIII).
Figure 35:
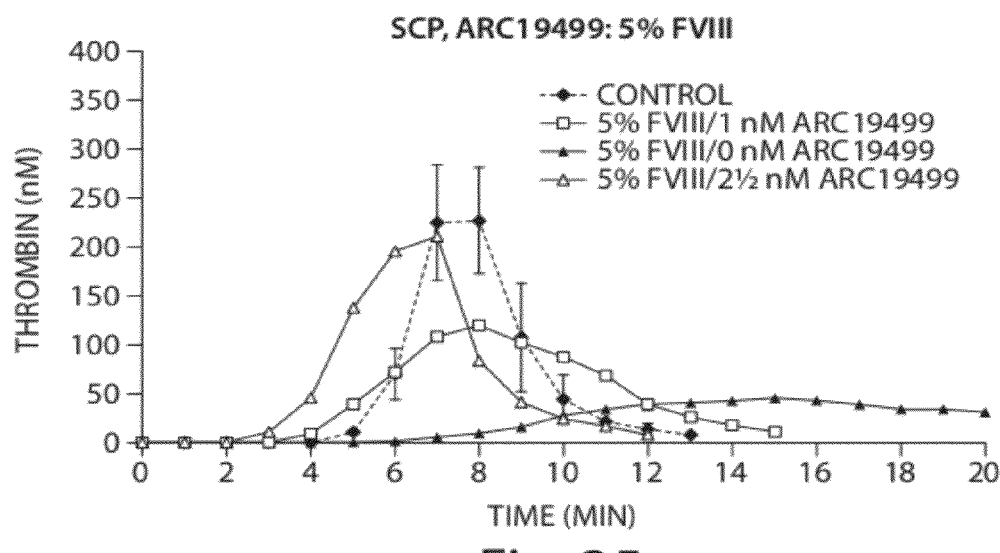
FIG. 35 is a graph that shows the effect of increasing ARC19499 concentrations on tissue factor (TF)-initiated thrombin generation in the presence of 5% Factor VIII (FVIII).
Figure 36:
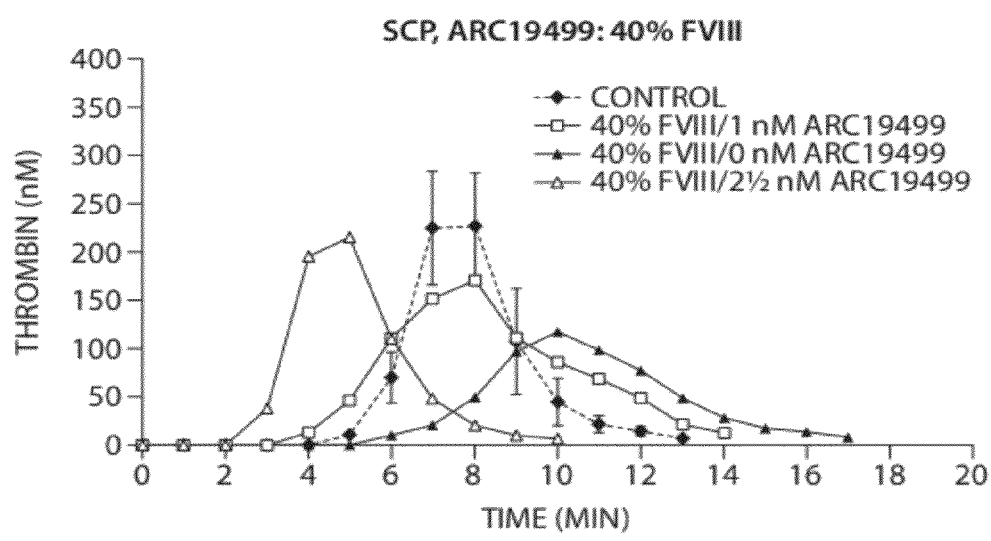
FIG. 36 is a graph that shows the effect of increasing ARC19499 concentrations on tissue factor (TF)-initiated thrombin generation in the presence of 40% Factor VIII (FVIII).

FIG. 32 shows additional synthetic coagulation proteome data for 0% FVIII in the presence of a series of ARC19499 concentrations (0, 1, 2.5, 5 and 10 nM) compared to a "healthy control" and a "No TFPI" control. FIG. 33 shows the data for 100% FVIII for the same range of ARC19499 concentrations. FIGS. 34, 35 and 36 show the data for 2%, 5% and 40% FVIII in the presence of 0, 1 and 2.5 nM ARC19499, respectively. Under all conditions, ARC19499 showed a significant procoagulant response, causing the initiation phase (lag time) to decrease and the peak thrombin to increase. In all cases of FVIII deficiency (0-40% FVIII), ARC19499 was able to restore a normal thrombin generation profile.

Example 14

This example demonstrates that in vitro activity of ARC19499 is specific for the presence of TFPI.

In this experiment, the ability of ARC19499 to affect thrombin generation in the calibrated automated thrombogram (CAT) assay, which measures the generation of thrombin over time following initiation of the tissue factor coagulation pathway, was tested in three different plasma conditions. In the first condition, increasing concentrations of ARC19499 were added to pooled normal plasma (PNP) and mixed with a solution containing tissue factor (TF) and phospholipids so that the TF concentration was either 0.1 or 1.0 µM in the final reaction volume (FIG. 37). Thrombin generation was initiated by the addition of a mixture containing calcium chloride and a fluorogenic substrate for thrombin. The reaction took place at 37° C., and fluorescence intensity was measured periodically over 1 hour. ARC19499 was tested at the following concentrations in the plasma: 0.1, 1, 10, 100 and 1000 nM.

Figure 37A:
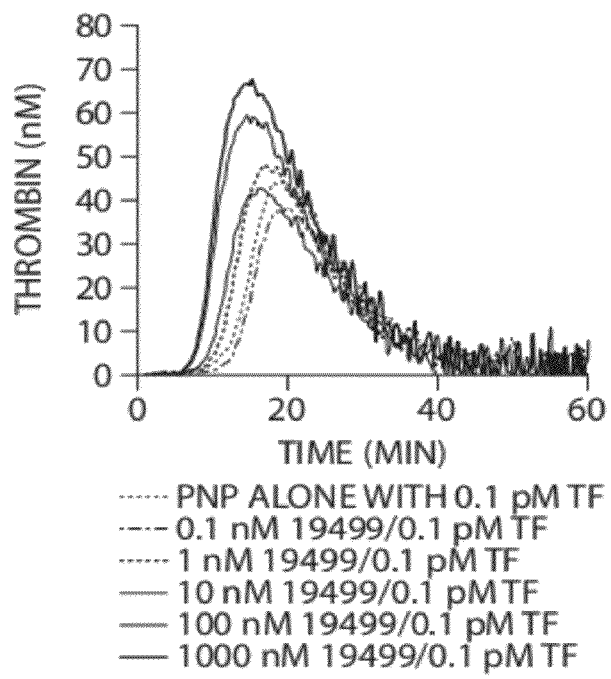
FIG. 37A) or 1.0 pM TF (FIG. 37B). The endogenous thrombin potential (ETP.
Figure 37B:
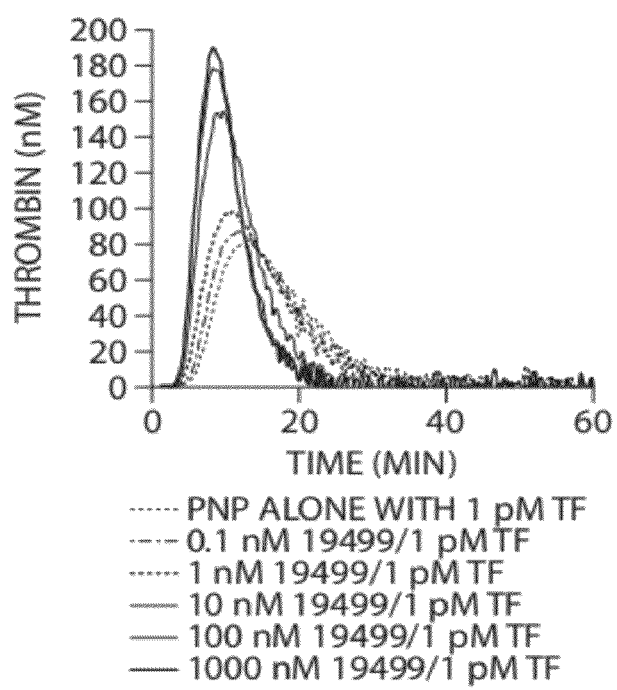
FIG. 37 is a series of graphs showing the activity of ARC19499 in the calibrated automated thrombogram (CAT) assay in pooled normal plasma (PNP) initiated with 0.1 pM tissue factor (TF.
FIG. 37C) and peak thrombin (FIG. 37D) both showed a dose-dependent increase with increasing concentrations of ARC19499 at both TF concentrations. The lag time (FIG. 37E) showed a dose-dependent decrease with increasing concentrations of ARC19499 at both TF concentrations.
Figure 37C:
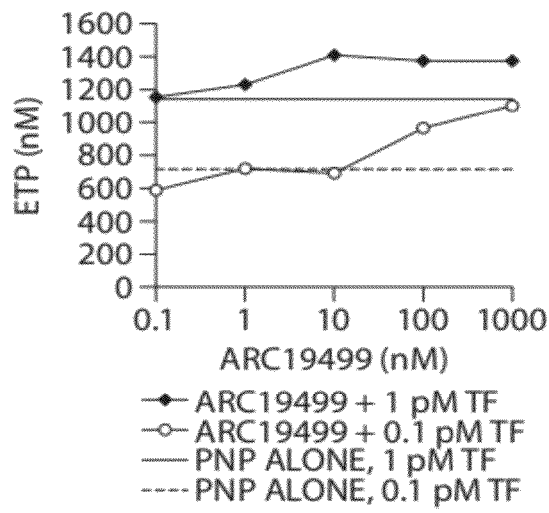
Figure 37D:
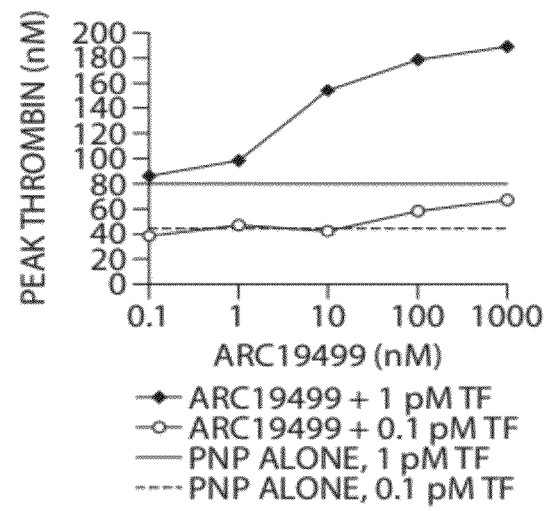
Figure 37E:
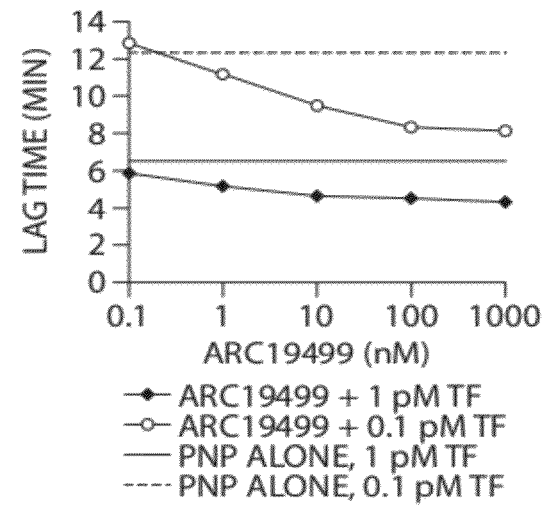

With either TF concentration, increasing ARC19499 increased the generation of thrombin in PNP plasma (FIG. 37A-B). Both the endogenous thrombin potential (ETP— area under the curve) and peak thrombin (highest level of thrombin produced at any one point in the assay) values increased in a dose-dependent manner with ARC19499 (FIG. 37C-D). The lag time (time it takes for thrombin generation to begin) decreased in a dose-dependent manner with ARC19499 (FIG. 37E). These results were observed at both concentrations of TF.

Figure 38A:
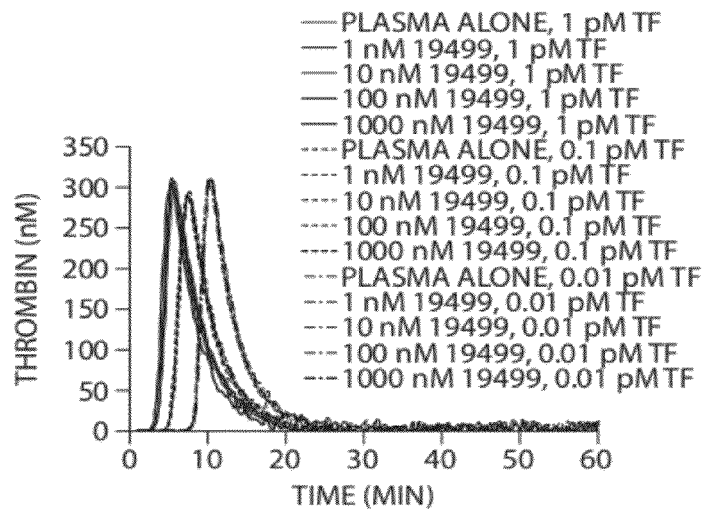
FIG. 38A shows thrombin generation curves at increasing ARC19499 concentrations with three different TF concentrations. The endogenous thrombin potential (ETP.
Figure 38B:
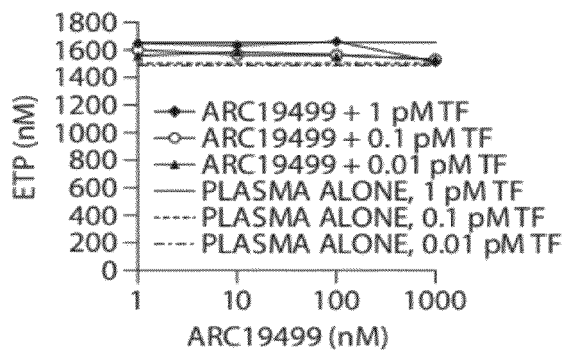
FIG. 38B), peak thrombin (FIG. 38C) and lag time (FIG. 38D) showed little or no change over all tested ARC19499 concentrations at all tested TF concentrations.
Figure 38C:
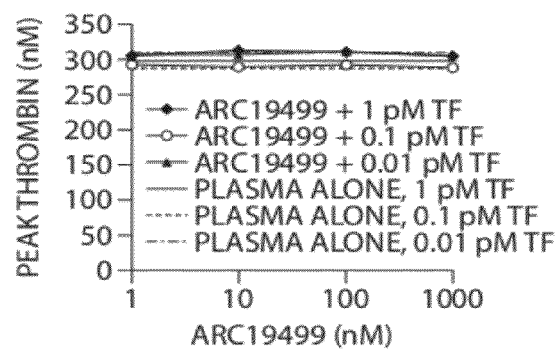
FIG. 38 is a series of graphs showing the activity of ARC19499 in the calibrated automated thrombogram (CAT) assay in TFPI-depleted plasma initiated with 0.01, 0.1 or 1.0 pM tissue factor (TF).
Figure 38D:
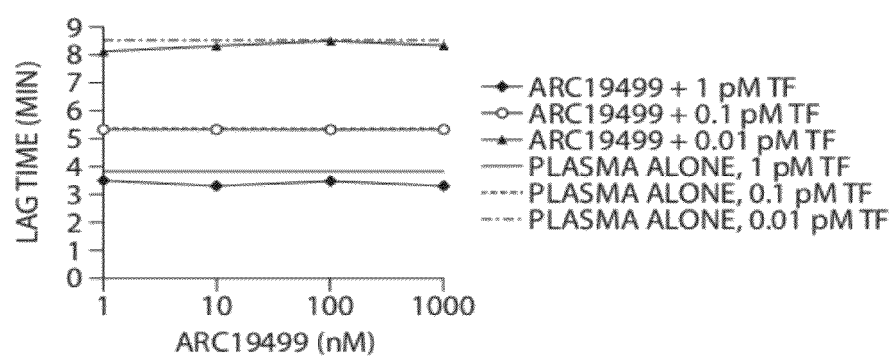
Figures 39A, 39B, 39C:
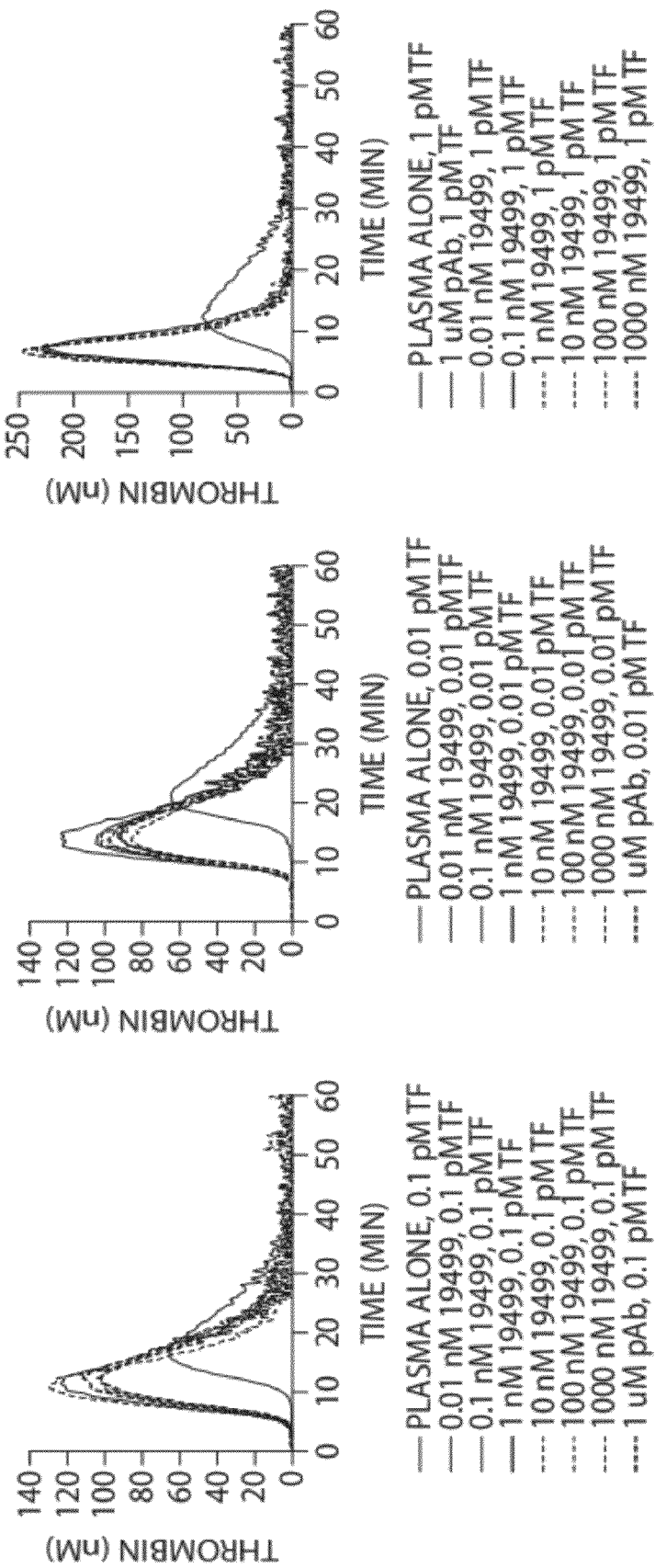
FIG. 39A), 0.1 pM TF (FIG. 39B) or 1.0 pM TF (FIG. 39C). The endogenous thrombin potential (ETP.

The CAT assay measuring ARC19499 activity was repeated in TFPI-depleted plasma. Plasma that was immunodepleted for TFPI and lyophilized was obtained from American Diagnostica (Stamford, Conn.) and resuspended prior to use. Thrombin generation was measured as described above with 0.01, 0.1 or 1.0 pM TF. The results in FIG. 38A show that the thrombin generation curves measured for each TF concentration were distinct from each other, but within a specific TF concentration there was essentially no difference in thrombin generation as the ARC19499 concentration was increased. This was also seen in the parameters measured in the CAT assay. There was little or no change in ETP, peak thrombin or lag time as the ARC19499 concentration increased (FIG. 38B-D), independent of TF concentration. ARC19499 activity was tested in a third set of plasma conditions. In this case, PNP was incubated with a polyclonal antibody against TFPI, in order to neutralize all TFPI activity. ARC19499 was then added to this antibody-treated plasma (FIG. 39). Again, thrombin generation was initiated with either 0.01, 0.1 or 1.0 pM TF. Addition of the polyclonal antibody enhanced thrombin generation at all three TF concentrations because the TFPI was neutralized; however, increasing concentrations of ARC19499 appeared to cause no further increases in thrombin generation (FIG. 39A-C). There was little to no effect on the ETP, peak thrombin or lag time when ARC19499 was added (FIG. 39D-F).

These experiments indicate that ARC19499 only has procoagulant activity when functioning TFPI is present in the plasma, and therefore, ARC19499 is specific for TFPI.

Example 15

This example demonstrates that ARC17480, ARC19498 and ARC19499 inhibit TFPI activity in vitro.

Figure 40D:
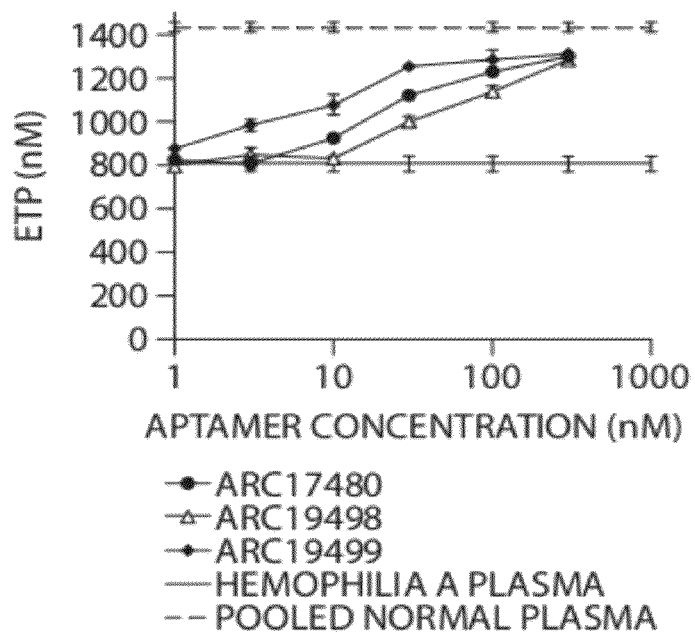
FIG. 40D) and peak thrombin (FIG. 40E) measured with various concentrations of ARC17480, ARC19498 and ARC19499 in hemophilia A plasma were similar to one another, with ARC19499 having slightly greater activity, reaching an ETP plateau close to normal plasma levels by 30 nM aptamer. The thrombin generation curves (FIG. 40A-C) are representative data. The ETP (FIG. 40D) and peak thrombin (FIG. 40E) data represent the mean±standard error, n=3.
Figure 40E:
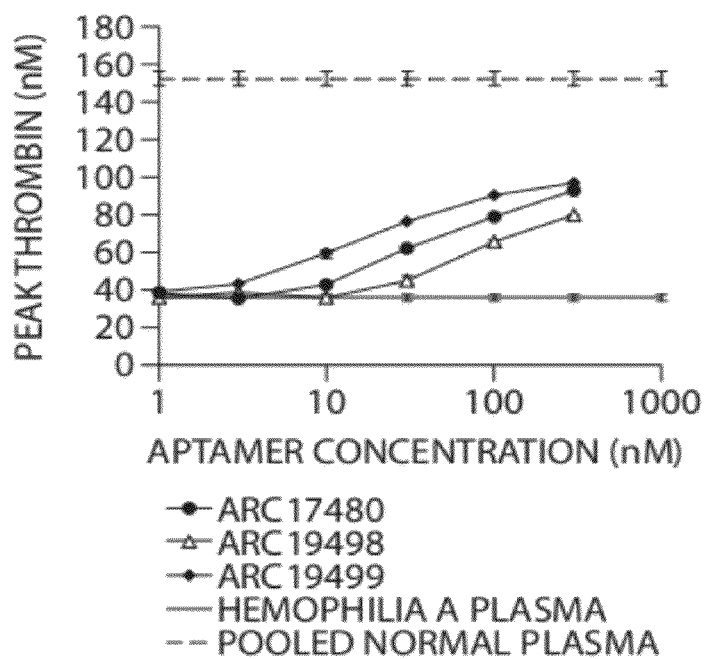
FIG. 40 is a series of graphs showing a calibrated automated thrombogram (CAT) assay with ARC17480 (FIG. 40A), ARC19498 (FIG. 40B) and ARC19499 (FIG. 40C) at various concentrations. The endogenous thrombin potential (ETP.

In this experiment, the inhibitory activity of TFPI aptamers (ARC17480, ARC19498 and ARC19499) were measured in vitro in pooled hemophilia A (Factor VIII-deficient) plasma in a calibrated automated thrombogram (CAT) assay. Aptamers were titrated at different concentrations in pooled hemophilia A plasma, and the amount of thrombin generated was compared to a pooled normal plasma control (FIG. 40A-C), using 1.0 pM TF in the final reaction. Both the endogenous thrombin potential (ETP), which is the area under the thrombin generation versus time curve, and the peak thrombin, which is the highest concentration of thrombin generated over the course of the experiment, provided indirect measures of aptamer inhibition of TFPI. All three aptamers had similar activity in this assay, with ARC19499 having slightly higher activity than the other two. ARC19499 corrected the ETP to near normal levels by 30 nM (FIG. 40D). Peak thrombin levels also increased with increasing concentrations of aptamer (FIG. 40E).

These results show that ARC17480, ARC19498 and ARC19499 inhibit TFPI activity in vitro.

Example 16

This example demonstrates that ARC19499 increases thrombin generation in normal human plasma treated with an anti-Factor VIII antibody to generate a hemophilia A-like state.

Figure 41:
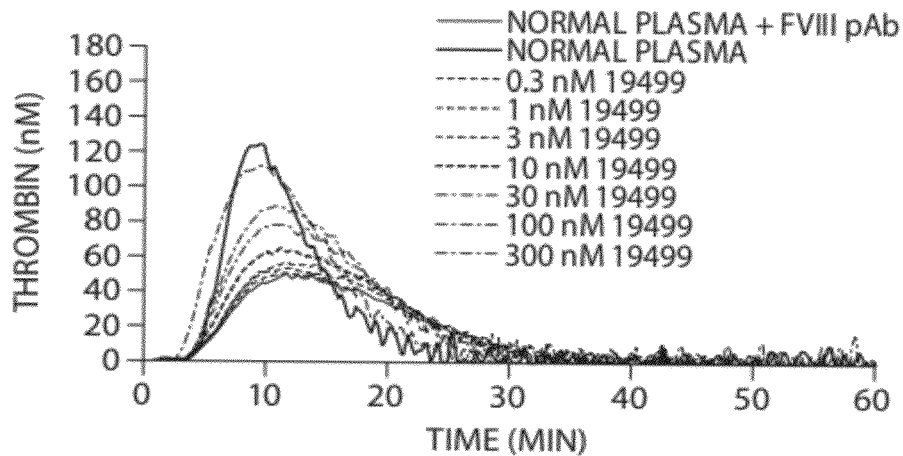
FIG. 41 is a graph of thrombin generation in platelet-poor normal plasma from a single, healthy volunteer. The plasma was treated with an anti-FVIII antibody to generate a hemophilia A-like state. ARC19499 showed a dose-dependent increase in thrombin generation in the antibody-treated plasma.

Platelet-poor plasma from a normal, healthy volunteer was treated with an anti-FVIII antibody to generate a hemophilia A-like state. Thrombin generation in this antibody-treated plasma was similar to that observed with hemophilia A plasma (FIG. 41). Addition of ARC19499 to the antibody-treated plasma resulted in a dose-dependent increase in thrombin generation. These results demonstrate that ARC19499 can correct thrombin generation in plasma with low FVIII levels that results from treatment with an anti-FVIII antibody.

Example 17

This example demonstrates that ARC17480 and ARC19499 inhibit TFPI activity in vitro and have biological activity.

The effects of the non-PEGylated core TFPI inhibitory aptamer ARC17480 and the PEGylated aptamer ARC19499 were evaluated for in vitro thrombin generation activity in hemophilia B (FIX-deficient) plasma using the calibrated automated thrombogram (CAT) assay.

Figure 42A:
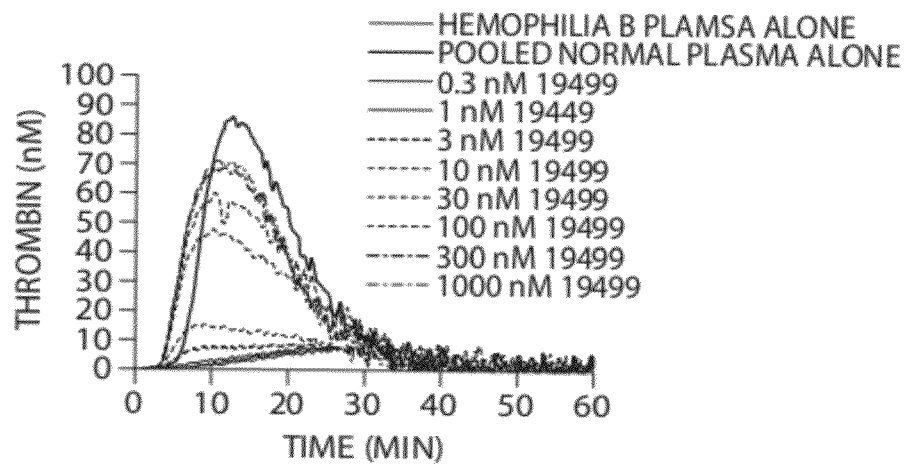
FIG. 42 is a series of graphs showing a calibrated automated thrombogram (CAT) assay with ARC19499 (FIG. 42A) and ARC17480 (FIG. 42B) at various concentrations in hemophilia B plasma.
Figure 42B:
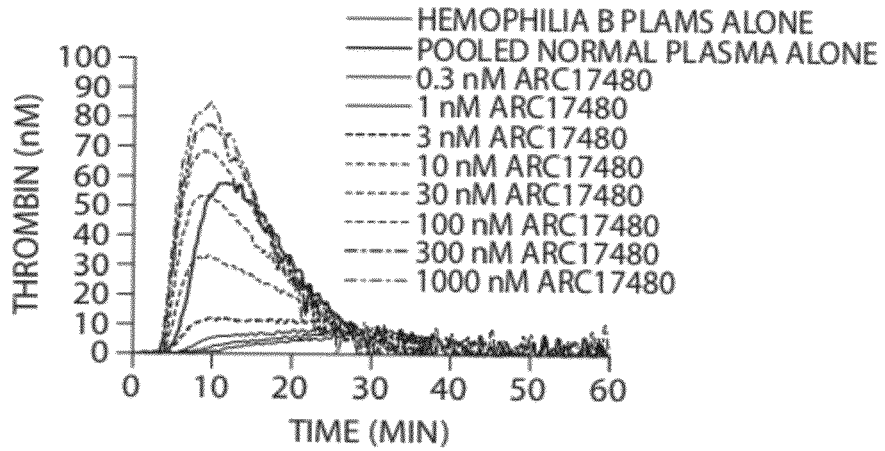
Figure 43:
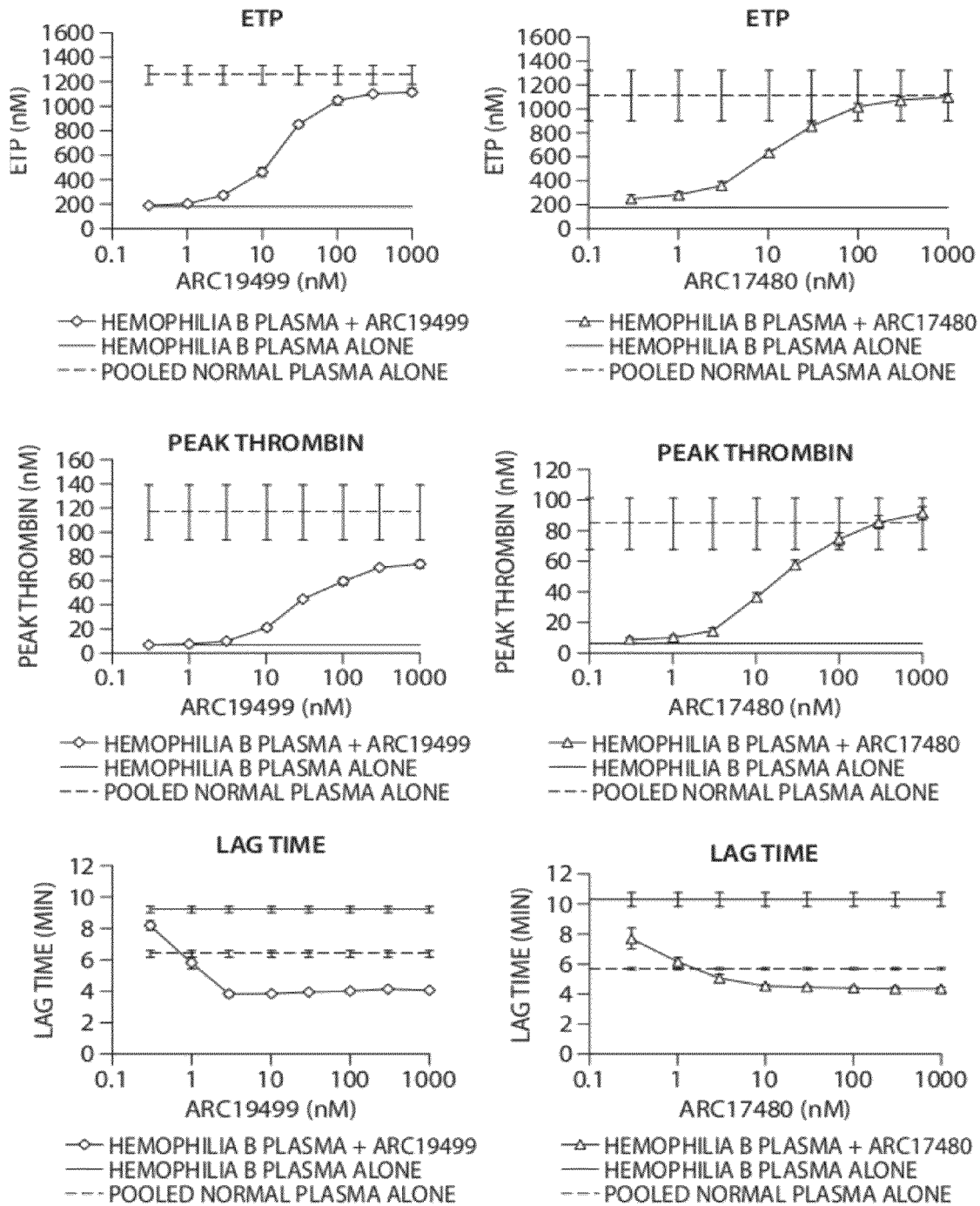
FIG. 43 is a series of graphs showing the effect of ARC19499 (diamonds) and ARC17480 (triangles) on endogenous thrombin potential (ETP), peak thrombin and lag time in hemophilia B plasma. The solid line designates the level of each parameter in the absence of any drug. The hatched line designates the level of each parameter in pooled normal plasma (PNP) without any additional drug. Data represent mean±standard error, n=3. Both aptamers behaved very similarly to each other in hemophilia B plasma.

These studies were performed in plasma pooled from two hemophilia B patients with <1% Factor IX levels (commercially available from George King Bio-Medical, Inc, Overland Park, Kans.). In this assay, plasma and aptamer were mixed together and added to a reagent containing phospholipids and tissue factor. Thrombin generation was initiated by the addition of a mixture containing calcium chloride and a fluorogenic substrate for thrombin. The reaction took place at 37° C., and fluorescence intensity was measured periodically over 1 hour. The final concentrations of tissue factor and phospholipids were 1 pM and 4 µM, respectively. Aptamers were tested at the following concentrations in the plasma: 0.3, 1, 3, 10, 30, 100, 300 and 1000 nM. Individual thrombin generation curves are shown in FIG. 42, illustrating the effects of increasing concentrations of ARC19499 (FIG. 42A) or ARC17480 (FIG. 42B) on the extent of thrombin generation in hemophilia B plasma compared to pooled normal plasma. The plot of ETP, peak thrombin and lag time are shown in FIG. 43. Results with ARC19499 are plotted on the left side, and results with ARC17480 are plotted on the right side.

The ETP and peak thrombin levels decreased ~85% and ~95%, respectively, in plasma from the hemophilia B pool compared to the pooled normal plasma, consistent with a deficiency in thrombin generation due to the loss of Factor IX. Both ARC17480 (triangles) and ARC19499 (diamonds) largely corrected the defect in thrombin generation, as measured by both of these parameters (FIG. 43). By 100 nM, both aptamers demonstrated an ETP nearly equivalent to that achieved with pooled normal plasma, and a nearly equivalent peak thrombin by 300 nM ARC17480 (FIG. 43). Peak thrombin plateaued by 300 nM ARC19499. ARC17480 and ARC19499 decreased the lag time in hemophilia B plasma, below what was achieved with pooled normal plasma and hemophilia B plasma without any drug (FIG. 43).

These results show that ARC17480 and ARC19499 inhibit TFPI with similar potency in hemophilia B plasma in vitro.

Example 18

This example demonstrates that ARC19499 inhibits TFPI activity in vitro and has biological activity compared to a negative control aptamer.

The ability of ARC19499 to enhance thrombin generation was tested in three platelet-poor hemophilia plasmas: plasma pooled from 7-8 patients with severe hemophilia A (<1%

FVIII levels; referred to as "hemophilia A plasma"), plasma from three different hemophilia A patients with high titers of anti-FVIII antibodies (≧160 Bethesda units (BU)/mL; referred to as "inhibitor plasma"), and plasma pooled from two patients with severe hemophilia B (<1% FIX levels; referred to as "hemophilia B plasma"). All plasmas were from George King Bio-Medical (Overland Park, Kans.). Thrombin generation was measured using the calibrated automated thrombogram (CAT) assay. In this assay, plasma and aptamer were mixed together and added to a reagent containing phospholipids and tissue factor. Thrombin generation was initiated by the addition of a mixture containing calcium chloride and a fluorogenic substrate for thrombin. The reaction took place at 37° C., and fluorescence intensity was measured periodically over 1 hour. The final concentrations of tissue factor and phospholipids were 1 pM and 4 µM, respectively. Thrombin generation in the presence of ARC19499 (0.3, 1, 3, 10, 30, 100, 300 and 1000 nM) was compared to negative control aptamer (0.1, 1, 10, 100 and 1000 nM). Plots of ETP, peak thrombin and lag time (mean±s.e.m.) are shown in FIG. 44.

Figure 44A:
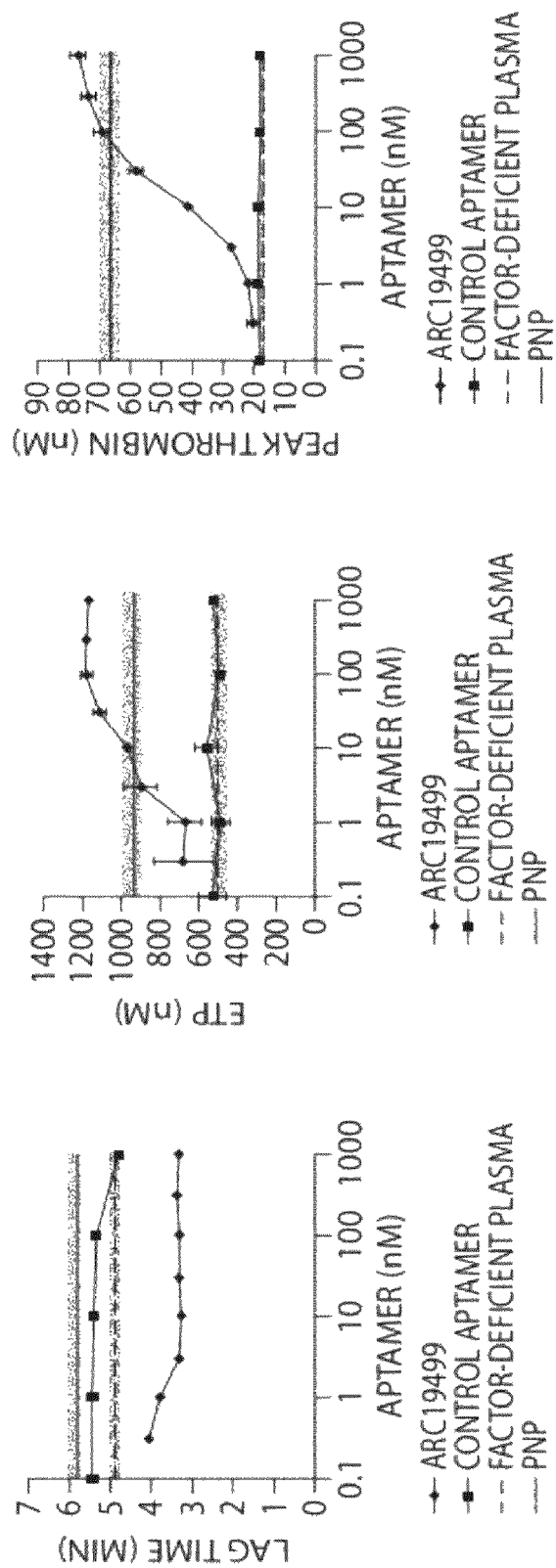
FIG. 44 is a series of graphs showing the effects of ARC19499 compared to a negative control aptamer on thrombin generation as measured by the calibrated automated thrombogram (CAT) assay in plasmas from patients with hemophilia A (FIG. 44A), hemophilia A with inhibitors (FIG. 44B) or hemophilia B (FIG. 44C). The results are given in terms of the lag time (left), endogenous thrombin potential (ETP) (middle) and peak thrombin concentration (right). In all graphs, lines represent activity of normal plasma (solid) and factor-deficient plasma (dashed) in the absence of aptamer, and shading around the lines represents the standard error of the mean.
Figure 44B:
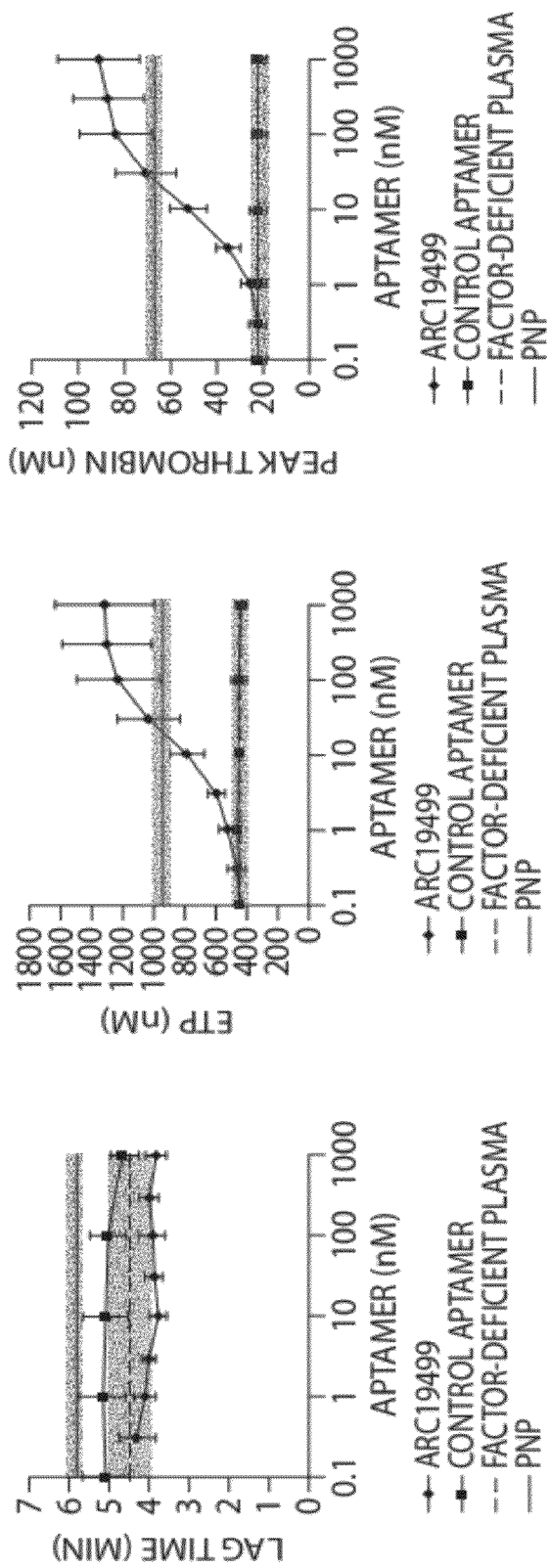
Figure 44C:
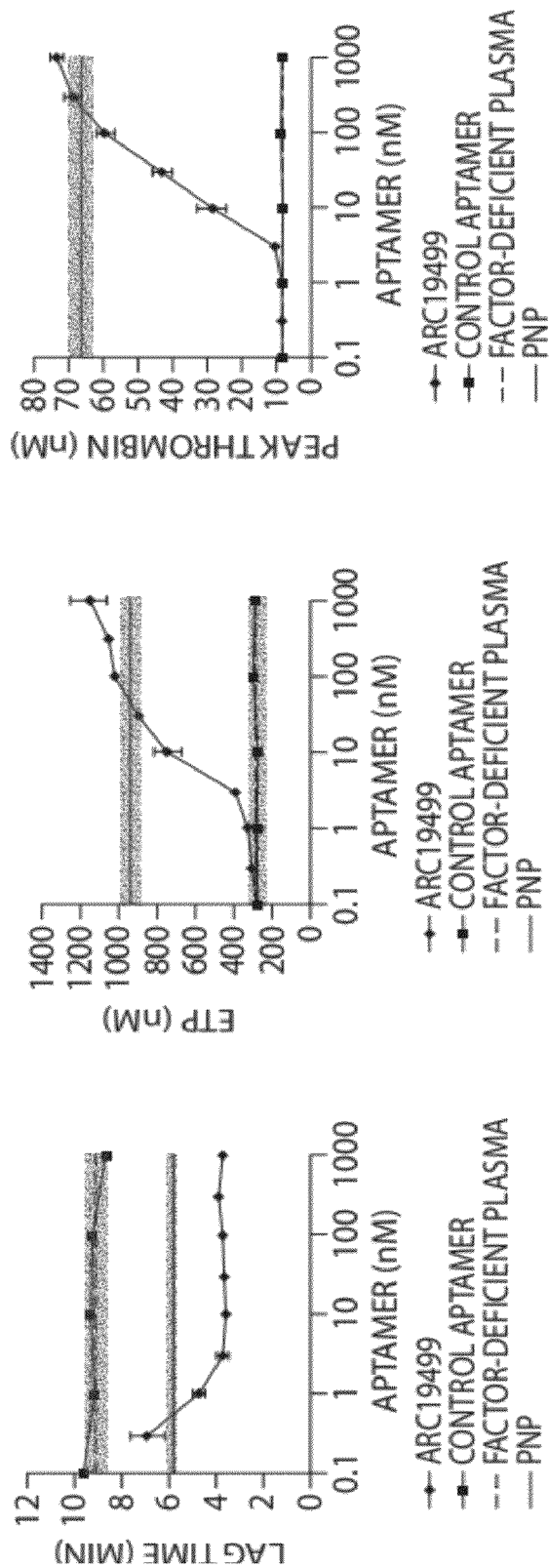
Figure 45A:
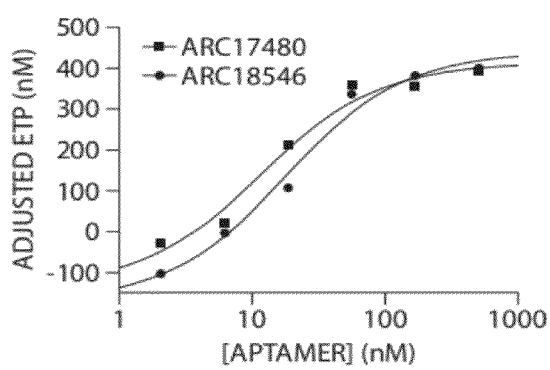
FIGS. 45A and C) and adjusted peak thrombin (FIGS. 45B and D) values are plotted as a function of aptamer concentration. The ETP and peak thrombin values for hemophilia plasma were subtracted from each value to give the adjusted values. ARC17480, ARC18546, ARC26835 and ARC31301 increase thrombin generation in a concentration-dependent manner in hemophilia A plasma.
Figure 45B:
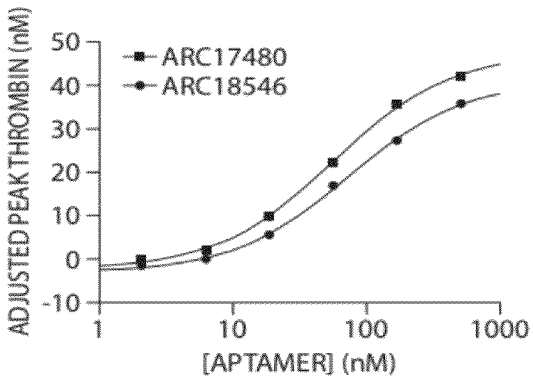
FIG. 45 depicts the results of thrombin generation experiments with ARC17480, ARC18546, ARC26835 and ARC31301 in hemophilia A plasma. Adjusted endogenous thrombin potential (ETP.
Figure 45C:
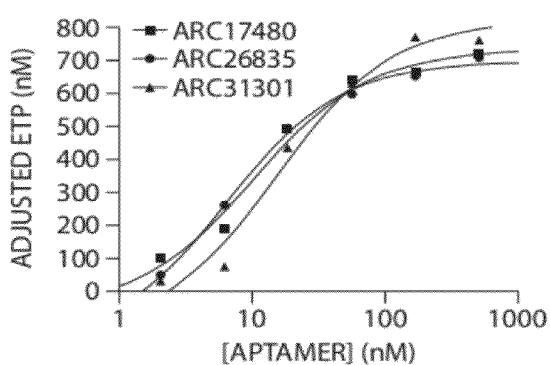
Figure 45D:
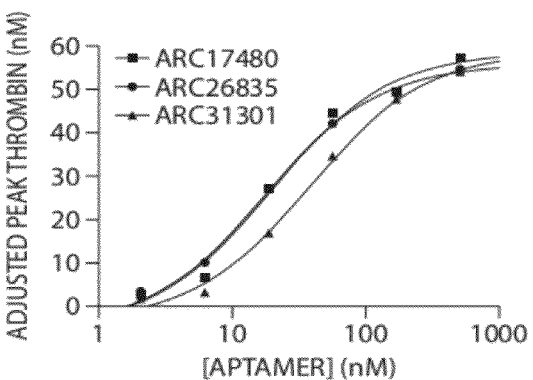
Figure 46A:
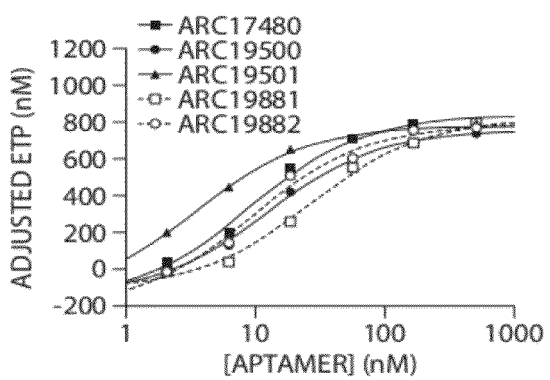
FIG. 46A) and adjusted peak thrombin (FIG. 46B) values are plotted as a function of aptamer concentration. The ETP and peak thrombin values for hemophilia plasma were subtracted from each value to give the adjusted values. ARC17480, ARC19500, ARC19501, ARC19881 and ARC19882 increase thrombin generation in a concentration-dependent manner in hemophilia A plasma.
Figure 46B:
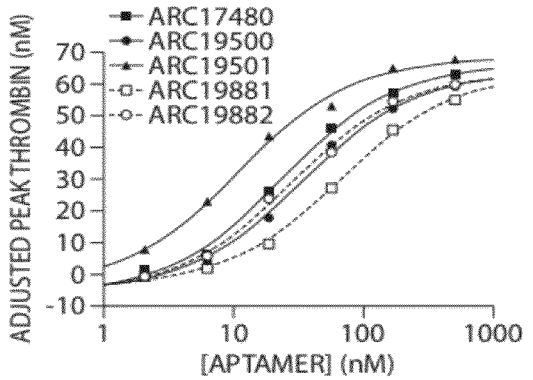
FIG. 46 depicts the results of thrombin generation experiments with ARC17480, ARC19500, ARC19501, ARC19881 and ARC19882 in hemophilia A plasma. Adjusted endogenous thrombin potential (ETP.

Hemophilia A plasma had a slightly shorter lag time and a markedly decreased ETP and peak thrombin (~50% and ~75%, respectively) compared to normal plasma. Increasing concentrations of ARC19499 largely corrected the defect in thrombin generation. ETP was corrected to near-normal levels with 3 nM ARC19499, and peak thrombin was corrected with 100 nM aptamer (FIG. 44A) Inhibitor plasma also had decreased ETP and peak thrombin (~50% and ~70%, respectively) compared to normal plasma. As with the severe hemophilia A plasma, ARC19499 increased thrombin generation in this plasma. With 30 nM ARC19499, both the ETP and peak thrombin were at normal levels (FIG. 44B). Hemophilia B had an even greater defect in thrombin generation, with significantly decreased ETP and peak thrombin (~70% and ~90%, respectively) and an increased lag time. As with the hemophilia A plasmas, increasing concentrations of ARC19499 improved thrombin generation in this plasma, achieving normal ETP levels with 30 nM ARC19499, and normal peak thrombin levels with 100-300 nM aptamer (FIG. 44C). Taken together, these results demonstrate that 30-100 nM ARC19499 is effective in restoring coagulation in three different types of hemophilia plasma. A negative control aptamer was also tested in the three different plasmas and demonstrated no correction of thrombin generation (FIG. 44).

The sequence of the negative control aptamer, ARC32603, used in this example was: mG-mG-mA-mA-mU-mA-mU-mA-dC-mU-mU-mG-mG-dC-mU-mG-dC-mU-mU-mA-mG-mG-mU-mG-dC-mG-mU-mA-mU-mA-mU-mA-3T (SEQ ID NO: 152).

Example 19

This example demonstrates that ARC17480, ARC26835, ARC19500, ARC19501, ARC31301, ARC18546, ARC19881 and ARC19882 have biological activity in the calibrated automated thrombogram (CAT) assay.

The TFPI-inhibitory activity of each aptamer was evaluated in the CAT assay in pooled hemophilia A plasma at 500 nM, 167 nM, 55.6 nM, 18.5 nM, 6.17 nM and 2.08 nM aptamer concentration. ARC17480 was included in every experiment as a control. For each aptamer, the endogenous thrombin potential (ETP) and peak thrombin values at each aptamer concentration were used for analysis. The ETP or peak thrombin value for hemophilia A plasma alone was subtracted from the corresponding value in the presence of aptamer for each molecule at each concentration. Then, the adjusted ETP and peak values were plotted as a function of aptamer concentration and fit to the equation y=(max/(1+$IC_{50}$/x))+int, where y=ETP or peak thrombin, x=concentration of aptamer, max=the maximum ETP or peak thrombin, and int=the y-intercept, to generate an $IC_{50}$ value for both the ETP and the peak thrombin. FIG. 45A-D and FIG. 46A-B show graphs of CAT experiments with ARC17480, ARC26835, ARC19500, ARC19501, ARC31301, ARC18546, ARC19881 and ARC19882. Both the adjusted endogenous thrombin potential (ETP) and peak thrombin are shown. These experiments demonstrate that ARC17480, ARC26835, ARC19500, ARC19501, ARC31301, ARC18546, ARC19881 and ARC19882 all functionally inhibited TFPI in the CAT assay, as evidenced by a concentration-dependent increase in both ETP and peak thrombin in hemophilia A plasma. These molecules all have similar activity in the CAT assay.

Example 20

This example demonstrates that the TFPI aptamers have biological activity.

In this experiment, the ability of ARC19499 to affect thrombin generation compared to that of NovoSeven® was tested using the calibrated automated thrombogram (CAT) assay. The CAT assay generates a number of parameters to compare thrombin generation. The lag time is a measure of the length of time that it takes for thrombin generation to begin. Peak thrombin is a measure of the highest amount of thrombin to be generated at any one point. The endogenous thrombin potential (ETP) is the area under the thrombin generation curve.

These studies were performed in the presence of three different plasmas: platelet-poor plasma from healthy volunteers, a pool of plasma from hemophilia A patients with <1% Factor VIII levels (commercially available from George King Bio-Medical, Inc, Overland Park, Kans.), and plasma from hemophilia A patients with a high titer of inhibitor antibody to Factor VIII (commercially available from George King Bio-Medical, Inc, Overland Park, Kans.). In the CAT assay, plasma and drug (either ARC19499 or NovoSeven®) were mixed together and added to a reagent containing phospholipids and tissue factor. Thrombin generation was initiated by the addition of a mixture containing calcium chloride and a fluorogenic substrate for thrombin. The reaction took place at 37° C., and fluorescence intensity was measured periodically over 1 hour. The final concentrations of tissue factor and phospholipids were 1 pM and 4 µM, respectively. The drugs were tested at the following concentrations in the plasma: 0.3, 1, 3, 10, 30, 100 and 300 nM.

In the plasma from healthy volunteers, there was no change in the ETP over the range of concentrations tested with both ARC19499 and NovoSeven® (FIG. 47A). The peak thrombin levels increased slightly at the higher doses, with ARC19499 and NovoSeven® behaving in a nearly identical manner (FIG. 47B). ARC19499 had no effect on the lag time of thrombin generation, while NovoSeven® demonstrated a dose-dependent decrease in lag time, reaching a minimum lag time by 30 nM (FIG. 47C).

The ETP and peak thrombin levels decreased ~40% and ~75%, respectively, in plasma from the hemophilia A pool, consistent with a deficiency in thrombin generation due to the loss of Factor VIII. ARC19499 and NovoSeven® largely corrected the defect in thrombin generation, as measured by both of these parameters. These agents demonstrated a nearly equivalent effect on ETP, reaching a maximum ETP by 30 nM (FIG. 48A). NovoSeven® had a slightly higher effect on peak thrombin reaching a maximal level by 30 nM. ARC19499 reached the same level of peak thrombin by 300 nM (FIG. 48B). As seen in the plasma from healthy volunteers, ARC19499 had no effect on the lag time, while NovoSeven® showed a dose-dependent decrease in lag time, reaching a maximum effect by 30 nM (FIG. 48C).

Similar results were seen in the plasma from patients with a high titer antibody. Both drugs increased ETP and peak thrombin in the same manner (FIGS. 49A-B). Again, ARC19499 had no effect on the lag time, while NovoSeven® showed a dose-dependent decrease of lag time (FIG. 49C). Standard error associated with the inhibitor plasma was higher than that seen in the healthy plasma or hemophilia A pool. This was most likely due to the difference in titers between the three inhibitor patients (160 BU/mL, 533 BU/mL and 584 BU/mL).

Overall, with the exception of the lag time, ARC19499 and NovoSeven® had very comparable effects on thrombin generation in all plasmas tested.

Example 21

This example demonstrates that the TFPI aptamers have biological activity.

In this experiment, the ability of ARC19499 to affect clot formation compared to that of NovoSeven® was tested using the thromboelastography (TEG®) assay. The TEG® assay measures the mechanical properties of a developing clot. In the TEG® assay, a cup containing the blood product and any activators oscillates freely around a pin that is attached to a torsion wire. As a clot develops, newly formed fibrin strands connect the oscillating cup to the stationary pin and begin to pull on the pin, thus generating force on the torsion wire. This force is converted to a signal by the computer to monitor clot formation, and is displayed as a tracing of signal height versus time. From this tracing, one can extract a number of parameters to measure various aspects of clot formation. The R-value measures the time that it takes for an initial clot to develop. The angle is a measure of the rate at which the clot forms. The maximum amplitude (MA) is a measure of clot strength and stability.

These studies were performed in citrated whole blood from healthy volunteers. In the first assay, the drugs were tested in untreated whole blood. In the second assay, the blood was first treated with a sheep polyclonal antibody against human Factor VIII for three hours at 37° C. prior to drug addition. In both assays, NovoSeven® or ARC19499 were added to the blood (antibody-treated or not) at final blood concentrations of 0.01, 0.1, 1, 10 or 100 nM. Activation of clotting occurred upon addition of tissue factor (Innovin) at a final dilution of 1:200000 (~6 fM) and calcium chloride at a final concentration of 11 mM.

In untreated blood, both ARC19499 and NovoSeven® demonstrated a dose-dependent, moderate decrease in R-value that appeared to reach a minimum value by 10 nM (FIG. 50A). The angle and MA values remained unchanged over the concentrations tested (FIG. 50B-C).

In the blood treated with Factor VIII antibody, both drugs had similar effects on the R-value. The R-value was prolonged in blood treated with antibody compared to untreated blood. As the ARC19499 or NovoSeven® concentration increased, the R-value was restored to the same level it was in untreated blood (FIG. 51A). Antibody treatment decreased the rate of clot formation in the blood, which is reported as the angle. NovoSeven® had a strong effect on the angle, increasing it linearly from 0.1 to 100 nM of NovoSeven®. This increase surpassed the angle achieved with untreated blood. ARC19499 also increased the angle, but the value appeared to plateau by 10 nM of aptamer, at a similar level as that achieved with untreated blood (FIG. 51B). The effect on MA was minimal with both drugs, primarily because there does not appear to be a large difference in the MA of whole blood, with or without FVIII antibody treatment. Both drugs resulted in MA values that fell between those achieved with untreated blood and those achieved with antibody-treated blood (FIG. 51C).

As seen in the CAT assay, ARC19499 and NovoSeven® had very comparable effects on clot formation in whole blood, whether the blood was lacking Factor VIII or not. The main difference between the two drugs was seen in the effect on the rate of clot formation (angle), with NovoSeven® showing a more linear increase in rate as the concentration increased, but ARC19499 did increase the rate as well.

Example 22

This example demonstrates that the TFPI aptamers have biological activity.

In this experiment, the synergy between ARC19499 and Factor VIII in thrombin generation was tested using the calibrated automated thrombogram (CAT) assay. These studies were performed in the presence of a pool of plasma from hemophilia A patients with <1% Factor VIII (FVIII) levels (commercially available from George King Bio-Medical, Inc, Overland Park, Kans.). Increasing concentrations of ARC19499 (from 1 to 300 nM) were analyzed in the presence of 0, 1.4, 2.5, 5, 14 and 140% Factor VIII (World Health Organization International Standard). The results were compared to the baseline responses for hemophilia A and pooled normal plasmas in the absence of ARC19499.

Figures 52A, 52B, 52C:
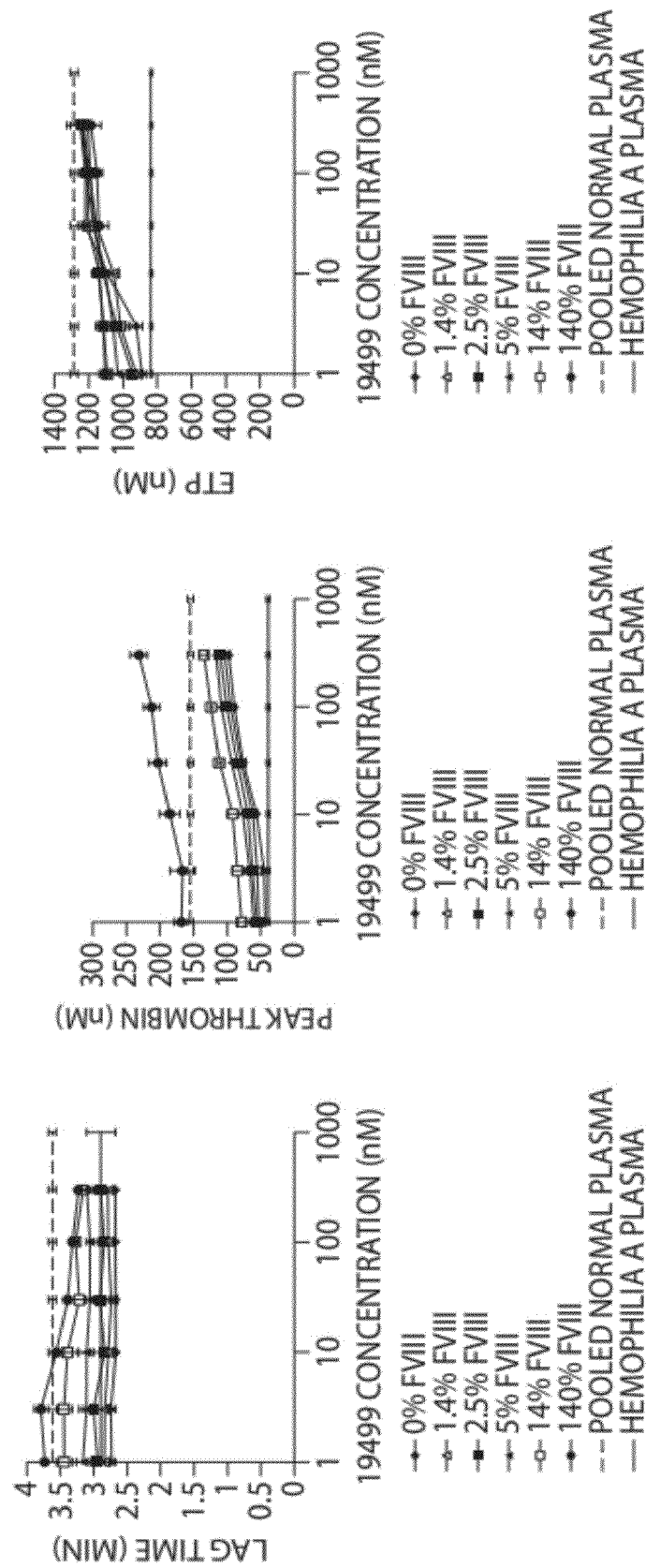
FIG. 52C). Each line represents the dose response of ARC19499 in the presence of a different percent of Factor VIII (filled diamonds, 0%; empty triangles, 1.4%; filled squares, 2.5%; filled triangles, 5%; empty squares, 14%; and filled circles, 140%). The dashed line designates level of each parameter in the presence of pooled normal plasma (PNP) alone. The solid line designates the level of each parameter in hemophilia A plasma without any additions. Data represent mean±standard error, n=3.
Figure 53A:
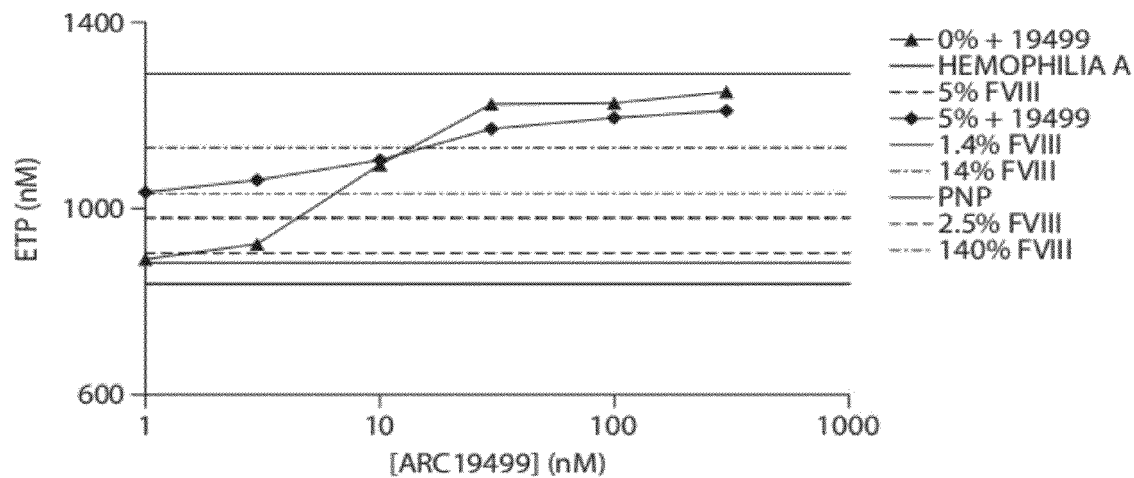
In FIG. 53A, the endogenous thrombin potential (ETP) is plotted as a function of ARC19499 concentration. The dashed lines represent the ETP after addition of different amounts of FVIII to hemophilia A plasma. The solid lines show that ARC19499 increases ETP in hemophilia A plasma (line with triangles) and hemophilia A plasma with 5% FVIII added (line with diamonds).
Figure 53B:
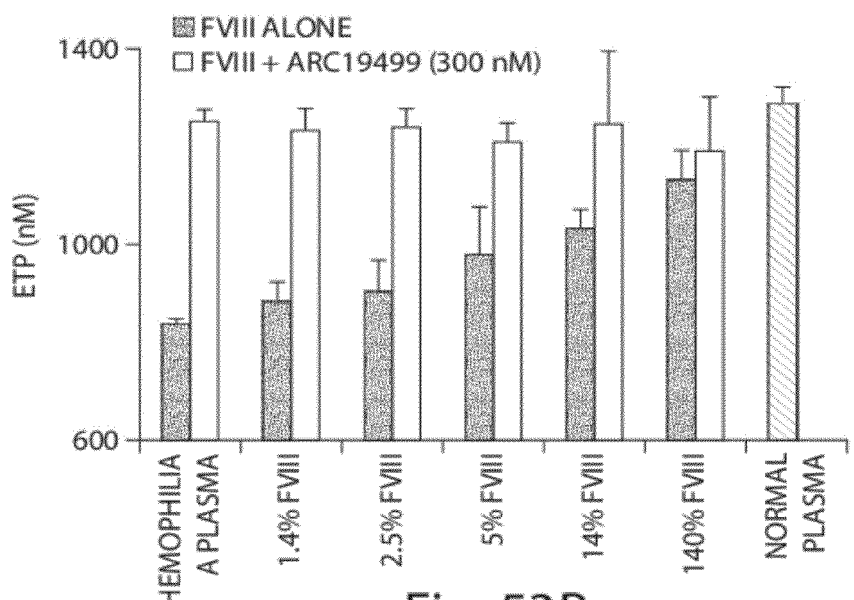
In FIG. 53B, the ETP is plotted versus FVIII concentration. ETP data is shown with and without the addition of 300 nM ARC19499.

Assuming the normal and hemophilia A plasmas are otherwise equivalent, the absence of Factor VIII in the hemophilia A plasma caused a marginal decrease in the baseline lag time for thrombin generation compared to normal plasma (FIG. 52A), a 3-4 fold decrease in peak thrombin concentration (FIG. 52B) and a 1.5-1.6 fold decrease in endogenous thrombin potential (ETP) (FIG. 52C) in this experiment. In the absence of Factor VIII, ARC19499 had little or no effect on the lag time for thrombin generation, but caused a dose-dependent increase in peak thrombin concentration and ETP. The addition of exogenous Factor VIII caused incremental changes in all parameters, with the largest effects observed on the peak thrombin concentration (FIG. 52B). Reconstitution with 140% Factor VIII restored this parameter to a level similar to that observed in normal plasma, with smaller improvements observed at 14% Factor VIII and below. Moreover, the incremental increase in peak thrombin caused by each Factor VIII concentration was nearly identical at all concentrations of ARC19499, suggesting that the effects of the two agents on thrombin generation are additive rather than synergistic. With ETP, Factor VIII flattened the ARC19499 dose-response curve with an additive effect observed only at the lower concentrations of ARC19499 (FIG. 52C). Once 10 nM of ARC19499 was reached, additional Factor VIII did not appear to have a benefit. FIG. 53A shows the ETP of hemophilia A plasma with different concentrations of FVIII added (dashed lines). Addition of ARC19499 resulted in a dose-dependent increase in thrombin generation in hemophilia A plasma and in hemophilia A plasma with 5% FVIII added. ARC19499 mediated a procoagulant effect in hemophilia A plasma that was similar to 14% FVIII at 1-10 nM aptamer when ETP was evaluated (FIG. 53A) or 10-30 nM when peak thrombin was evaluated. When a saturating amount of ARC19499 (300 nM) was added to plasma with different concentrations of FVIII, thrombin generation levels were near to that observed with normal plasma, indicating that ARC19499 does not have a severe prothrombotic effect (FIG. 53B). Even with 140% Factor VIII, ETP levels of normal plasma were never reached. By this measure, therefore, the addition of exogenous Factor VIII appeared to obviate the need for a bypassing agent like ARC19499, rather than facilitate its action. Interestingly, ARC19499 appeared to decrease lag time at the higher concentrations of Factor VIII (FIG. 52A).

The inhibition of TFPI in this case may enable more rapid, Factor VIII-dependent propagation of thrombin generation.

Example 23

This example demonstrates that ARC19499 can improve coagulation in a spatial model of clot formation, in hemophilia plasma activated with immobilized tissue factor.

Figure 54A:
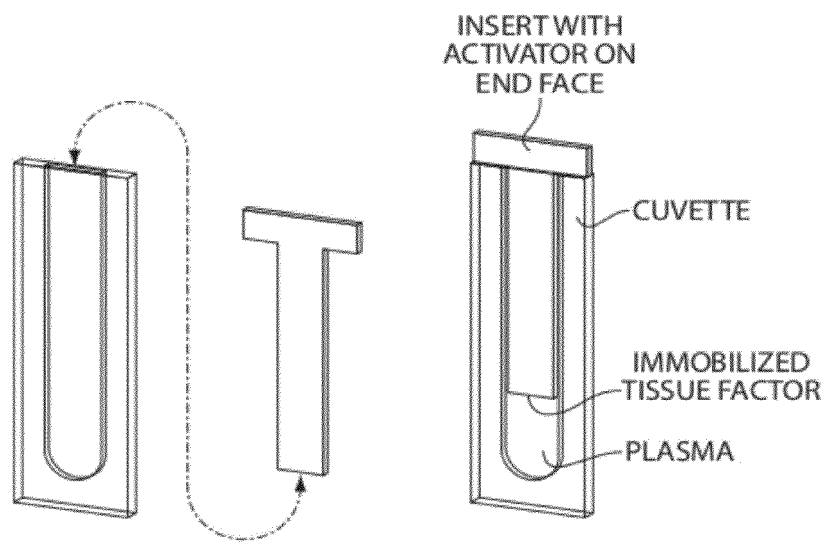
FIG. 54A is a diagram of the spatial clotting chamber.
Figure 54B:
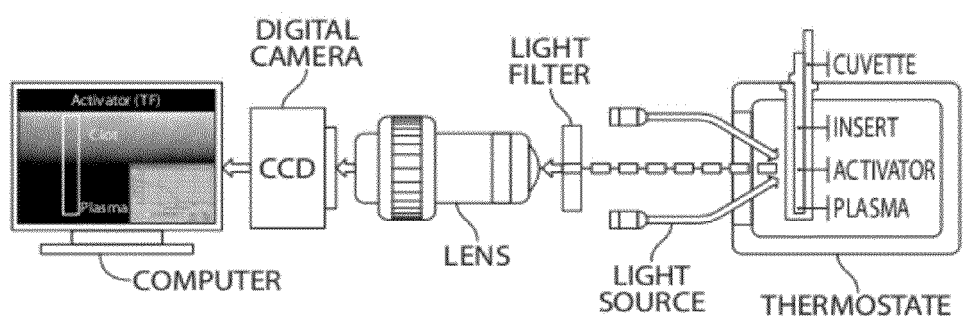
FIG. 54B is a schematic illustration of the components of the system for measuring clot progression in the chamber.
Figure 57A:
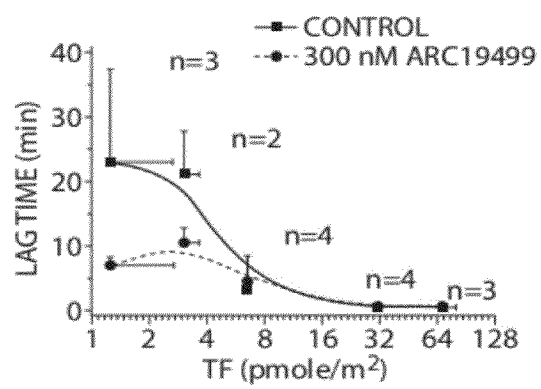
FIG. 57 is a series of graphs showing the lag time (FIG. 57A), $V_{initial}$ (FIG. 57B), $V_{stationary}$ (FIG. 57C) and clot size after 60 minutes (FIG. 57D) in normal pooled plasma, each plotted as a function of tissue factor density in the presence (circles) and absence (squares) of ARC19499.
Figure 57B:
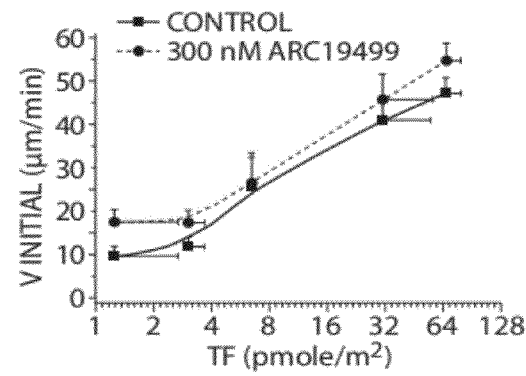
Figure 57C:
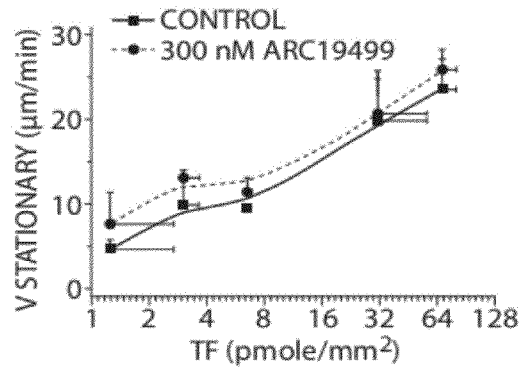
Figure 57D:
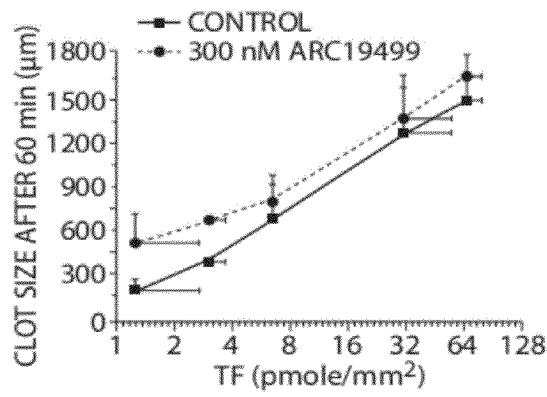
Figure 58A:
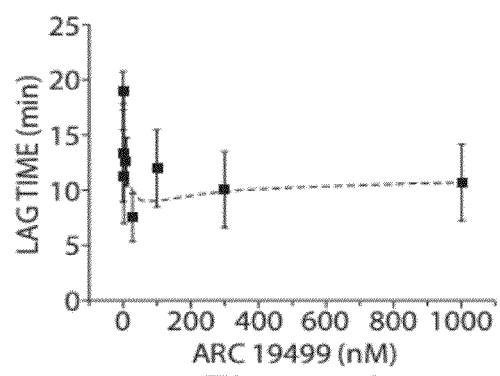
FIG. 58 is a series of graphs showing the lag time (FIG. 58A), $V_{initial}$ (FIG. 58B), $V_{stationary}$ (FIG. 58C) and clot size after 60 minutes (FIG. 58D) in normal pooled plasma, each plotted as a function of ARC19499 concentration under conditions of low surface tissue factor density.
Figure 58B:
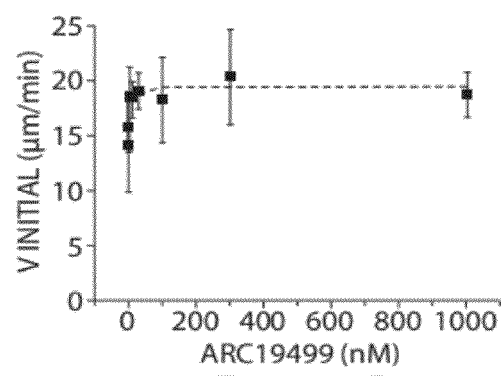
Figure 58C:
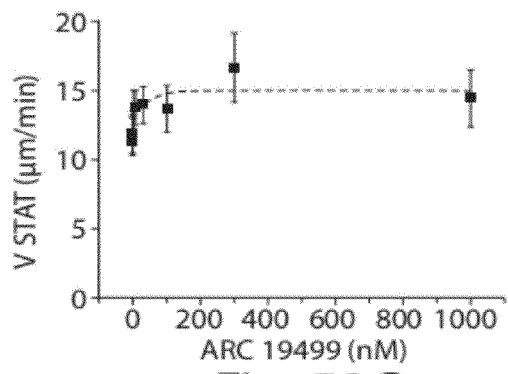
Figure 58D:
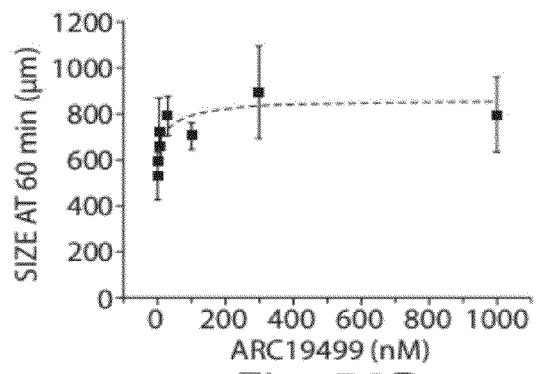
Figure 59A:
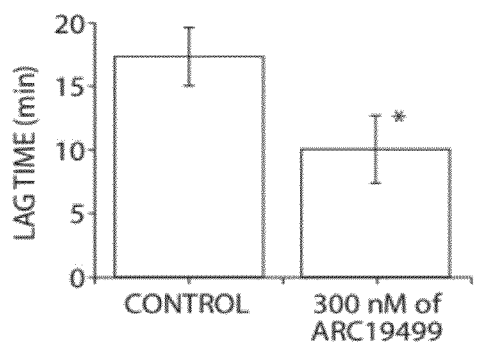
FIG. 59 is a series of graphs illustrating the effect of ARC19499 on the lag time (FIG. 59A), $V_{initial}$ (FIG. 59B), $V_{stationary}$ (FIG. 59C) and clot size after 60 minutes (FIG. 59D) in normal pooled plasma under conditions of low surface tissue factor density. An asterisk indicates a statistically significant difference±ARC19499 ($P<0.05$).
Figure 59B:
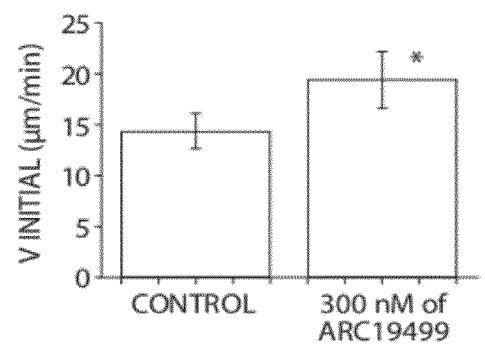
Figure 59C:
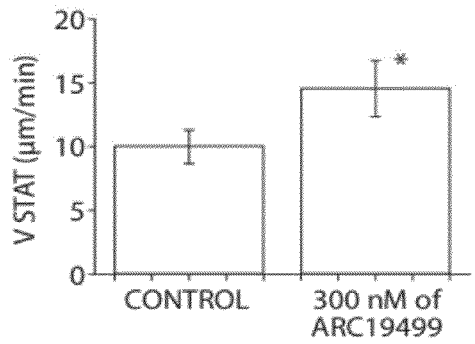
Figure 59D:
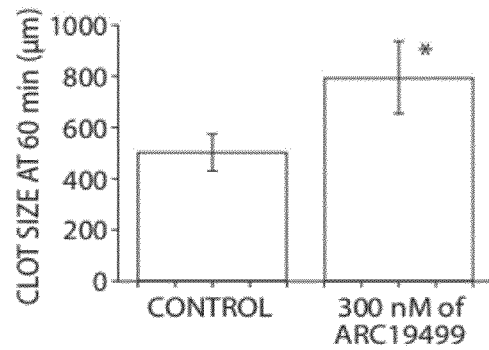
Figure 60A:
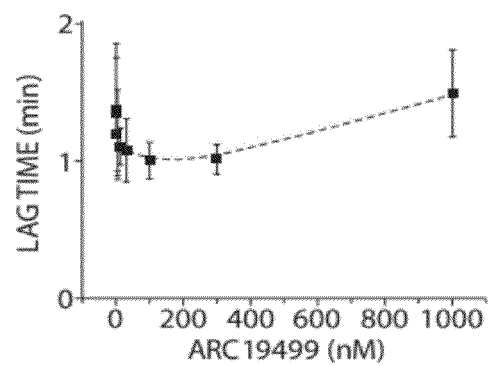
FIG. 60 is a series of graphs showing the lag time (FIG. 60A), $V_{initial}$ (FIG. 60B), $V_{stationary}$ (FIG. 60C) and clot size after 60 minutes (FIG. 60D) in normal pooled plasma, each plotted as a function of ARC19499 concentration under conditions of medium surface tissue factor density.
Figure 60B:
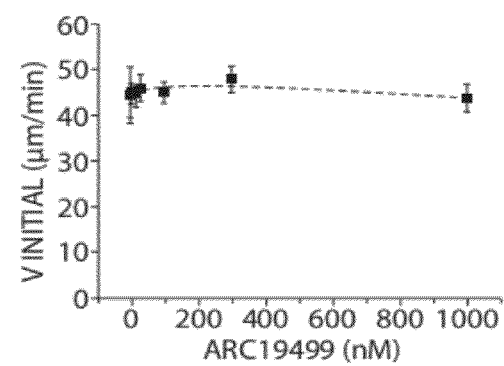
Figure 60C:
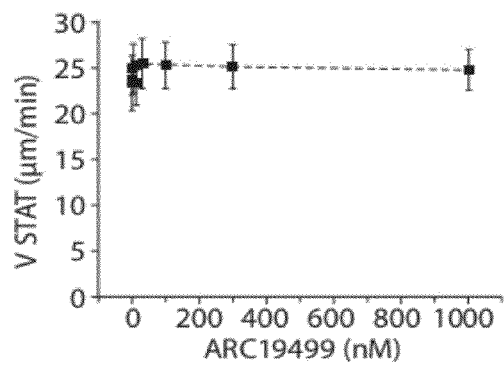
Figure 60D:
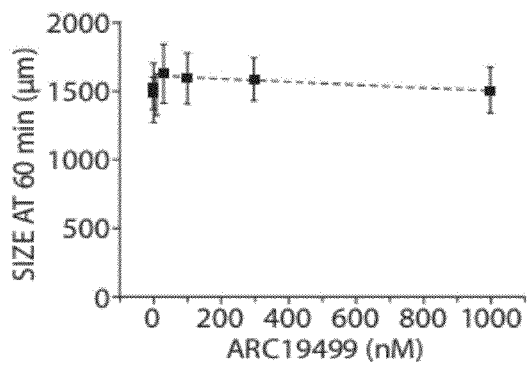
Figure 61A:
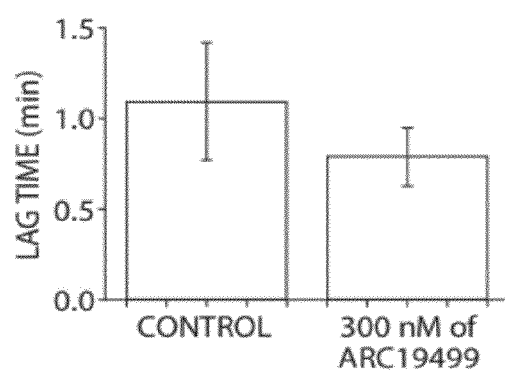
FIG. 61 is a series of graphs illustrating the effect of ARC19499 on the lag time (FIG. 61A), $V_{initial}$ (FIG. 61B), $V_{stationary}$ (FIG. 61C) and clot size after 60 minutes (FIG. 61D) in normal pooled plasma under conditions of medium surface tissue factor density. An asterisk indicates a statistically significant difference±ARC19499 ($P<0.05$).
Figure 61B:
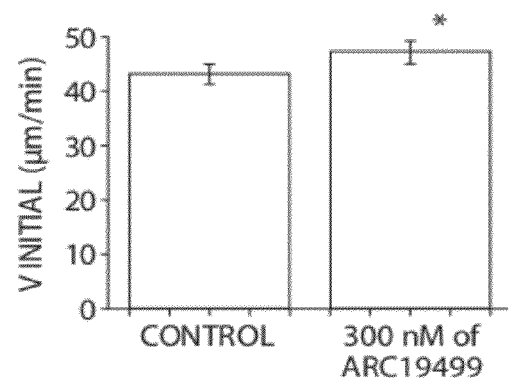
Figure 61C:
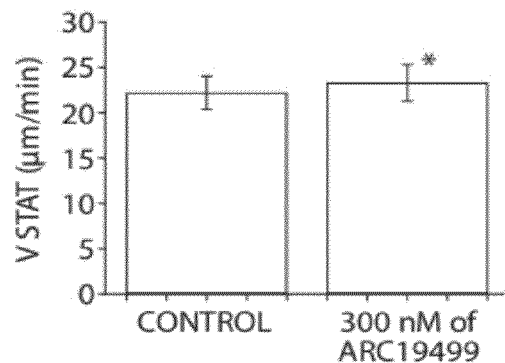
Figure 61D:
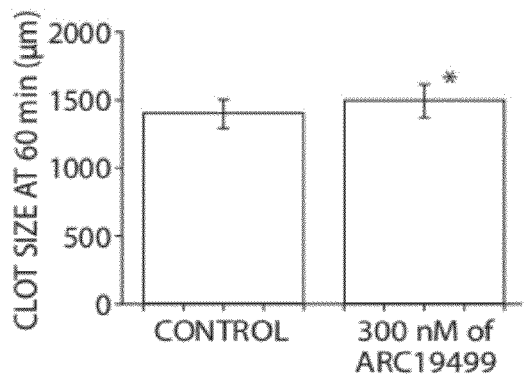

The key property of the spatial experimental model is that blood plasma clotting is activated by a surface covered with immobilized tissue factor (TF). The fibrin gel then propagates into the bulk of plasma. Clotting takes place in a specially designed chamber (FIG. 54A). Plasma samples are loaded into the well of the chamber that is subsequently placed in the thermostat. All experiments are performed at 37° C. Clotting is initiated by immersion of an insert with TF immobilized on its end face into the chamber. Clot formation is registered by light scattering from fibrin gel using a CCD camera (FIG. 54B). The chamber is uniformly illuminated with monochromatic light and images are captured every 15 seconds. The acquired series of images is then processed by computer and parameters of spatial dynamics of blood clotting are calculated.

For the purposes of this set of experiments, surfaces were derivatized with TF densities in the range of 1-100 pmole/m$^2$. The density of TF on the surface was characterized by the ability to activate Factor X (Enzyme Research Laboratories) in the presence of excess Factor VIIa (Novoseven®; Novo Nordisk) using a chromogenic Factor Xa substrate S-2765 (Chromogenix). The rate of S-2765 cleavage was measured by light absorption (405 nm) and compared to a calibration curve prepared using a set of TF standard solutions (American Diagnostica) to calculate TF concentration.

Each light scattering image was processed by calculating the mean light scattering intensity (based on pixel intensity) along a perpendicular drawn to activating surface. The data from each image was depicted as a single contour line on a plot of light scattering intensity versus distance from the activating surface (FIG. 55). Clot propagation was depicted qualitatively by successive contour lines of increasing light scattering intensity, determined from images taken at consecutive timepoints up to 90 minutes (FIG. 55), or quantitatively, by plotting clot size versus time (FIG. 56). The clot size for each image was determined as the coordinate (in micrometers or millimeters) along the contour line where the scattering intensity is half-maximal. Based on clot size versus time plots, the following parameters were calculated: lag time (delay between contact of plasma with activator and beginning of clot formation), initial velocity of clot growth ($\alpha$ or $V_{initial}$; mean slope of the clot size versus time curve over the first 10 minutes after the lag time), spatial or stationary velocity of clot growth ($\beta$ or $V_{stationary}$; mean slope over the next 30 minutes) and clot size after 60 minutes of the experiment (an integral parameter of clot formation efficiency). For each experiment, four perpendiculars were drawn from different points along the activator surface. Profiles of clot size versus time were analyzed and four values of each clotting parameter were obtained and then averaged to obtain means.

This study was conducted primarily using freshly prepared plasma (rather than commercial or frozen plasma) from normal donors and hemophilia A patients. Blood was collected from healthy volunteers and hemophilia A patients at a 9:1 v/v ratio into a solution containing 3.8% sodium citrate plus 0.2 mg/ml CTI (Institute of Protein Research, Russian Academy of Sciences), then it was processed by centrifugation at 1,500 g for 15 minutes to obtain platelet-poor plasma. It was additionally centrifuged at 10,000 g for 5 minutes to obtain platelet-free plasma. Fresh pools of normal plasma were prepared from 3 healthy donors each. At 15 minutes before an experiment, 300 µL of plasma was supplemented with 18 µL of ARC19499 or recombinant Factor VIIa (alternatively designated rVIIa or Novoseven®). In control experiments lacking ARC19499 or Factor rVIIa, plasma was supplemented with the same volume of phosphate buffered saline. Plasma was recalcified by the addition of 60 µL 1 M CaCl$_2$, mixed, and 300 µL of recalcified plasma was placed in the experimental chamber. The insert with the TF-derivatized surface was then placed in the chamber to initiate clotting (FIG. 54A).

The result of a typical spatial clot formation experiment, activated by 1 pmole/m$^2$ of TF density in normal pooled plasma, without and with 300 nM of ARC19499 is shown in FIGS. 55A and B, respectively. The plots show contours of light scattering as a function of distance from the activator. The time between two contours is 2.5 minutes and the total time of each experiment is 90 minutes. The enhancement in light scattering at each timepoint in FIG. 55B compared to FIG. 55A indicates that addition of ARC19499 improved spatial clot formation. However, the effects of ARC19499 on clot formation are more clearly seen in a plot of clot size versus time (FIG. 56) derived from the processed scattering data, where improvements in lag time, $V_{initial}$ ($\alpha$) and clot size at 60 minutes are observable.

Clot formation parameters were plotted as a function of TF surface density in FIG. 57. Vertical error bars indicate standard deviations (SD) for clot parameters while "n" is the number of experiments performed at a specific TF density. Horizontal bars are SD for determinations of TF density (n=2 for each activator series). FIG. 57A shows averaged lag time dependence on activator TF density. The magnitude of TFPI inhibition by ARC19499 depended on TF density and became more significant as the density decreased (up to 2.5-fold shortening of the lag time at TF densities of 1-3 pmole/m$^2$). FIG. 57B shows the averaged initial clot growth velocity dependence on activator TF density. Again, the effect of ARC19499 was significant only at low TF densities (1-3 pmole/m$^2$) where a ~1.8-fold increase of the initial velocity was observed. FIG. 57C illustrates the stationary clot growth velocity dependence on activator TF density; ARC19499 had little effect on clot propagation velocity throughout the entire range of activators. Finally, FIG. 57D shows the averaged clot size after 60 minutes. Inhibition of TFPI affected clot size at densities of 1-4 pmole/m$^2$ TF; ARC19499 effects became insignificant as the TF density increased. Based on these data, two TF densities were chosen for further studies of ARC19499: low, 1-2 pmole/m$^2$, and medium, 10-20 pmole/m$^2$. Several lots of activators were prepared for each of these TF densities; the mean values for the low and medium density activators were 2.0±0.68 (n=22 lots) and 20.6±8.90 pmole/m$^2$ (n=5 lots), respectively.

The influence of different ARC19499 concentrations (from 0 to 1000 nM) on spatial clotting in normal pooled plasma was evaluated to examine the dose-dependence of ARC19499 effects. FIG. 58 shows means and standard errors of the mean (SEM) for experiments with different normal plasma pools (n=4) and low surface TF densities. Lag time (FIG. 58A) decreased with increasing ARC19499 concentration up to 30 nM, and then stabilized. Initial velocity (FIG. 58B) increased by ~30% with increasing ARC19499 concentration, while stationary velocity (FIG. 58C) was not significantly affected throughout the entire range of concentrations. There was a detectable increase in clot size at 60 minutes (FIG. 58D) with increasing ARC19499 concentration. For all affected parameters, maximal effects of ARC19499 were clearly achieved by 300 nM, and the concentration of half-maximal effect was <10 nM. FIG. 59 shows means (±SEM) of clotting parameters for 0 and 300 nM of ARC19499 at low TF density combining the raw data from FIGS. 57 and 58 (n=6). To calculate the statistical significance of the ARC19499 effect, the difference between each parameter value, with and without ARC19499, was calculated for each experiment, and the distribution of these differences was compared with zero using the t-test. Asterisks indicate statistical significance (P<0.05), that the difference between values±ARC19499 was different from zero. The effects on all four parameters were statistically significant, although the effects on lag time and clot size were the largest.

FIG. 60 shows mean parameters (±SEM) for experiments with different normal plasma pools (n=3) and medium surface TF densities, plotted as a function of ARC19499 concentration. The effects of ARC19499 on clotting were less substantial in this experiment. FIG. 61 shows the statistical analysis comparing 0 and 300 nM ARC19499 for all four clotting parameters. Although some of the differences appear statistically significant (indicated by asterisk), the effects of ARC19499 on clotting in normal plasma activated by medium TF density were very small.

Figure 62A:
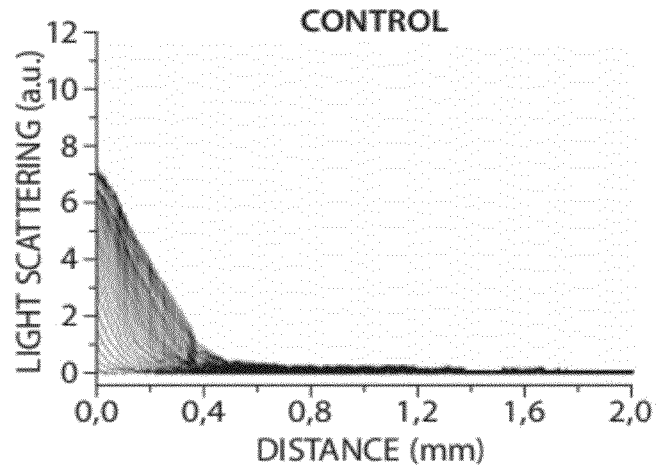
FIG. 62 compares clot propagation in normal pooled plasma (FIG. 62A) to normal pooled plasma containing 100 nM ARC19499 (FIG. 62B) or 100 nM recombinant factor VIIa (rVIIa or Novoseven®.
FIG. 62C) under conditions of low surface tissue factor density.
Figure 62B:
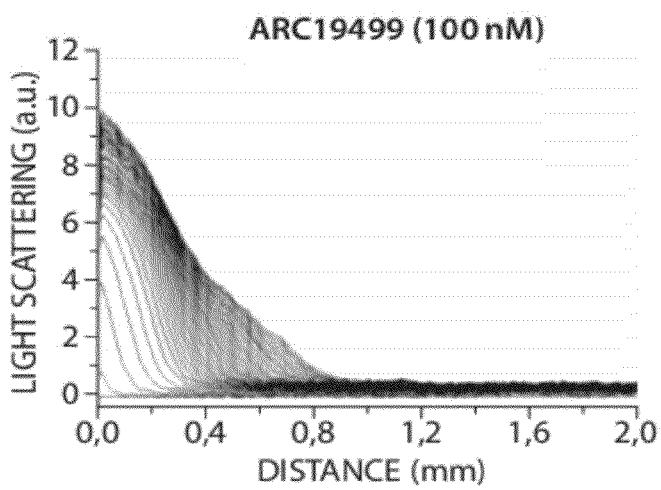
Figure 62C:
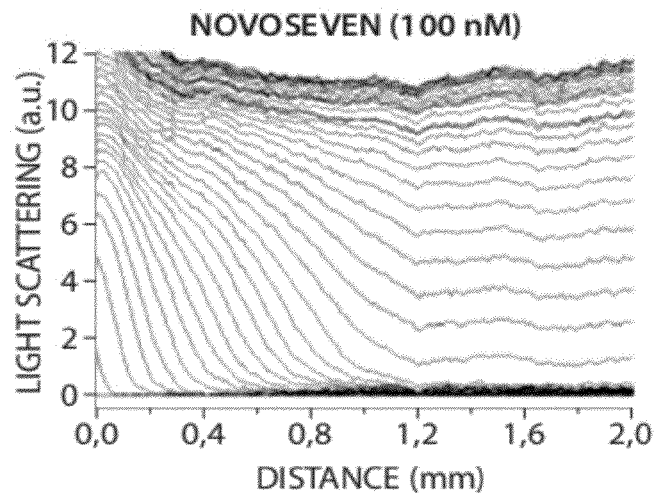
Figure 63:
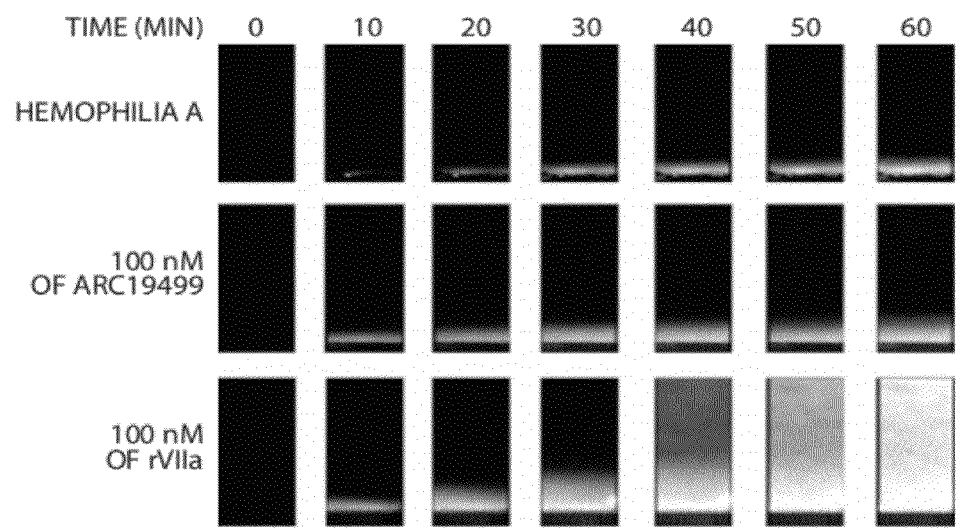
FIG. 63 is an illustration showing a series of light scattering images from the spatial clotting model. Each row depicts clot propagation from a surface (bottom) over time 0, 10, 20, 30, 40, 50 and 60 minutes. The top row shows clot propagation in severe hemophilia A plasma, followed by severe hemophilia A plasma containing 100 nM ARC19499 in the second row and severe hemophilia A plasma containing 100 nM recombinant factor VIIa (rVIIa) in the third row.
Figure 64:
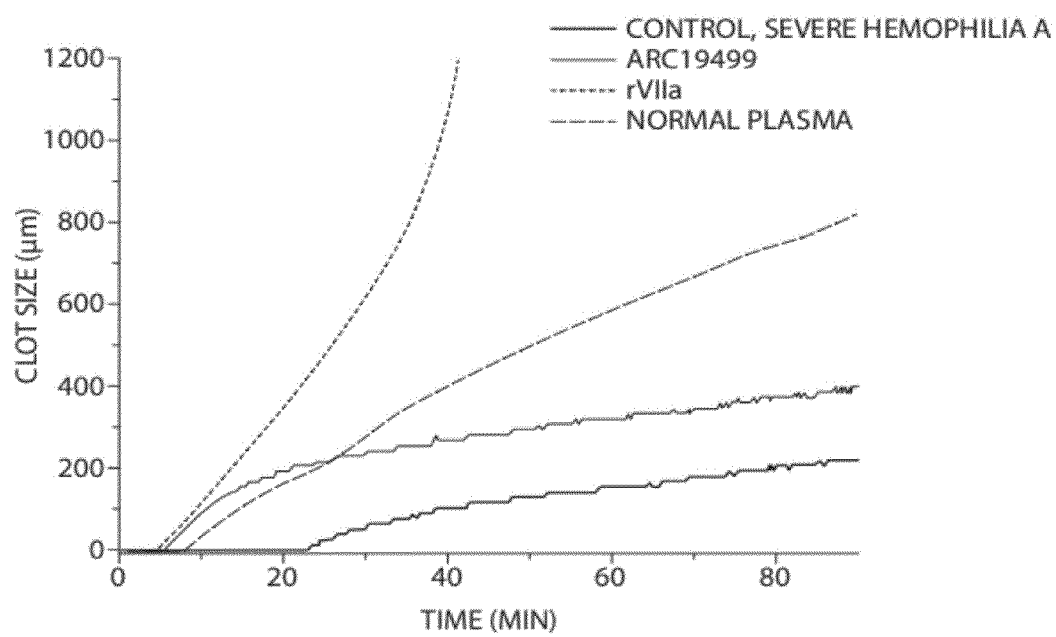
FIG. 64 is a graph of clot size versus time, in normal plasma (dark grey, dashed line), severe hemophilia A plasma (black, solid line), severe hemophilia A plasma containing 100 nM ARC19499 (light grey, solid line) or 100 nM recombinant factor VIIa (rVIIa) (light grey, dashed line).
Figure 66A:
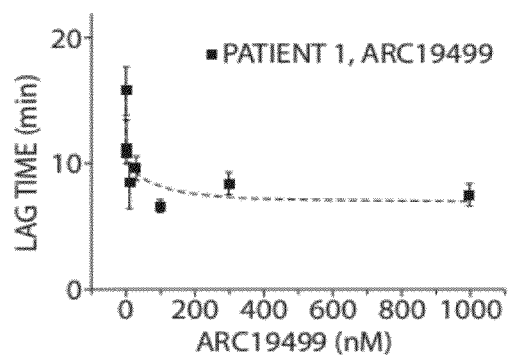
FIG. 66 shows the effects of ARC19499 or recombinant factor VIIa (rVIIa), titrated into severe hemophilia A plasma from Patient 1, on spatial clot formation activated with low surface tissue factor density. The effects of ARC19499 and rVIIa on lag time are depicted in FIGS. 66A and B, respectively, while the effects of ARC19499 and rVIIa on $V_{initial}$ are depicted in FIGS. 66C and D, respectively.
Figure 66B:
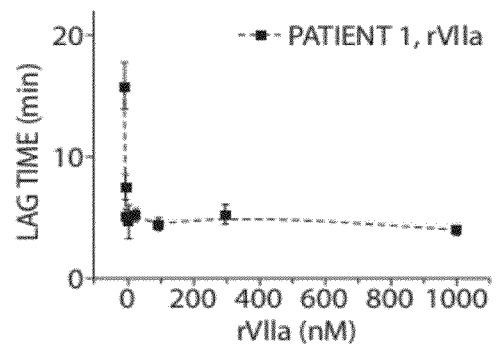
Figure 66C:
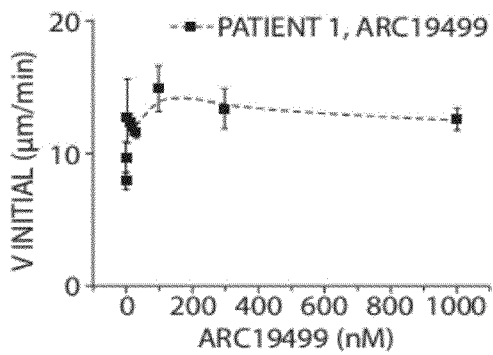
Figure 66D:
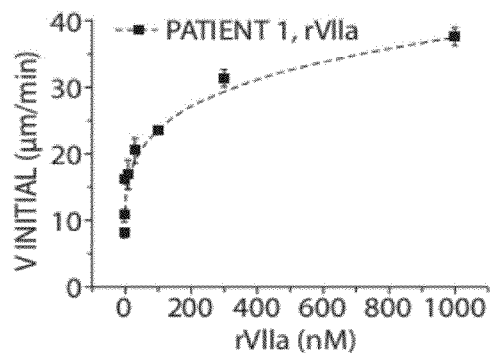
Figure 67A:
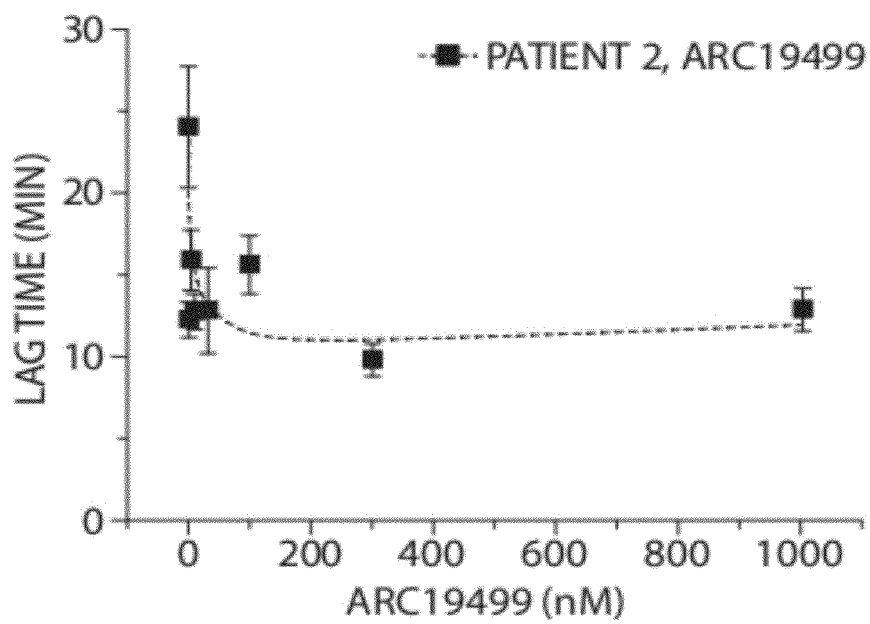
FIG. 67 shows the effects of ARC19499 or recombinant factor VIIa (rVIIa), titrated into severe hemophilia A plasma from Patient 2, on spatial clot formation activated with low surface tissue factor density. The effects of ARC19499 and rVIIa on lag time are depicted in FIGS. 67A and B, respectively, while the effects of ARC19499 and rVIIa on $V_{initial}$ are depicted in FIGS. 67C and D, respectively.
Figure 67B:
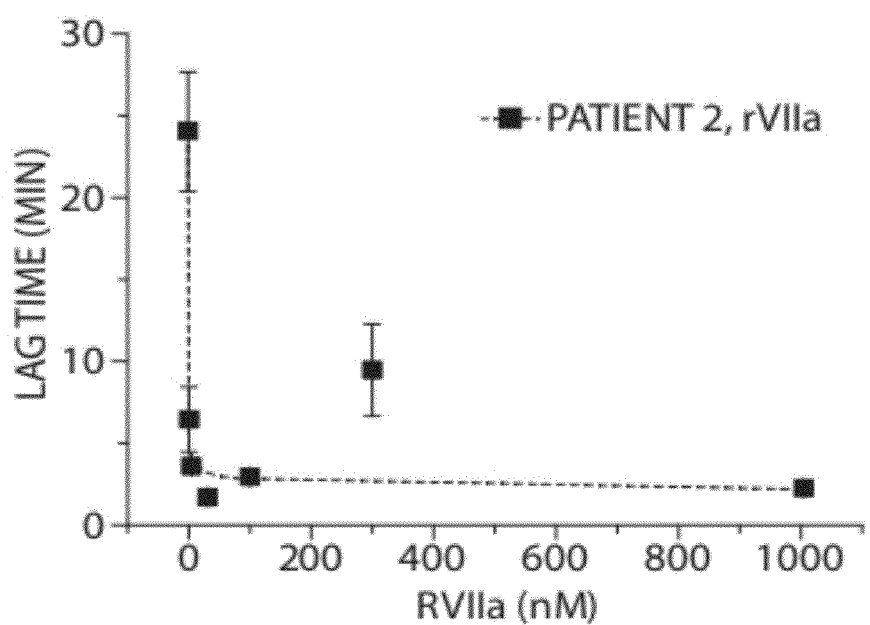
Figure 67C:
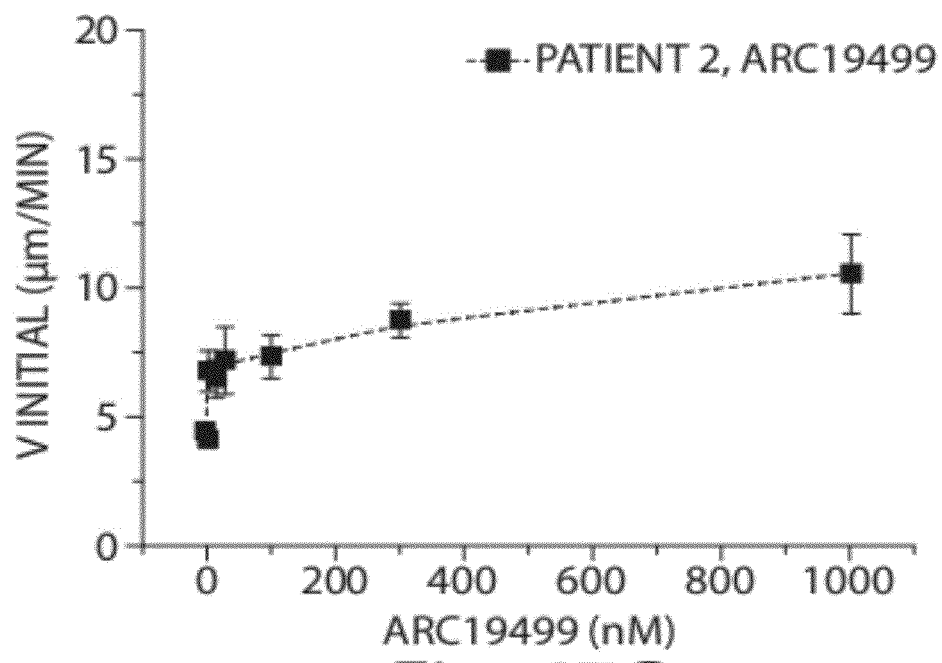
Figure 67D:
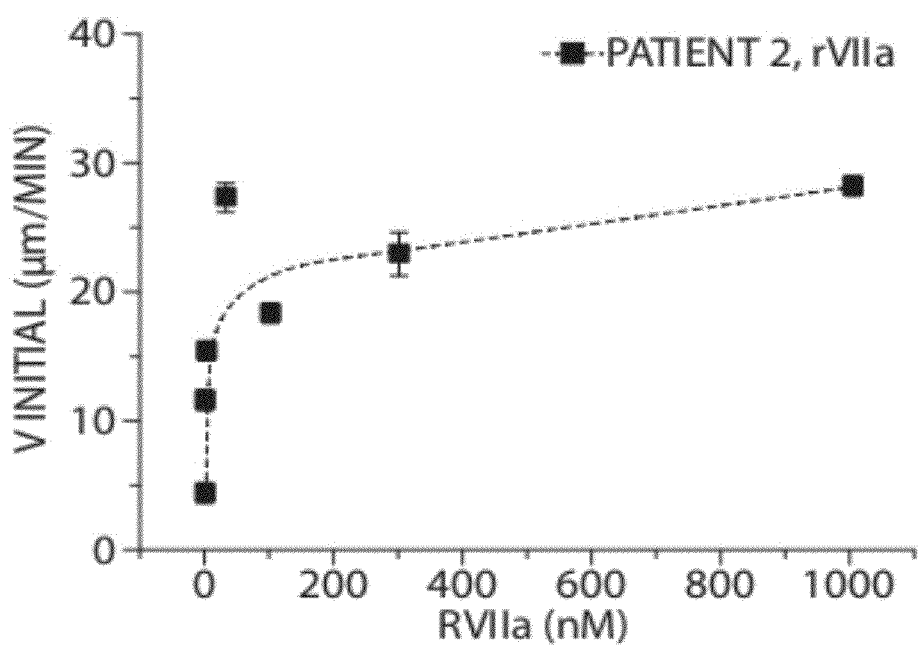
Figure 68A:
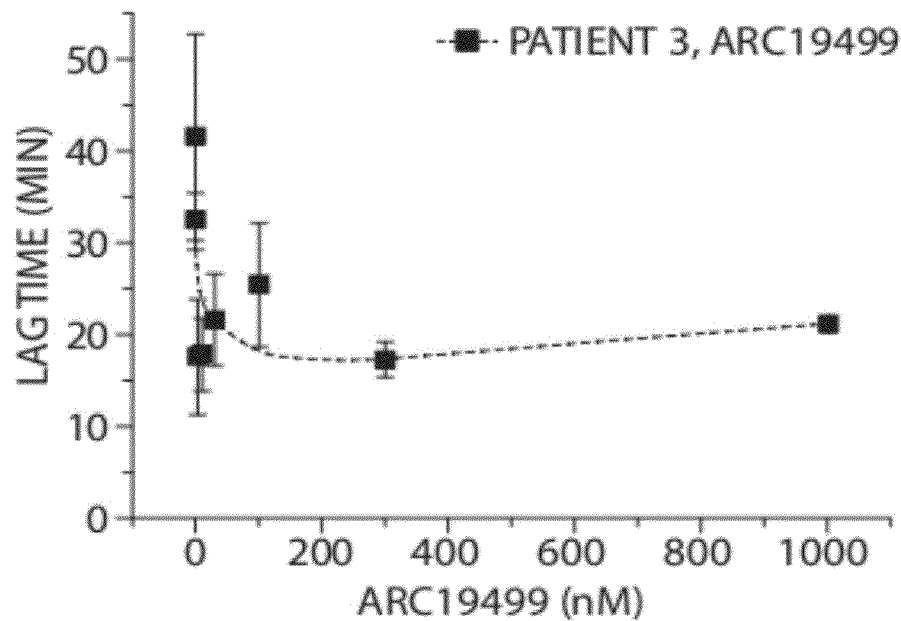
FIG. 68 shows the effects of ARC19499 or recombinant factor VIIa (rVIIa), titrated into severe hemophilia A plasma from Patient 3, on spatial clot formation activated with low surface tissue factor density. The effects of ARC19499 and rVIIa on lag time are depicted in FIGS. 68A and B, respectively, while the effects of ARC19499 and rVIIa on $V_{initial}$ are depicted in FIGS. 68C and D, respectively.
Figure 68B:
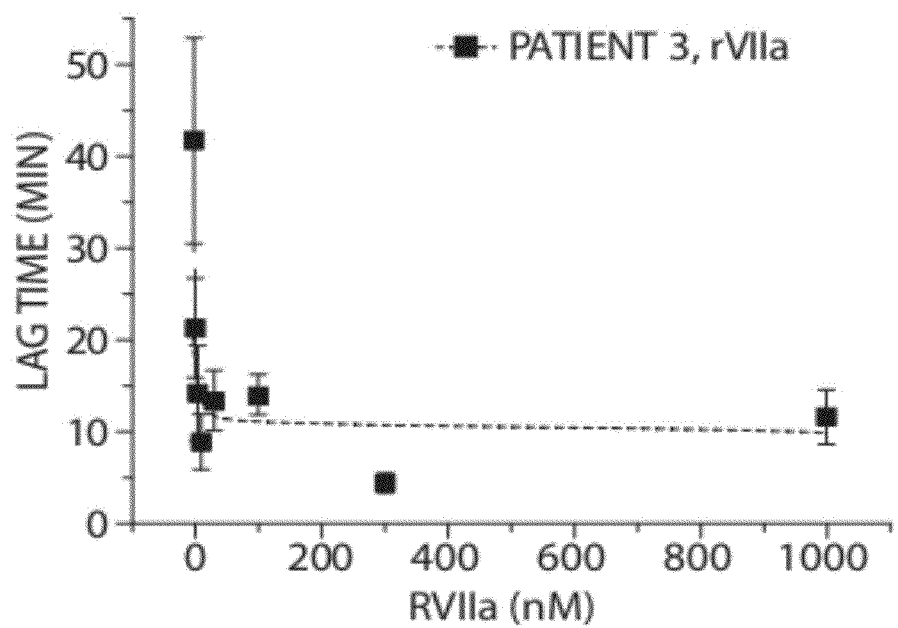
Figure 68C:
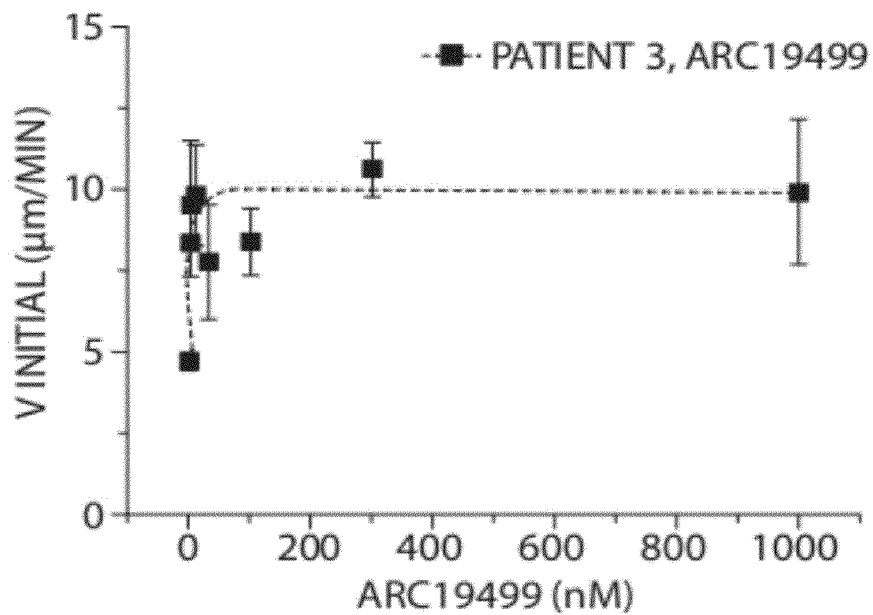
Figure 68D:
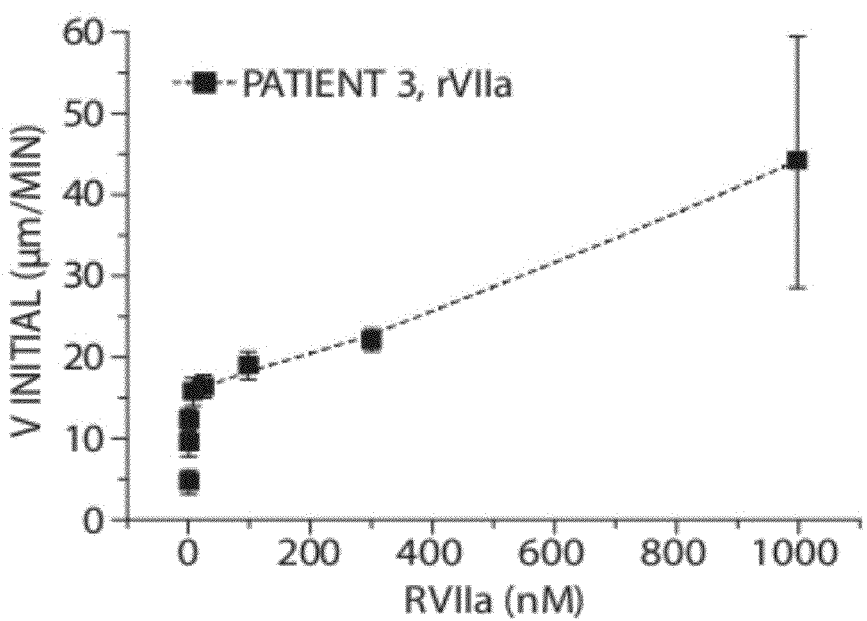

Typical spatial clot formation activated by low density TF in hemophilia A plasma is shown in FIG. 62. The plots show profiles of light scattering as a function of distance from the activator for hemophilia A plasma alone (FIG. 62A) and hemophilia A plasma containing 100 nM ARC19499 (FIG. 62B) or 100 nM rVIIa (FIG. 62C). Example light scattering images from which this data was derived are shown in FIG. 63, and a plot of clot size versus time derived from the processed data is shown in FIG. 64, with a normal plasma profile included for comparison. Based on these data, ARC19499 improved spatial clot formation by shortening lag time and increasing clot size. As shown in FIG. 64, 100 nM ARC19499 partially normalized clot formation, facilitating clot propagation from the activating surface. In contrast, 100 nM rVIIa stimulated potent TF-independent clotting. Rather than stimulating normalization of spatial clot propagation from the activating surface, rVIIa at this concentration induced clotting throughout the reaction chamber.

Figure 69:
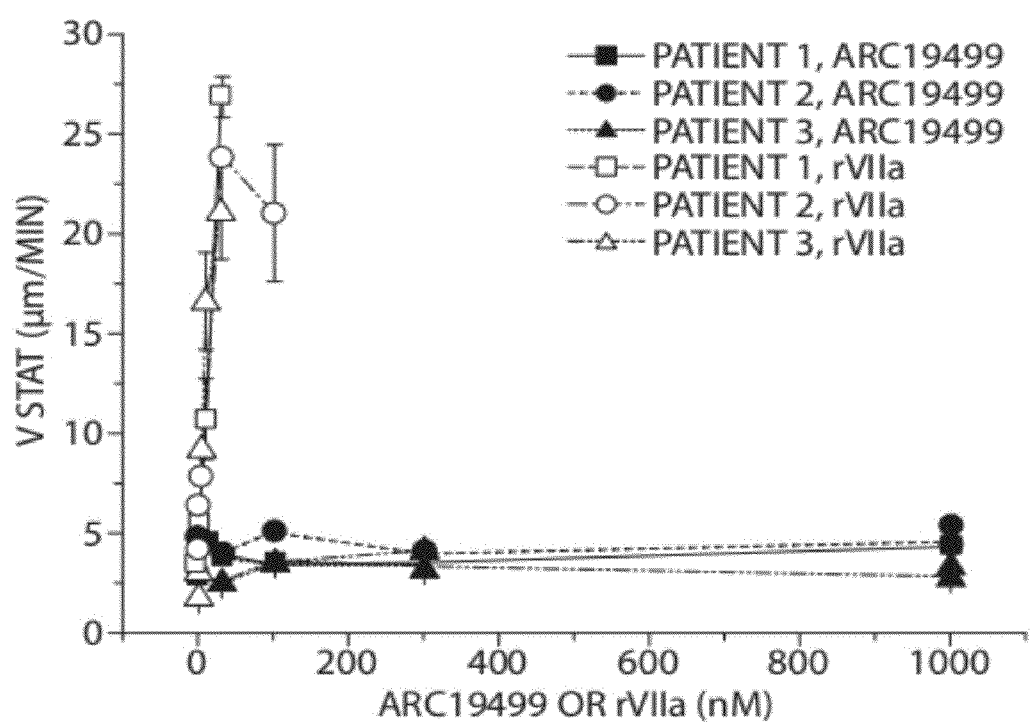
FIG. 69 shows the effects of ARC19499 (black symbols) or recombinant factor VIIa (rVIIa; grey symbols) on $V_{stationary}$ in hemophilia A plasma samples from Patients 1-3, activated with low surface tissue factor density.
Figure 70A:
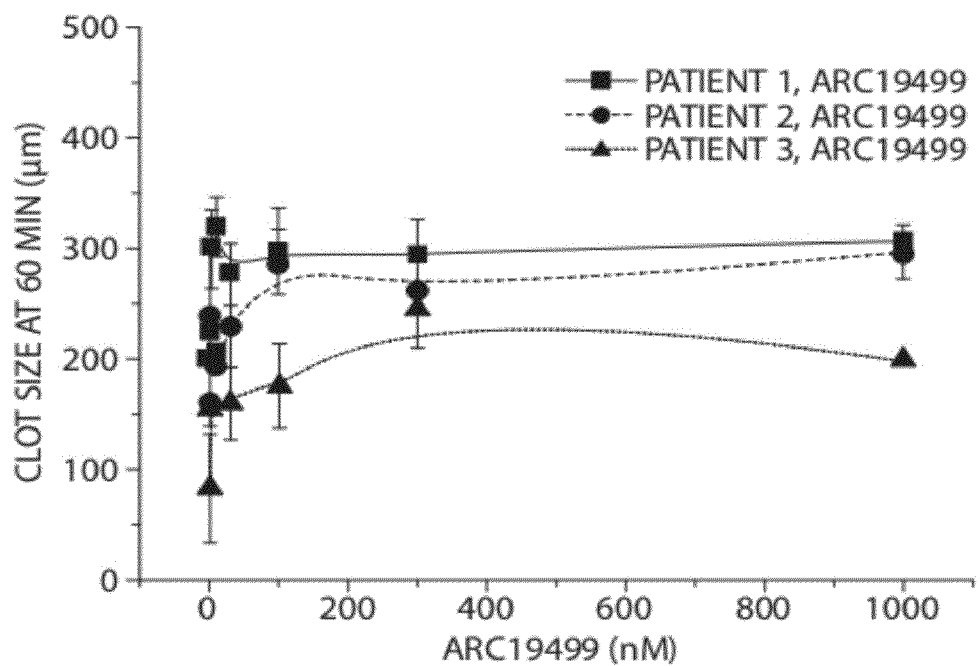
FIG. 70 shows the effects of ARC19499 (FIG. 70A) or recombinant factor VIIa (rVIIa.
FIG. 70B) on clot size at 60 minutes in hemophilia A plasma samples from Patients 1-3, activated with low surface tissue factor density.
Figure 70B:
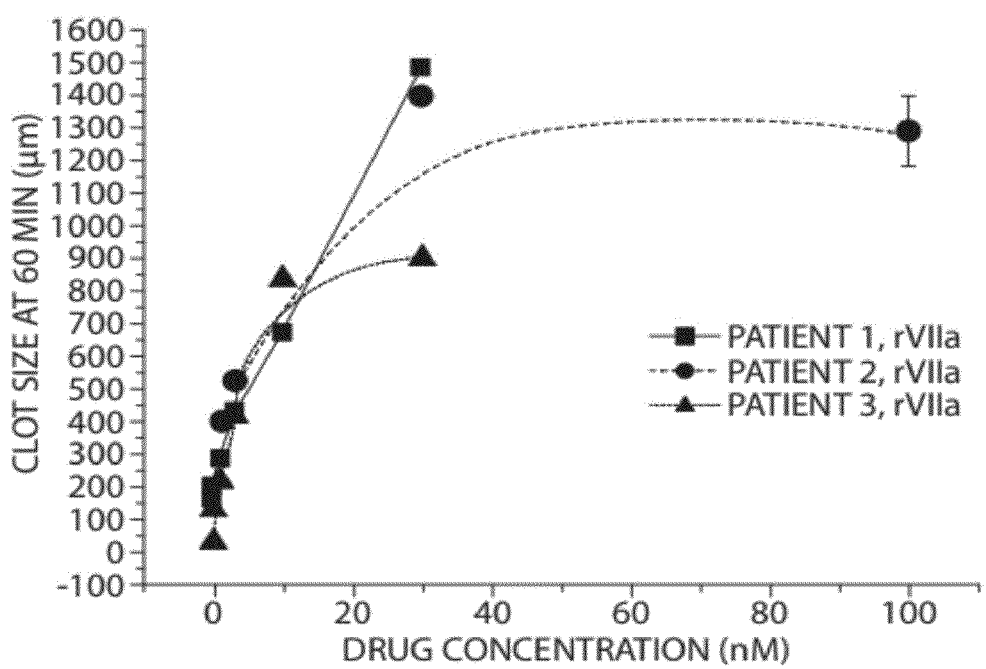
Figure 71A:
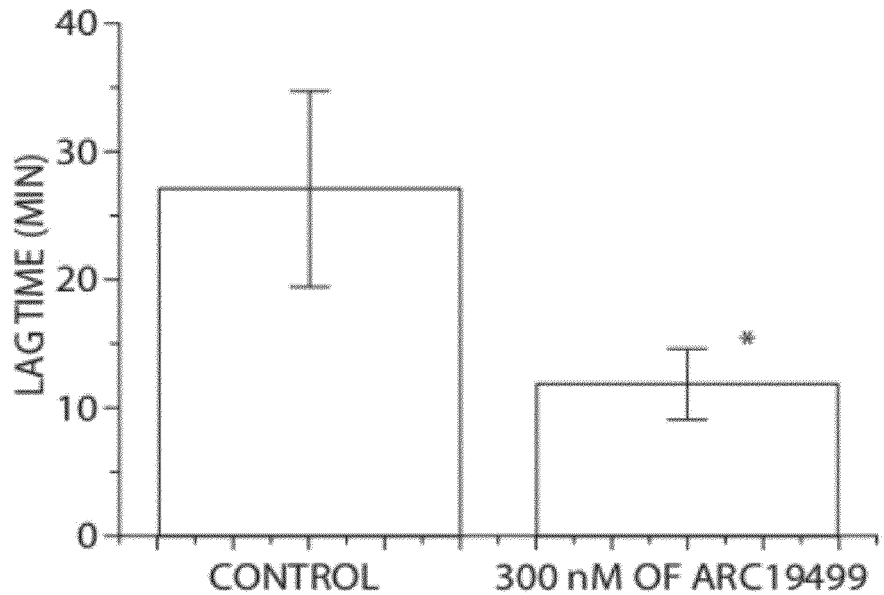
FIG. 71 is a series of graphs illustrating the effect of 300 nM ARC19499 on the average lag time (FIG. 71A), $V_{initial}$ (FIG. 71B), $V_{stationary}$ (FIG. 71C) and clot size after 60 minutes (FIG. 71D) in hemophilia A plasma activated with low surface tissue factor density (n=3). An asterisk indicates a statistically significant difference±ARC19499 ($P<0.05$).
Figure 71B:
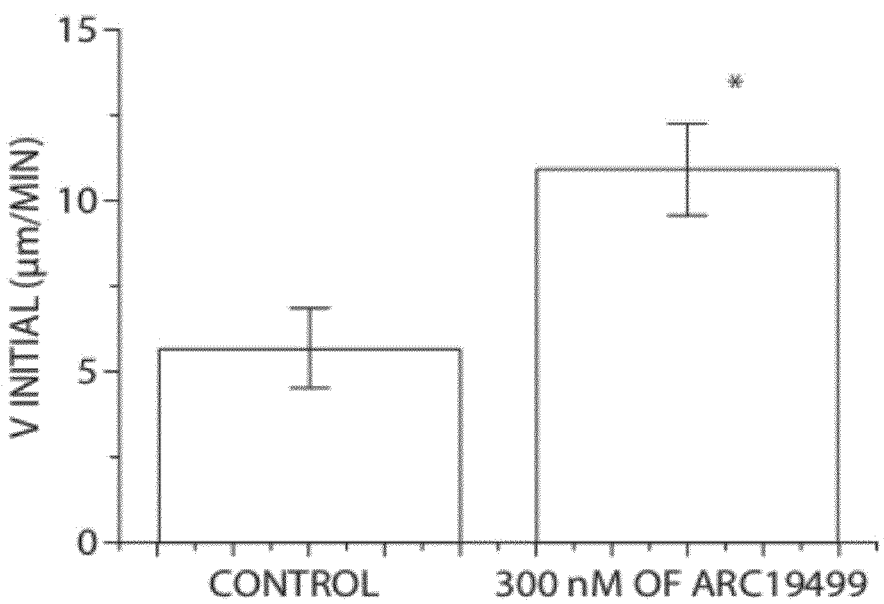
Figure 71C:
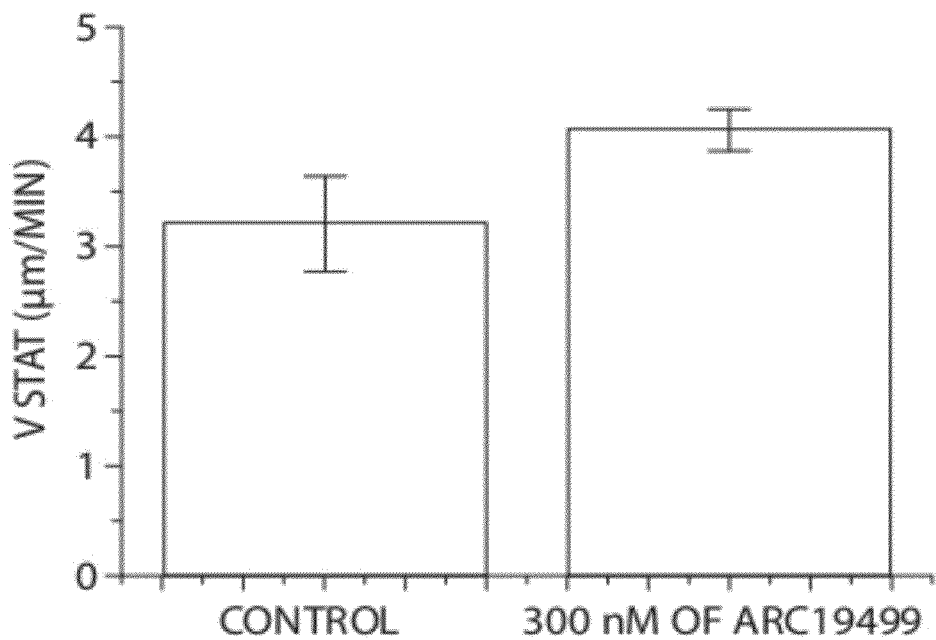
Figure 71D:
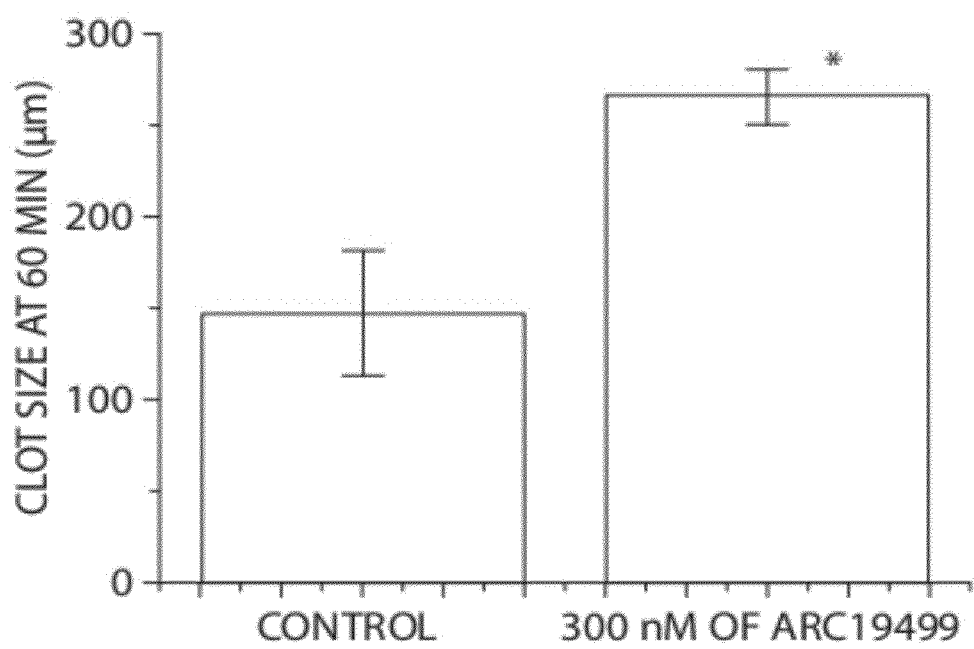
Figure 72A:
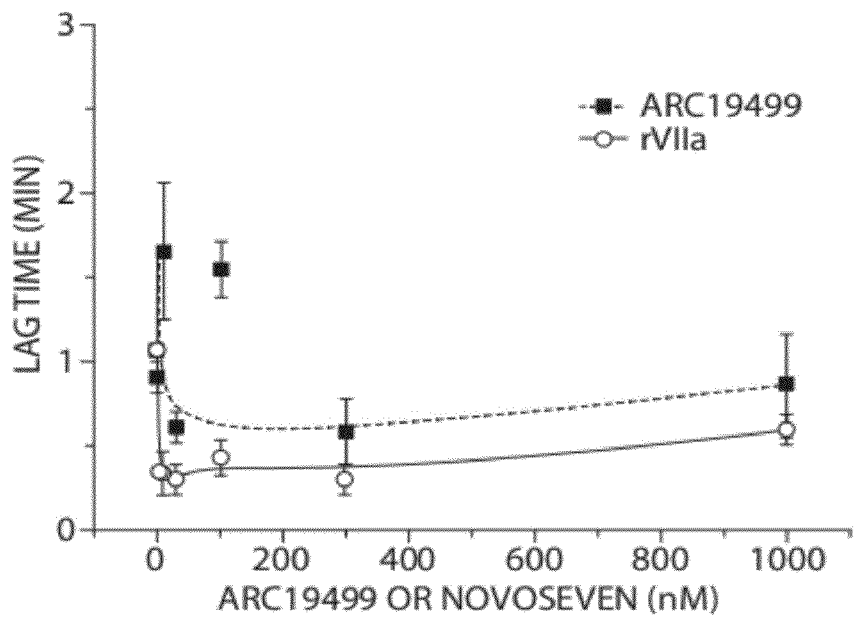
FIG. 72 is a series of graphs showing the lag time (FIG. 72A), $V_{initial}$ (FIG. 72B), $V_{stationary}$ (FIG. 72C) and clot size after 60 minutes (FIG. 72D) in hemophilia A plasma from Patient 4 activated with medium surface tissue factor density. Each parameter is plotted as a function of ARC19499 (squares) or recombinant factor VIIa (rVIIa; circles).
Figure 72B:
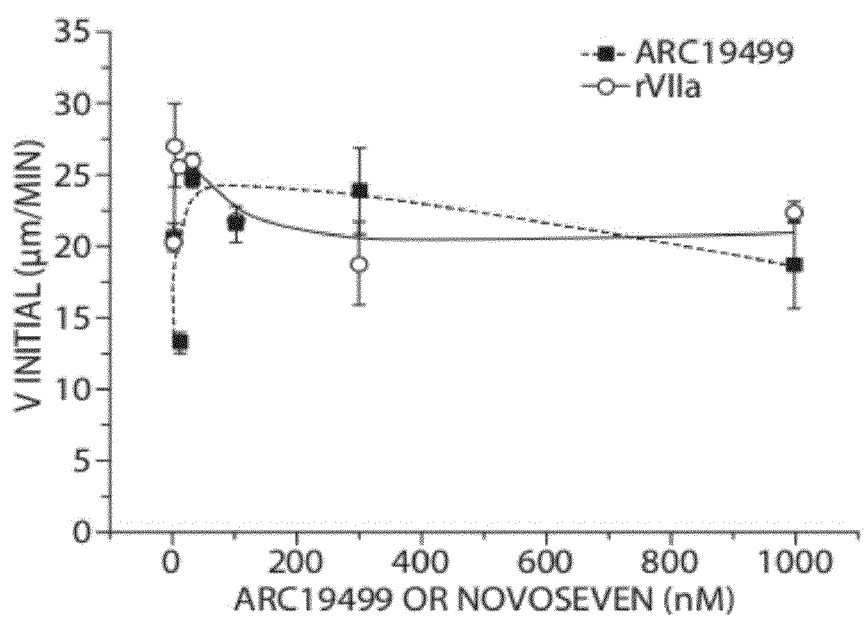
Figure 72C:
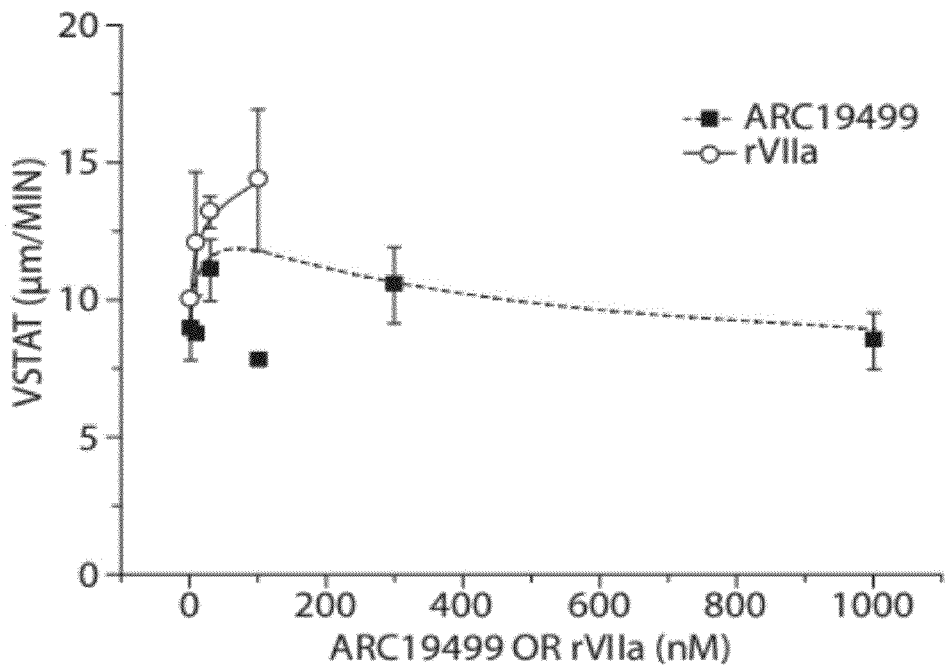
Figure 72D:
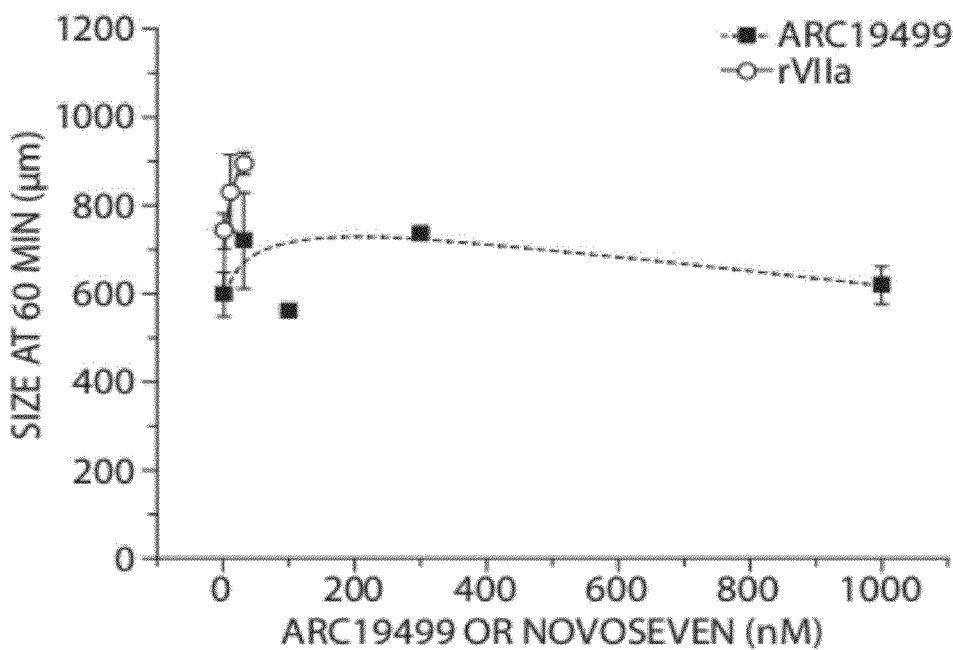
Figure 73A:
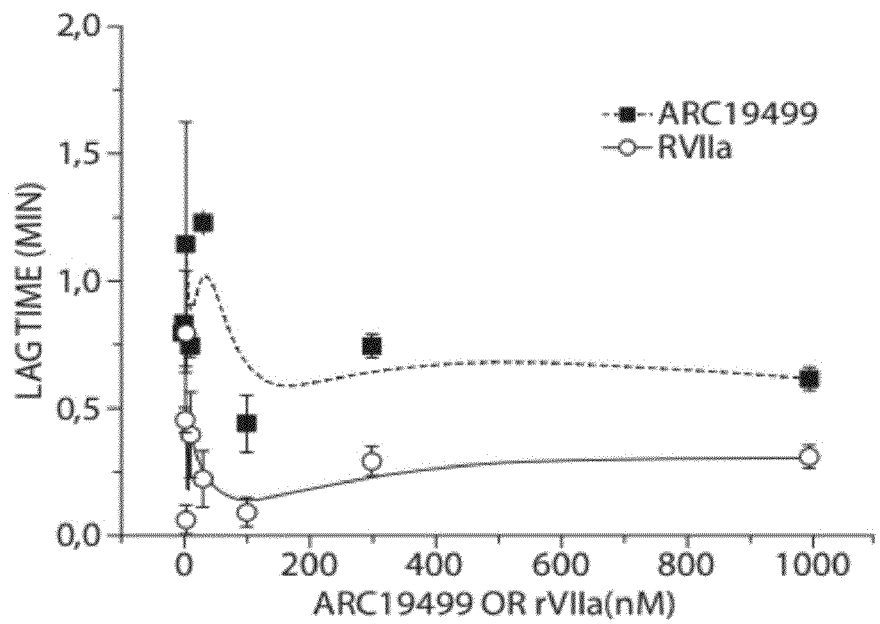
FIG. 73 is a series of graphs showing the lag time (FIG. 73A), $V_{initial}$ (FIG. 73B), $V_{stationary}$ (FIG. 73C) and clot size after 60 minutes (FIG. 73D) in hemophilia A plasma from Patient 5 activated with medium surface tissue factor density. Each parameter is plotted as a function of ARC19499 (squares) or recombinant factor VIIa (rVIIa; circles).
Figure 73B:
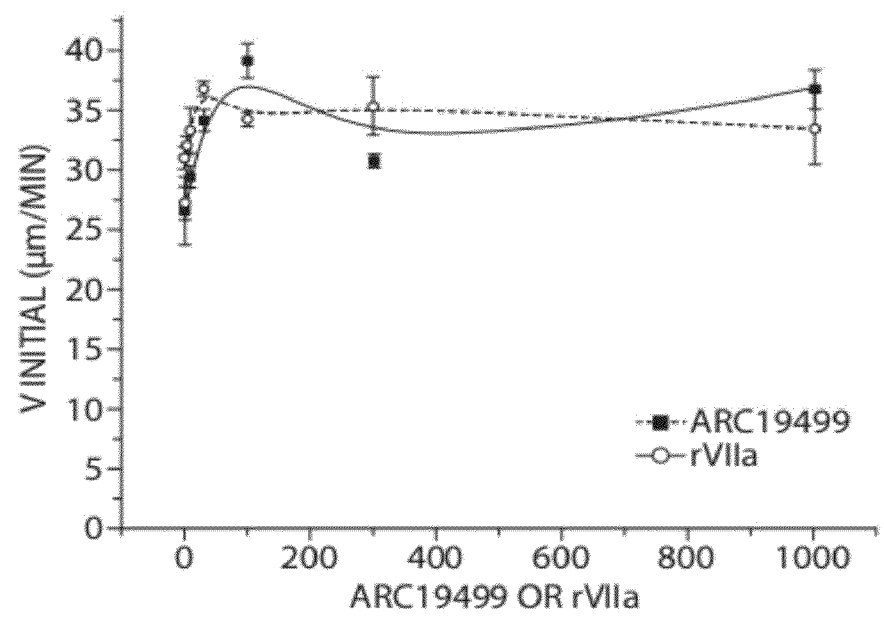
Figure 73C:
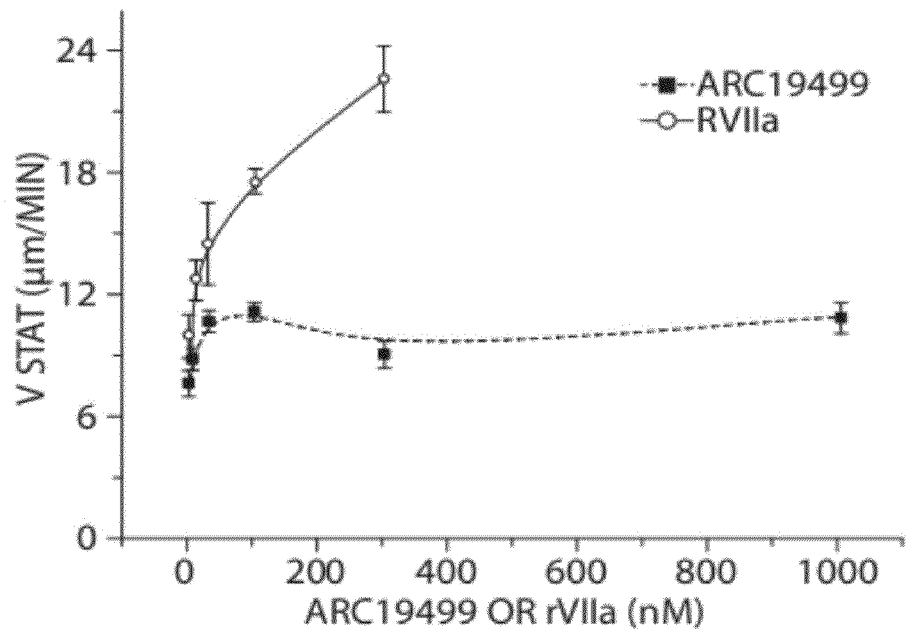
Figure 73D:
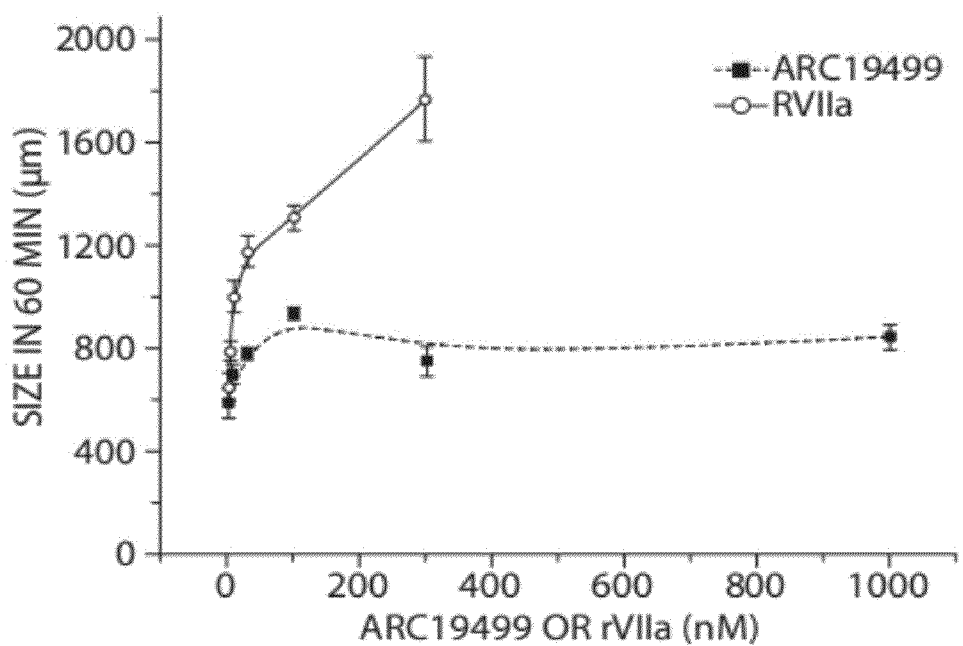
Figure 74A:
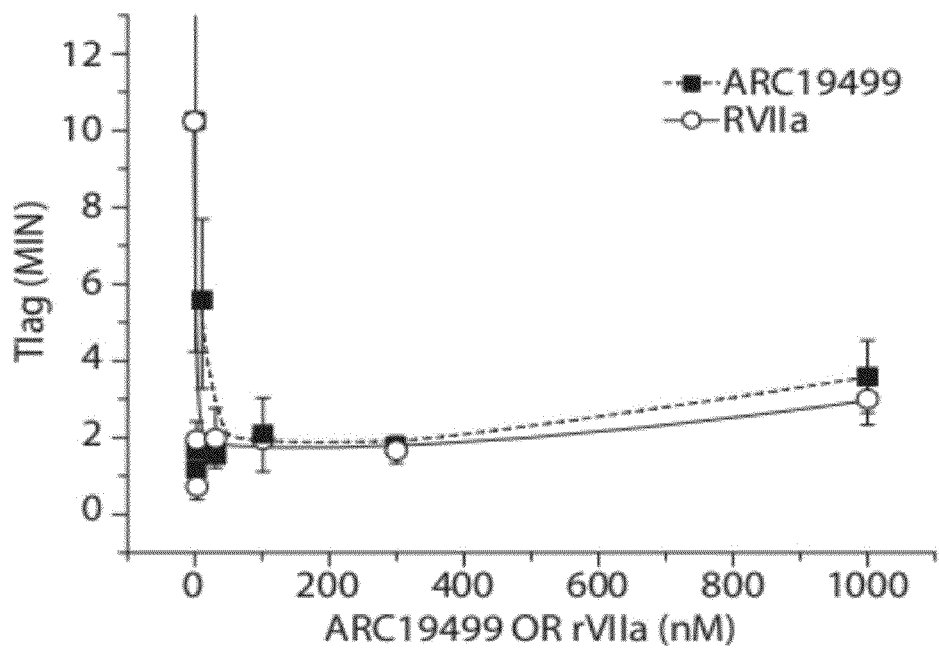
FIG. 74 is a series of graphs showing the lag time (FIG. 74A), $V_{initial}$ (FIG. 74B), $V_{stationary}$ (FIG. 74C) and clot size after 60 minutes (FIG. 74D) in hemophilia A plasma from Patient 6 activated with medium surface tissue factor density. Each parameter is plotted as a function of ARC19499 (squares) or recombinant factor VIIa (rVIIa; circles).
Figure 74B:
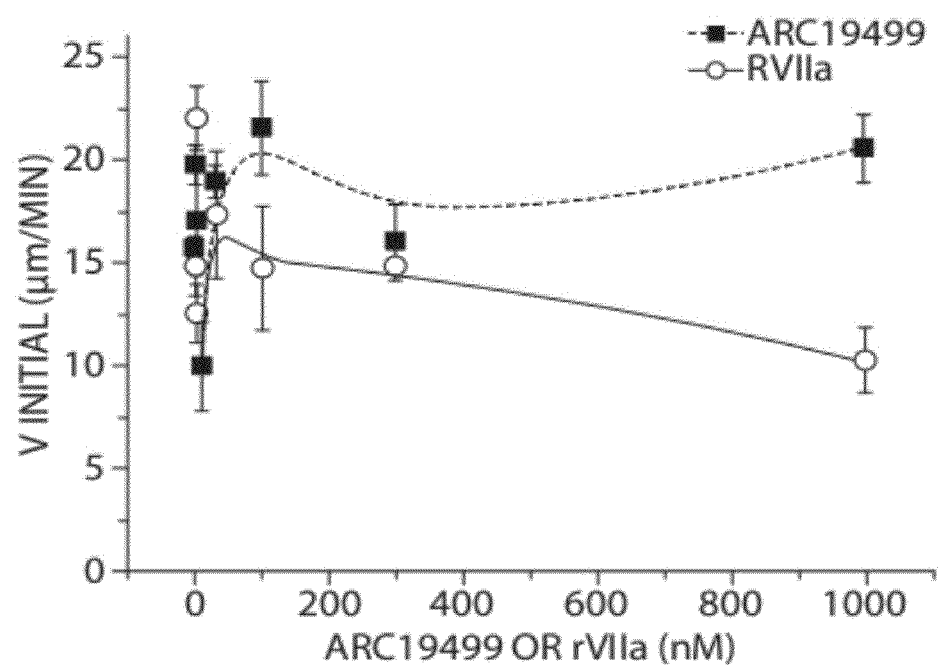
Figure 74C:
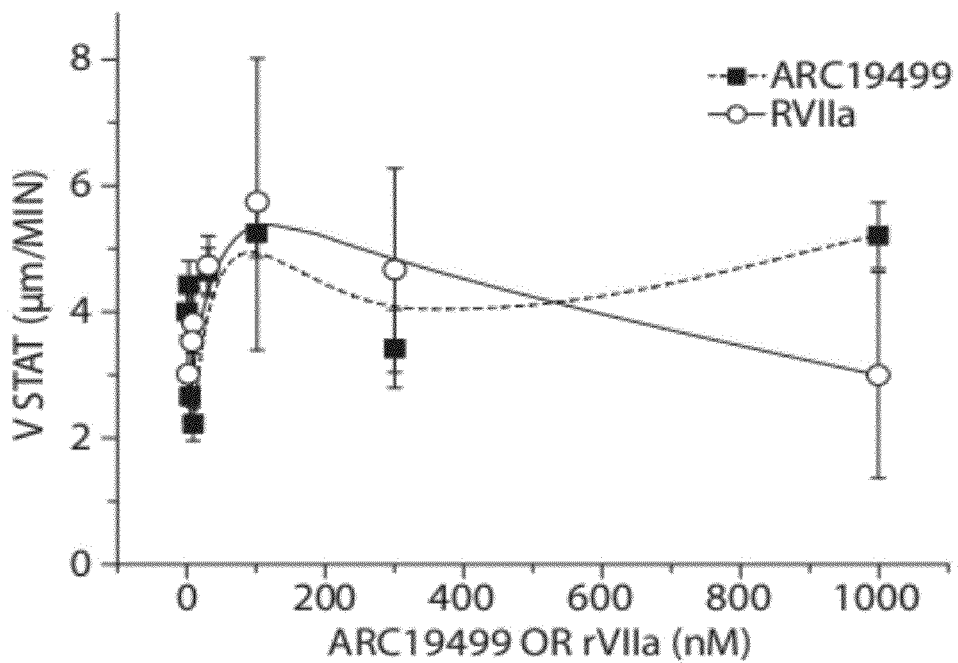
Figure 74D:
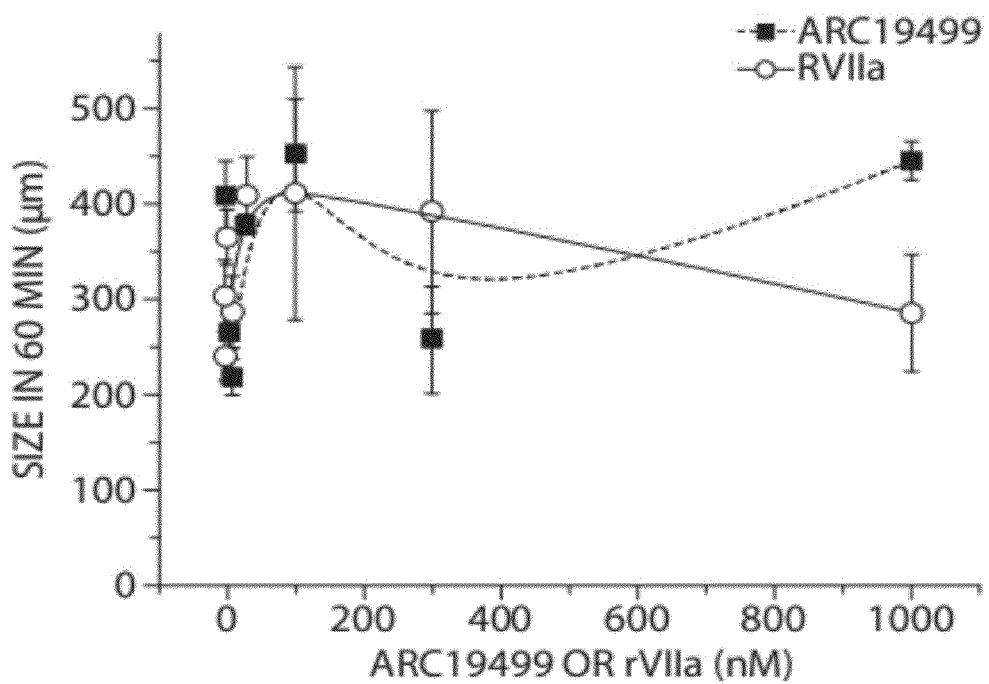
Figure 75A:
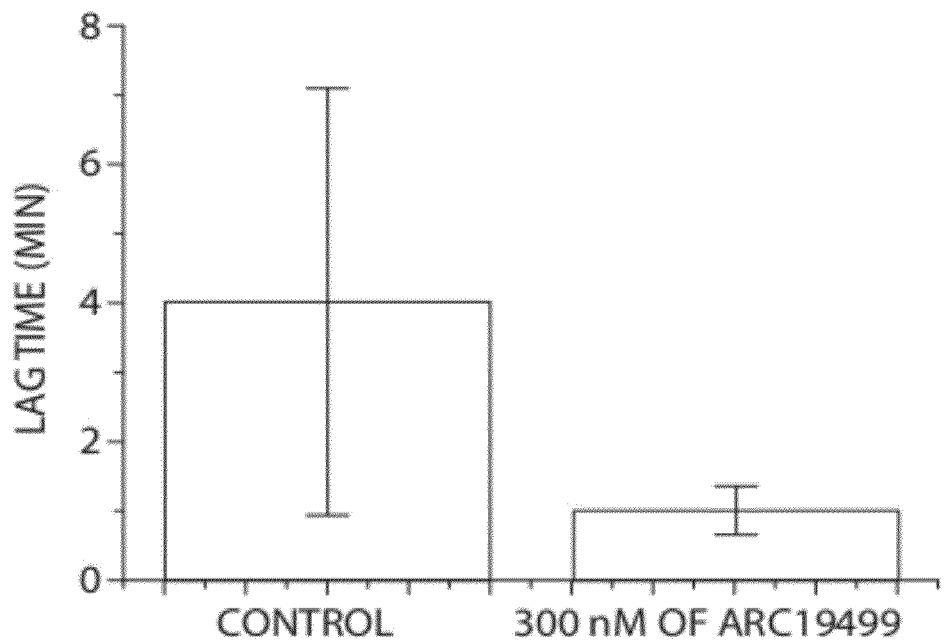
FIG. 75 is a series of graphs illustrating the effect of 300 nM ARC19499 on the average lag time (FIG. 75A), $V_{initial}$ (FIG. 75B), $V_{stationary}$ (FIG. 75C) and clot size after 60 minutes (FIG. 75D) in hemophilia A plasma activated with medium surface tissue factor density (n=3).
Figure 75B:
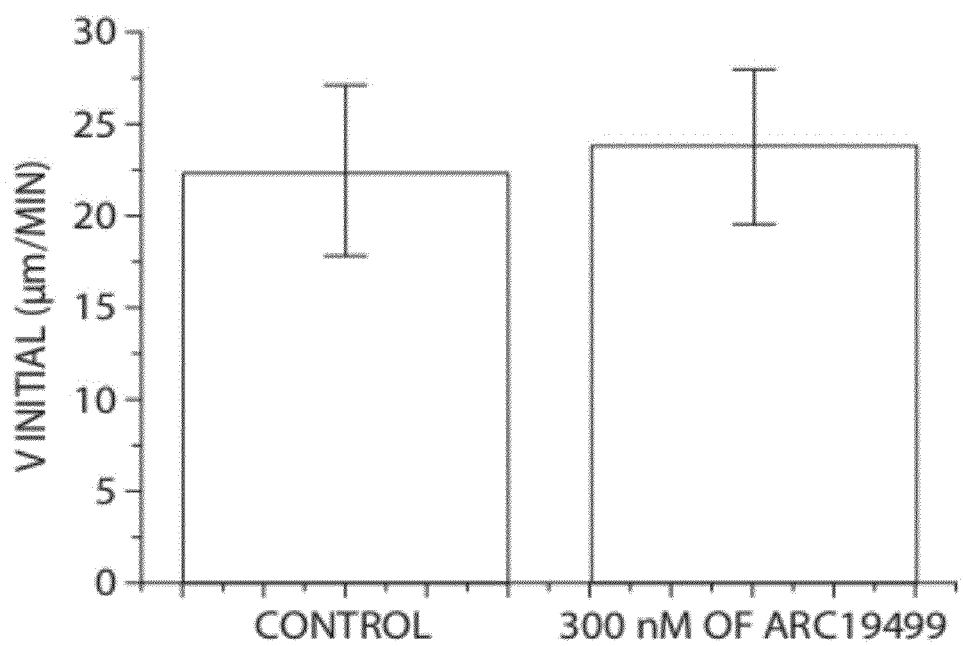
Figure 75C:
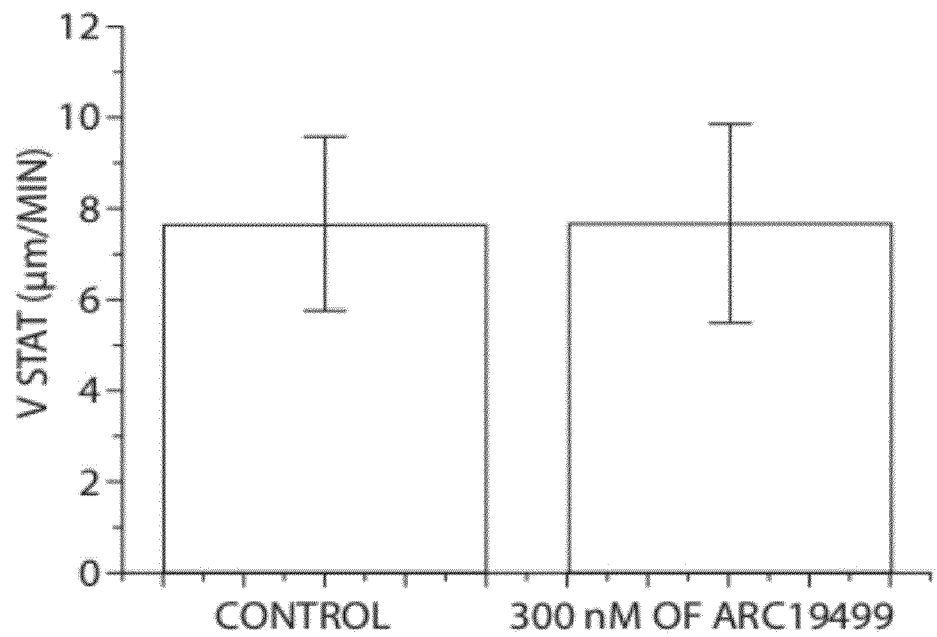
Figure 75D:
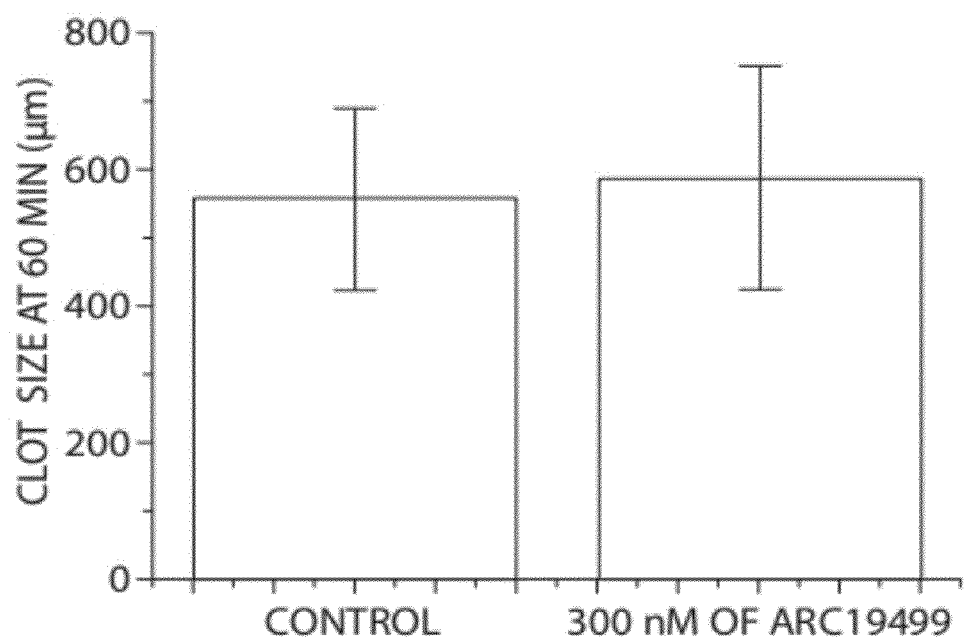
Figure 76A:
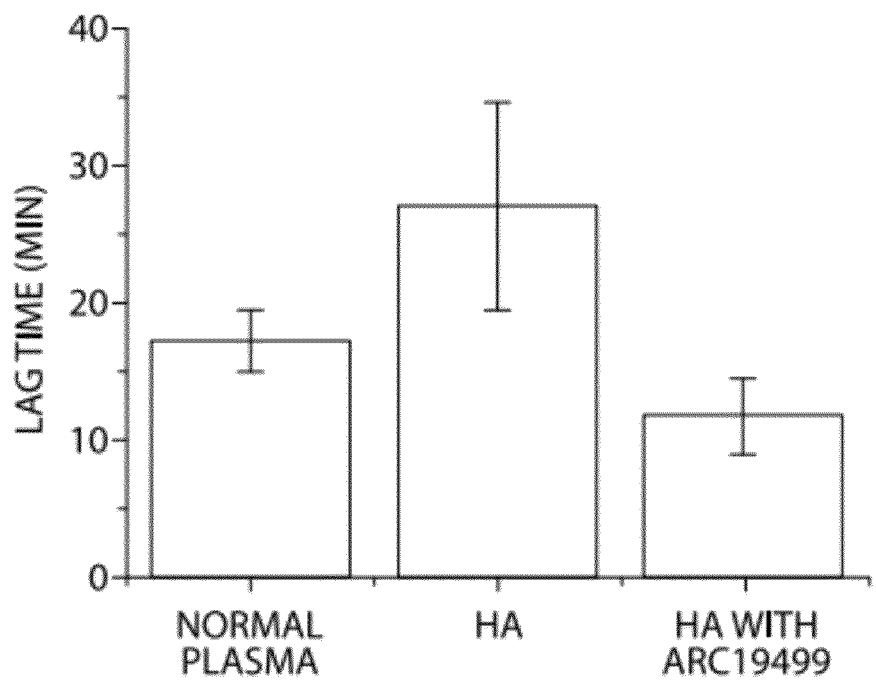
FIG. 76 is a series of graphs illustrating the lag time (FIG. 76A), $V_{initial}$ (FIG. 76B), $V_{stationary}$ (FIG. 76C) and clot size after 60 minutes (FIG. 76D) in normal plasma compared to hemophilia A plasma or hemophilia A plasma containing 300 nM ARC19499, activated with low surface tissue factor density.
Figure 76B:
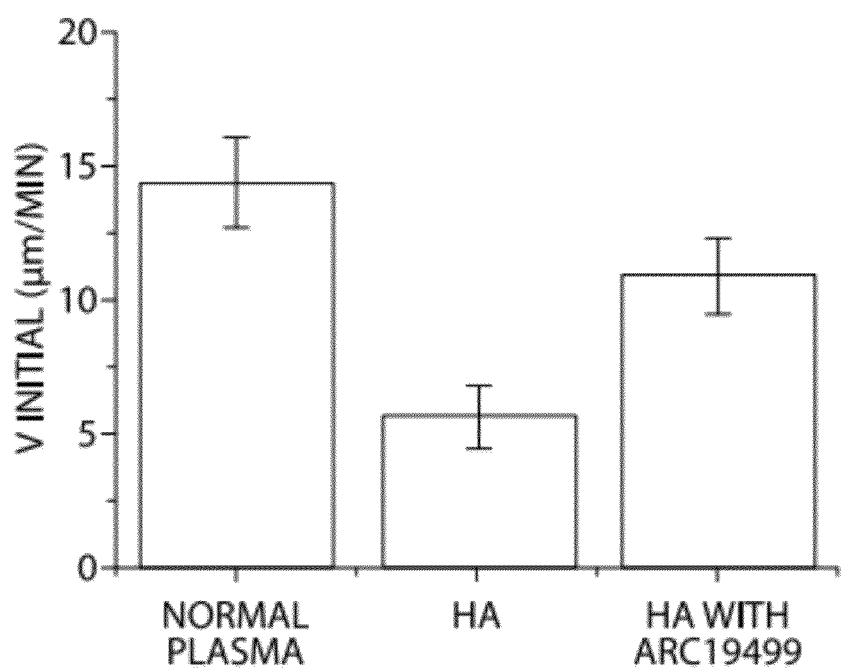
Figure 76C:
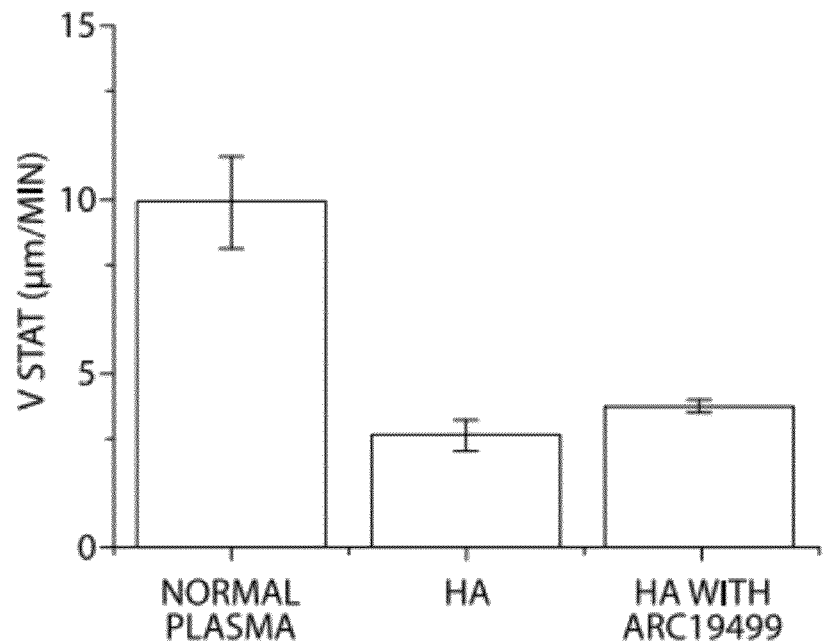
Figure 76D:
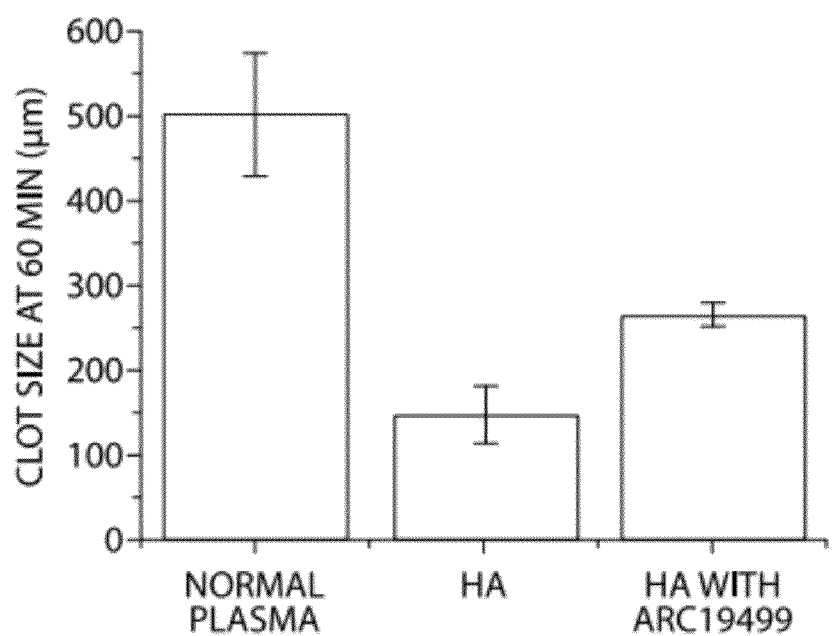

Further experiments characterized the concentration-dependent effects of ARC19499 in various hemophilia patient plasmas. The demographics of the patient pool from which samples were drawn are shown in the table in FIG. 65. All of the patients had severe (<1%) or moderate (1-5%) FVIII deficiencies. FIGS. 66, 67 and 68 show the effects of ARC19499 and rVIIa on spatial clot formation activated by low density TF in plasmas of patients #1, #2 and #3, respectively. The error bars henceforth indicate SEM for n=4 regions along the propagating fibrin clot front within a single experiment. Panels A and B of these figures show the lag time dependence on ARC19499 and rVIIa concentrations, respectively. The lag time decreased 2-fold with increasing concentrations of ARC19499 from 0 up to 30 nM, with no significant further change in lag time at higher ARC19499 concentrations. Panels C and D of the same figures show the initial velocity dependence on ARC19499 and rVIIa concentrations, respectively. The initial velocity increased 2-fold with increasing concentrations of ARC19499 from 0 up to 30 nM, with no significant further change at higher ARC19499 concentrations. FIG. 69 shows stationary clot growth velocity dependence on ARC19499 and rVIIa concentrations for all 3 patients in one graph. ARC19499 had no effect on stationary velocity through the whole investigated range of concentrations, while addition of rVIIa led to a strong increase of this parameter. Finally, FIG. 70 shows the dependence of clot size at 60 minutes on ARC19499 (FIG. 70A) and rVIIa (FIG. 70B). The clot size at 60 minutes increased 1.5-2 fold with increasing concentrations of ARC19499 from 0 up to 30 nM, with no significant further change at higher ARC19499 concentrations. A statistical analysis of the low TF density data, comparing each parameter for 0 and 300 nM ARC19499, is shown in FIG. 71. ARC19499 had significant effects on lag time (FIG. 71A), initial velocity (FIG. 71B) and clot size at 60 minutes (FIG. 71D), but no effect on stationary velocity (FIG. 71C).

FIGS. 72, 73 and 74 show the effects of ARC19499 and rVIIa on spatial clot formation activated by medium density TF in plasmas of patients #4, #5 and #6, respectively. ARC19499 had little effect on clotting parameters for the medium density activator through the entire range of concentrations tested. A statistical analysis of the medium TF density data comparing each parameter for 0 and 300 nM ARC19499 is shown in FIG. 75. ARC19499 had no significant effect on any of the four clotting parameters under these conditions.

Figure 77:
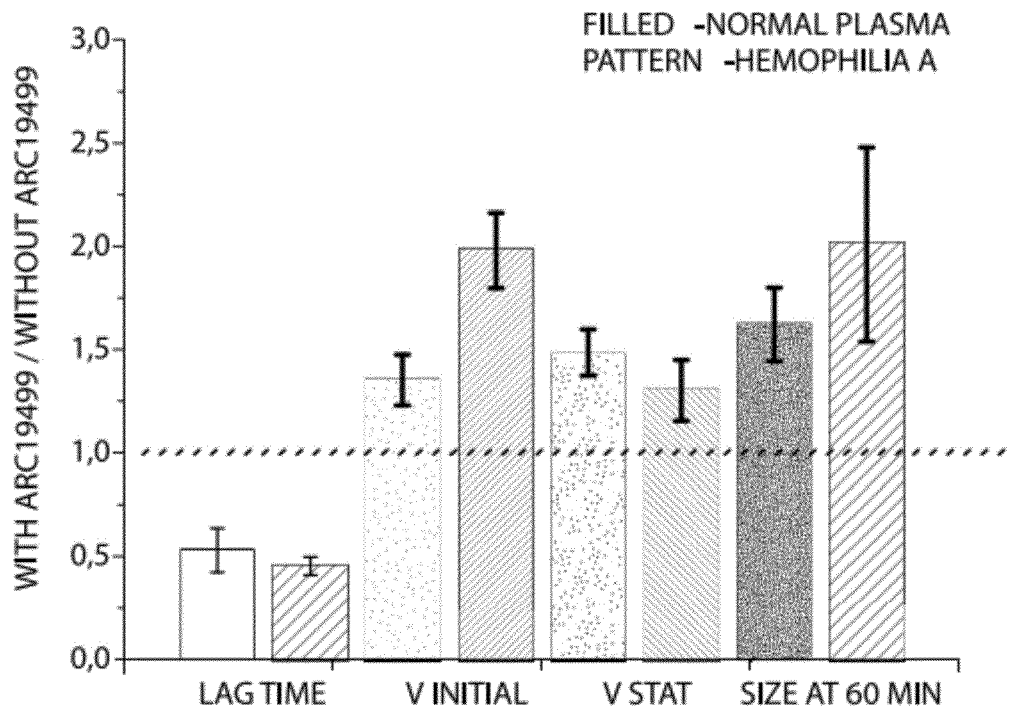
FIG. 77 is a bar graph illustrating the efficiency of ARC19499 in promoting clot propagation in normal plasma (solid bars) versus hemophilia A plasma (hatched bars) as reflected in the lag time (white), $V_{initial}$ (light grey), $V_{stationary}$ (medium grey) and clot size after 60 minutes (black). Efficiency is defined as the ratio of the parameter determined in the presence of 300 nM ARC19499 to the parameter in the absence of ARC19499.

To estimate the extent of clotting normalization by ARC19499 under conditions of low TF density, FIG. 76 shows the mean parameters of clotting for hemophilia A and hemophilia A with 300 nM of ARC19499 in comparison to normal plasma. ARC19499 shortened the lag time below the normal level and normalized the initial velocity, but had no effect on stationary velocity. ARC19499 increased the clot size at 60 minutes approximately 2-fold from 30% up to 60% of the normal value. In order to check whether ARC19499 effects differ in normal and hemophilia A plasma, the ratios with and without 300 nM of ARC19499 were plotted for all four clotting parameters [ratio=(Parameter)$_{+ARC19499}$/(Parameter)$_{-ARC19499}$] (FIG. 77). In both hemophilia A and normal plasmas, the lag time ratio was ~0.5, indicating that the addition of 300 nM ARC19499 decreased the lag time by about half in each. The ratios for $V_{stationary}$ were also similar between plasmas. However, larger ratios were observed for $V_{initial}$ and clot time at 60 minutes in hemophilia A plasma compared to normal plasma, suggesting that the maximal effect of ARC19499 in hemophilia A plasma slightly exceeded that in normal plasma.

Figure 78:
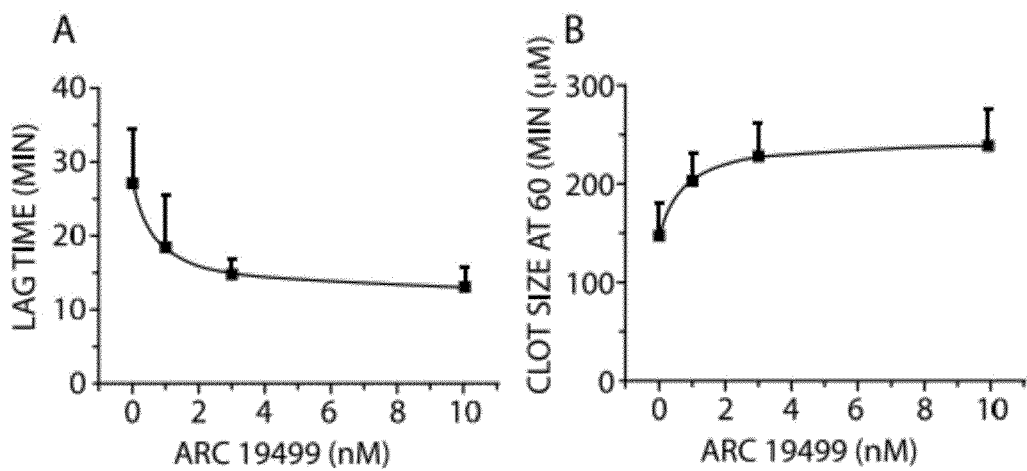
FIG. 78 illustrates the concentration dependence of the lag time (FIG. 78A) and clot size at 60 minutes (FIG. 78B) on ARC19499 in hemophilia A plasma activated with low surface tissue factor density. These data were used to calculate the $IC_{50}$ values shown in the table below the graphs.

To determine an $IC_{50}$ for ARC19499 in hemophilia A plasma, we plotted mean lag time and clot size as a function of ARC19499 concentration (up to 10 nM) for low TF density (FIG. 78). The half-maximal effect, calculated by curve-fitting, was ~0.7 nM for both parameters.

Figure 79:
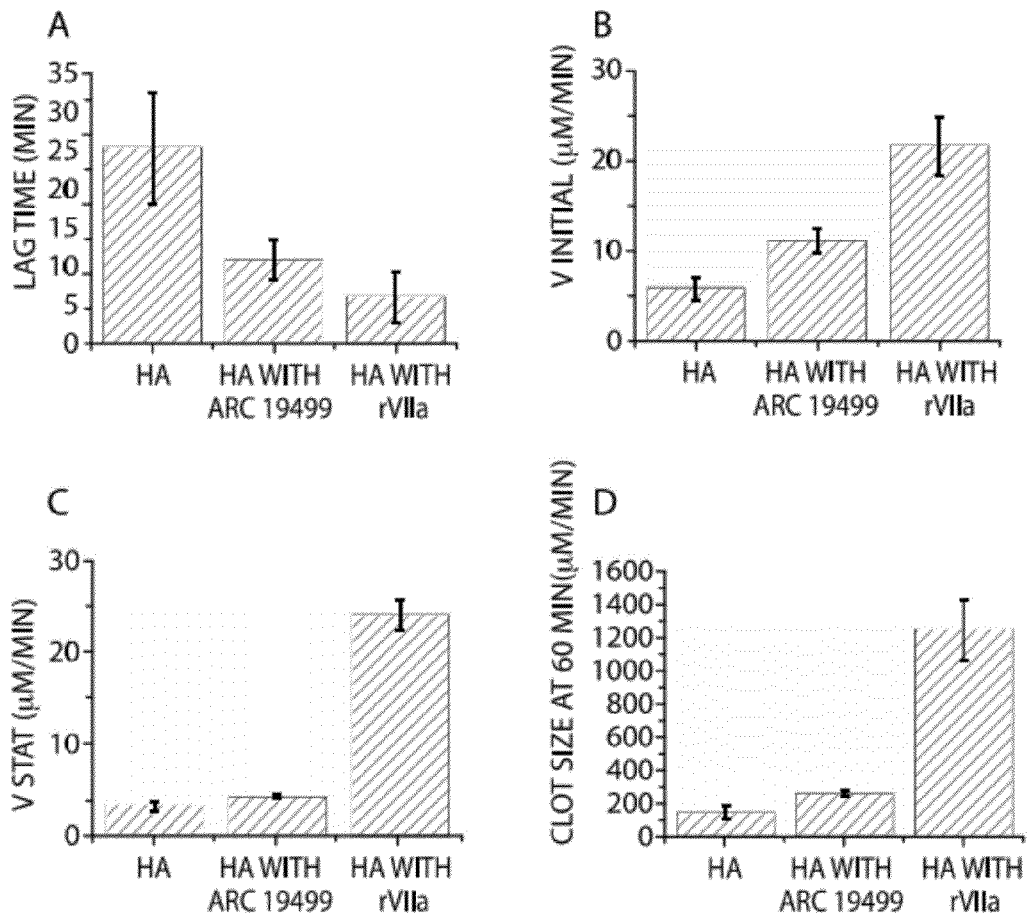
FIG. 79 is a series of graphs illustrating the lag time (FIG. 79A), $V_{initial}$ (FIG. 79B), $V_{stationary}$ (FIG. 79C) and clot size after 60 minutes (FIG. 79D) in hemophilia A plasma alone compared to hemophilia A plasma containing 300 nM ARC19499 or 300 nM recombinant factor VIIa (rVIIa), activated with low surface tissue factor density.

FIG. 79 compares clotting parameters for hemophilia A plasma alone with 300 nM ARC19499 or with 30 nM rVIIa. FIG. 79A-D show lag time, initial clot growth velocity, stationary velocity and clot size after 60 minutes, respectively. In contrast to rVIIa, ARC19499 increased clot size primarily by shortening the lag time and increasing initial velocity; it had no effect on spatial propagation stage ($V_{stationary}$).

Figure 80:
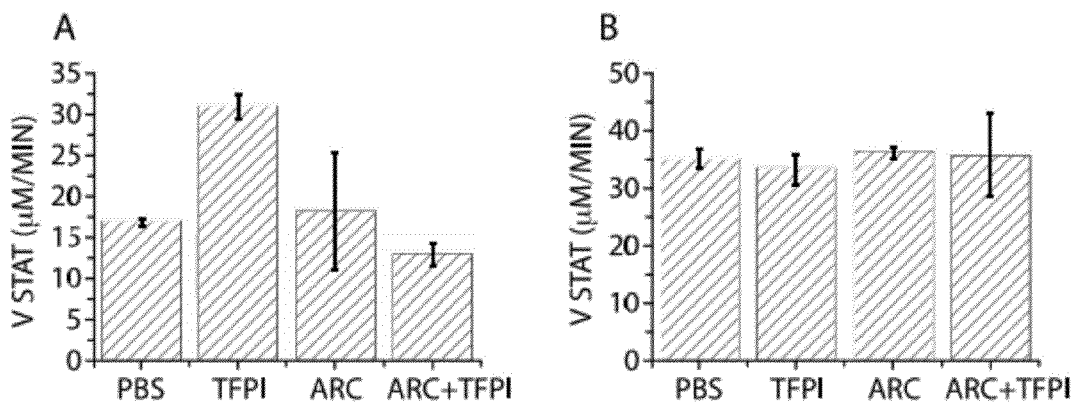
FIG. 80 compares the lag time (FIG. 80A) and $V_{initial}$ (FIG. 80B) in TFPI depleted plasma activated with low surface tissue factor density. Each graph shows parameters measured in TFPI depleted plasma alone ("PBS"), TFPI depleted plasma supplemented with ±10 nM recombinant TFPI ("TFPI"), TFPI depleted plasma containing 300 nM ARC19499 ("ARC"), and TFPI depleted plasma supplemented with 10 nM recombinant TFPI and 300 nM ARC19499 ("ARC+TFPI").

Experiments at low TF density in TFPI-depleted plasma were also performed to gain insight into the mechanism of action of ARC19499 and into the regulation of spatial clotting by TFPI. Lyophilized TFPI-depleted plasma was purchased from American Diagnostica, resuspended in deionized water, and CTI added to 0.2 mg/mL. Recombinant TFPI (rTFPI; R&D Systems) was added into plasma at the concentration of 0 or 10 nM, with or without ARC19499 (0 or 300 nM), for measurement of spatial clot formation in the presence of low TF surface density. The addition of rTFPI significantly increased the lag time (FIG. 80) in the absence of ARC19499, but had no effect in the presence of 300 nM ARC19499, suggesting that it was completely inhibited. ARC19499 had no effect on clotting in TFPI-depleted plasma in the absence of supplementary rTFPI, indicating that its effects are TFPI-specific. Neither rTFPI or ARC19499 had any effect on initial velocity in this experiment.

In conclusion, ARC19499 significantly improved clotting in normal and hemophilia A plasma in the spatially heterogeneous system at low TF density (1-3 pmole/m$^2$). The lag time was shortened, and initial velocity of spatial propagation and clot size at 60 minutes were increased by ARC19499 up to 2-fold, with little effect on spatial propagation velocity far from the activator. In hemophilia A plasma, this resulted in complete normalization of the lag time and initial velocity parameters, while clot size at 60 minutes was partially normalized (increases from 30% to 60% of normal upon addition of ARC19499). With increases in TF density, the effects of the aptamer became smaller and there was almost no effect at TF>20 pmole/m$^2$. The action of ARC19499 on clotting in this experiment at low TF density was TFPI-specific, since ARC19499 had no effect on clotting in TFPI-deficient plasma.

Example 24

This example demonstrates that ARC19499 can improve clotting in whole blood and cell-free (plasma) clot-time assays, in samples collected from hemophilia A and hemophilia B patients.

Blood samples (20 mL) were collected from 12 subjects, including seven severe hemophilia A (subjects #1, 3, 5, 8, 10, 11 and 12) subjects, two severe hemophilia B (#4 and 9) subjects and three healthy controls (#2, 6 and 7). Blood was collected into 0.5 mM EDTA and 0.1 mg/mL corn trypsin inhibitor (CTI; Haematologic Technologies Inc.). Approximately half of each sample was used for whole blood assays, while the other half was centrifuged to prepare platelet poor plasma (PPP).

The TF-activated clotting time (TF-ACT) is a whole blood assay performed using the Hemochron® Response Whole Blood Coagulation System (International Technidyne Corp.), a commonly used system for measuring patient responses to unfractionated heparin and protamine. Standard ACTs measured by this instrument use tubes containing an activator of the "contact" or "intrinsic" pathway of coagulation (e.g., celite or kaolin). However, for TF-ACTs, the tubes designed for measuring standard ACTs were rinsed of contact-activating reagent. In its place was added 12 µL of 1 M CaCl$_2$, a desired amount of ARC19499, and 2 µL of 5 nM relipidated, recombinant TF (Haematologic Technologies). Upon the addition of 2 mL whole blood to this mixture, the clot time was measured on the Hemochron® Response instrument as for a standard ACT. The results are shown in tabular format in FIG. 81. An average baseline TF-ACT of 335±22 seconds was observed in normal subjects. Moderate decreases in TF-ACT (up to 75 seconds), indicative of a procoagulant effect, were observed in these individuals for ARC19499 concentrations ranging from 44 to 700 nM. The two hemophilia B subjects showed baseline TF-ACTs of 528 and 580 seconds. The TF-ACT decreased by 160-205 seconds at 88 nM ARC19499 in these two individuals, then increased moderately at higher ARC19499 concentrations (up to 350 nM). A relatively broad range of baseline TF-ACT values was observed in the hemophilia A group, with an average value of 578±140 seconds. Substantial ARC19499-dependent shortening of the TF-ACT was observed in 6 of 7 of these individuals, and in two of these (subjects #1 and 11) values in the normal range or below were observed. Only a moderate decrease of up to 47 seconds was observed in subject #12, but this subject also displayed the shortest baseline TF-ACT (328 seconds) of the group. These data suggest that TFPI suppression by ARC19499 was able to improve clotting activity in a simple, whole blood clotting assay.

Dilute prothrombin time (dPT) assays were performed on PPP prepared from the same blood samples as described for the TF-ACT assays. The standard prothrombin time (PT) is performed by adding thromboplastin, consisting of tissue factor (~1 nM), calcium chloride and phospholipids, to plasma to evaluate the integrity of the "tissue factor" or "extrinsic" pathway of coagulation. The clot time in a normal plasma sample measured using the standard PT protocol is typically ~11 seconds. The PT is commonly used for measuring patient responses to warfarin, and is largely insensitive to deficiencies in contact pathway factors like FVIII and FIX. In contrast to the standard PT, the dPT uses a very low TF concentration and clot times measured by this assay are sensitive to factors in both the TF and contact pathways. In this particular experiment, thromboplastin reagent (Innovin; Dade-Behring) was diluted in tris-buffered saline (20 mM tris, pH 7.5, 150 mM NaCl) to reach a concentration of 0.3 pM TF. The dPT was performed by mixing 120 µL of PPP with 60 µL of the dilute TF solution and incubating at 37° C. for 3 minutes before adding 60 µL of 25 mM CaCl$_2$ to the plasma/TF mixture. Clotting time was recorded on an ACL-8000 coagulometer (from Instrumentation Laboratory, Bedford, Mass.) and the data for all subjects is shown in tabular format in FIG. 82. Baseline clot times in PPP samples from all normal and hemophilia B subjects, and 6 of 7 hemophilia A subjects were >360 seconds, which was the pre-set, maximum measurable clot time on the coagulometer. One hemophilia A subject (#10) displayed a baseline dPT of 169 seconds. Increasing concentrations of ARC19499 added to the PPP typically resulted in decreased dPT clot times. In PPP from normal subjects, 2 nM ARC19499 was sufficient to significantly lower the clot time (avg=278±15 seconds) relative to baseline, but had no apparent effect in plasma from hemophilia A or B subjects. However, 8 nM ARC19499 lowered the clot time in PPP from nearly all subjects. Exceptions were observed in PPP from subject #10, where a low baseline dPT was observed, and #12, who appeared unresponsive to ARC19499. Excluding these two individuals, the average clot time in the hemophilia A group for 8 nM ARC19499 was 188±8 seconds. The average clot times for the normal and hemophilia B groups under the same conditions were 204±37 seconds and 226±22 seconds, respectively. Higher ARC19499 concentrations caused only moderate, further decreases in clot times. Average clot times at 500 nM ARC19499 were 179±6 seconds, 200±21 seconds and 161±3 seconds for the normal, hemophilia A (excluding #10 and #12) and hemophilia B groups, respectively. These data indicate that TFPI suppression by ARC19499 was able to improve clotting activity in a simple, plasma-based clotting assay.

Example 25

This example demonstrates that ARC19499 can improve clotting in whole blood samples from hemophilia A and hemophilia B patients, as measured by rotation thromboelastometry (ROTEM).

Blood samples were collected from 39 healthy volunteers (27 male and 12 female) and 40 hemophilia patients (all male). Of the 40 hemophilia patients, 3 hemophilia B (HB) patients and 28 hemophilia A (HA) patients were diagnosed as severe (baseline factor activity <1%), one HA and one HB patient suffered from moderately severe hemophilia (baseline factor activity 1-5%), four HA and two HB patients had mild hemophilia (baseline factor activity >5%). Using a 21-gauge butterfly needle, blood samples were drawn into plastic Vacuette tubes (Greiner Bio-One) containing 3.8% sodium citrate at a volume ratio of 1:9.

Coagulation was analyzed by ROTEM (Pentapharm GmbH), which is based on the original thromboelastography system (TEG™). In a typical ROTEM experiment, blood is incubated at 37° C. in a heated cup. As fibrin forms between the cup and the pin, the impedance of the rotation of the pin is detected and a trace is generated, indicating clot formation over time. The following parameters may be analyzed from the ROTEM trace: the clotting time (CT), the clot formation time (CFT), the maximum clot firmness (MCF) and the alpha angle (alpha). The clotting time (CT) characterizes the period from analysis start until initiation of the clot. The clot formation time (CFT) describes the subsequent period until an amplitude of 20 mm is reached. The alpha angle is given by the angle between the center line and a tangent to the curve through the 2 mm amplitude point. Both the CFT and the alpha angle denote the speed of clot development. The MCF is calculated from the maximum amplitude of the ROTEM trace and describes clot stability and strength; the MCF is largely dependent on fibrinogen and platelet function.

In this set of experiments, 300 µL of ARC19499-spiked whole blood (0, 0.2, 0.6, 2, 6, 20, 60, 200 or 600 nM ARC19499) was transferred into pre-warmed plastic cups. Blood samples were recalcified using 20 µL 0.2 M $CaCl_2$ and coagulation was activated by ~33 fM tissue factor (TF) (Innovin, Dade Behring, diluted 1:200,000). All analyses were performed at 37° C. Measurement was performed either without corn trypsin inhibitor (CTI) or with the addition of 100 µg/mL of CTI (Haematologic Technologies Inc). Comparisons between different concentrations of ARC19499 in any of the measured parameters were calculated with the Wilcoxon signed rank test with a Bonferroni Correction. To compare healthy controls to patients, a Mann-Whitney U-test was used. To analyze the correlation of hemostatic parameters to Factor VIII (FVIII) activity, the Spearman's rank correlation coefficient was used. A p-value smaller or equal to 0.05 was considered statistically significant.

Figure 83:
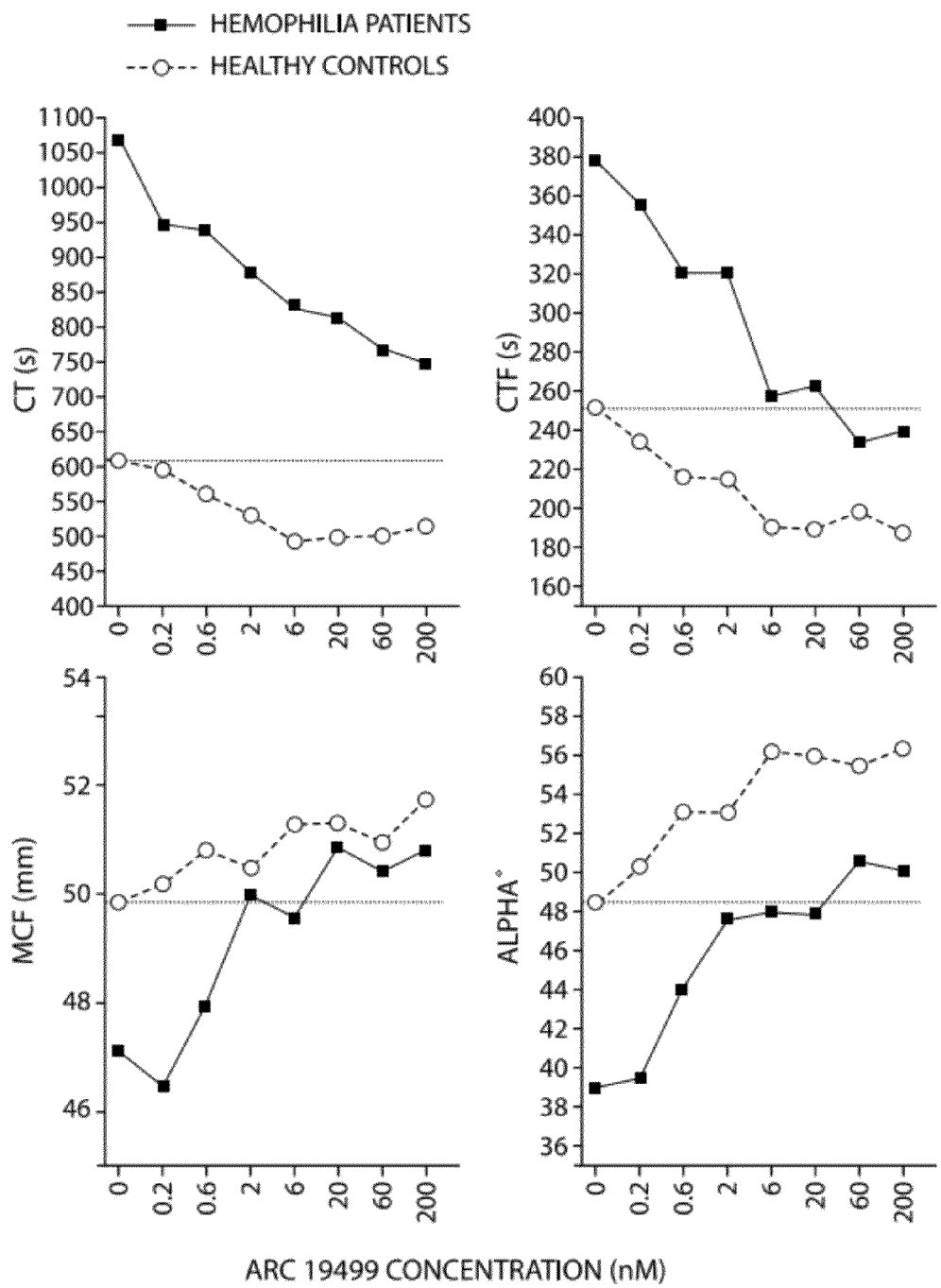
FIG. 83 shows the effect of different ARC19499 concentrations on ROTEM parameters in whole blood samples (without corn trypsin inhibitor (CTI)) from hemophilia patients (filled squares) and healthy controls (empty circles). The following parameters were analyzed: the clotting time (CT), the clot formation time (CFT), the maximum clot firmness (MCF) and the alpha angle (alpha).

The baseline whole blood clotting profile of hemophilia patients was characterized by a prolonged initiation phase (as shown by a prolonged CT) and a diminished propagation phase of whole blood clotting (prolonged CFT and a lower alpha angle) compared to healthy controls (p<0.01 for all) in the absence of CTI (FIG. 83).

Concentrations of ARC19499 $\geq$2 nM enhanced whole blood coagulation significantly in both hemophilia patients and healthy controls (p<0.01). The maximum hemostatic effect of ARC19499 was achieved with concentrations $\geq$60 nM. In hemophilia blood, ARC19499 decreased the CFT and increased the alpha angle to values equal to those of healthy controls (p>0.4). The clot time was substantially improved by ARC19499, but not fully normalized. The MCF, though not significantly different between controls and patients, was significantly augmented by ARC19499 (p<0.05 for 0 nM ARC19499 compared to $\geq$2 nM in hemophilia patients and 200 nM in healthy controls).

Figure 84:
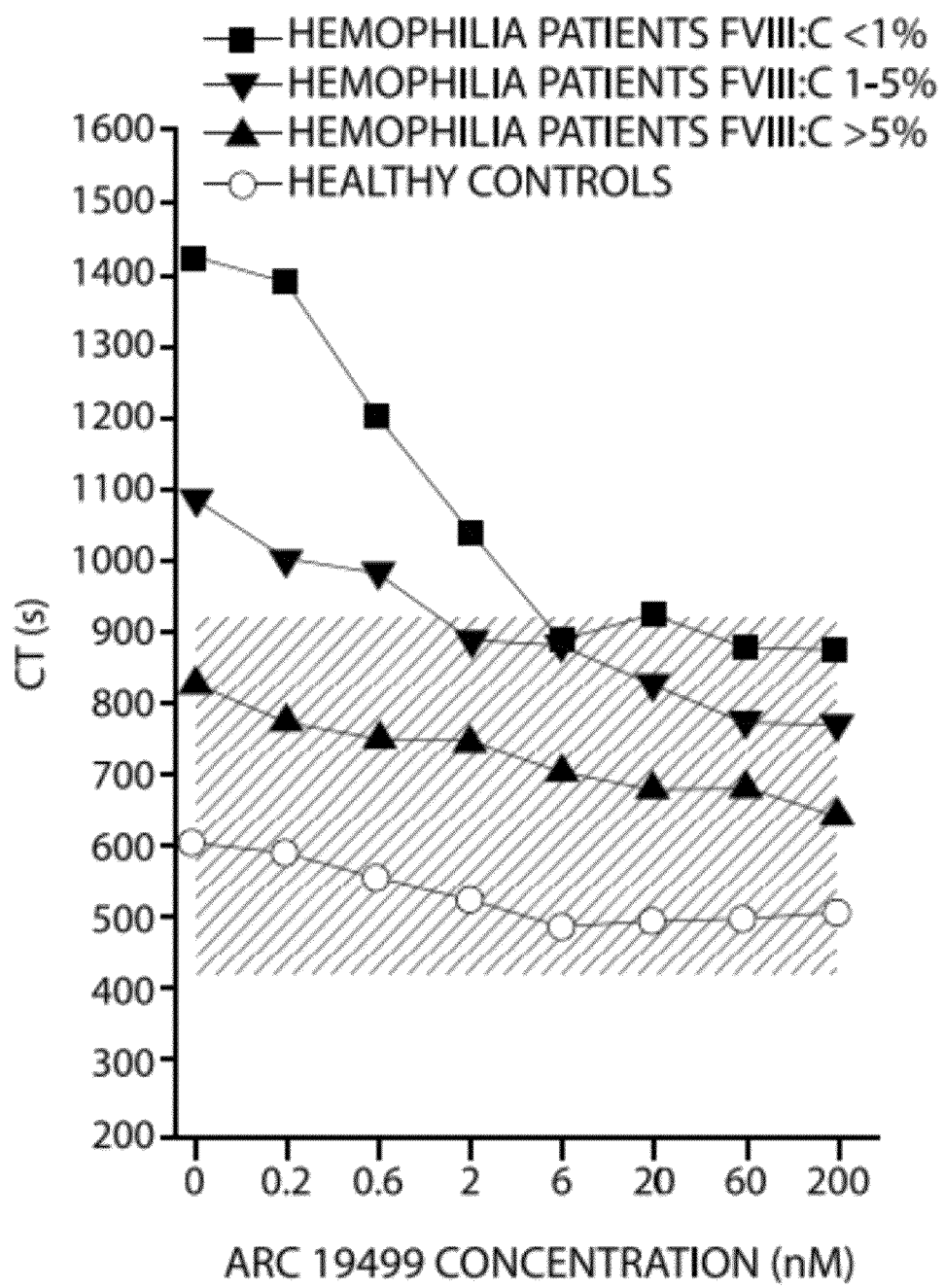
FIG. 84 shows the effect of different ARC19499 concentrations on the clotting time (CT) in blood samples from healthy controls (empty circles) compared to hemophilia A patients stratified according to FVIII level: <1% (filled squares), 1-5% (filled, inverted triangles), >5% (filled triangles). The hatched region indicates the range in healthy controls.

A comparison between FVIII coagulant activity (FVIII:C) activity levels in the hemophilia A patient samples and baseline CT indicated a significant correlation (p<0.01). Therefore, the hemophilia A patient CT data were stratified into three groups (<1% FVIII:C, 1-5% FVIII:C, and >5% FVIII:C) and replotted next to the healthy control CT data (FIG. 84). As previously indicated, concentrations $\geq$2 nM ARC19499 significantly shortened the clotting time (p<0.01). The CT values for hemophilia patients and healthy controls remained significantly different (p<0.05), but ARC19499 shortened the CT of hemophilia patients by a maximum up to 38%, and those of healthy controls by up to 19%, compared to baseline values. ARC19499 had the largest effect on the CT in patients with measured FVIII:C <1%. Although the CT of patients with FVIII:C <1% was not entirely normalized, ARC19499 shortened the CT to the range of healthy controls and to values equal those of patients with an FVIII:C >5%.

Figure 85:
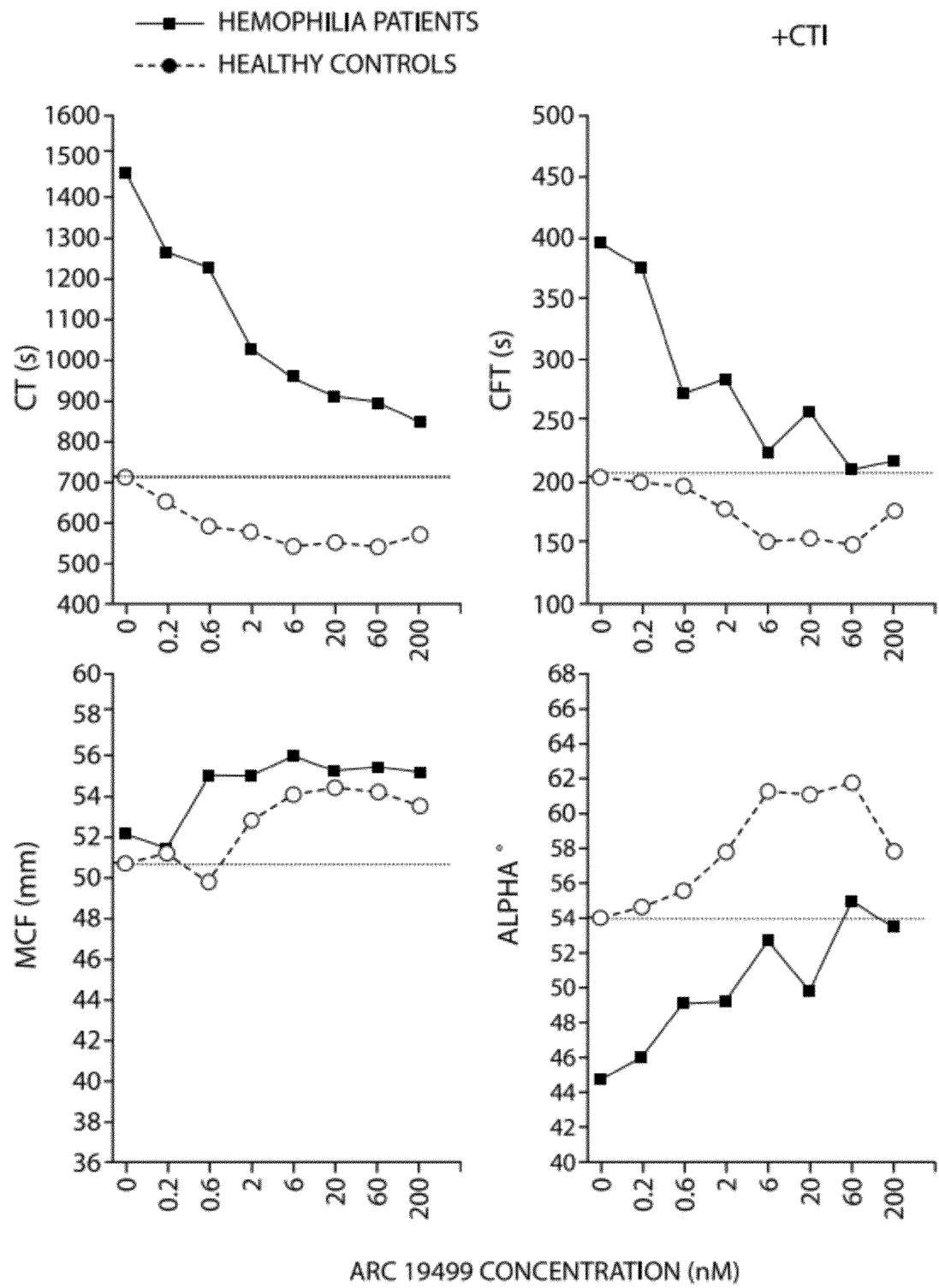
FIG. 85 shows the effect of different ARC19499 concentrations on ROTEM parameters in whole blood samples (with corn trypsin inhibitor (CTI)) from hemophilia patients (filled squares) and healthy controls (empty circles). The following parameters were analyzed: the clotting time (CT), the clot formation time (CFT), the maximum clot firmness (MCF) and the alpha angle (alpha).

Additional ROTEM analyses were performed in blood containing CTI using samples from 28 hemophilia patients and 11 healthy male controls. Again, the coagulation profiles were significantly different for patients and healthy controls (p<0.01) for all parameters except the MCF (FIG. 85). Similar to the measurements in the absence of CTI, addition of ARC19499 to blood containing CTI significantly shortened the CT and CFT, and raised the alpha angle and MCF (concentrations $\geq$20 nM, p$\leq$0.01). In blood containing CTI, the pro-haemostatic effect was more pronounced than in blood without CTI. Upon addition of 200 nM of ARC19499 to blood containing CTI, the CT was not only shortened significantly (p<0.01) but was also no longer different from the baseline CT of healthy controls (p=0.06). ARC19499 also normalized the CFT and the alpha angle in CTI whole blood, as previously observed in whole blood lacking CTI. ROTEM parameters of hemophilic blood spiked with $\geq$60 nM of ARC19499 were equal to baseline values of healthy controls (p>0.1).

Figure 86:
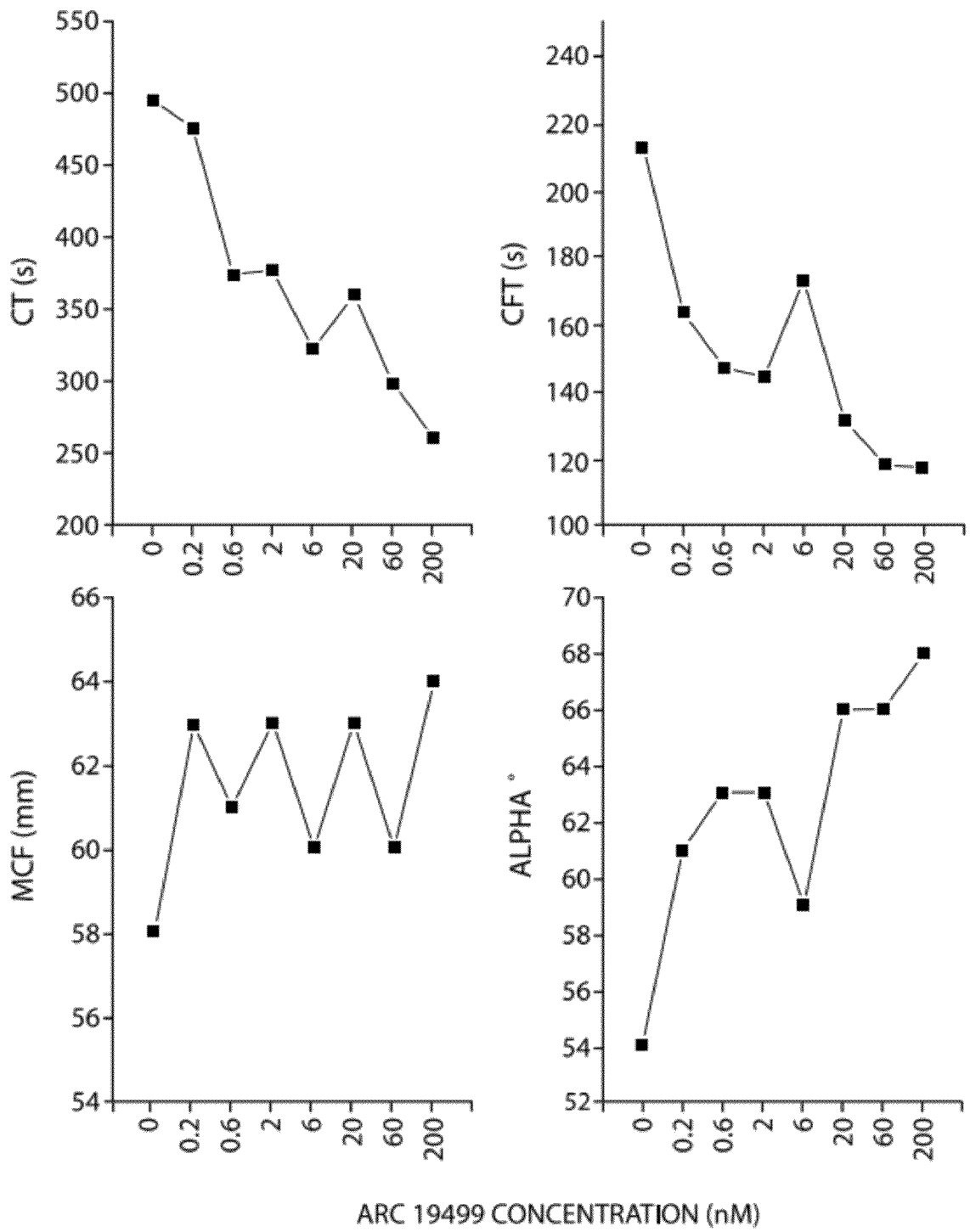
FIG. 86 shows the effect of different ARC19499 concentrations on ROTEM parameters in whole blood samples from a single patient with acquired hemophilia A. The following parameters were analyzed: the clotting time (CT), the clot formation time (CFT), the maximum clot firmness (MCF) and the alpha angle (alpha).

One patient with acquired hemophilia A was recruited. This patient showed a FVIII:C activity of 7%, 8.5 BU/mL FVIII inhibitor and an elevated aPTT of 63 seconds. This patient had received two infusions of FVIII bypassing activity (FEIBA), the most recent one within 8 hours of venipuncture. As a consequence, the CT and CFT of this patient were already normal (patient values: CT=496 seconds, CFT=213 seconds; healthy control mean values: CT=607 seconds, CFT=251 seconds). ARC19499 shortened the CT and CFT further, and even more than in controls and hereditary hemophilia patients (CT: 47% vs. 19% and 30%, CFT: 45% vs. 38% and 22%). ARC19499 also increased the alpha angle, as shown in FIG. 86.

Figure 87:
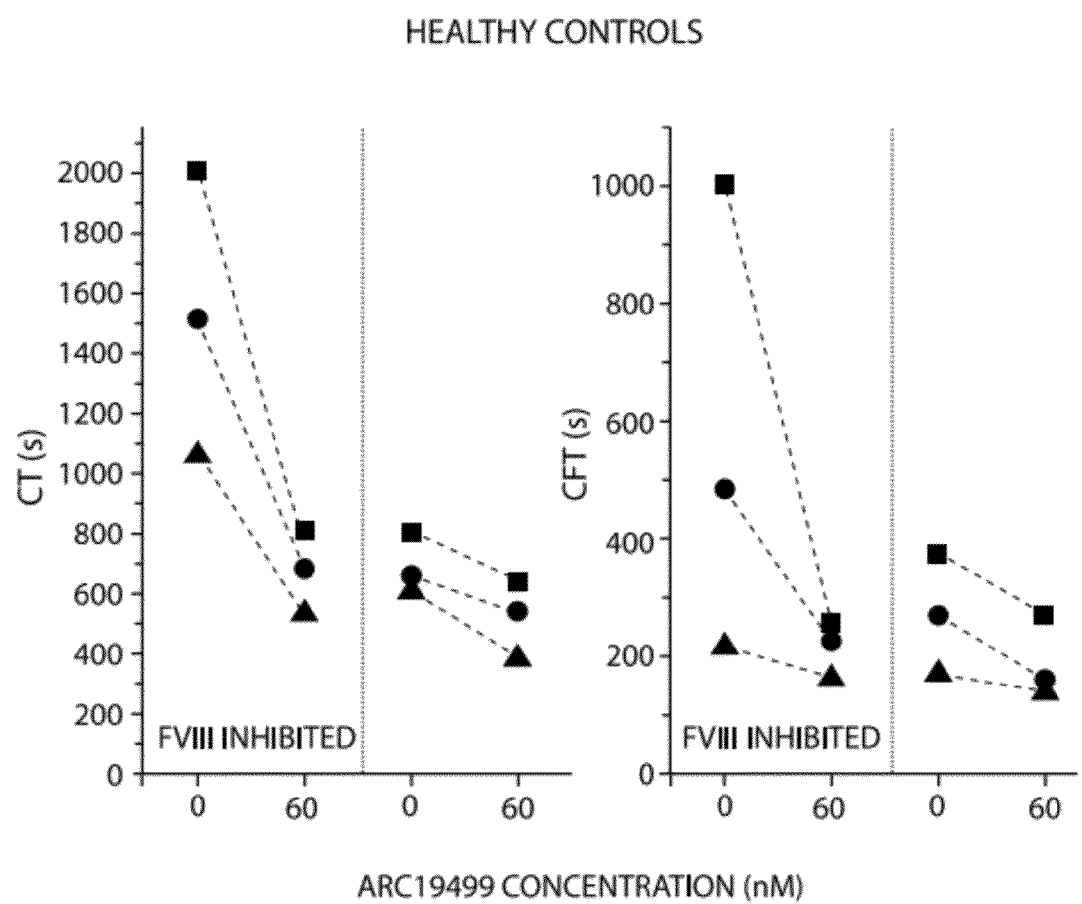
FIG. 87 shows ROTEM parameters for healthy control blood pre-incubated with a neutralizing FVIII antibody. Graphs show clotting time (CT) (left panel) and clot formation time (CFT) (right panel) in the same controls; on the left side of each graph, values after inhibition by an FVIII antibody are depicted.

Since patients with acquired hemophilia are extremely rare, the ROTEM experiment was repeated on normal blood that had been treated with a neutralizing antibody to FVIII. Blood from healthy controls was pre-incubated with a sheep antihuman FVIII polyclonal antibody (specific activity 2300 BU/mg; Haematologic Technologies Inc). FIG. 87 shows the CT (left panel) and the CFT (right panel) in the same controls; on the left side of each graph, values after inhibition by the FVIII antibody are depicted. The addition of 60 nM ARC19499 normalized both the CT and the CFT in antibody-treated blood.

These data show that ARC19499 had a procoagulant effect on clotting in blood samples from healthy controls and hemophilia patients, as measured by ROTEM. Additionally, ARC19499 was able to normalize ROTEM clotting parameters in blood from hemophilia patients.

Example 26

This example demonstrates that ARC19499 can improve thrombin generation in plasma samples from hemophilia A and hemophilia B patients, as measured by calibrated automated thrombography (CAT).

Blood samples were collected from 39 healthy volunteers (27 male and 12 female) and 40 hemophilia patients (all male). Of the 40 hemophilia patients, 3 hemophilia B (HB) patients and 28 hemophilia A (HA) patients were diagnosed as severe (baseline factor activity <1%), one HA and one HB patient suffered from moderately severe hemophilia (baseline factor activity 1-5%), and four HA and two HB patients had mild hemophilia (baseline factor activity >5%). Using a 21-gauge butterfly needle, blood samples were drawn into plastic Vacuette tubes (Greiner Bio-One) containing 3.8% sodium citrate at a volume ratio of 1:9. Platelet poor plasma (PPP) was prepared from these samples by two room temperature centrifugation steps, with the first spin at 1700×g for 10 minutes followed by a second spin at 18,000×g for 15 minutes. PPP containing 100 µg/mL corn trypsin inhibitor (CTI; Haematologic Technologies Inc.) was spiked with different ARC19499 concentrations (0, 0.2, 0.6, 2, 6, 20, 60, 200 or 600 nM ARC19499) for use in the assay.

CAT assays were performed by adding 80 µL of PPP to 204 of a mixture of tissue factor (TF) and phospholipids (PPP-Reagent Low, Thrombinoscope BV) in a 96 well microtiter plate. The final concentrations of TF and phospholipids were 1 pM and 4 µM, respectively. The reaction was started by adding 20 µL of fluorogenic substrate (FluCa Kit, Thrombinoscope BV) and fluorescence was detected using a Fluoroskan Ascent fluorometer (Thermo Fisher Scientific). Analysis by Thrombinoscope software resulted in thrombin generation curves with thrombin (nM) on the y-axis and time (minutes) on the x-axis. The software determined values for a number of parameters including: lag time (minutes; time till onset of initial thrombin generation); endogenous thrombin potential (ETP; nM; area under the thrombin generation curve); peak thrombin (nM; highest amount of thrombin generated at any one point of the assay); time to peak (minutes; time reach peak thrombin concentration); and start tail (minutes; point in time when the end thrombin generation is reached). Comparisons between different concentrations of ARC19499 in any of the measured parameters were calculated with the Wilcoxon signed rank test with a Bonferroni Correction. To compare healthy controls to patients, a Mann-Whitney U-test was used. A p-value smaller or equal to 0.05 was considered statistically significant.

Figure 88:
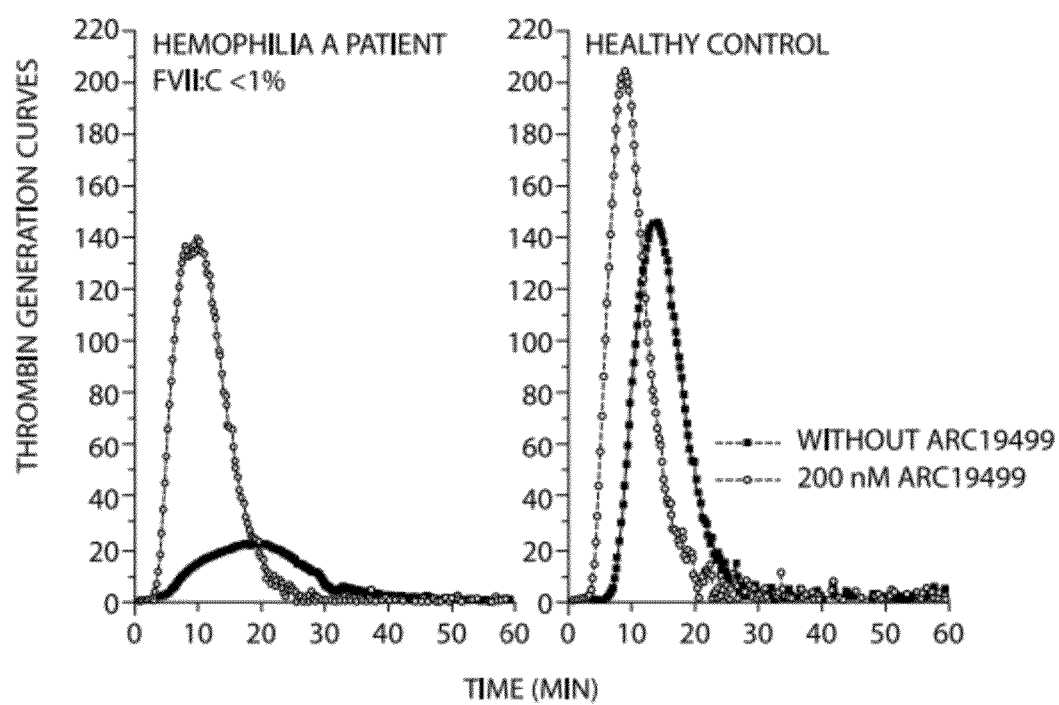
FIG. 88 shows thrombin generation curves from the calibrated automated thrombogram (CAT) assay in plasma from a representative severe hemophilia A patient (left panel) and a healthy control (right panel). Both graphs show results in the presence (empty circles) and absence (filled squares) of 200 nM ARC19499.

Examples of CAT data are shown in FIG. 88 for a representative hemophilia A patient (left panel) and a healthy control (right panel), comparing thrombin generation in the presence and absence of 200 nM of ARC19499. The addition of ARC19499 normalized the thrombin generation curve in the hemophilia A patient sample and augmented thrombin generation in the healthy control sample.

Figure 89:
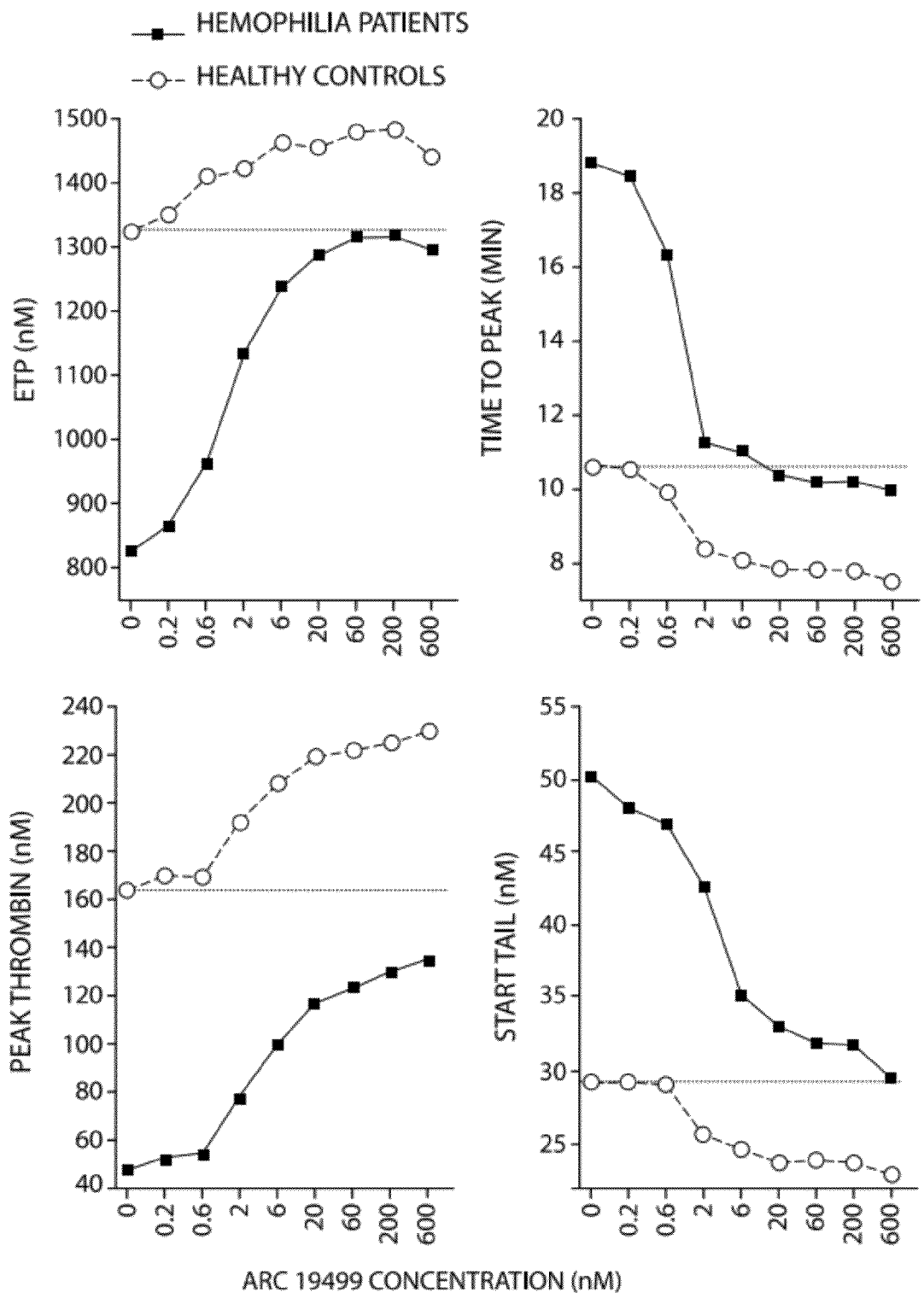
FIG. 89 shows plots of calibrated automated thrombogram (CAT) parameters versus ARC19499 concentration, including the endogenous thrombin potential (ETP), time to peak, peak thrombin concentration and start tail. In each graph, the response to ARC19499 in plasma from hemophilia patients (filled squares) is compared to healthy controls (empty circles).
Figure 90:
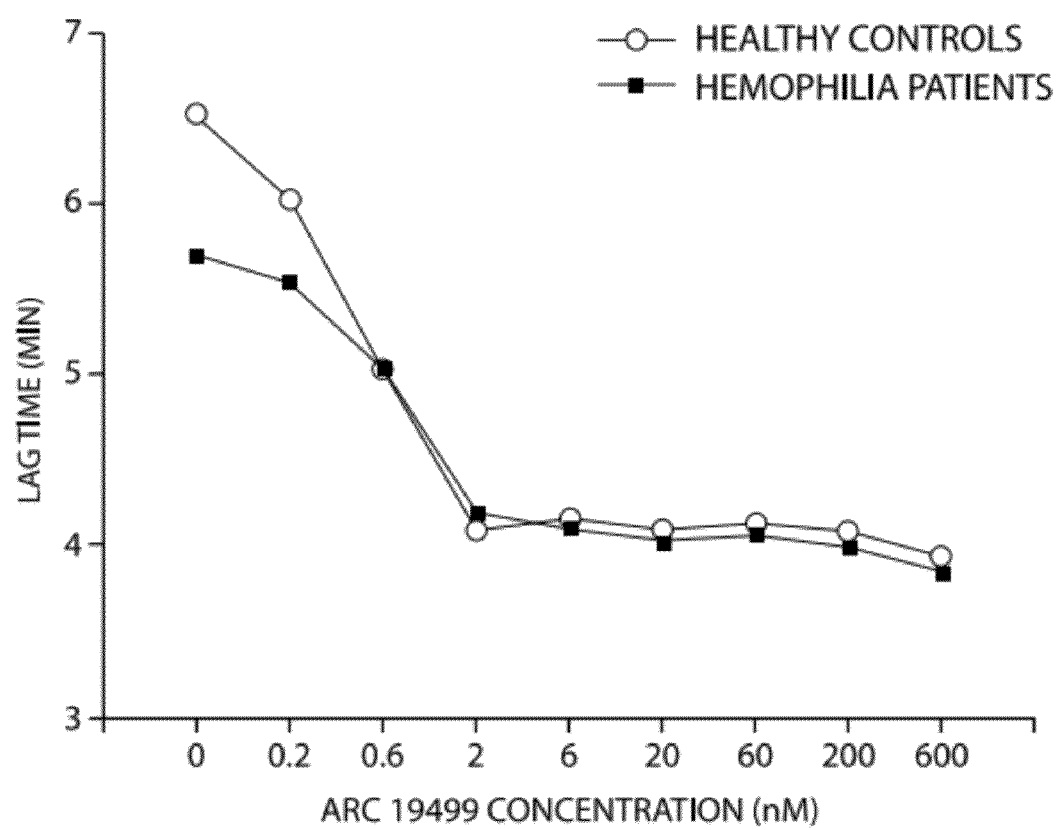
FIG. 90 is a plot of calibrated automated thrombogram (CAT) lag time versus ARC19499 concentration, comparing the response in hemophilia patients (filled squares) to healthy controls (empty circles).

Average CAT parameters for all hemophilia patients and healthy male controls are shown in FIG. 89. At baseline, the hemophilia patient group displayed a prolonged time to peak, a lower peak thrombin generation and a severely compromised ETP. In the absence of ARC19499, the following CAT parameters were significantly different between healthy male controls and hemophilia patients: time to peak, peak thrombin generation, ETP and start tail (p<0.001). There was no significant difference in the lag time between healthy controls and hemophilia patients (FIG. 90). The addition of ARC19499 significantly enhanced all of the parameters assessed by the CAT assay (FIGS. 89 and 90). Concentrations above 60 nM of ARC19499 normalized CAT parameters in hemophilia patients. There was no longer a significant difference between baseline values of healthy controls and values measured with addition of ≧60 nM ARC19499 in hemophilia patients in the following CAT parameters: start tail, time to peak and ETP (p>0.05) (FIG. 89). Peak thrombin remained significantly different between patients and controls, but 600 nM of ARC19499 augmented peak thrombin by 185% in hemophilia patients, from 47 nM at baseline to 135 nM, thus reaching the normal range of healthy controls (healthy controls mean peak thrombin 167 nM, minimum 100 nM, maximum 297 nM). ARC19499 shortened the lag time significantly in both groups (p<0.001 for concentrations above 0.6 nM) but differences between the groups continued to be not significant (FIG. 90).

Figure 91:
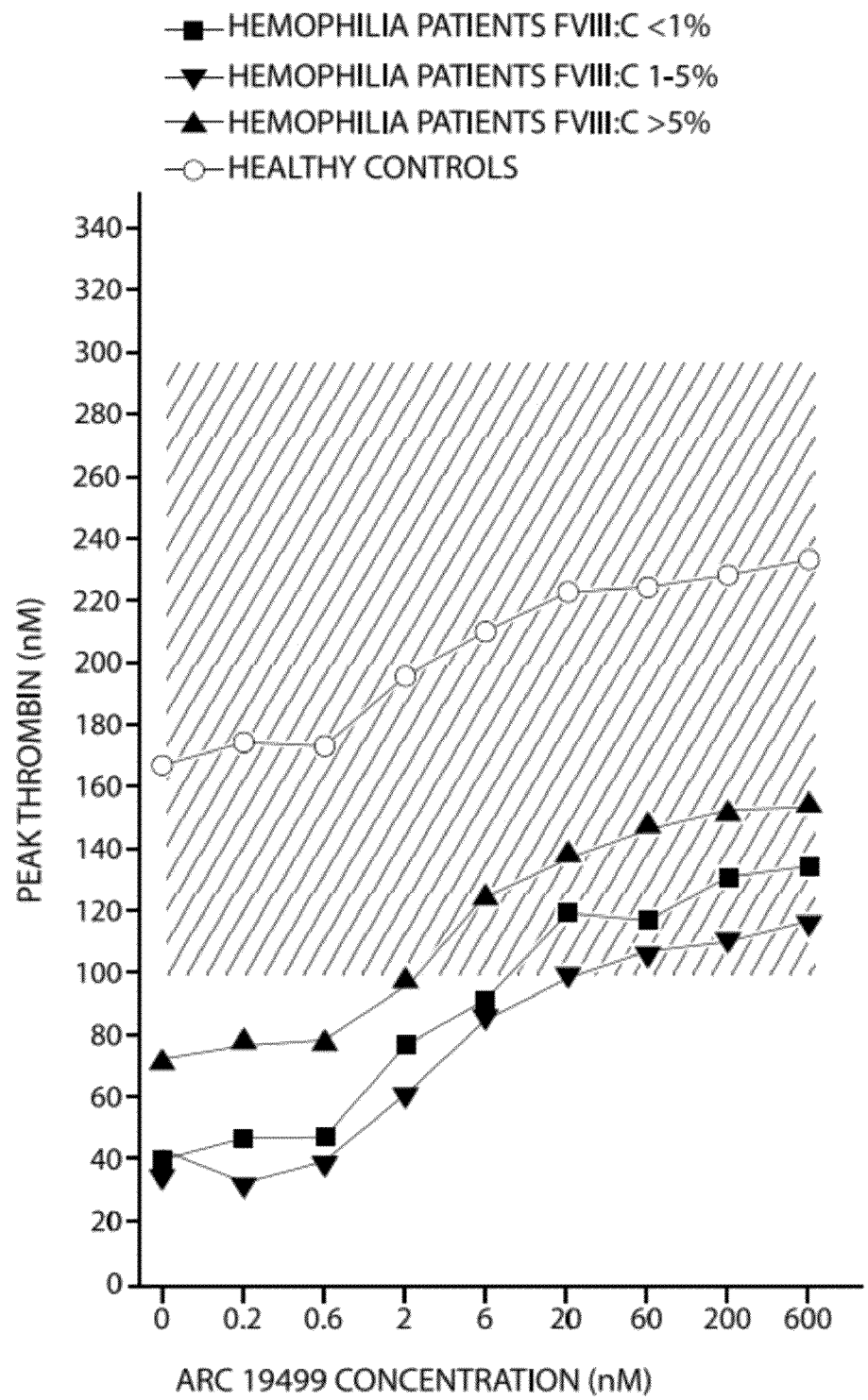
FIG. 91 shows the effect of different ARC19499 concentrations on peak thrombin in plasma samples from healthy controls (empty circles) compared to hemophilia A patients stratified according to FVIII level: <1% (filled squares), 1-5% (filled, inverted triangles), >5% (filled triangles). The hatched region indicates the range observed in healthy controls.

FIG. 91 shows peak thrombin data stratified into three groups (<1% FVIII coagulant activity (FVIII:C), 1-5% FVIII:C, and >5% FVIII:C) and replotted next to the healthy control peak thrombin data. Increasing concentrations of ARC19499 augmented peak thrombin generation in all four groups. ARC19499 did not completely normalize peak thrombin in the <1% FVIII:C plasma relative to the average healthy control value at baseline, but values at ≧60 nM ARC19499 reached higher than the baseline of patients with >5% FVIII:C concentration and into the range of values observed for healthy controls (hatched region in FIG. 91).

Figure 92:
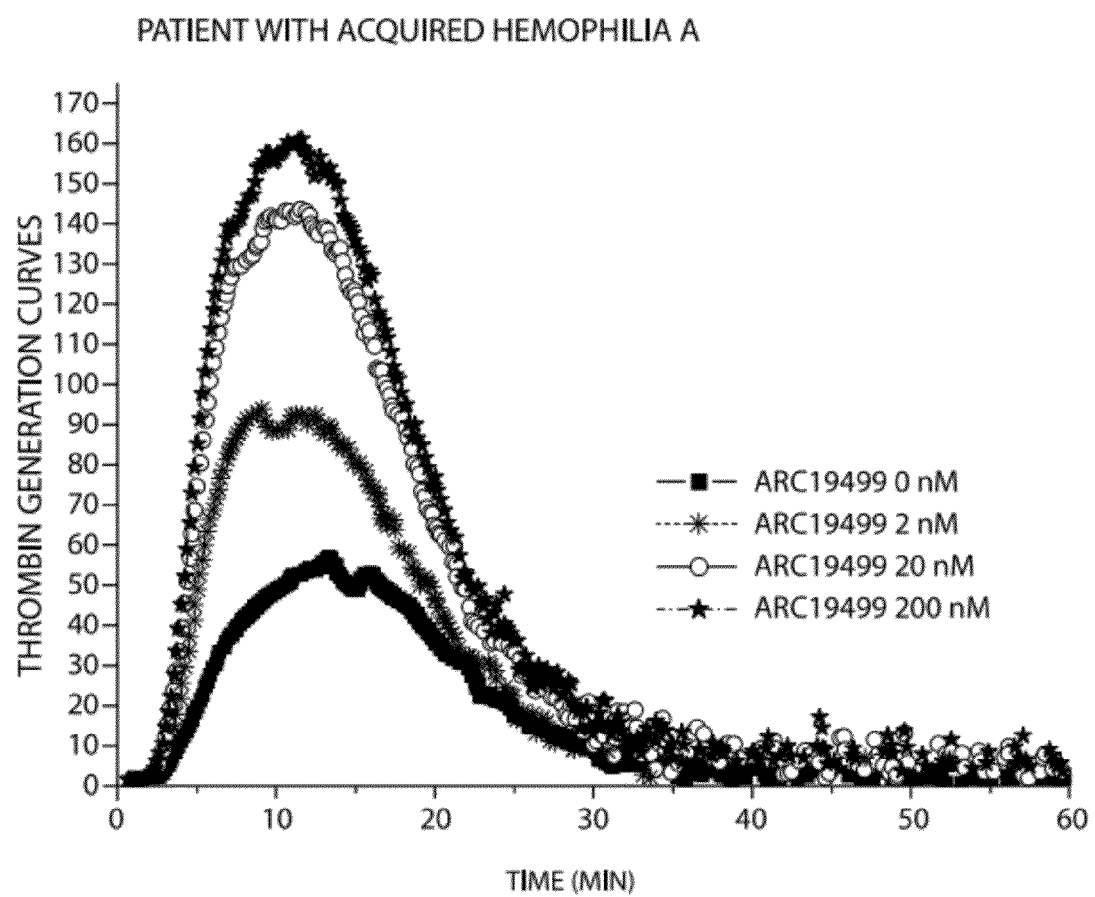
FIG. 92 shows thrombin generation curves in plasma from a single patient with acquired hemophilia A containing 0 nM (filled squares), 2 nM (asterisks), 20 nM (empty circles) or 200 nM (filled stars) of ARC19499.

CAT assays were also performed on ARC19499-spiked samples from a patient with acquired hemophilia. This patient showed a FVIII:C activity of 7%, 8.5 BU/mL FVIII inhibitor and an elevated aPTT of 63 seconds. This patient had received two infusions of FVIII bypassing activity (FEIBA), the most recent one within 8 hours of venipuncture. As a consequence, ROTEM parameters of clotting in this patient were already normal (patient values: CT=496 seconds, CFT=213 seconds; healthy control mean values: CT=607 seconds, CFT=251 seconds). Thrombin generation curves measured in the presence of 0, 2, 20 and 200 nM ARC19499 are shown in FIG. 92. Although this patient displayed normal ROTEM values, baseline CAT values were severely compromised. As for patients with inherited hemophilia, increasing concentrations of ARC19499 normalized thrombin generation in samples from this patient. ARC19499 had the largest influence on the peak thrombin and the ETP of the patient, both of which increased more than 2.5 fold. Peak thrombin was normalized (peak thrombin: baseline 54 nM-max 165 nM; mean baseline value of healthy controls: 164 nM). Moreover ARC19499 (200 nM) increased the ETP to values above those of healthy controls (ETP: baseline 973 nM-max 2577 nM; mean baseline healthy controls: ETP 1322 nM).

Figure 93:
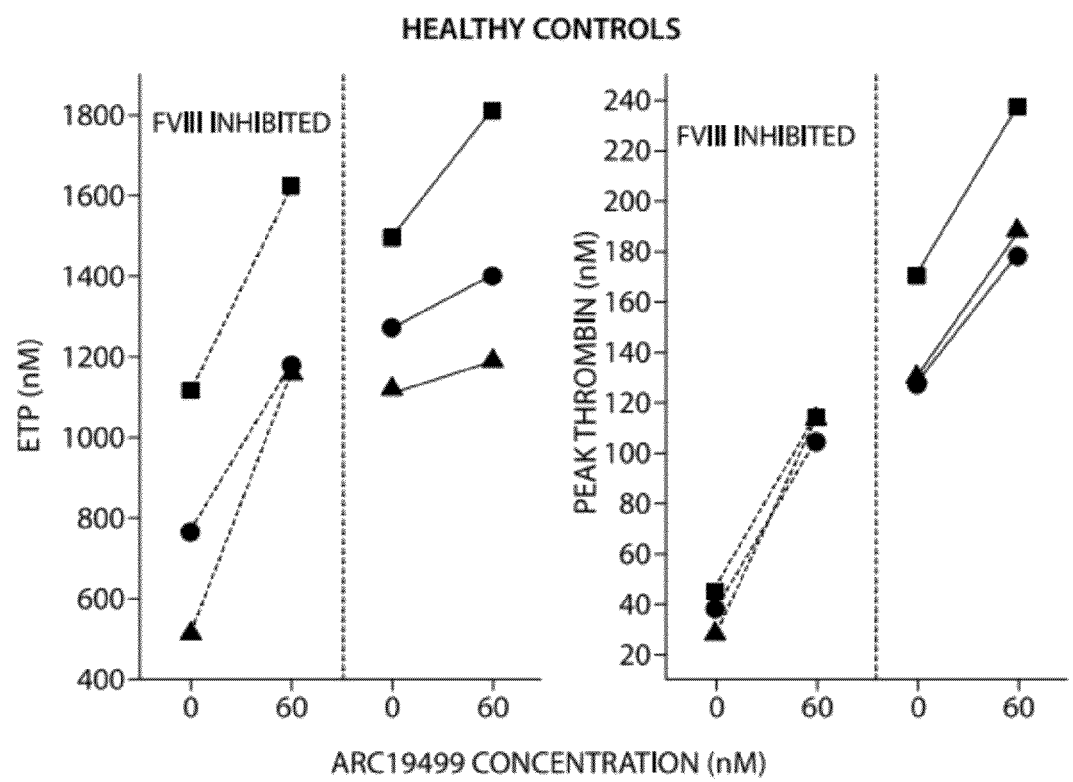
FIG. 93 shows calibrated automated thrombogram (CAT) parameters for healthy control plasma pre-incubated with a neutralizing FVIII antibody. Graphs show endogenous thrombin potential (ETP) (left panel) and peak thrombin (right panel) in the same controls; on the left side of each graph, values after inhibition by an FVIII antibody are depicted.
Figure 94:
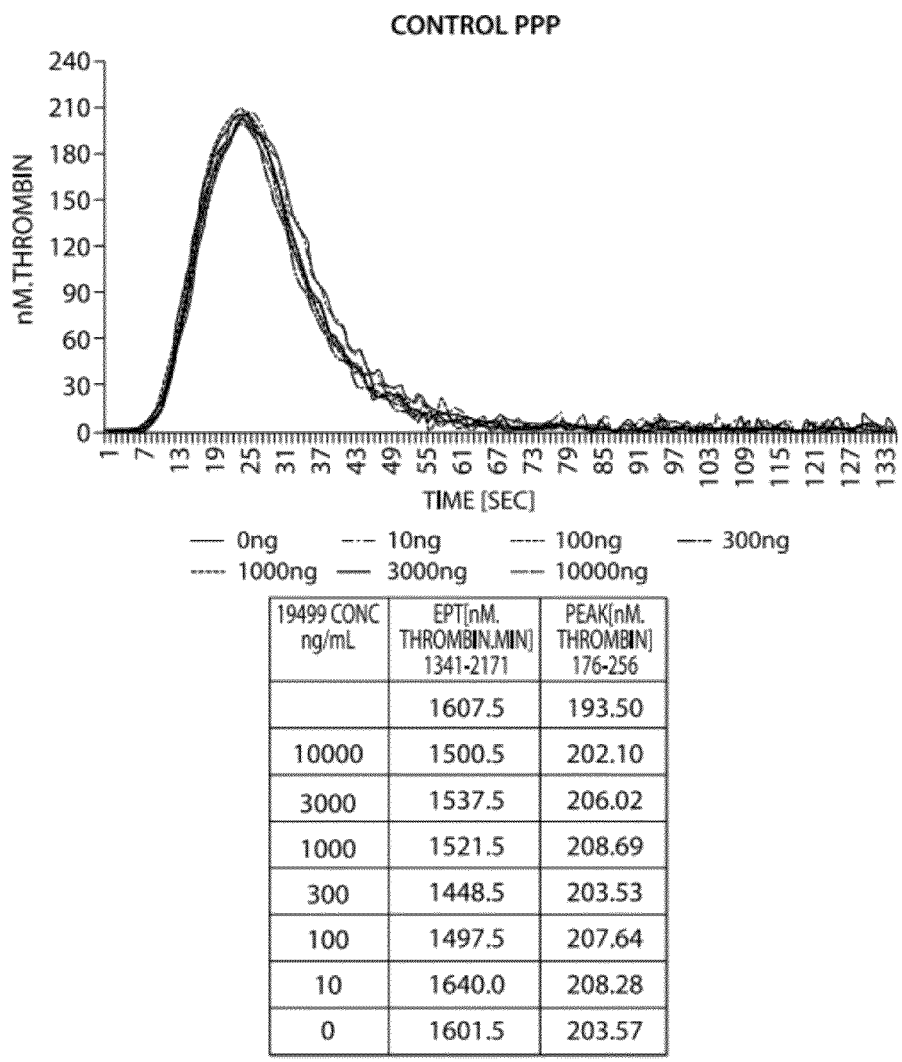
FIG. 94 shows representative calibrated automated thrombogram (CAT) data from a healthy volunteer (ARC HV 01).
Figure 95:
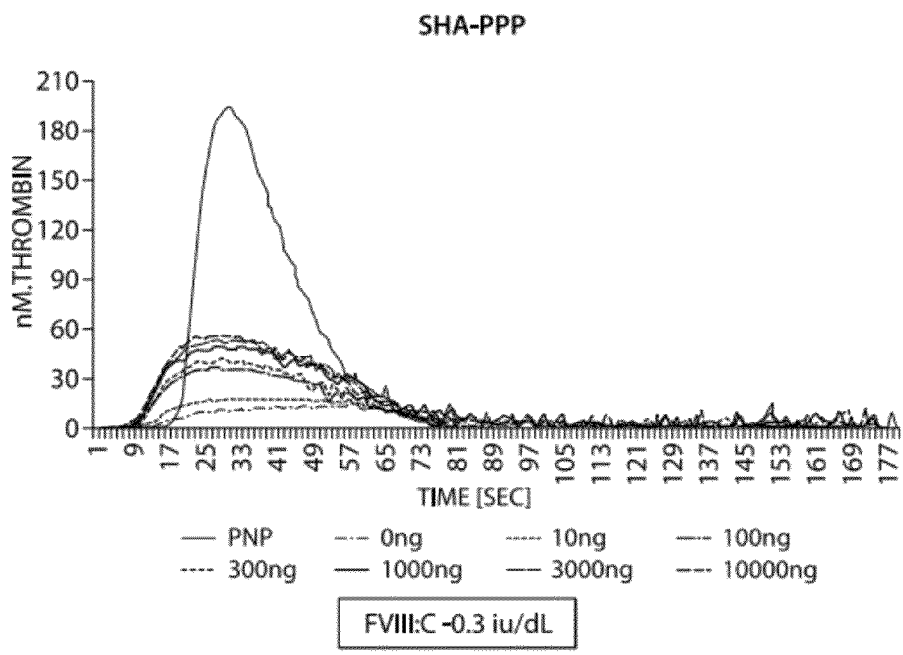
FIG. 95 shows representative calibrated automated thrombogram (CAT) data from a patient with severe hemophilia A (ARC SHA 05).
Figure 96:
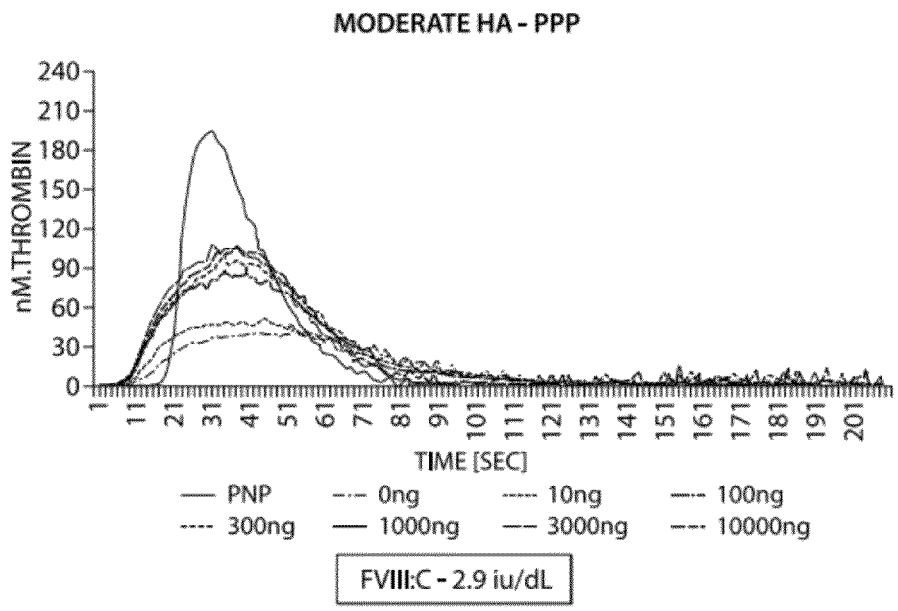
FIG. 96 shows representative calibrated automated thrombogram (CAT) data from a patient with moderate hemophilia A (ARC MoHA 01).
Figure 97:
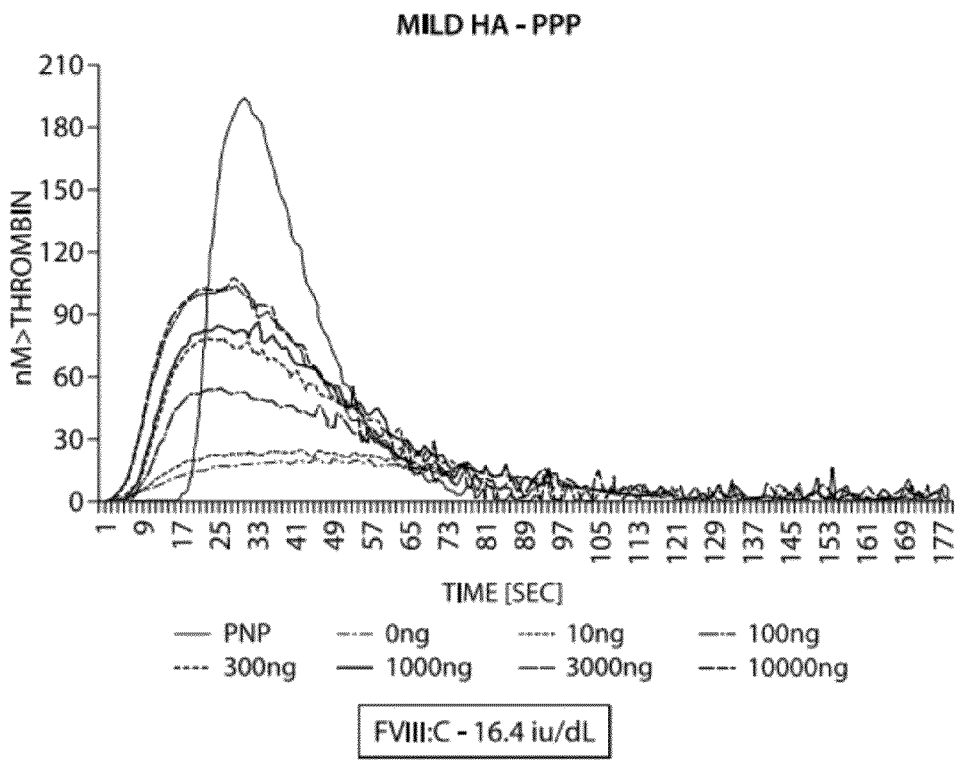
FIG. 97 shows representative calibrated automated thrombogram (CAT) data from a patient with mild hemophilia A (ARC MiHA 03).

The CAT experiment was repeated on normal plasma that had been treated with a neutralizing antibody to FVIII. PPP from healthy controls was pre-incubated with a sheep antihuman FVIII polyclonal antibody (specific activity 2300 BU/mg; Haematologic Technologies Inc). FIG. 93 shows the ETP (left panel) and the peak thrombin (right panel) in the same controls; on the left side of each graph, values after inhibition by the FVIII antibody are depicted. The addition of 60 nM ARC19499 normalized both the ETP and the peak thrombin in antibody-treated plasma.

These data show that ARC19499 had a procoagulant effect on thrombin generation in blood samples from healthy controls and hemophilia patients, as measured by CAT. Additionally, ARC19499 was able to normalize CAT parameters in plasma from hemophilia patients.

Example 27

This example demonstrates that ARC19499 can improve thrombin generation times (TGT) in plasma samples from severe, moderate and mild hemophilia A patients, and severe hemophilia B patients, as measured by calibrated automated thrombogram (CAT).

Blood was collected into 3.2 mL Vacuette tubes containing 3.2% sodium citrate and 250 µL 1.3 mg/mL corn trypsin inhibitor (CTI); the final CTI concentration was 100 µg/mL. Samples were collected from patients with severe (<1% FVIII; n=10), moderate (1-5% FVIII; n=7) and mild (5-40% FVIII; n=5) hemophilia A, patients with severe hemophilia B (<1% FIX, n=5) and healthy volunteers (n=10). To prepare platelet poor plasma (PPP) for CAT assays, tubes were centrifuged at 2500×g for 15 minutes, the supernatant transferred to fresh Eppendorf tubes, then centrifuged again at 11000×g for 5 minutes. Plasma was either used immediately or frozen at −80° C. for later use. To analyze the effects of ARC19499 on thrombin generation, ARC19499 was added to plasma at concentrations of 10, 100, 300, 1000, 3000 or 10,000 ng/mL (0.9, 9.0, 27.1, 90.3, 271 or 903 nM).

Thrombin generation time (TGT) assays were performed by calibrated automated thrombography (CAT) on a Thrombinoscope instrument (Thrombinoscope, Maastricht, The Netherlands) consisting of a Thermo Scientific Fluoroskan Ascent Microplate Fluorometer (serial no. 374-90031C) programmed with Thrombinoscope software version 2.6. 80 µL plasma was mixed with 20 µL relipidated recombinant tissue factor (TF; final concentration 1 pM) and the assay was initiated by the addition of 20 µL FluCa substrate. Analysis of the data by Thrombinoscope software resulted in thrombin generation curves with thrombin (nM) on the y-axis and time (minutes) on the x-axis. The software determined values for a number of parameters including: lag time (minutes; time till onset of initial thrombin generation), endogenous thrombin potential (ETP; nM; area under the thrombin generation curve), peak thrombin (nM; highest amount of thrombin generated at any one point of the assay) and time to peak (minutes; time reach peak thrombin concentration). All measurements were performed in duplicate. Differences in means of each group were tested using a student's t-test or ANOVA, as appropriate.

Figures 1, 98:
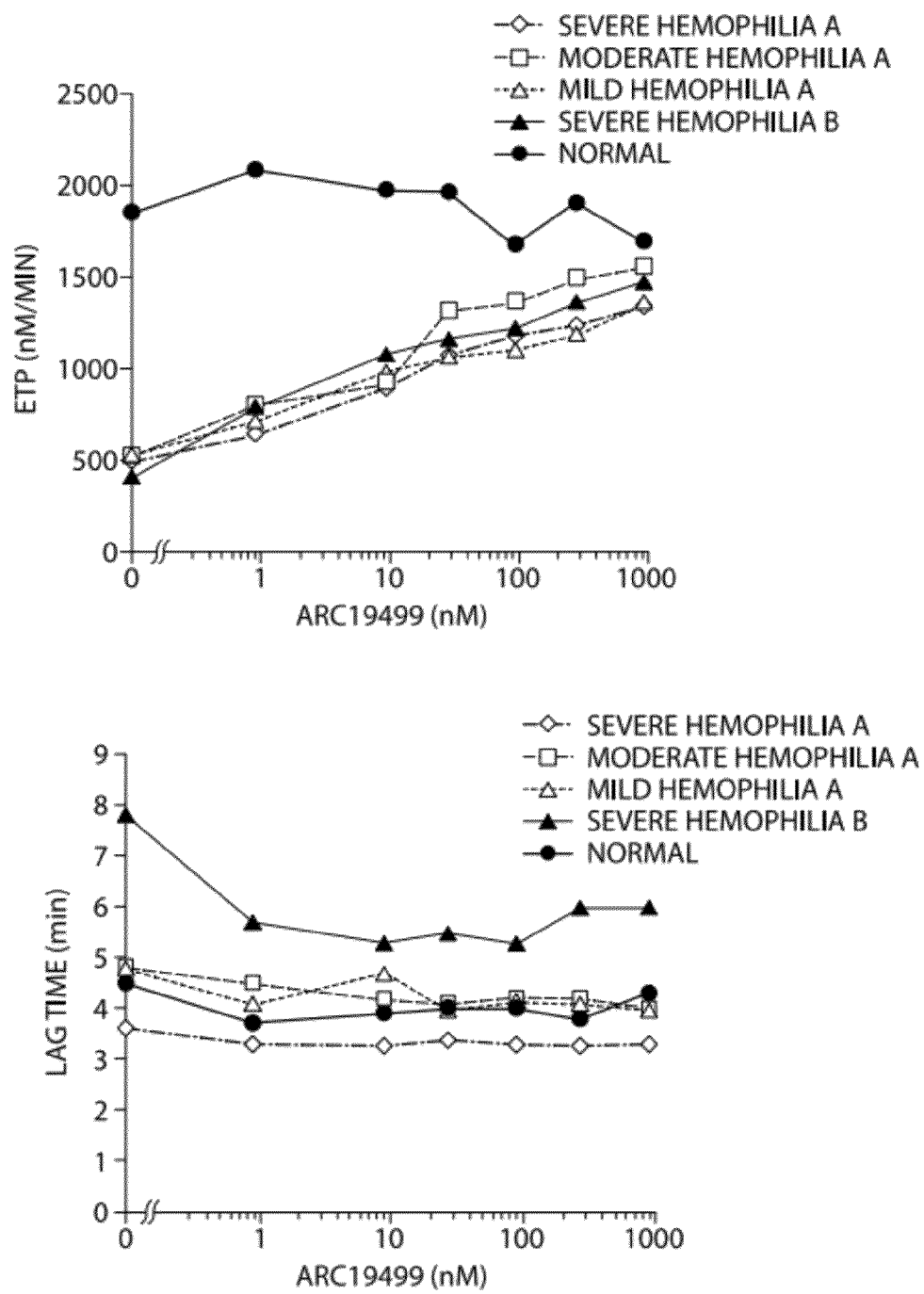
FIG. 98 is a series of graphs depicting median calibrated automated thrombogram (CAT) parameters (endogenous thrombin potential (ETP), peak thrombin, lag time and time to peak) measured in fresh plasma samples from patients with severe hemophilia A (empty diamonds), moderate hemophilia A (empty squares), mild hemophilia A (empty triangles) or severe hemophilia B (filled triangles) compared to healthy controls (filled circles).
Figures 2, 98:
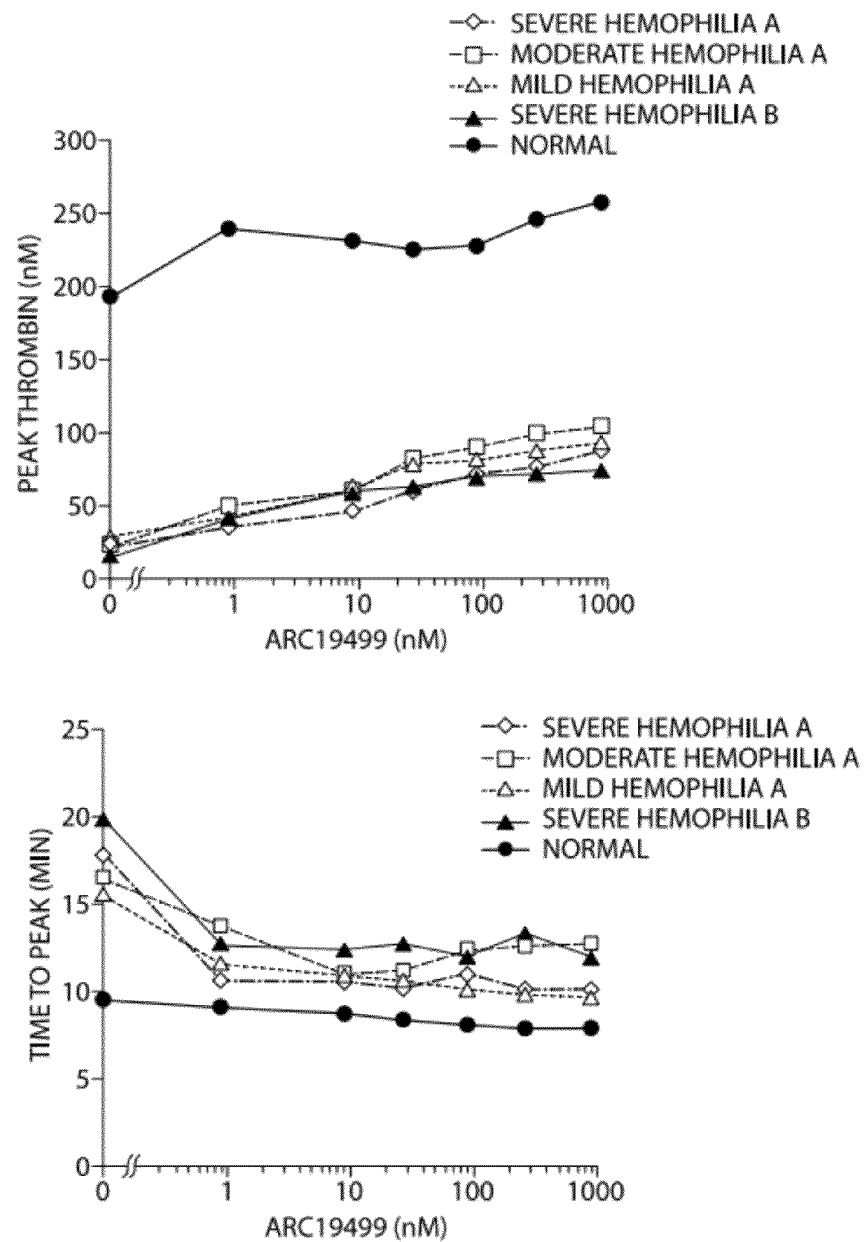
Figures 1, 99:
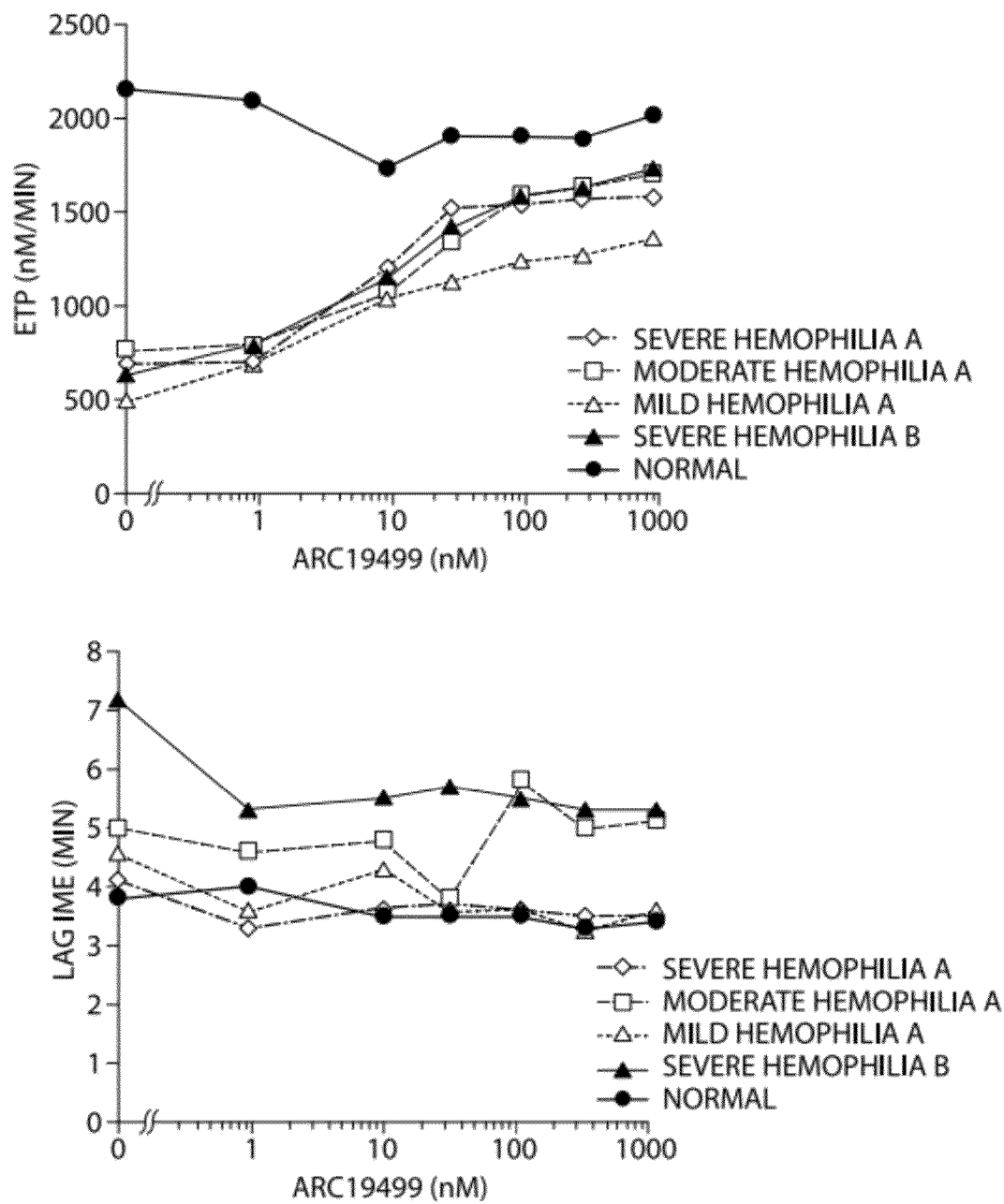
FIG. 99 is a series of graphs depicting median calibrated automated thrombogram (CAT) parameters (endogenous thrombin potential (ETP), peak thrombin, lag time and time to peak) measured in frozen/thawed plasma samples from patients with severe hemophilia A (empty diamonds), moderate hemophilia A (empty squares), mild hemophilia A (empty triangles) or severe hemophilia B (filled triangles) compared to healthy controls (filled circles).
Figures 2, 99:
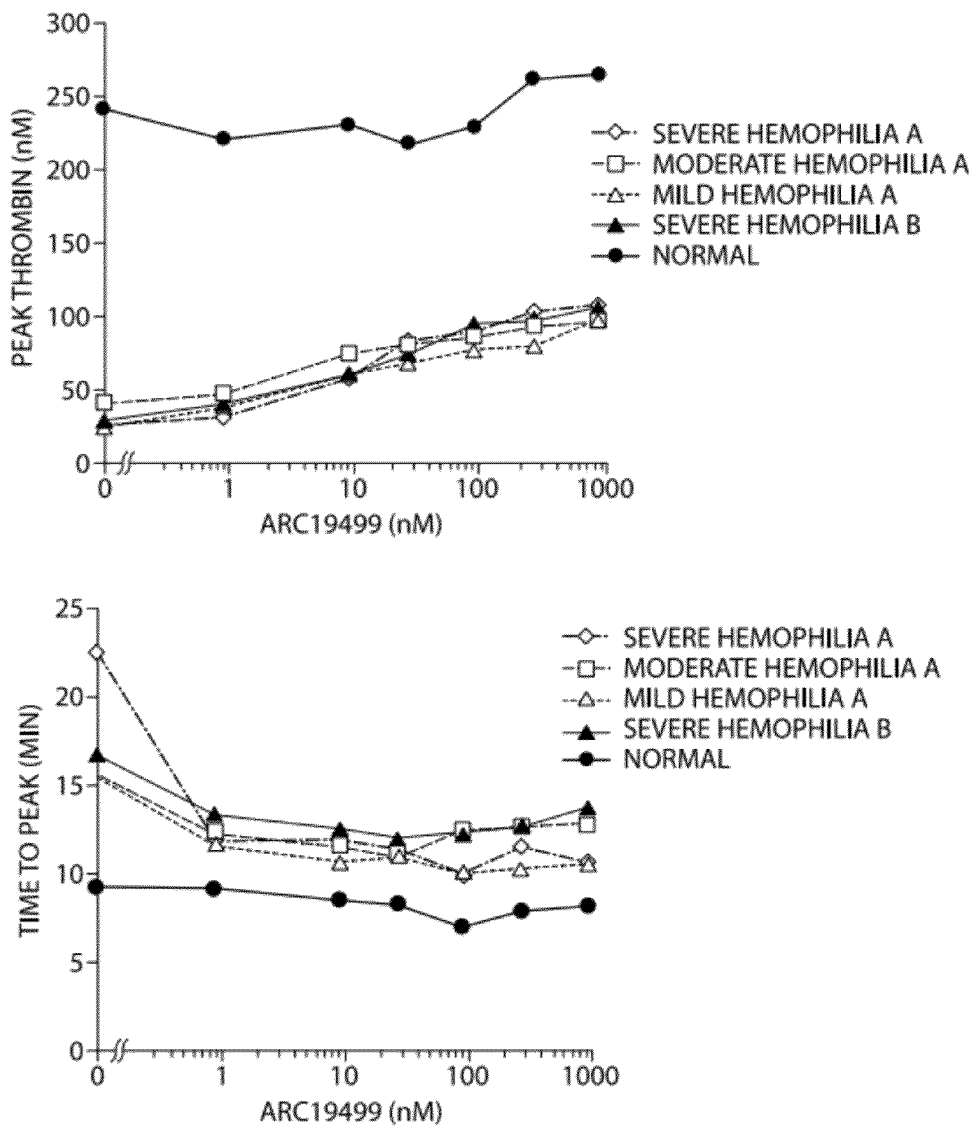
Figure 100:
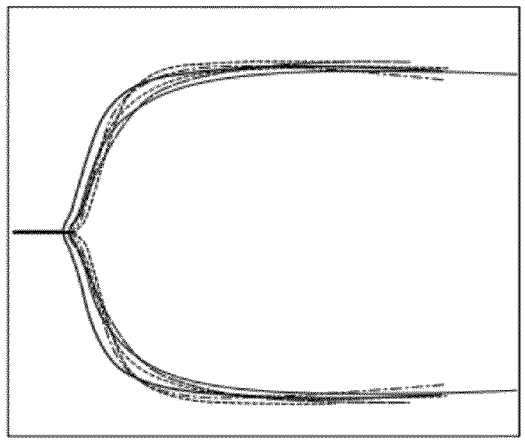
FIG. 100 shows representative whole blood thromboelastography (TEG®) data from a healthy volunteer (ARC HV 01).
Figure 101:
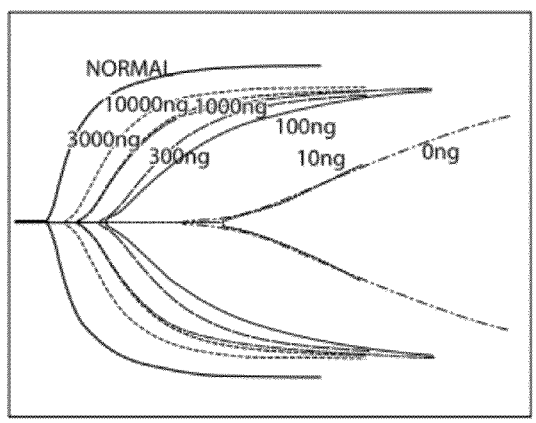
FIG. 101 shows representative whole blood thromboelastography (TEG®) data from a patient with severe hemophilia A (ARC SHA 02).
Figure 102:
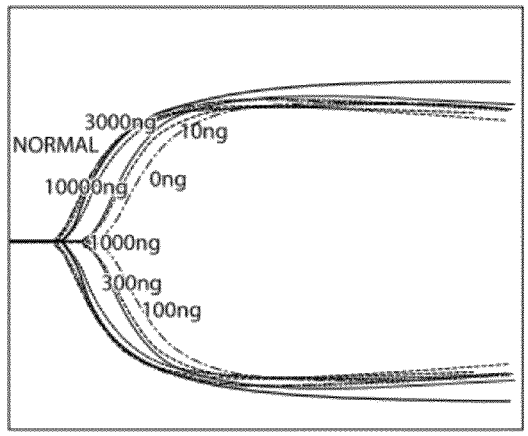
FIG. 102 shows representative whole blood thromboelastography (TEG®) data from a patient with moderate hemophilia A (ARC MoHA 01).
Figure 103:
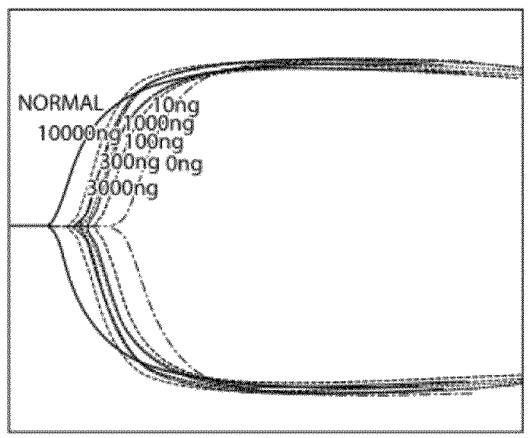
FIG. 103 shows representative whole blood thromboelastography (TEG®) data from a patient with mild hemophilia A (ARC MiHA 01).

FIGS. 94-97 show representative CAT data from a healthy volunteer (HV), a patient with severe hemophilia A (SHA), a patient with moderate hemophilia A (MoHA) and a patient with mild hemophilia A (MiHA). Median data for healthy volunteers, all three hemophilia A patient groups, and the severe hemophilia B patient group are shown in FIG. 98 for experiments performed in freshly processed plasma. Baseline ETP and peak thrombin parameters were decreased in all hemophilia patient groups compared to healthy controls, and the time to peak was increased. The severity of FVIII deficiency had no effect on observed thrombin generation, as baseline parameter values were essentially indistinguishable between the 3 hemophilia A patient groups. FVIII deficiency had little effect on the baseline lag time compared to healthy controls, but FIX deficiency resulted in ~2-fold prolongation of the lag time at baseline. Freezing the plasma had little effect on thrombin generation as similar CAT parameter values were observed in plasma samples that had undergone freeze-thaw (FIG. 99).

As shown in the individual (FIGS. 95-97) and median data plots (FIGS. 98 and 99), the addition of ARC19499 improved thrombin generation in hemophilia plasma. The ETP increased with increasing ARC19499 concentrations up to 10,000 ng/mL (903 nM) reaching a normal level in all hemophilia groups (FIGS. 98 and 99). A trend toward improvement was also observed in the peak thrombin. Although normalization of this parameter was not achieved, 3-5-fold improvements were observed in all patient groups. ARC19499 had little effect on the lag time in any of the hemophilia A patient groups, but it did slightly improve the lag time in plasma from hemophilia B. A slight improvement in time to peak was also observed in all of the patient groups. In healthy volunteer plasma, the addition of ARC19499 had little effect on any of the CAT parameters.

Median CAT data with interquartile ranges are presented for fresh and frozen plasma in the following tables: Table 3, severe hemophilia A (SHA); Table 4, moderate hemophilia A (MoHA); Table 5, mild hemophilia A (MiHA); Table 6, severe hemophilia B (SHB); and Table 7, normal. Taken together, the data show that ARC19499 improved thrombin generation in hemophilia A patient plasma of all severity levels, and in severe hemophilia B plasma.

TABLE 3

TGT on Citrated PPP with CTI - SHA (n = 10)

| ARC19499 | ETP[nM/min] | | | | Peak[nM] | | | |
|---|---|---|---|---|---|---|---|---|
| | Fresh | | Frozen | | Fresh | | Frozen | |
| ng/mL | Median | IQR | Median | IQR | Median | IQR | Median | IQR |
| 10000 | 1347 | 1260-1538 | 1587 | 1244-1763 | 88 | 63-119 | 107 | 86-139 |
| 3000 | 1233 | 1117-1425 | 1569 | 1094-1716 | 76 | 56-103 | 103 | 77-132 |
| 1000 | 1171 | 1019-1335 | 1546 | 1019-1711 | 71 | 50-95 | 90 | 67-125 |
| 300 | 1078 | 825-1206 | 1522 | 916-1657 | 60 | 44-77 | 83 | 58-117 |
| 100 | 896 | 741-1137 | 1206 | 726-1469 | 46 | 36-76 | 58 | 42-94 |
| 10 | 638 | 564-978 | 705 | 516-1169 | 34 | 23-48 | 31 | 19-62 |
| 0 | 489 | 292-711 | 685 | 247-847 | 21 | 13-29 | 26 | 10-35 |

| ARC19499 | Lag time [min] | | | | TT peak[min] | | | |
|---|---|---|---|---|---|---|---|---|
| | Fresh | | Frozen | | Fresh | | Frozen | |
| ng/mL | Median | IQR | Median | IQR | Median | IQR | Median | IQR |
| 10000 | 3.3 | 3.2-4.2 | 3.5 | 2.9-3.8 | 10.1 | 8.6-12.1 | 10.6 | 9.1-13.0 |
| 3000 | 3.3 | 3.2-3.7 | 3.5 | 2.6-4.1 | 10.1 | 9.6-11.7 | 11.5 | 9.3-13.0 |
| 1000 | 3.3 | 3.24-3.8 | 3.6 | 3.0-3.8 | 11 | 9.6-11.7 | 9.9 | 9.4-11.4 |
| 300 | 3.4 | 3.3-3.8 | 3.7 | 2.9-4.0 | 10.1 | 9.5-12.5 | 11.3 | 9.9-11.9 |
| 100 | 3.3 | 2.5-3.7 | 3.6 | 3.0-4.2 | 10.5 | 9.3-12.3 | 11.9 | 10.8-12.7 |
| 10 | 3.3 | 3.0-3.5 | 3.3 | 2.5-4 | 10.6 | 9.3-13.6 | 11.8 | 9.2-14.1 |
| 0 | 3.6 | 3.4-4.3 | 4.1 | 3.6-5.7 | 17.8 | 16.2-22.9 | 22.5 | 15.5-24.8 |

TABLE 4

TGT on Citrated PPP with CTI - MoHA (n = 7)

| ARC19499 ng/mL | ETP[nM/min] Fresh Median | IQR | ETP[nM/min] Frozen Median | IQR | Peak[nM] Fresh Median | IQR | Peak[nM] Frozen Median | IQR |
|---|---|---|---|---|---|---|---|---|
| 10000 | 1548 | 1468-1672 | 1706 | 1406-2062 | 102.71 | 86-134 | 97 | 87-133 |
| 3000 | 1498 | 1331-1538 | 1637 | 1188-2054 | 99.39 | 68-130 | 94 | 88-130 |
| 1000 | 1366 | 1235-1603 | 1589 | 1212-2058 | 88.92 | 58-134 | 86 | 80-126 |
| 300 | 1314.5 | 965-1781 | 1349 | 1099-1762 | 81.25 | 57-90 | 81 | 68-108 |
| 100 | 919 | 835-1792 | 1085 | 939-1763 | 58.77 | 48-85 | 74 | 51-100 |
| 10 | 806 | 576-1102 | 796 | 740-1308 | 49.19 | 27-60 | 47 | 34-87 |
| 0 | 517.9 | 384-872 | 764 | 392-1105 | 22.62 | 16-42 | 41 | 16-64 |

| ARC19499 ng/ml | Lag time [min] Fresh Median | IQR | Lag time [min] Frozen Median | IQR | TT peak[min] Fresh Median | IQR | TT peak[min] Frozen Median | IQR |
|---|---|---|---|---|---|---|---|---|
| 10000 | 4 | 3.5-4.8 | 5.1 | 4.0-5.6 | 12.7 | 10.5-13.6 | 12.8 | 11.3-14.7 |
| 3000 | 4.2 | 4.0-4.8 | 5 | 3.3-5.5 | 12.5 | 10.3-13.4 | 12.6 | 11.3-13.1 |
| 1000 | 4.2 | 4.8-5.8 | 5.8 | 4.6-6.0 | 12.3 | 10.5-12.6 | 12.4 | 11.3-14.1 |
| 300 | 4.1 | 3.6-4.3 | 3.8 | 3-5.33 | 11.2 | 10.3-13.3 | 11.0 | 9.5-12.2 |
| 100 | 4.2 | 3.5-4.7 | 4.8 | 3.3-5.5 | 11.0 | 10.8-13.3 | 11.5 | 10-14.1 |
| 10 | 4.5 | 3.6-4.6 | 4.6 | 3.3-6.0 | 13.7 | 10.5-14.6 | 12.2 | 11.3-14.6 |
| 0 | 4.8 | 4-5.8.9 | 5.0 | 4.2-7 | 16.4 | 15-2.3 | 15.5 | 13.5-16.8 |

TABLE 5

TGT on Citrated PPP with CTI - Mild HA PPP (n = 5)

| ARC19499 ng/ml | ETP[nM/min] Fresh Median | IQR | ETP[nM/min] Frozen Median | IQR | Peak[nM] Fresh Median | IQR | Peak[nM] Frozen Median | IQR |
|---|---|---|---|---|---|---|---|---|
| 10000 | 1366 | 1081-1472 | 1361 | 1271-1708 | 93 | 75-138 | 98 | 87-112 |
| 3000 | 1187 | 913-1412 | 1273 | 1226-1520 | 87 | 65-116 | 81 | 72-97 |
| 1000 | 1097 | 871-1398 | 1245 | 1156-1330 | 82 | 62-102 | 77 | 72-88 |
| 300 | 1069 | 804-1317 | 1136 | 1026-1201 | 78 | 54-80 | 69 | 59-76 |
| 100 | 986 | 643-1149 | 1045 | 753-1145 | 62 | 37-77 | 61 | 40-67 |
| 10 | 709 | 421-1000 | 692 | 551-1068 | 42 | 19-52 | 39 | 25-58 |
| 0 | 532 | 337-823 | 493 | 372-800 | 28 | 14-37 | 25 | 16-41 |

| ARC19499 ng/ml | Lag time [min] Fresh Median | IQR | Lag time [min] Frozen Median | IQR | TT peak[min] Fresh Median | IQR | TT peak[min] Frozen Median | IQR |
|---|---|---|---|---|---|---|---|---|
| 10000 | 4 | 2.4-5.2 | 3.6 | 3-5.6 | 9.6 | 8-11.5 | 10.5 | 9.3-13.5 |
| 3000 | 4.1 | 2.1-5.1 | 3.3 | 2.3-5.7 | 9.8 | 8.8-11.5 | 10.3 | 9-12.4 |
| 1000 | 4.1 | 3-5.2 | 3.6 | 3.2-5.7 | 10.1 | 9-11.7 | 10.1 | 9.6-12.6 |
| 300 | 4 | 3.2-5.1 | 3.6 | 3.42-5.5 | 10.6 | 9.3-11.8 | 11 | 10.3-13.1 |
| 100 | 4.7 | 3.1-5.5 | 4.3 | 3.3-5.5 | 10.8 | 9.2-16.4 | 10.6 | 10.1-14.3 |
| 10 | 4.1 | 2.3-6 | 3.6 | 2.6-6.5 | 11.6 | 11.5-17.1 | 11.6 | 10.7-17.5 |
| 0 | 4.8 | 2.5-8.9 | 4.6 | 3.9-10.4 | 15.6 | 14.0-22 1 | 15.6 | 13.1-24.5 |

TABLE 6

TGT on Citrated PPP with CTI - SHB PPP (n = 5)

| ARC19499 ng/ml | ETP[nM/min] Fresh Median | IQR | ETP[nM/min] Frozen Median | IQR | Peak[nM] Fresh Median | IQR | Peak[nM] Frozen Median | IQR |
|---|---|---|---|---|---|---|---|---|
| 10000 | 1484 | 1129-1592 | 1736 | 1312-1850 | 74.3 | 70.5-117 | 106.1 | 77-122 |
| 3000 | 1360.7 | 1074-1459 | 1635 | 1229-1702 | 70.5 | 59-102 | 97.9 | 75-111 |
| 1000 | 1217.5 | 949-1435 | 1587.5 | 1200-1667 | 68.4 | 57.1-98.2 | 94.6 | 74-107 |

TABLE 6-continued

TGT on Citrated PPP with CTI - SHB PPP (n = 5)

| | | | | | | | | |
|---|---|---|---|---|---|---|---|---|
| 300 | 1167 | 893-1353 | 1429 | 999-1493 | 62.1 | 53.5-97.2 | 74.3 | 61-104 |
| 100 | 1075 | 671-1228 | 1154.5 | 850-1340 | 58.5 | 40.7-85 | 60.1 | 50-92 |
| 10 | 787.5 | 431-852 | 794.9 | 550-981 | 40 | 21.7-46.6 | 41 | 32-64 |
| 0 | 403 | 186-473 | 642 | 189-722 | 14.9 | 9.2-25.5 | 29.3 | 9-35 |

| | Lag time [min] | | | | TT peak[min] | | | |
|---|---|---|---|---|---|---|---|---|
| ARC19499 | Fresh | | Frozen | | Fresh | | Frozen | |
| ng/ml | Median | IQR | Median | IQR | Median | IQR | Median | IQR |
| 10000 | 6 | 4.7-6.3 | 5.3 | 4.9-6.4 | 12 | 11.3-14.8 | 13.7 | 12-14.5 |
| 3000 | 6 | 4.7-6 | 5.3 | 5-5.7 | 13.3 | 10.9-15.7 | 12.7 | 11.8-4.3 |
| 1000 | 5.3 | 4.6-6.3 | 5.5 | 4.5-6.5 | 12 | 10.1-14.6 | 12.3 | 11.4-4.4 |
| 300 | 5.5 | 4.9-5.9 | 5.7 | 5.3-5.8 | 12.7 | 9.8-14.5 | 12 | 11-13.8 |
| 100 | 5.3 | 4.7-6.2 | 5.5 | 5.1-6 | 12.3 | 9.9-15.1 | 12.5 | 10.9-3.7 |
| 10 | 5.7 | 4.9-6.8 | 5.3 | 5.1-6.5 | 12.7 | 11.1-19.7 | 13.3 | 11.2-4.3 |
| 0 | 7.8 | 6.4-9.6 | 7.2 | 5.8-8.8 | 19.8 | 14.2-23.4 | 16.7 | 14.6-8.8 |

TABLE 7

TGT on Citrated PPP with CTI - Normal PPP (n = 10)

| | ETP[nM/min] | | | | Peak[nM] | | | |
|---|---|---|---|---|---|---|---|---|
| ARC19499 | Fresh | | Frozen | | Fresh | | Frozen | |
| ng/ml | Median | IQR | Median | IQR | Median | IQR | Median | IQR |
| 10000 | 1696 | 1464-2286 | 2018 | 1455-2395 | 257 | 227-286 | 265 | 197-274 |
| 3000 | 1903 | 1788-2424 | 1897 | 1746-2356 | 245 | 205-270 | 261 | 210-272 |
| 1000 | 1680 | 1545-2072 | 1901 | 1283-2374 | 227 | 188-290 | 229 | 182-263 |
| 300 | 1964 | 1533-2245 | 1903 | 1548-2245 | 225 | 199-245 | 217 | 183-288 |
| 100 | 1973 | 1529-2231 | 1730 | 1512-2266 | 230 | 200-238 | 230 | 189-287 |
| 10 | 2087 | 1530-2125 | 2092 | 1611-2189 | 239 | 204-274 | 220 | 204-269 |
| 0 | 1847 | 1517-2329 | 2159 | 1745-2462 | 192 | 161-298 | 241 | 182-300 |

| | Lag time [min] | | | | TT peak[min] | | | |
|---|---|---|---|---|---|---|---|---|
| ARC19499 | Fresh | | Frozen | | Fresh | | Frozen | |
| ng/ml | Median | IQR | Median | IQR | Median | IQR | Median | IQR |
| 10000 | 4.3 | 3.7-4.6 | 3.4 | 3-3.5 | 7.9 | 6.7-8.9 | 8.1 | 7.2-9.4 |
| 3000 | 3.8 | 3.6-4.5 | 3.3 | 3.1-3.9 | 7.9 | 7.5-8.8 | 7.9 | 7.5-8.4 |
| 1000 | 4 | 3.5-4.6 | 3.5 | 3.3-3.9 | 8 | 7.7-9 | 7.0 | 7.4-8.7 |
| 300 | 4 | 3.5-4.7 | 3.5 | 3.2-3.9 | 8.3 | 7.9-9.3 | 8.2 | 7.3-9 |
| 100 | 3.9 | 3.3-4.4 | 3.5 | 3.1-3.9 | 8.7 | 7.9-8.9 | 8.5 | 6-10.3 |
| 10 | 3.7 | 3.4-5.1 | 4 | 3.2-5 | 9 | 7.9-10.8 | 9.1 | 7.2-10 |
| 0 | 4.5 | 3.7-4.6 | 3.8 | 3.2-4.7 | 9.5 | 7.1-10.4 | 9.2 | 7.5-9.9 |

Example 28

This example demonstrates that ARC19499 can improve clotting in whole blood and plasma samples from hemophilia A and hemophilia B patients, as measured by thromboelastography (TEG).

Blood was collected into 3.2 mL Vacuette tubes containing 3.2% sodium citrate and 250 μL 1.3 mg/mL corn trypsin inhibitor (CTI); the final CTI concentration was 100 μg/mL. Samples were collected from patients with severe (<1% FVIII; n=10), moderate (1-5% FVIII; n=7) and mild (5-40% FVIII; n=5) hemophilia A, patients with severe hemophilia B (<1% FIX, n=5) and healthy volunteers (n=10). To prepare platelet poor plasma (PPP) for CAT assays, tubes were centrifuged at 2500×g for 15 minutes, the supernatant transferred to fresh Eppendorf tubes, then centrifuged again at 11000×g for 5 minutes. Plasma was either used immediately or frozen at −80° C. for later use. To analyze the effects of ARC19499 on thrombin generation, ARC19499 was added to plasma at concentrations of 10, 100, 300, 1000, 3000 or 10,000 ng/mL (0.9, 9.0, 27.1, 90.3, 271 or 903 nM).

Thromboelastography (TEG) assays were performed using a TEG 5000 series instrument from Haemoscope. Whole blood TEG assays were performed by adding 300 μL whole blood to 40 μL 9 pM tissue factor (TF) and 20 μL 0.2 M $CaCl_2$ in a disposable reaction cup. Amplitude versus time traces were analyzed to obtain the R-time (length of time to initiate clot formation, amplitude=2 mm), K-value (measure of the speed of clot formation, equal to the time required to reach an amplitude of 20 mm) and the angle (another measure of the speed of clot formation, calculated from the tangent of the amplitude tracing drawn with its origin set to the R-time). Plasma TEG assays were performed similarly, except that supplementary phospholipids (PL) were included. In these assays 300 μL PPP was mixed with 10 μL 38 pM TF, 30 μL 48 μM PL (20% phosphatidyl serine, 20% phosphatidyl ethanolamine, 60% phosphatidyl choline; Avanti Polar Lipids) and 20 μL 0.2 M $CaCl_2$. The final PL concentration in these reactions was 4 μM.

Figure 104:
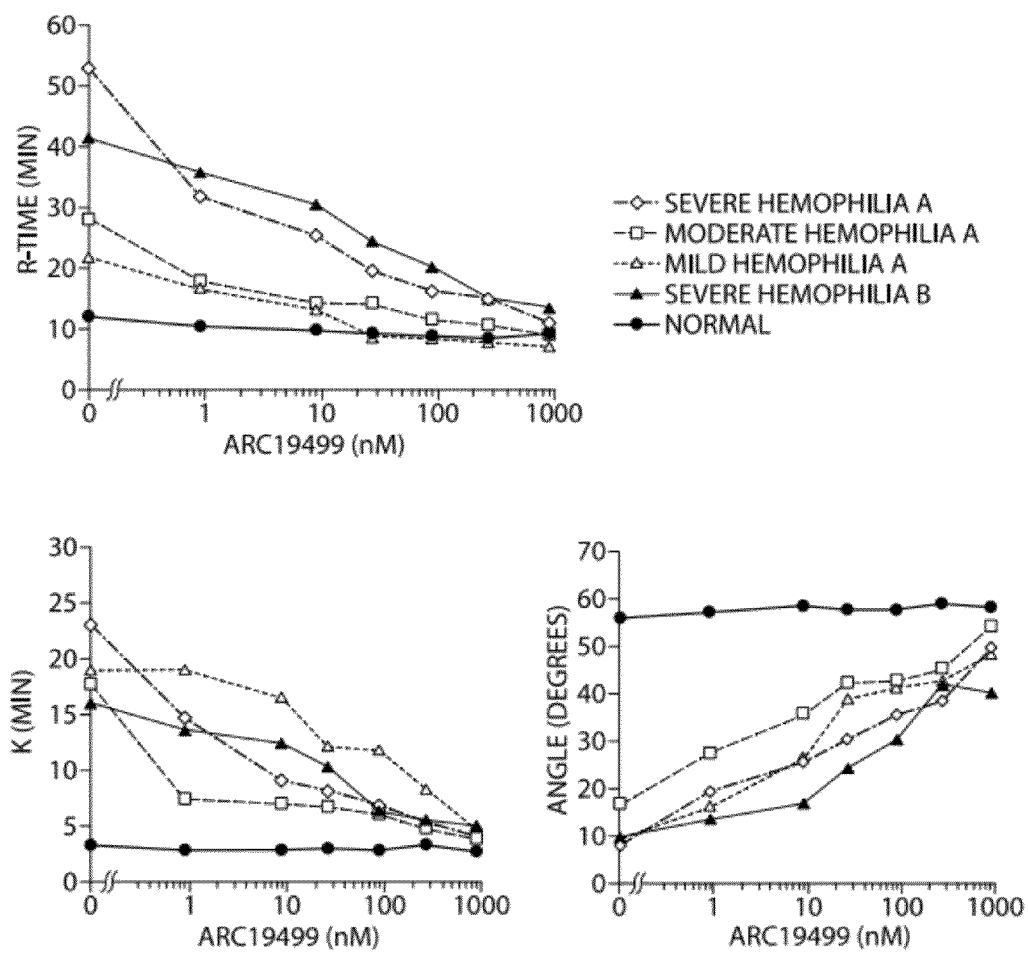
FIG. 104 is a series of graphs depicting median thromboelastography (TEG®) parameters (R-time, K and angle) measured in whole blood samples from patients with severe hemophilia A (empty diamonds), moderate hemophilia A (empty squares), mild hemophilia A (empty triangles) or severe hemophilia B (filled triangles) compared to healthy controls (filled circles).

FIGS. 100-103 show representative whole blood TEG data from a healthy volunteer (HV), a patient with severe hemophilia A (SHA), a patient with moderate hemophilia A (MoHA) and a patient with mild hemophilia A (MiHA). Median data for healthy volunteers, all three hemophilia A patient groups, and the severe hemophilia B patient group are shown in FIG. 104. The baseline R-time values were elevated in all hemophilia patient groups compared to healthy controls, indicating a delay in clot initiation, with the most significant effect observed in the severe hemophilia A and B samples. Additionally, the K-values were increased and angles decreased in hemophilia patient samples compared to healthy controls. Both of these effects indicate less rapid clot formation compared to normal, although the effects were similar in all patient groups regardless of the severity of factor deficiency.

As shown in the individual (FIGS. 101-103) and median data plots (FIG. 104), the addition of ARC19499 improved clot formation in whole blood, as measured by TEG. Increasing concentrations of ARC19499 (up to 10,000 ng/mL, 903 nM) substantially normalized all of the TEG parameters in all of the patient groups (FIG. 104). ARC19499 restored normal clot initiation (R-time) and development (K value and angle).

Figure 105:
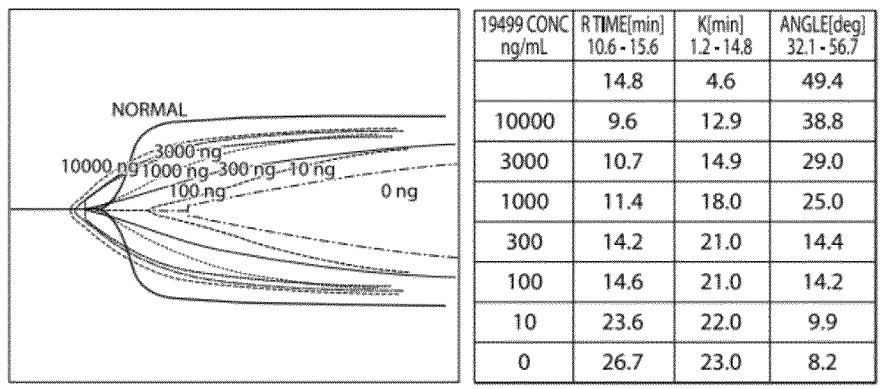
FIG. 105 shows representative plasma thromboelastography (TEG®) data from a patient with severe hemophilia A (ARC SHA 02).
Figure 106:
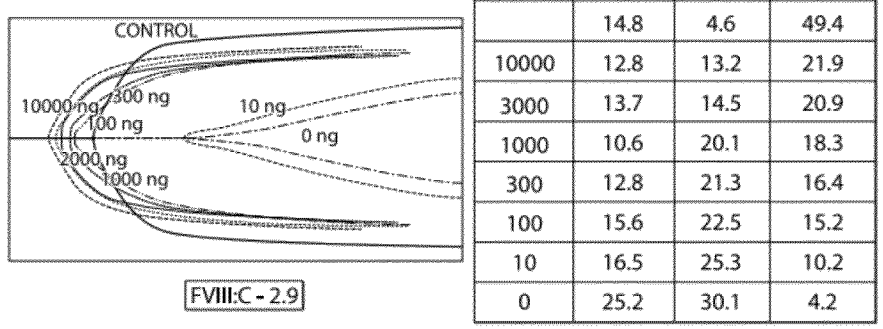
FIG. 106 shows representative plasma thromboelastography (TEG®) data from a patient with moderate hemophilia A (ARC MoHA 01).
Figure 107:
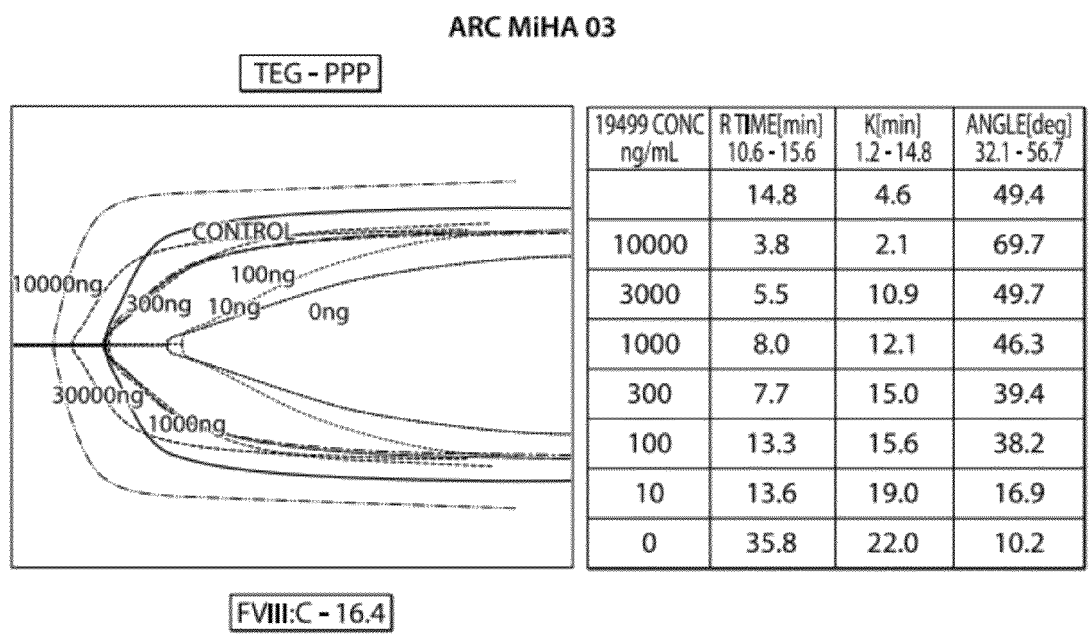
FIG. 107 shows representative plasma thromboelastography (TEG®) data from a patient with mild hemophilia A (ARC MiHA 03).
Figure 108:
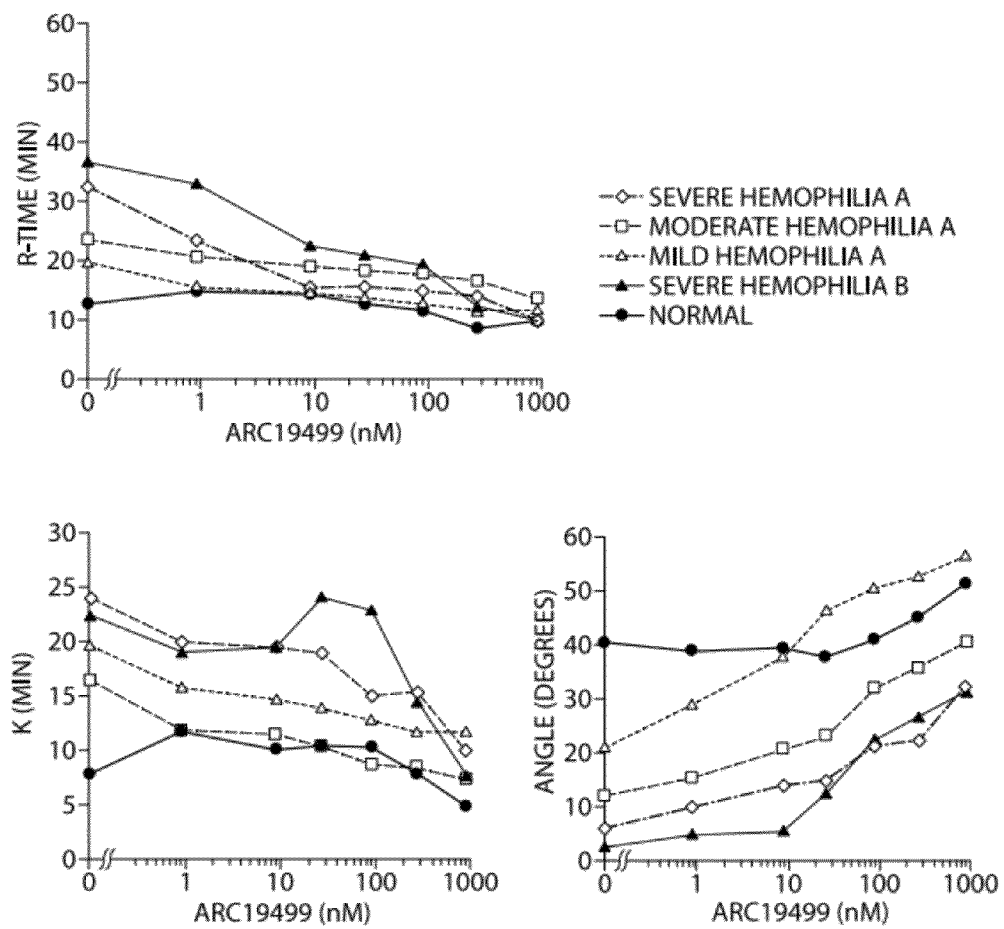
FIG. 108 is a series of graphs depicting median thromboelastography (TEG®) parameters (R-time, K and angle) measured in plasma samples from patients with severe hemophilia A (empty diamonds), moderate hemophilia A (empty squares), mild hemophilia A (empty triangles) or severe hemophilia B (filled triangles) compared to healthy controls (filled circles).

Similar results were observed in plasma TEG assays. Individual plasma TEG data from representative patients with severe hemophilia A (SHA), moderate hemophilia A (MoHA) mild hemophilia A (MiHA) are shown in FIGS. 105-107, and the median data are presented in FIG. 108. Baseline clotting effects in hemophilia plasma samples showed a trend toward correlation with disease severity in all three TEG parameters, with the most substantial effects observed for severe hemophilia A and B samples (FIG. 108). The addition of ARC19499 improved all three parameters describing clot formation. Increasing concentrations of ARC19499 appeared to normalize clotting in all of the patient groups, as measured by R-time and K-value. In contrast, while ARC19499 appeared to normalize the angle in both mild and moderate hemophilia A groups, the angle in the severe hemophilia A and B groups did not fully correct even at the highest ARC19499 concentration tested. Nevertheless, substantial improvement was observed in all of the groups.

Median data with interquartile ranges are presented for whole blood TEG measurements in the following tables: Table 8, severe hemophilia A (SHA); Table 9, moderate hemophilia A (MoHA); Table 10, mild hemophilia A (MiHA); Table 11, severe hemophilia B (SHB); and Table 12, normal. Additional tables show median data with interquartile ranges for plasma TEG measurements: Table 13, severe hemophilia A (SHA); Table 14, moderate hemophilia A (MoHA); Table 15, mild hemophilia A (MiHA); Table 16, severe hemophilia B (SHB); and Table 17, normal. In all of the tables, the expected normal range for each parameter is shown in italics in the column heading. Taken together, the data show that ARC19499 improves clot formation in hemophilia A patient plasma of all severity levels, and in severe hemophilia B plasma.

TABLE 8

TEG on Citrated Blood with CTI - SHA (n = 10)

| ARC 19499 | R time [min] 10.6-15.6 | | K [min] 1.2-14.8 | | Angle [deg] 32.1-56.7 | |
|---|---|---|---|---|---|---|
| (ng/ml) | Median | IQR | Median | IQR | Median | IQR |
| 10000 | 11.1 | 10.2-18.3 | 4 | 3.3-6.6 | 49.6 | 33.3-54.2 |
| 3000 | 15.2 | 11.2-20.4 | 5.3 | 3.6-7.5 | 38.7 | 31.2-50.8 |
| 1000 | 16.4 | 13.5-21.8 | 6.8 | 4.4-9.0 | 35.7 | 25.6-47.5 |
| 300 | 19.7 | 16.4-29.0 | 8.2 | 5.4-10.4 | 30.7 | 23.6-36.3 |
| 100 | 25.3 | 19.6-33.0 | 9 | 6.3-12.6 | 25.8 | 17.1-33.1 |
| 10 | 31.9 | 25.9-50.9 | 14.7 | 11.3-25.3 | 19.5 | 11.0-20.1 |
| 0 | 53 | 43.8-73.0 | 23 | 15.8-29.9 | 8.2 | 5.0-13.15 |

TABLE 9

TEG on Citrated Blood with CTI - MoHA (n = 7)

| ARC 19499 | R time [min] 5.9-16.3 | | K [min] 1.7-5.3 | | Angle [deg] 48.5-59 | |
|---|---|---|---|---|---|---|
| (ng/ml) | Median | IQR | Median | IQR | Median | IQR |
| 10000 | 9 | 4.5-12.4 | 3.8 | 3.2-4.8 | 54.1 | 51-59 |
| 3000 | 10.7 | 7.7-16.1 | 4.7 | 3.6-6.1 | 45.3 | 43.6-52 |
| 1000 | 11.6 | 6.75-17 | 6 | 3.9-10.4 | 43 | 29.7-50.3 |
| 300 | 14.1 | 6.0-16.2 | 6.7 | 3.8-10.8 | 42.5 | 30.4-48.7 |
| 100 | 14.3 | 10.2-17.8 | 7 | 6.0-9.2 | 35.9 | 29.1-40.1 |
| 10 | 18 | 11.2-21.5 | 7.4 | 4.0-10.1 | 27.7 | 26.6-37.8 |
| 0 | 28.1 | 21.7-37.5 | 17.6 | 6.8-20.8 | 17.1 | 9.3-23.6 |

TABLE 10

TEG on Citrated Blood with CTI - MiHA (n = 5)

| ARC 19499 | R time [min] 5.9-16.3 | | K [min] 1.7-5.3 | | Angle [deg] 48.5-59 | |
|---|---|---|---|---|---|---|
| (ng/ml) | Median | IQR | Median | IQR | Median | IQR |
| 10000 | 7.3 | 5.5-13.8 | 4.7 | 2.7-6.8 | 48.7 | 38.4-62.8 |
| 3000 | 7.8 | 6.5-17.2 | 8.3 | 6.4-12.4 | 42.8 | 30.0-47.6 |
| 1000 | 8.6 | 7.9-14.5 | 11.8 | 8.0-12.6 | 41.5 | 22.0-48.9 |
| 300 | 8.9 | 7.8-23.1 | 12.1 | 9.7-18.5 | 39.1 | 21.4-41.0 |
| 100 | 13.3 | 10.5-24.9 | 16.6 | 9.3-22.4 | 26.8 | 13.0-41.2 |
| 10 | 16.8 | 11.8-38.7 | 19 | 10.0-32.0 | 16.5 | 11.8-30.0 |
| 0 | 22 | 15.9-46.1 | 19 | 10.8-23.8 | 9.7 | 5.5-28.0 |

TABLE 11

TEG on Citrated Blood with CTI - SHB (n = 5)

| ARC 19499 | R time [min] 5.9-16.3 | | K [min] 1.7-5.3 | | Angle [deg] 48.5-67.9 | |
|---|---|---|---|---|---|---|
| (ng/ml) | Median | IQR | Median | IQR | Median | IQR |
| 10000 | 13.5 | 10.3-16.9 | 4.9 | 4.2-6.4 | 40.3 | 36-46.6 |
| 3000 | 15.2 | 12.2-18.6 | 5.5 | 5-6.4 | 41.9 | 36.3-42.6 |

TABLE 11-continued

TEG on Citrated Blood with CTI - SHB (n = 5)

| ARC 19499 (ng/ml) | R time [min] 5.9-16.3 | | K [min] 1.7-5.3 | | Angle [deg] 48.5-67.9 | |
|---|---|---|---|---|---|---|
| | Median | IQR | Median | IQR | Median | IQR |
| 1000 | 20.3 | 17.6-21.2 | 6.3 | 5.4-10.2 | 30.7 | 21.6-39.6 |
| 300 | 24.6 | 22.3-31.8 | 10.3 | 8-15.5 | 24.7 | 17.9-28.9 |
| 100 | 30.4 | 24.9-34.9 | 12.5 | 9.5-14 | 17 | 14.1-24.9 |
| 10 | 35.8 | 30.3-39.2 | 13.7 | 11.8-16.3 | 13.7 | 11.8-16.3 |
| 0 | 41.6 | 39.9-57.8 | 16 | 14.4-31.8 | 10.04 | 6.2-12.5 |

TABLE 12

TEG on Citrated Blood with CTI - HV (n = 10)

| ARC 19499 (ng/ml) | R time [min] 5.9-16.3 | | K [min] 1.7-5.3 | | Angle [deg] 48.5-67.9 | |
|---|---|---|---|---|---|---|
| | Median | IQR | Median | IQR | Median | IQR |
| 10000 | 9.3 | 8.7-10.3 | 2.7 | 2.1-3.5 | 58.2 | 51.7-61.6 |
| 3000 | 8.5 | 8.3-11.2 | 3.2 | 2.3-4.0 | 58.9 | 56.7-60.9 |
| 1000 | 8.8 | 8.4-10.5 | 2.8 | 2.2-3.2 | 57.8 | 54.8-63.6 |
| 300 | 9.3 | 8.4-11.2 | 2.9 | 2.6-3.4 | 57.8 | 54.2-61.2 |
| 100 | 9.9 | 7.2-12.2 | 2.8 | 2.3-4.5 | 58.5 | 50.0-62.6 |
| 10 | 10.4 | 9.4-11.5 | 2.8 | 2.3-3.1 | 57.1 | 52.0-62.6 |
| 0 | 12 | 8.6-12.9 | 3.2 | 2.8-4.2 | 56 | 51.6-57.9 |

TABLE 13

TEG on Citrated PPP with CTI - SHA (n = 10)

| ARC 19499 (ng/ml) | R time [min] 10.6-15.6 | | K [min] 1.2-14.8 | | Angle [deg] 32.1-56.7 | |
|---|---|---|---|---|---|---|
| | Median | IQR | Median | IQR | Median | IQR |
| 10000 | 10.3 | 8.9-21.5 | 10 | 7.5-14.7 | 32.3 | 24.1-38.5 |
| 3000 | 14.2 | 10.4-23.8 | 15.4 | 10.9-17.3 | 22.3 | 16.5-25.7 |
| 1000 | 15 | 15.7-25.7 | 15.1 | 12.1-19.0 | 21.2 | 18.8-23.9 |
| 300 | 15.7 | 9.8-29.5 | 19 | 7.8-21.0 | 14.9 | 11.6-16.8 |
| 100 | 15.8 | 14.3-34.1 | 19.6 | 18.3-21.0 | 14 | 10.7-14.4 |
| 10 | 23.6 | 15.7-29.8 | 20 | 19.8-23.0 | 9.9 | 8.8-10.7 |
| 0 | 32.6 | 25.5-55.4 | 24.1 | 20.4-27.3 | 6.1 | 4.4-7.9 |

TABLE 14

TEG on Citrated PPP with CTI - MoHA (n = 7)

| ARC 19499 (ng/ml) | R time [min] 10.6-15.6 | | K [min] 1.2-14.8 | | Angle [deg] 32.1-56.7 | |
|---|---|---|---|---|---|---|
| | Median | IQR | Median | IQR | Median | IQR |
| 10000 | 13.8 | 11.5-15.2 | 7.3 | 4.9-9.9 | 40.4 | 35.8-45.6 |
| 3000 | 16.8 | 10.6-21 | 8.5 | 5.9-8.9 | 35.6 | 30.9-40.2 |
| 1000 | 17.9 | 12-22.1 | 8.7 | 5.1-10.1 | 32 | 27.1-36.2 |
| 300 | 18.5 | 12.6-22.5 | 10.4 | 7.4-12.3 | 23 | 17.3-29.1 |
| 100 | 19.1 | 11.9-23.5 | 11.5 | 9.3-14.4 | 20.7 | 19.2-24.6 |
| 10 | 20.9 | 13.8-25.6 | 11.9 | 9.6-14.4 | 15.2 | 13.1-18.7 |
| 0 | 23.6 | 18.2-28.1 | 16.5 | 13-18 | 12 | 7.9-14 |

TABLE 15

TEG on Citrated PPP with CTI - MiHA (n = 5)

| ARC 19499 (ng/ml) | R time [min] 10.6-15.6 | | K [min] 1.2-14.8 | | Angle [deg] 32.1-56.7 | |
|---|---|---|---|---|---|---|
| | Median | IQR | Median | IQR | Median | IQR |
| 10000 | 11.8 | 3.4-11.9 | 3.3 | 1.3-3.8 | 56.6 | 53.3-73.9 |
| 3000 | 11.8 | 5.2-13.9 | 3.4 | 2.0-4.0 | 52.6 | 51.3-66.4 |
| 1000 | 12.8 | 4.0-14.9 | 3.4 | 2.3-4.9 | 50.6 | 47.8-62.0 |
| 300 | 14 | 3.7-18.6 | 3.7 | 3.5-3.8 | 46.4 | 44.1-52.6 |
| 100 | 14.7 | 5.6-21.7 | 5 | 3.8-6.2 | 37.9 | 34.5-41.1 |
| 10 | 15.8 | 13.9-22.0 | 7.4 | 4.2-10.1 | 29.1 | 23.5-35.1 |
| 0 | 19.8 | 17.7-26.9 | 9.6 | 4.6-12.2 | 21.1 | 16.2-35.0 |

TABLE 16

TEG on Citrated PPP with CTI - SHB (n = 5)

| ARC 19499 (ng/ml) | R time [min] 10.6-15.6 | | K [min] 1.2-14.8 | | Angle [deg] 32.1-56.7 | |
|---|---|---|---|---|---|---|
| | Median | IQR | Median | IQR | Median | IQR |
| 10000 | 10.2 | 8.2-14.3 | 7.7 | 4.8-17.7 | 31.2 | 20.6-49.9 |
| 3000 | 12.3 | 9.7-16.9 | 14.5 | 6.5-23.2 | 26.6 | 17.2-24.1 |
| 1000 | 19.2 | 12.7-21.8 | 23 | 8.5-26.5 | 22.4 | 12.1-30.4 |
| 300 | 21 | 12.5-28.5 | 24.2 | 14.3-28.8 | 12.5 | 5.2-20.4 |
| 100 | 22.6 | 13.6-31.6 | 19.6 | 16.8-27.4 | 5.3 | 4.9-15.3 |
| 10 | 33.1 | 16.9-38.3 | 19.1 | 17.1-28.4 | 4.8 | 3.7-14.1 |
| 0 | 36.7 | 27.9-44.5 | 22.5 | 20.5-59.9 | 2.6 | 1.5-7.6 |

TABLE 17

TEG on Citrated PPP with CTI - HV (n = 10)

| ARC 19499 (ng/ml) | R time [min] 10.6-15.6 | | K [min] 1.2-14.8 | | Angle [deg] 32.1-56.7 | |
|---|---|---|---|---|---|---|
| | Median | IQR | Median | IQR | Median | IQR |
| 10000 | 9.8 | 6.7-13.2 | 4.8 | 3.5-6.4 | 51.2 | 50.0-53.2 |
| 3000 | 8.7 | 7.0-10.7 | 7.8 | 5.2-10.8 | 45 | 44.0-49.9 |
| 1000 | 11.6 | 11.0-12.1 | 10.3 | 5.8-10.5 | 40.9 | 39.9-42.0 |
| 300 | 12.7 | 12.1-13.8 | 10.4 | 6.5-11.3 | 37.7 | 36.5-40.3 |
| 100 | 14.3 | 13.1-15.3 | 10.1 | 5.9-11.2 | 39.3 | 39.6-49.0 |
| 10 | 15 | 13.1-15.7 | 11.7 | 10.1-11.9 | 38.8 | 38.2-44.7 |
| 0 | 12.7 | 12.1-14.3 | 7.9 | 4.9-11.3 | 40.3 | 38.5-48.3 |

Example 29

This example demonstrates that the in vitro activity of ARC19499 can be reversed.

Figure 109A:
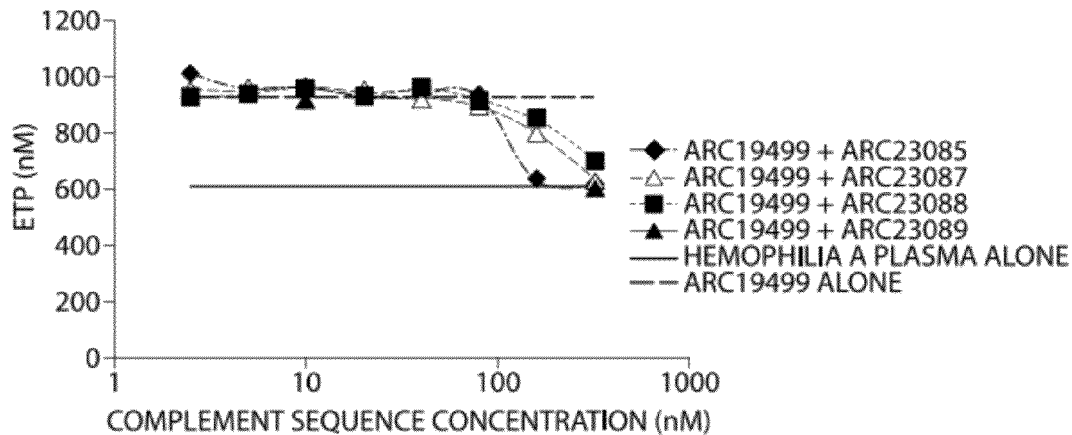
FIG. 109A) and peak thrombin (FIG. 109B). Addition of ARC23085 (filled diamonds), ARC23087 (empty triangles), ARC23088 (filled squares) and ARC23089 (filled triangles) can reverse this improvement at concentrations $\geq$100 nM, reaching similar levels to the absence of ARC19499.
Figure 109B:
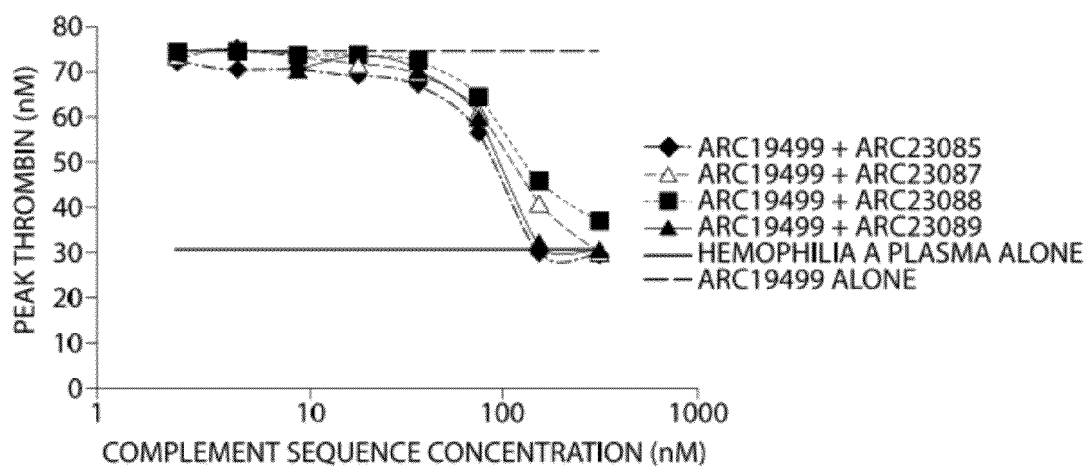
FIG. 109 is a series of graphs showing that ARC19499 activity can be reversed. ARC19499 (dashed line) improved thrombin generation in the calibrated automated thrombogram (CAT) assay compared to hemophilia A plasma alone (solid line), as measured by endogenous thrombin potential (ETP.
In FIG. 109C, R-values from the thromboelastography (TEG®) assay showed that 500 nM ARC19499 shortens the R-value that is prolonged in hemophilia A plasma. 1 µM ARC23085 partially reversed this improvement with and without a 5 minute preincubation at 37° C. ARC23087 reversed the improvement with the addition of a 5 minute preincubation at 37° C. ARC23088 showed little reversal at either condition. ARC23089 also reversed the ARC19499 improvement with a 5 minute preincubation at 37° C.

Four reversal agents (ARC23085, ARC23087, ARC23088 and ARC23089) were mixed with ARC19499 and tested in both the calibrated automated thrombogram (CAT) and the thromboelastography (TEG®) assays in hemophilia A plasma (FIG. 109).

For the CAT assay, ARC19499 was incubated with each reversal agent individually for 5 minutes at 37° C. The mixture was then added to hemophilia A plasma at a final concentration of 100 nM ARC19499 and increasing concentrations of ARC23085, ARC23087, ARC23088, or ARC23089 (2.5, 5, 10, 20, 40, 80, 160, and 320 nM). The CAT assay was then performed as previously described using a final TF concentration of 1.0 pM. ARC19499 alone improved the ETP of hemophilia A plasma from ~600 nM to ~900 nM (FIG.

109A). All four tested reversal agents blocked this improvement when tested at concentrations >80 nM. ARC23085 and ARC23089 almost completely reversed ARC19499 activity at 160 nM, while ARC23087 and ARC23088 almost completely reversed ARC19499 activity at 320 nM. Looking at peak thrombin (FIG. 109B), the four reversal agents showed a similar partial reversal of ARC19499 activity at 80 nM. Again, by 160 nM, ARC23085 and ARC23089 completely reversed ARC19499 activity, while the other two reversal agents did so by 320 nM.

Figure 109C:
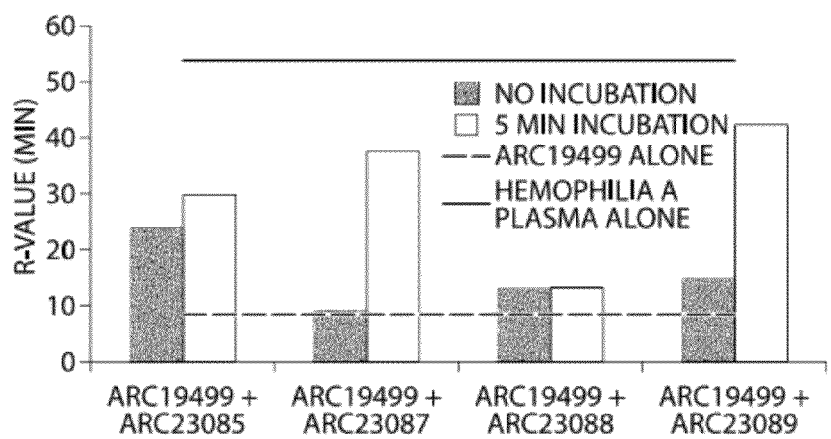

For the TEG® assay, ARC19499 and one of each of the four reversal agents were mixed with hemophilia A plasma, and clotting was initiated with the addition of TF and $CaCl_2$. This was performed with and without a 5 minute preincubation of ARC19499 and the additional reversal agent at 37° C. When ARC19499 was tested alone, the aptamer corrected the prolonged R-value of hemophilia A plasma from 54 minutes to 8.3 minutes (FIG. 109C). ARC23085 partially reversed this improvement with R-values of 30 and 24 minutes with and without the 5 minute preincubation, respectively. ARC23087 demonstrated no ability to reverse ARC19499 when there was no preincubation, but with the incubation it did reverse ARC19499 activity, resulting in an R-value of 38 minutes. ARC23088 demonstrated little to no ability to reverse ARC19499 activity in this assay, independent of any preincubation. Similar to ARC23087, ARC23089 showed little ability to reverse ARC19499 activity when there was no preincubation. But, when the reversal agent was incubated with ARC19499 prior to the assay, it reversed ARC19499 activity almost completely, resulting in an R-value of 42 minutes (FIG. 109C).

These experiments indicate that the in vitro activity of ARC19499 can be reversed.

Example 30

This example demonstrates that ARC19499 does not inhibit the in vitro anti-coagulant activity of low molecular weight heparin (LMWH).

Figure 110A:
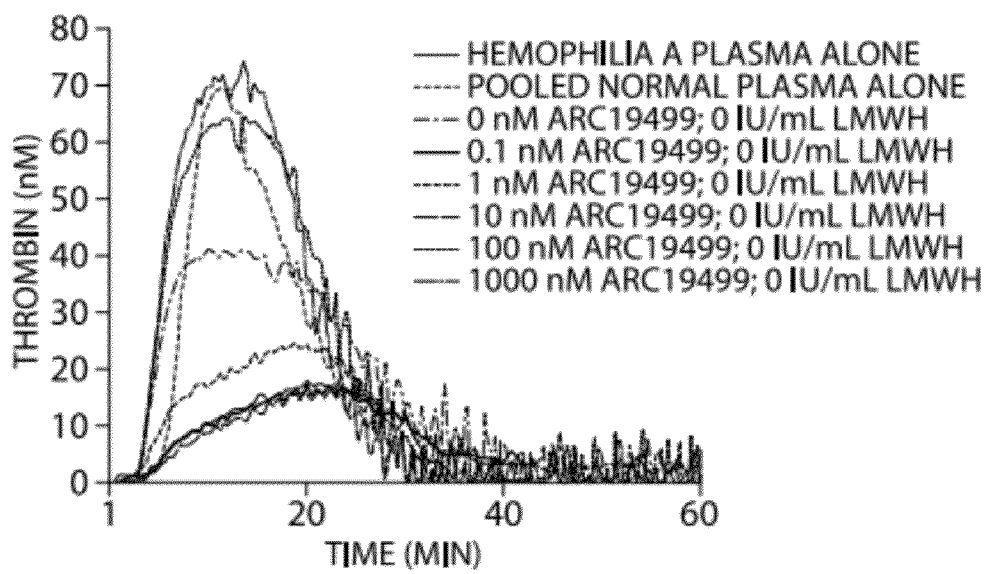
FIG. 110 is a series of thrombin generation curves from the calibrated automated thrombogram (CAT) assay showing the activity of ARC19499 in hemophilia A plasma in the presence of 0.00 (FIG. 110A), 0.156 (FIG. 110B), 0.312 (FIG. 110C), 0.625 (FIG. 110D), 1.25 (FIG. 110E), 2.50 (FIG. 110F) or 5.00 IU/mL (FIG. 110G) low molecular weight heparin (LMWH).
Figure 110B:
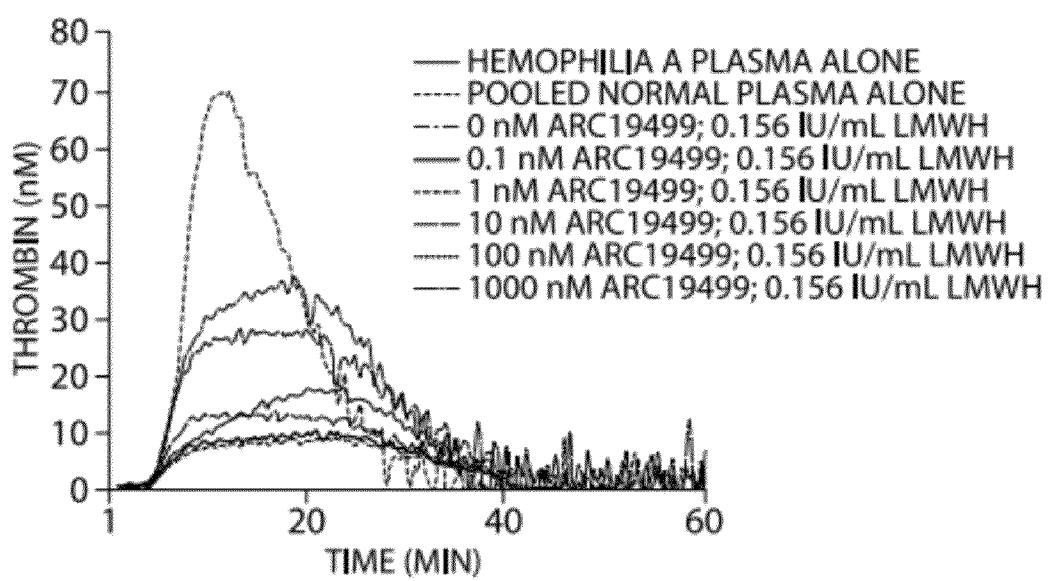
Figure 110C:
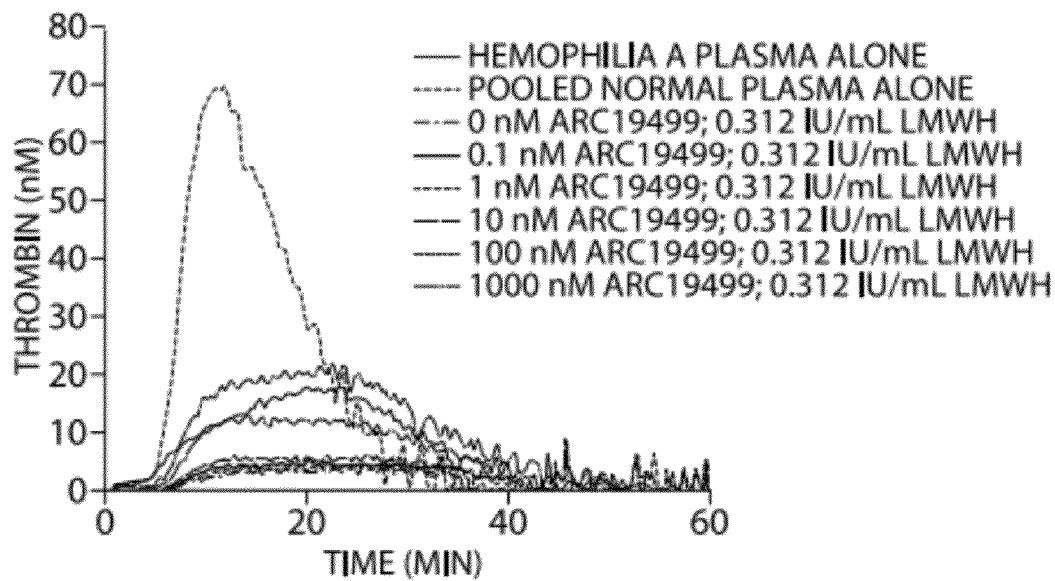
Figure 110D:
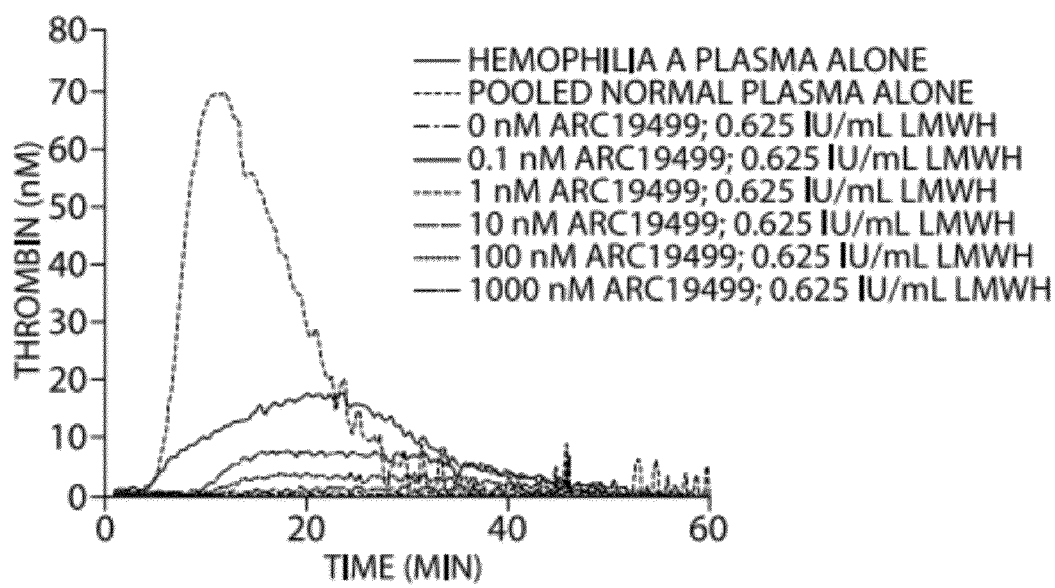
Figure 110E:
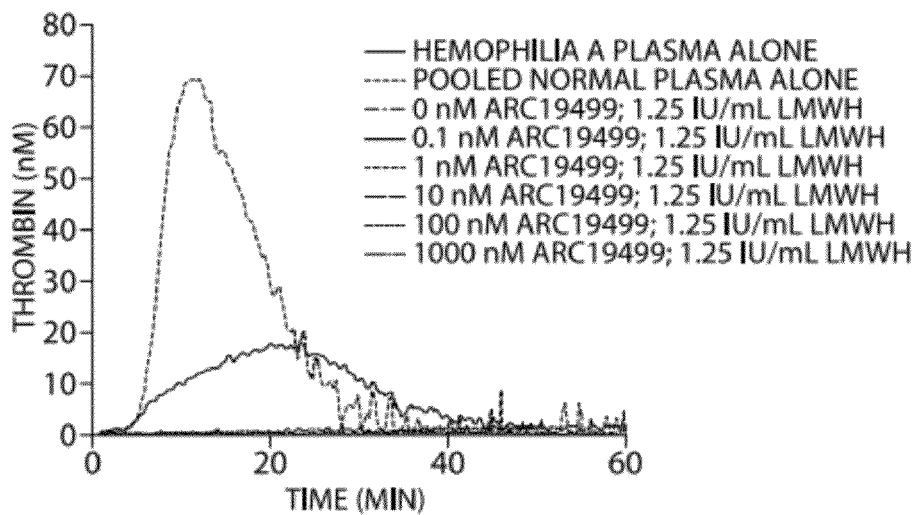
Figure 110F:
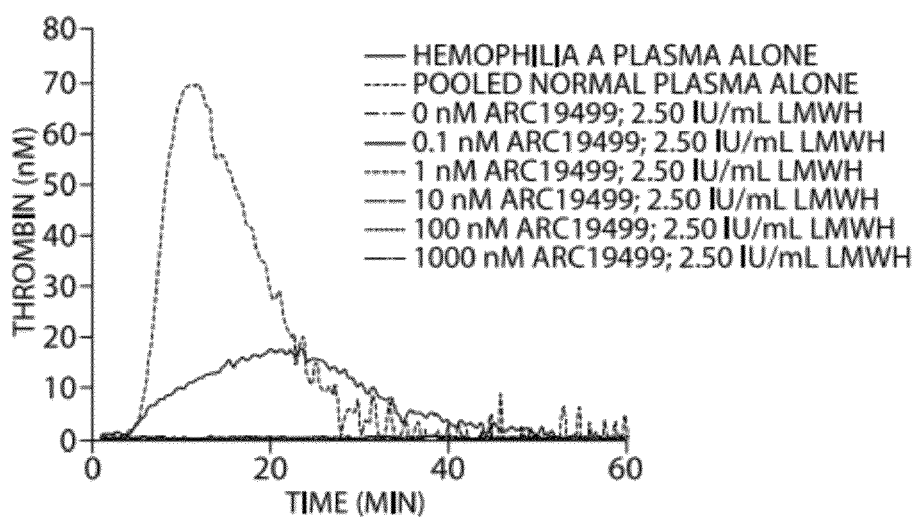
Figure 110G:
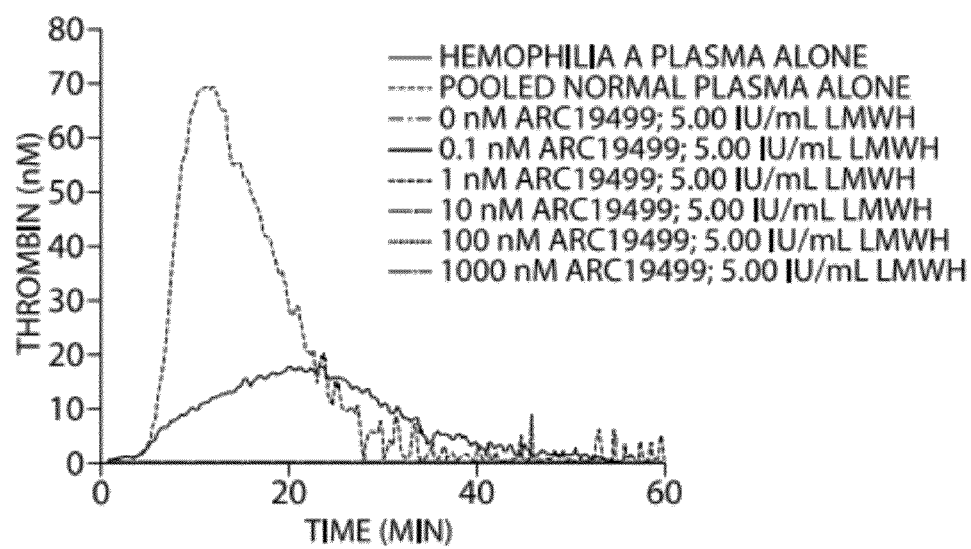

In this assay, increasing concentrations of ARC19499 and increasing concentrations of LMWH were mixed together and added to hemophilia A plasma. The thrombin generation ability of these plasma mixtures was analyzed using the calibrated automated thrombogram (CAT) assay. FIG. 110 shows the thrombin generation curves of the increasing aptamer concentrations in the presence of each LMWH concentration. ARC19499 was tested at 0.1, 1, 10, 100 and 1000 nM. LMWH was tested at 0 (FIG. 110A), 0.156 (FIG. 110B), 0.312 (FIG. 110C), 0.625 (FIG. 110D), 1.25 (FIG. 110E), 2.5 (FIG. 110F) and 5.0 IU (international units)/mL (FIG. 110G).

Figure 111A:
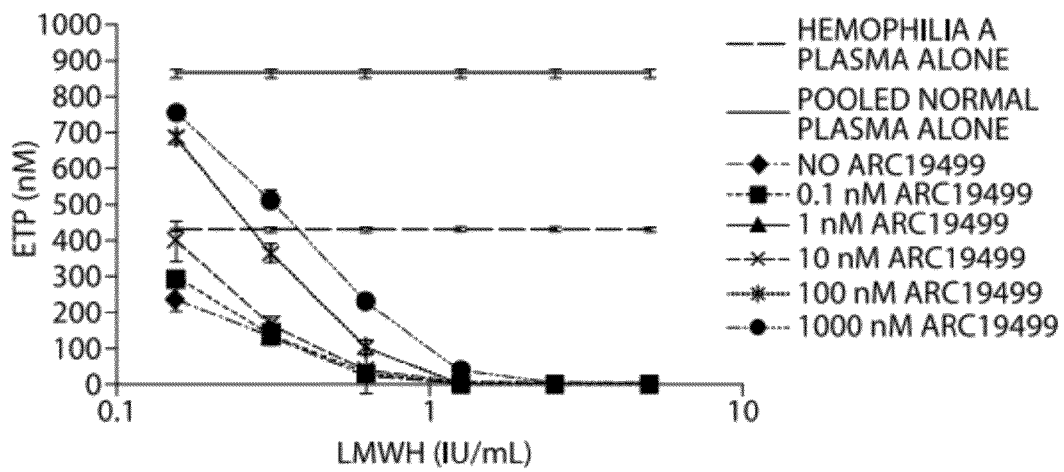
FIG. 111A) and peak thrombin (FIG. 111B) from calibrated automated thrombogram (CAT) assays performed in hemophilia A plasma with increasing concentrations of both ARC19499 and LMWH. The concentration of LMWH is denoted on the x-axis in units of IU/mL. At therapeutic doses of LMWH ($\geq$1.25 IU/mL), the procoagulant activity of ARC19499 was reversed.
Figure 111B:
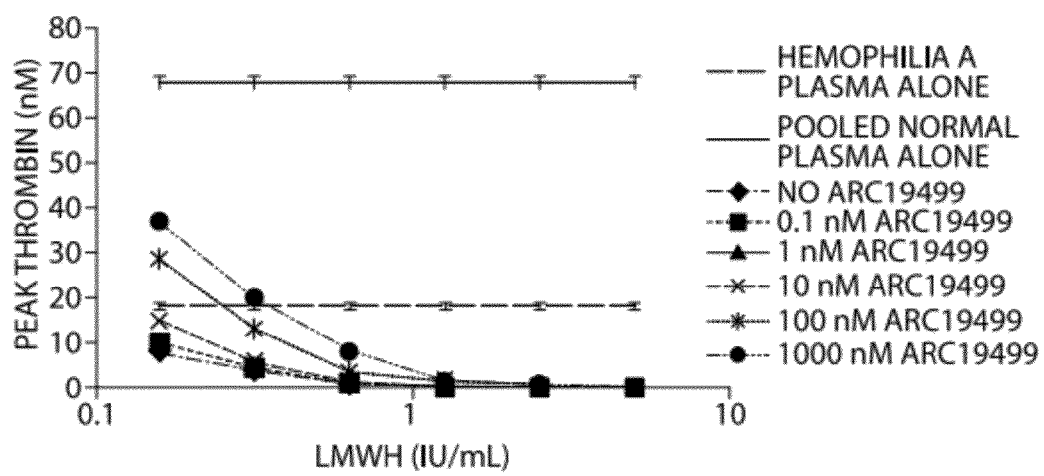
FIG. 111 is a series of graphs showing the endogenous thrombin potential (ETP.
Figure 112A:
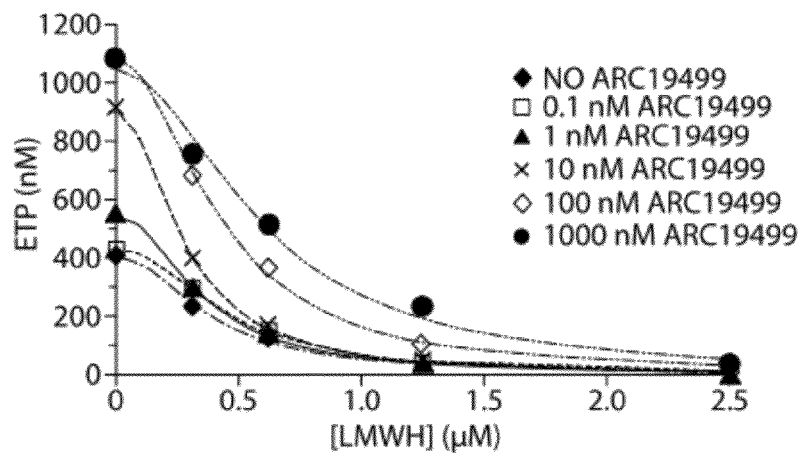
FIG. 112A) and peak thrombin (FIG. 112B) from calibrated automated thrombogram (CAT) assays performed in hemophilia A plasma with increasing concentrations of both ARC19499 and LMWH. The concentration of LMWH is denoted on the x-axis in units of µM. The data in these graphs were analyzed by curve-fitting to generate estimates of LMWH $IC_{50}$ in the presence of various ARC19499 concentrations. The $IC_{50}$ values may be found in the table below the graphs.
Figure 112B:
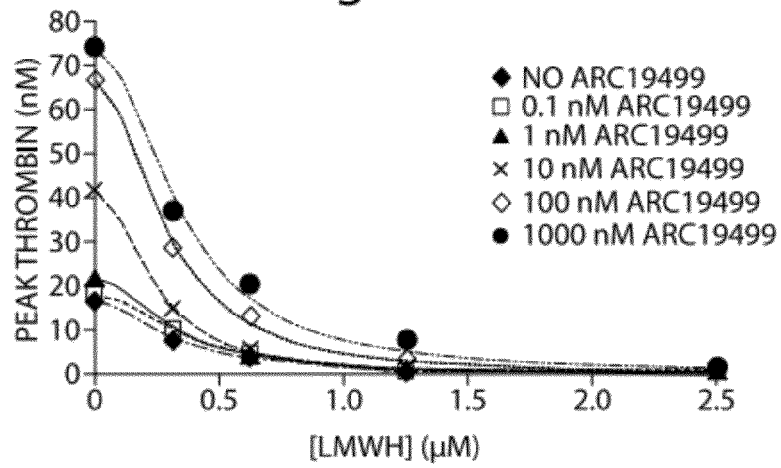
FIG. 112 is a series of graphs showing the endogenous thrombin potential (ETP.

In FIG. 111A, the ETP values for each combination were plotted along the y-axis, with the LMWH concentrations on the x-axis. The same was true for peak thrombin values in FIG. 111B. In both cases, therapeutic doses of LMWH (0.5-1.0 IU/mL) strongly inhibited thrombin generation, and higher concentrations almost completely prevented any thrombin from being generated, even in the presence of up to 1000 nM ARC19499 (FIG. 111). $IC_{50}$ values of 381±24.3 nM and 299±18.0 nM for LMWH were calculated from the ETP and peak thrombin data, respectively, in the absence of ARC19499, and these results are consistent with previous measurements (Robert et al., Is thrombin generation the new rapid, reliable and relevant pharmacological tool for the development of anticoagulant drugs?, *Pharmacol Res.* 2009; 59:160-166). Increasing concentrations of ARC19499 did not appear to significantly alter the $IC_{50}$ of LMWH (FIG. 112), indicating that ARC19499 does not interfere with the anticoagulant activity of LMWH.

This experiment indicates that even in the presence of 1000 nM ARC19499, therapeutic doses of LMWH still remain anti-coagulant in an in vitro assay.

Example 31

This example demonstrates that the TFPI aptamers are stable to serum nucleases.

In this experiment, 50 µM of each aptamer was incubated in 90% pooled human, cynomolgus monkey or rat serum for 72 hours at 37° C. Samples were analyzed by HPLC and the percent remaining as a function of incubation time was determined, as shown in FIG. 113.

Figure 113A:
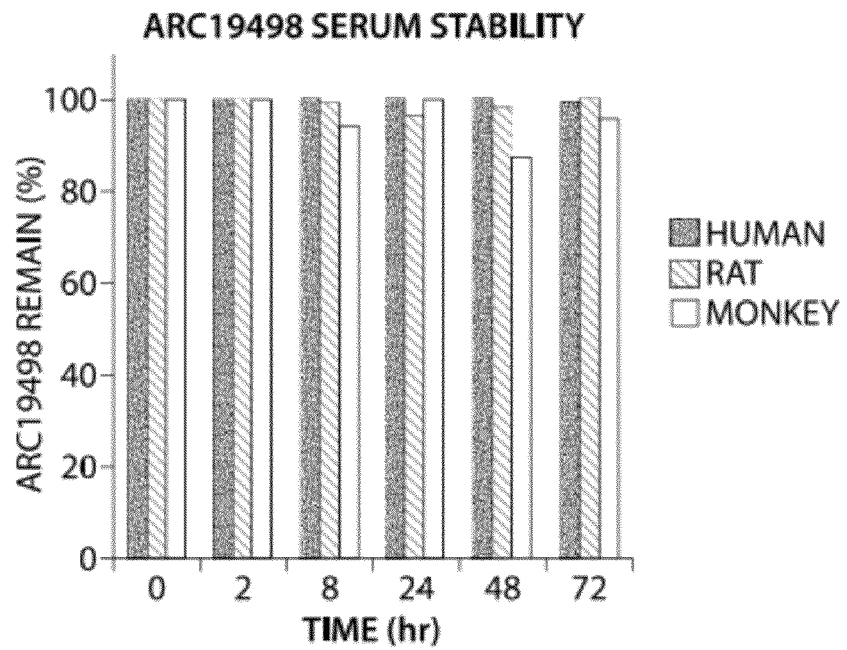
FIG. 113 is a series of graphs showing the in vitro stability of several TFPI aptamers in serum. The stability of ARC19498 (FIG. 113A), ARC19499 (FIG. 113B), ARC19500 (FIG. 113C), ARC19501 (FIG. 113D), ARC19881 (FIG. 113E) and ARC19882 (FIG. 113F) in human, monkey and rat serum were measured over the course of 72 hours.
Figure 113B:
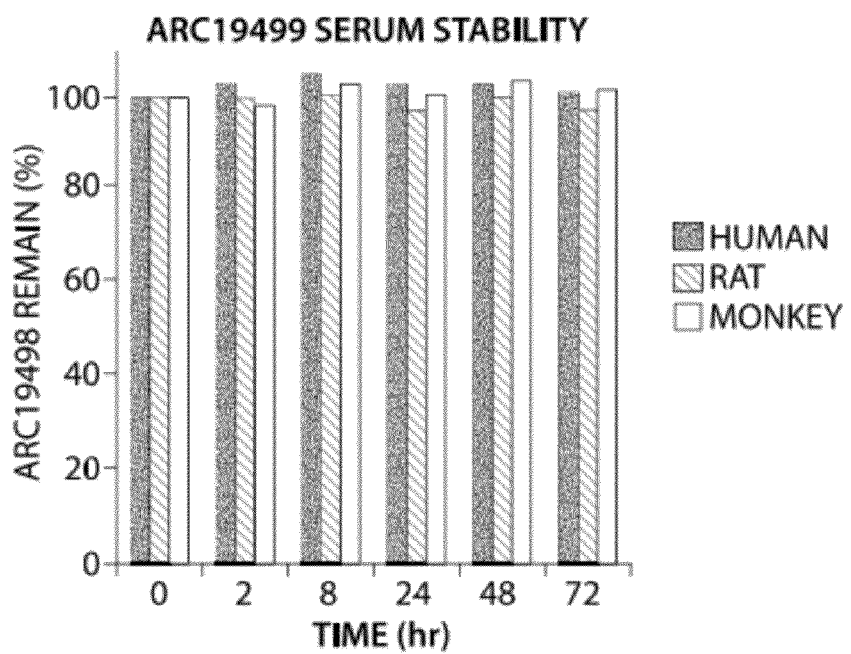
Figure 113C:
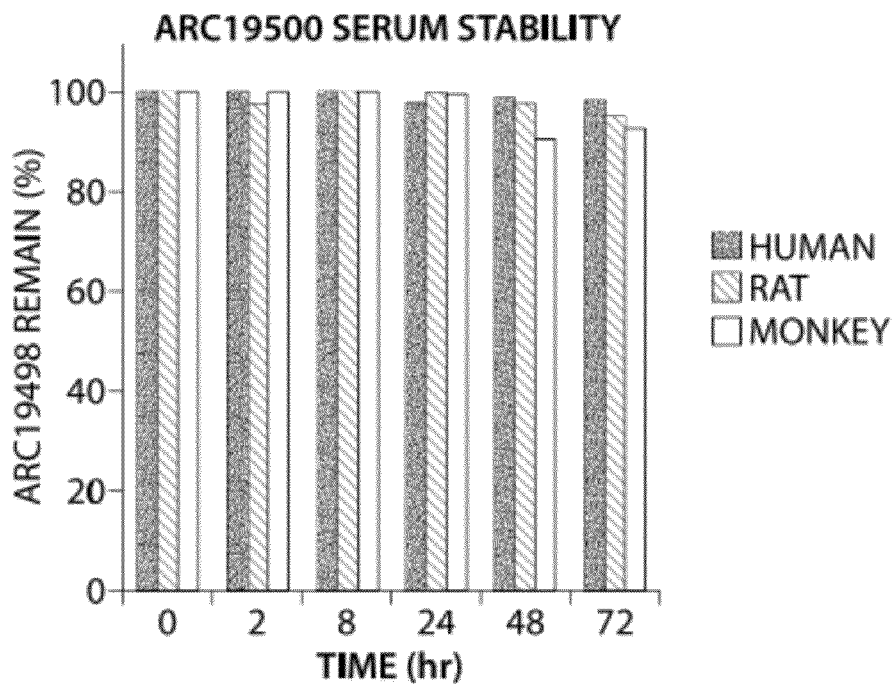

Both ARC19498 and ARC19499 were >95% stable over the course of 72 hours in human, monkey and rat serum (FIGS. 113A and 113B).

Figure 113D:
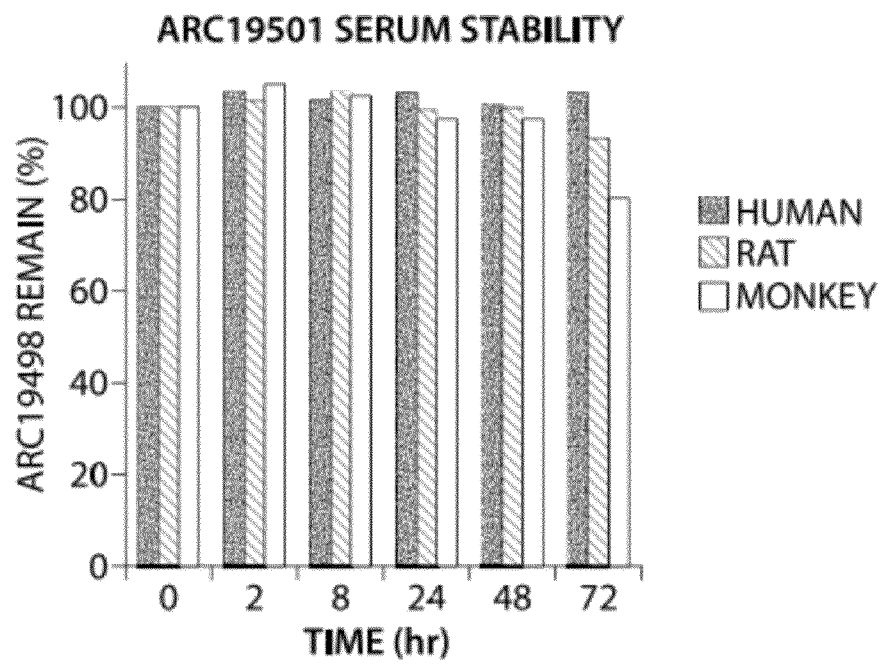
Figure 113E:
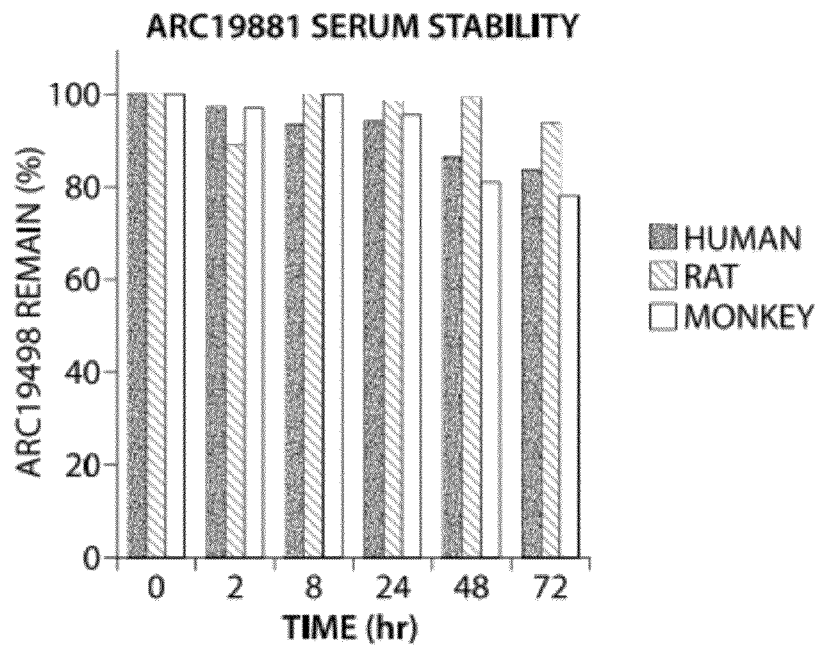

ARC19500 was >92% stable over the course of 72 hours in human, monkey and rat serum (FIG. 113C), and ARC19501 was >80% stable over the course of 72 hours in human, monkey and rat serum (FIG. 113D).

Figure 113F:
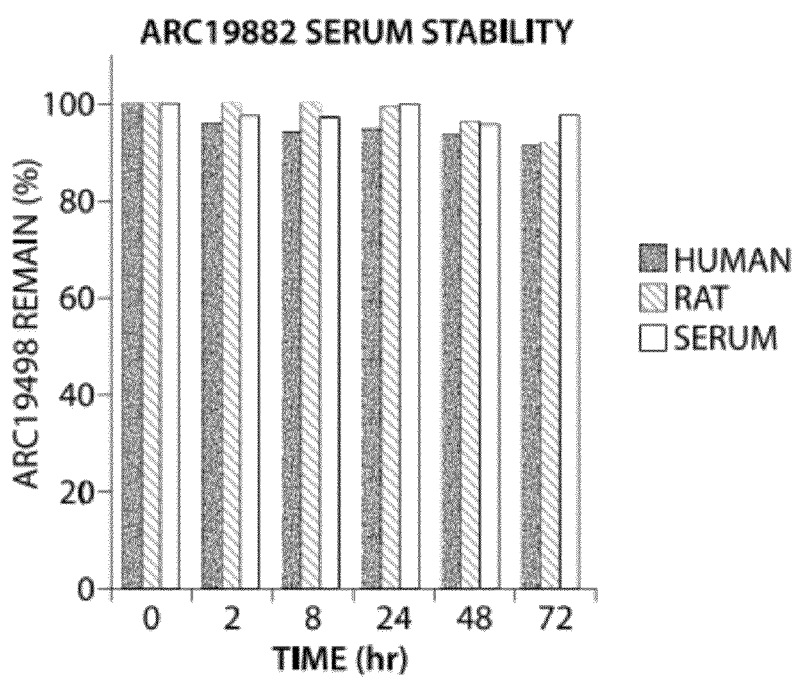

ARC19881 was >78% stable over the course of 72 hours in human, monkey and rat serum (FIG. 113E), and ARC19882 was >91% stable over the course of 72 hours in human, monkey and rat serum (FIG. 113F).

Example 32

This example demonstrates that the TFPI aptamers have biological activity.

In this experiment, a non-human primate model of hemophilia A was created by injecting cynomolgus monkeys with a single intravenous (IV) bolus of sheep polyclonal antibody against human Factor VIII (20 mg; 50,000 Bethesda Units). 3.5 hours after the IV injection, the monkeys were treated with either saline (1 mL/kg), recombinant Factor VIIa (rFVIIa) (NovoSeven®; 90 µg/kg bolus) or ARC19499 (either a 600 µg/kg, 300 µg/kg or 100 µg/kg bolus). Citrated blood samples were acquired before antibody administration (baseline), 2.5 hours after antibody administration, 15 minutes after drug/saline treatment (time=3.75 hours), and 1 and 2 hours after drug/saline treatment (time=4.5 and 5.5 hours, respectively). Blood was processed to generate plasma, and citrated plasma samples were assayed for prothrombin time (PT), activated partial thromboplastin time (aPTT), Factor VIII function and thromboelastography (TEG®). The saline-treated monkey received a treatment of ARC19499 (600 µg/kg) after the 5.5 hour time point was drawn. Fifteen minutes after receiving this treatment, another citrated blood sample was drawn and processed for plasma.

Figure 114:
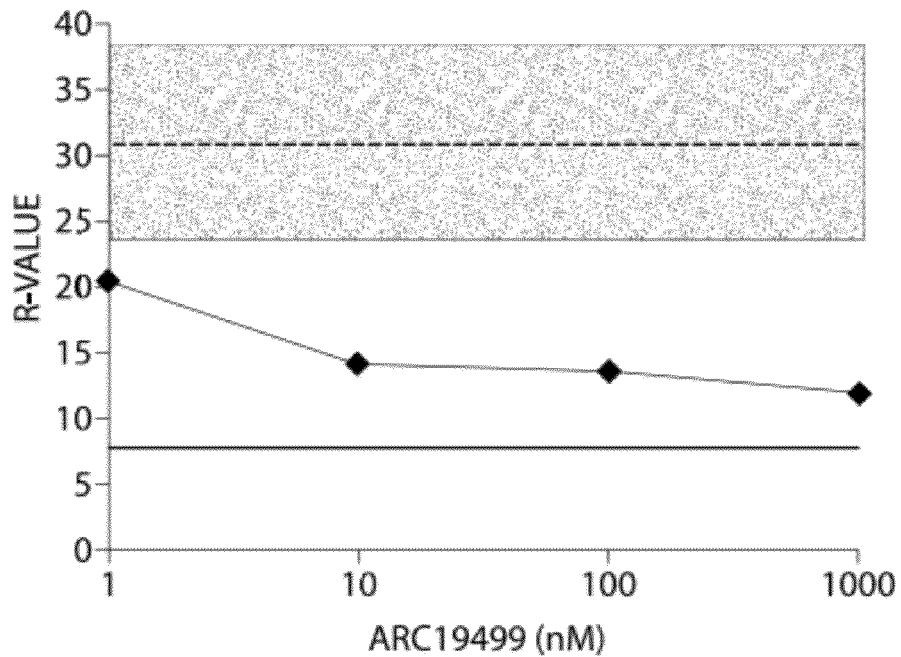
FIG. 114 is a graph of a thromboelastography (TEG®) assay where plasma from cynomolgus monkeys that were treated previously with an anti-human FVIII antibody was mixed with increasing concentrations of ARC19499 and assayed for activity. The solid line represents plasma from untreated monkeys and the dashed line represents plasma from antibody treated monkeys, both in the absence of aptamer. The data represents mean±standard error, with the shaded areas representing the standard error of the non-aptamer samples.

In order to ensure that ARC19499 inhibits monkey TFPI, plasma taken from monkeys after antibody treatment were mixed, ex vivo, with increasing concentrations of ARC19499 from 1 to 1000 nM, and tested in a TEG® assay (FIG. 114). The plasma mixed with aptamer was compared to plasma without aptamer, both before and after antibody treatment (solid and dashed lines, respectively). Antibody treatment alone prolonged the R-value. The addition of ARC19499 to this antibody-treated plasma corrected the R-value to near baseline levels, suggesting the aptamer was cross-reactive with monkey plasma.

Figure 115:
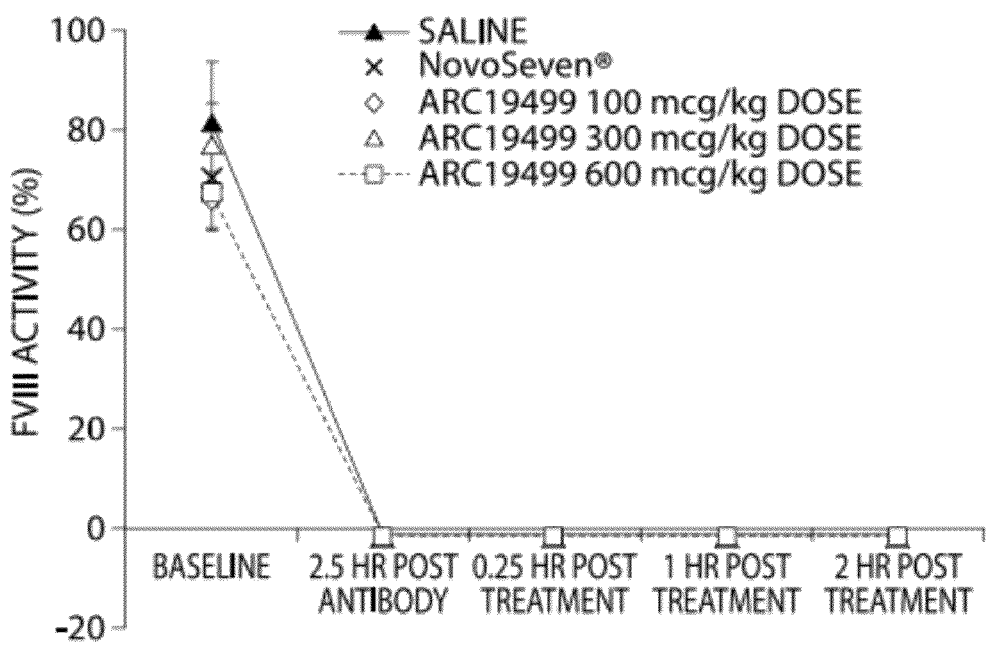
FIG. 115 is a graph showing that regardless of treatment following Factor VIII antibody injection in cynomolgus monkeys, Factor VIII activity decreased to <1% and remained there for the duration of the study (5.5 hours). Data represent mean±standard error, n=3–6.
Figure 116:
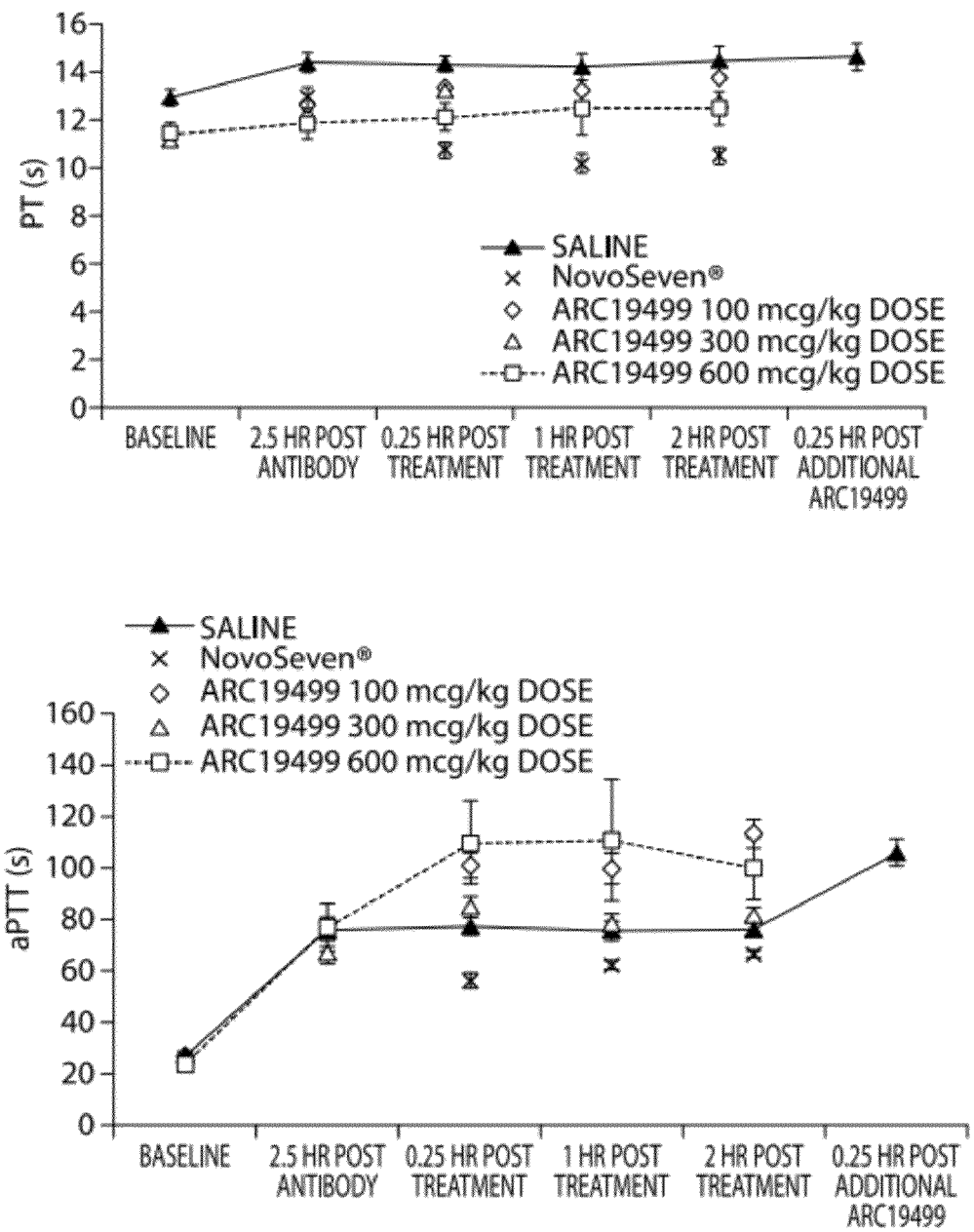
FIG. 116 is a series of graphs showing prothrombin (PT) and activated partial thromboplastin (aPTT) times before and after ARC19499 treatment in cynomolgus monkeys.
Figure 117A:
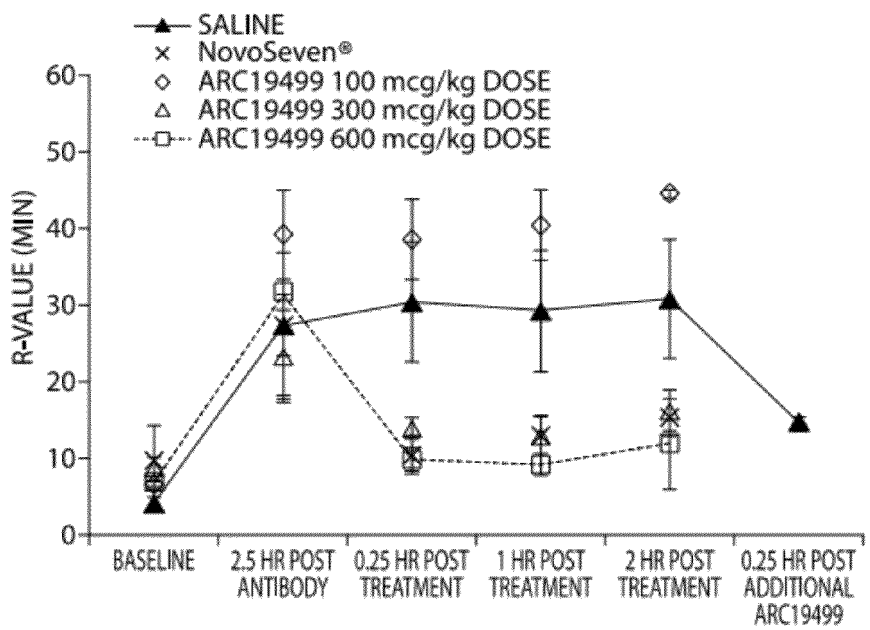
FIG. 117 is a series of graphs from thromboelastography (TEG®) analysis showing that R-values (FIG. 117A), a measure of clot time; angles (FIG. 117B), a measure of rate of clot formation; and maximum amplitudes (MA.
FIG. 117C), a measure of clot strength, determined in monkeys treated with saline (filled triangles), NovoSeven® (x), 600 µg/kg ARC19499 (empty squares), 300 µg/kg ARC19499 (empty triangles) or 100 µg/kg ARC19499 (empty diamonds). The time course of the study is denoted on the x-axis. Data represent mean±standard error, n=3–6.
Figure 117B:
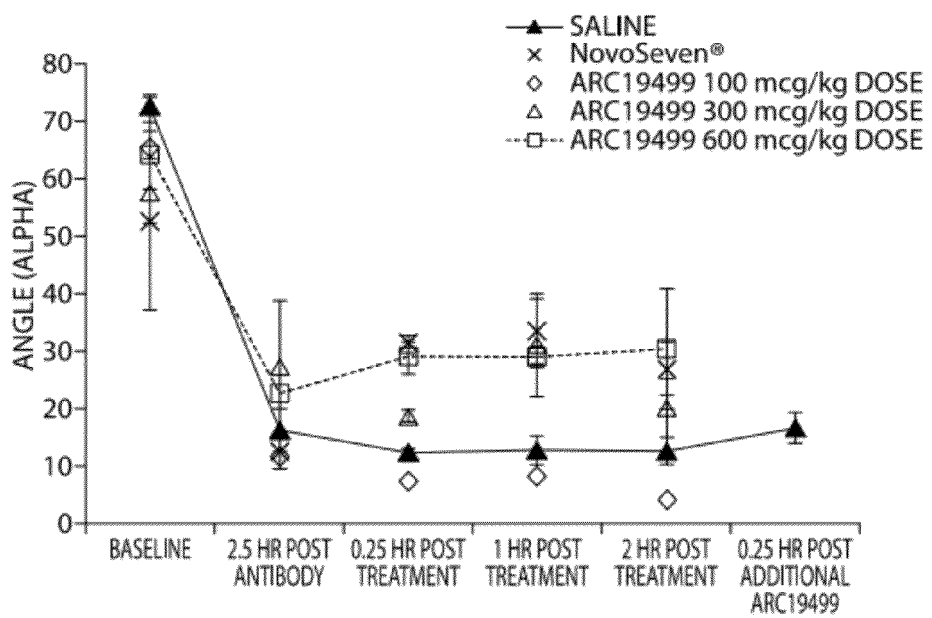
Figure 117C:
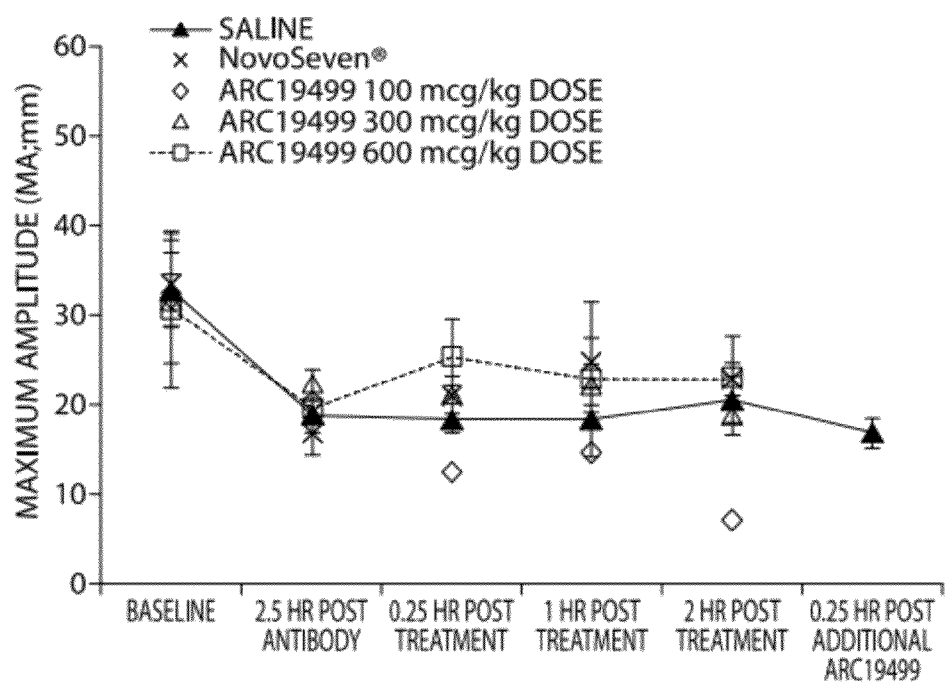

In the plasma sample withdrawn 2.5 hours after antibody injection, Factor VIII levels were below 0.6% and remained there for the course of the 5.5 hour assay (FIG. 115). As expected, the PT, which is insensitive to FVIII, remained unchanged after antibody administration (FIG. 116A); however, upon injection of rFVIIa, there was a slight dip in PT values from 13.0±0.4 to 10.7±0.4 seconds. aPTT values increased after administration of the Factor VIII antibody (FIG. 116B). As seen in the PT assay, rFVIIa administration resulted in a decrease in clotting time in the aPTT assay. There was no change to the aPTT values upon saline treatment. ARC19499 treatment (at all concentrations) resulted in a prolongation in aPTT. The saline-treated animal that received an ARC19499 bolus after the 5.5 hour time point also showed a prolongation in aPTT after aptamer administration. The effect of ARC19499 treatment on clot development in this hemophilia A-like model was assayed using tissue factor (TF)-activated TEG®. In all animals tested, antibody administration resulted in a prolongation in R-value (FIG. 117A). Saline treatment had no further effect on the R-value, while both rFVIIa and the 600 µg/kg and 300 µg/kg ARC19499 treatments resulted in a decrease in R-value to levels close to baseline. The 100 µg/kg dose of ARC19499 was an ineffective dose and did not have a positive effect on the R-value. In the saline-treated monkey, the additional injection of ARC19499 at the end of the study had an immediate effect on decreasing the R-value. The angle (FIG. 117B) and maximum amplitude (MA) (FIG. 117C) were both reduced after antibody administration. The 600 µg/kg and 300 µg/kg ARC19499 treatments appeared to have similar increasing effects on the angle as NovoSeven®; whereas, the 100 µg/kg ARC19499 treatment behaved similarly to the saline treatment (FIG. 117B). All of the treatments, including saline, appeared to have no additional effect on MA (FIG. 117C).

Figure 118A:
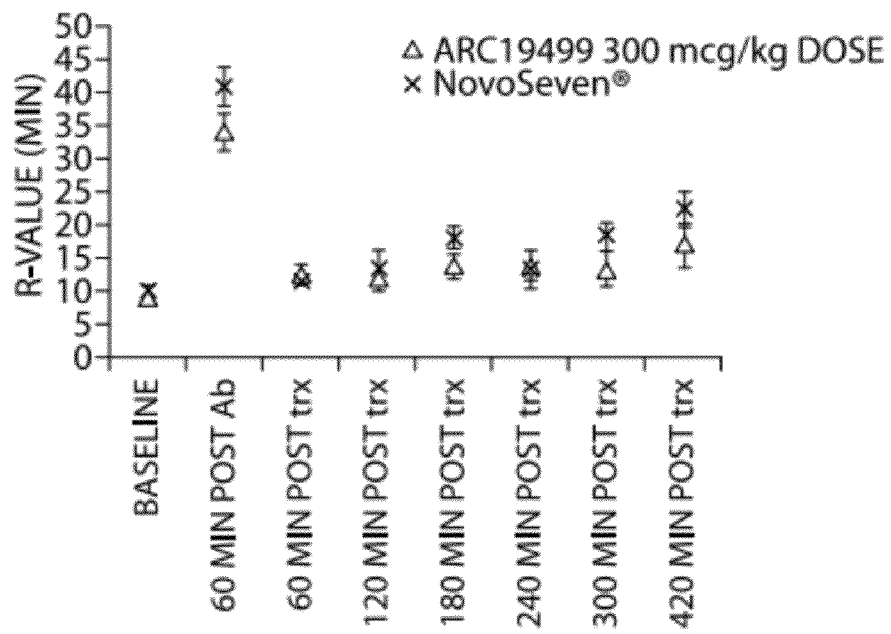
FIG. 118 is a series of graphs from thromboelastography (TEG®) analysis showing that R-values (FIG. 118A), a measure of clot time; angles (FIG. 118B), a measure of rate of clot formation; and maximum amplitude (MA.
FIG. 118C), a measure of clot strength, were determined in additional monkeys treated with NovoSeven® (x) or 300 µg/kg ARC19499 (triangles) for a longer time course than in FIG. 117. The time course of the study is denoted on the x-axis. Data represent mean±standard error, n=5 for NovoSeven® treatment and n=6 for ARC19499 treatment.
Figure 118B:
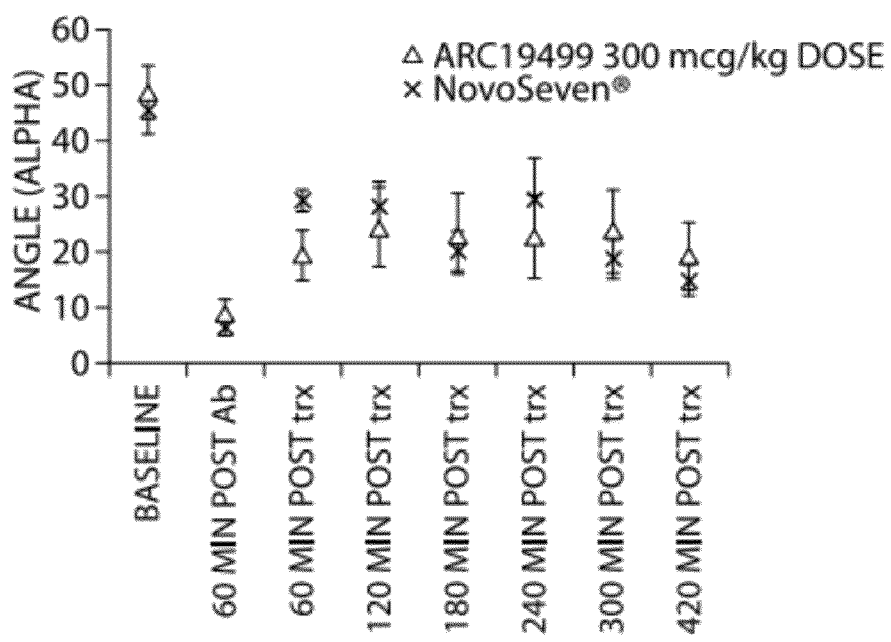
Figure 118C:
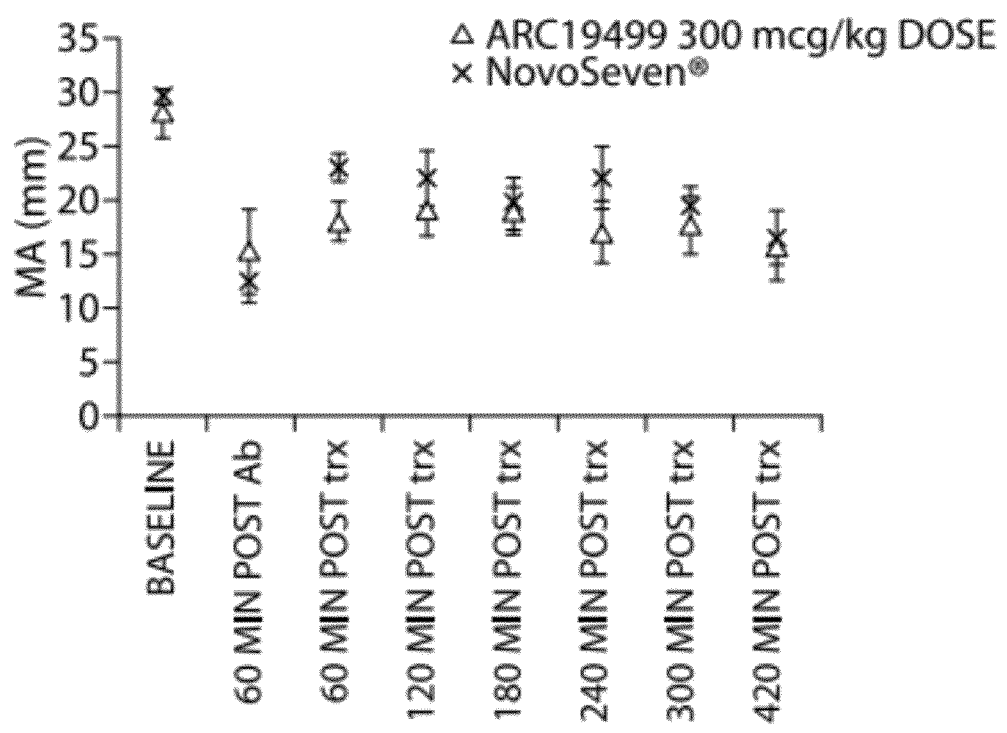

In a second set of related experiments, monkeys were treated with the same concentration of anti-FVIII antibody followed by 300 µg/kg ARC19499 or 90 µg/kg NovoSeven® 1 hour later. Citrated blood samples were acquired and processed for plasma at baseline, 60 minutes after antibody administration, and 60, 120, 180, 240, 300 and 420 minutes after drug administration. Plasma samples were tested using the TF-activated TEG® assay as described above. As before, antibody administration resulted in increased R-values (FIG. 118A), and decreased angle and MA values (FIG. 118B-C). ARC19499 and NovoSeven® behaved in very similar manners, restoring the R-values to near-baseline levels and improving both the angle and MA values (FIG. 118).

Taken together, the Factor VIII, aPTT and TEG® all indicate the successful induction of a hemophilia A-like state in these monkeys. The moderate prolongation of the aPTT upon injection of ARC19499 most likely reflects further, non-specific inhibition of the intrinsic cascade, which has been previously observed with other aptamers. However, the clear correction of the clot time (R-value) in TF-activated plasma measured by the TEG® assay suggests that the hemostatic defect due to loss of Factor VIII was successfully bypassed by ARC19499 inhibition of TFPI.

Figure 119:
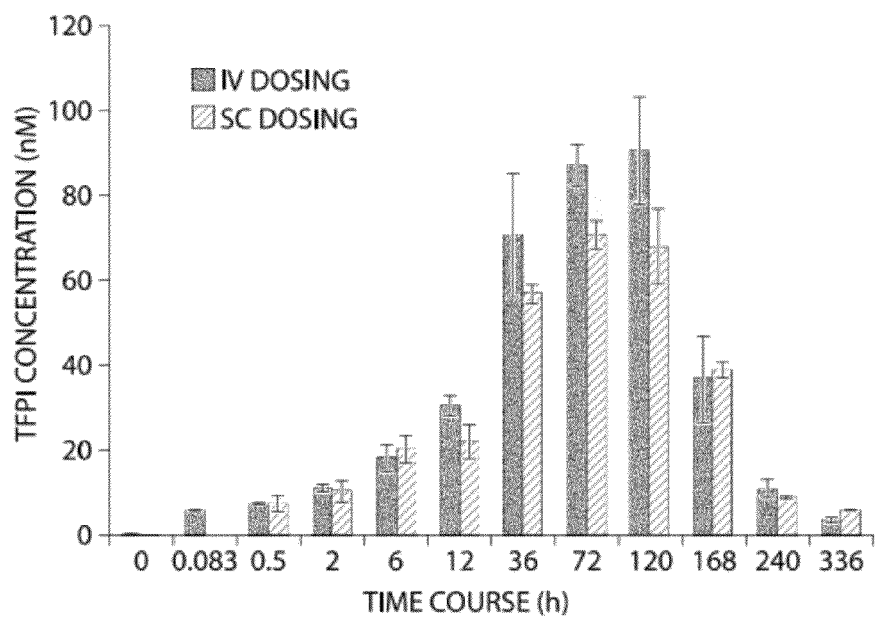
FIG. 119 is a graph showing TFPI levels in cynomolgus monkeys following a 20 mg/kg intravenous (IV, solid) or subcutaneous (SC, hatched) dose of ARC19499 in nM on the y-axis. The time course is denoted on the x-axis. The pattern of TFPI release was very similar for both IV and SC dosing. Data represent mean±standard error, n=3.

An additional observation of ARC19499 treatment was that it appeared to result in an increase in plasma levels of TFPI. In a preliminary experiment, TFPI concentrations in samples from these cynomolgus experiments mentioned above, following ARC19499 treatment, exceeded the upper limit of quantitation of the TFPI ELISA when diluted 1:40. This effect was analyzed more closely by measuring the TFPI levels in EDTA-plasma samples from cynomolgus monkeys that received a very high dose (20 mg/kg) of ARC19499 either via IV or subcutaneous (SC) administration. Blood samples were drawn periodically over two weeks, which enabled the assessment of changes in TFPI plasma concentrations following a more prolonged exposure to ARC19499. TFPI concentrations were measured in serially diluted plasma samples (diluted up to 1:1600) at the following timepoints: pre-dose, 0.083 (IV only), 0.5, 2, 6, 12, 36, 72, 120, 168, 240 and 336 hours post-dose. In animals treated with either an IV or SC dose of ARC19499, TFPI levels increased immediately from ~0.2 nM (pre-dose) to 5-7 nM at the first time point, then more gradually over time to peak levels of 91±12 and 71±2 nM, respectively (FIG. 119). The pattern of TFPI levels was similar in the monkeys treated with either the IV or SC dose, increasing to peak levels at 72-120 hours followed by a gradual decline. However, the ARC19499 $t_{max}$ estimates were 5 minutes and 24 hours for the IV and SC doses, respectively (data not shown). Thus, although ARC19499 stimulated an increase in plasma TFPI in vivo, the changes in TFPI and ARC19499 concentrations over time do not necessarily correlate. The mechanism for the increase in TFPI is unknown, but it is possible that the initial exposure to ARC19499 caused the rapid release of TFPI from the endothelial surface while subsequent increases were due to slow release of TFPI from intracellular stores, upregulation of TFPI expression, and/or inhibition of TFPI clearance mechanisms. This increase in plasma TFPI levels upon aptamer treatment was specific for ARC19499. An aptamer against a target other than TFPI did not appear to increase TFPI levels, especially not to the same level as ARC19499 (data not shown).

Example 33

This example demonstrates that ARC19499 shortens bleeding time in a non-human primate (NHP) model of hemophilia A and that this shortened bleeding time is reflected in most cases by a concomitant correction in the thromboelastography (TEG®) R-value (a measure of the time to initial clot formation) from the prolonged R-value associated with hemophilia A and present in the NHP model described below.

Bleeding time, with and without ARC19499 treatment, was assessed in a NHP model of hemophilia A in which cynomolgus monkeys were dosed with an anti-FVIII antibody (FVIII Ab) to induce a hemophilia A-like state. As diagramed in FIG. 120, bleeding time was measured at the beginning of the experiment (baseline), and then 2.5 hours after FVIII Ab administration. Treatment with 1 mg/kg bolus doses of ARC19499 were then begun. Bleeding time was measured 1 hour after the first ARC19499 dose for all groups of monkeys. For those monkeys whose bleeding times had not corrected, bleeding time was again assessed 17 minutes after the second ARC19499 dose. For those monkeys whose bleeding times still had not corrected, bleeding time was again assessed 17 minutes after the third ARC19499 dose (groups 3 and 4).

Figure 120:
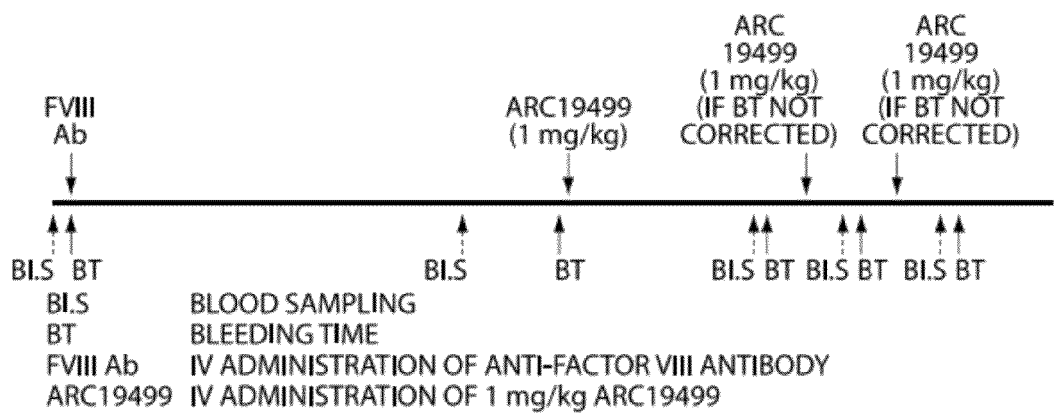
Figure 121A:
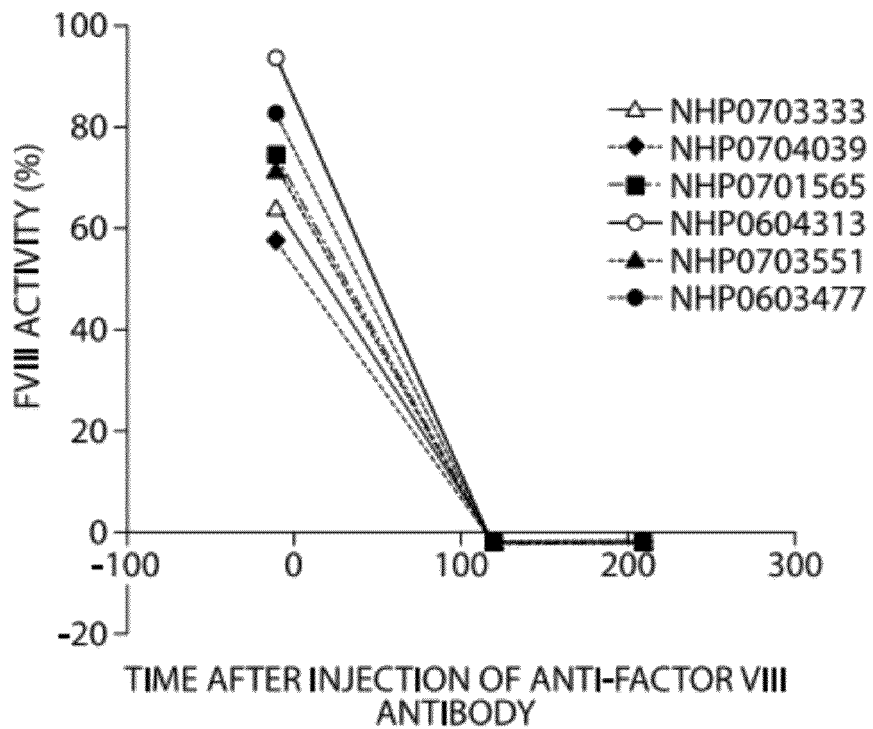
Figure 121B:
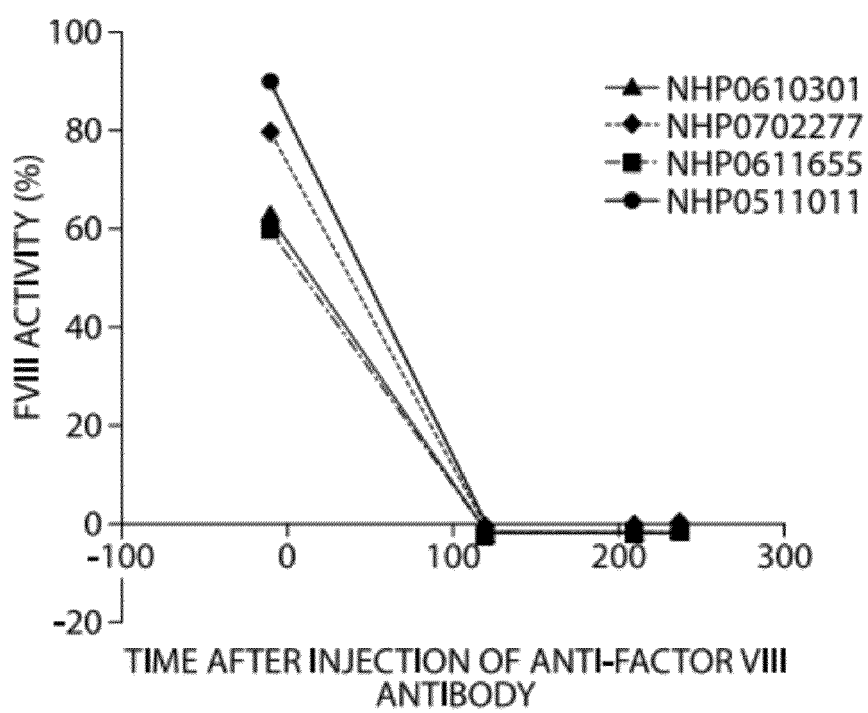
Figure 121C:
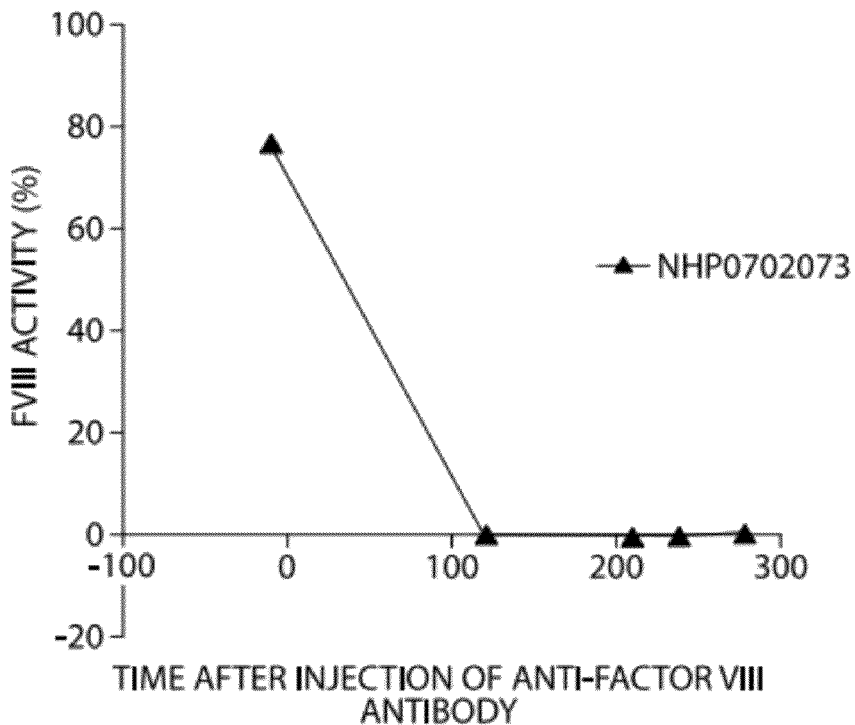
Figure 121D:
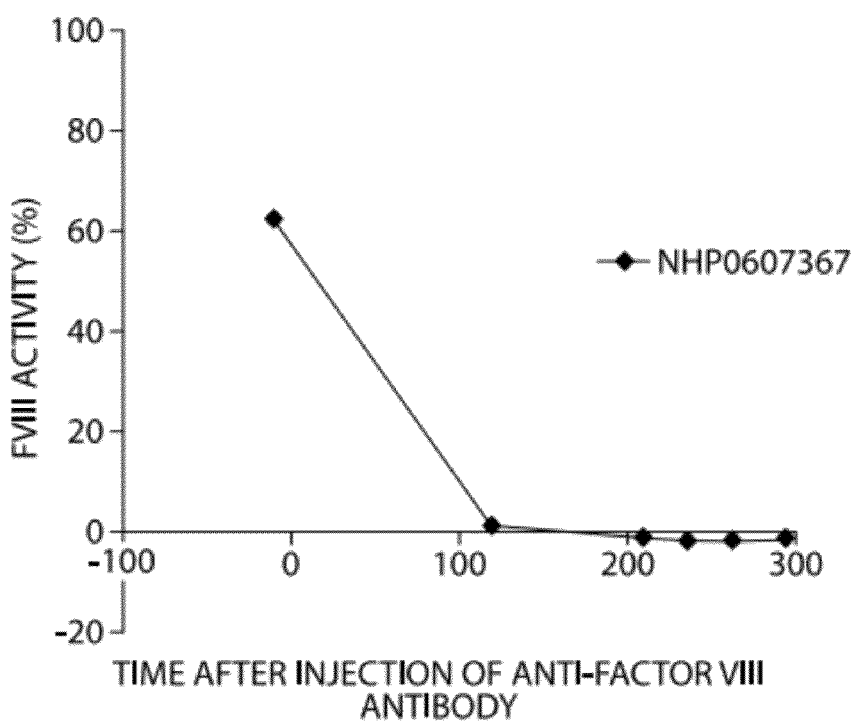

For bleeding time assessment and collection of blood samples, a monkey was anesthetized, and a line was placed in the femoral vein for blood pressure determinations and the saphenous vein on the opposite side from the saphenous vein used for the bleeding time assessment was catheterized with a 22 gauge catheter for dosing and sampling. The schedule for bleeding time assessment and related FVIII Ab and ARC19499 dosing and blood sampling are indicated in FIG. 120. A pre-treatment baseline blood sample and a bleeding time (pre-treatment bleeding time, $BT_0$) were taken 10 and 5 minutes, respectively, before dosing with FVIII Ab. Blood samples were taken by first withdrawing approximately 3-4 mL of blood mixed with saline, which was then set aside. An undiluted blood sample was then taken using a syringe. The collected blood was immediately injected into citrate-containing tubes and inverted ten times to mix. A sample of the citrated whole blood was analyzed by TEG® and the remaining citrated blood was processed to obtain plasma for analysis. The first blood-saline sample was then injected back into the monkey, followed by a flush of saline equivalent to the volume of blood sample taken.

The saphenous vein was exposed for the bleeding time assessment. A 22 gauge 1 inch hypodermic needle (Kendall Monoject, Kendall Healthcare, Mansfield, Mass.) was carefully bent at the bevel to a 90° C. angle using a hemostat; the bend was 5 mm from the tip of the needle. The needle was inserted into the exposed vein up to the bend in the needle, puncturing only one wall of the vein. Blood was wicked away from the vein using Surgicutt Bleeding Time Blotting Paper (ITC, Edison, N.J.); care was taken to not touch the actual puncture site. Time was measured from the moment bleeding began until cessation of bleeding, as determined by inability to wick away blood. Blood pressure readings were taken one to five minutes before and after bleeding time assessment. After bleeding time assessment, the wound was closed with Gluture (Abbott Labs, Abbott Park, Ill.).

FVIII Ab (sheep anti-human FVIII polyclonal antibody, Lot Y1217, from Haematologic Technologies Inc (Essex Junction, Vt.)) was administered to monkeys intravenously (IV) as a single slow bolus dose via a 22 gauge catheter placed in the saphenous vein on the opposite side from the saphenous vein used for the bleeding time assessment. It was kept frozen at −80° C. until use, and was thawed and re-frozen no more than 3 times before use. Each monkey received 12,642 Bethesda units/kg of FVIII Ab. Two hours after the FVIII Ab was given, another blood sample was taken; 30 minutes later the bleeding time was assessed (post FVIII bleeding time, $BT_{FVIII}$). A first dose of ARC19499 was administered IV as a single slow bolus. In all cases prior to dosing of either the Factor VIII Ab or ARC19499, 0.5-1.0 mL of fluid were removed from the catheter, the FVIII Ab or ARC19499 was administered, and the catheter was then flushed with 2-3 mL warm saline. A blood sample was taken 55 minutes later. One hour after the administration of the first ARC19499 dose, the bleeding time was assessed (post first ARC19499 dose bleeding time, $BT_1$). Determination was then made as to whether the bleeding time had been corrected by the first dose of ARC19499. Correction was considered to have been attained if the difference between the pre-treatment baseline and post first ARC19499 dose bleeding times was less than half the difference between the pre-treatment baseline and post FVIII bleeding times (i.e., $(BT_1-BT_0)/(BT_{FVIII}-BT_0)<0.5$). If the bleeding time was successfully corrected, the bleeding time study was completed for that animal. If the bleeding time was not corrected, a second dose of 1 mg/kg ARC19499 was administered ten minutes after the initiation of the prior bleeding time assessment. A blood sample was taken 12 minutes later; a bleeding time assessment was begun 17 minutes after the second ARC19499 injection (post second ARC19499 dose bleeding time, $BT_2$). Determination was then made as to whether the bleeding time had been corrected by the second dose of ARC19499. If the bleeding time was successfully corrected, the bleeding time study was completed for that animal. If the bleeding time was not corrected, a third dose of 1 mg/kg ARC19499 was administered ten minutes after the initiation of the prior bleeding time assessment. A blood sample was taken 12 minutes later; a bleeding time assessment was begun 17 minutes after the second ARC19499 injection (post third ARC19499 dose bleeding time, $BT_3$). Determination was then made as to whether the bleeding time had been corrected by the third dose of ARC19499. Regardless of whether the bleeding time was successfully corrected, the bleeding time study was completed for that animal. If the bleeding time was not corrected, a fourth dose of 3 mg/kg ARC19499 was administered 14 minutes after the initiation of the prior bleeding time assessment; a blood sample was taken for whole blood TEG® analysis but no further bleeding times were assessed due to lack of available vein of type similar to that used in the study. Additional ARC19499 (1 to 3 mg/kg) was administered prior to recovery of each animal as a precaution against bleeding over the next 24 hours. The actual time points for blood sampling, compound dosing and bleeding time assessment for each animal are within 5 minutes of the time point reported.

FVIIIa activity levels in citrated plasma from monkeys in this study were measured using the Coamatic FVIII assay from Chromogenix (Diapharma, Columbus Ohio). Samples acquired during the study were compared to a standard curve generated from a pool of the pre-treatment baseline plasma samples. All samples and standards were diluted 80× in reaction buffer provided by the kit. The reaction was carried out as per the manufacturer's instructions, reading the change in absorbance at 405 nm over 45 minutes. The FVIII activity levels associated with the cynomolgus monkey plasma samples are shown in Table 18 and FIG. 121 (Table 18A and FIG. 121A: Group 1: monkeys whose bleeding times were corrected with one dose of 1 mg/kg ARC19499; Table 18B and FIG. 121B: Group 2: monkeys whose bleeding times were corrected with two doses of 1 mg/kg ARC19499; Table 18C and FIG. 121C: Group 3: monkey whose bleeding time was corrected with three doses of 1 mg/kg ARC19499; Table 18D and FIG. 121D: Group 4: monkey whose bleeding time was not corrected with three doses of 1 mg/kg ARC19499). Prior to antibody treatment, the plasma from all monkeys had very high FVIII activity levels, varying from 57.6% to 93.5% (Table 18). After antibody treatment, this activity dropped to below measurable levels (less than 0.1%) in all animals, and remained low for the course of the assay (FIG. 121). Most importantly, there was no difference noted by this assay in the level of FVIII inactivation between the different groups of animals, indicating that the dose of ARC19499 required to correct the bleeding time was not a related to differing levels of FVIII activity post FVIII Ab administration.

TABLE 18

| | | | | | | | |
|---|---|---|---|---|---|---|---|
| FVIII activity levels | | | | | | | |
| A. Group 1: Monkeys Whose Bleeding Times were Corrected by One Dose of 1 mg/kg ARC19499 | | | | | | | |
| | Time point (min) | NHP 0703333 % | NHP 0704039 % | NHP 0701565 % | NHP 0604313 % | NHP 0703551 % | NHP 0603477 % |
| Baseline | −10 | 64.4 | 57.6 | 74.1 | 93.5 | 71.8 | 82.4 |
| 2 hr post FVIII ab treatment | 120 | −1.6 | −2.2 | −1.8 | −1.5 | −1.8 | −2.6 |

TABLE 18-continued

| FVIII activity levels | | | | | | | |
|---|---|---|---|---|---|---|---|
| 55 min post first ARC19499 treatment | 210 | −1.5 | −2.1 | −1.8 | −2.2 | −1.6 | −2.3 |

B. Group 2: Monkeys Whose Bleeding Times were Corrected by Two Doses of 1 mg/kg ARC19499

| | Time point (min) | NHP 0610301 % | NHP 0702277 % | NHP 0611655 % | NHP 0511011 % |
|---|---|---|---|---|---|
| Baseline | −10 | 63.0 | 79.6 | 59.5 | 89.7 |
| 2 hr post FVIII ab treatment | 120 | −2.1 | −0.3 | −2.3 | −2.0 |
| 55 min post first ARC19499 treatment | 210 | −2.2 | −0.1 | −2.2 | −1.9 |
| 12 min post second ARC19499 treatment | 237 | ns | 0.1 | −2.2 | −1.7 |

C. Group 3: Monkey Whose Bleeding Time was Corrected by Three Doses of 1 mg/kg ARC19499

| | Time point (min) | NHP0702073 % |
|---|---|---|
| Baseline | −10 | 76.8 |
| 2 hr post FVIII ab treatment | 120 | 0.0 |
| 55 min post first ARC19499 treatment | 210 | −0.2 |
| 12 min post second ARC19499 treatment | 239 | −0.3 |
| 12 min post third ARC19499 treatment | 278 | 0.3 |

D. Group 4: Monkey Whose Bleeding Time was Not Corrected by Three Doses of 1 mg/kg ARC19499

| | Time point (min) | NHP0607367 % |
|---|---|---|
| Baseline | −10 | 62.5 |
| 2 hr post FVIII ab treatment | 120 | 0.8 |
| 55 min post first ARC19499 treatment | 210 | −1.4 |
| 12 min post second ARC19499 treatment | 237 | −2.0 |
| 12 min post third ARC19499 treatment | 264 | −2.0 |
| 12 min post fourth ARC19499 treatment | 296 | −1.7 |

The mean group bleeding times (±SEM) for Group 1 monkeys (whose bleeding times were corrected with one dose of 1 mg/kg ARC19499) are shown in Table 19. The mean group bleeding times for this group are also plotted against the time points of the blood samples in FIG. 122 (FIG. 122A: in seconds, FIG. 122B: in terms of % of baseline bleeding time). Treatment with the anti-FVIII antibody resulted in a prolongation of the group mean bleeding time to 203±15% of the baseline group mean bleeding time. Treatment of the monkeys with 1 mg/kg ARC19499 corrected the group mean bleeding time back to essentially baseline levels (102±11% of the baseline group mean bleeding time). Individual bleeding times for Group 1 monkeys are shown in Table 20; the individual monkey bleeding times at each time point are also plotted in FIG. 123 (FIG. 123A: in seconds, FIG. 123B: in terms of % of baseline bleeding time). All monkeys in this group showed a prolongation of their bleeding times in response to administration of FVIII Ab compared to their baseline bleeding times (range: 162 to 252% of the baseline bleeding time). All monkeys in this group also exhibited a correction of their bleeding times in response to administration of 1 mg/kg ARC19499 compared to their baseline bleeding times (range: 82 to 152% of the baseline bleeding time).

TABLE 19

Mean Bleeding Times in Monkeys Whose Bleeding Times were Corrected by One Dose of 1 mg/kg ARC19499 (Group 1)
Group 1: Mean Bleeding Times

|  | Time point (min) | Mean (sec) | SEM (sec) |
|---|---|---|---|
| Baseline | −5 | 41 | 5.1 |
| 2.5 hr post FVIII ab treatment | 150 | 84 | 13 |
| 1 hr post ARC19499 treatment | 215 | 40 | 3.5 |

TABLE 20

Individual Bleeding Times in Monkeys Whose Bleeding Times were Corrected by One Dose of 1 mg/kg ARC19499 (Group 1)
Group 1: Individual Bleeding Times

|  | Time point (min) | NHP 0703333 (sec) | NHP 0704039 (sec) | NHP 0701565 (sec) | NHP 0604313 (sec) | NHP 0703551 (sec) | NHP 0603477 (sec) |
|---|---|---|---|---|---|---|---|
| Baseline | −5 | 36 | 23 | 45 | 42 | 41 | 61 |
| 2.5 hr post FVIII ab treatment | 150 | 62 | 58 | 85 | 68 | 85 | 145 |
| 1 hr post ARC19499 treatment | 215 | 31 | 35 | 37 | 47 | 38 | 54 |

The mean group bleeding times (±SEM) for Group 2 monkeys (whose bleeding times were corrected with two doses of 1 mg/kg ARC19499) are shown in Table 21. The mean group bleeding times for this group are also plotted against the time points of the blood samples in FIG. 124 (FIG. 124A: in seconds, FIG. 124B: in terms of % of baseline bleeding time). Treatment with the anti-FVIII antibody resulted in a prolongation of the group mean bleeding time to 195±26% of the baseline group mean bleeding time. After treatment of the monkeys with 1 mg/kg ARC19499, the group mean bleeding time did decrease, but only to 175±20% of the baseline group mean bleeding time. An additional dose of 1 mg/kg ARC19499 subsequently reduced the group mean bleeding time to essentially baseline levels (94±17% of the baseline group mean bleeding time). Individual bleeding times for Group 2 monkeys are shown in Table 22; the individual monkey bleeding times at each time point are also plotted in FIG. 125 (FIG. 125A: in seconds, FIG. 125B: in terms of % of baseline bleeding time). All monkeys in this group showed a prolongation of their bleeding times in response to administration of FVIII ab compared to their baseline pre-treatment bleeding times (range: 143 to 263% of the baseline bleeding time). After administration of 1 mg/kg ARC19499, three of the monkeys exhibited a slight decrease in their bleeding times while one monkey showed a small increase in bleeding time. All monkeys in this group exhibited a correction of their bleeding times in response to a second dose of 1 mg/kg ARC19499 (range: 61 to 138% of baseline bleeding time).

TABLE 21

Mean Bleeding Times in Monkeys Whose Bleeding Times Were Corrected by Two Doses of 1 mg/kg ARC19499 (Group 2)
Group 2: Mean Bleeding Times

|  | Time point (min) | Mean (sec) | SEM (sec) |
|---|---|---|---|
| Baseline | −5 | 35 | 12 |
| 2.5 hr post FVIII ab treatment | 150 | 62 | 13 |
| 1 hr post first ARC19499 treatment | 215 | 59 | 16 |
| 17 min post second ARC19499 treatment | 242 | 31 | 8.4 |

TABLE 22

Individual Bleeding Times in Monkeys Whose Bleeding Times Were Corrected by Two Doses of 1 mg/kg ARC19499 (Group 2)
Group 2: Individual Bleeding Times

|  | Time point (min) | NHP 0610301 (sec) | NHP 0702277 (sec) | NHP 0611655 (sec) | NHP 0511011 (sec) |
|---|---|---|---|---|---|
| Baseline | −5 | 29 | 23 | 70 | 19 |
| 2.5 hr post FVIII ab treatment | 150 | 60 | 38 | 100 | 50 |
| 1 hr post first ARC19499 treatment | 215 | 50 | 33 | 107 | 44 |

TABLE 22-continued

Individual Bleeding Times in Monkeys Whose Bleeding Times
Were Corrected by Two Doses of 1 mg/kg ARC19499 (Group 2)
Group 2: Individual Bleeding Times

| Time point (min) | NHP 0610301 (sec) | NHP 0702277 (sec) | NHP 0611655 (sec) | NHP 0511011 (sec) |
|---|---|---|---|---|
| 17 min post second ARC19499 treatment | 242 | 40 | 14 | 50 | 20 |

The bleeding times for the Group 3 monkey are shown in Table 23; the bleeding times are also plotted against the time points of the blood samples in FIG. 126 (FIG. 126A: in seconds, FIG. 126B: in terms of % of baseline bleeding time). This monkey showed a prolongation of its bleeding time in response to administration of FVIII Ab to 220% of the baseline bleeding time. In response to treatment with 1 mg/kg dose of ARC19499, the bleeding time increased to 330% of the baseline. Treatment of this monkey with two doses of 1 mg/kg ARC19499 produced a reduction of the bleed time to 210% of the baseline bleeding time. To confirm that this second dose had indeed not corrected the bleeding time, an additional bleeding time assessment was performed 38 minutes after administration of the second ARC19499 dose. This bleeding time of 45 seconds was very close to the 42 seconds measured 12 minutes after the second dose of ARC19499 was given, confirming that the bleeding time had not been corrected by the two doses of ARC19499. An additional dose of 1 mg/kg ARC19499 corrected the bleeding time to 85% of the baseline bleeding time.

TABLE 23

Bleeding Times in Monkey Whose Bleeding
Time was Corrected by Three Doses of
1 mg/kg ARC19499 (Group 3)
Group 3: Bleeding Times

| | Time point (min) | NHP0702073 (sec) |
|---|---|---|
| Baseline | −5 | 20 |
| 2.5 hr post FVIII ab treatment | 150 | 44 |
| 1 hr post first ARC19499 treatment | 215 | 66 |
| 17 min post second ARC19499 treatment | 243 | 42 |
| 37 min post second ARC19499 treatment | 263 | 45 |
| 17 min post third ARC19499 treatment | 282 | 17 |

The bleeding times for the Group 4 monkey are shown in Table 24; the bleeding times are also plotted against the time points of the blood samples in FIG. 127 (FIG. 127A: in seconds, FIG. 127B: in terms of % of baseline bleeding time). This monkey showed a prolongation of its bleeding time in response to administration of FVIII Ab to 143% of the baseline bleeding time. In response to treatment with 1 mg/kg dose of ARC19499, the bleeding time increased markedly to 193% of the baseline bleeding time. The bleeding time after treatment of this monkey with two doses of 1 mg/kg ARC19499 then decreased to 154% of the baseline bleeding time. An additional dose of 1 mg/kg ARC19499 failed to significantly change the bleeding time, which was now 159% of the baseline bleeding time. No additional bleeding time assessments could be done on this animal due to a lack sufficient available vein consistent with that used for previous assessments.

TABLE 24

Bleeding Times in Monkey Whose Bleeding
Time was Not Corrected by Three Doses
of 1 mg/kg ARC19499 (Group 4)
Group 4: Bleeding Times

| | Time point (min) | NHP0607367 (sec) |
|---|---|---|
| Baseline | −5 | 56 |
| 2.5 hr post FVIII ab treatment | 150 | 80 |
| 1 hr post first ARC19499 treatment | 215 | 108 |
| 17 min post second ARC19499 treatment | 243 | 86 |
| 17 min post third ARC19499 treatment | 273 | 89 |

The coagulation status of the cynomolgus whole blood was analyzed using the TEG® assay on citrated whole blood samples. To initiate the clotting reaction, 330 µL citrated whole blood was added to a disposable cup (Haemonetics Corp, cat no. 6211) containing 20 µL 0.2 M [Haemonetics Corporation (Braintree, Mass.)] and 10 µL tissue factor (TF) (final dilution of 1:200000 at 37° C.) Innovin (Dade-Behring, Newark, Del.) was used as a tissue factor (TF) source, reconstituted in water as per manufacturer recommendation, and diluted 1:5555 in 0.9% saline prior to use. Reconstituted stock Innovin was stored at 4° C. for less than 4 weeks. The time to initial clot formation (R-value) was measured using the Haemoscope TEG® 5000 system (Haemonetics Corporation, Braintree, Mass.).

The mean group R-values (±SEM) for Group 1 monkeys (whose bleeding times were corrected with one dose of 1 mg/kg ARC19499) are shown in Table 25. The mean group R-values are also plotted against the time points of the blood sample (FIG. 128). Treatment with FVIII Ab resulted in a prolongation of the group mean R-value to about 4.8 times the group mean R-value at baseline. While treatment of the monkeys with 1 mg/kg ARC19499 reduced the group mean R-value from that obtained after FVIII Ab treatment, this R-value was still about 3.2 times the group mean baseline R-value. Individual R-values for Group 1 monkeys are shown in Table 26; the individual R-values are also plotted against the time points of the blood sample in FIG. 129. All monkeys in this group showed a prolongation of their R-values in response to administration of FVIII ab compared to their baseline pre-treatment R-values (range 2.9 to 9.4-fold). All but one of the monkeys in this group also exhibited a reduction of their R-values in response to administration of 1 mg/kg ARC19499 compared to their baseline pre-treatment R-values (range 1.4 to 5.3-fold). One monkey, NHP0701565, showed a slight increase in the R-value after administration of 1 mg/kg ARC19499.

TABLE 25

Mean Whole Blood TEG ® R-values in Monkeys Whose Bleeding Times were Corrected by One Dose of 1 mg/kg ARC19499 (Group 1)
Group 1: Mean Whole Blood TEG ® R-values

| | Time point (min) | Mean (min) | SEM (min) |
|---|---|---|---|
| Baseline | −10 | 5.6 | 0.93 |
| 2 hr post FVIII ab treatment | 120 | 27 | 3.3 |
| 55 min post ARC19499 treatment | 210 | 18 | 4.8 |

TABLE 26

Individual Whole Blood TEG ® R-values in Monkeys Whose Bleeding Times were Corrected by One Dose of 1 mg/kg ARC19499 (Group 1)
Group 1: Individual Whole Blood TEG ® R-values

| | Time point (min) | NHP 0703333 (min) | NHP 0704039 (min) | NHP 0701565 (min) | NHP 0604313 (min) | NHP 0703551 (min) | NHP 0603477 (min) |
|---|---|---|---|---|---|---|---|
| Baseline | −10 | 8.5 | ns | 6.0 | 2.2 | 5.0 | 6.2 |
| 2 hr post FVIII ab treatment | 120 | 38.6 | 28.8 | 34 | 20.7 | 22.6 | 17.8 |
| 55 min post ARC19499 treatment | 210 | 29.4 | 10.9 | 35.5 | 11.6 | 9.8 | 8.4 |

The mean group R-values (±SEM) for Group 2 monkeys (whose bleeding times were corrected with two doses of 1 mg/kg ARC19499) are shown in Table 27. The mean group R-values are also plotted against the time points of the blood samples in FIG. 130. Treatment with the anti-FVIII antibody resulted in a prolongation of the group mean R-value to about 5.9 times the group mean R-value at baseline. In response to treatment with 1 mg/kg dose of ARC19499, which did not correct the bleed time, the group mean R-value was reduced to about 4.0 times the baseline group mean R-value. Treatment of the monkeys with two doses of 1 mg/kg ARC19499, which did correct the bleed time in this group, further reduced the group mean R-value from that obtained after FVIII Ab treatment, although this R-value was still about 3.5 times the baseline group mean R-value. Individual R-values for Group 2 monkeys are shown in Table 28; the individual R-values are also plotted against the time points of the blood sample in FIG. 131. All monkeys in this group showed a prolongation of their R-values in response to administration of FVIII Ab compared to their baseline pre-treatment R-values at baseline (range 4.0 to 9.1-fold). All but one of the monkeys in this group also exhibited a reduction of their R-values in response to administration of 1 mg/kg ARC19499 compared to their baseline pre-treatment R-values (range 2.4 to 5.0-fold); treatment of these monkeys with two doses of 1 mg/kg ARC19499, which did correct all of the bleed times in this group, reduced further the R-values in two of these monkeys, and slightly increased the R-value in the third monkey. One monkey, NHP0611655, showed a 103% increase in the R-value compared with the R-value post FVIII Ab injection after administration of 1 mg/kg ARC19499; treatment of this monkey with an additional 1 mg/kg ARC19499, which did correct the bleeding time, produced a decrease in the R-value to 6.4 times the baseline R-value.

TABLE 27

Mean Whole Blood TEG ® R-values in Monkeys Whose Bleeding Times were Corrected by Two Doses of 1 mg/kg ARC19499 (Group 2)
Group 2: Mean Whole Blood TEG ® R-values

| | Time point (min) | Mean (min) | SEM (min) |
|---|---|---|---|
| Baseline | −10 | 6.0 | 1.0 |
| 2 hr post FVIII ab treatment | 120 | 36 | 4.5 |
| 55 min post first ARC19499 treatment | 210 | 24 | 8.7 |
| 12 min post second ARC19499 treatment | 237 | 21 | 7.1 |

TABLE 28

Individual Whole Blood TEG ® R-values in Monkeys Whose Bleeding Times were Corrected by Two Doses of 1 mg/kg ARC19499 (Group 2)
Group 2: Individual Whole Blood TEG ® R-values

| | Time point (min) | NHP 0610301 (min) | NHP 0702277 (min) | NHP 0611655 (min) | NHP 0511011 (min) |
|---|---|---|---|---|---|
| Baseline | −10 | ns | 8.1 | 6.0 | 4.0 |
| 2 hr post FVIII ab treatment | 120 | 46.3 | 35.8 | 24.1 | 36.2 |
| 55 min post first ARC19499 treatment | 210 | 8.2 | 19.8 | 48.9 | 19.9 |
| 12 min post ARC19499 treatment | 237 | 6.7 | 11.9 | 38.3 | 25.6 |

The R-values for the Group 3 monkey are shown in Table 29; the R-values are also plotted against the time points of the blood samples in FIG. 132. This monkey showed, in response to administration of FVIII Ab, a prolongation of its R-value to 7.6 times its baseline R-value. In response to treatment with a 1 mg/kg dose of ARC19499, which did not correct the bleed time, the R-value was reduced to 6.1-fold of the baseline R-value. Treatment of this monkey with two doses of 1 mg/kg ARC19499, which also did not correct the bleed time in this monkey, further reduced the R-value slightly, to 5.8 times that of the baseline. An additional dose of 1 mg/kg ARC19499, which did correct the bleed time, reduced the R-value to 3 times the baseline R-value.

TABLE 29

Whole Blood TEG ® R-values in a Monkey Whose
Bleeding Time was Corrected by Three
Doses of 1 mg/kg ARC19499 (Group 3)
Group 3: Whole Blood TEG ® R-values

|  | Time point (min) | NHP0702073 (min) |
| --- | --- | --- |
| Baseline | −10 | 3.9 |
| 2 hr post FVIII ab treatment | 120 | 29.5 |
| 55 min post first ARC19499 treatment | 210 | 23.6 |
| 12 min post second ARC19499 treatment | 239 | 22.5 |
| 12 min post third ARC19499 treatment | 278 | 11.8 |

The R-values for the Group 4 monkey are shown in Table 30; the R-values are also plotted against the time points of the blood samples in FIG. 133. This monkey showed, in response to administration of FVIII Ab, a prolongation to 2.9-fold times its baseline R-value. In response to treatment with 1 mg/kg dose of ARC19499, which did not correct the bleed time, the R-value was reduced to 1.6 fold times the baseline R-value. Treatment of this monkey with two doses of 1 mg/kg ARC19499, which also did not correct the bleed time in this monkey, further reduced the R-value slightly, to 1.5-fold times the baseline R-value. An additional dose of 1 mg/kg ARC19499, which still did not correct the bleed time, reduced the R-value slightly more to 1.2 times the baseline R-value. A fourth dose of 3 mg/kg ARC19499 had little effect on the R-value, which was now 1.1 times the pre-treatment baseline R-value. No additional bleeding time assessments could be done on this animal due to a lack sufficient available vein consistent with that used for previous assessments.

TABLE 30

Whole Blood TEG ® R-values in a Monkey Whose
Bleeding Time was Not Corrected by Three
Doses of 1 mg/kg ARC19499 (Group 4)
Group 4: Whole Blood TEG ® R-values

|  | Time point (min) | NHP0607367 (min) |
| --- | --- | --- |
| Baseline | −10 | 7.2 |
| 2 hr post FVIII ab treatment | 120 | 21.2 |
| 55 min post first ARC19499 treatment | 210 | 11.2 |
| 12 min post second ARC19499 treatment | 237 | 10.7 |
| 12 min post third ARC19499 treatment | 264 | 8.8 |
| 12 min post fourth ARC19499 treatment | 296 | 8.1 |

The coagulation status of the cynomolgus plasma was also analyzed using the TEG® assay on plasma from the citrated blood samples. Citrated whole blood samples were kept at room temperature until plasma processing. Samples were centrifuged at 2,000×g for 15 minutes at room temperature. The plasma was removed and immediately stored at −80° C. until shipped for analysis. Prior to analysis, plasma samples were thawed rapidly at 37° C. To initiate the clotting reaction, 330 μL citrated plasma was added to a disposable cup (Haemonetics Corporation, Braintree, Mass., cat no. 6211) containing 20 μL 0.2 M (Haemonetics Corporation (Braintree, Mass.)) and 10 μL TF (final dilution of 1:200000 at 37° C.) Innovin (Dade-Behring, Newark, Del.) was used as a tissue factor (TF) source, reconstituted in water as per manufacturer recommendation, and diluted 1:5555 in 0.9% saline prior to use. Reconstituted stock Innovin was stored at 4° C. for less than 4 weeks. The time to initial clot formation (R-value) was measured using the Haemoscope TEG® 5000 system (Haemonetics Corporation, Braintree, Mass.).

The mean group R-values (±SEM) of plasma samples from Group 1 monkeys (whose bleeding times were corrected with one dose of 1 mg/kg ARC19499) are shown in Table 31. The mean group R-values are also plotted against the time points of the plasma sample (FIG. 134). Treatment with FVIII Ab resulted in a prolongation of the group mean R-value to about 2.8 times the group mean R-value at baseline. While treatment of the monkeys with 1 mg/kg ARC19499 reduced the group mean R-value from that obtained after FVIII Ab treatment, this R-value was still about 1.9 times the group mean baseline R-value. Individual R-values for Group 1 monkeys are shown in Table 32; the individual R-values are also plotted against the time points of the plasma sample in FIG. 135. All monkeys in this group showed a prolongation of their R-values in response to administration of FVIII Ab compared to their baseline pre-treatment R-values (range 1.7 to 5.1-fold). All but one of the monkeys in this group also exhibited a reduction of their R-values in response to administration of 1 mg/kg ARC19499 compared to their baseline pre-treatment R-values (range 1.3 to 1.8-fold). One monkey, NHP0603477, showed a 50% increase in the R-value compared with the R-value post FVIII Ab injection after administration of 1 mg/kg ARC19499; the whole blood TEG® analysis had instead shown a 53% decrease in the R-value compared with the R-value post FVIII Ab injection after administration of 1 mg/kg ARC19499. The plasma TEG® analysis of NHP0701565, whose whole blood TEG® analysis had shown a slight increase in R-value in response to administration of 1 mg/kg ARC19499, was actually 66% below the R-value post FVIII Ab injection after administration of 1 mg/kg ARC19499.

TABLE 31

Mean Plasma TEG ® R-values in Monkeys Whose
Bleeding Times were Corrected by one
Dose of 1 mg/kg ARC19499 (Group 1)
Group 1: Mean Plasma TEG ® R-values

|  | Time point (min) | Mean (min) | SEM (min) |
|---|---|---|---|
| Baseline | −10 | 5.4 | 0.37 |
| 2 hr post FVIII ab treatment | 120 | 15 | 1.6 |
| 55 min post ARC19499 treatment | 210 | 10 | 1.7 |

TABLE 32

Individual Plasma TEG ® R-values in Monkeys Whose Bleeding Times were
Corrected by One Dose of 1 mg/kg ARC19499 (Group 1)
Group 1: Individual Plasma TEG ® R-values

|  | Time point (min) | NHP 0703333 (min) | NHP 0704039 (min) | NHP 0701565 (min) | NHP 0604313 (min) | NHP 0703551 (min) | NHP 0603477 (min) |
|---|---|---|---|---|---|---|---|
| Baseline | −10 | 5.0 | 6.0 | 4.3 | 4.6 | 6.3 | 6.4 |
| 2 hr post FVIII ab treatment | 120 | 12.2 | 16.6 | 21.9 | 15.5 | 14.1 | 10.8 |
| 55 min post ARC19499 treatment | 210 | 9.2 | 7.8 | 7.4 | ns | ns | 16.2 |

The mean group R-values (±SEM) of plasma samples from Group 2 monkeys (whose bleeding times were corrected with two doses of 1 mg/kg ARC19499) are shown in Table 33. The mean group R-values are also plotted against the time points of the blood samples in FIG. 136. Treatment with the anti-FVIII antibody resulted in a prolongation of the group mean R-value to about 4.0-fold of the group mean R-value at baseline. In response to treatment with 1 mg/kg dose of ARC19499, which did not correct the bleed time, the group mean R-value was reduced to about 2.2-fold times the baseline group mean R-value. Treatment of the monkeys with two doses of 1 mg/kg ARC19499, which did correct the bleed time in this group, did not significantly reduce further the group mean R-value from that obtained after FVIII Ab treatment. Individual R-values for Group 2 monkeys are shown in Table 34; the individual R-values are also plotted against the time points of the blood sample in FIG. 137. All monkeys in this group showed a prolongation of their R-values in response to administration of FVIII Ab compared to their baseline pre-treatment R-values at baseline (range 1.1 to 6.4-fold). In response to treatment with 1 mg/kg dose of ARC19499, which did not correct the bleed times, the plasma R-values of all monkeys in this group were reduced over the baseline group mean R-value (range 0.5 to 4.5-fold). Treatment of the monkeys with two doses of 1 mg/kg ARC19499, which did correct all of the bleed times in this group, produced unchanged or further reduced R-values, although in two monkeys the R-values were still higher than those at the pre-treatment baseline (range 0.5 to 3.2-fold).

TABLE 33

Mean Plasma TEG ® R-values in Monkeys Whose
Bleeding Times were Corrected by Two
Doses of 1 mg/kg ARC19499 (Group 2)
Group 2: Mean Plasma TEG ® R-values

|  | Time point (min) | Mean (min) | SEM (min) |
|---|---|---|---|
| Baseline | −10 | 5.8 | 0.6 |
| 2 hr post FVIII ab treatment | 120 | 23 | 6.5 |
| 55 min post first ARC19499 treatment | 210 | 13 | 4.5 |
| 12 min post second ARC19499 treatment | 237 | 12 | 3.7 |

TABLE 34

Individual Plasma TEG ® R-values in Monkeys
Whose Bleeding Times were Corrected by Two
Doses of 1 mg/kg ARC19499 (Group 2)
Group 2: Individual Plasma TEG ® R-values

|  | Time point (min) | NHP 0610301 (min) | NHP 0702277 (min) | NHP 0611655 (min) | NHP 0511011 (min) |
|---|---|---|---|---|---|
| Baseline | −10 | 4.6 | 7.2 | 5.3 | 6.0 |
| 2 hr post FVIII ab treatment | 120 | 15.4 | 8.1 | 33.9 | 33.7 |
| 55 min post first ARC19499 treatment | 210 | 7.6 | 3.5 | 23.7 | 16.8 |
| 12 min post ARC19499 treatment | 237 | ns | 3.9 | 17.2 | 16.5 |

The R-values of the plasma samples from the Group 3 monkey are shown in Table 35; the R-values are also plotted against the time points of the blood samples in FIG. 138. This monkey showed, in response to administration of FVIII Ab, a prolongation of its R-value to 3.5 fold times its baseline R-value. In response to treatment with 1 mg/kg dose of ARC19499, which did not correct the bleed time, the R-value was reduced to 1.3 times the baseline R-value. Treatment of this monkey with two doses of 1 mg/kg ARC19499, which also did not correct the bleed time in this monkey, further reduced the R-value to 1.1 times that of the baseline. An additional dose of 1 mg/kg ARC19499, which did correct the bleed time, reduced the R-value to 0.9 times the baseline R-value.

TABLE 35

Plasma TEG ® R-values in a Monkey Whose Bleeding Time was Corrected by Three Doses of 1 mg/kg ARC19499 (Group 3)
Group 3: Plasma TEG ® R-values

|  | Time point (min) | NHP0702073 (min) |
|---|---|---|
| Baseline | −10 | 4.7 |
| 2 hr post FVIII ab treatment | 120 | 16.4 |
| 55 min post first ARC19499 treatment | 210 | 6.2 |
| 12 min post second ARC19499 treatment | 239 | 5.2 |
| 12 min post third ARC19499 treatment | 278 | 4.4 |

The R-values of plasma samples from the Group 4 monkey are shown in Table 36; the R-values are also plotted against the time points of the blood samples in FIG. 139. This monkey showed, in response to administration of FVIII Ab, a prolongation to 2.9 times its baseline R-value. In response to treatment with 1 mg/kg dose of ARC19499, which did not correct the bleed time, the R-value was reduced over the baseline R-value to 1.1 times the baseline R-value. Plasma from blood taken after treatment of this monkey with two doses of 1 mg/kg ARC19499, which also did not correct the bleed time in this monkey, exhibited a slightly higher R-value of 1.2 times the baseline R-value. An additional dose of 1 mg/kg ARC19499, which still did not correct the bleed time, reduced the R-value slightly more to 1.0 times the baseline R-value. A fourth dose of 3 mg/kg ARC19499 reduced the R-value to below the pre-treatment baseline (0.9 times the pre-treatment baseline R-value). No additional bleeding time assessments could be done on this animal due to a lack sufficient available vein consistent with that used for previous assessments.

TABLE 36

Plasma TEG ® R-values in a Monkey Whose Bleeding Time was Not Corrected by Three Doses of 1 mg/kg ARC19499 (Group 4)
Group 4: Plasma TEG ® R-values

|  | Time point (min) | NHP0607367 (min) |
|---|---|---|
| Baseline | −10 | 6.4 |
| 2 hr post FVIII ab treatment | 120 | 18.5 |
| 55 min post first ARC19499 treatment | 210 | 6.8 |
| 12 min post second ARC19499 treatment | 237 | 7.5 |
| 12 min post third ARC19499 treatment | 264 | 6.2 |
| 12 min post fourth ARC19499 treatment | 296 | 5.8 |

The above example shows that monkeys treated with the FVIII Ab exhibited prolonged bleeding after puncture of the saphenous vein, an observation consistent with the prolonged bleeding that is the hallmark of hemophilia. In a majority of monkeys tested in this study (11 of 12), treatment with up to 3 mg/kg ARC19499 corrected this prolonged bleeding time. Six of the monkeys only required one dose of 1 mg/kg ARC19499 to exhibit this correction; bleeding time in four other monkeys was corrected with two doses of 1 mg/kg ARC19499. R-values in TEG® analysis of the whole blood from these monkeys exhibited the expected elevation after FVIII Ab administration; this elevation was reduced towards baseline levels after treatment with ARC19499; a similar pattern was seen in the analysis of the plasma from these blood samples. These data show that ARC19499 can correct prolonged bleeding in a model of induced hemophilia, supporting the potential clinical utility of ARC19499 as a successful therapeutic in the treatment of inhibitor and non-inhibitor hemophilia A patients.

Example 34

This example is an evaluation of tolerated and non-tolerated substitutions in ARC17480 through aptamer medicinal chemistry.

Molecules were generated for testing with modifications at the 2'-position or within the phosphate backbone of residues in ARC17480, as shown in Table 37 below and in FIGS. 140 and 141. Each individual 2'-deoxy residue in ARC17480 was replaced by the corresponding 2'-methoxy or 2'-fluoro containing residue, resulting in ARC18538-ARC18541 and ARC19493-ARC19496, respectively (FIG. 140). Additionally, some molecules with multiple 2'-deoxy to 2'-methoxy and/or 2'-deoxy to 2'-fluoro residues were generated at the four deoxycytidine residues in ARC17480 at positions 9, 14, 16 and 25, resulting in ARC18545, ARC18546, ARC18549, ARC19476, ARC19477, ARC19478, ARC19484, ARC19490 and ARC19491 (FIG. 140). Each individual 2'-methoxy residue in ARC17480 was replaced by the corresponding 2'-deoxy residue, with 2'-methoxyuridine residues replaced with both 2'-deoxythymidine and 2'-deoxyuridine residues, resulting in ARC19448-ARC19475 and ARC33867-ARC33877 (FIG. 140). The phosphate between each pair of nucleotides in ARC17480 was replaced individually with a phosphorothioate, resulting in ARC19416-ARC19447 (FIG. 141).

The modified ARC17480 molecules were assayed for binding and function. The assays used for this evaluation were the calibrated automated thrombogram (CAT) assay, a dot-blot binding-competition assay and a FXa activity assay.

The results of these assays are summarized in Table 37 and depicted in FIG. 142. A substitution was considered tolerated for activity if it met the criteria of at least two of the three assays that were carried out. Substitutions that were tolerated ("yes") and not tolerated ("no") are identified in Table 37. The experimental details and the criteria used for each assay are described in the following paragraphs.

The TFPI-inhibitory activity of each molecule was evaluated in the CAT assay in pooled hemophilia A plasma at 500 nM, 166.67 nM, 55.56 nM, 18.52 nM, 6.17 nM and 2.08 nM aptamer concentration. ARC17480 was included in every experiment as a control. For each molecule, the endogenous thrombin potential (ETP) and peak thrombin values at each aptamer concentration were used for analysis. The ETP or peak thrombin value for hemophilia A plasma alone was subtracted from the corresponding value in the presence of aptamer for each molecule at each concentration. Then, the corrected ETP and peak values were plotted as a function of aptamer concentration and fit to the equation y=(max/(1+ $IC_{50}$/x))+int, where y=ETP or peak thrombin, x=concentration of aptamer, max=the maximum ETP or peak thrombin, and int=the y-intercept, to generate an $IC_{50}$ value for both the ETP and the peak thrombin. The $IC_{50}$ of each aptamer was compared to the $IC_{50}$ of ARC17480 that was evaluated in the same experiment. A substitution was considered tolerated in the CAT assay if both the ETP and peak thrombin $IC_{50}$ of that molecule were not more than 5-fold greater than that of ARC17480 evaluated in the same experiment. Tolerated substitutions are indicated in Table 37 as meeting the assay criteria ("yes") or not meeting the assay criteria ("no").

Each molecule was evaluated for binding to tissue factor pathway inhibitor (TFPI) in a binding-competition assay. For these experiments, 10 nM human TFPI (American Diagnostica, Stamford, Conn., catalog #4500PC) was incubated with trace amounts of radiolabeled ARC17480 and 5000 nM, 1666.67 nM, 555.56 nM, 185.19 nM, 61.73 nM, 20.58 nM, 6.86 nM, 2.29 nM, 0.76 nM or 0.25 nM of unlabeled competitor aptamer. ARC17480 was included as a competitor in every experiment as a control. For each molecule, the percentage of radiolabeled ARC17480 bound at each competitor aptamer concentration was used for analysis. The percentage of radiolabeled ARC17480 bound was plotted as a function of aptamer concentration and fit to the equation y=(max/(1+x/ $IC_{50}$))+int, where y=the percentage of radiolabeled ARC17480 bound, x=the concentration of aptamer, max=the maximum radiolabeled ARC17480 bound, and int=the y-intercept, to generate an $IC_{50}$ value for binding-competition. The $IC_{50}$ of each aptamer was compared to the $IC_{50}$ of ARC17480 that was evaluated in the same experiment. A substitution was considered tolerated in the binding-competition assay if the $IC_{50}$ of that molecule was not more than 5-fold greater than that of ARC17480 evaluated in the same experiment. Tolerated substitutions are indicated in Table 37 as meeting the assay criteria ("yes") or not meeting the assay criteria ("no").

Each molecule was evaluated for inhibition of TFPI in a Factor Xa (FXa) activity assay. The ability of FXa to cleave a chromogenic substrate was measured in the presence and absence of TFPI, with or without the addition of aptamer. For these experiments, 2 nM human FXa was incubated with 8 nM human TFPI. Then, 500 µIM chromogenic substrate and aptamers were added and FXa cleavage of the substrate was measured by absorbance at 405 nm ($A_{405}$) as a function of time. Aptamers were tested at 500 nM, 125 nM, 31.25 nM, 7.81 nM, 1.95 nM and 0.49 nM concentrations. ARC17480 was included as a control in each experiment. For each aptamer concentration, the $A_{405}$ was plotted as a function of time and the linear region of each curve was fit to the equation y=mx+b, where y=$A_{405}$, x=the aptamer concentration, m=the rate of substrate cleavage, and b=the y-intercept, to generate a rate of FXa substrate cleavage. The rate of FXa substrate cleavage in the presence of TFPI and the absence of aptamer was subtracted from the corresponding value in the presence of both TFPI and aptamer for each molecule at each concentration. Then, the corrected rates were plotted as a function of aptamer concentration and fit to the equation y=($V_{max}$/(1+ $IC_{50}$/x)), where y=the rate of substrate cleavage, x=concentration of aptamer, and $V_{max}$=the maximum rate of substrate cleavage, to generate an $IC_{50}$ and maximum ($V_{max}$) value. The $IC_{50}$ and $V_{max}$ values of each aptamer were compared to the $IC_{50}$ and $V_{max}$ values of ARC17480 that was evaluated in the same experiment. A substitution was considered tolerated in the FXa activity assay if the $IC_{50}$ of that molecule was not more than 5-fold greater than that of ARC17480 evaluated in the same experiment and the $V_{max}$ value was not less than 80% of the $V_{max}$ value of the ARC17480 evaluated in the same experiment. Tolerated substitutions are indicated in Table 37 as meeting the assay criteria ("yes") or not meeting the assay criteria ("no").

This example demonstrates that multiple individual 2'-substitutions in ARC17480 are tolerated for binding and activity, and that some combinations of 2'-substitutions are also tolerated (Table 37 and FIG. 142). This example also demonstrates that a phosphorothioate substitution is tolerated between each pair of nucleotides in ARC17480 (Table 37). Additional combinations of tolerated 2'-substitutions and/or phosphorothioate substitutions in ARC17480 will likely be tolerated for binding and activity.

TABLE 37

Tolerated and Non-tolerated Substitutions in ARC17480

| SEQ ID NO: | ARC # | Sequence (5' → 3') (3T = inverted dT; s = phosphorothioate; mN = 2'-methoxy-containing residue; dN = deoxy residue; fN = 2'-fluoro-containing residue) | Meets Criteria? | | | Substitution(s) Tolerated |
|---|---|---|---|---|---|---|
| | | | CAT Assay | Binding-competition Assay | FXa Activity Assay | |
| 19 | 18538 | mGmGmAmAmUmAmUmAmCmU mUmGmGdCmUdCmGmUmUmA mGmGmUmGdCmGmUmAmUmA mUmA3T | NO | NO | NO | NO |
| 20 | 18539 | mGmGmAmAmUmAmUmAdCmU mUmGmGmCmUdCmGmUmUmA | YES | YES | YES | YES |

TABLE 37-continued

Tolerated and Non-tolerated Substitutions in ARC17480

| SEQ ID NO: | ARC # | Sequence (5' → 3') (3T = inverted dT; s = phosphorothioate; mN = 2'-methoxy-containing residue; dN = deoxy residue; fN = 2'-fluoro-containing residue) | C

TABLE 37-continued

Tolerated and Non-tolerated Substitutions in ARC17480

| SEQ ID NO: | ARC # | Sequence (5' → 3') (3T = inverted dT; s = phosphorothioate; mN = 2'-methoxy-containing residue; dN = deoxy residue; fN = 2'-fluoro-containing residue) | Meets Criteria? | | | |
|---|---|---|---|---|---|---|
| | | | CAT Assay | Binding-competition Assay | FXa Activity Assay | Substitution(s) Tolerated |
| | |

TABLE 37-continued

Tolerated and Non-tolerated Substitutions in ARC17480

| SEQ ID NO: | ARC # | Sequence (5' → 3') (3T = inverted dT; s = phosphorothioate; mN = 2'-methoxy-containing residue; dN = deoxy residue; fN = 2'-fluoro-containing residue) | CAT Assay | Binding-competition Assay | FXa Activity Assay | Meets Criteria? Substitution(s) Tolerated |
|---|---|---|---|---|---|---|
| | | mGmGmUmGdCdGmUmAmUmA mUmA3T | | | | |
| 49 | 19470 | mGmGmAmAmUmAmUmAdCmU mUmGmGdCmUdCmGmUmUmA mGmGmUmGdCmGdTmAmUmA mUmA3T | YES | YES | YES | YES |
| 50 | 19471 | mGmGmAmAmUmAmUmAdCmU mUmGmGdCmUdCmGmUmUmA mGmGmUmGdCmGmGdAmUmA mUmA3T | YES | YES | YES | YES |
| 51 | 19472 | mGmGmAmAmUmAmUmAdCmU mUmGmGdCmUdCmGmUmUmA mGmGmUmGdCmGmUmAdTmA mUmA3T | YES | YES | YES | YES |
| 52 | 19473 | mGmGmAmAmUmAmUmAdCmU mUmGmGdCmUdCmGmUmUmA mGmGmUmGdCmGmUmAmUdA mUmA3T | YES | YES | YES | YES |
| 53 | 19474 | mGmGmAmAmUmAmUmAdCmU mUmGmGdCmUdCmGmUmUmA mGmGmUmGdCmGmUmAmUmA dTmA3T | YES | YES | YES | YES |
| 54 | 19475 | mGmGmAmAmUmAmUmAdCmU mUmGmGdCmUdCmGmUmUmA mGmGmUmGdCmGmUmAmUmA mUdA3T | YES | YES | YES | YES |
| 55 | 33867 | mGmGmAmAdUmAmUmAdCmUm UmGmGdCmUdCmGmUmUmAm GmGmUmGdCmGmUmAmUmAm UmA3T | YES | YES | YES | YES |
| 56 | 33868 | mGmGmAmAmUmAdUmAdCmUm UmGmGdCmUdCmGmUmUmAm GmGmUmGdCmGmUmAmUmAm UmA3T | YES | YES | YES | YES |
| 57 | 33869 | mGmGmAmAmUmAmUmAdCdUm UmGmGdCmUdCmGmUmUmAm GmGmUmGdCmGmUmAmUmAm UmA3T | NO | NO | NO | NO |
| 58 | 33870 | mGmGmAmAmUmAmUmAdCmUd UmGmGdCmUdCmGmUmUmAm GmGmUmGdCmGmUmAmUmAm UmA3T | YES | NO | YES | YES |
| 59 | 33871 | mGmGmAmAmUmAmUmAdCmU mUmGmGdCdUdCmGmUmUmAm GmGmUmGdCmGmUmAmUmAm UmA3T | YES | YES | YES | YES |
| 60 | 33872 | mGmGmAmAmUmAmUmAdCmU mUmGmGdCmUdCmGdUmUmAm GmGmUmGdCmGmUmAmUmAm UmA3T | YES | YES | YES | YES |
| 61 | 33873 | mGmGmAmAmUmAmUmAdCmU mUmGmGdCmUdCmGmUdUmAm GmGmUmGdCmGmUmAmUmAm UmA3T | YES | YES | YES | YES |
| 62 | 33874 | mGmGmAmAmUmAmUmAdCmU mUmGmGdCmUdCmGmUmUmA | YES | YES | YES | YES |

TABLE 37-continued

Tolerated and Non-tolerated Substitutions in ARC17480

| SEQ ID NO: | ARC # | Sequence (5' → 3') (3T = inverted dT; s = phosphorothioate; mN = 2'-methoxy-containing residue; dN = deoxy residue; fN = 2'-fluoro-containing residue) | CAT Assay | Meets Criteria? Binding-competition Assay | FXa Activity Assay | Substitution(s) Tolerated |
|---|---|---|---|---|---|---|
| | | mGmGdUmGdCmGmUmAmUmA

TABLE 37-continued

Tolerated and Non-tolerated Substitutions in ARC17480

| SEQ ID NO: | ARC # | Sequence (5' → 3') (3T = in

TABLE 37-continued

Tolerated and Non-tolerated Substitutions in ARC17480

| SEQ ID NO: | ARC # | Sequence (5' → 3') (3T = inverted dT; s = phosphorothioate; mN = 2'-methoxy-containing residue; dN = deoxy residue; fN = 2'-fluoro-containing residue) | CAT Assay | Binding-competition Assay | FXa Activity Assay | Substi-tution(s) Tolerated |
|---|---|---|---|---|---|---|
| | | mGmGmUmGdCmGmUmAmUmA mUmA3T | | | | |
| 90 | 19432 | mGmGmAmAmUmAmUmAdCmU mUmGmGdCmUdCmGsmUmUmA mGmGmUmGdCmGmUmAmUmA mUmA3T | YES | YES | YES | YES |
| 91 | 19433 | mGmGmAmAmUmAmUmAdCmU mUmGmGdCmUdCmGmUsmUmA mGmGmUmGdCmGmUmAmUmA mUmA3T | YES | YES | YES | YES |
| 92 | 19434 | mGmGmAmAmUmAmUmAdCmU mUmGmGdCmUdCmGmUmUsmA mGmGmUmGdCmGmUmAmUmA mUmA3T | YES | YES | YES | YES |
| 93 | 19435 | mGmGmAmAmUmAmUmAdCmU mUmGmGdCmUdCmGmUmUmAs mGmGmUmGdCmGmUmAmUmA mUmA3T | YES | YES | YES | YES |
| 94 | 19436 | mGmGmAmAmUmAmUmAdCmU mUmGmGdCmUdCmGmUmUmA mGsmGmUmGdCmGmUmAmUm AmUmA3T | YES | YES | YES | YES |
| 95 | 19437 | mGmGmAmAmUmAmUmAdCmU mUmGmGdCmUdCmGmUmUmA mGmGsmUmGdCmGmUmAmUm AmUmA3T | YES | YES | YES | YES |
| 96 | 19438 | mGmGmAmAmUmAmUmAdCmU mUmGmGdCmUdCmGmUmUmA mGmGmUsmGdCmGmUmAmUm AmUmA3T | YES | YES | YES | YES |
| 97 | 19439 | mGmGmAmAmUmAmUmAdCmU mUmGmGdCmUdCmGmUmUmA mGmGmUmGsdCmGmUmAmUm AmUmA3T | YES | YES | YES | YES |
| 98 | 19440 | mGmGmAmAmUmAmUmAdCmU mUmGmGdCmUdCmGmUmUmA mGmGmUmGdCsmGmUmAmUm AmUmA3T | YES | YES | YES | YES |
| 99 | 19441 | mGmGmAmAmUmAmUmAdCmU mUmGmGdCmUdCmGmUmUmA mGmGmUmGdCmGsmUmAmUm AmUmA3T | YES | YES | YES | YES |
| 100 | 19442 | mGmGmAmAmUmAmUmAdCmU mUmGmGdCmUdCmGmUmUmA mGmGmUmGdCmGmUsmAmUm AmUmA3T | YES | YES | YES | YES |
| 101 | 19443 | mGmGmAmAmUmAmUmAdCmU mUmGmGdCmUdCmGmUmUmA mGmGmUmGdCmGmUmAsmUm AmUmA3T | YES | YES | YES | YES |
| 102 | 19444 | mGmGmAmAmUmAmUmAdCmU mUmGmGdCmUdCmGmUmUmA mGmGmUmGdCmGmUmAmUsm AmUmA3T | YES | YES | YES | YES |
| 103 | 19445 | mGmGmAmAmUmAmUmAdCmU mUmGmGdCmUdCmGmUmUmA | YES | YES | YES | YES |

TABLE 37-continued

Tolerated and Non-tolerated Substitutions in ARC17480

| SEQ ID NO: | ARC # | Sequence (5' → 3') (3T = inverted dT; s = phosphorothioate; mN = 2'-methoxy-containing residue; dN = deoxy residue; fN = 2'-fluoro-containing residue) | Binding-CAT Assay | Meets Criteria? competition Assay | FXa Activity Assay | Substitution(s) Tolerated |
|---|---|---|---|---|---|---|
| | | mGmGmUmGdCmGmUmAmUmA smUmA3T | | | | |
| 104 | 19446 | mGmGmAmAmUmAmUmAdCmU mUmGmGdCmUdCmGmUmUmA mGmGmUmGdCmGmUmAmUmA mUsmA3T | YES | YES | YES | YES |
| 105 | 19447 | mGmGmAmAmUmAmUmAdCmU mUmGmGdCmUdCmGmUmUmA mGmGmUmGdCmGmUmAmUmA mUmAs3T | YES | YES | YES | YES |

Example 35

This example is an evaluation of tolerated and non-tolerated deletions in ARC17480.

Molecules were generated for testing with single or multiple residues deleted in the ARC17480 sequence, as shown in Table 38 below and in FIG. 143. Each individual residue in ARC17480 was deleted one at a time, resulting in ARC32301, ARC33120-ARC33143, and ARC18555. In cases where two adjacent nucleotides were identical, the corresponding double deletion was also generated, resulting in ARC32302 and ARC33144-ARC33148. Additionally, molecules with multiple deletions were generated, resulting in ARC32303, ARC32305, ARC32306, ARC32307, ARC33889, ARC33890, ARC33891, ARC33895, ARC33900 and ARC33907.

The ARC17480 molecules with deletions were assayed for binding and function. The assays used for this evaluation were the calibrated automated thrombogram (CAT) assay, a dot-blot binding-competition assay and a FXa activity assay. The results of these assays are summarized in Table 38 and FIG. 144. A substitution was considered tolerated for activity if it met the criteria of at least two of the three assays that were carried out. Substitutions that were tolerated ("yes") and not tolerated ("no") are identified in Table 38. The experimental details and the criteria used for each assay are described in the following paragraphs.

The TFPI-inhibitory activity of each molecule was evaluated in the CAT assay in pooled hemophilia A plasma at 500 nM, 166.67 nM, 55.56 nM, 18.52 nM, 6.17 nM and 2.08 nM aptamer concentration. ARC17480 was included in every experiment as a control. For each molecule, the endogenous thrombin potential (ETP) and peak thrombin values at each aptamer concentration were used for analysis. The ETP or peak thrombin value for hemophilia A plasma alone was subtracted from the corresponding value in the presence of aptamer for each molecule at each concentration. Then, the corrected ETP and peak values were plotted as a function of aptamer concentration and fit to the equation $y=(max/(1+IC_{50}/x))+int$, where $y=$ETP or peak thrombin, $x=$concentration of aptamer, max=the maximum ETP or peak thrombin, and int=the y-intercept, to generate an $IC_{50}$ value for both the ETP and the peak thrombin. The $IC_{50}$ of each aptamer was compared to the $IC_{50}$ of ARC17480 that was evaluated in the same experiment. A substitution was considered tolerated in the CAT assay if both the ETP and peak thrombin $IC_{50}$ of that molecule were not more than 5-fold greater than that of ARC17480 evaluated in the same experiment. Tolerated substitutions are indicated in Table 38 as meeting the assay criteria ("yes") or not meeting the assay criteria ("no").

Each molecule was evaluated for binding to tissue factor pathway inhibitor (TFPI) in a binding-competition assay. For these experiments, 10 nM human TFPI (American Diagnostica, Stamford, Conn., catalog #4500PC) was incubated with trace amounts of radiolabeled ARC17480 and 5000 nM, 1666.67 nM, 555.56 nM, 185.19 nM, 61.73 nM, 20.58 nM, 6.86 nM, 2.29 nM, 0.76 nM or 0.25 nM of unlabeled competitor aptamer. ARC17480 was included as a competitor in every experiment as a control. For each molecule, the percentage of radiolabeled ARC17480 bound at each competitor aptamer concentration was used for analysis. The percentage of radiolabeled ARC17480 bound was plotted as a function of aptamer concentration and fit to the equation $y=(max/(1+x/IC_{50}))+int$, where $y=$the percentage of radiolabeled ARC17480 bound, $x=$the concentration of aptamer, max=the maximum radiolabeled ARC17480 bound, and int=the y-intercept, to generate an $IC_{50}$ value for binding-competition. The $IC_{50}$ of each aptamer was compared to the $IC_{50}$ of ARC17480 that was evaluated in the same experiment. A substitution was considered tolerated in the binding-competition assay if the $IC_{50}$ of that molecule was not more than 5-fold greater than that of ARC17480 evaluated in the same experiment. Tolerated substitutions are indicated in Table 38 as meeting the assay criteria ("yes") or not meeting the assay criteria ("no").

Each molecule was evaluated for inhibition of TFPI in a Factor Xa (FXa) activity assay. The ability of FXa to cleave a chromogenic substrate was measured in the presence and absence of TFPI, with or without the addition of aptamer. For these experiments, 2 nM human FXa was incubated with 8 nM human TFPI. Then, 500 µM chromogenic substrate and aptamers were added and FXa cleavage of the substrate was measured by absorbance at 405 nm ($A_{405}$) as a function of time. Aptamers were tested at 500 nM, 125 nM, 31.25 nM, 7.81 nM, 1.95 nM and 0.49 nM concentrations. ARC17480 was included as a control in each experiment. For each aptamer concentration, the $A_{405}$ was plotted as a function of time and the linear region of each curve was fit to the equation $y=mx+b$, where $y=A_{405}$, $x=$the aptamer concentration, m=the rate of substrate cleavage, and b=the y-intercept, to generate a rate of FXa substrate cleavage. The rate of FXa substrate cleavage in the presence of TFPI and the absence of aptamer was subtracted from the corresponding value in the presence of both TFPI and aptamer for each molecule at each concentration. Then, the corrected rates were plotted as a function of aptamer concentration and fit to the equation y=($V_{max}$/(1+ $IC_{50}$/x)), where y=the rate of substrate cleavage, x=concentration of aptamer, and $V_{max}$=the maximum rate of substrate cleavage, to generate an $IC_{50}$ and maximum ($V_{max}$) value. The $IC_{50}$ and $V_{max}$ values of each aptamer were compared to the $IC_{50}$ and max values of ARC17480 that was evaluated in the same experiment. A substitution was considered tolerated in the FXa activity assay if the $IC_{50}$ of that molecule was not more than 5-fold greater than that of ARC17480 evaluated in the same experiment and the $V_{max}$ value was not less than 80% of the $V_{max}$ value of the ARC17480 evaluated in the same experiment. Tolerated substitutions are indicated in Table 38 as meeting the assay criteria ("yes") or not meeting the assay criteria ("no").

This example demonstrates that multiple individual deletions in ARC17480 are tolerated for binding and activity, and that some combinations of deletions are also tolerated (Table 38 and FIG. 144). ARC33889 and ARC33895 each tolerate a total of seven deletions at their 5'- and 3'-ends, resulting in core molecules that are twenty-five nucleotides long. Additional combinations of deletions in ARC17480 may be tolerated for binding and activity, with or without additional changes in the molecule.

TABLE 38

Tolerated and Non-tolerated Deletions in ARC17480

| SEQ ID NO: | ARC # | Sequence (5' → 3') (3T = inverted dT; mN = 2'-methoxy-containing residue; dN = deoxy residue) | Meets Criteria? CAT Assay | Binding-competition Assay | FXa Activity Assay | Substitution(s) Tolerated |
|---|---|---|---|---|---|---|
| 106 | 32301 | mGmAmAmUmAmUmAdCmUmU mGmGdCmUdCmGmUmUmAm GmGmUmGdCmGmUmAmUmA mUmA3T | YES | YES | YES | YES |
| 107 | 33120 | mGmGmAmUmAmUmAdCmUm UmGmGdCmUdCmGmUmUmAm GmGmUmGdCmGmUmAmUmA mUmA3T | YES | YES | YES | YES |
| 108 | 33121 | mGmGmAmAmAmUmAdCmUm UmGmGdCmUdCmGmUmUmAm GmGmUmGdCmGmUmAmUmA mUmA3T | YES | YES | YES | YES |
| 109 | 33122 | mGmGmAmAmUmUmAdCmUm UmGmGdCmUdCmGmUmUmAm GmGmUmGdCmGmUmAmUmA mUmA3T | NO | YES | YES | YES |
| 110 | 33123 | mGmGmAmAmUmAmAdCmUm UmGmGdCmUdCmGmUmUmAm GmGmUmGdCmGmUmAmUmA mUmA3T | NO | NO | NO | NO |
| 111 | 33124 | mGmGmAmAmUmAmUdCmUm UmGmGdCmUdCmGmUmUmAm GmGmUmGdCmGmUmAmUmA mUmA3T | NO | NO | NO | NO |
| 112 | 33125 | mGmGmAmAmUmAmUmAmUm UmGmGdCmUdCmGmUmUmAm GmGmUmGdCmGmUmAmUmA mUmA3T | NO | NO | NO | NO |
| 113 | 33126 | mGmGmAmAmUmAmUmAdCm UmGmGdCmUdCmGmUmUmAm GmGmUmGdCmGmUmAmUmA mUmA3T | NO | NO | NO | NO |
| 114 | 33127 | mGmGmAmAmUmAmUmAdCm UmUmGdCmUdCmGmUmUmAm GmGmUmGdCmGmUmAmUmA mUmA3T | NO | NO | NO | NO |
| 115 | 33128 | mGmGmAmAmUmAmUmAdCm UmUmGmGmUdCmGmUmUmA mGmGmUmGdCmGmUmAmUm AmUmA3T | NO | NO | NO | NO |
| 116 | 33129 | mGmGmAmAmUmAmUmAdCm UmUmGmGdCdCmGmUmUmAm | NO | NO | NO | NO |

TABLE 38-continued Tolerated and Non-tolerated Deletions in ARC17480

| SEQ ID NO: | ARC # | Sequence (5' → 3') (3T = inverted dT; mN = 2'-methoxy-containing residue; dN = deoxy residue) | CAT Assay | Binding-competition Assay | FXa Activity Assay | Substitution(s) Tolerated |
|---|---|---|---|---|---|---|
| | | GmGmUmGdCmGmUmAmUmAmUmA3T | | | | |
| 117 | 33130 | mGmGmAmAmUmAmUmAdCmUmUmGmGdCmUmGmUmUmAmGmGmUmGdCmGmUmAmUmAmUmA3T | NO | NO | NO | NO |
| 118 | 33131 | mGmGmAmAmUmAmUmAdCmUmUmGmGdCmUdCmUmUmAmGmGmUmGdCmGmUmAmUmAmUmA3T | NO | NO | NO | NO |
| 119 | 33132 | mGmGmAmAmUmAmUmAdCmUmUmGmGdCmUdCmGmUmAmGmGmUmGdCmGmUmAmUmAmUmA3T | NO | NO | YES | NO |
| 120 | 33133 | mGmGmAmAmUmAmUmAdCmUmUmGmGdCmUdCmGmUmUmGmGmUmGdCmGmUmAmUmAmUmA3T | NO | NO | NO | NO |
| 121 | 33134 | mGmGmAmAmUmAmUmAdCmUmUmGmGdCmUdCmGmUmUmAmGmUmGdCmGmUmAmUmAmUmA3T | NO | NO | NO | NO |
| 122 | 33135 | mGmGmAmAmUmAmUmAdCmUmUmGmGdCmUdCmGmUmUmAmGmGmGdCmGmUmAmUmAmUmA3T | NO | NO | NO | NO |
| 123 | 33136 | mGmGmAmAmUmAmUmAdCmUmUmGmGdCmUdCmGmUmUmAmGmGmUdCmGmUmAmUmAmUmA3T | NO | NO | NO | NO |
| 124 | 33137 | mGmGmAmAmUmAmUmAdCmUmUmGmGdCmUdCmGmUmUmAmGmGmUmGmGmUmAmUmAmUmA3T | NO | NO | NO | NO |
| 125 | 33138 | mGmGmAmAmUmAmUmAdCmUmUmGmGdCmUdCmGmUmUmAmGmGmUmGdCmUmAmUmAmUmA3T | NO | NO | NO | NO |
| 126 | 33139 | mGmGmAmAmUmAmUmAdCmUmUmGmGdCmUdCmGmUmUmAmGmGmUmGdCmGmAmUmAmUmA3T | NO | NO | NO | NO |
| 127 | 33140 | mGmGmAmAmUmAmUmAdCmUmUmGmGdCmUdCmGmUmUmAmGmGmUmGdCmGmUmUmAmUmA3T | NO | NO | NO | NO |
| 128 | 33141 | mGmGmAmAmUmAmUmAdCmUmUmGmGdCmUdCmGmUmUmAmGmGmUmGdCmGmUmAmAmUmA3T | NO | YES | YES | YES |
| 129 | 33142 | mGmGmAmAmUmAmUmAdCmUmUmGmGdCmUdCmGmUmUmAmGmGmUmGdCmGmUmAmUmUmA3T | YES | YES | YES | YES |
| 130 | 33143 | mGmGmAmAmUmAmUmAdCmUmUmGmGdCmUdCmGmUmUmAmGmGmUmGdCmGmUmAmUmAmA3T | YES | YES | YES | YES |

TABLE 38-continued

Tolerated and Non-tolerated Deletions in ARC17480

| SEQ ID NO: | ARC # | Sequence (5' → 3') (3T = inverted dT; mN = 2'-methoxy-containing residue; dN = deoxy residue) | Meets Criteria? CAT Assay | Binding-competition Assay | FXa Activity Assay | Substitution(s) Tolerated |
|---|---|---|---|---|---|---|
| 131 | 18555 | mGmGmAmAmUmAmUmAdCmUmUmGmGdCmUdCmGmUmUmAmGmGmUmGdCmGmUmAmUmAmU3T | YES | YES | YES | YES |
| 132 | 32302 | mAmAmUmAmUmAdCmUmUmGmGdCmUdCmGmUmUmAmGmGmUmGdCmGmUmAmUmAmUmA3T | YES | YES | YES | YES |
| 133 | 33144 | mGmUmUmAmUmAdCmUmUmGmGdCmUdCmGmUmUmAmGmGmUmGdCmGmUmAmUmAmUmA3T | YES | YES | YES | YES |
| 134 | 33145 | mGmGmAmAmUmAmUmAdCmGmGdCmUdCmGmUmUmAmGmGmUmGdCmGmUmAmUmAmUmA3T | NO | NO | NO | NO |
| 135 | 33146 | mGmGmAmAmUmAmUmAdCmUmUdCmUdCmGmUmUmAmGmGmUmGdCmGmUmAmUmAmUmA3T | NO | NO | NO | NO |
| 136 | 33147 | mGmGmAmAmUmAmUmAdCmUmUmGmGdCmUdCmGmAmGmGmUmGdCmGmUmAmUmAmUmA3T | NO | NO | NO | NO |
| 137 | 33148 | mGmGmAmAmUmAmUmAdCmUmUmGmGdCmUdCmGmUmUmAmUmGdCmGmUmAmUmAmUmA3T | NO | NO | NO | NO |
| 138 | 32303 | mAmUmAmUmAdCmUmUmGmGdCmUdCmGmUmUmAmGmGmUmGdCmGmUmAmUmAmUmA3T | YES | YES | YES | YES |
| 139 | 32305 | mGmAmAmUmAmUmAdCmUmUmGmGdCmUdCmGmUmUmAmGmGmUmGdCmGmUmAmUmAmU3T | YES | YES | YES | YES |
| 140 | 32306 | mAmAmUmAmUmAdCmUmUmGmGdCmUdCmGmUmUmAmGmGmUmGdCmGmUmAmUmA3T | YES | YES | YES | YES |
| 141 | 32307 | mAmUmAmUmAdCmUmUmGmGdCmUdCmGmUmUmAmGmGmUmGdCmGmUmAmU3T | YES | YES | YES | YES |
| 142 | 33889 | mUmAmUmAdCmUmUmGmGdCmUdCmGmUmUmAmGmGmUmGdCmGmUmAmU3T | YES | NO | YES | YES |
| 143 | 33890 | mAmUmAmUmAdCmUmUmGmGdCmUdCmGmUmUmAmGmGmUmGdCmGmUmAmUmA3T | YES | YES | YES | YES |
| 144 | 33891 | mUmAmUmAdCmUmUmGmGdCmUdCmGmUmUmAmGmGmUmGdCmGmUmAmUmA3T | YES | YES | YES | YES |
| 145 | 33895 | mAmUmAdCmUmUmGmGdCmUdCmGmUmUmAmGmGmUmGdCmGmUmAmUmA3T | YES | YES | YES | YES |

TABLE 38-continued

Tolerated and Non-tolerated Deletions in ARC17480

| SEQ ID NO: | ARC # | Sequence (5' → 3') (3T = inverted dT; mN = 2'-methoxy-containing residue; dN = deoxy residue) | CAT Assay | Binding-competition Assay | FXa Activity Assay | Substitution(s) Tolerated |
|---|---|---|---|---|---|---|
| 146 | 33900 | mUmUmAdCmUmUmGmGdCmU dCmGmUmUmAmGmGmUmGd CmGmUmAmUmA3T | YES | YES | YES | YES |
| 147 | 33907 | mGmGmAmAmUmAdCmUmUm GmGdCmUdCmGmUmUmAmG mGmUmGdCmGmUmAmUmAm UmA3T | YES | YES | YES | YES |

Example 36

This example demonstrates that 3'-truncated derivatives of ARC19499 have functional activity in the CAT assay.

ARC21383, ARC21385, ARC21387 and ARC21389 have successive single deletions at their 3'-end relative to ARC19499 (Table 39). These molecules are pegylated at their 5'-ends with a 40 kDa PEG. These molecules were added to hemophilia A plasma at different concentrations (300 nM-1.2 nM) and thrombin generation was measured. ARC19499 was used as a control in the experiment. These 3'-truncated molecules all had activity in the CAT assay that was similar to that observed with ARC19499, with respect to both endogenous thrombin potential (ETP; FIG. 145A) and peak thrombin (FIG. 145B).

This example demonstrates that ARC19499 can be truncated by removal of the 3'-3T and the three 3'-end core nucleotides and still retain activity in the CAT assay that is similar to that of the parent molecule ARC19499.

TABLE 39

3'-truncated versions of ARC19499

| SEQ ID NO: | ARC # | Sequence (5' → 3') (mN = 2'-methoxy-containing residue; dN = deoxy residue; nh = amine linker; PEG40K = 40 kDa PEG) |
|---|---|---|
| 148 | 21383 | PEG40KnhmGmGmAmAmUmAmUmAd CmUmUmGmGdCmUdCmGmUmUmA mGmGmUmGdCmGmUmAmUmAmUm A |
| 149 | 21385 | PEG40KnhmGmGmAmAmUmAmUmAd CmUmUmGmGdCmUdCmGmUmUmA mGmGmUmGdCmGmUmAmUmAmU |
| 150 | 21387 | PEG40KnhmGmGmAmAmUmAmUmAd CmUmUmGmGdCmUdCmGmUmUmA mGmGmUmGdCmGmUmAmUmA |
| 151 | 21389 | PEG40KnhmGmGmAmAmUmAmUmAd CmUmUmGmGdCmUdCmGmUmUmA mGmGmUmGdCmGmUmAmU |

Example 37

This example describes a strategy for identifying aptamers that bind at least in part to or otherwise interact with one or more portions of tissue factor pathway inhibitor (TFPI). For these experiments, a partial TFPI protein or peptide that comprises the region of TFPI that is to be targeted is used as a selection target. Any portion of the TFPI protein can be used for this type of experiment. For example, a TFPI protein that only contains the K3 and C-terminal domains of full-length TFPI (K3-C TFPI; amino acids 182-276) is the target for selection. A nucleic acid pool is incubated with K3-C TFPI to allow binding to occur, the mixture is partitioned to separate bound nucleic acids from unbound nucleic acids, and the bound nucleic acids are eluted from the protein and amplified. This process is optionally repeated for multiple cycles until an aptamer is identified. For some cycles, full-length TFPI is used as the target to ensure that the aptamer binds to the K3-C-terminal region of the protein in the context of the full-length protein. These experiments result in the identification of TFPI-binding aptamers whose binding epitope is contained, for example, within the K3-C-terminal region of the protein.

Example 38

This example describes a strategy for identifying aptamers that bind at least in part to or otherwise interact with one or more portions of tissue factor pathway inhibitor (TFPI). For these experiments, full-length TFPI is used as a selection target and a portion of TFPI or a ligand that binds to TFPI is used to elute aptamers that bind to a portion of the TFPI protein. A protein or peptide that contains only a portion of TFPI could also be used as the selection target. For example, a peptide comprised of amino acids 150-190 of TFPI is used for elution. A nucleic acid pool is incubated with full-length TFPI to allow binding to occur, the mixture is partitioned to separate bound nucleic acids from unbound nucleic acids, bound nucleic acids are eluted from the protein by incubation with the TFPI 150-190 peptide, and amplified. This process is repeated for multiple cycles until an aptamer is identified. These experiments result in the identification of TFPI-binding aptamers whose binding epitope contains, for example, all or part of the 150-190 region of TFPI.

Example 39

This example describes a strategy for identifying aptamers that bind at least in part to or otherwise interact with one or more portions of tissue factor pathway inhibitor (TFPI). For these experiments, full-length TFPI is used as a selection target and a ligand that binds to TFPI is included in the selection to block epitopes from aptamer binding to drive aptamer binding to alternative sites on the protein. A protein or peptide that contains only a portion of TFPI could also be used as the selection target. The blocking ligand is included in the selection step and/or in the partitioning step as a capture method or as a washing reagent. For example, an antibody that binds to the C-terminus of TFPI is included in the selection. A nucleic acid pool is incubated with TFPI in the presence of the antibody to allow binding to occur, the mixture is partitioned to separate bound nucleic acids from unbound nucleic acids, and bound nucleic acids are eluted from the protein and amplified. This process is repeated for multiple cycles until an aptamer is identified. Some cycles include the antibody in the washing solution during the partitioning step and some cycles use the antibody as a partitioning method to capture TFPI-aptamer complexes, in conjunction with or instead of inclusion of the antibody in the binding step. These experiments result in the identification of TFPI-binding aptamers whose binding epitope is not contained, for example, within the antibody-binding region at the C-terminus of TFPI.

Example 40

This example describes a strategy for identifying aptamers that bind at least in part to or otherwise interact with one or more portions of tissue factor pathway inhibitor (TFPI). For these experiments, full-length TFPI is used as a selection target and a partitioning step is employed that separates aptamers with a desired functional property away from nucleic acids that do not have that functional property. A protein or peptide that contains only a portion of TFPI could also be used as the selection target. For example, the desired aptamer functional property is inhibition of TFPI interaction with Factor Xa (FXa). For these experiments, a nucleic acid pool is incubated with TFPI under conditions that allow for binding and then partitioned to separate unbound nucleic acids from aptamers that are bound to TFPI. The TFPI-bound aptamers are then incubated with FXa that is bound to a hydrophobic plate. Free TFPI and TFPI bound with aptamers that do not interfere with the TFPI-FXa interaction bind to FXa on the plate, while TFPI bound with aptamers that do interfere with the TFPI-FXa interaction do not bind to the plate. Aptamers from the unbound TFPI-aptamer complexes are then amplified. This process is repeated for multiple cycles until an aptamer is identified. These experiments result, for example, in the identification of aptamers that bind to a region of the TFPI protein that mediates inhibition of the functional interaction between TFPI and FXa.

Example 41

This example describes a strategy for identifying antibodies that bind at least in part to or otherwise interact with one or more portions of tissue factor pathway inhibitor (TFPI). The antigen can be any one or more portions of TFPI that are of interest. For example, the antigen may be a TFPI protein that only contains the K3 and C-terminal domains of full-length TFPI (K3-C TFPI; amino acids 182-276). The antigen is expressed in an expression system or is synthesized on an automated protein synthesizer. Mice are then immunized with the antigen in solution. Antibody producing cells are then isolated from the immunized mice and fused with myeloma cells to form monoclonal antibody-producing hybridomas. The hybridomas are then cultured in a selective medium. The resulting cells are then plated by serial dilution and assayed for the production of antibodies that specifically bind to the antigen. Selected monoclonal antibody secreting hybridomas are then cultured. Antibodies are then purified from the culture media supernatants of hybridoma cells. These experiments result in the identification of TFPI-binding antibodies whose binding epitope is contained, for example, within the K3-C-terminal region of the protein.

The invention having now been described by way of written description and example, those of skill in the art will recognize that the invention can be practiced in a variety of embodiments and that the description and examples above are for purposes of illustration and not limitation of the following claims.

What is claimed is:

1. An aptamer that binds to tissue factor pathway inhibitor (TFPI), wherein the aptamer comprises a nucleic acid sequence selected from the group consisting of SEQ ID NOs.: 4, 1, 2, 3, 5, 6, 7, 8, 9 and 10.

2. The aptamer of claim 1, wherein the TFPI is human TFPI.

3. The aptamer of claim 1, wherein the aptamer has a dissociation constant for human TFPI of 100 nM or less.

4. The aptamer of claim 1, wherein the aptamer comprises at least one chemical modification.

5. The aptamer of claim 4, wherein the modification is selected from the group consisting of: a chemical substitution at a sugar position, a chemical substitution at an internucleotide linkage, and a chemical substitution at a base position.

6. The aptamer of claim 4, wherein the modification is selected from the group consisting of: incorporation of a modified nucleotide; a 3' cap; a 5' cap; conjugation to a polyalkylene oxide compound with a molecular weight of greater than 10 kD; conjugation to a lipophilic compound; incorporation of a CpG motif; and incorporation of a phosphorothioate or phosphorodithioate into the phosphate backbone.

7. The aptamer of claim 6, wherein the polyalkylene oxide compound is polyethylene glycol.

8. The aptamer of claim 6, wherein the 3' cap is an inverted deoxythymidine cap.

9. The aptamer of claim 1 or a salt thereof comprising the nucleic acid sequence set forth below: mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA (SEQ ID NO: 1) (ARC26835), wherein "dN" is a deoxynucleotide and "in mN" is a 2'-OMe containing nucleotide.

10. The aptamer of claim 1 or a salt thereof comprising the nucleic acid sequence set forth below: mG-mG-mA-mA-mU-mA-mU-mA-dC-mU-mU-mG-mG-dC-mU-dC-mG-mU-mU-mA-mG mG-mU-mG-dC-mG-mU-mA-mU-mA-mU-mA-3T (SEQ ID NO: 2) (ARC17480), wherein "3T" is an inverted deoxythymidine, "dN" is a deoxynucleotide and "mN" is a 2'-OMe containing nucleotide.

11. The aptamer of claim 1 or a salt thereof comprising the nucleic acid sequence set forth below: NH$_2$-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 3) (ARC19498), wherein "NH$_2$" is from a 5'-hexylamine linker phosphoramidite, "3T" is an inverted deoxythymidine, "dN" is a deoxynucleotide and "mN" is a 2'-OMe containing nucleotide.

12. The aptamer of claim 1 or a salt thereof comprising the nucleic acid sequence set forth below: PEG40K-NH-mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 4) (ARC19499), wherein "NH" is from a 5'-hexylamine linker phosphoramidite, "PEG" is a polyethylene glycol, "3T" is an inverted deoxythymidine, "dN" is a deoxynucleotide and "mN" is a 2'-OMe containing nucleotide.

13. A pharmaceutical composition comprising a therapeutically effective amount of the aptamer of claim 1 or a salt thereof, and a pharmaceutically acceptable carrier or diluent.

14. A method for treating, delaying the progression of or ameliorating a bleeding disorder mediated by TFPI, comprising administering to a subject the composition of claim 13.

15. The method of claim 14, wherein the subject is a mammal.

16. The method of claim 15, wherein the mammal is a human.

17. The method of claim 14, wherein the bleeding disorder is selected from the group consisting of: congenital or acquired coagulation factor deficiencies, hemophilia A; hemophilia B; hemophilia C; hemophilia A with inhibitors; deficiency of α2-plasmin inhibitor; deficiency of plasminogen activator inhibitor 1; multiple coagulation factor deficiency; functional coagulation factor abnormalities; joint hemorrhage; spontaneous bleeding; hemorrhagic stroke; intracranial hemorrhage; lacerations; hemorrhage associate with trauma; acute traumatic coagulopathy; coagulopathy associated with cancer; von Willebrand's Disease; disseminated intravascular coagulation; liver disease; menorrhagia; thrombocytopenia and hemorrhage associated with the use of anticoagulants.

18. The method of claim 14, wherein the composition is administered prior to, during and/or after a medical procedure.

19. The method of claim 14, wherein the composition is administered in combination with another drug.

20. The method of claim 14, wherein the composition is administered in combination with another therapy.

21. A kit comprising the aptamer of claim 1.

22. An aptamer or a salt thereof that binds to tissue factor pathway inhibitor (TFPI), wherein the aptamer comprises the following structure:

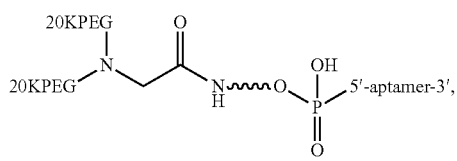

wherein HN〜〜〜PO$_3$H is from a 5'-amine linker phosphoramidite, and wherein the aptamer comprises the nucleic acid sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 2), wherein "3T" is an inverted deoxythymidine, "dN" is a deoxynucleotide and "mN" is a 2'-O Methyl containing nucleotide, and wherein 20 KPEG is a mPEG moiety having a molecular weight of 20 kDa.

23. The aptamer of claim 22, wherein the linker is selected from the group consisting of: 2-18 consecutive CH$_2$ groups, 2-12 consecutive CH$_2$ groups, 4-8 consecutive CH$_2$ groups and 6 consecutive CH$_2$ groups.

24. An aptamer or a salt thereof that binds to tissue factor pathway inhibitor (TFPI), wherein the aptamer comprises the following structure:

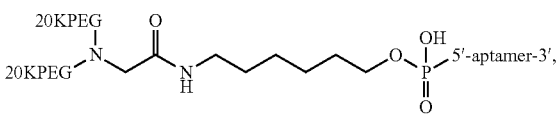

wherein the aptamer comprises the nucleic acid sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 2), wherein "3T" is an inverted deoxythymidine, "dN" is a deoxynucleotide and "mN" is a 2'-O Methyl containing nucleotide, and wherein 20 KPEG is a mPEG moiety having a molecular weight of 20 kDa.

25. An aptamer or a salt thereof that binds to tissue factor pathway inhibitor (TFPI), wherein the aptamer comprises the following structure:

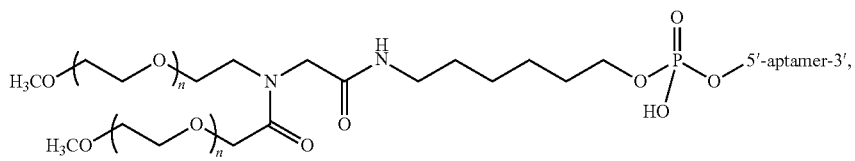

wherein the aptamer comprises the nucleic acid sequence of mG-mG-mA-mA-mU-mA-mU-mA-dC-mU-mU-mG-mG-dC-mU-dC-mG-mU-mU-mA-mG-mG-mU-mG-dC-mG-mU-mA-mU-mA-mU-mA-3T (SEQ ID NO: 2), Wherein "n" is approximately 450, "3T" is an inverted deoxythymidine, "dN" is a deoxynucleotide and "mN" is a 2'-O Methyl containing nucleotide.

26. An aptamer that binds to a human tissue factor pathway inhibitor (TFPI) polypeptide having the amino acid sequence of SEQ ID NO: 11, wherein the aptamer has at least 70% identity to the entire sequence of any one of SEQ ID NOS: 1-10, wherein the aptamer modulates TFPI-mediated inhibition of blood coagulation, and wherein the aptamer competes for binding to TFPI with a reference aptamer comprising a nucleic acid sequence selected from the group consisting of: SEQ ID NO: 4 (ARC19499), SEQ ID NO: 1 (ARC26835), SEQ ID NO: 2 (ARC17480), SEQ ID NO: 3 (ARC19498), SEQ ID NO: 5 (ARC19500), SEQ ID NO:6 (ARC19501), SEQ ID NO: 7 (ARC31301), SEQ ID NO: 8 (ARC18546), SEQ ID NO: 9 (ARC19881) and SEQ ID NO: 10 (ARC19882).

27. An aptamer that binds to a region on a human tissue factor pathway inhibitor (TFPI) polypeptide comprising one or more portions of SEQ ID NO: 11, wherein the one or more portions is selected from the group consisting of: residues 240-260, amino acid residues 245-265, amino acid residues 250-270, amino acid residues 255-275, amino acid residues 260-276, amino acid residues 240-276, and amino acid residues 242-276.

28. An aptamer with at least 70% identity to the entire sequence of any one of SEQ ID NOS: 1-10 and that binds to human tissue factor pathway inhibitor (TFPI) and exhibits one or more of the following properties:
   a) competes for binding to TFPI with any one of SEQ ID NOS: 1-10;
   b) inhibits TFPI inhibition of Factor Xa;
   c) increases thrombin generation in hemophilia plasma;
   d) inhibits TFPI inhibition of the intrinsic tenase complex;
   e) restores normal hemostasis, as measured by thromboelastography (TEG) in whole blood and plasma;
   f) restores normal clotting, as indicated by shorter clot time, more rapid clot formation or more stable clot development, as measured by thromboelastography (TEG) or rotational thromboelastometry (ROTEM) in whole blood and plasma; or
   g) decreases the clot time, as measured by dilute prothrombin time (dPT), tissue factor activated clotting time (TF-ACT) or any other TFPI-sensitive clot-time measurement.

29. An aptamer with at least 70% identity to the entire sequence of any one of SEQ ID NOS: 1-10 and that binds to human tissue factor pathway inhibitor wherein the aptamer competes for binding to TFPI with a reference aptamer selected from the group consisting of: SEQ ID NO: 4, SEQ ID NO: 1, SEQ ID NO: 2, SEQ ID NO: 3, SEQ ID NO: 5, SEQ ID NO: 6, SEQ ID NO: 7, SEQ ID NO: 8, SEQ ID NO: 9 and SEQ ID NO: 10.

30. An aptamer that binds to tissue factor pathway inhibitor (TFPI) with at least 70% identity to the entire sequence of any one of SEQ ID NOs 1-10 and wherein the aptamer competes, either directly or indirectly, for binding to TFPI with a reference antibody selected from the group consisting of: AD4903.

31. An aptamer that binds to human tissue factor pathway inhibitor (UPI) and comprises a stem and loop motif having the nucleotide sequence of SEQ ID NO: 4, wherein:
   a) any one or more of nucleotides 1, 2, 3, 4, 6, 8, 11, 12, 13, 17, 20, 21, 22, 24, 28, 30 and 32 may be modified from a 2'-OMe substitution to a 2'-deoxy substitution;
   b) any one or more of nucleotides 5, 7, 15, 19, 23, 27, 29 and 31 may be modified from a 2'-OMe uracil to either a 2'-deoxy uracil or a 2'-deoxy thymine;
   c) nucleotide 18 may be modified from a 2'-OMe uracil to a 2'-deoxy uracil; and/or
   d) any one or more of nucleotides 14, 16 and 25 may be modified from a 2'-deoxy cytosine to either a 2'-OMe cytosine or a 2'-fluoro cytosine.

32. An aptamer that binds to tissue factor pathway inhibitor (TFPI), wherein the aptamer comprises the primary nucleotide sequence: ggaauauacu uggcucguua ggugcguaua ua (SEQ ID NO: 153).

33. The aptamer of claim 32, wherein the aptamer has at least one chemical modification.

34. The aptamer of claim 33, wherein the modification is selected from the group consisting of: chemical substitution at a sugar position, a chemical substitution at an internucleotide linkage, and a chemical substitution at a base position.

35. The aptamer of claim 34, wherein the modification is selected from the group consisting of: incorporation of a modified nucleotide; a nucleotide cap; conjugation to a polyalkylene oxide compound with a molecular weight of greater than 10 kD; conjugation to a lipophilic compound; incorporation of a CpG motif; and incorporation of a phosphorothioate or phosphorodithioate into the phosphate backbone.

36. The aptamer of claim 35, wherein the polyalkylene oxide compound is polyethylene glycol.

* * * * *

UNITED STATES PATENT AND TRADEMARK OFFICE
CERTIFICATE OF CORRECTION

PATENT NO. : 8,252,913 B2  Page 1 of 1
APPLICATION NO. : 12/858369
DATED : August 28, 2012
INVENTOR(S) : Robert G. Schaub et al.

It is certified that error appears in the above-identified patent and that said Letters Patent is hereby corrected as shown below:

In the claims:

Claim 9, Column 375, Line 26: please delete "in" before -- mN --

Claim 10, Column 375, Line 36: please insert a -- - -- between the first and second "mG"

Claim 25, Column 377, Line 13: please replace "Wherein" with -- wherein --

Claim 31, Column 378, Line 24: please delete "(UPI)" and replace with -- (TFPI) --

Signed and Sealed this
Twenty-seventh Day of November, 2012

David J. Kappos
*Director of the United States Patent and Trademark Office*